US011001559B2

(12) United States Patent
Sintim

(10) Patent No.: US 11,001,559 B2
(45) Date of Patent: May 11, 2021

(54) 4-SUBSTITUTED AMINOISOQUINOLINE DERIVATIVES

(71) Applicant: Purdue Research Foundation, West Lafayette, IN (US)

(72) Inventor: Herman O. Sintim, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/325,022

(22) PCT Filed: Aug. 15, 2017

(86) PCT No.: PCT/US2017/046843
§ 371 (c)(1),
(2) Date: Feb. 12, 2019

(87) PCT Pub. No.: WO2018/035072
PCT Pub. Date: Feb. 22, 2018

(65) Prior Publication Data
US 2019/0177278 A1  Jun. 13, 2019

Related U.S. Application Data

(60) Provisional application No. 62/461,295, filed on Feb. 21, 2017, provisional application No. 62/375,154, filed on Aug. 15, 2016.

(51) Int. Cl.
| | |
|---|---|
| C07D 471/04 | (2006.01) |
| C07D 401/06 | (2006.01) |
| C07D 217/22 | (2006.01) |
| C07D 401/12 | (2006.01) |
| C07D 487/04 | (2006.01) |
| C07D 417/04 | (2006.01) |
| C07D 471/10 | (2006.01) |
| C07D 473/32 | (2006.01) |
| C07D 413/04 | (2006.01) |
| C07D 239/95 | (2006.01) |
| C07D 213/73 | (2006.01) |
| C07D 239/84 | (2006.01) |
| C07D 401/04 | (2006.01) |
| C07D 403/04 | (2006.01) |
| C07D 417/12 | (2006.01) |
| C07D 401/10 | (2006.01) |
| C07D 403/10 | (2006.01) |
| A61P 35/00 | (2006.01) |
| C07D 209/49 | (2006.01) |
| C07D 221/02 | (2006.01) |
| C07D 233/10 | (2006.01) |
| C07D 271/06 | (2006.01) |
| C07D 413/06 | (2006.01) |

(52) U.S. Cl.
CPC ............ *C07D 217/22* (2013.01); *A61P 35/00* (2018.01); *C07D 209/49* (2013.01); *C07D 213/73* (2013.01); *C07D 221/02* (2013.01); *C07D 233/10* (2013.01); *C07D 239/84* (2013.01); *C07D 239/95* (2013.01); *C07D 271/06* (2013.01); *C07D 401/04* (2013.01); *C07D 401/06* (2013.01); *C07D 401/10* (2013.01); *C07D 401/12* (2013.01); *C07D 403/04* (2013.01); *C07D 403/10* (2013.01); *C07D 413/04* (2013.01); *C07D 413/06* (2013.01); *C07D 417/04* (2013.01); *C07D 417/12* (2013.01); *C07D 471/04* (2013.01); *C07D 471/10* (2013.01); *C07D 473/32* (2013.01); *C07D 487/04* (2013.01)

(58) Field of Classification Search
CPC ........................... C07D 401/05; C07D 471/04
See application file for complete search history.

(56) References Cited

U.S. PATENT DOCUMENTS

| | | |
|---|---|---|
| 8,461,167 B2 | 6/2013 | Wang et al. |
| 2005/0137213 A1 | 6/2005 | Cai et al. |
| 2009/0285782 A1 | 11/2009 | Gao et al. |
| 2010/0080772 A1 | 4/2010 | Belema et al. |
| 2010/0160283 A1 | 6/2010 | Chaffee et al. |
| 2011/0081316 A1 | 7/2011 | Messersmith et al. |
| 2013/0196975 A1 | 8/2013 | Wunberg et al. |
| 2015/0057263 A1 | 2/2015 | Brown et al. |

FOREIGN PATENT DOCUMENTS

| | | |
|---|---|---|
| WO | 20030024931 A1 | 3/2003 |
| WO | 2011041634 A1 | 4/2011 |
| WO | 20140194667 A1 | 12/2014 |
| WO | 2016/014674 A1 | 1/2016 |
| WO | 20160014674 A1 | 1/2016 |

OTHER PUBLICATIONS

Yang et al. J.Med.Chem. vol. 56,p. 1641-1655 (Year: 2013).*
Partial Machine Translation for WO 2014/194667 (Year: 2014).*
Supplementary European Search Report from counterpart European Patent Application No. 17 841 957.8, completed on Nov. 29, 2019.
Kaitsiotou et al., "Inhibitors to Overcome Secondary Mutations in the Stem Cell Factor Receptor KIT", J. Med. Chem., vol. 60, No. 21, Oct. 9, 2017, pp. 8801-8815.
Ma et al., "Identification of New FLT3 Inhibitors that Potently Inhibit AML Cell Lines via an Azo Click-it/Staple-it Approach", ACS med. Chem. Lett., vol. 8, No. 5, Apr. 14, 2017, pp. 492-597.
Dixit et al., "New Approach for the Synthesis of 3H-Pyrrolo[2, 3-c] Isoquinoline Derivatives", vol., 68, No. 18, May 1, 2012, pp. 3560-3565.
Desai et al., "Rapid Discovery of a Novel Series of Ab1 Kinase Inhibitors by Application of an Integrated Microfluidic Synthesis and Screening Platform", J. Med. Chem., vol. 56, No. 7, Apr. 11, 2013, pp. 3033-3047.

(Continued)

*Primary Examiner* — Emily A Bernhardt
(74) *Attorney, Agent, or Firm* — Miles & Stockbridge P.C.; Ajay Jagtiani

(57) ABSTRACT

This invention relates to 4-substituted isoquinoline compounds and their derivatives and uses thereof for treatment of cancer, for example, acute myeloid leukemia.

2 Claims, 20 Drawing Sheets

(56) References Cited

OTHER PUBLICATIONS

Bridges et al., "Tyroasine Kynase Inhibitors", J. Med. Chem., vol. 39, No. 1, Jan. 1, 1996, pp. 267-276.
Ife et al., "Reversible Inhibitors of the Gastric(H+/K+)-ATPase", J. Med. Chem., vol. 38, No. 14, Jan. 1, 1995, pp. 2762-2773.
Doig et al., "Rational Design of Inhibitors of the Bacterial Cell Wall Synthetic Enzyme GlmU using Virtual Screening and Lead-Hopping", Bioorg.Med. Chem., vol. 22, No. 21, Nov. 1, 2014, pp. 6256-6269.
International Search Report dated Nov. 16, 2017, mailed in corresponding International Patent Application No. PCT/US2017/046843.
Gainor, J.F., et al., "Ponatinib: Accelerated Disapproval," The Oncologist, vol. 20(8), pp. 847-848, 2015.
Talbert, D.R., et al., "A Multi-parameter In Vitro Screen in Human Stem Cell-Derived Cardiomyocytes Identifies Ponatinib-Induced Structural and Functional Cardiac Toxicity," Society of Toxicology, vol. 143(1), pp. 147-155, 2015.
Freireich, E.J., et al., "Quantitative Comparison of Toxicity of Anticancer Agents in Mouse, Rat, Hamster, Dog, Monkey and Man," Cancer Chemother. Rep. vol. 50(4), pp. 219-244,1966.
Scientific Tables, Geigy Pharmaceuticals, Ardley, New York, pp. 537-538, 1970.
Communication pursuant to Article 34(3) EPC, Examination Report dated Nov. 11, 2020 issued in corresponding European Patent Application No. 17 841 957.8.
First Examination Report dated by Intellectual Property India on Dec. 14, 2020 in related Indian Application No. 201927009684.

* cited by examiner compound 1703

Wherein R is alkyl, aryl or heteroalkyl; and Y is

X = halogen
R = alkyl, aryl, heteroalkyl, heteroaryl
Y= alkyl, aryl, halogen, CN, amide, heteroalkyl, heteroaryl etc

4-SUBSTITUTED AMINOISOQUINOLINE DERIVATIVES

CROSS REFERENCE TO RELATED APPLICATIONS

This application is a National Phase Application of PCT International Application No. PCT/US2017/046843, filed Aug. 15, 2017, which claims the benefit of U.S. Provisional Application Ser. No. 62/461,295, filed on Feb. 21, 2016 and U.S. Provisional Application Ser. No. 62/375,154, filed on Aug. 15, 2016, all of which are incorporated herein by reference in their entirety.

TECHNICAL FIELD

This invention relates to 4-substituted aminoisoquinoline compounds and their derivatives and uses thereof for treatment of cancer, for example, acute myeloid leukemia.

BACKGROUND

In human cells there are over 500 kinases regulating important processes, such as cell cycle regulation, proliferation, apoptosis and migration. Inhibitors of protein kinases have the potential to treat many diseases that are controlled by disregulation of protein kinases. Thus far over twenty kinase inhibitors have been approved by the FDA to treat various diseases.

Ponatinib, an approved FDA drug, is a 7-alkynyl imidazo [1,5-b]pyridazine compound and it is used against CML. Ponatinib, however, has toxic side effects and about 40% of patients on ponatinib developed some form of thrombosis. The FDA temporarily halted the sale of ponatinib in 2014 due to this adverse issue and it is now given as a drug of last resort for CML patients who have ABL (T315I) mutation and have not responded to any other therapy (Gainor, J. F. et al., Ponatinib: Accelerated Disapproval, *Oncologist*, 20 (8), 847-848 (2015); Talbert, D. R. et al., *Toxicol. Sci*, 143 (1), 147-155 (2015).

In the efforts to develop kinase inhibitors against several disease-related kinases, it is discovered that 4-substituted isoquinolines are privileged kinases inhibitors. Further, the substitution pattern of these 4-substituted isoquinolines play critical roles in kinase selectivity and hence cancer selectivity. 4-Alkynyl-substituted aminoisoquinolines in particular have shown exceptional activity against various kinases and potently inhibit cancer proliferation. This important discovery has facilitated the tailoring of 4-substituted aminoisoquinoline into compounds that inhibit various cancers. Additionally, the 4-alkynyl-substituted 1- or 3-amino isoquinolines can be tuned for selectivity and toxicity and hence represent a new-generation alkyne-containing kinase inhibitors with desirable drug-like properties.

SUMMARY OF THE INVENTION

In one aspect, the present invention features a compound represented by a compound of formula (IV)

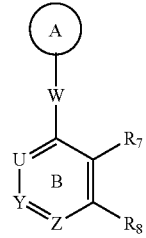

(IV)

wherein
W is NR', alkene, alkyne, $C_{1-8}$ alkyl, heteroalkyl containing 1-8 carbon and hetero atoms, cycloalkyl, heterocycloalkyl, aryl, or heteroaryl, wherein cycloalkyl, hetereocycloalkyl, aryl, and heteroaryl optionally form a fused aryl or heteroaryl group with Ring A;
U, Y, and Z are each N or $CR_6$, wherein $R_6$ is H or $NR_aR_b$;
$R_7$ and $R_8$ are each independently H, alkyl, alkenyl, alkynyl, halo, nitro, $OR_c$, $SR_c$, CN, haloalkyl, O-haloalkyl, $(CO)R_d$, $NR_aR_b$, $NH(CO)R_d$, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl;
or $R_7$ and $R_8$, together with the carbon atoms to which they are attached, form a cycloalkyl, heterocycloalkyl, aryl, or heteroaryl group, each optionally substituted with substituents independently selected from the group consisting of alkyl, cycloalkyl, alkenyl, alkynyl, halo, nitro, $OR_c$, $SR_c$, CN, haloalkyl, O-haloalkyl, $NR_aR_b$, $(CO)R_d$, $(CO)OR_c$, $(CO)NR_aR_b$, $SO_2NR_aR_b$, and —$C(CH_3)(=N-NHC(NH)NH_2)$;
Ring A is a 5- or 6-membered aryl or heteroaryl group, wherein Ring A is optionally substituted with substituents selected from the group consisting of alkyl, alkenyl, alkynyl, cycloalkyl, heterocycloalkyl, halo, nitro, $OR_c$, $SR_c$, CN, haloalkyl, O-haloalkyl, $NR_mR_n$, $(CO)R_d$, $(CO)OR_c$, $SO_2NR_mR_n$, $(CO)NR_mR_n$, $C(NH)NR_mR_n$, $NH(CO)R_d$, $NH(CO)OR_c$, $NH(CO)NR_mR_n$, aryl, heteroaryl;
$R_m$ and $R_n$ are each independently
H, OH,
alkyl, —$(CH_2)_p$-T, -aryl-$(CH_2)_p$-T, —$(CH_2)_p$-aryl-T, -heteroaryl-$(CH_2)_p$-T, —$(CH_2)_p$-heteroaryl-T, each optionally substituted with alkyl, halo, nitro, CN, haloalkyl, O-haloalkyl, $OR_c$, $SR_c$, $NR_aR_b$, $(CO)R_d$, $NH(CO)R_d$, $NH(CO)OR_c$, $NH(CO)NR_aR_b$, $NHC(NH)NH_2$, $(CO)OR_c$, $(CO)NR_aR_b$, $SO_2NR_aR_b$, arylamino, or heteroarylamino,
or $R_m$ and $R_n$, together with the nitrogen atom they are attached, form a heterocycloalkyl group, optionally substituted with alkyl, cycloalkyl, heterocycloalkyl, aryl, heteroaryl, halo, nitro, CN, $OR_c$, $SR_c$, $COR_d$, $NR_aR_b$, $NH(CO)R_d$, $NH(CO)OR_c$, $NH(CO)NR_aR_b$, a guanidine group, $(CO)OR_c$, or $(CO)NR_aR_b$;
T is $NR_aR_b$, $OR_c$, $SR_c$, O—$(CH_2)_q$—$NR_aR_b$, cycloalkyl, heterocycloalkyl, aryl, heteroaryl, a guanidine group, or an isonicotinimidamide group;
R' is H, alkyl, or cycloalkyl;
$R_a$, $R_b$, $R_c$, and $R_d$ are each independently H, alkyl, alkenyl, cycloalkyl, heterocycloalkyl, aryl, heteroaryl, —$(CH_2)_q$-cycloalkyl, —$(CH)_q$-heterocycloalkyl, —$(CH_2)_q$-aryl, —$(CH)_q$-heteroaryl, —(CO)-alkyl, —(CO)-cycloalkyl, —(CO)-heterocycloalkyl, —$(SO_2)$-alkyl, —$(SO_2)$-cycloalkyl, or —$(SO_2)$-heterocycloalkyl, or $R_a$ and $R_b$, together with the nitrogen atom to which they are attached, form a heterocycloalkyl group, wherein cycloalkyl, heterocycloalkyl, aryl and heteroaryl are each optionally substituted with a group consisting of alkyl, halo, nitro, CN, haloalkyl, O-haloalkyl, OH, O-alkyl, SH, S-alkyl, $NH_2$, NH(alkyl), and $N(alkyl)_2$; and p and q are each independently 0-8;

or a pharmaceutically acceptable salt, N-oxide, hydrate, solvate, tautomer, or optical isomer thereof.

In another aspect, the present invention is directed to a pharmaceutical composition comprising one or more compounds as described herein, or a pharmaceutically acceptable salt, N-oxide, hydrate, solvate, tautomer, or optical isomer thereof, and a pharmaceutically acceptable carrier or diluent.

In yet another aspect, the present invention is directed to a method of treating, inhibiting, suppressing, or reducing the severity of cancer in a subject in need thereof, wherein the method comprises administering to the subject a therapeutically effective amount of a compound as described herein, or a pharmaceutically acceptable salt, N-oxide, hydrate, solvate, tautomer, or optical isomer thereof, or a pharmaceutical composition containing one or more compounds as described herein.

In yet another aspect, the present invention is directed to a method of treating, inhibiting, suppressing, or reducing the severity of a disease or a disorder associated with protein kinase in a subject in need thereof, wherein the method comprises administering to the subject a therapeutically effective amount of a compound as described herein, or a pharmaceutically acceptable salt, N-oxide, hydrate, solvate, tautomer, or optical isomer thereof, or a pharmaceutical composition containing one or more compounds as described herein.

The details of one or more embodiments of the invention are set forth in the accompa-nying the description below. Other features, objects, and advantages of the invention will be apparent from the description and drawings, and from the claims.

BRIEF DESCRIPTION OF THE DRAWINGS

FIG. 8A: Dose-response curves of HSW1651 against FLT3 and important FLT3 mutants. FIGS. 8B and 8C: Western Blot analyses of p-FLT3/total FLT3 (FIG. 8B) and p-STAT5/STAT5 (FIG. 8C) protein expression in MV4-11 after treatment with HSM1651 and DMSO vehicle (V) control. Scanned images were analyzed using image J software.

FIG. 17A: Phospho-FLT3/FLT3, PhosphoSRC/SRC and phospho-STAT3/STAT3; and FIG. 17B: phospho-STAT5/STAT5 and phospho-p-38/p-38. Cells were treated with DMSO vehicle (V), HSN286 (9 nM and 45 nM) for 6 h, 24 h and 48 h. Western Blot with anti-rabbit or anti-mouse antibody. Scanned images were analyzed using image J software.

DETAILED DESCRIPTION

Figure 1:
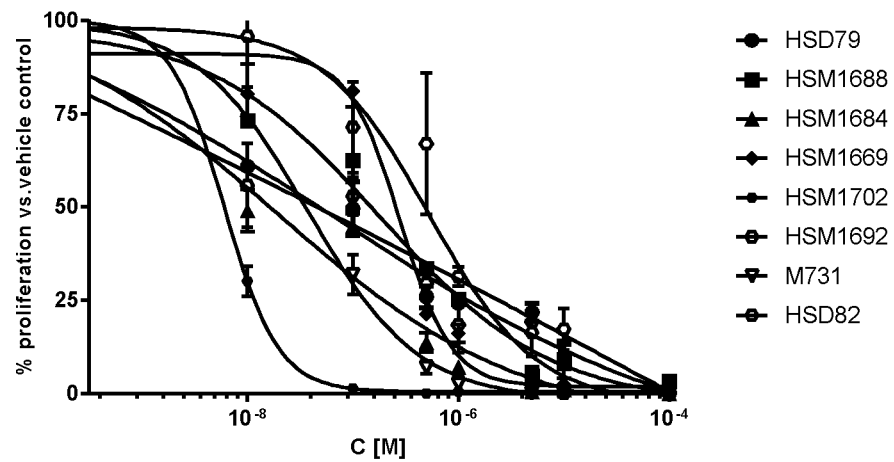
FIG. 1 depicts that the length of the amide head group, substitution pattern, and relative position to the alkyne moiety remarkably affects the anticancer activity against MV4-11 cell line (AML cell line).
Figure 1:
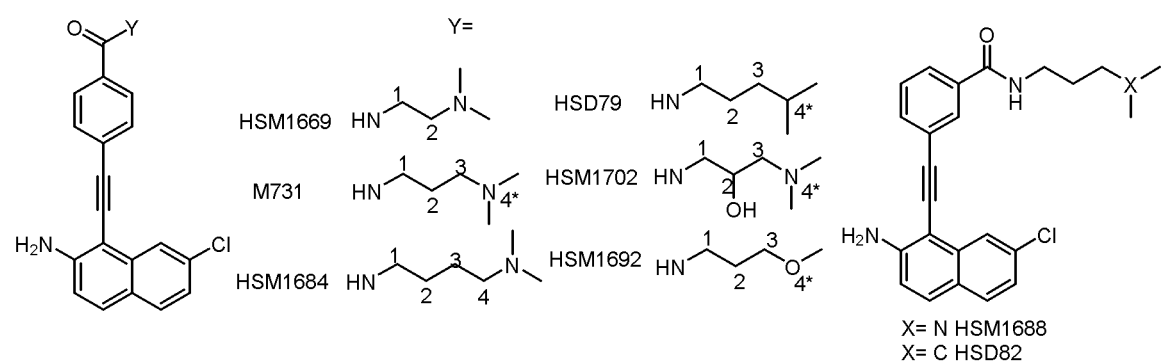
Figure 2:
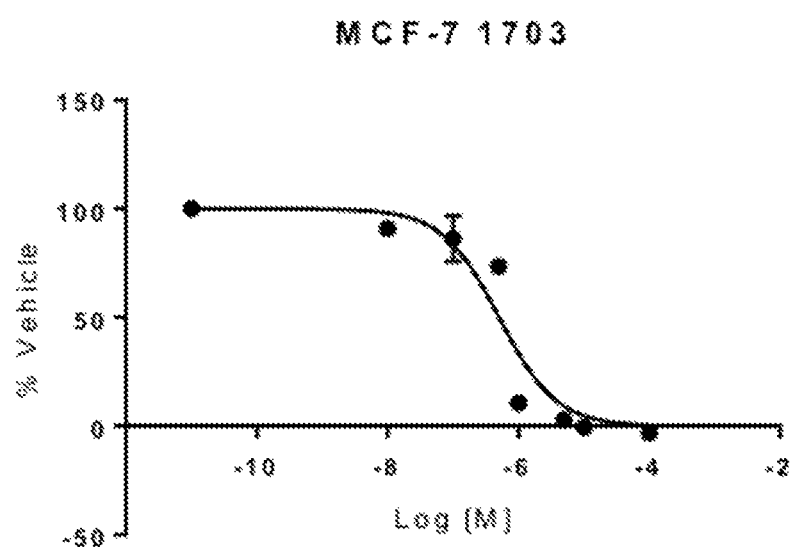
FIG. 2 depicts that Compound 1703 is potent against MCF-7 cell lines.
Figure 2:
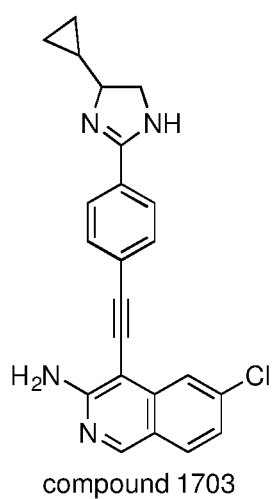
Figure 3:
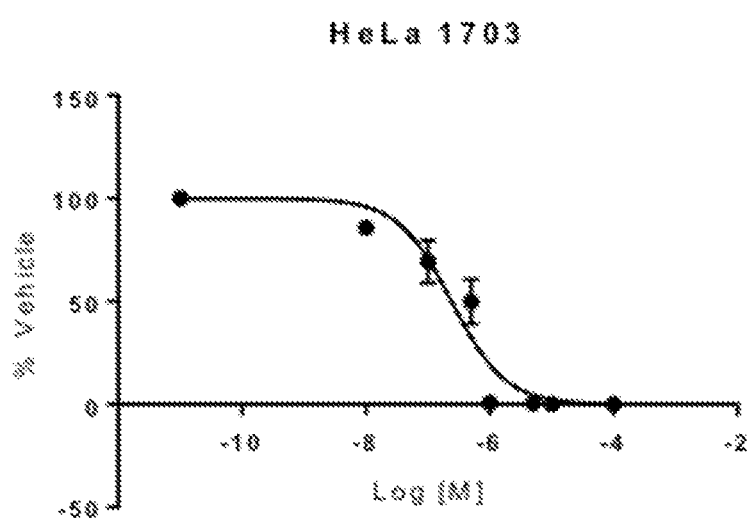
FIG. 3 depicts that Compound 1703 is potent against HeLa cell lines.

In one aspect, the present invention features a compound represented by a compound of formula (IV)

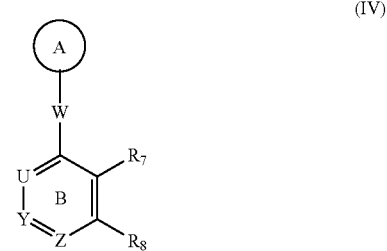

(IV)

wherein

W is NR', alkene, alkyne, $C_{1-8}$ alkyl, heteroalkyl containing 1-8 carbon and hetero atoms, cycloalkyl, heterocycloalkyl, aryl, or heteroaryl, wherein cycloalkyl, hetereocycloalkyl, aryl, and heteroaryl optionally form a fused aryl or heteroaryl group with Ring A;

U, Y, and Z are each N or $CR_6$, wherein $R_6$ is H or $NR_aR_b$;

$R_7$, and $R_8$ are each independently H, alkyl, alkenyl, alkynyl, halo, nitro, $OR_c$, $SR_c$, CN, haloalkyl, O-haloalkyl, $(CO)R_d$, $NR_aR_b$, $NH(CO)R_d$, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl;

or $R_7$ and $R_8$, together with the carbon atoms to which they are attached, form a cycloalkyl, heterocycloalkyl, aryl, or heteroaryl group, each optionally substituted with substituents independently selected from the group consisting of alkyl, cycloalkyl, alkenyl, alkynyl, halo, nitro, $OR_c$, $SR_c$, CN, haloalkyl, O-haloalkyl, $NR_aR_b$, $(CO)R_d$, $(CO)OR_c$, $(CO)NR_aR_b$, $SO_2NR_aR_b$, and $—C(CH_3)(=N—NHC(NH)NH_2$; Ring A is a 5- or 6-membered aryl or heteroaryl group, wherein Ring A is optionally substituted with substituents selected from the group consisting of alkyl, alkenyl, alkynyl, cycloalkyl, heterocycloalkyl, halo, nitro, $OR_c$, $SR_c$, CN, haloalkyl, O-haloalkyl, $NR_mR_n$, $(CO)R_d$, $(CO)OR_c$, $SO_2NR_mR_n$, $(CO)NR_mR_n$, $C(NH)NR_mR_n$, $NH(CO)R_d$, $NH(CO)OR_c$, $NH(CO)NR_mR_n$, aryl, heteroaryl;

$R_m$ and $R_n$ are each independently

H, OH, alkyl, $—(CH_2)_p$-T, -aryl-$(CH_2)_p$-T, $—(CH_2)_p$-aryl-T, -heteroaryl-$(CH_2)_p$-T, $—(CH_2)_p$ heteroaryl-T, each optionally substituted with alkyl, halo, nitro, CN, haloalkyl, O-haloalkyl, $OR_c$, $SR_c$, $NR_aR_b$, $(CO)R_d$, $NH(CO)R_d$, $NH(CO)OR_c$, $NH(CO)NR_aR_b$, $NHC(NH)NH_2$, $(CO)OR_c$, $(CO)NR_aR_b$, $SO_2NR_aR_b$, arylamino, or heteroarylamino, or $R_m$ and $R_n$, together with the nitrogen atom they are attached, form a heterocycloalkyl group, optionally substituted with alkyl, cycloalkyl, heterocycloalkyl, aryl, heteroaryl, halo, nitro, CN, $OR_c$, $SR_c$, $COR_d$, $NR_aR_b$, $NH(CO)R_d$, $NH(CO)OR_c$, $NH(CO)NR_aR_b$, a guanidine group, $(CO)OR_c$, or $(CO)NR_aR_b$;

T is $NR_aR_b$, $OR_c$, $SR_c$, $O—(CH_2)_q—NR_aR_b$, cycloalkyl, heterocycloalkyl, aryl, heteroaryl, a guanidine group, or an isonicotinimidamide group;

R' is H, alkyl, or cycloalkyl;

$R_a$, $R_b$, $R_c$, and $R_d$ are each independently H, alkyl, alkenyl, cycloalkyl, heterocycloalkyl, aryl, heteroaryl, $—(CH_2)_q$-cycloalkyl, $—(CH)_q$-heterocycloalkyl, $—(CH_2)_q$-aryl, $—(CH)_q$-heteroaryl, $—(CO)$-alkyl, $—(CO)$-cycloalkyl, $—(CO)$-heterocycloalkyl, $—(SO_2)$-alkyl, $—(SO_2)$-cycloalkyl, or $—(SO_2)$-heterocycloalkyl, or $R_a$ and $R_b$, together with the nitrogen atom to which they are attached, form a heterocycloalkyl group, wherein cycloalkyl, heterocycloalkyl, aryl and heteroaryl are each optionally substituted with a group consisting of alkyl, halo, nitro, CN, haloalkyl, O-haloalkyl, OH, O-alkyl, SH, S-alkyl, $NH_2$, NH(alkyl), and N(alkyl)$_2$; and p and q are each independently 0-8;

or a pharmaceutically acceptable salt, N-oxide, hydrate, solvate, tautomer, or optical isomer thereof.

In some embodiments, the compound of the invention is represented by a compound of formula (V)

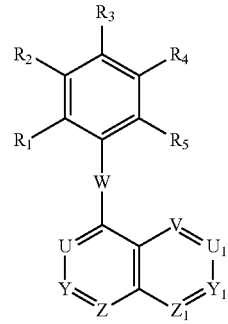

(V)

wherein

W is NR', $—C≡C—$, or a heterocycloalkyl group containing a 5- or 6-membered ring, wherein R' is H or alkyl;

U, Y, and Z are each N or $CR_6$, wherein $R_6$ is H or $NR_aR_b$;

V, $U_1$, $Y_1$, and $Z_1$ are each N or $CR_6$;

$R_1$, $R_2$, and $R_6'$ are each independently H, alkyl, cycloalkyl, halo, nitro, $OR_c$, $SR_c$, CN, haloalkyl, O-haloalkyl, or $NR_aR_b$;

$R_3$, $R_4$, and $R_5$ are each independently H, alkyl, cycloalkyl, heterocycloalkyl, halo, nitro, $OR_c$, $SR_c$, CN, haloalkyl, O-haloalkyl, $NR_mR_n$, $(CO)R_d$, $(CO)OR_c$, $SO_2NR_mR_n$, $(CO)NR_mR_n$, $C(NH)NR_mR_n$, $NH(CO)R_d$, $NH(CO)OR_c$, $NH(CO)NR_mR_n$, aryl, or heteroaryl;

$R_m$ and $R_n$ are each independently

H, OH, alkyl, $—(CH_2)_p$-T, -aryl-$(CH_2)_p$-T, $—(CH_2)_p$-aryl-T, -heteroaryl-$(CH_2)_p$-T, $—(CH_2)_p$ heteroaryl-T, each optionally substituted with alkyl, cycloalkyl, halo, nitro, CN, haloalkyl, O-haloalkyl, $OR_c$, $SR_c$, $(CO)R_d$, $NR_aR_b$, $NH(CO)R_d$, $NH(CO)OR_c$, $NH(CO)NR_aR_b$, $NHC(NH)NH_2$, $(CO)OR_c$, $(CO)NR_aR_b$, and $SO_2NR_aR_b$, or $R_m$ and $R_n$, together with the nitrogen atom they are attached, form a heterocycloalkyl group, optionally substituted with alkyl, cycloalkyl, heterocycloalkyl, aryl, heteroaryl, halo, nitro, CN, $OR_c$, $SR_c$, $COR_d$, $NR_aR_b$, $NH(CO)R_d$, $NH(CO)OR_c$, $NH(CO)NR_aR_b$, a guanidine group, $(CO)OR_c$, and $(CO)NR_aR_b$;

T is $NR_aR_b$, $OR_c$, $SR_c$, $O—(CH_2)_q—NR_aR_b$, cycloalkyl, heterocycloalkyl, aryl, heteroaryl, a guanidine group, or an isonicotinimidamide group;

$R_a$, $R_b$, $R_c$, and $R_d$ are each independently H, alkyl, alkenyl, cycloalkyl, heterocycloalkyl, aryl, heteroaryl, $—(CH_2)_q$-cycloalkyl, $—(CH)_q$-heterocycloalkyl, $—(CH_2)_q$-aryl, $—(CH)_q$-heteroaryl, $—(CO)$-alkyl, $—(CO)$-cycloalkyl, or $—(CO)$-heterocycloalkyl, or $R_a$ and $R_b$, together with the nitrogen atom to which they are attached, form a heterocycloalkyl group, wherein cycloalkyl, heterocycloalkyl, aryl and heteroaryl are each optioncally substituted with a group consisting of alkyl, halo, nitro, CN, haloalkyl, O-haloalkyl, OH, O-alkyl, SH, S-alkyl, $NH_2$, NH(alkyl), and N(alkyl)$_2$; and p and q are each independently 0-5.

or a pharmaceutically acceptable salt, N-oxide, hydrate, solvate, tautomer, or optical isomer thereof.

In some embodiments, $R_6$ is $NR_aR_b$.

In some embodiments, one of $R_3$, $R_4$, and $R_5$ is heterocycloalkyl, CN, $NR_mR_n$, $(CO)R_d$, $(CO)OR_c$, $SO_2NR_mR_n$, $(CO)NR_mR_n$, $C(NH)NR_mR_n$, or $NH(CO)R_d$.

In some embodiments, one of $R_3$, $R_4$, and $R_5$ is (CO)$NR_mR_n$.

In some embodiments, $R_m$ is H and $R_n$ is —$(CH_2)_p$-T, -aryl-$(CH_2)_p$-T, —$(CH_2)_p$-aryl-T, or -heteroaryl-$(CH_2)_p$-T, each optionally substituted with alkyl, halo, and $OR_c$.

In some embodiments, T is $NR_aR_b$, O—$(CH_2)_q$—$NR_aR_b$, heterocycloalkyl, aryl, or heteroaryl.

In some embodiments, $R_m$ and $R_n$, together with the nitrogen atom they are attached, form a heterocycloalkyl group, optionally substituted with alkyl, cycloalkyl, heterocycloalkyl, $NR_aR_b$, NH(CO)$R_d$, NH(CO)$OR_c$, and NH(CO)$NR_aR_b$.

In some embodiments, $R_1$ and $R_2$ are each independently H, alkyl, halo, CN, $OR_c$, $SR_c$, or $NR_aR_b$.

In some embodiments, the compound of the invention is a compound of the formula:

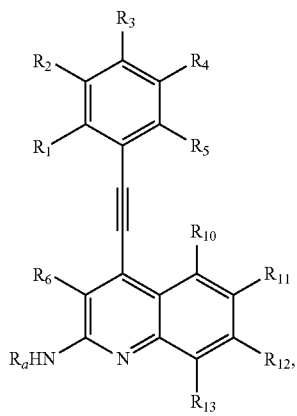

(XII$_a$)

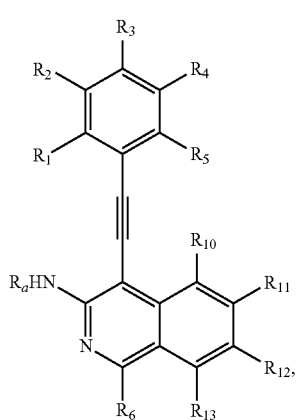

(XII$_b$)

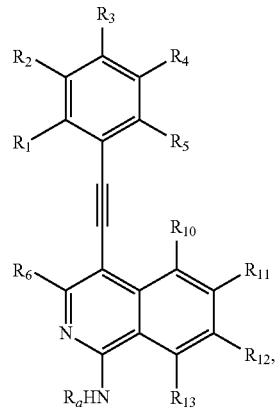

(XII$_c$)

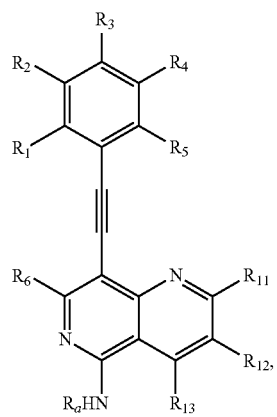

(XII$_d$)

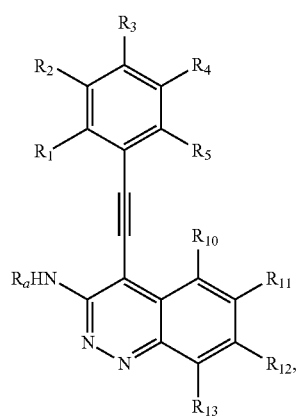

(XII$_e$)

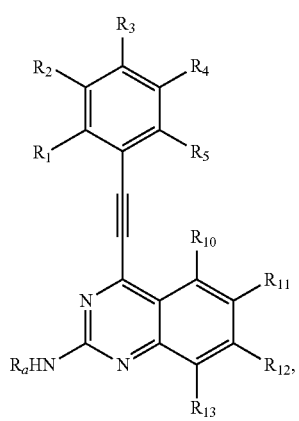
(XII<sub>f</sub>)
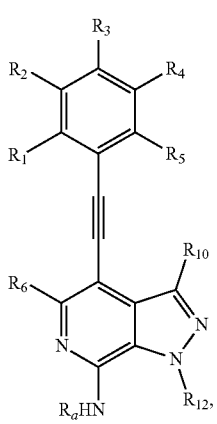
(XII<sub>i</sub>)
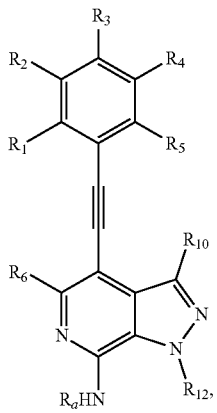
(XII<sub>j</sub>)
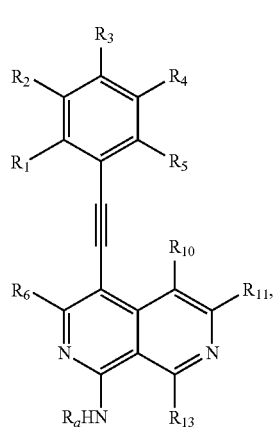
(XII<sub>g</sub>)
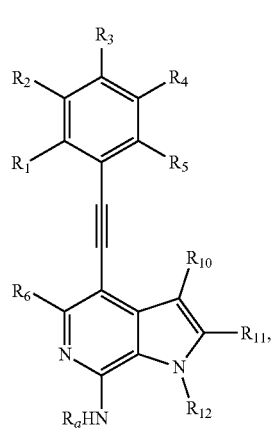
(XII<sub>k</sub>)
(XII<sub>h</sub>)

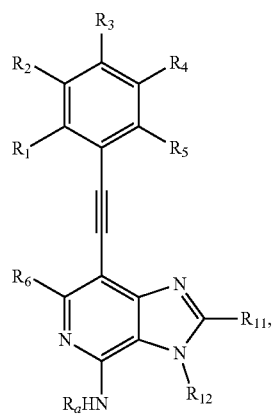
(XII_l)
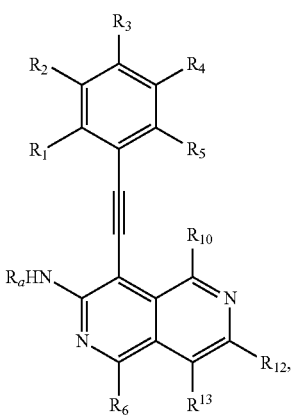
(XII_o)
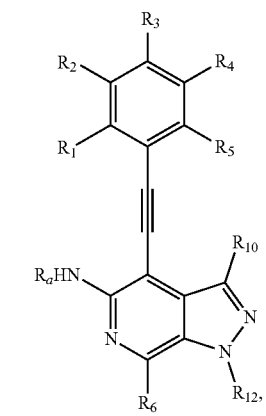
(XII_m)
(XII_p)
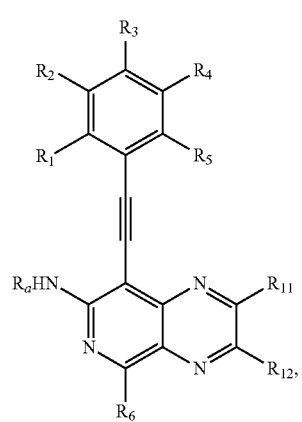
(XII_n)
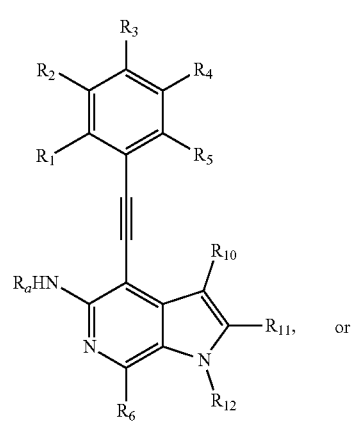
(XII_q) or -continued

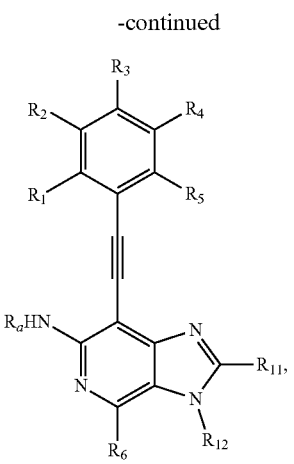

(XII$_r$)

wherein
R$_1$, R$_2$ R$_{10}$, R$_{11}$, R$_{12}$, and R$_{13}$ are each independently H, alkyl, cycloalkyl, halo, nitro, OR$_c$, SR$_c$, CN, haloalkyl, O-haloalkyl, or NR$_a$R$_b$;
R$_3$, R$_4$, and R$_5$ are each independently H, alkyl, cycloalkyl, heterocycloalkyl, halo, nitro, OR$_c$, SR, CN, haloalkyl, O-haloalkyl, NR$_m$R$_n$, (CO)R$_d$, (CO)OR$_c$, SO$_2$NR$_m$R$_n$, (CO)NR$_m$R$_n$, C(NH)NR$_m$R$_n$, NH(CO)R$_d$, NH(CO)OR$_c$, NH(CO)NR$_m$R$_n$, aryl, or heteroaryl;
R$_6$ is H or NR$_a$R$_b$;
R$_m$ and R$_n$, are each independently
H, OH,
alkyl, —(CH$_2$)$_p$-T, -aryl-(CH$_2$)$_p$-T, —(CH$_2$)$_p$-aryl-T, -heteroaryl-(CH$_2$)$_p$-T, —(CH$_2$)$_p$ heteroaryl-T, each optionally substituted with alkyl, cycloalkyl, halo, nitro, CN, haloalkyl, O-haloalkyl, OR$_c$, SR$_c$, (CO)R$_d$, NR$_a$R$_b$, NH(CO)R$_d$, NH(CO)OR$_c$, NH(CO)NR$_a$R$_b$, NHC(NH)NH$_2$, (CO)OR$_c$, (CO)NR$_a$R$_b$, and SO$_2$NR$_a$R$_b$,
or R$_m$ and R$_n$ together with the nitrogen atom they are attached, form a heterocycloalkyl group, optionally substituted with alkyl, cycloalkyl, heterocycloalkyl, aryl, heteroaryl, halo, nitro, CN, OR$_c$, SR$_c$, COR$_d$, NR$_a$R$_b$, NH(CO)R$_d$, NH(CO)OR$_c$, NH(CO)NR$_a$R$_b$, a guanidine group, (CO)OR$_c$, and (CO)NR$_a$R$_b$;
T is NR$_a$R$_b$, OR$_c$, SR$_c$, O—(CH$_2$)$_q$—NR$_a$R$_b$, cycloalkyl, heterocycloalkyl, aryl, heteroaryl, a guanidine group, or an isonicotinimidamide group;
R$_a$, R$_b$, R$_c$, and R$_d$ are each independently H, alkyl, alkenyl, cycloalkyl, heterocycloalkyl, aryl, heteroaryl, —(CH$_2$)$_q$-cycloalkyl, —(CH)$_q$-heterocycloalkyl, —(CH$_2$)$_q$-aryl, —(CH)$_q$-heteroaryl, —(CO)-alkyl, —(CO)-cycloalkyl, or —(CO)-heterocycloalkyl, or R$_a$ and R$_b$, together with the nitrogen atom to which they are attached, form a heterocycloalkyl group, wherein cycloalkyl, heterocycloalkyl, aryl and heteroaryl are each optioncally substituted with a group consisting of alkyl, halo, nitro, CN, haloalkyl, O-haloalkyl, OH, O-alkyl, SH, S-alkyl, NH$_2$, NH(alkyl), and N(alkyl)$_2$; and
p and q are each independently 0-5;
or a pharmaceutically acceptable salt, N-oxide, hydrate, solvate, tautomer, or optical isomer thereof.

In some embodiments, R$_6$ is NR$_a$R$_b$.

In some embodiments, one of R$_3$, R$_4$, and R$_5$ is heterocycloalkyl, CN, NR$_m$R$_n$, (CO)R$_d$, (CO)OR$_c$, SO$_2$NR$_m$R$_n$, (CO)NR$_m$R$_n$, C(NH)NR$_m$R$_n$, or NH(CO)R$_d$.

In some embodiments, one of R$_3$, R$_4$, and R$_5$ is (CO)NR$_m$R$_n$.

In some embodiments, R$_m$ is H and R$_n$ is —(CH$_2$)$_p$-T, -aryl-(CH$_2$)$_p$-T, —(CH$_2$)$_p$-aryl-T, or -heteroaryl-(CH$_2$)$_p$-T, each optionally substituted with alkyl, halo, and OR$_c$.

In some embodiments, T is NR$_a$R$_b$, O—(CH$_2$)$_q$—NR$_a$R$_b$, heterocycloalkyl, aryl, or heteroaryl.

In some embodiments, R$_m$ and R$_n$, together with the nitrogen atom they are attached, form a heterocycloalkyl group, optionally substituted with alkyl, cycloalkyl, heterocycloalkyl, NR$_a$R$_b$, NH(CO)R$_d$, NH(CO)OR$_c$, and NH(CO)NR$_a$R$_b$.

In some embodiments, R$_1$ and R$_2$ are each independently H, alkyl, halo, CN, OR$_c$, SR$_c$, or NR$_a$R$_b$.

In some embodiments, the compound of the invention is a compound of the following formula

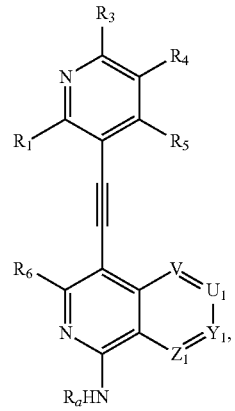

(XIII$_a$)

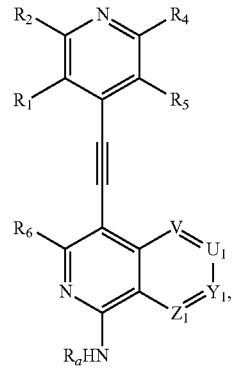

(XIII$_b$)

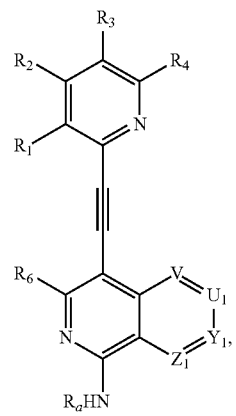

(XIII$_c$)

(XIII_d)
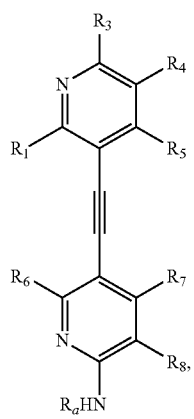
(XIII_e)
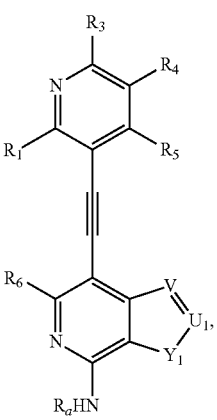
(XIII_f)
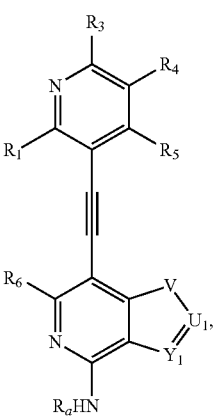
(XIII_g)
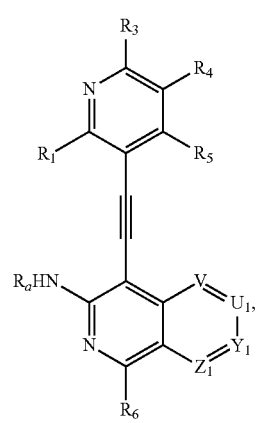
(XIII_h)
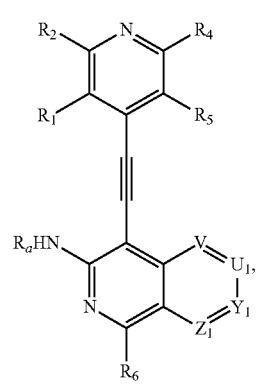
(XIII_i)
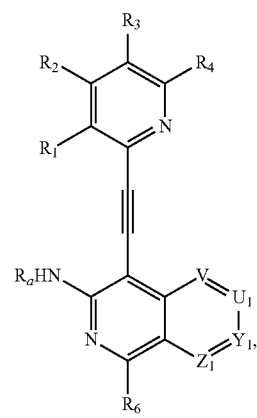
(XIII_j)
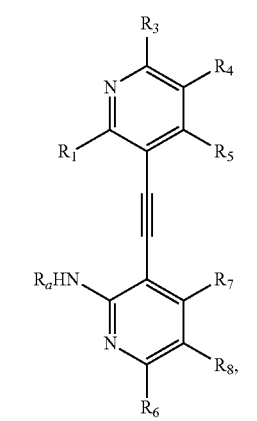

-continued

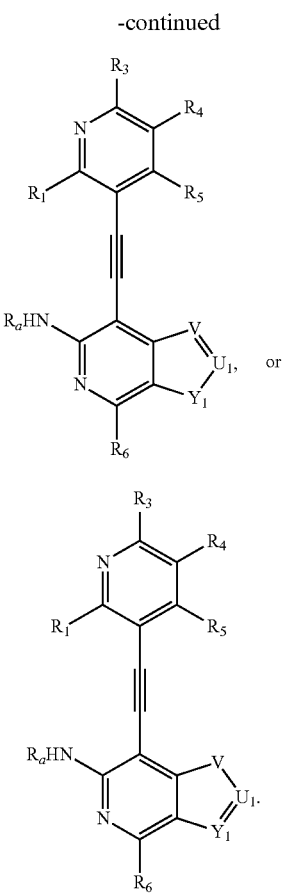

wherein
- $V$, $U_1$, $Y_1$, and $Z_1$ are each N or $CR_6'$;
- $R_1$, $R_2$, and $R_6'$ are each independently H, alkyl, cycloalkyl, halo, nitro, $OR_c$, $SR_c$, CN, haloalkyl, O-haloalkyl, or $NR_aR_b$;
- $R_3$, $R_4$, and $R_5$ are each independently H, alkyl, cycloalkyl, heterocycloalkyl, halo, nitro, $OR_c$, $SR_c$, CN, haloalkyl, O-haloalkyl, $NR_mR_n$, $(CO)R_d$, $(CO)OR_c$, $SO_2NR_mR_n$, $(CO)NR_mR_n$, $C(NH)NR_mR_n$, $NH(CO)R_d$, $NH(CO)OR_c$, $NH(CO)NR_mR_n$, aryl, or heteroaryl;
- $R_6$ is H or $NR_aR_b$;
- $R_7$ and $R_8$ are each independently H, alkyl, alkenyl, alkynyl, halo, nitro, $OR_c$, $SR_c$, CN, haloalkyl, O-haloalkyl, $(CO)R_d$, $NR_aR_b$, $NH(CO)R_d$, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl;
- $R_m$ and $R_n$ are each independently H, OH, alkyl, $-(CH_2)_p$-T, -aryl-$(CH_2)_p$-T, $-(CH_2)_p$-aryl-T, -heteroaryl-$(CH_2)_p$-T, $-(CH_2)_p$-heteroaryl-T, each optionally substituted with alkyl, cycloalkyl, halo, nitro, CN, haloalkyl, O-haloalkyl, $OR_c$, $SR_c$, $(CO)R_d$, $NR_aR_b$, $NH(CO)R_d$, $NH(CO)OR_c$, $NH(CO)NR_aR_b$, $NHC(NH)NH_2$, $(CO)OR_c$, $(CO)NR_aR_b$, and $SO_2NR_aR_b$,
- or $R_m$ and $R_n$, together with the nitrogen atom they are attached, form a heterocycloalkyl group, optionally substituted with alkyl, cycloalkyl, heterocycloalkyl, aryl, heteroaryl, halo, nitro, CN, $OR_c$, $SR_c$, $COR_d$, $NR_aR_b$, $NH(CO)R_d$, $NH(CO)OR_c$, $NH(CO)NR_aR_b$, a guanidine group, $(CO)OR_c$, and $(CO)NR_aR_b$;
- T is $NR_aR_b$, $OR_c$, $SR_c$, $O-(CH_2)_q-NR_aR_b$, cycloalkyl, heterocycloalkyl, aryl, heteroaryl, a guanidine group, or an isonicotinimidamide group;
- $R_a$, $R_b$, $R_c$, and $R_d$ are each independently H, alkyl, alkenyl, cycloalkyl, heterocycloalkyl, aryl, heteroaryl, $-(CH_2)_q$-cycloalkyl, $-(CH)_q$-heterocycloalkyl, $-(CH_2)_q$-aryl, $-(CH)_q$-heteroaryl, $-(CO)$-alkyl, $-(CO)$-cycloalkyl, or $-(CO)$-heterocycloalkyl, or $R_a$ and $R_b$, together with the nitrogen atom to which they are attached, form a heterocycloalkyl group, wherein cycloalkyl, heterocycloalkyl, aryl and heteroaryl are each optioncally substituted with a group consisting of alkyl, halo, nitro, CN, haloalkyl, O-haloalkyl, OH, O-alkyl, SH, S-alkyl, $NH_2$, NH(alkyl), and N(alkyl)$_2$; and
- p and q are each independently 0-5;

or a pharmaceutically acceptable salt, N-oxide, hydrate, solvate, tautomer, or optical isomer thereof.

In some embodiments, $R_6$ is $NR_aR_b$.

In some embodiments, one of $R_3$, $R_4$, and $R_5$ is heterocycloalkyl, CN, $NR_mR_n$, $(CO)R_d$, $(CO)OR_c$, $SO_2NR_mR_n$, $(CO)NR_mR_n$, $C(NH)NR_mR_n$, or $NH(CO)R_d$.

In some embodiments, one of $R_3$, $R_4$, and $R_5$ is $(CO)NR_mR_n$.

In some embodiments, $R_m$ is H and $R_n$ is $-(CH_2)_p$-T, -aryl-$(CH_2)_p$-T, $-(CH_2)_p$-aryl-T, or -heteroaryl-$(CH_2)_p$-T, each optionally substituted with alkyl, halo, and $OR_c$.

In some embodiments, T is $NR_aR_b$, $O-(CH_2)_q-NR_aR_b$, heterocycloalkyl, aryl, or heteroaryl.

In some embodiments, $R_m$ and $R_n$, together with the nitrogen atom they are attached, form a heterocycloalkyl group, optionally substituted with alkyl, cycloalkyl, heterocycloalkyl, $NR_aR_b$, $NH(CO)R_d$, $NH(CO)OR_c$, and $NH(CO)NR_aR_b$.

In some embodiments, $R_1$ and $R_2$ are each independently H, alkyl, halo, CN, $OR_c$, $SR_c$, or $NR_aR_b$.

In some embodiments, the compound is a compound of the following formula:

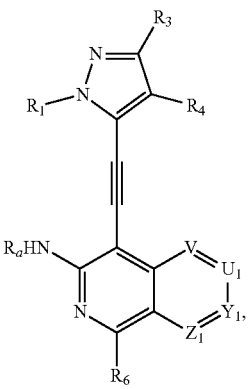

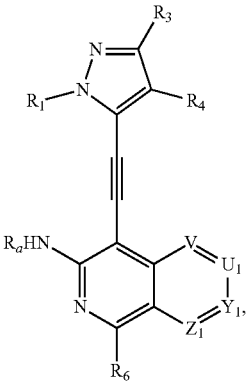

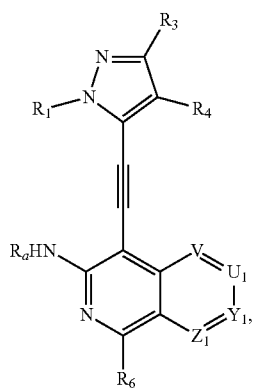
(XIVc)
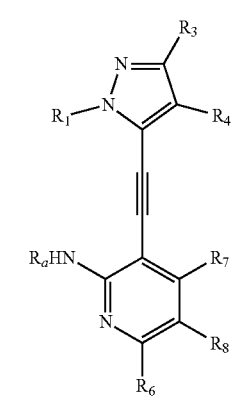
(XIVd)
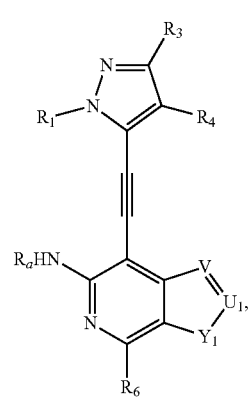
(XIVe)
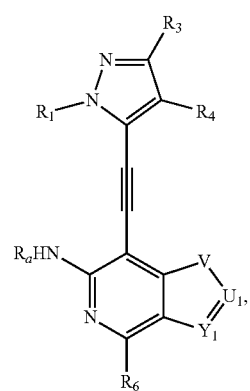
(XIVf)
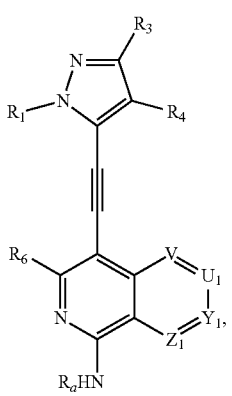
(XIVg)
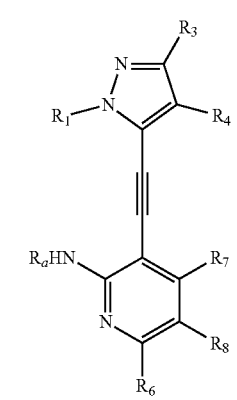
(XIVh)
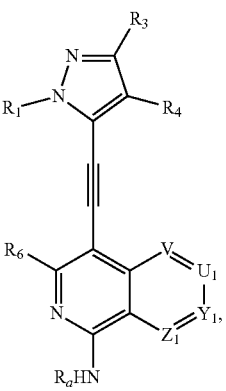
(XIVi)
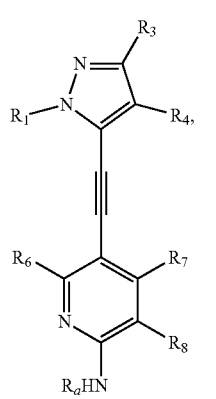
(XIVj)

-continued

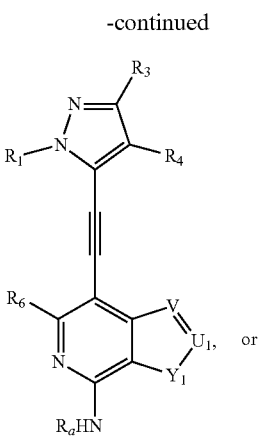
(XIV$_k$)

or

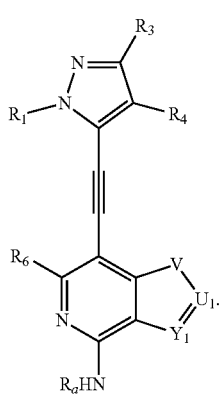
(XIV$_l$)

wherein
V, U$_1$, Y$_1$, and Z$_1$ are each N or CR$_6$';
R$_1$, R$_2$, and R$_6$' are each independently H, alkyl, cycloalkyl, halo, nitro, OR$_c$, SR$_c$, CN, haloalkyl, O-haloalkyl, or NR$_a$R$_b$;
R$_3$, R$_4$, and R$_5$ are each independently H, alkyl, cycloalkyl, heterocycloalkyl, halo, nitro, OR$_c$, SR$_c$, CN, haloalkyl, O-haloalkyl, NR$_m$R$_n$, (CO)R$_d$, (CO)OR$_c$, SO$_2$NR$_m$R$_n$, (CO)NR$_m$R$_n$, C(NH)NR$_m$R$_n$, NH(CO)R$_d$, NH(CO)OR$_c$, NH(CO)NR$_m$R$_n$, aryl, or heteroaryl;
R$_6$ is H or NR$_a$R$_b$;
R$_7$ and R$_8$ are each independently H, alkyl, alkenyl, alkynyl, halo, nitro, OR$_c$, SR$_c$, CN, haloalkyl, O-haloalkyl, (CO)R$_d$, NR$_a$R$_b$, NH(CO)R$_d$, NH(CO)OR$_c$, NH(CO)NR$_a$R$_b$, (CO)OR$_c$, (CO)NR$_a$R$_b$, SO$_2$NR$_a$R$_b$, cycloalkyl, heterocycloalkyl, aryl, or heteroaryl;
R$_m$ and R$_n$ are each independently
H, OH,
alkyl, —(CH$_2$)$_p$-T, -aryl-(CH$_2$)$_p$-T, —(CH$_2$)$_p$-aryl-T, -heteroaryl-(CH$_2$)$_p$-T, —(CH$_2$)$_p$ heteroaryl-T, each optionally substituted with alkyl, cycloalkyl, halo, nitro, CN, haloalkyl, O-haloalkyl, OR$_c$, SR$_c$, (CO)R$_d$, NR$_a$R$_b$, NH(CO)R$_d$, NH(CO)OR$_c$, NH(CO)NR$_a$R$_b$, NHC(NH) NH$_2$, (CO)OR$_c$, (CO)NR$_a$R$_b$, and SO$_2$NR$_a$R$_b$,
or R$_m$ and R$_n$, together with the nitrogen atom they are attached, form a heterocycloalkyl group, optionally substituted with alkyl, cycloalkyl, heterocycloalkyl, aryl, heteroaryl, halo, nitro, CN, OR$_c$, SR$_c$, COR$_d$, NR$_a$R$_b$, NH(CO)R$_d$, NH(CO)OR$_c$, NH(CO)NR$_a$R$_b$, a guanidine group, (CO)OR$_c$, and (CO)NR$_a$R$_b$;
T is NR$_a$R$_b$, OR$_c$, SR$_c$, O—(CH$_2$)$_q$—NR$_a$R$_b$, cycloalkyl, heterocycloalkyl, aryl, heteroaryl, a guanidine group, or an isonicotinimidamide group;

R$_a$, R$_b$, R$_c$, and R$_d$ are each independently H, alkyl, alkenyl, cycloalkyl, heterocycloalkyl, aryl, heteroaryl, —(CH$_2$)$_q$-cycloalkyl, —(CH)$_q$-heterocycloalkyl, —(CH$_2$)$_q$-aryl, —(CH)$_q$-heteroaryl, —(CO)-alkyl, —(CO)-cycloalkyl, or —(CO)-heterocycloalkyl, or R$_a$ and R$_b$, together with the nitrogen atom to which they are attached, form a heterocycloalkyl group, wherein cycloalkyl, heterocycloalkyl, aryl and heteroaryl are each optionally substituted with a group consisting of alkyl, halo, nitro, CN, haloalkyl, O-haloalkyl, OH, O-alkyl, SH, S-alkyl, NH$_2$, NH(alkyl), and N(alkyl)$_2$; and
p and q are each independently 0-5;
or a pharmaceutically acceptable salt, N-oxide, hydrate, solvate, tautomer, or optical isomer thereof.

In some embodiments, R$_6$ is NR$_a$R$_b$.
In some embodiments, one of R$_3$, R$_4$, and R$_5$ is heterocycloalkyl, CN, NR$_m$R$_n$, (CO)R$_d$, (CO)OR$_c$, SO$_2$NR$_m$R$_n$, (CO)NR$_m$R$_n$, C(NH)NR$_m$R$_n$, or NH(CO)R$_d$.
In some embodiments, one of R$_3$, R$_4$, and R$_5$ is (CO)NR$_m$R$_n$.
In some embodiments, R$_m$ is H and R$_n$ is —(CH$_2$)$_p$-T, -aryl-(CH$_2$)$_p$-T, —(CH$_2$)$_p$-aryl-T, or -heteroaryl-(CH$_2$)$_p$-T, each optionally substituted with alkyl, halo, and OR$_c$.
In some embodiments, T is NR$_a$R$_b$, O—(CH$_2$)$_q$—NR$_a$R$_b$, heterocycloalkyl, aryl, or heteroaryl.
In some embodiments, R$_m$ and R$_n$, together with the nitrogen atom they are attached, form a heterocycloalkyl group, optionally substituted with alkyl, cycloalkyl, heterocycloalkyl, NR$_a$R$_b$, NH(CO)R$_d$, NH(CO)OR$_c$, and NH(CO) NR$_a$R$_b$.
In some embodiments, R$_1$ and R$_2$ are each independently H, alkyl, halo, CN, OR$_c$, SR$_c$, or NR$_a$R$_b$.
In some embodiments, the compound is a compound of formula (XV)

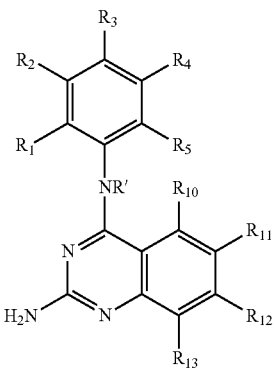
(XV)

wherein
R' is H or alkyl;
R$_1$, R$_2$, R$_{10}$, R$_{11}$, R$_{12}$, and R$_{13}$ are each independently H, alkyl, cycloalkyl, halo, nitro, OR$_c$, SR$_c$, CN, haloalkyl, O-haloalkyl, or NR$_a$R$_b$;
R$_3$, R$_4$, and R$_5$ are each independently H, alkyl, cycloalkyl, heterocycloalkyl, halo, nitro, OR$_c$, SR$_c$, CN, haloalkyl, O-haloalkyl, NR$_m$R$_n$, (CO)R$_d$, (CO)OR$_c$, SO$_2$NR$_m$R$_n$, (CO)NR$_m$R$_n$, C(NH)NR$_m$R$_n$, NH(CO)R$_d$, NH(CO)OR$_c$, NH(CO)NR$_m$R$_n$, aryl, or heteroaryl;
R$_m$ and R$_n$ are each independently
H, OH,
alkyl, —(CH$_2$)$_p$-T, -aryl-(CH$_2$)$_p$-T, —(CH$_2$)$_p$-aryl-T, -heteroaryl-(CH$_2$)$_p$-T, —(CH$_2$)$_p$ heteroaryl-T, each optionally substituted with alkyl, cycloalkyl, halo, nitro, CN, haloalkyl, O-haloalkyl, OR$_c$, SR$_c$, (CO)R$_d$, NR$_a$R$_b$, NH(CO)R$_d$, NH(CO)OR$_c$, NH(CO)NR$_a$R$_b$, NHC(NH)NH$_2$, (CO)OR$_c$, (CO)NR$_a$R$_b$, and SO$_2$NR$_a$R$_b$, or R$_m$ and R$_n$, together with the nitrogen atom they are attached, form a heterocycloalkyl group, optionally substituted with alkyl, cycloalkyl, heterocycloalkyl, aryl, heteroaryl, halo, nitro, CN, OR$_c$, SR$_c$, COR$_d$, NR$_a$R$_b$, NH(CO)R$_d$, NH(CO)OR$_c$, NH(CO)NR$_a$R$_b$, a guanidine group, (CO)OR$_c$, and (CO)NR$_a$R$_b$;

T is NR$_a$R$_b$, OR$_c$, SR$_c$, O—(CH$_2$)$_q$—NR$_a$R$_b$, cycloalkyl, heterocycloalkyl, aryl, heteroaryl, a guanidine group, or an isonicotinimidamide group;

R$_a$, R$_b$, R$_c$, and R$_d$ are each independently H, alkyl, alkenyl, cycloalkyl, heterocycloalkyl, aryl, heteroaryl, —(CH$_2$)$_q$-cycloalkyl, —(CH)$_q$-heterocycloalkyl, —(CH$_2$)$_q$-aryl, —(CH)$_q$-heteroaryl, —(CO)-alkyl, —(CO)-cycloalkyl, or —(CO)-heterocycloalkyl, or R$_a$ and R$_b$, together with the nitrogen atom to which they are attached, form a heterocycloalkyl group, wherein cycloalkyl, heterocycloalkyl, aryl and heteroaryl are each optionally substituted with a group consisting of alkyl, halo, nitro, CN, haloalkyl, O-haloalkyl, OH, O-alkyl, SH, S-alkyl, NH$_2$, NH(alkyl), and N(alkyl)$_2$; and p and q are each independently 0-5.

or a pharmaceutically acceptable salt, N-oxide, hydrate, solvate

In some embodiments, R' is H.

In some embodiments, one of R$_3$, R$_4$, and R$_5$ is heterocycloalkyl, CN, NR$_m$R$_n$, (CO)R$_d$, (CO)OR$_c$, SO$_2$NR$_m$R$_n$, (CO)NR$_m$R$_n$, C(NH)NR$_m$R$_n$, or NH(CO)R$_d$.

In some embodiments, one of R$_3$, R$_4$, and R$_5$ is (CO)NR$_m$R$_n$.

In some embodiments, R$_m$ is H and R$_n$ is —(CH$_2$)$_p$-T, -aryl-(CH$_2$)$_p$-T, —(CH$_2$)$_p$-aryl-T, or -heteroaryl-(CH$_2$)$_p$-T, each optionally substituted with alkyl, halo, and OR$_c$.

In some embodiments, T is NR$_a$R$_b$, O—(CH$_2$)$_q$—NR$_a$R$_b$, heterocycloalkyl, aryl, or heteroaryl.

In some embodiments, R$_m$ and R$_n$, together with the nitrogen atom they are attached, form a heterocycloalkyl group, optionally substituted with alkyl, cycloalkyl, heterocycloalkyl, NR$_a$R$_b$, NH(CO)R$_d$, NH(CO)OR$_c$, and NH(CO)NR$_a$R$_b$.

In some embodiments, R$_1$ and R$_2$ are each independently H, alkyl, halo, CN, OR$_c$, SR$_c$, or NR$_a$R$_b$.

The present invention provides a compound represented by formula (I):

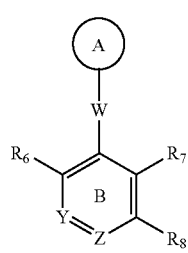

(I)

wherein

Ring A is a 5- or 6-membered aryl or heteroaryl group, optionally substituted;

Y and Z are each N or CR$_9$, wherein R$_9$ is H, alkyl, halo, nitro, OH, SH, CN, O-alkyl, haloalkyl, O-haloalkyl, S-alkyl, (CO)-alkyl, (CO)-alkenyl, NR$_a$R$_b$, (CO)OR$_c$, (CO)NR$_a$R$_b$, or SO$_2$NR$_a$R$_b$, wherein R$_a$, R$_b$, and R$_c$ are H or alkyl;

W is azo, alkene, alkyne, C$_{1-8}$ alkyl, heteroalkyl containing 1-8 carbon and hetero atoms, cycloalkyl, heterocycloalkyl, aryl, or heteroaryl, wherein cycloalkyl, hetereocycloalkyl, aryl, and heteroaryl optionally form a fused aryl or heteroaryl group with Ring A;

R$_6$, R$_7$, and R$_8$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, NH(CO)-alkyl, NH(CO)OR$_c$, NH(CO)NR$_a$R$_b$, (CO)OR$_c$, (CO)NR$_a$R$_b$, SO$_2$NR$_a$R$_b$, cycloalkyl, heterocycloalkyl, aryl, or heteroaryl;

or R$_7$ and R$_8$, together with the carbon atoms to which they are attached, form a cycloalkyl, heterocycloalkyl, aryl, or heteroaryl group, each optionally substituted with substituents independently selected from alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, (CO)OR$_c$, (CO)NR$_a$R$_b$, SO$_2$NR$_a$R$_b$, —C(CH$_3$)(=N—NHC(NH)NH$_2$, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, alkylamino, —NH(CO)-alkyl, or —NH(CO)-alkenyl;

wherein Ring A is optionally substituted with substituents independently selected from:

alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, NH(CO)-alkyl, NH(CO)OR$_c$, NH(CO)NR$_a$R$_b$, (CO)OR$_c$, SO$_2$NR$_a$R$_b$;

cycloalkyl, heterocycloalkyl, aryl, or heteroaryl, each optionally substituted with substituents independently selected from alkyl, aminoalkyl, heterocycloalkyl-alkyl, heterocycloalkyl, cycloalkyl-alkyl, and cycloalkyl; and (CO)NR$_m$R$_n$ or CNH)NR$_m$R$_n$, wherein R$_m$ and R$_n$ are each independently H, alkyl, —(CH$_2$)$_p$-T, cycloalkyl, heterocycloaryl, aryl, or heteroaryl, wherein —(CH$_2$)$_p$-T, cycloalkyl, heterocycloaryl, aryl, and heteroaryl are each optionally substituted with alkyl, halo, nitro, CN, OH, SH, O-alkyl, S-alkyl, (CO)-alkyl, (CO)-alkenyl, NR$_a$R$_b$, (CO)OR$_c$, (CO)NR$_a$R$_b$, SO$_2$NR$_a$R$_b$, cycloalkylamino, heterocycloalkylamino, arylamino, or heteroarylamino;

or R$_m$ and R$_n$, together with the nitrogen atom they are attached, form a heterocycloalkyl or heteroaryl group, optionally substituted with alkyl, halo, nitro, CN, OH, SH, O-alkyl, S-alkyl, —CO-alkyl, —CO-alkenyl, NR$_a$R$_b$, (CO)OR$_c$, or (CO)NR$_a$R$_b$;

wherein p is 0-8; and wherein T is NR$_a$R$_b$, O-alkyl, cycloalkyl, heterocycloalkyl, aryl, heteroaryl, cycloalkylamino, heterocycloalkylamino, arylamino, heteroarylamino, a guanidine group, or an isonicotinimidamide group;

or a pharmaceutically acceptable salt, N-oxide, hydrate, solvate, tautomer, or optical isomer thereof.

In some embodiment, Y is N.

In some embodiment, Z is CH.

In some embodiment, W is azo, —CH=CH—, —C≡C—, a phenyl group, or a 5- or 6-membered heteroaryl group. In other embodiments, W is azo. In certain embodiments, W is —C≡C—.

In some embodiment, R$_6$ is (CO)NR$_m$R$_n$. In other embodiments, wherein R$_6$ is C(NH)NR$_m$R$_n$.

In some embodiments, $R_6$ is $NH_2$.

In some embodiments, the compound of formula (I) is represented by the following formulas:

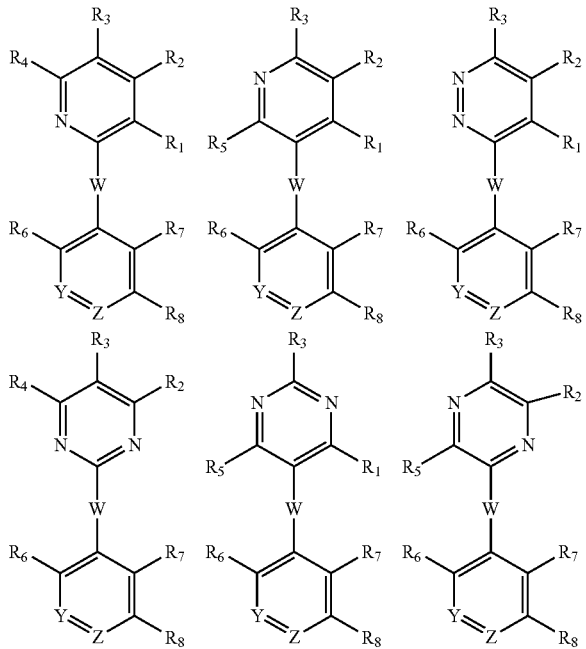

wherein
- $R_1$ and $R_2$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, NH(CO)-alkyl, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl;
- $R_3$ is:
- H or CN;
- cycloalkyl, heterocycloalkyl, aryl, or heteroaryl, each optionally substituted with substituents independently selected from alkyl, aminoalkyl, heterocycloalkyl-alkyl, heterocycloalkyl, cycloalkyl-alkyl, and cycloalkyl; and
- $(CO)NR_mR_n$ or $C(NH)NR_mR_n$ wherein $R_m$ and $R_n$ are each independently H, alkyl, $-(CH_2)_p$-T, cycloalkyl, heterocycloaryl, aryl, or heteroaryl, wherein $-(CH_2)_p$-T, cycloalkyl, heterocycloaryl, aryl, and heteroaryl are each optionally substituted with alkyl, halo, nitro, CN, OH, SH, O-alkyl, S-alkyl, (CO)-alkyl, (CO)-alkenyl, $NR_aR_b$, $(CO)OR_c$, $(CO)NR_aR_b$, $SO_2NR_aR_b$, cycloalkylamino, heterocycloalkylamino, arylamino, or heteroarylamino;
- or $R_m$ and $R_n$ together with the nitrogen atom they are attached, form a heterocycloalkyl or heteroaryl group, optionally substituted with alkyl, halo, nitro, CN, OH, SH, O-alkyl, S-alkyl, —CO-alkyl, —CO-alkenyl, $NR_aR_b$, $(CO)OR_c$, or $(CO)NR_aR_b$;
- p is 0-8; and
- T is $NR_aR_b$, O-alkyl, cycloalkyl, heterocycloalkyl, aryl, heteroaryl, cycloalkylamino, heterocycloalkylamino, arylamino, heteroarylamino, a guanidine group, or an isonicotinimidamide group.

In some embodiments, the compound of formula (I) is represented by the following formulas:

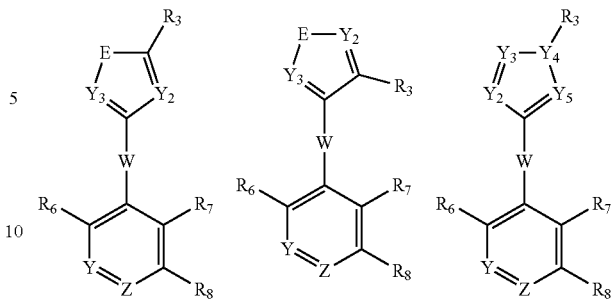

wherein
- E, $Y_2$, $Y_3$, $Y_4$, and $Y_5$ are each O, S, N, or $NR_{14}$, wherein $R_{14}$ is H, alkyl, (CO)-alkyl, $(CO)OR_c$, $(CO)NR_aR_b$, or $SO_2NR_aR_b$;
- $R_3$ is:
- H or CN;
- cycloalkyl, heterocycloalkyl, aryl, or heteroaryl, each optionally substituted with substituents independently selected from alkyl, aminoalkyl, heterocycloalkyl-alkyl, heterocycloalkyl, cycloalkyl-alkyl, and cycloalkyl; and
- $(CO)NR_mR_n$ or $C(NH)NR_mR_n$, wherein $R_m$ and $R_n$ are each independently H, alkyl, $-(CH_2)_p$-T, cycloalkyl, heterocycloaryl, aryl, or heteroaryl, wherein $-(CH_2)_p$-T, cycloalkyl, heterocycloaryl, aryl, and heteroaryl are each optionally substituted with alkyl, halo, nitro, CN, OH, SH, O-alkyl, S-alkyl, (CO)-alkyl, (CO)-alkenyl, $NR_aR_b$, $(CO)OR_c$, $(CO)NR_aR_b$, $SO_2NR_aR_b$, cycloalkylamino, heterocycloalkylamino, arylamino, or heteroarylamino;
- or $R_m$ and $R_n$, together with the nitrogen atom they are attached, form a heterocycloalkyl or heteroaryl group, optionally substituted with alkyl, halo, nitro, CN, OH, SH, O-alkyl, S-alkyl, —CO-alkyl, —CO-alkenyl, $NR_aR_b$, $(CO)OR_c$, or $(CO)NR_aR_b$;
- p is 0-8; and
- T is $NR_aR_b$, O-alkyl, cycloalkyl, heterocycloalkyl, aryl, heteroaryl, cycloalkylamino, heterocycloalkylamino, arylamino, heteroarylamino, a guanidine group, or an isonicotinimidamide group.

In some embodiments, a compound of formula (I) is represented by formula (Ia)

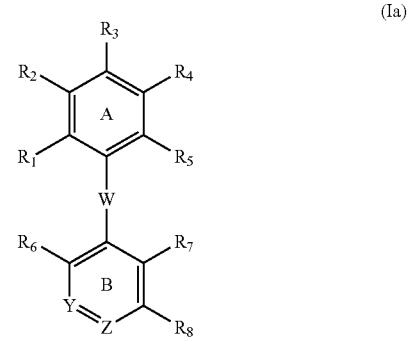

(Ia)

wherein
$R_1$, $R_2$, $R_4$, and $R_5$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, NH(CO)-alkyl, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl;

$R_3$ is:

H or CN;

cycloalkyl, heterocycloalkyl, aryl, or heteroaryl, each optionally substituted with substituents independently selected from alkyl, aminoalkyl, heterocycloalkyl-alkyl, heterocycloalkyl, cycloalkyl-alkyl, and cycloalkyl; and $(CO)NR_mR_n$ or $C(NH)NR_mR_n$, wherein $R_m$ and $R_n$ are each independently H, alkyl, —$(CH_2)_p$-T, cycloalkyl, heterocycloaryl, aryl, or heteroaryl, wherein —$(CH_2)_p$-T, cycloalkyl, heterocycloaryl, aryl, and heteroaryl are each optionally substituted with alkyl, halo, nitro, CN, OH, SH, O-alkyl, S-alkyl, (CO)-alkyl, (CO)-alkenyl, $NR_aR_b$, $(CO)OR_c$, $(CO)NR_aR_b$, $SO_2NR_aR_b$, cycloalkylamino, heterocycloalkylamino, arylamino, or heteroarylamino;

or $R_m$ and $R_n$, together with the nitrogen atom they are attached, form a heterocycloalkyl or heteroaryl group, optionally substituted with alkyl, halo, nitro, CN, OH, SH, O-alkyl, S-alkyl, —CO-alkyl, —CO-alkenyl, $NR_aR_b$, $(CO)OR_c$, or $(CO)NR_aR_b$;

p is 0-8; and

T is $NR_aR_b$, O-alkyl, cycloalkyl, heterocycloalkyl, aryl, heteroaryl, cycloalkylamino, heterocycloalkylamino, arylamino, heteroarylamino, a guanidine group, or an isonicotinimidamide group.

In some embodiments, the compound of formula (Ia) is represented by a compound of formula (II)

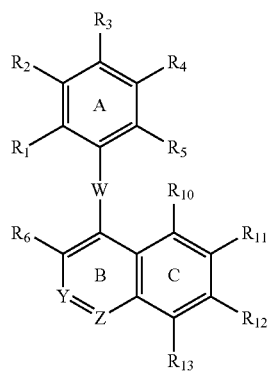

(II)

wherein $R_{10}$, $R_{11}$, $R_{12}$, and $R_{13}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, $(CO)OR_c$, $(CO)NR_aR_b$, $SO_2NR_aR_b$, —$C(CH_3)(=N—NHC(NH)NH_2$, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, dialkylamino, —NH(CO)-alkyl, or —NH(CO)— alkenyl.

In some embodiments, $R_6$, $R_{10}$, $R_{11}$, $R_{12}$, and $R_{13}$ are each independently H, alkyl, alkynyl, halo, OH, CN, amino, alkylamino, or di-alkylamino.

In some embodiments, $R_{11}$ is alkynyl, optionally substituted with amino, alkylamino, dialkylamino, or —NH(CO)-alkyl. In other embodiments, $R_{11}$ is halo. In certain embodiments, $R_{11}$ is chloro.

In some embodiments, $R_6$ is $NH_2$.

In some embodiments, $R_1$, $R_2$, $R_4$, and $R_5$ are each H.

In some embodiments, $R_3$ is CN. In other embodiments, $R_3$ is heterocycloalkyl or heteroaryl, optionally substituted with alkyl, aminoalkyl, heterocycloalkyl-alkyl, heterocycloalkyl, cycloalkyl-alkyl, and cycloalkyl.

In some embodiments, $R_3$ is $(CO)NR_mR_n$. In other embodiments, $R_3$ is $C(NH)NR_mR_n$. In some embodiments, $R_m$ is H and $R_n$ is heterocycloalkyl. In some embodiments, $R_m$ is H and $R_n$ is $(CH_2)_p$-T, optionally substituted with alkyl, halo, or OH. In some embodiments, p is 1-4.

In some embodiments, T is $NR_aR_b$ or O-alkyl. In some embodiments, T is —N(alkyl)$_2$. In certain embodiments, T is $N(CH_3)_2$. In other embodiments, T is $OCH_3$. In some embodiments, T is heterocycloalkylamino, a guanidine group, or an isonicotinimidamide group. In some embodiments, T is heterocycloalkyl. In certain embodiments, T is a 5- or 6-membered heterocycloalkyl group. In some embodiments, T is piperidine or pyrrolidine.

In some embodiments, $R_m$ is H and R, is aryl or heteroaryl. In other embodiments, $R_m$ and R, together with the nitrogen atom they are attached, form a heterocycloalkyl group. In some embodiments, $R_m$ and $R_n$ are independently alkyl.

In some embodiments, the compound of formula (II) is represented by a compound of formula (III)

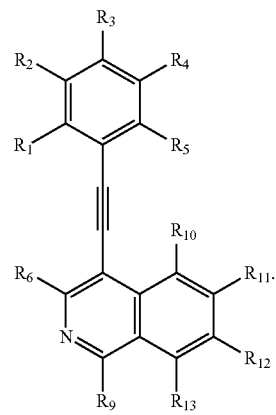

(III)

In some embodiments, the compound of formula (I) is represented by a compound of formulas $IV_a$-$IV_f$:

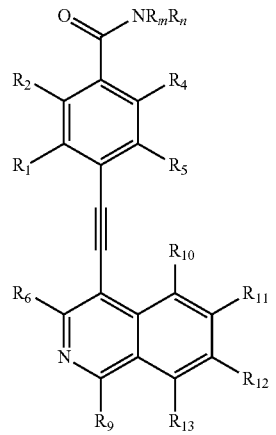

($IV_a$)

-continued

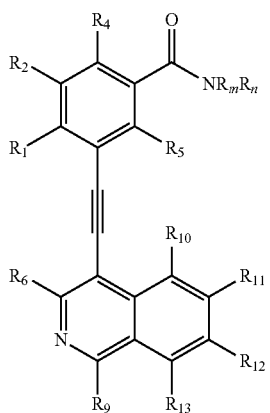

(IV$_b$)

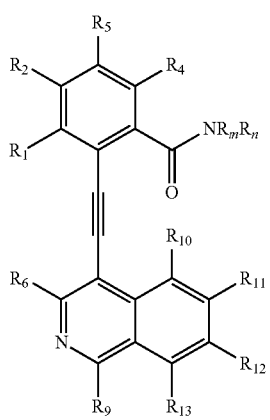

(IV$_c$)

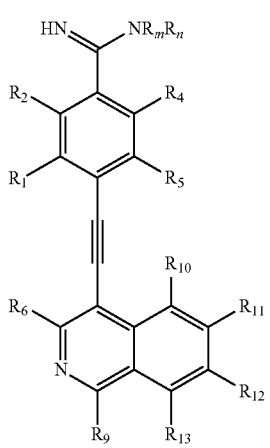

(IV$_d$)

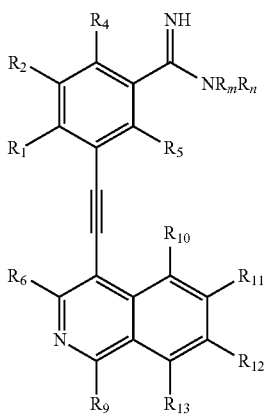

(IV$_e$)

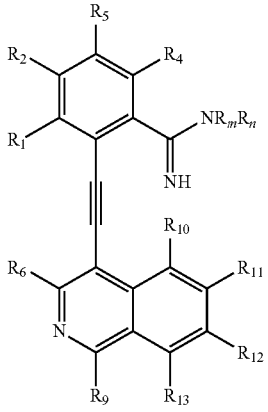

(IV$_f$)

wherein
R$_1$, R$_2$, R$_4$, R$_5$, R$_{10}$, and R$_{13}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, NH(CO)-alkyl, NH(CO)OR$_c$, NH(CO)NR$_a$R$_b$, (CO)OR$_c$, (CO)NR$_a$R$_b$, SO$_2$NR$_a$R$_b$, cycloalkyl, heterocycloalkyl, aryl, or heteroaryl; and
R$_{11}$ and R$_{12}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, (CO)OR$_c$, (CO)NR$_a$R$_b$, SO$_2$NR$_a$R$_b$, —C(CH$_3$)(=N—NHC(NH)NH$_2$, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, dialkylamino, —NH(CO)-alkyl, or —NH(CO)— alkenyl.

In some embodiments, R$_m$ is H and R$_n$ is (CH$_2$)$_p$-T, optionally substituted with OH. In other embodiments, R$_m$ and R$_n$ are independently alkyl. In some embodiments, p is 1-4. In some embodiments, T is NR$_a$R$_b$ or O-alkyl. In certain embodiments, T is N(CH$_3$)$_2$. In other embodiments, T is OCH$_3$. In some embodiments, T is heterocycloalkyl. In some embodiments, T is a 5- or 6-membered heterocycloalkyl group. In certain embodiments, T is piperidine or pyrrolidine.

In some embodiments, R$_m$ and R$_n$, together with the nitrogen atom they are attached, form a 5- or 6-membered heterocycloalkyl group.

In some embodiments, R$_6$ is NH$_2$.

In some embodiments, R$_{11}$ is halo. In certain embodiments, R$_{11}$ is chloro.

In some embodiments, the compound of the invention is
HSM1610
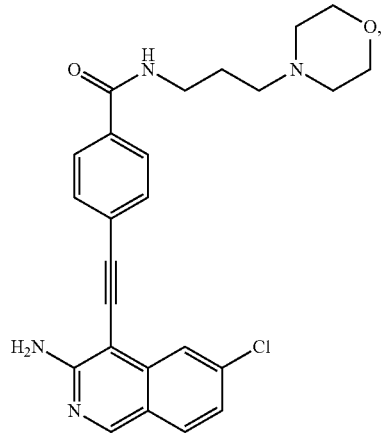
HSM1688
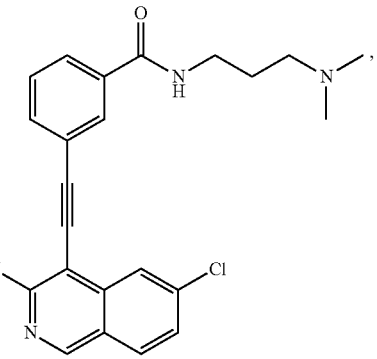
HSM1661
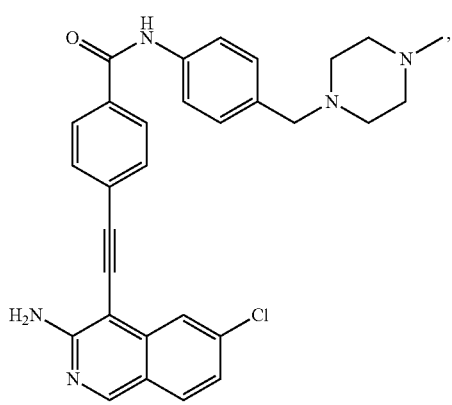
HSM1673
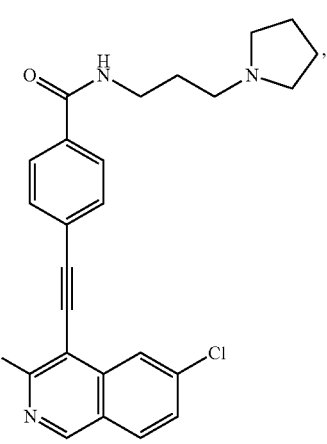
HSM1651
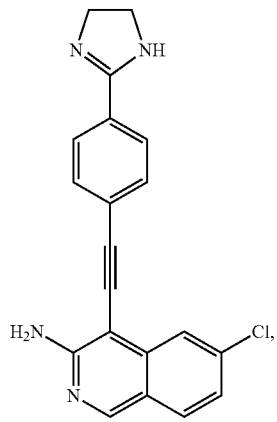
HSM1674
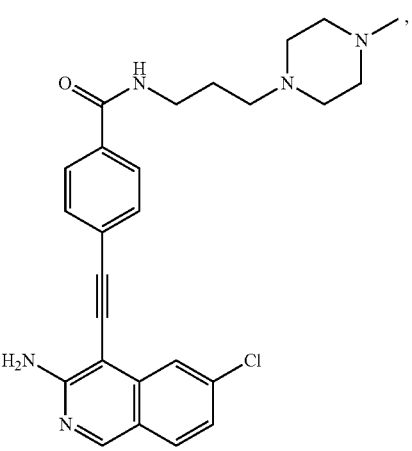

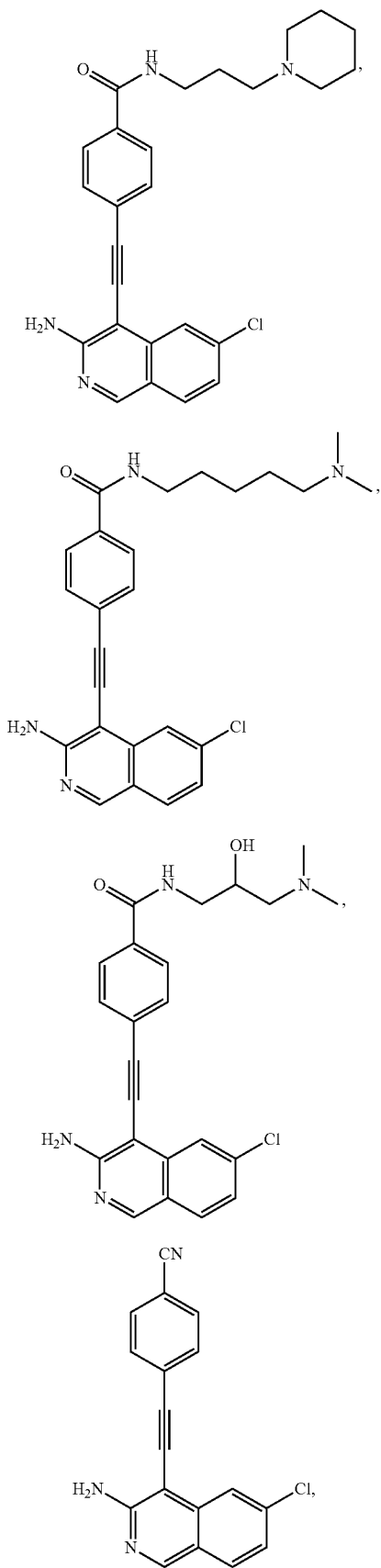
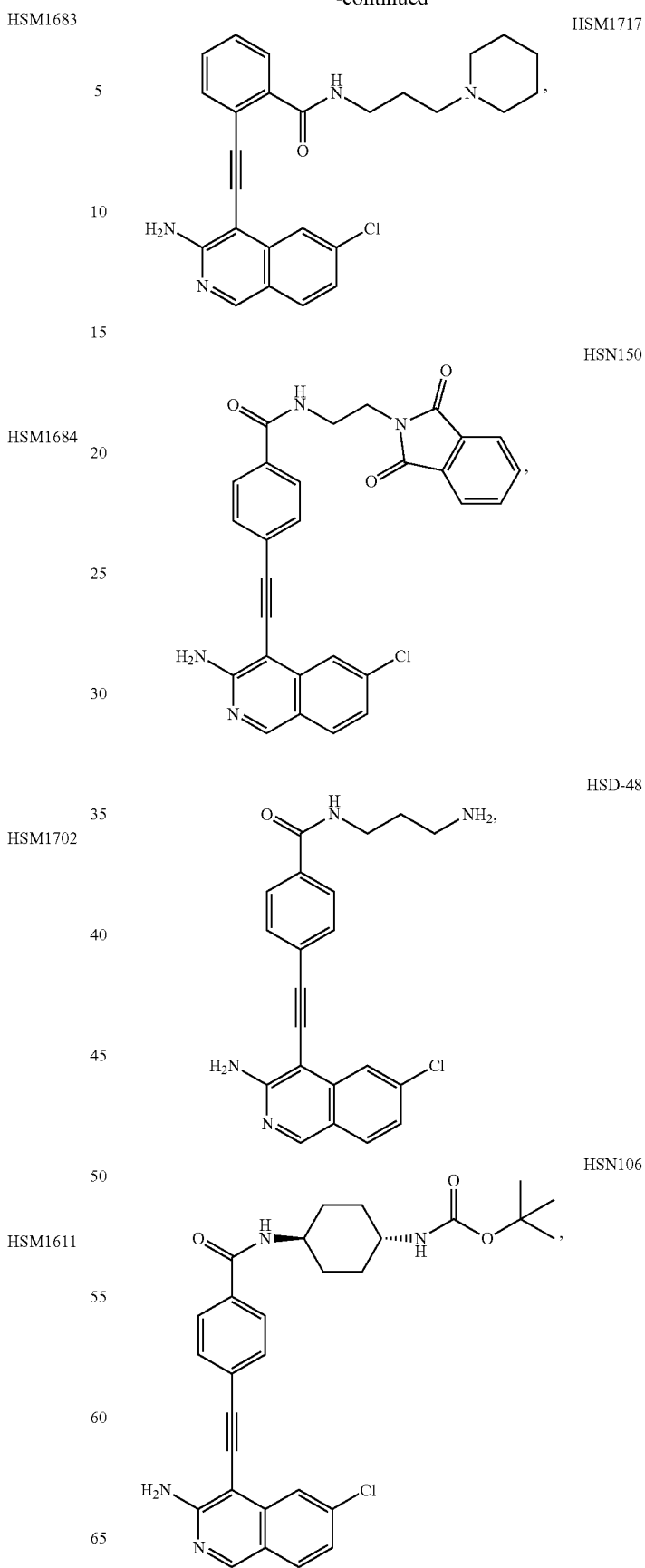

HSN139
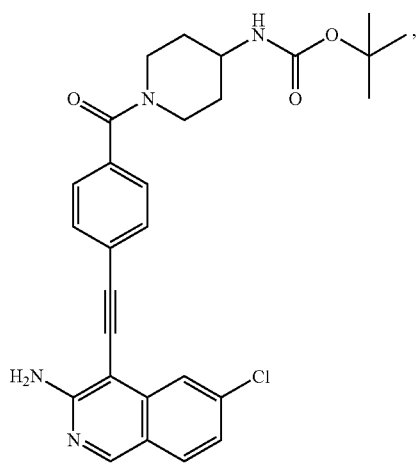
HSN135
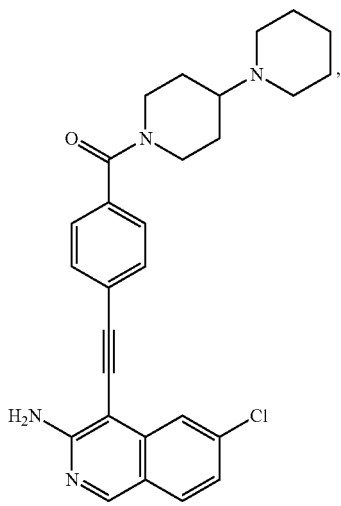
HSN105
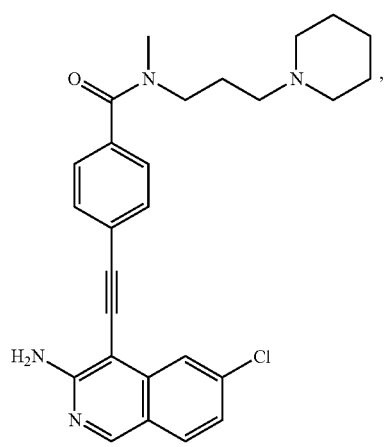
HSN129
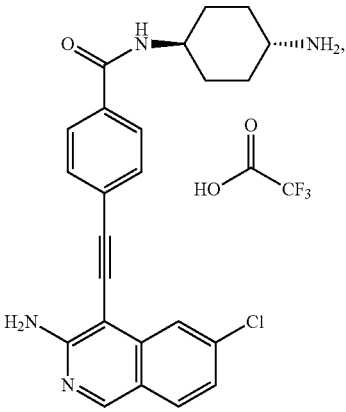
HSN136
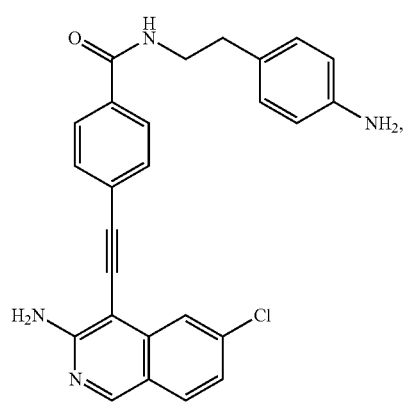
HSN137
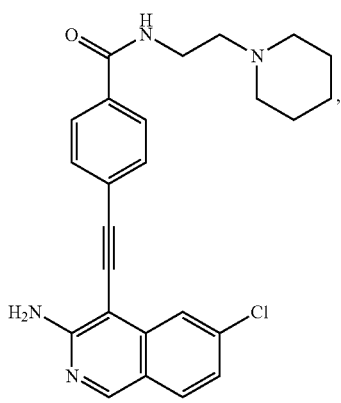

HSN157
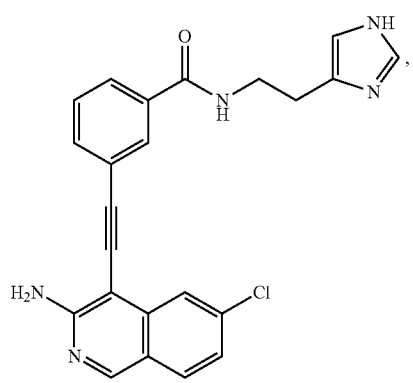
HSN169A
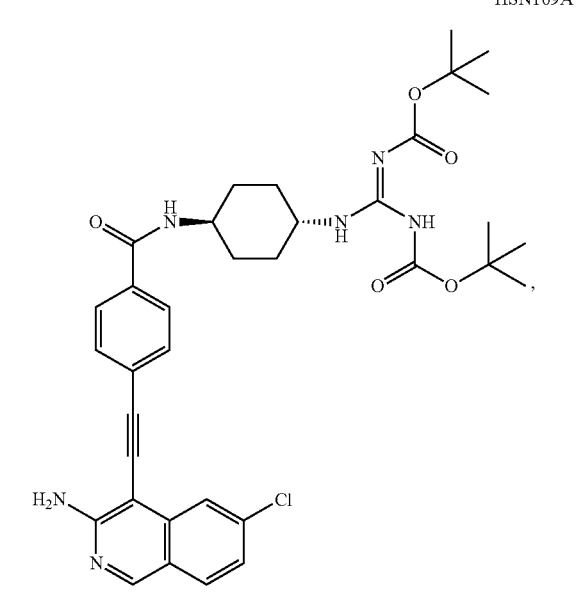
HSN145
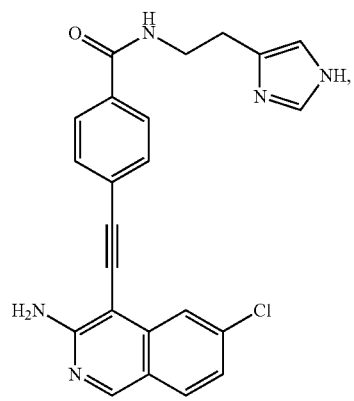
HSN169B
HCl
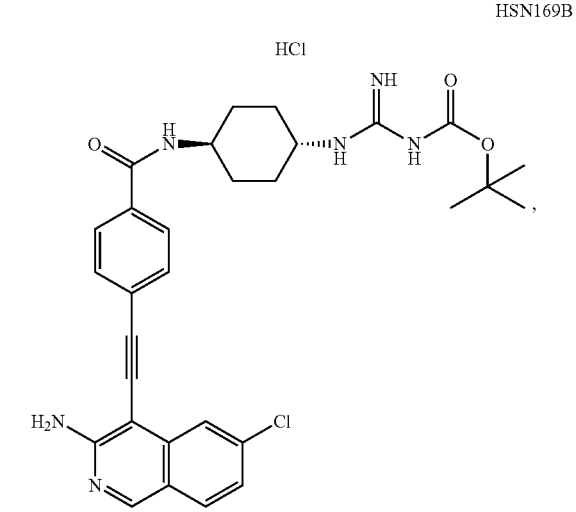
HSN159
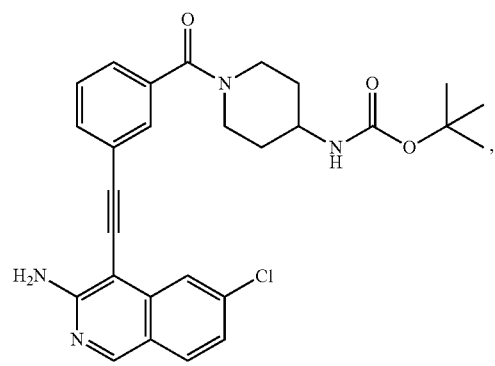
HSN172
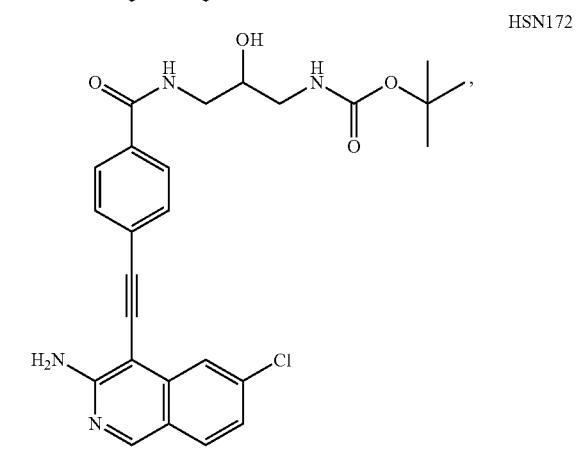

-continued
HSN174
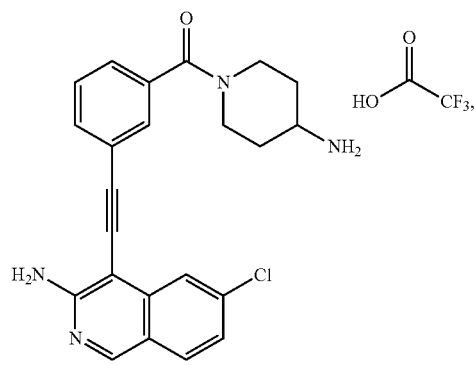
HSN177
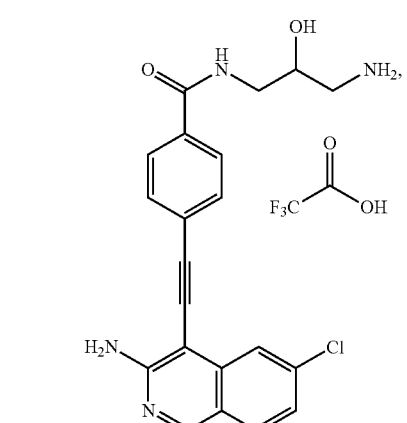
HSN178
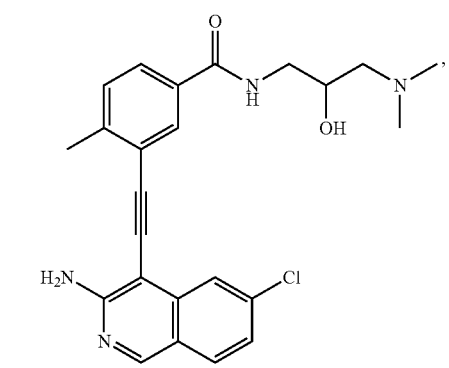
HSN181
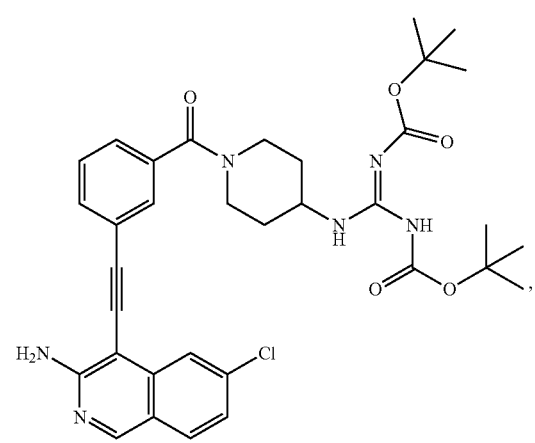
-continued
HSN184
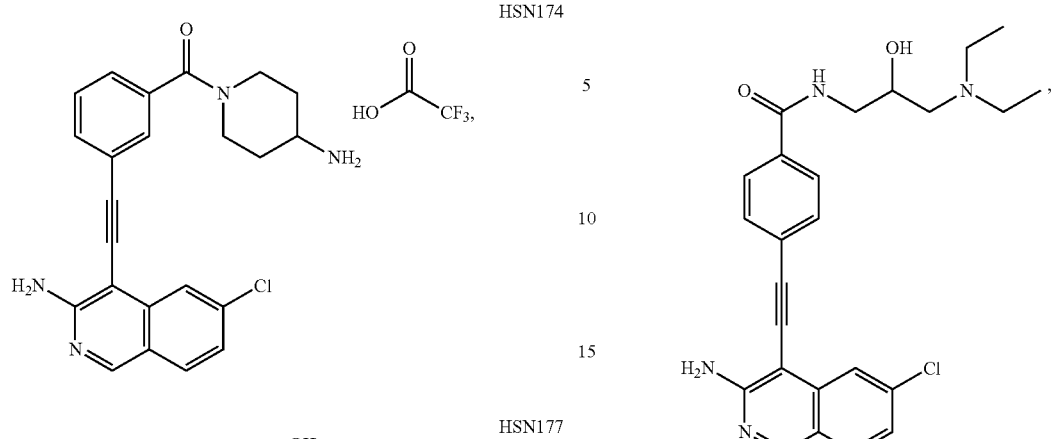
HSN185
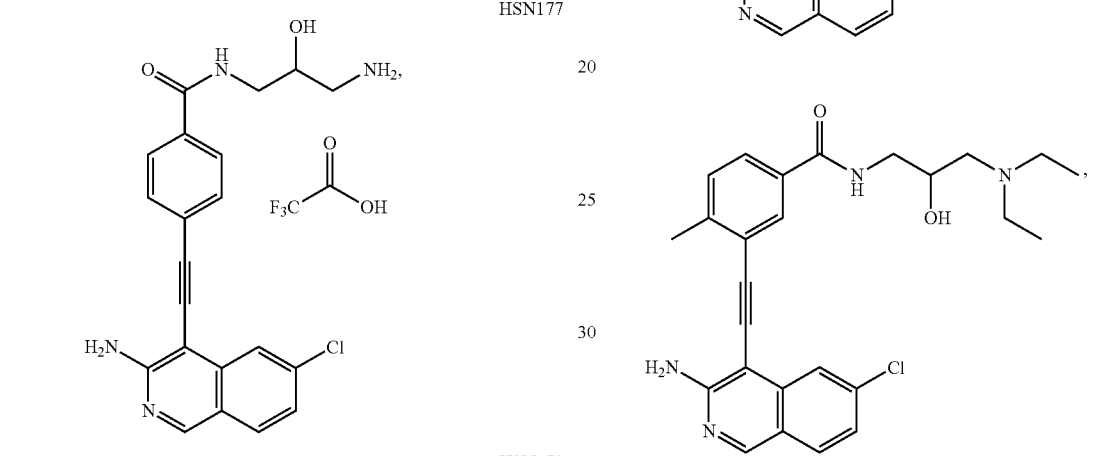
HSN187
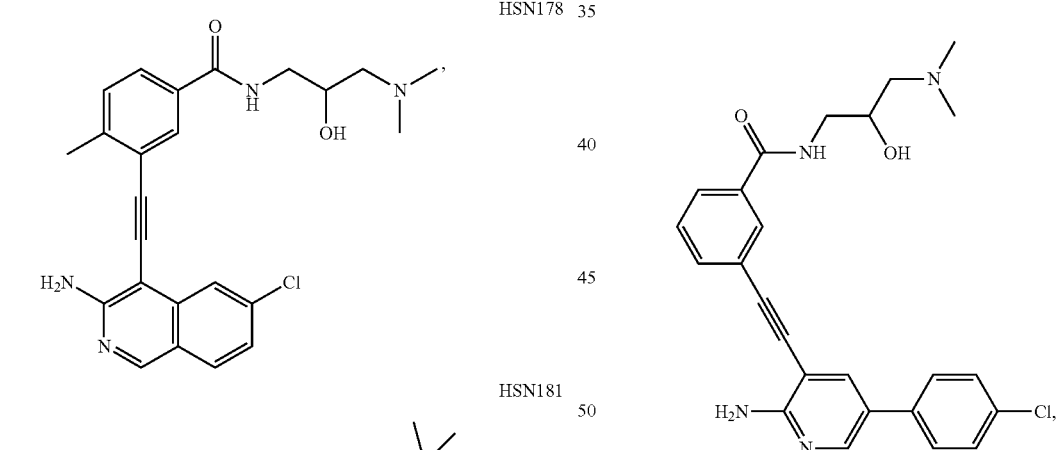
HSN189
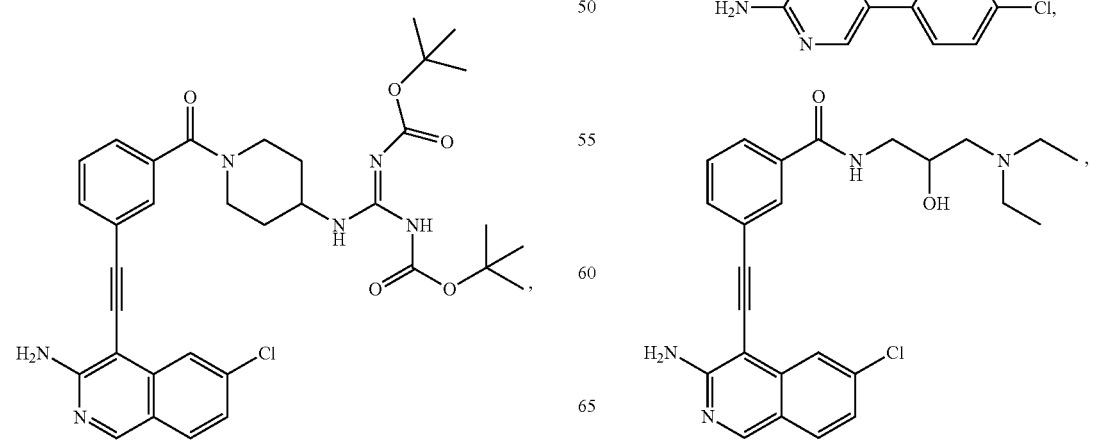

-continued
HSN198
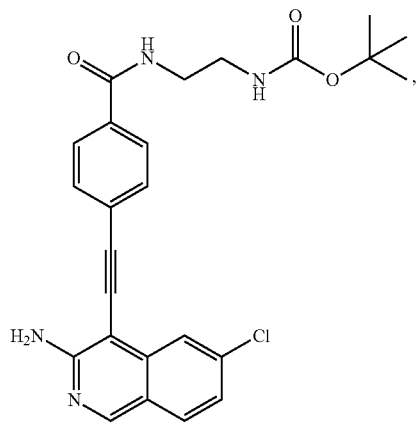
HSN202
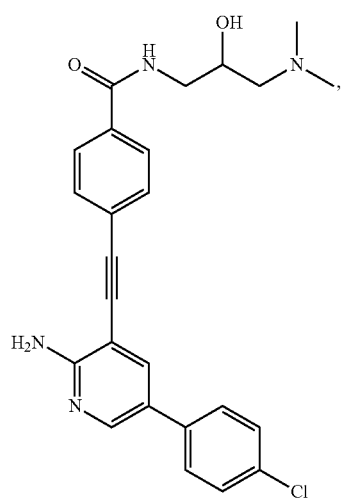
HSN204
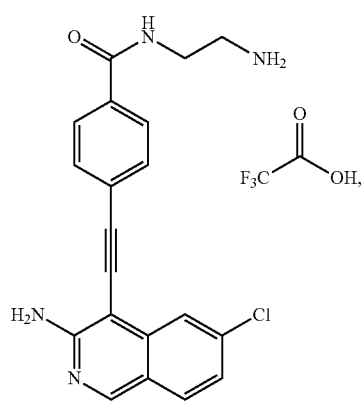
-continued
HSN206
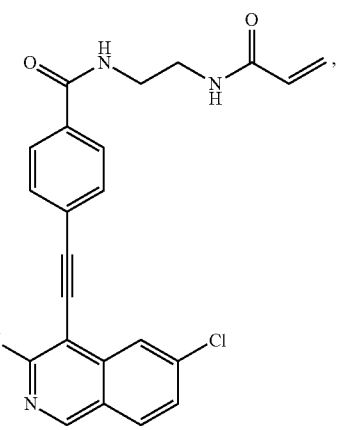
HSN221
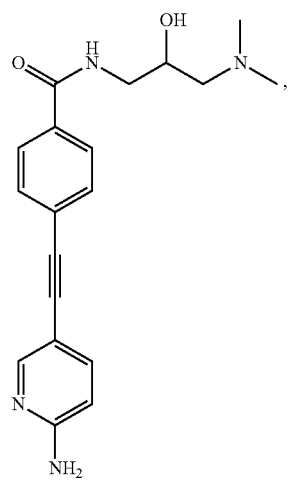
HSN222
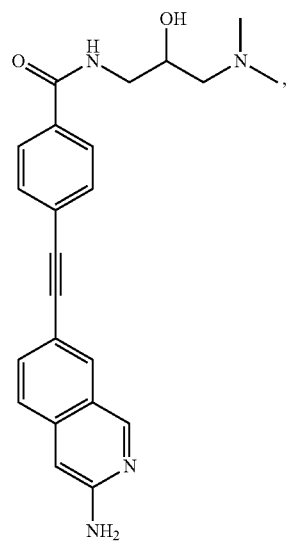

43
-continued
HSN225
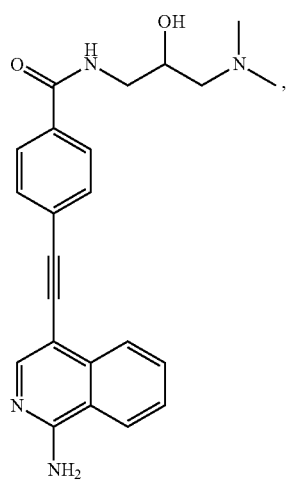
HSN233
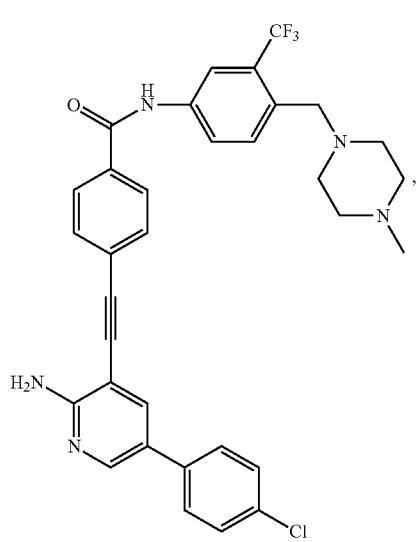
HSN1669
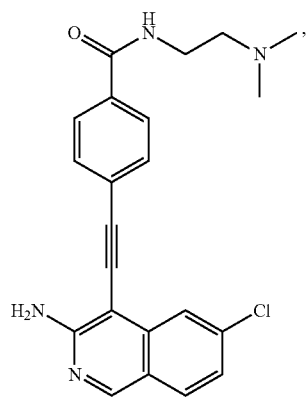
44
-continued
HSM1690
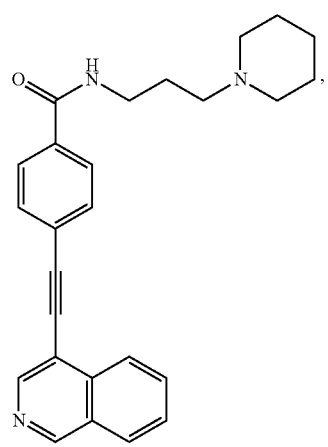
HSM1725
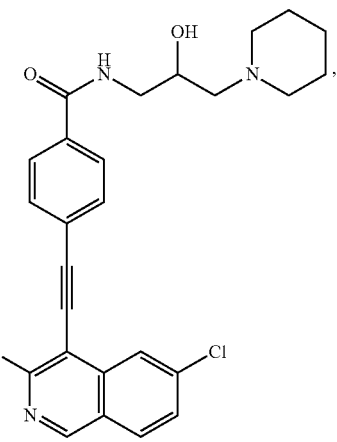
HSM1692
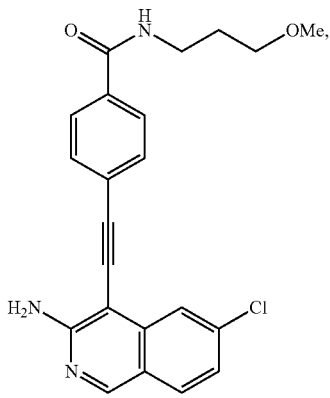

HSM1693
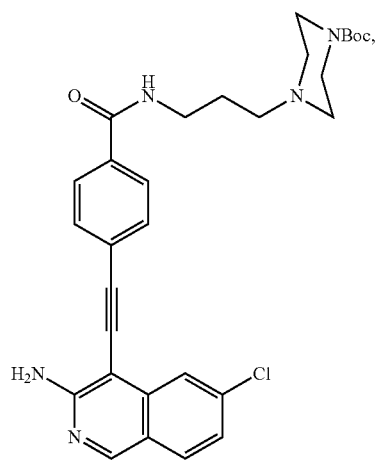
HSM1750
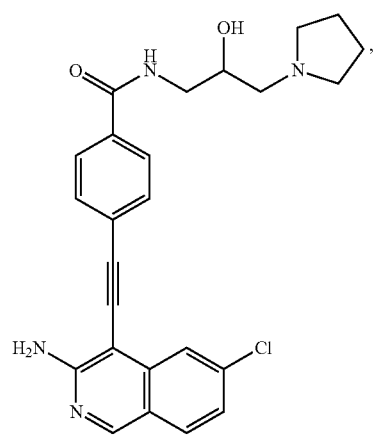
HSM1751
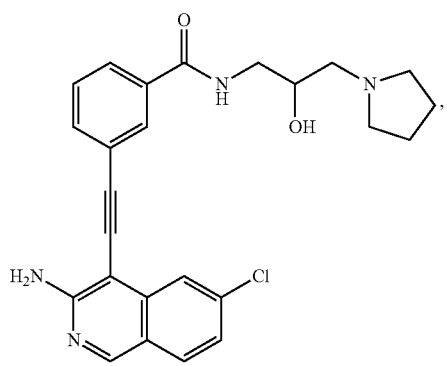
HSM1764
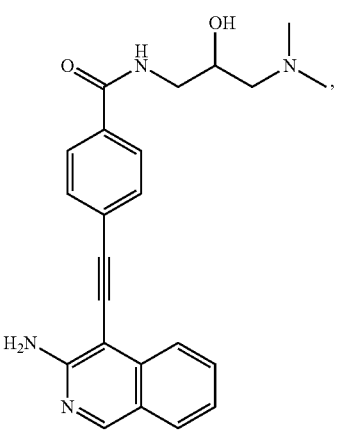
HSM1766
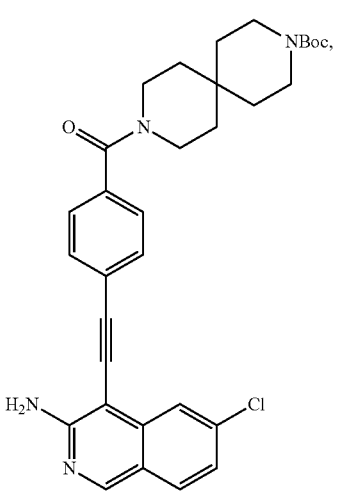
HSM1773
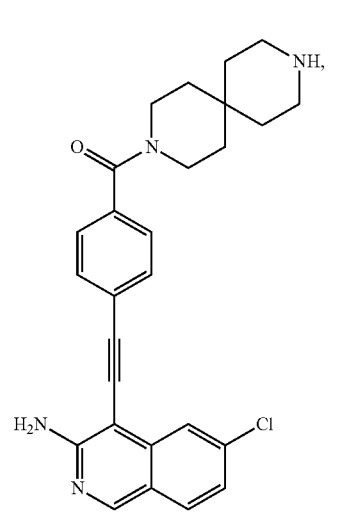

HSN304
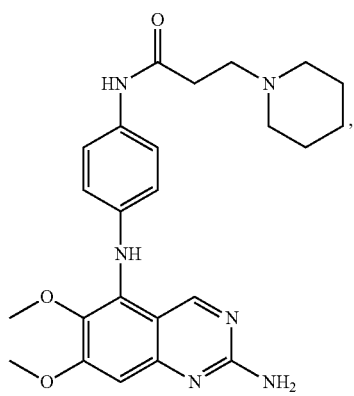
HSN305
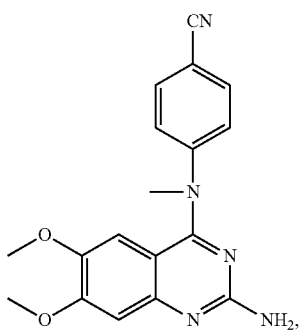
HSN284
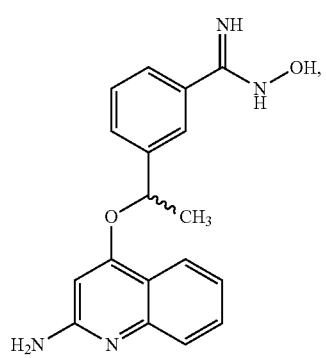
HSN315
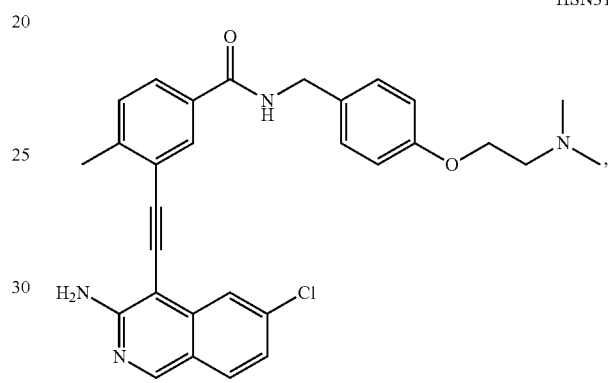
HSN253
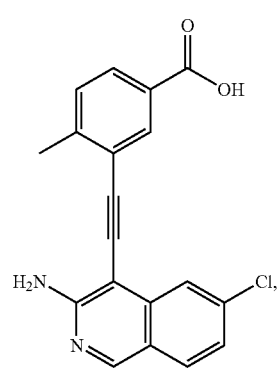
HSN312
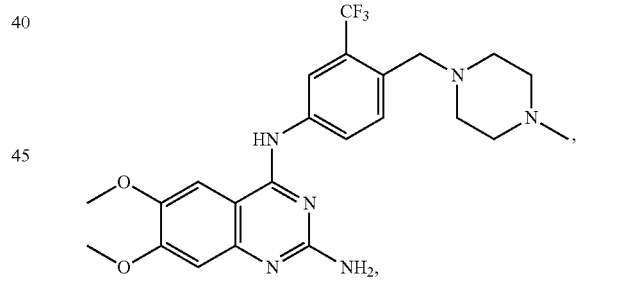
HSN266
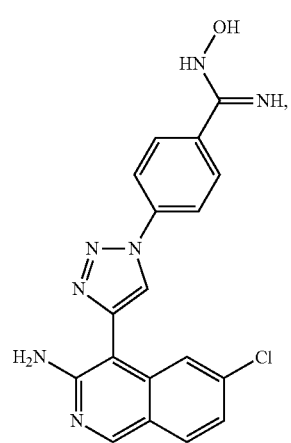
HSN314
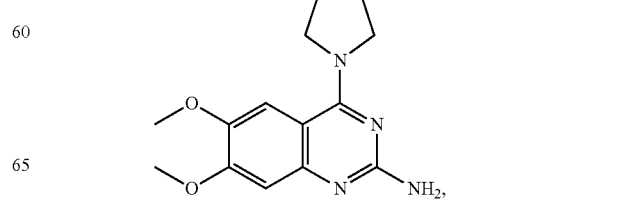

HSN335
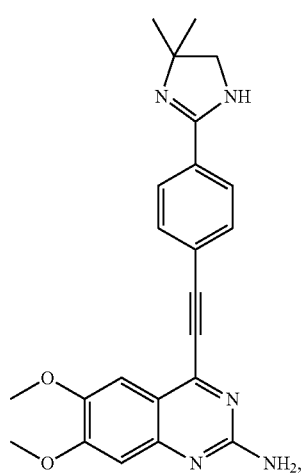
HSM1721
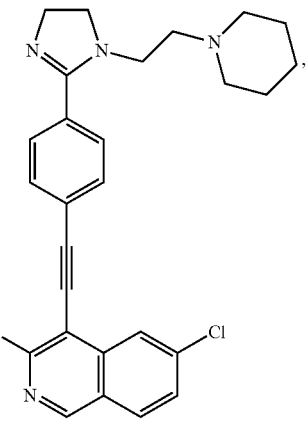
HSN336
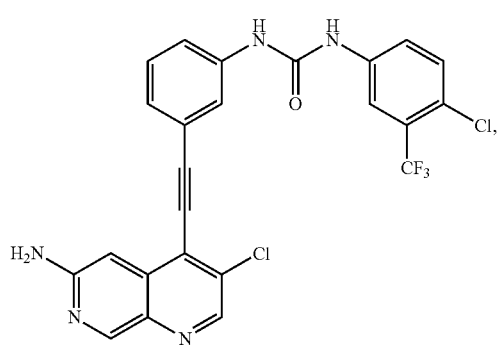
HSM1726
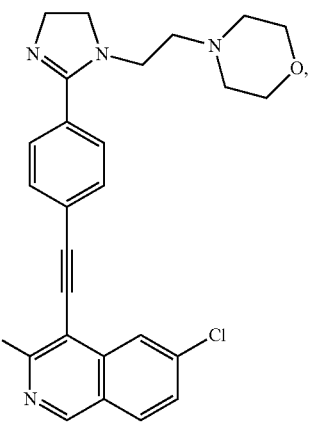
HSM1703
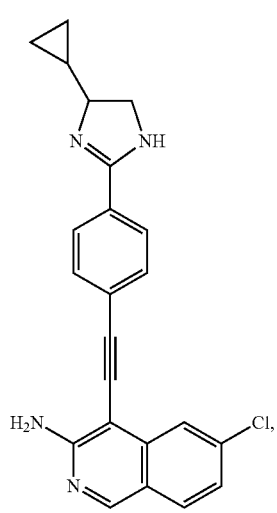
HSM1743
HSM1765
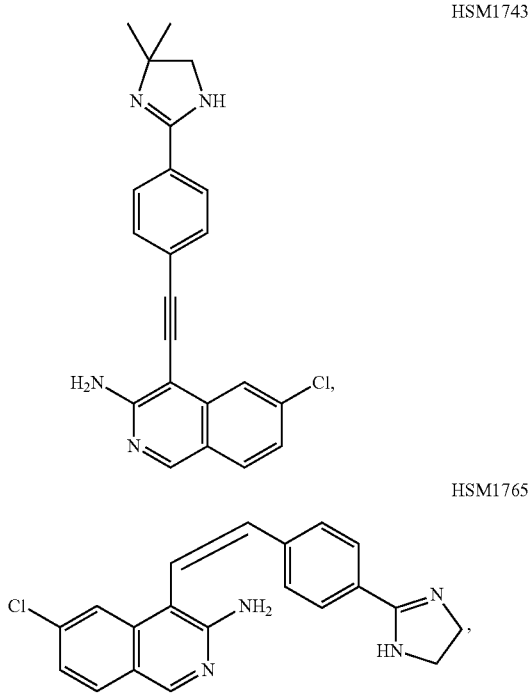

-continued
HSM1777
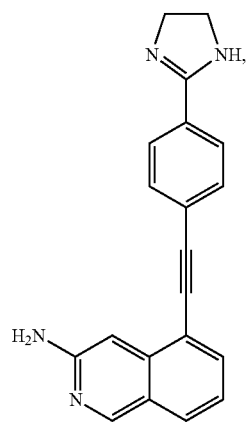
HSM1778
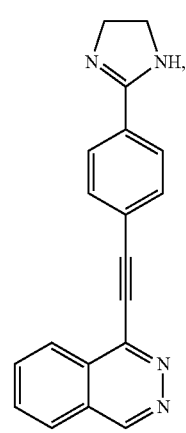
HSM1780
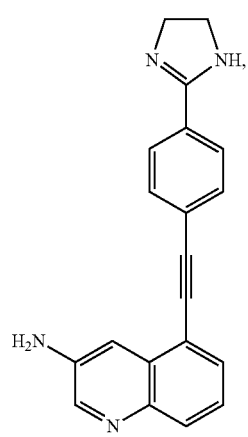
-continued
HSM1781
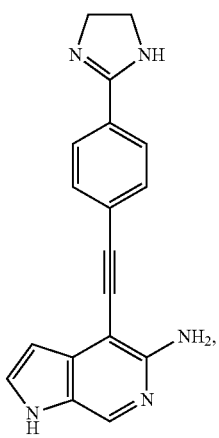
HSM1796
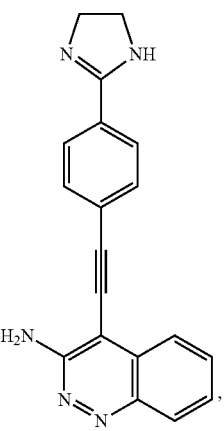
HSM1809
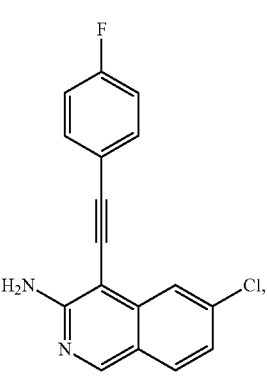
HSM1617
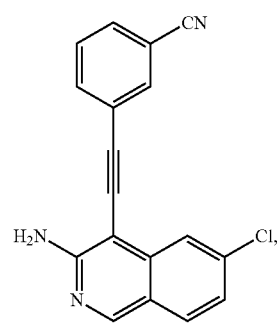

-continued
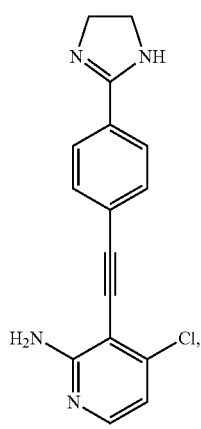
HSM1798
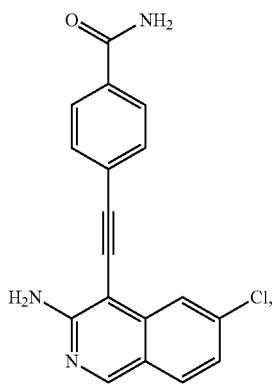
HSM1800
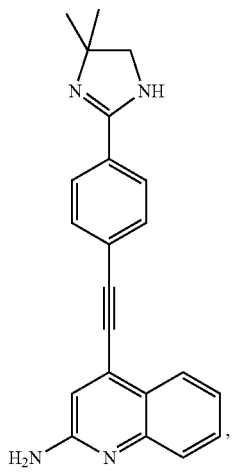
HSM1813
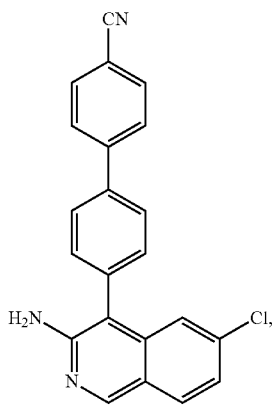
HSM1840
HSM1820
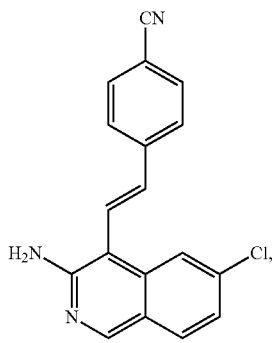
HSM1841
HSM1819
HSM1842

HSM1844
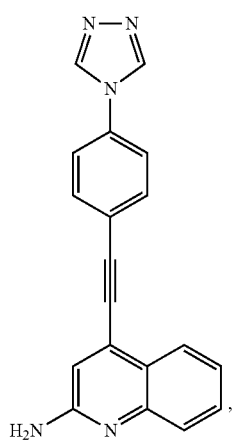
HSM1879
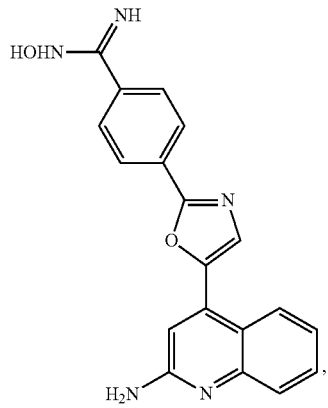
HSM1859
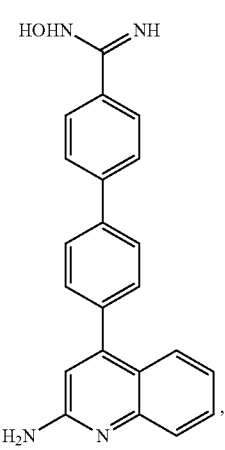
HSM1880
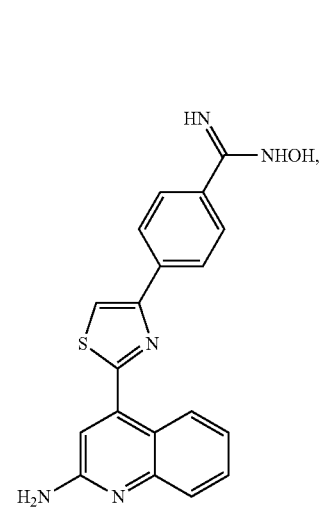
HSM1866
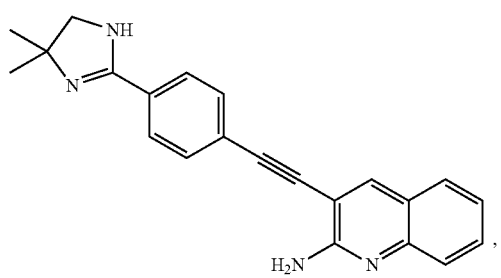
HSM1870
HSM1881
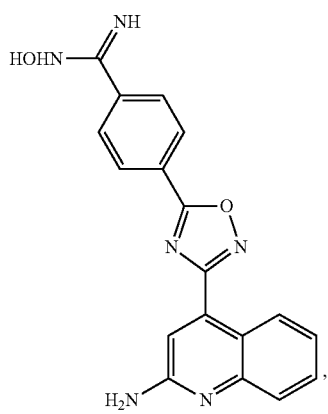

57
-continued
HSN335
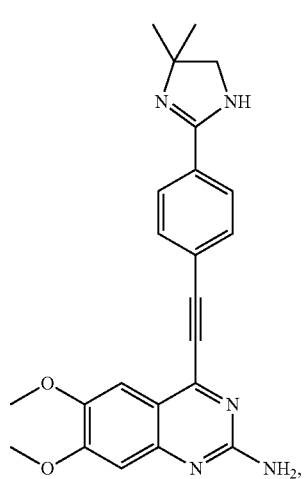
HSN360
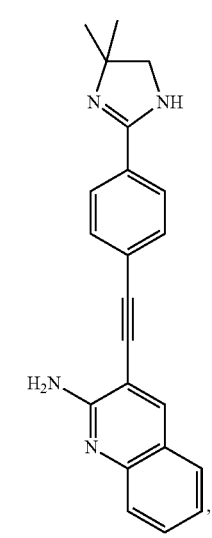
HSN99
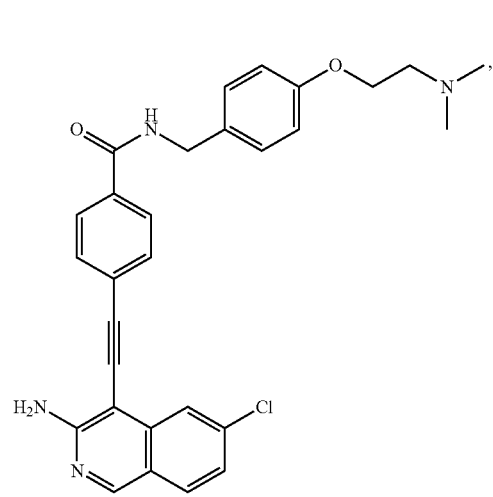
58
-continued
HSN161
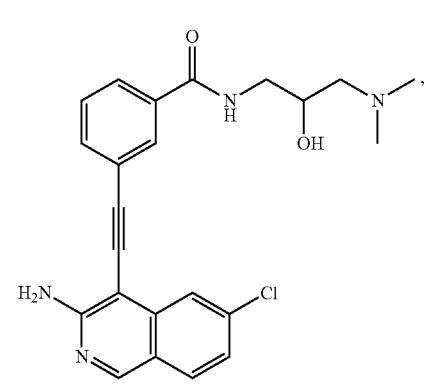
HSN165
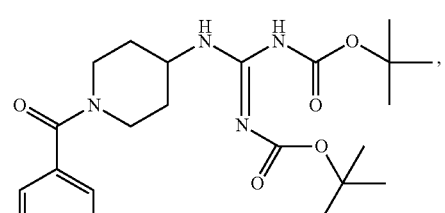
HSN225
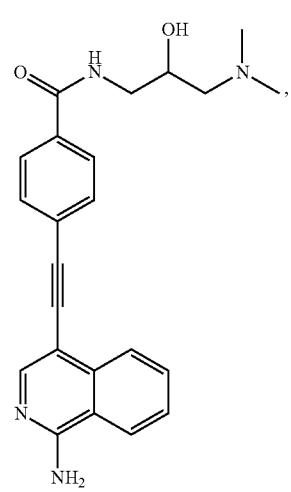

HSM1795
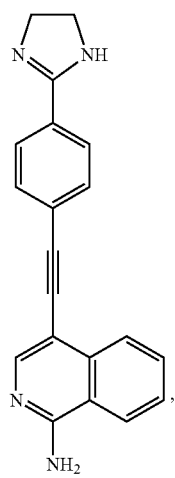
HSN370
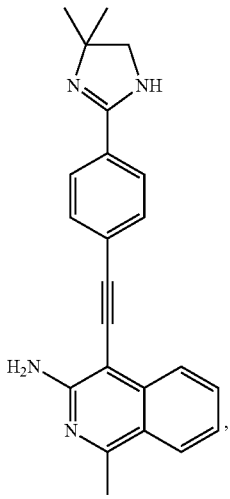
HSM1803
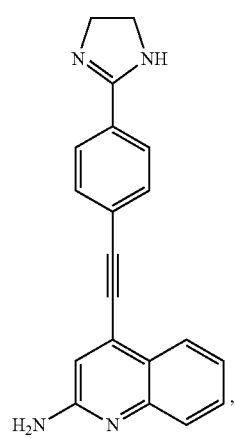
HSN368
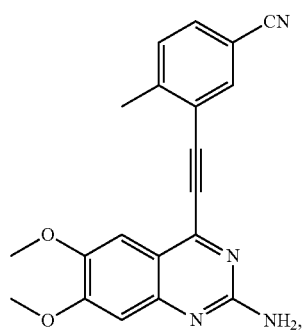
HSN364
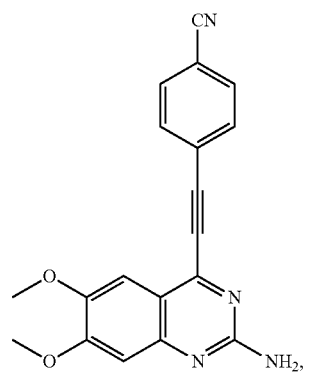
HSD-33
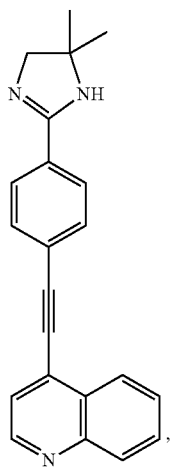

HSD-39
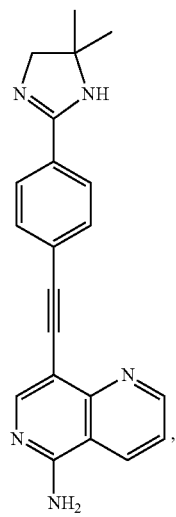
HSD-42
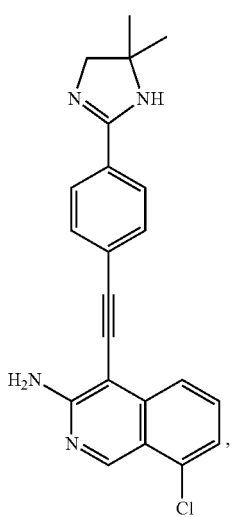
HSD-43
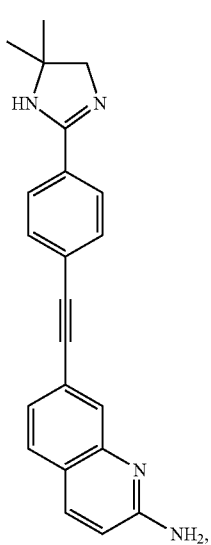
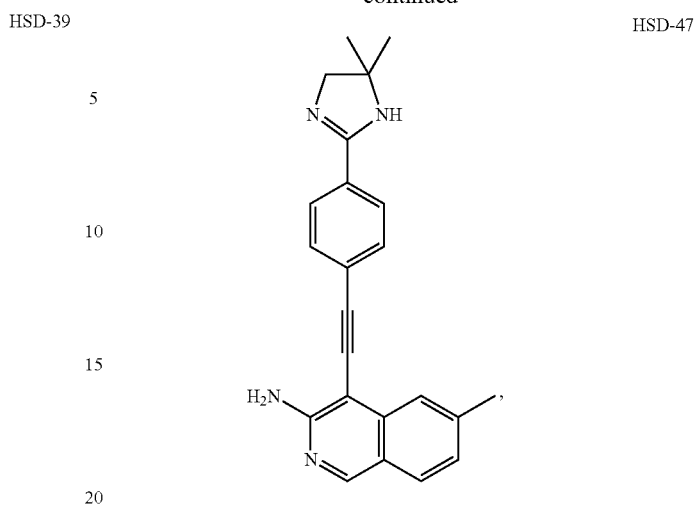

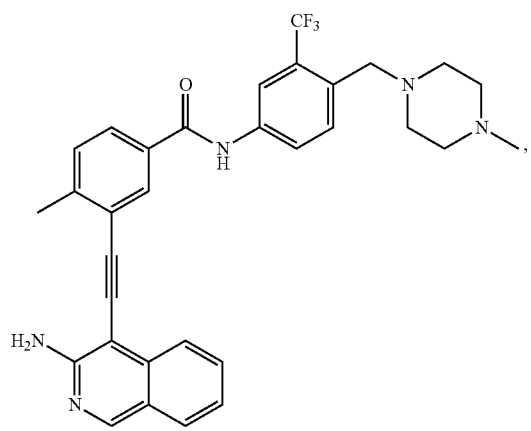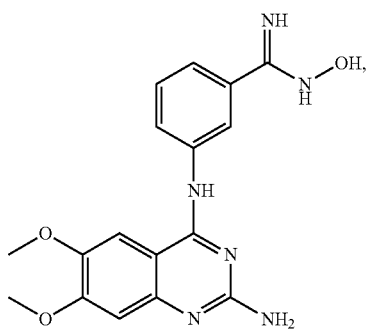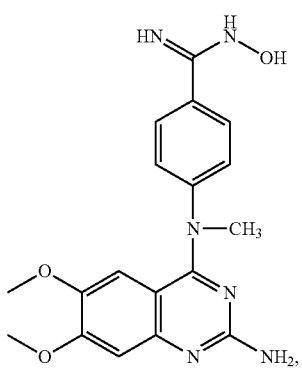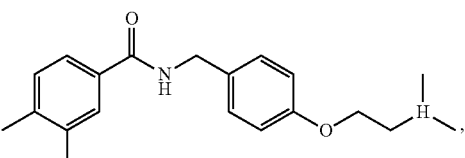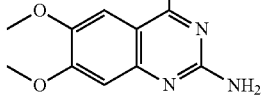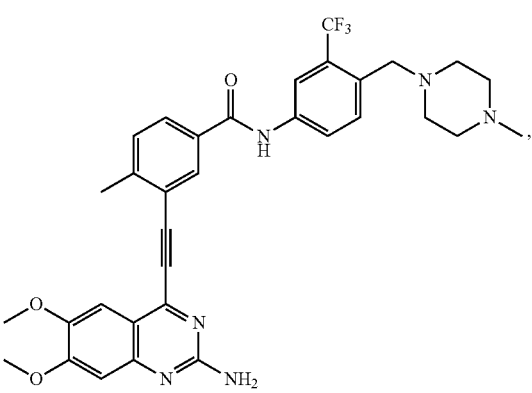

-continued
HSN329
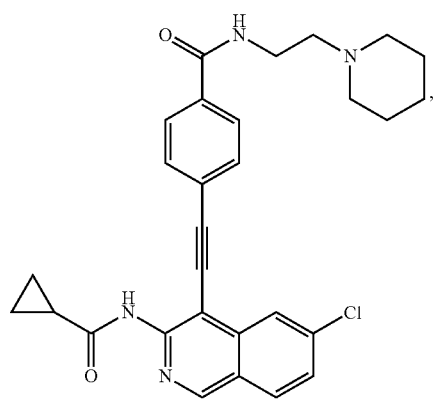
HSN357
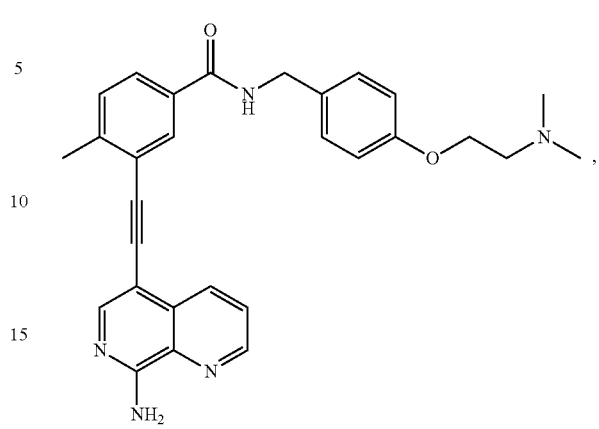
HSN333
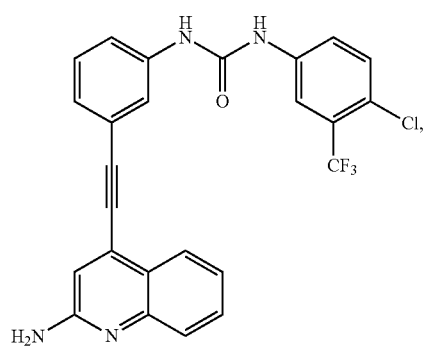
HSN334
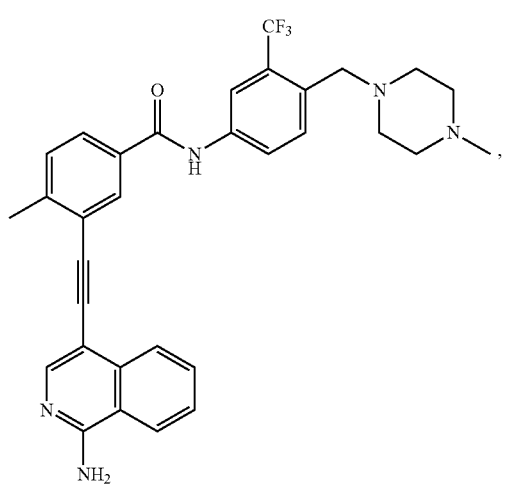
HSN356
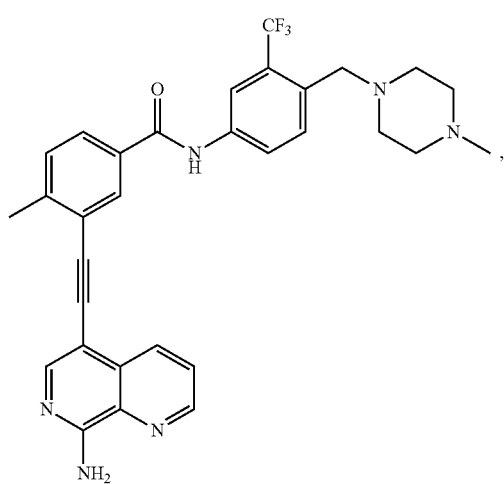
HSN286
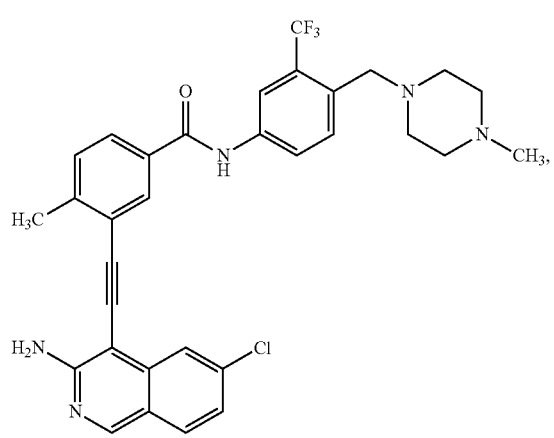

HSN285
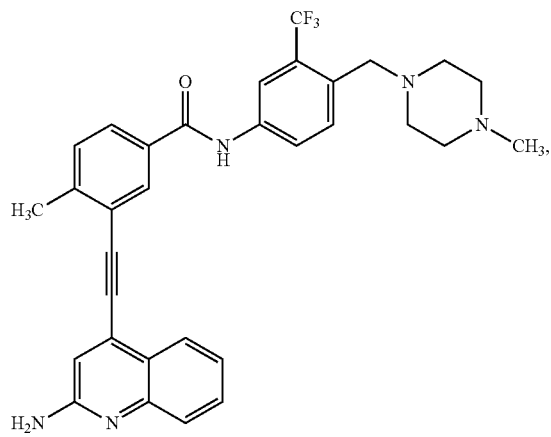
HSN353
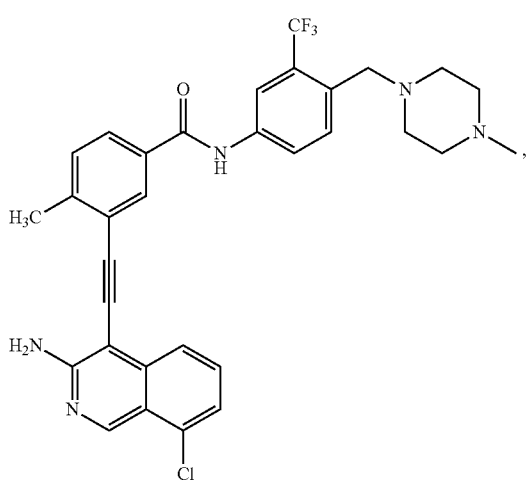
HSN247
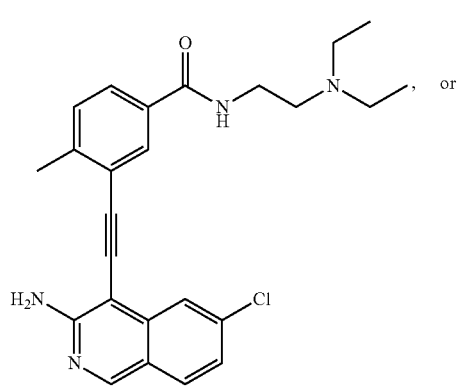
HSN248
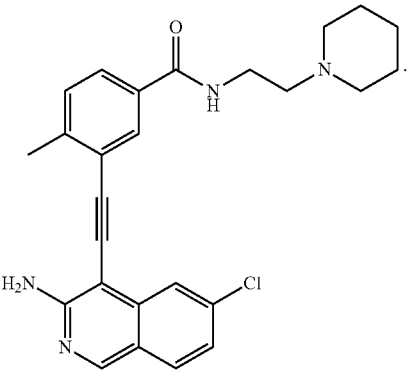
In some embodiments, the compound of the invention is
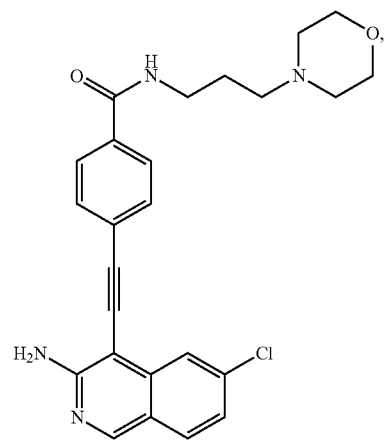
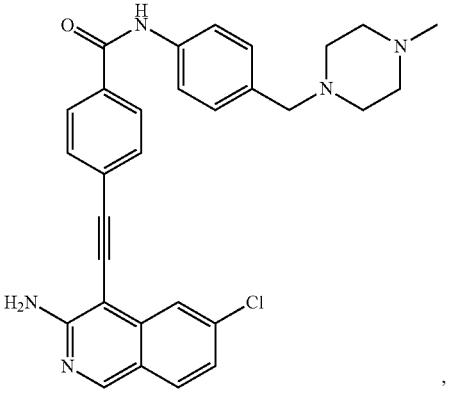

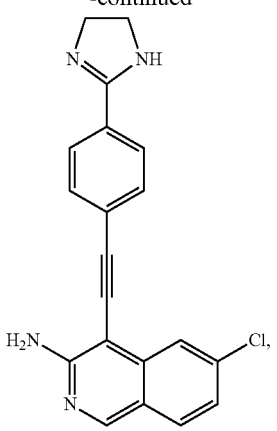
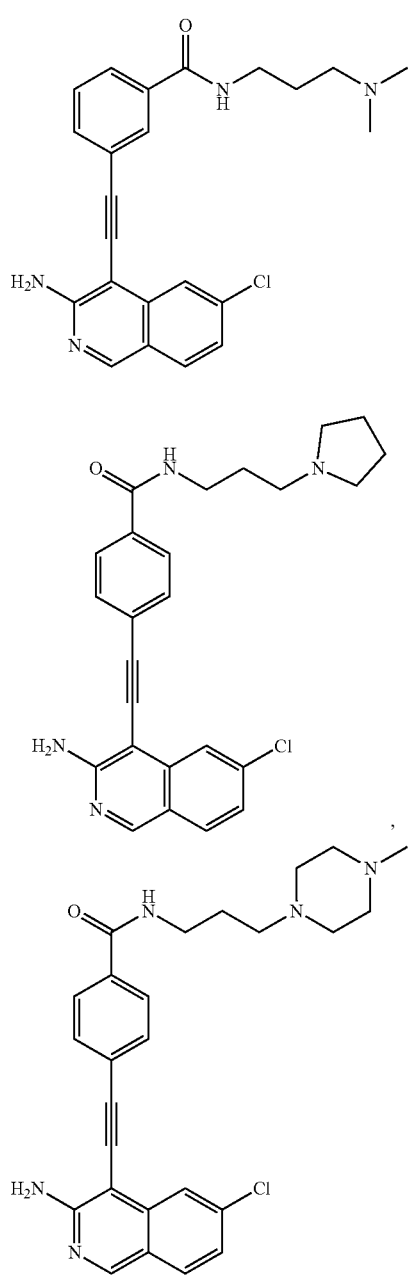
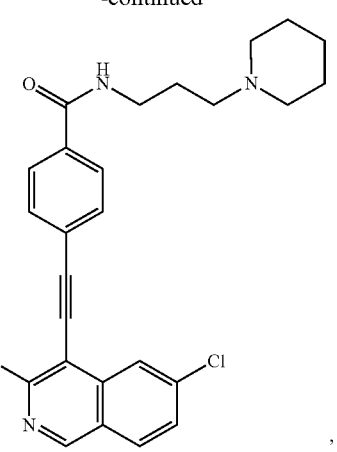

71
-continued
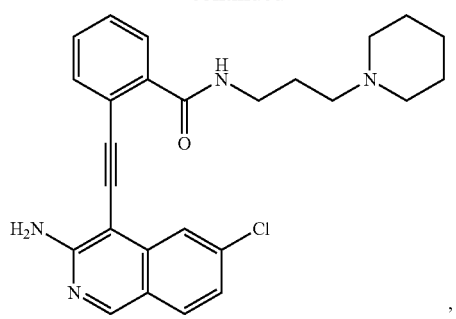
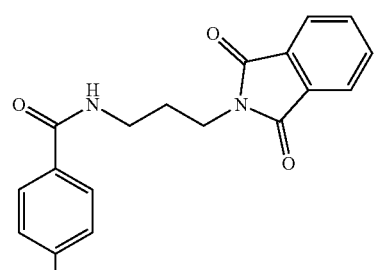
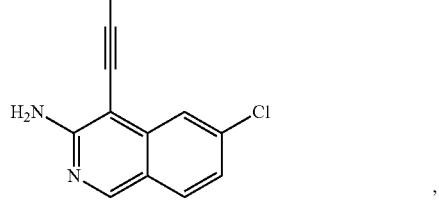
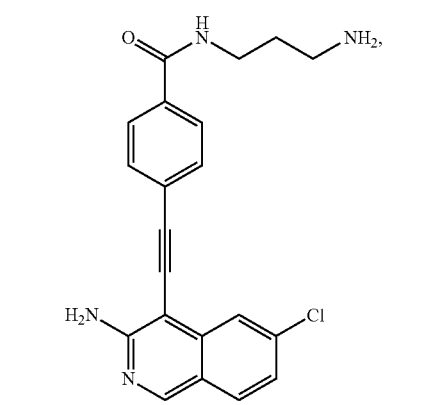
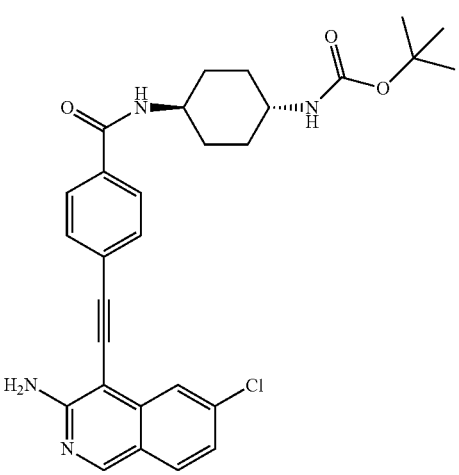
72
-continued
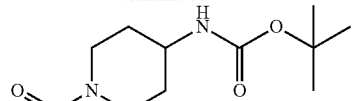
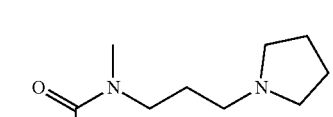

73
-continued
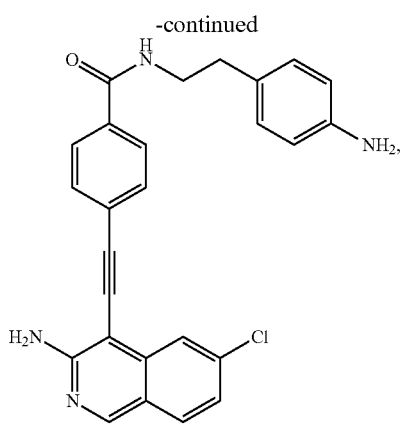
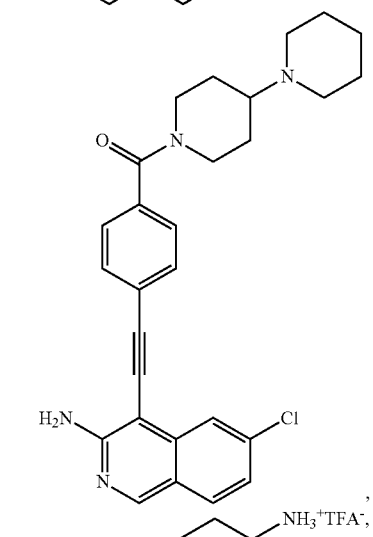
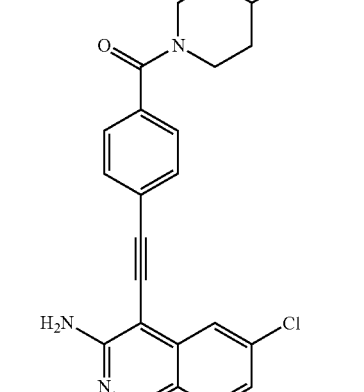
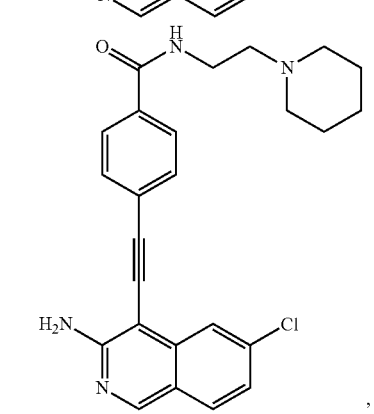
74
-continued
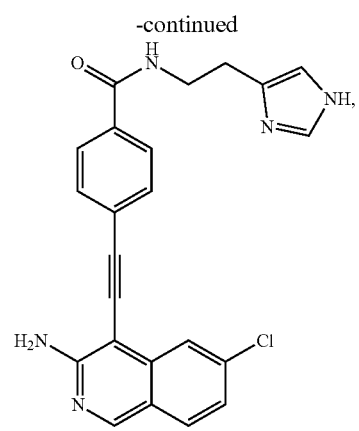
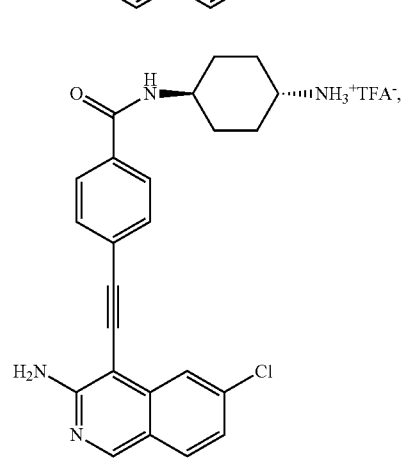
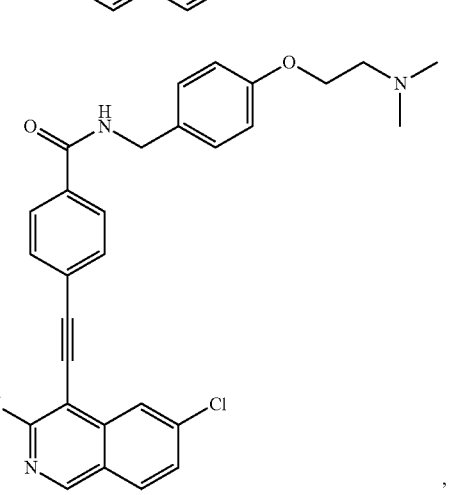
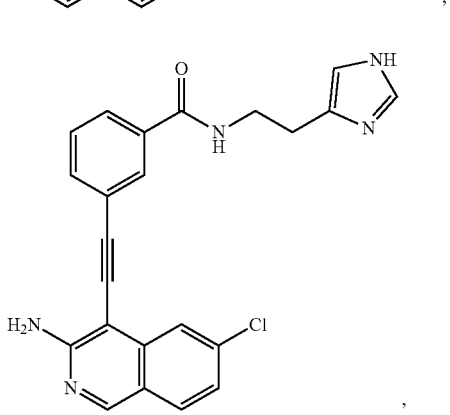

75
-continued
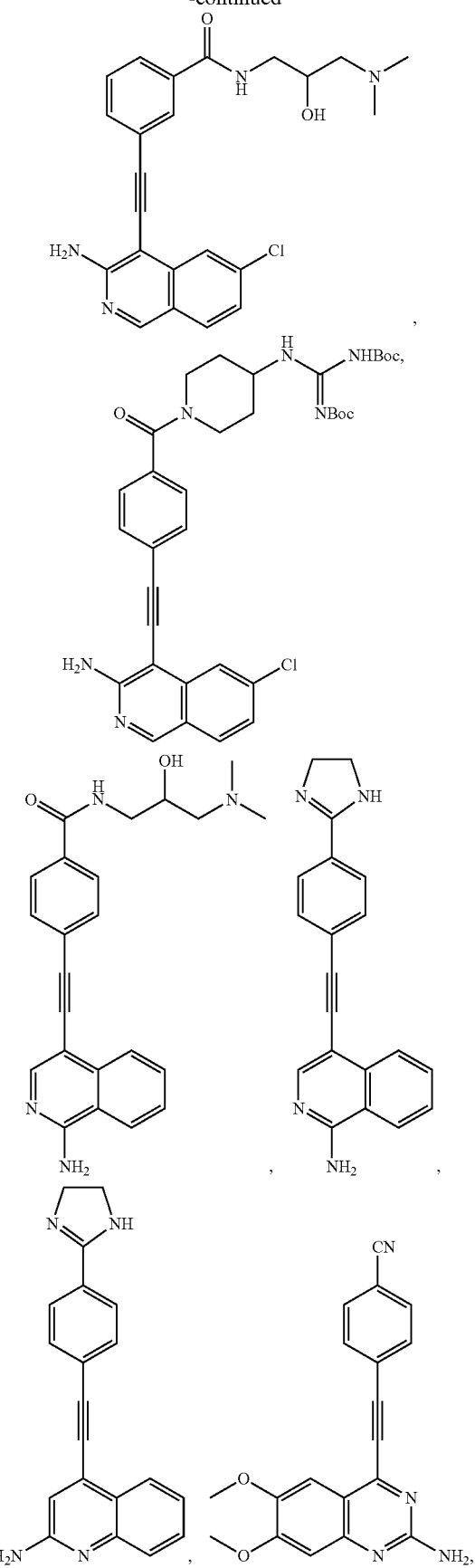
76
-continued
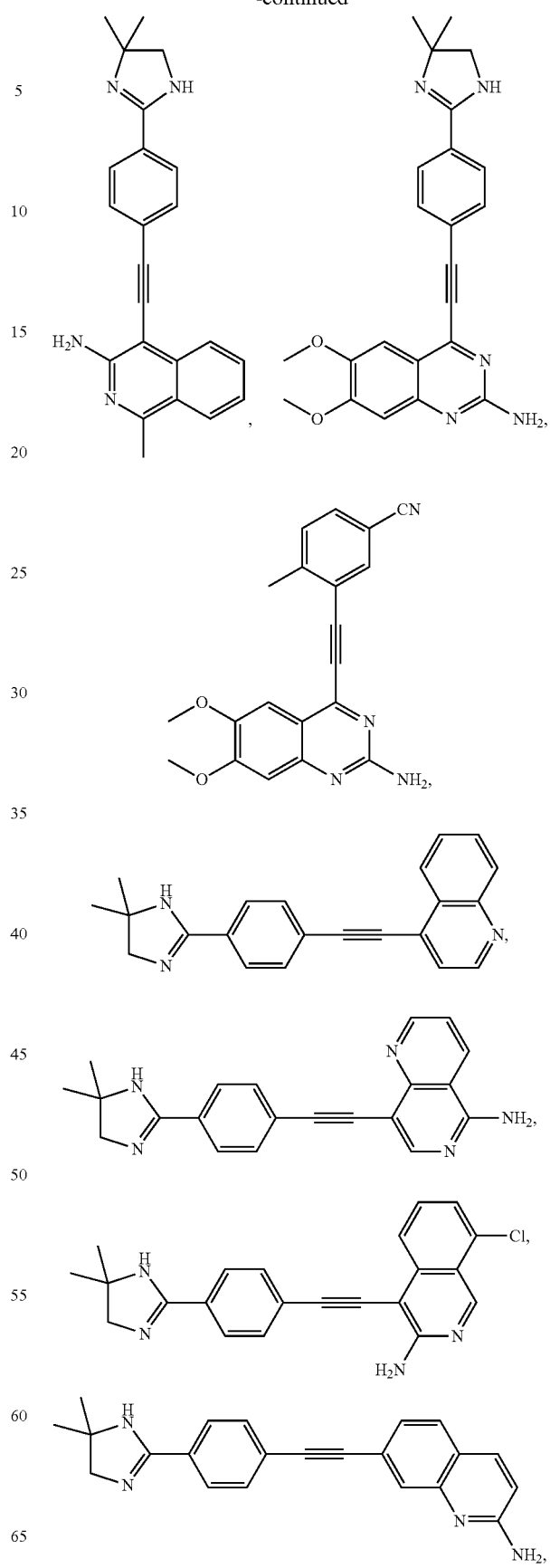

77
-continued
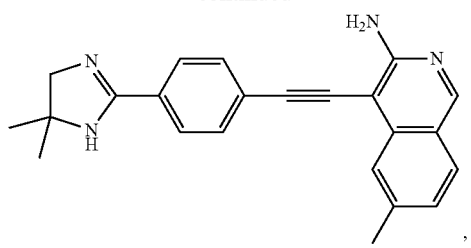
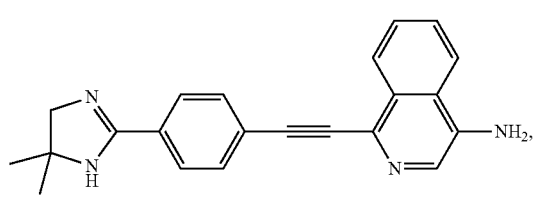
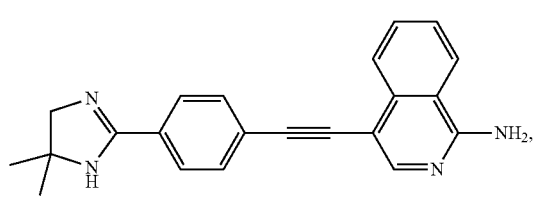
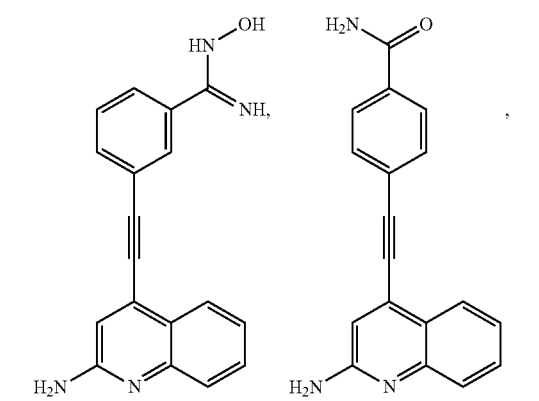
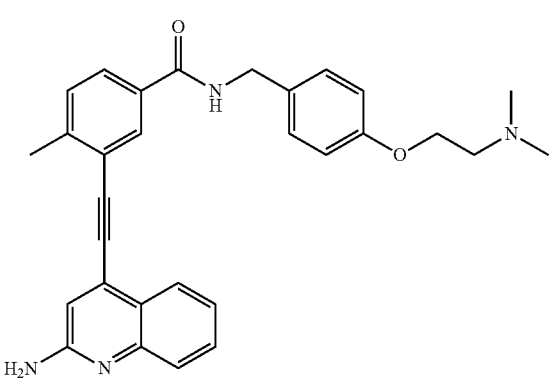
78
-continued
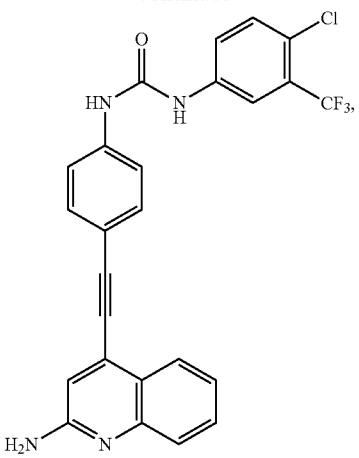
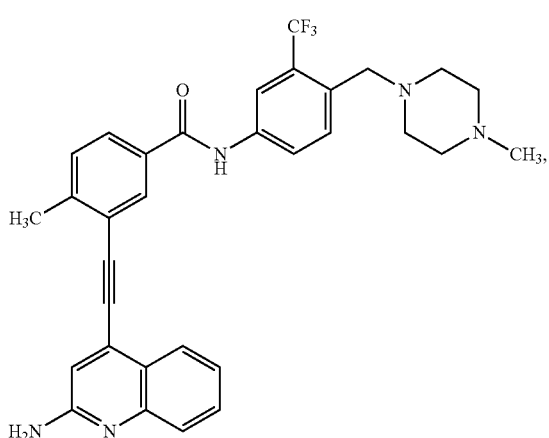
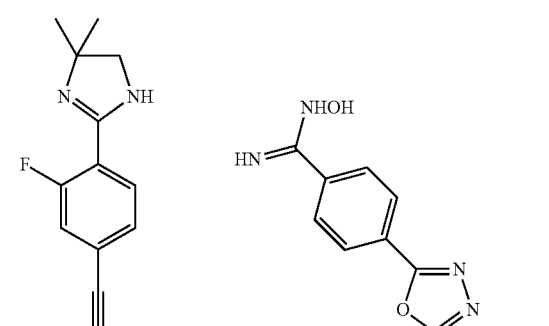
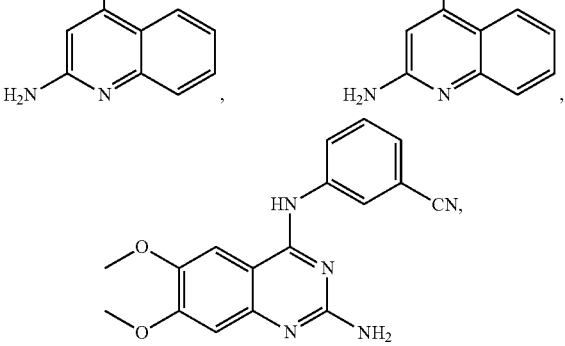

79
-continued
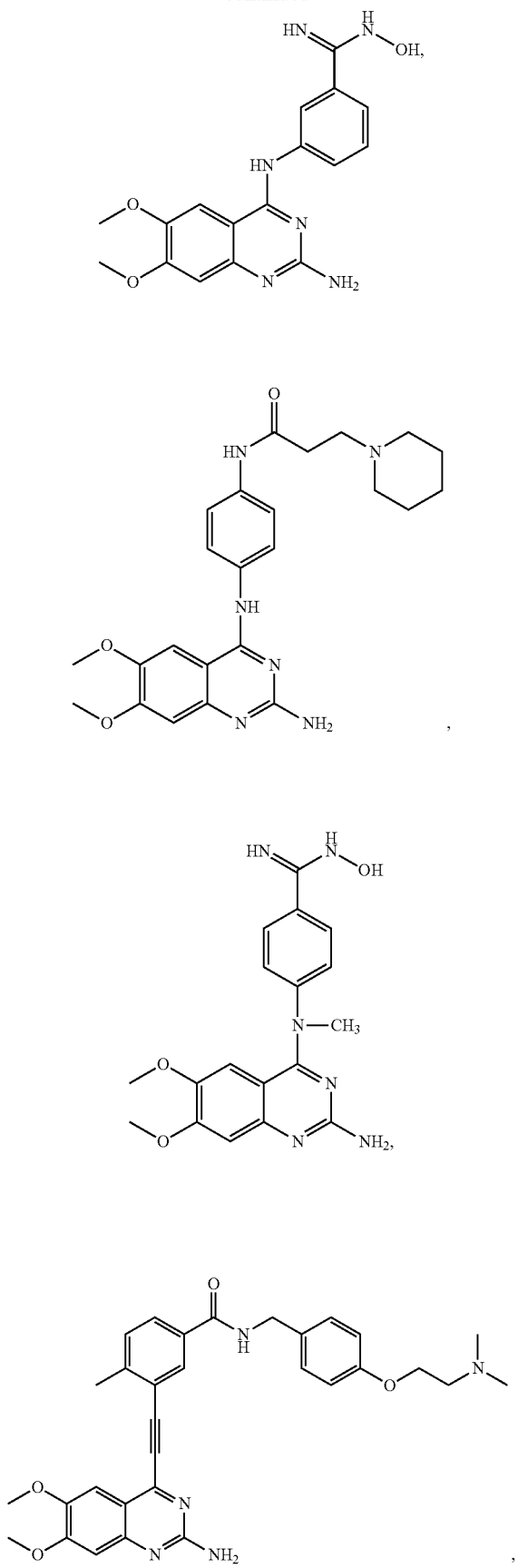
80
-continued
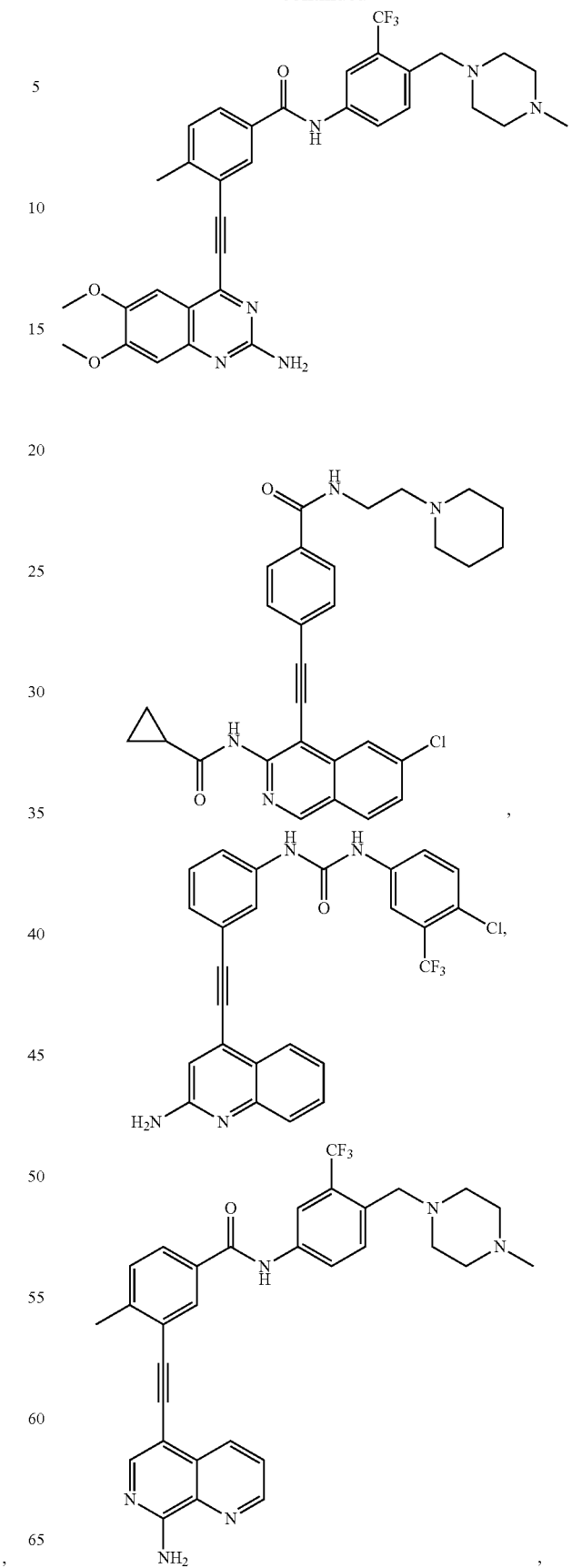

81
-continued
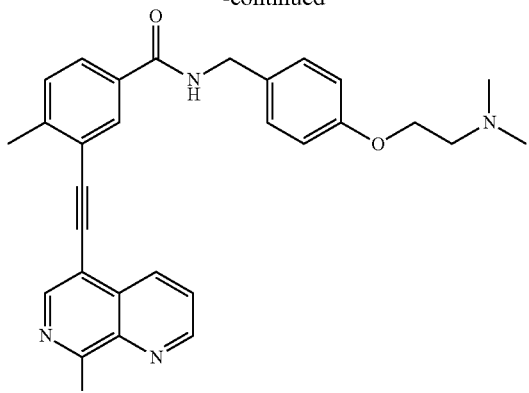
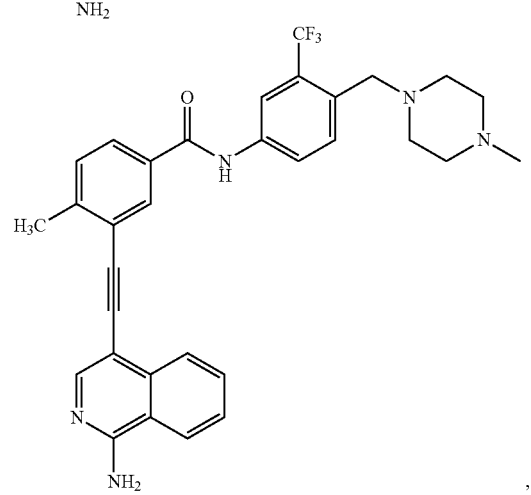
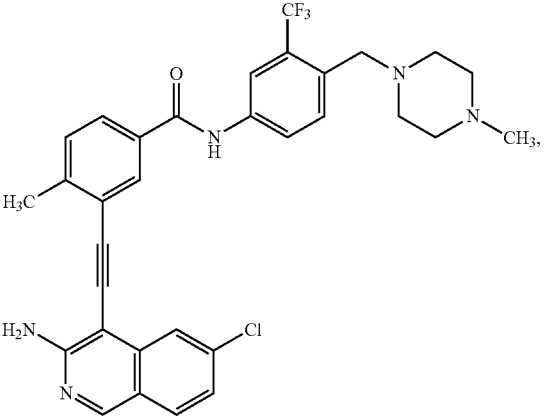
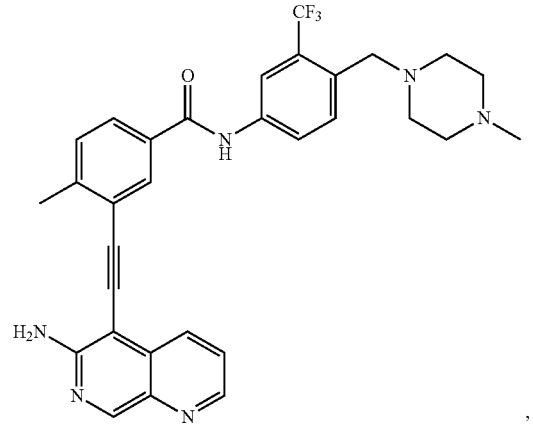
,
82
-continued
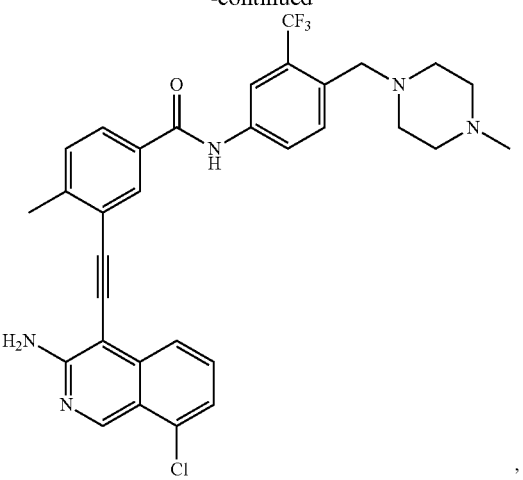
,
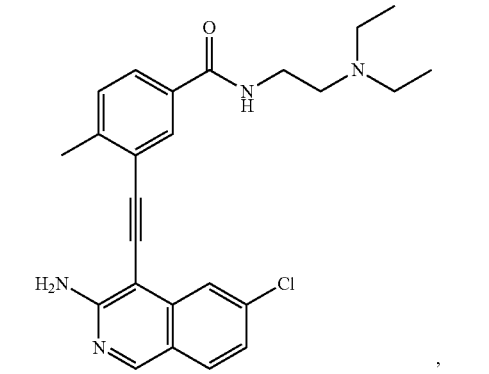
,
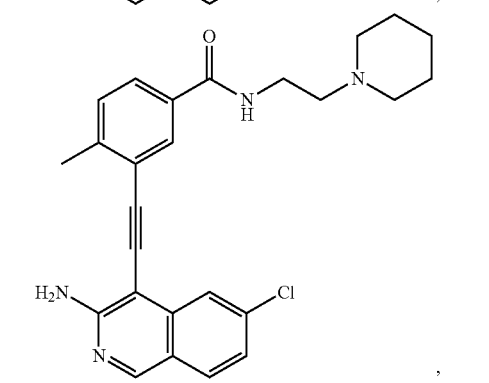
,
In some embodiments, the compound of the invention is
mxc 1611
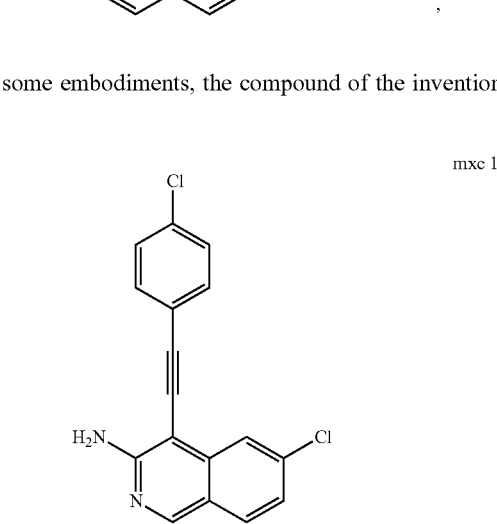

mxc 1688
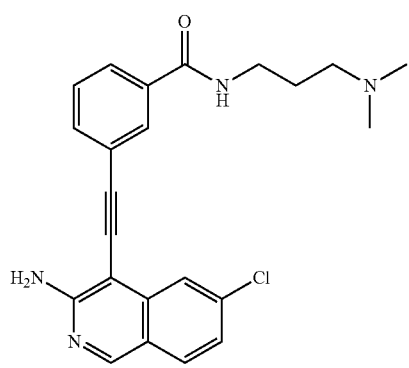
mxc 1651
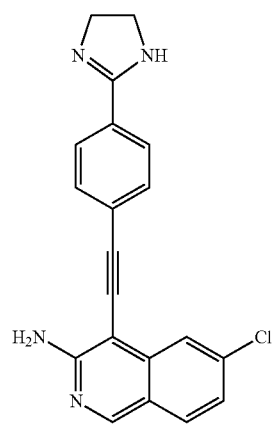
mxc 1610
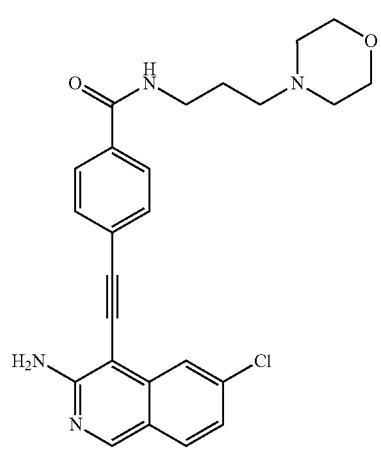
mxc 1669
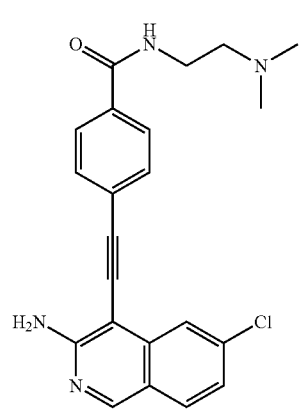
mxc 1674
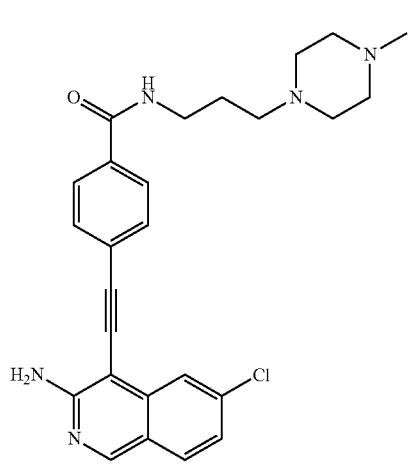
mxc 1673
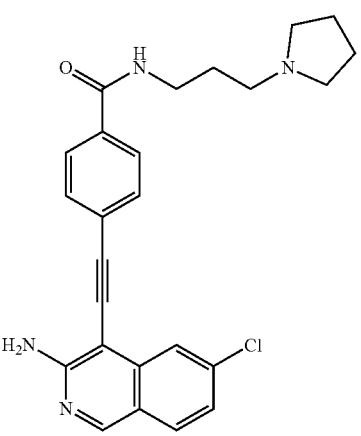

-continued
mxc 1683
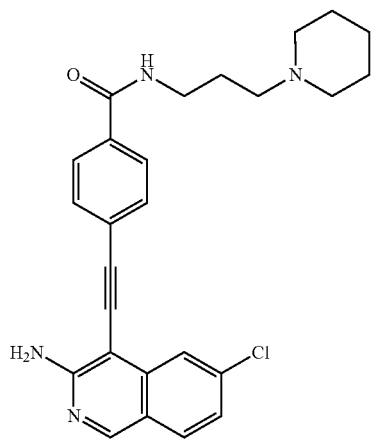
NN-I-66
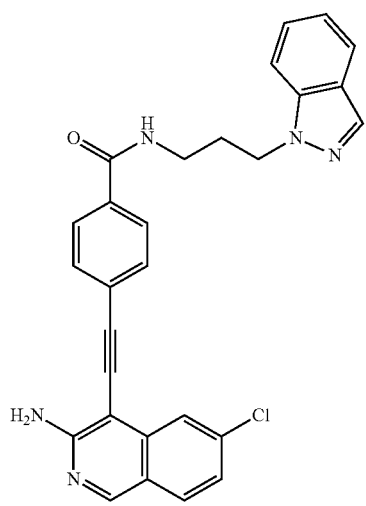
NN-I-64
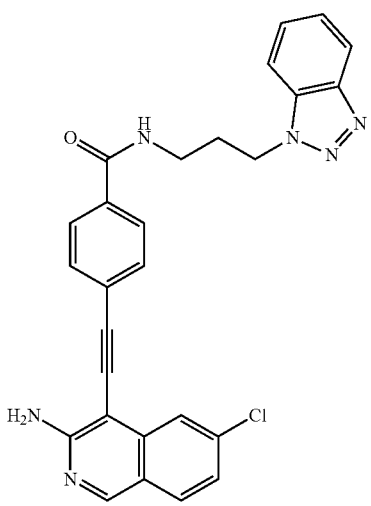
-continued
NN-I-67
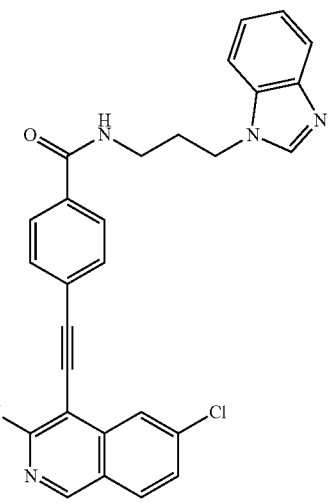
mxc 1661
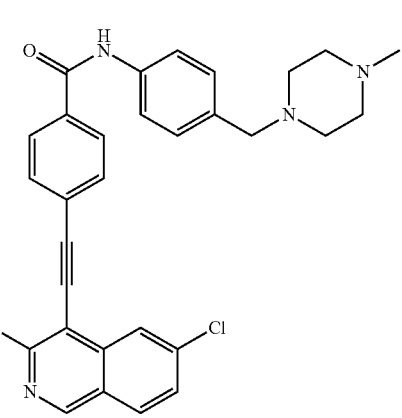
mxc 1683c
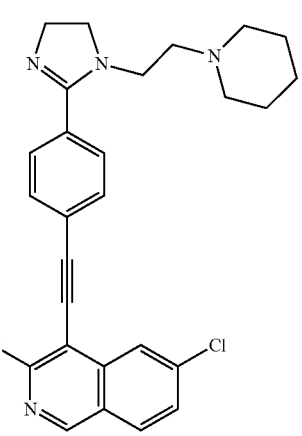

mxc 1684
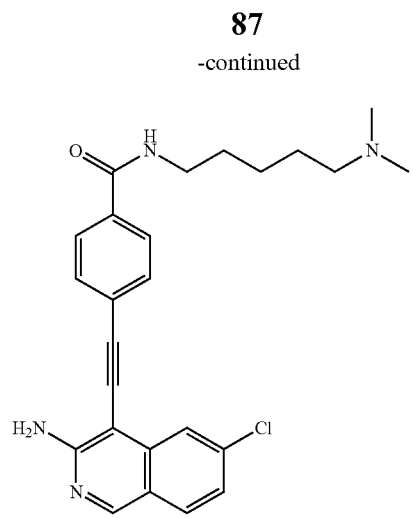
mxc 1703
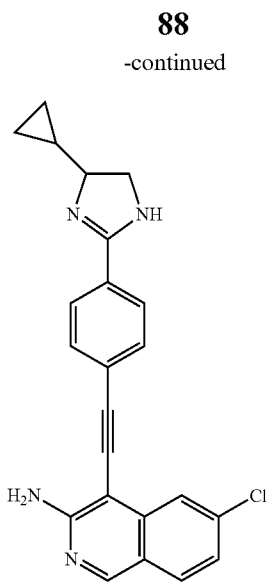
DBGI-29
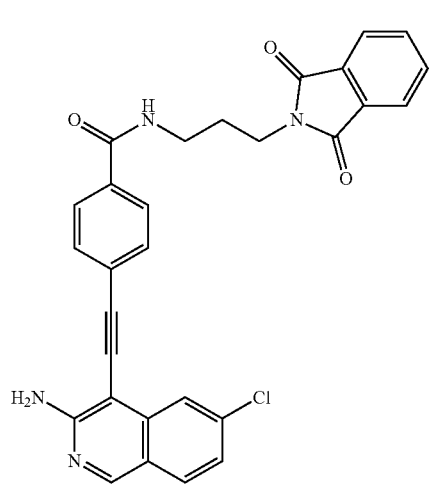
DBGI
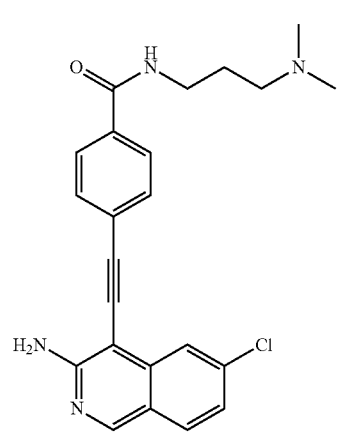
mxc 1683b
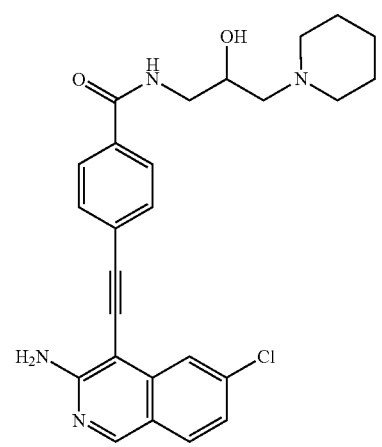
DBGI-48
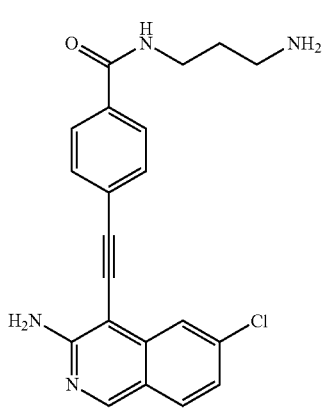 [SMILES: NCCCNC(=O)c1ccc(C#Cc2c(N)ncc3ccc(Cl)cc23)cc1]

89
-continued
mxc 1692
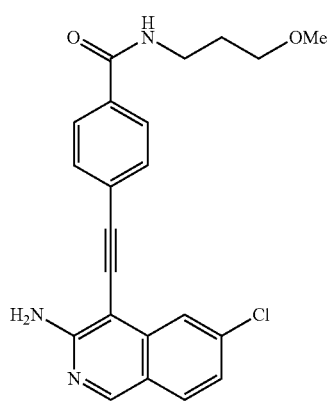
90
-continued
mxc 1702
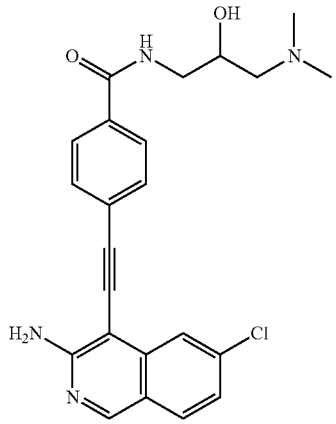
mxc 1690
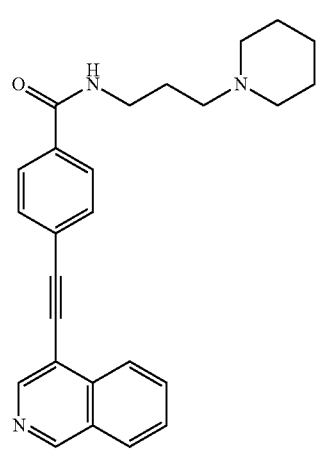
NN-I-106
mxc 1693
NN-I-99
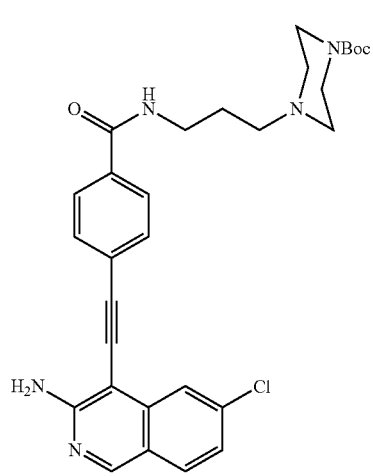

NN-I-105
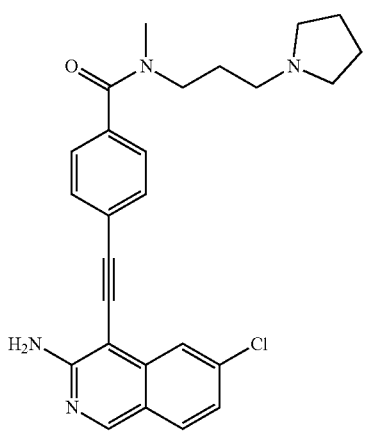
mxc 1707
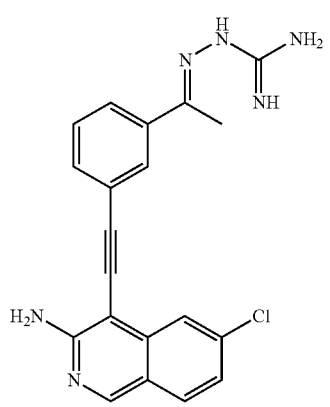
In some embodiments, the compound of the invention is
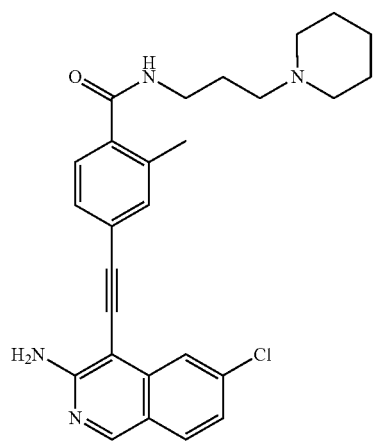
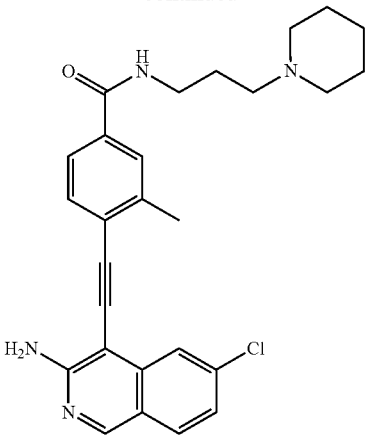
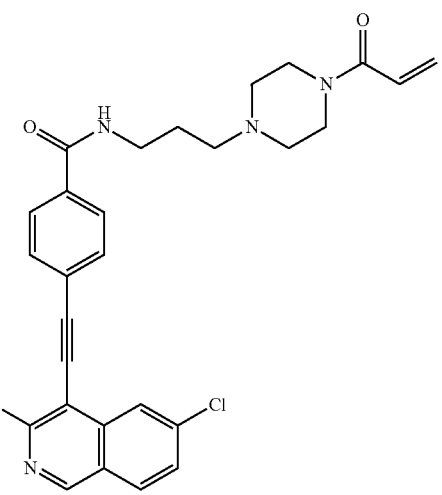
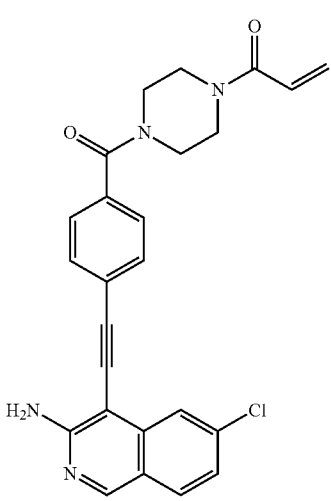

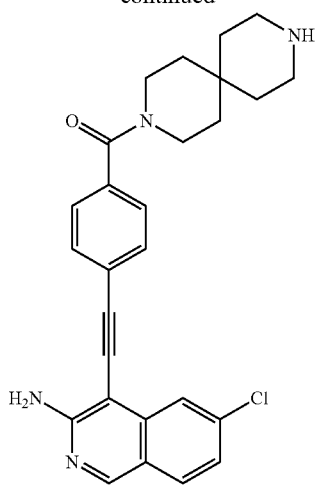
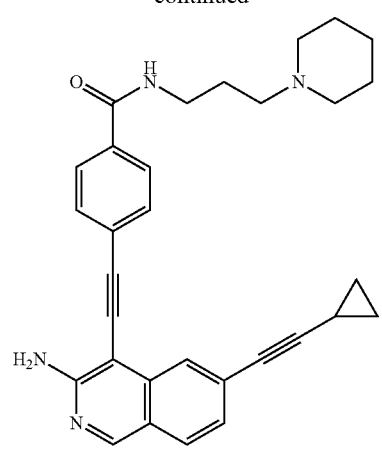
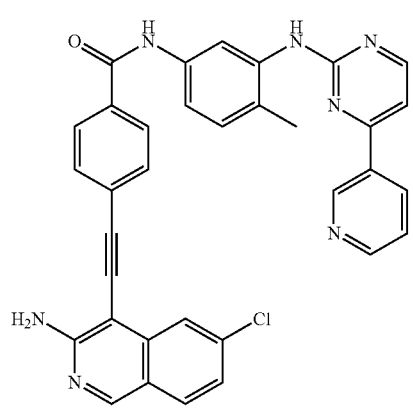
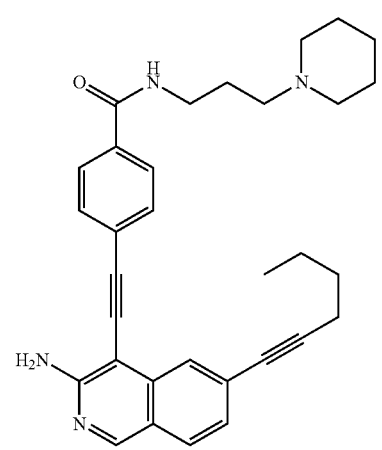
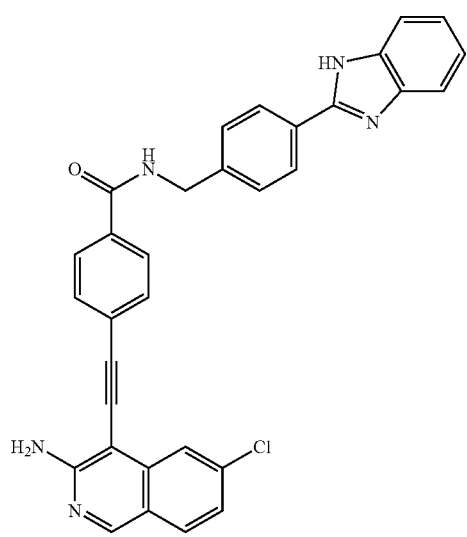

95
-continued
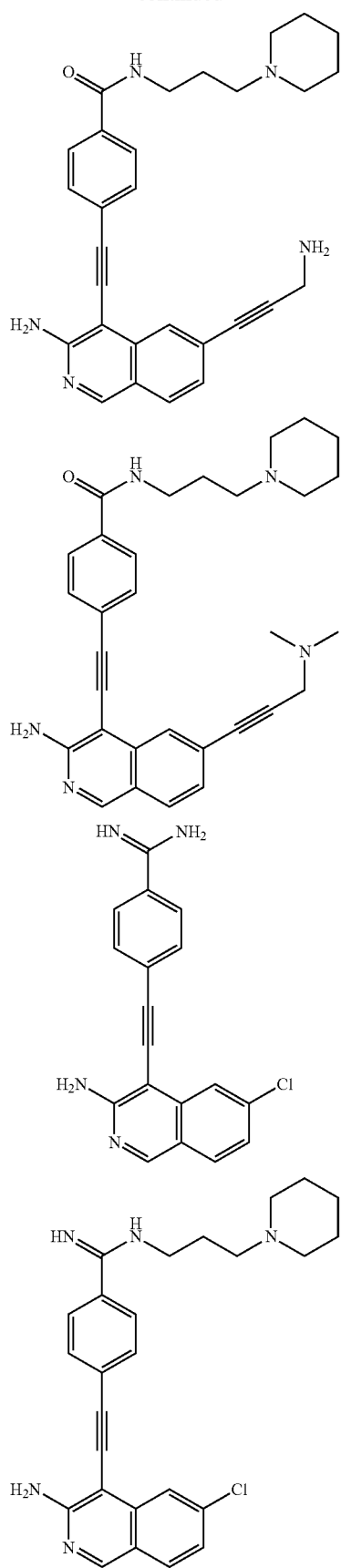
96
-continued
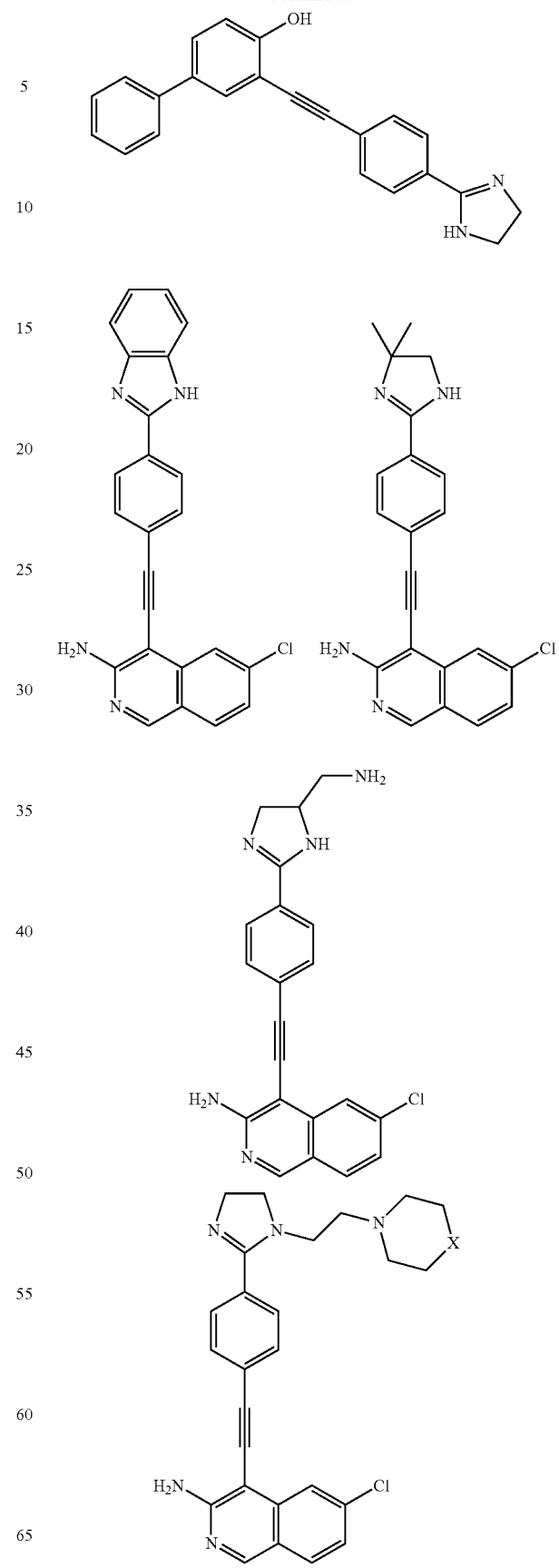

97
-continued
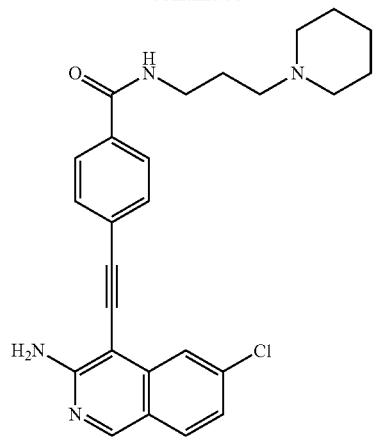
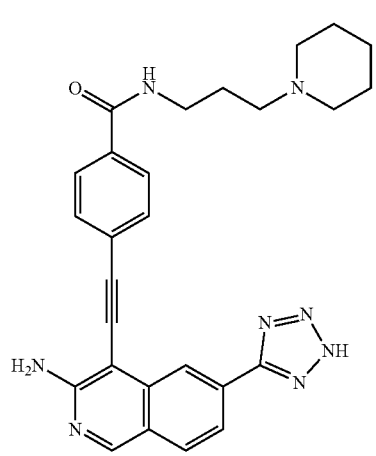
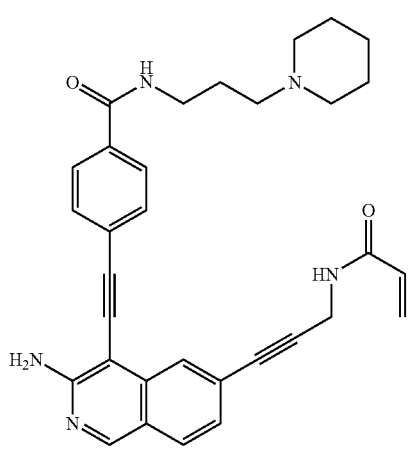
98
-continued
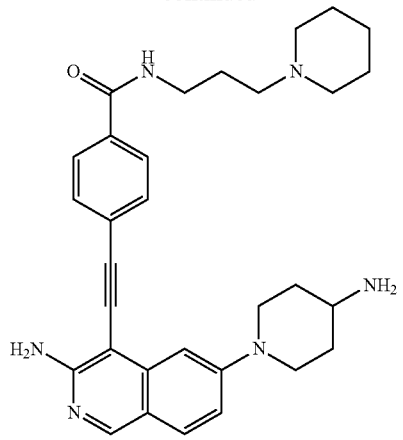
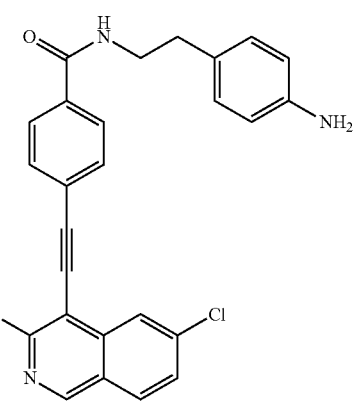
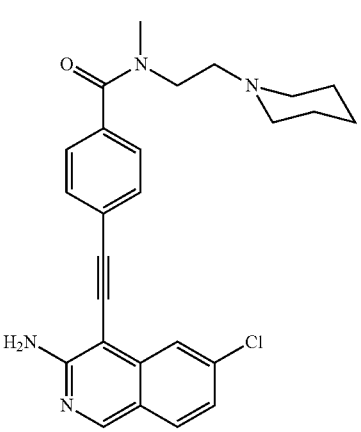

99
-continued
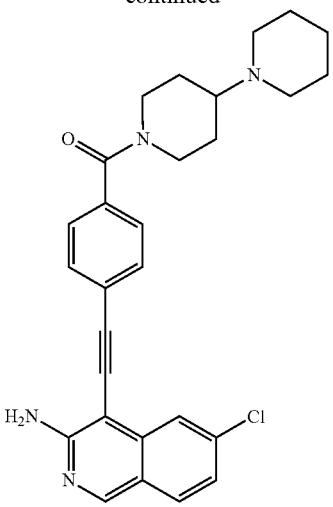
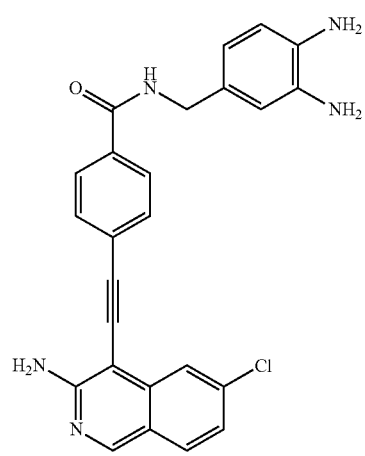
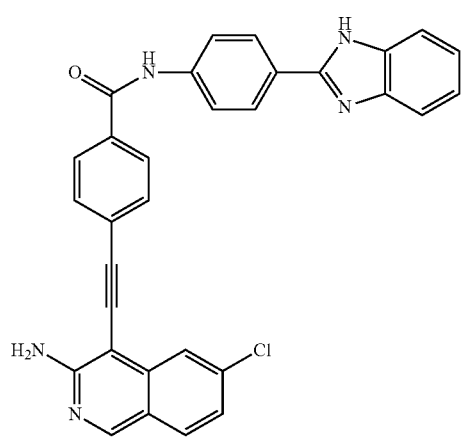
100
-continued
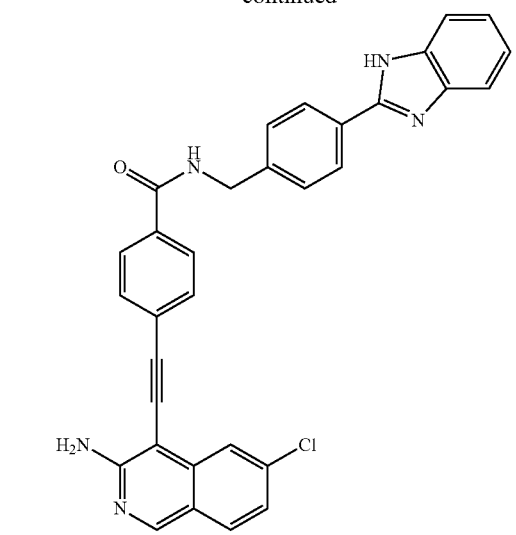
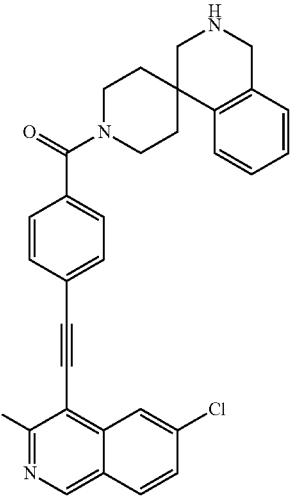
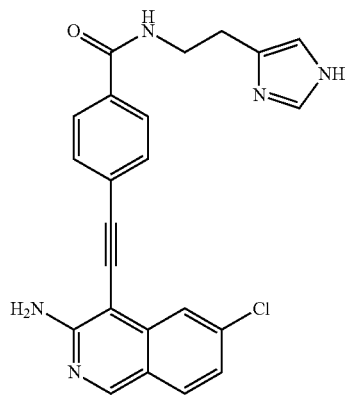

101
-continued
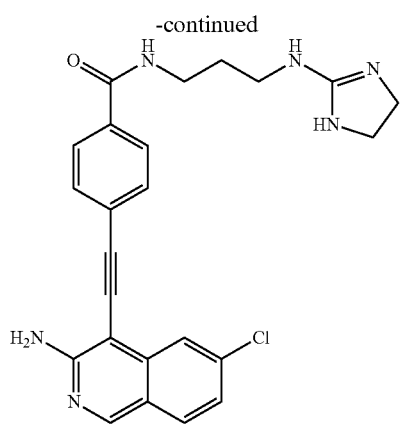
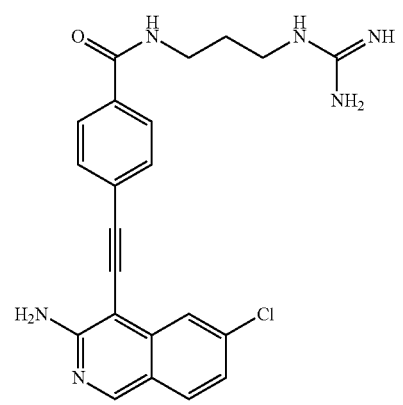
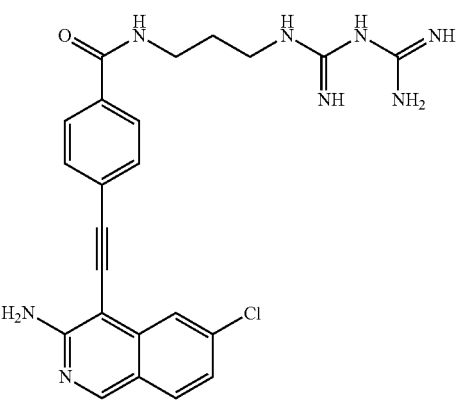
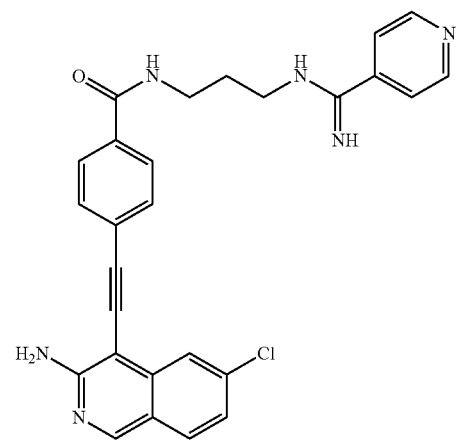
102
-continued
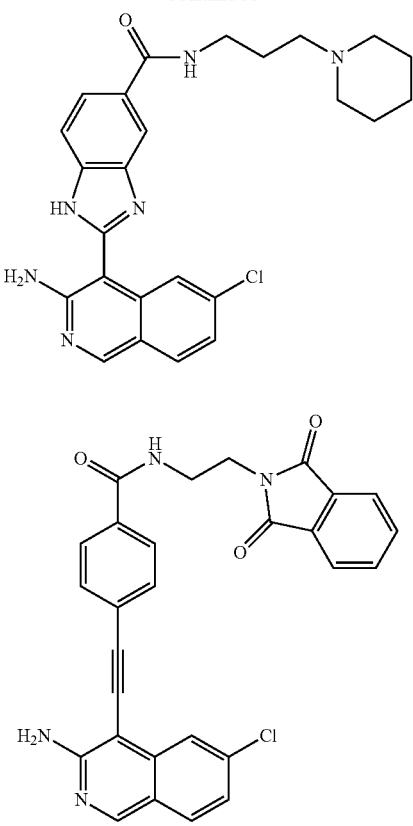
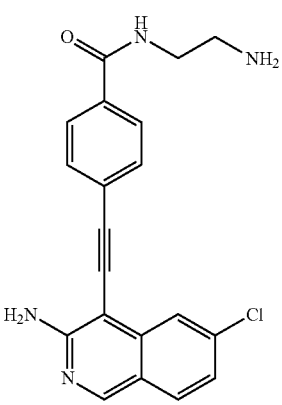
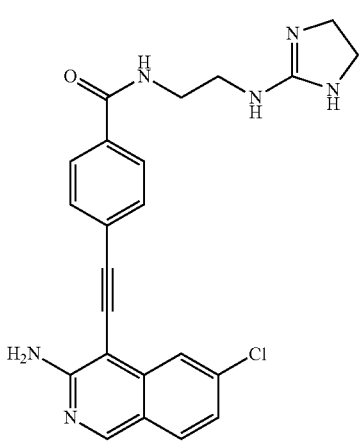

103
-continued
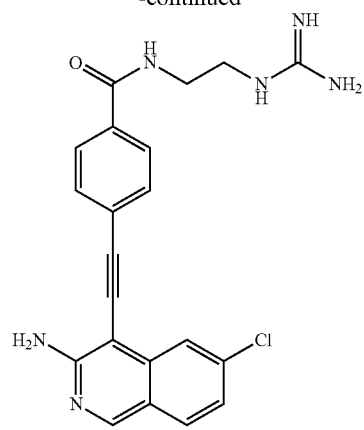
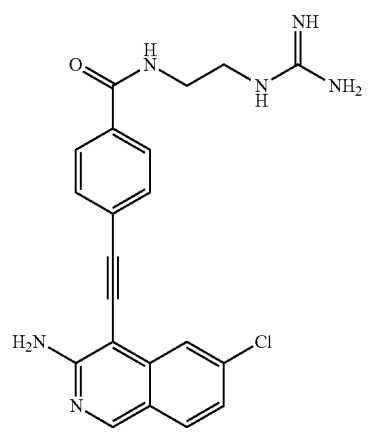
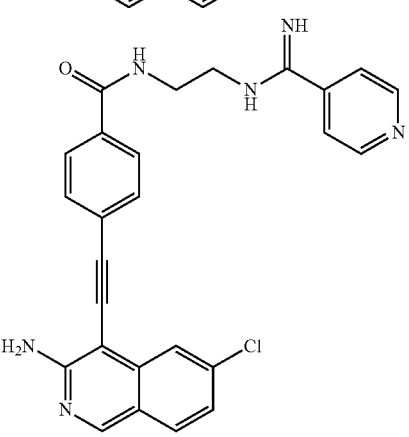
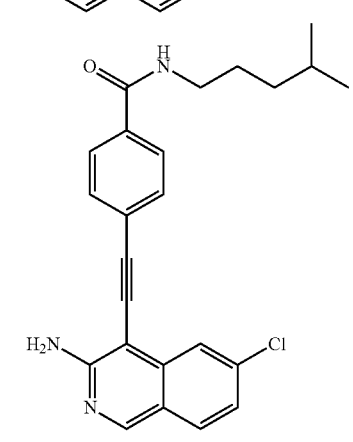
104
-continued
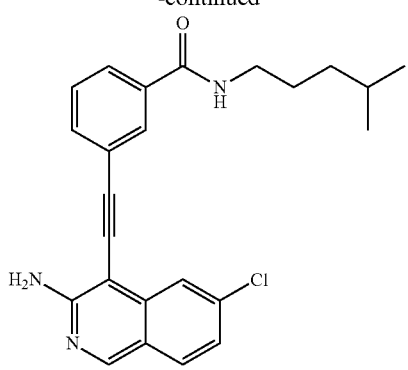
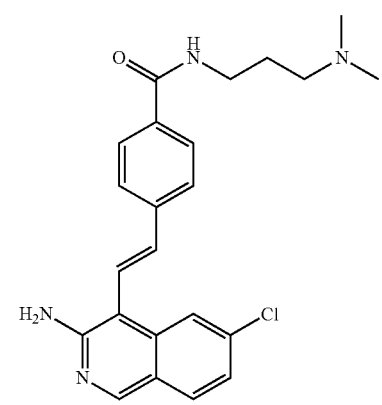
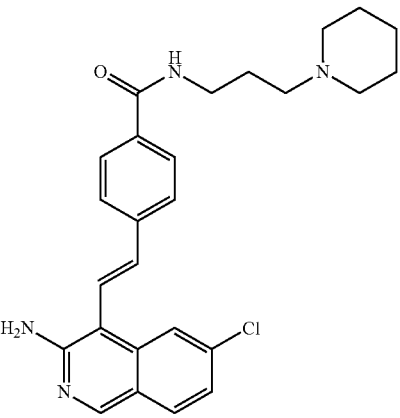
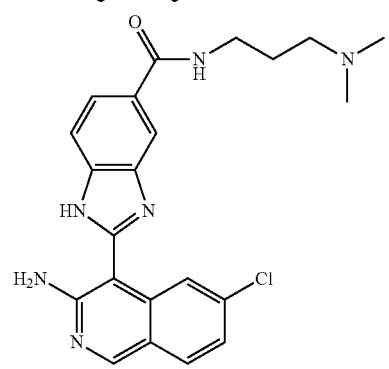

In some embodiments, the compound of the invention is
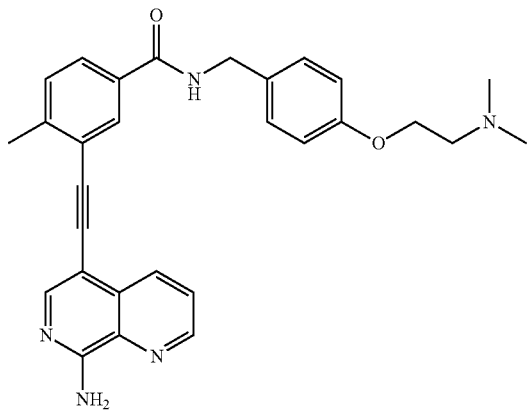
HSN357
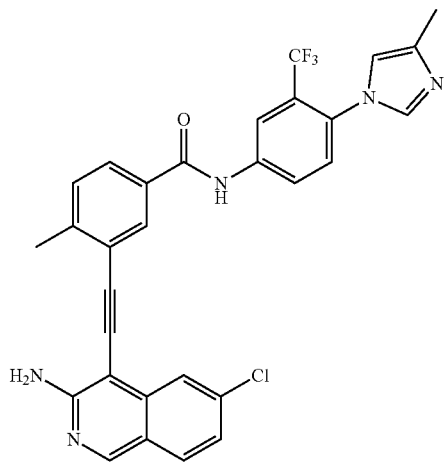
HSN380
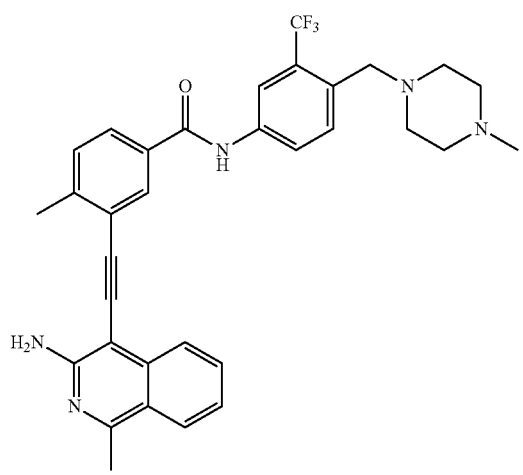
HSN375
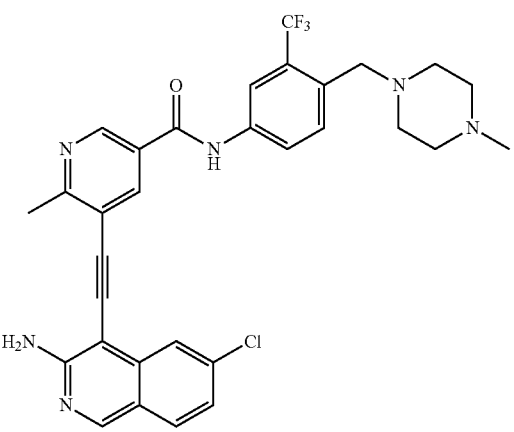
HSN387
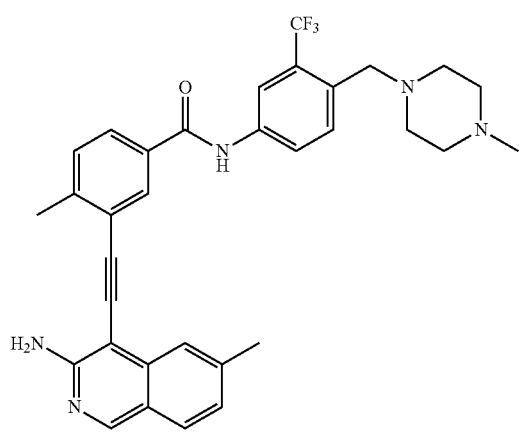
HSN379
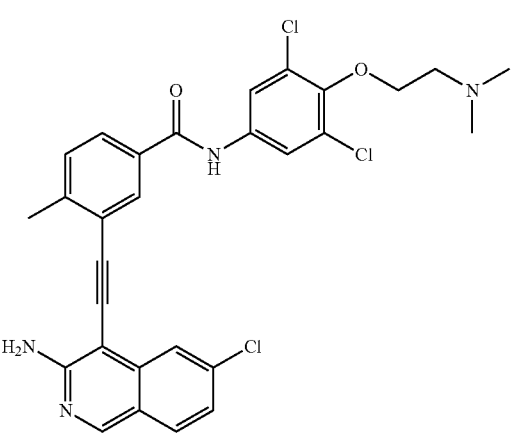
HSN391

HSN392
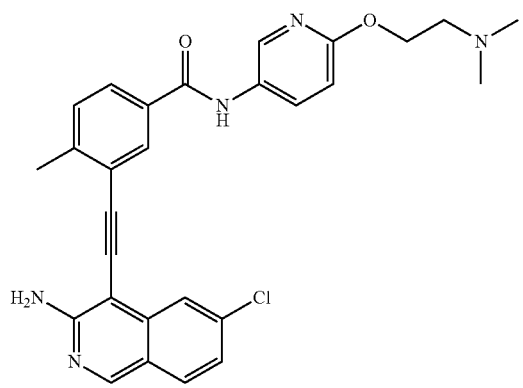
HSN400
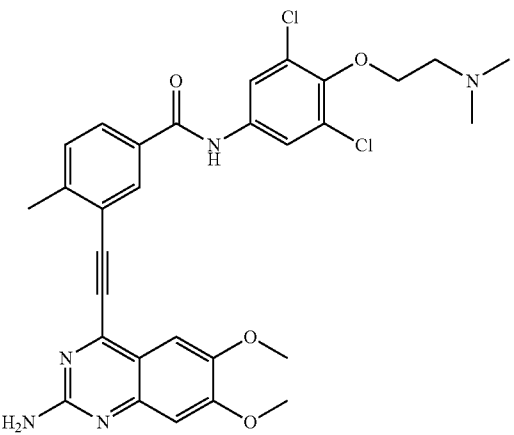
HSN393
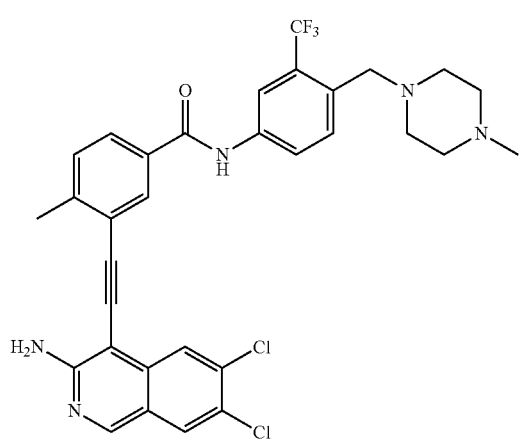
HSN401
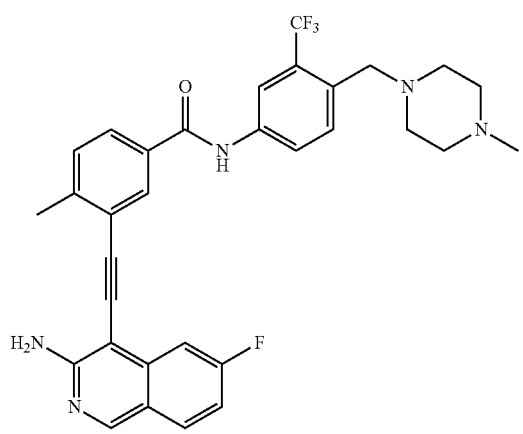
HSN394
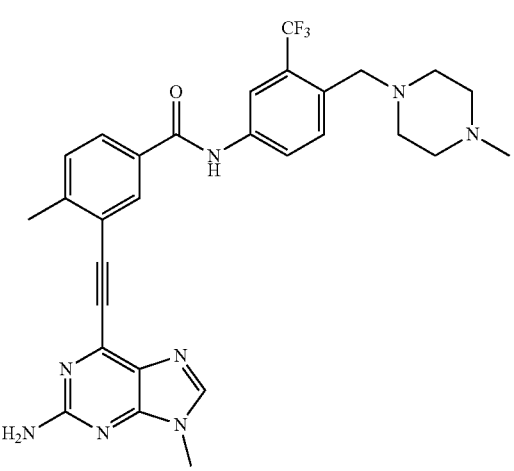
HSN403

HSN404
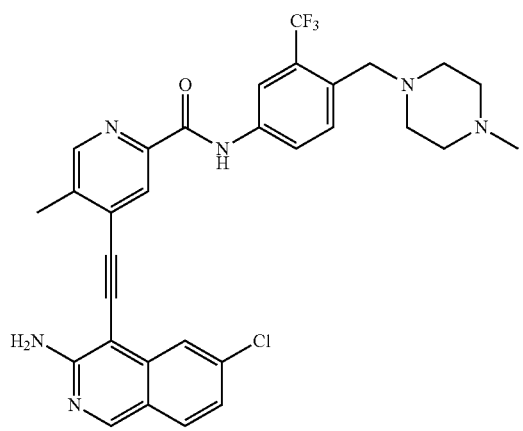
HSN405
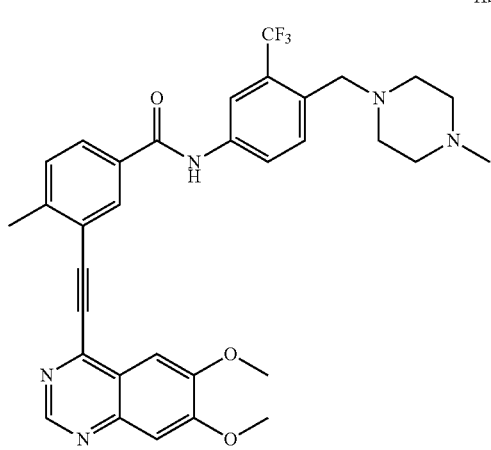
HSN408
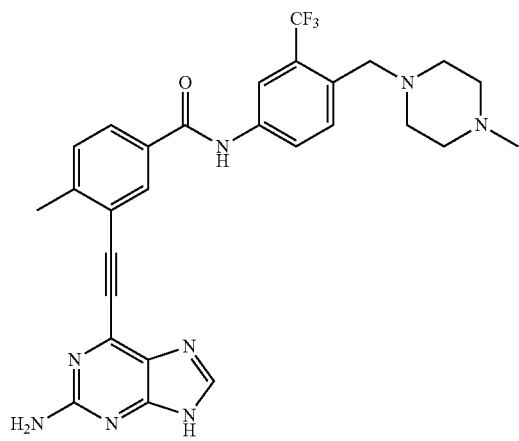
HSN409
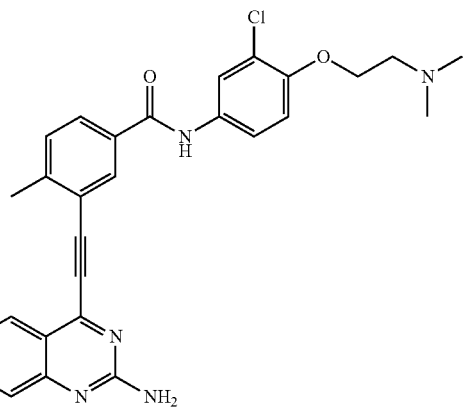
HSN415
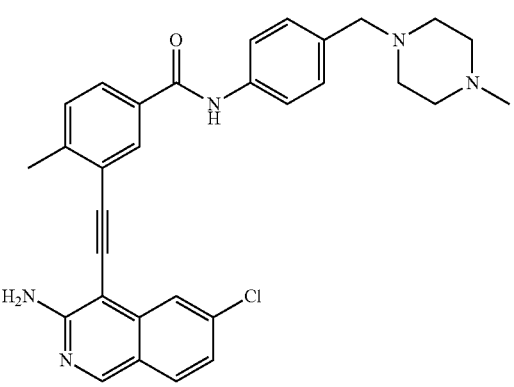
HSN416
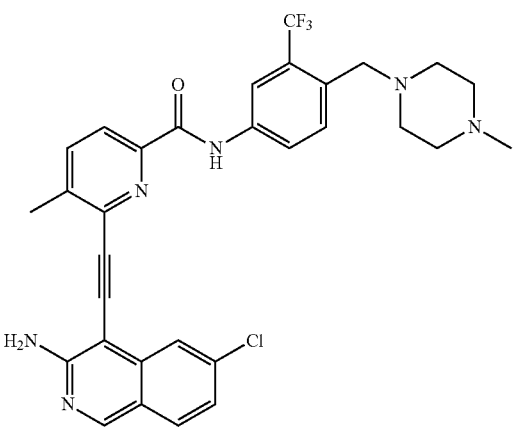

-continued
HSN421
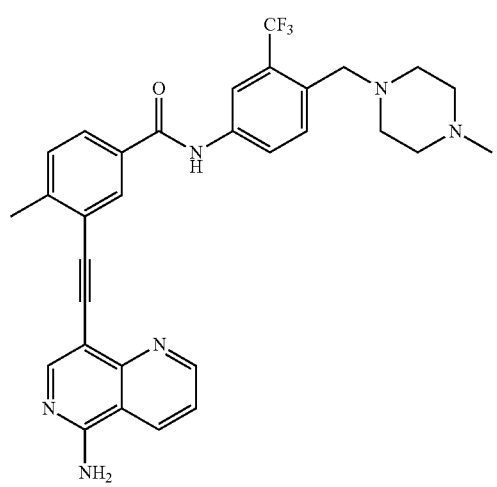
HSN422
HSN423
-continued
HSN431
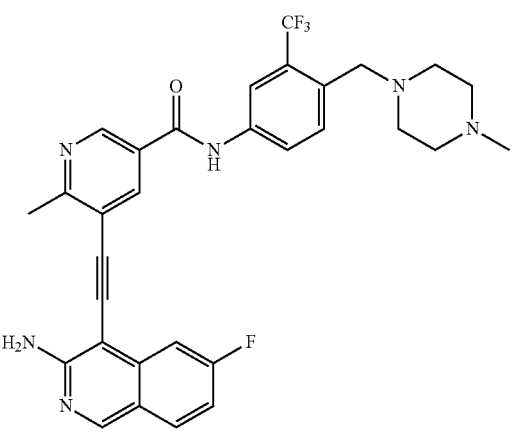
HSN432
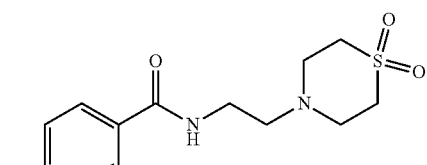
HSN433
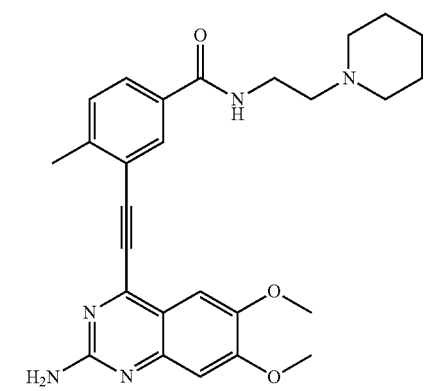
HSN434
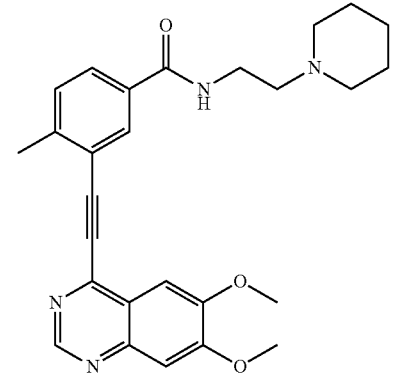

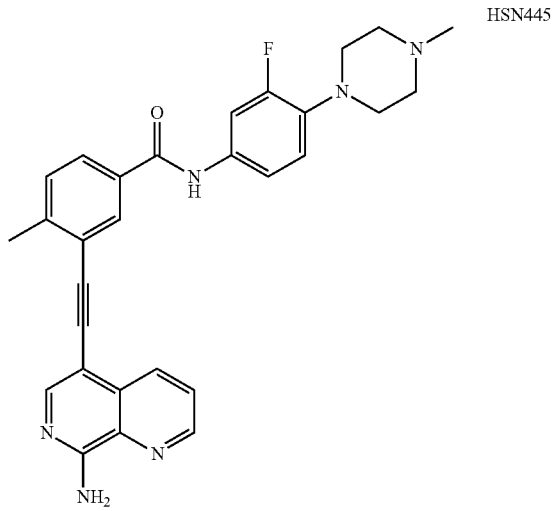
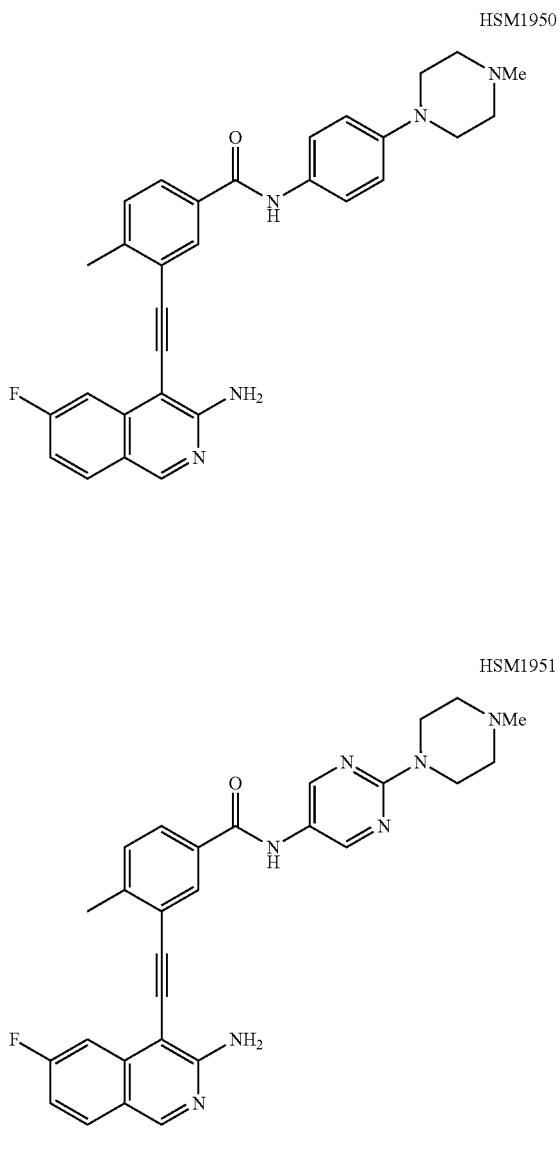
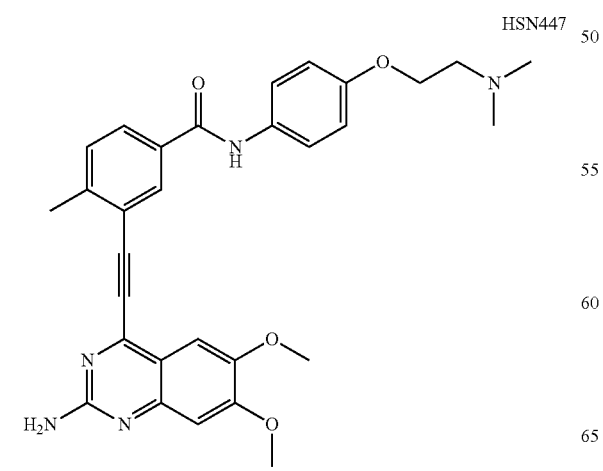
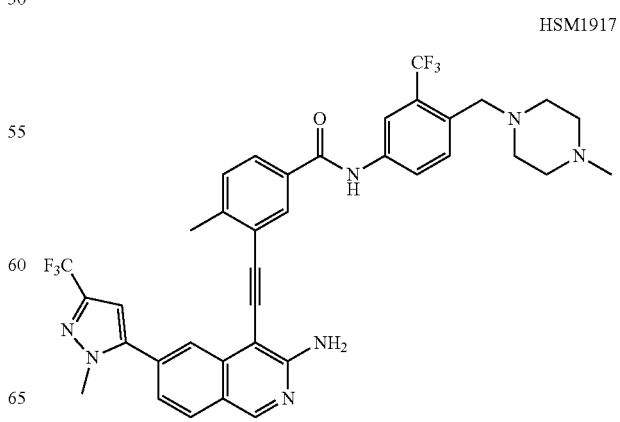

HSM1918
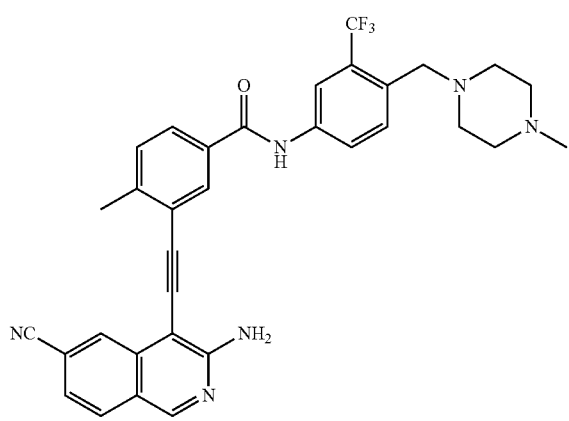
HSL41
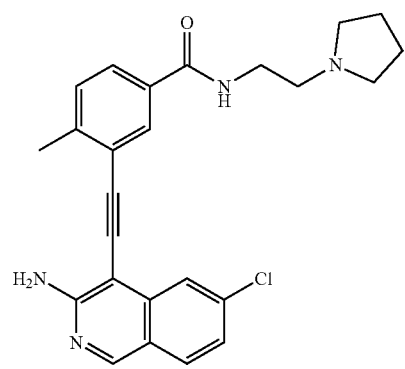
HSL43
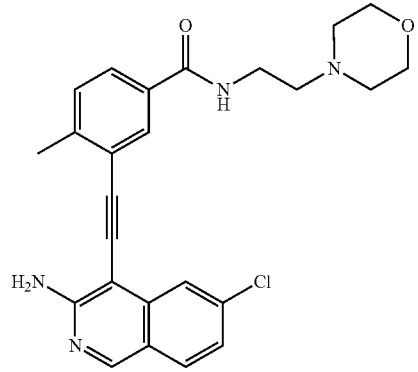
HSL44
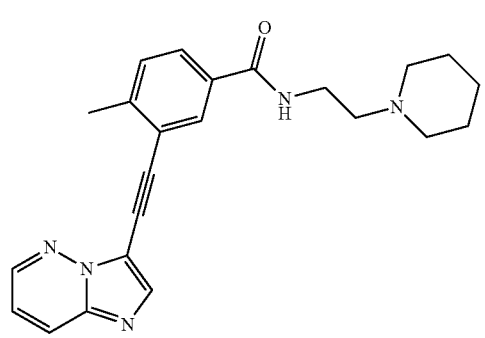
HSL58
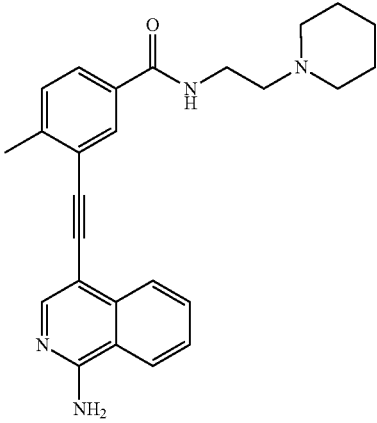
HSL45
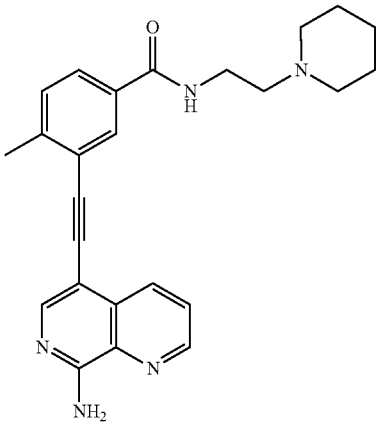
HSL47
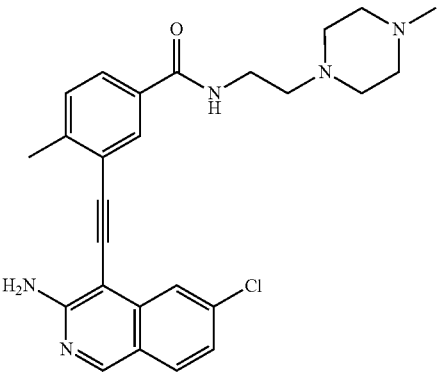
HSL56
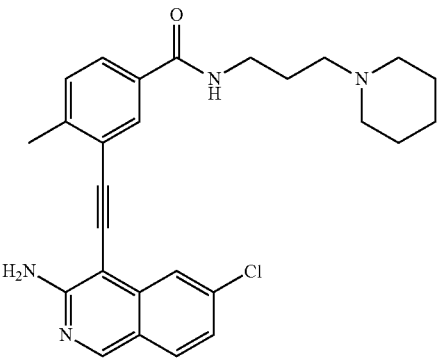

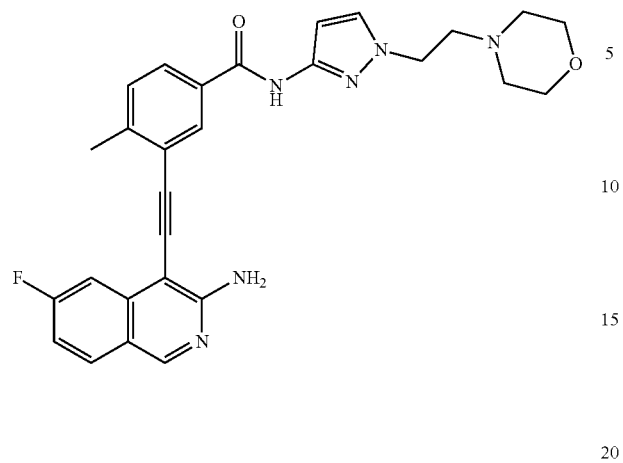
HSM1956
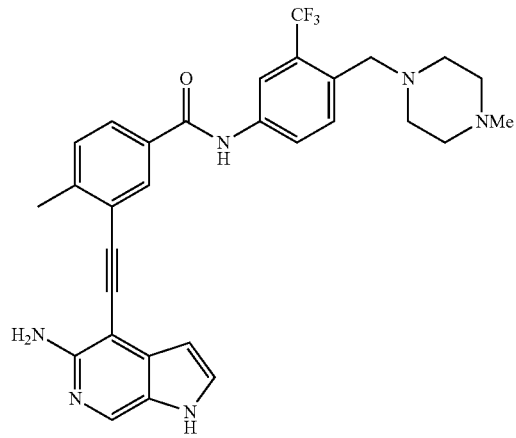
HSM2000
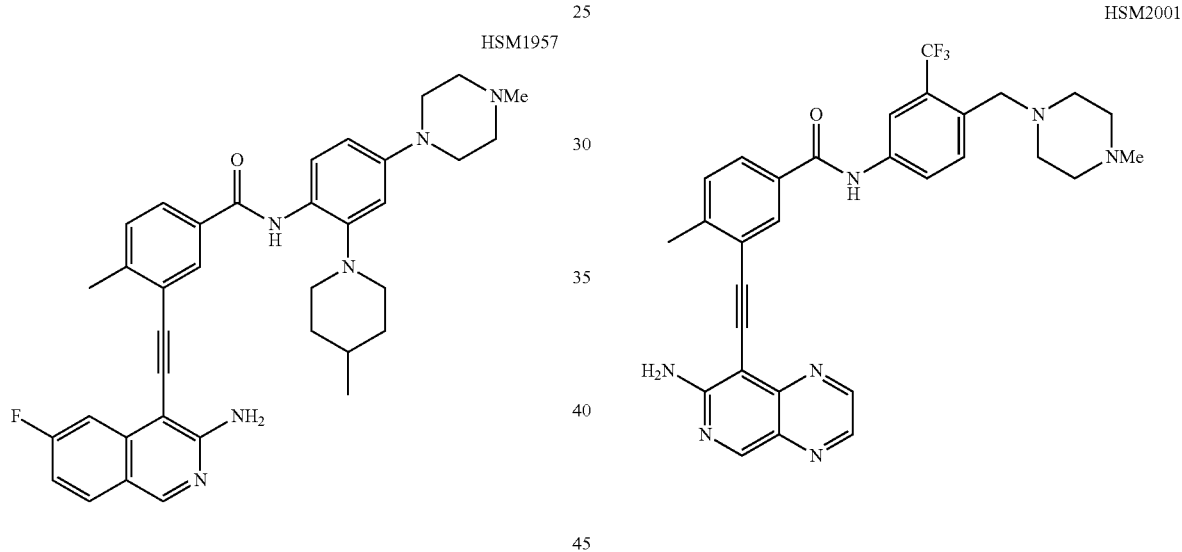
HSM1957
HSM2001
HSM1958
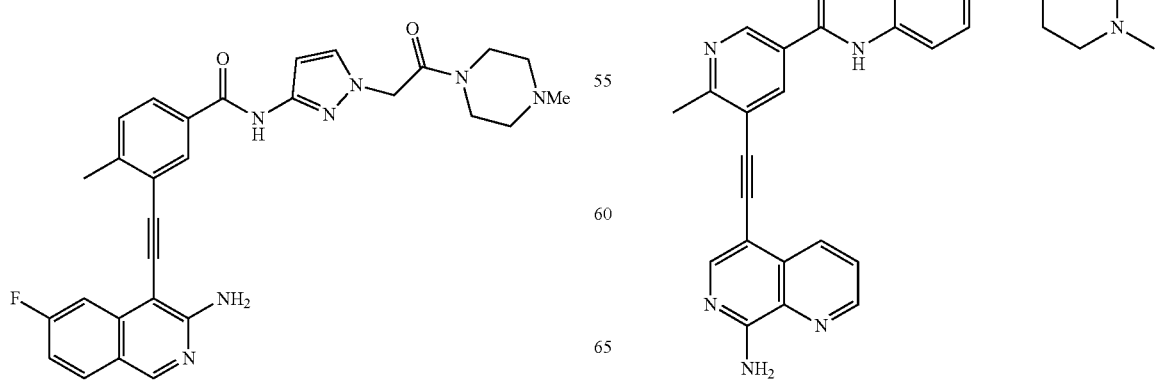
HSN459

-continued
HSN461
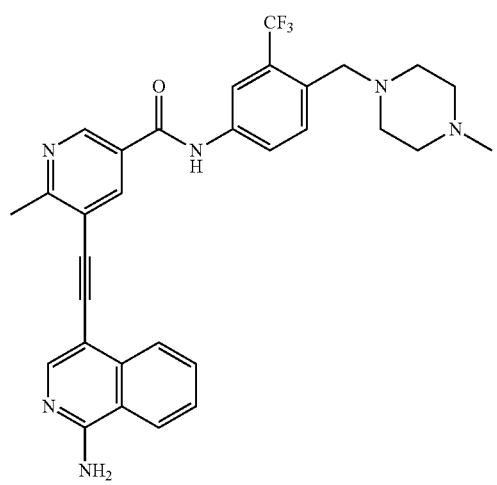
HSN485
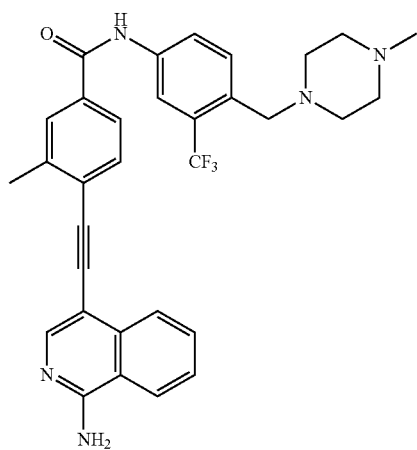
HSN489
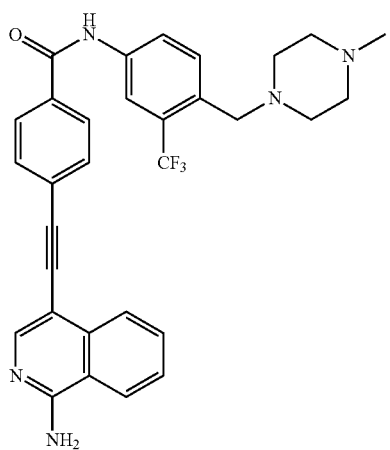
-continued
HSN482
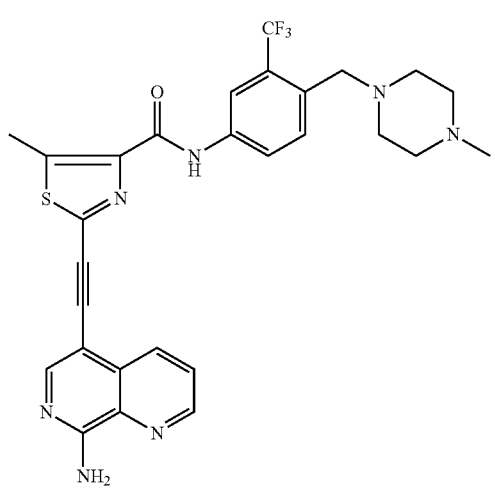
HSN486
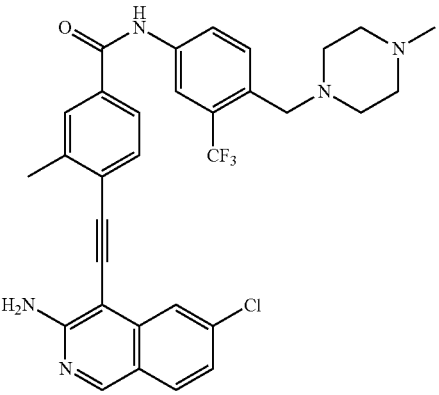
HSN490
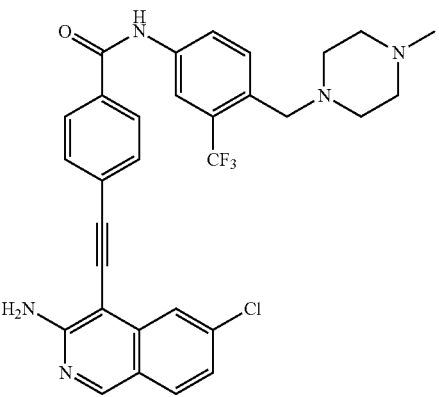

121
-continued
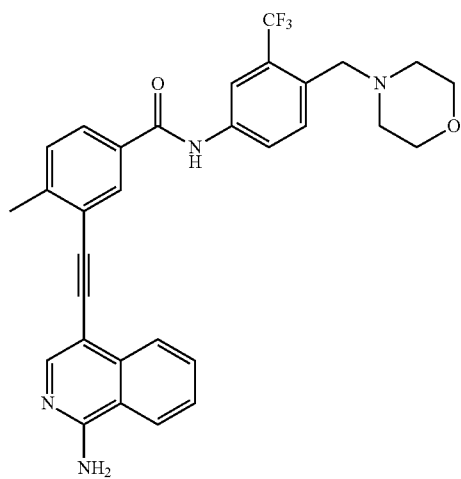
HSN514
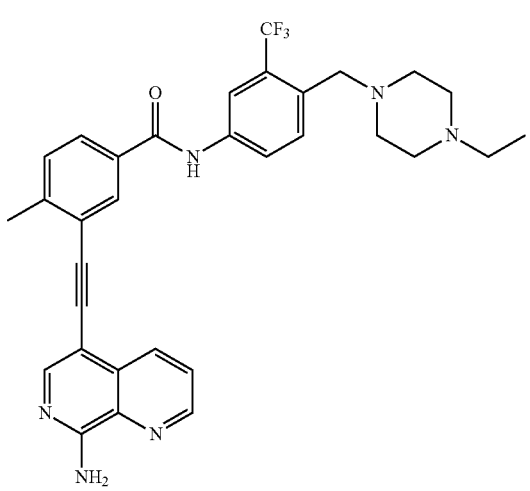
HSN515
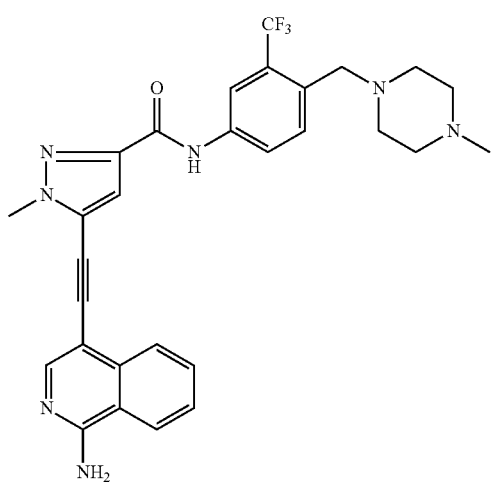
HSN516
122
-continued
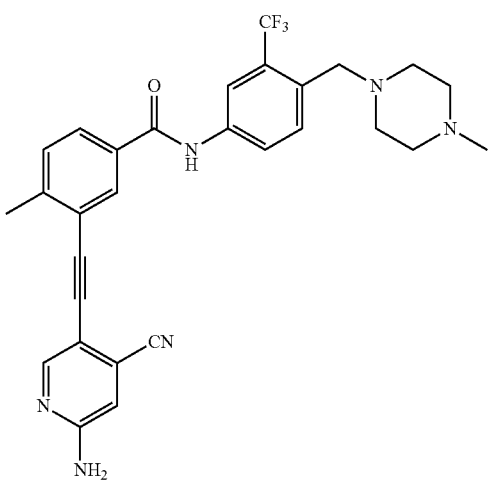
HSN517
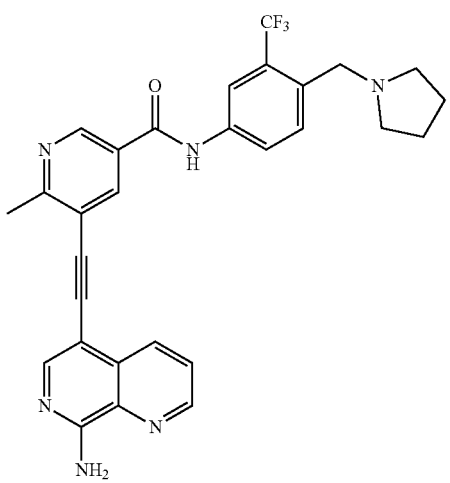
HSN533
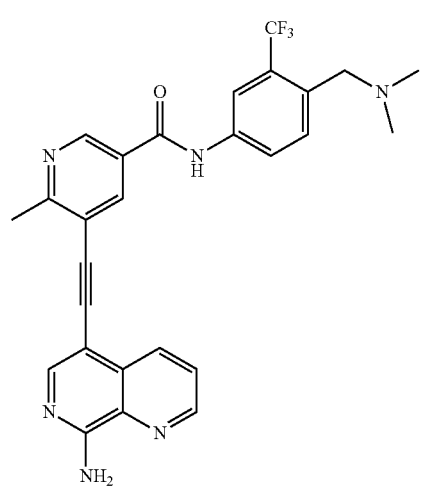
HSN534

-continued
HSN535
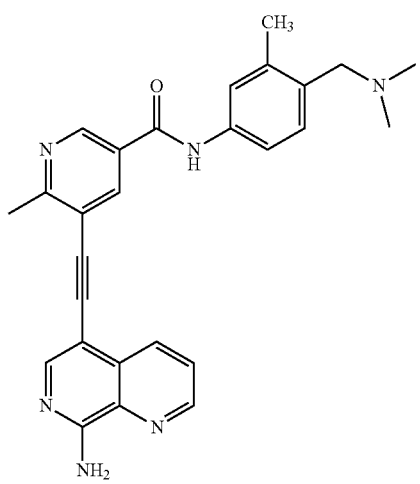
HSN544
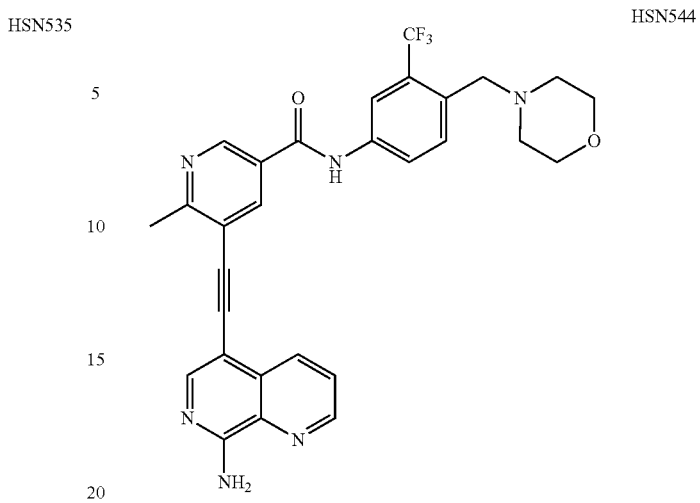
HSN536
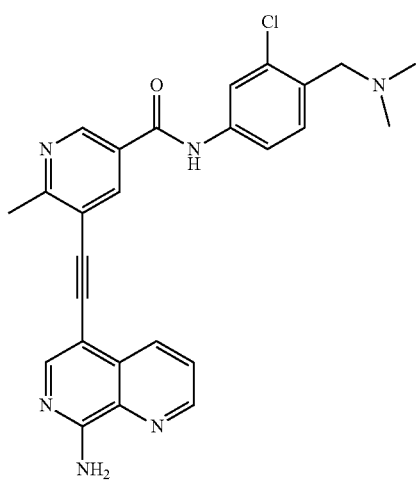
HSN545
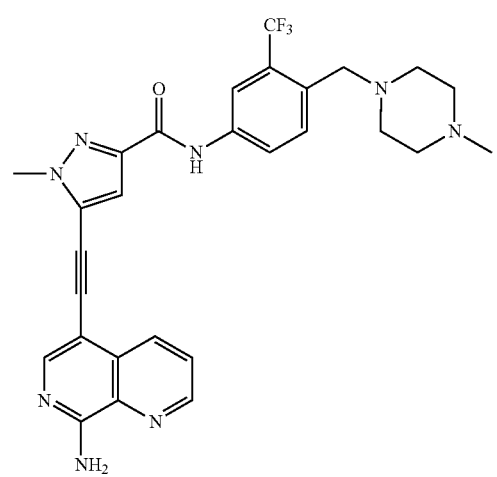
HSN543
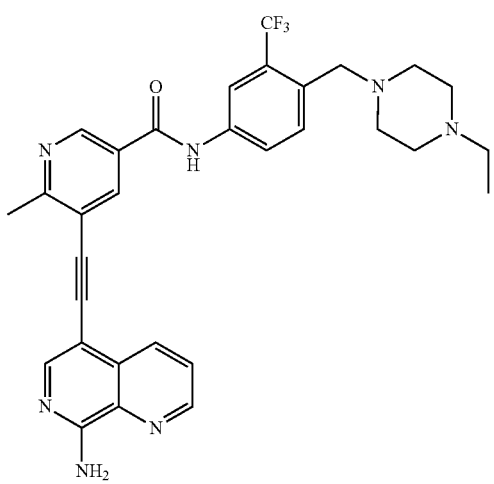
HSN548
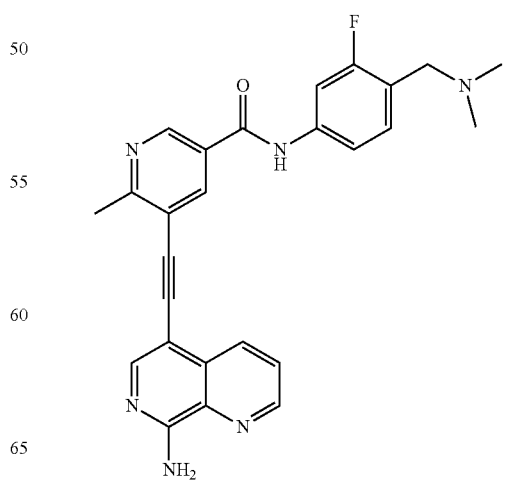

-continued
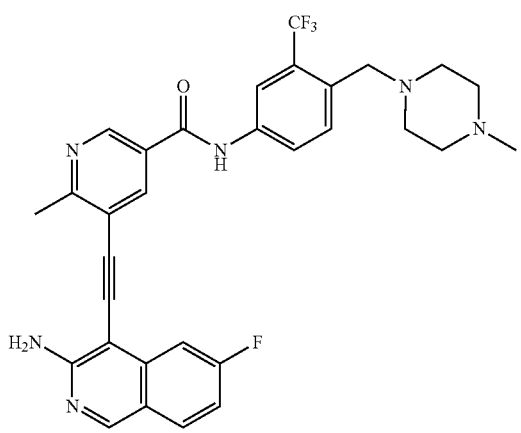
HSN431
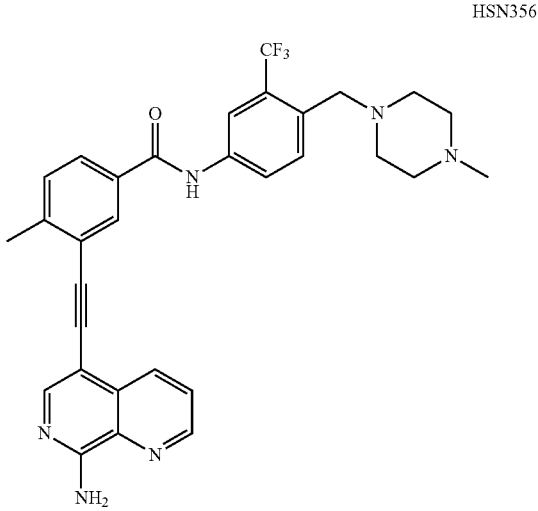
HSN431b
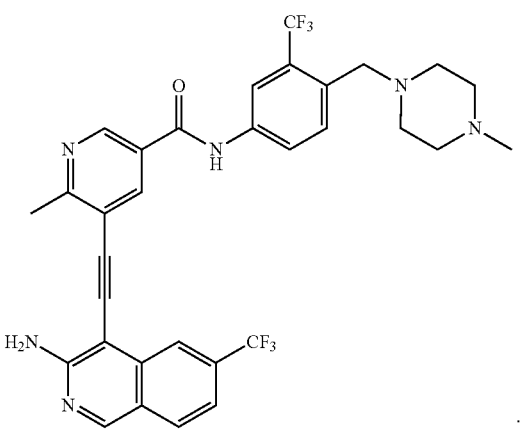
HSN431c
In some embodiments, the compound of the invention is
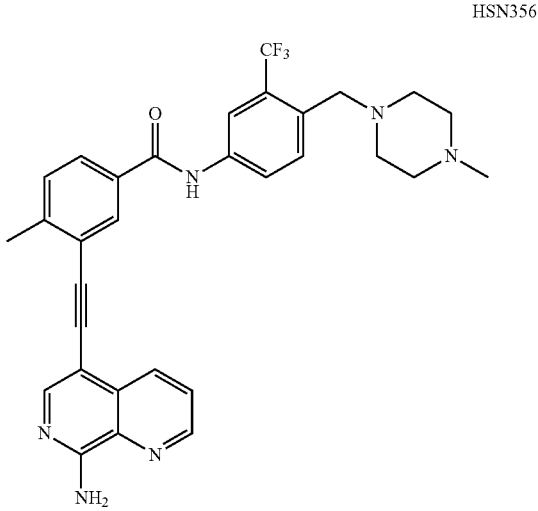
HSN356
HSN334
HSN286

-continued
HSN461
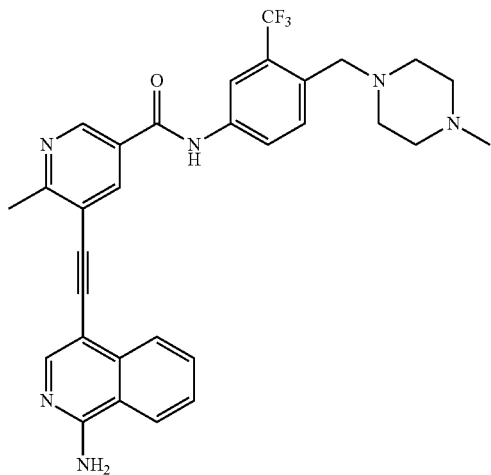
In some embodiments, the compound of the invention is
HSN286
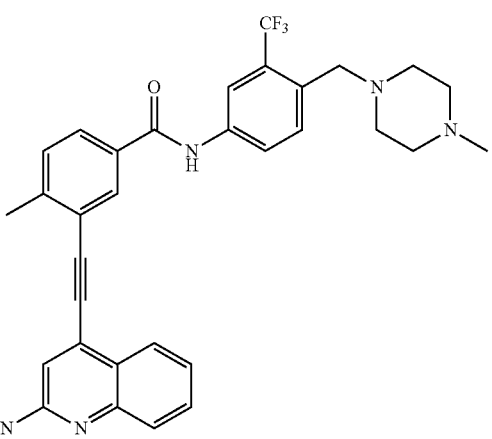
HSN459
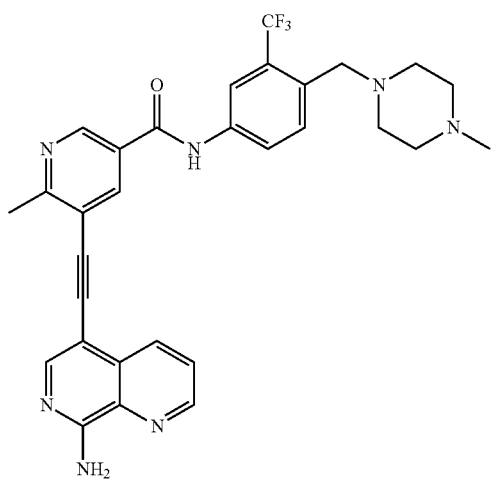
HSN325
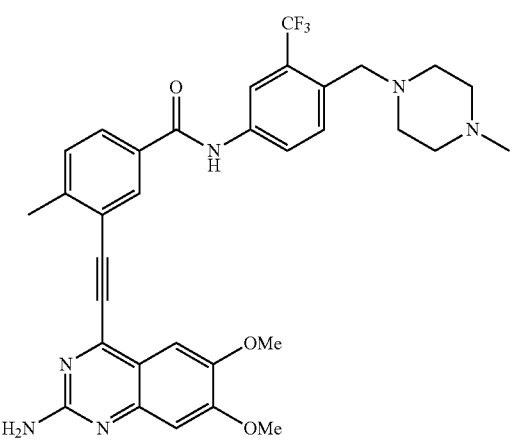
HSN431
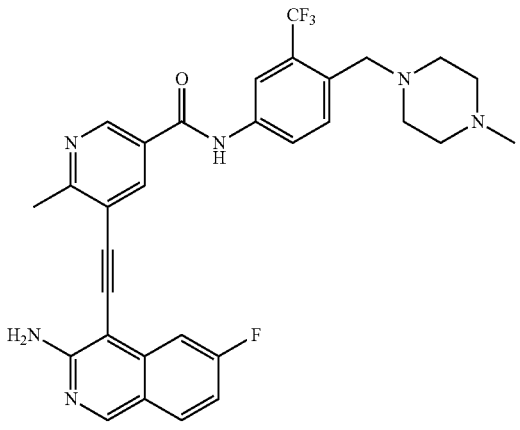
HSN352
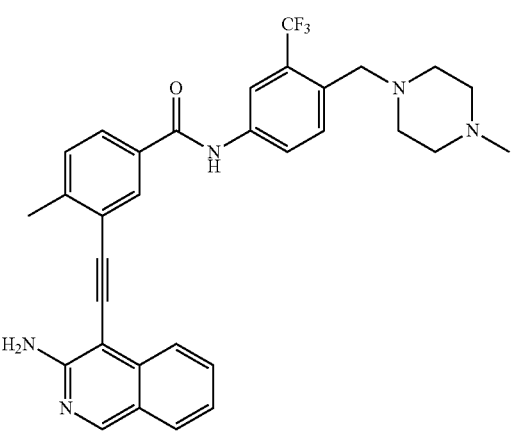

-continued
HSN353
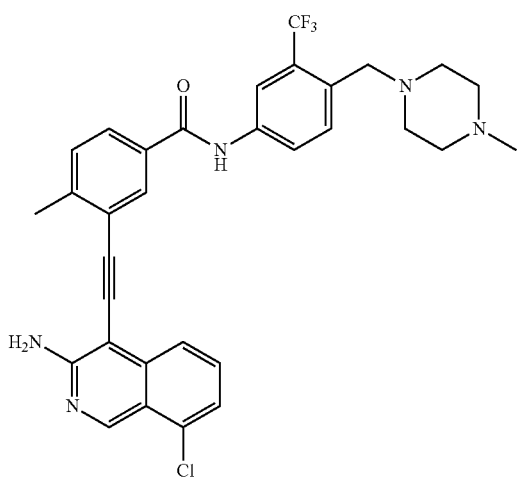
HSN379
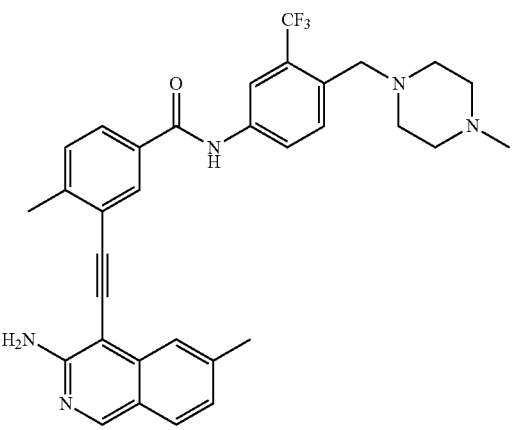
HSN248
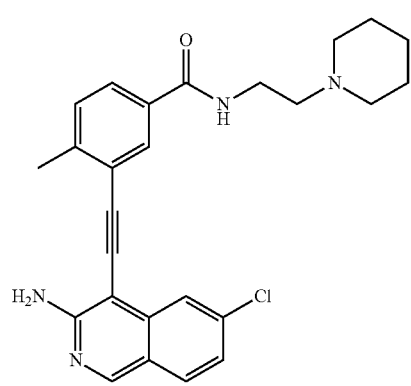
HSM1702
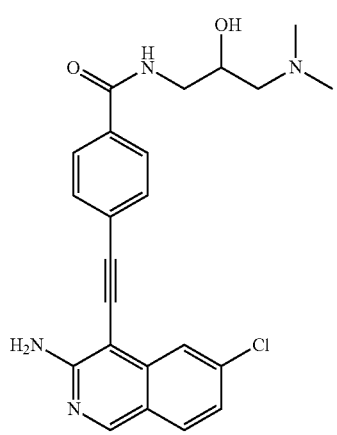
HSN247
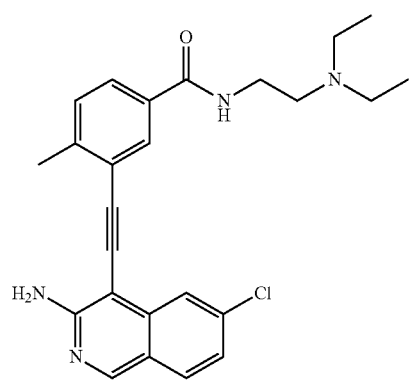
HSN178
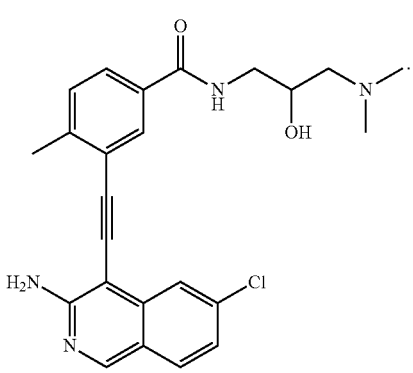

In some embodiments, the compound of the invention is
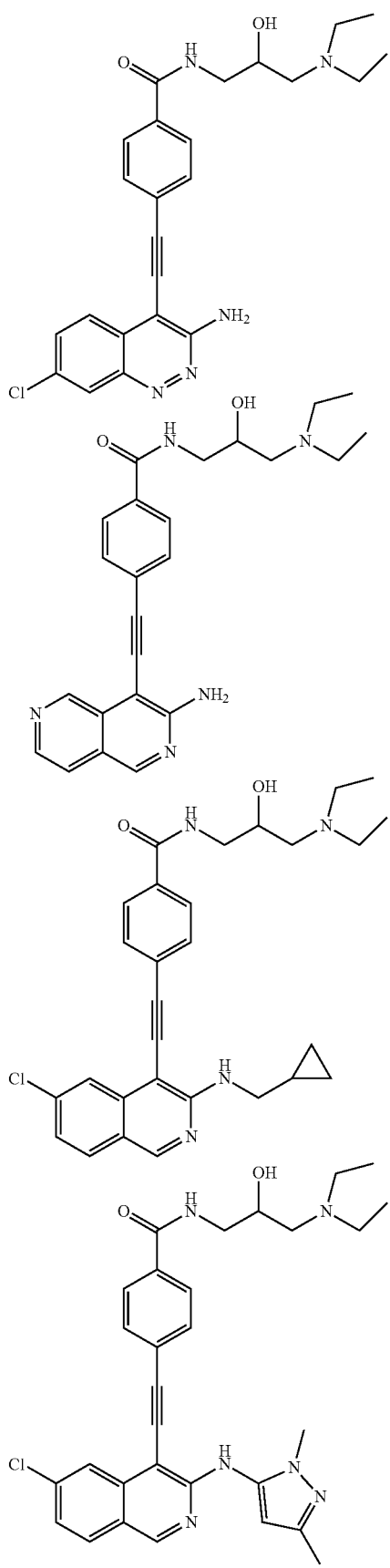
-continued
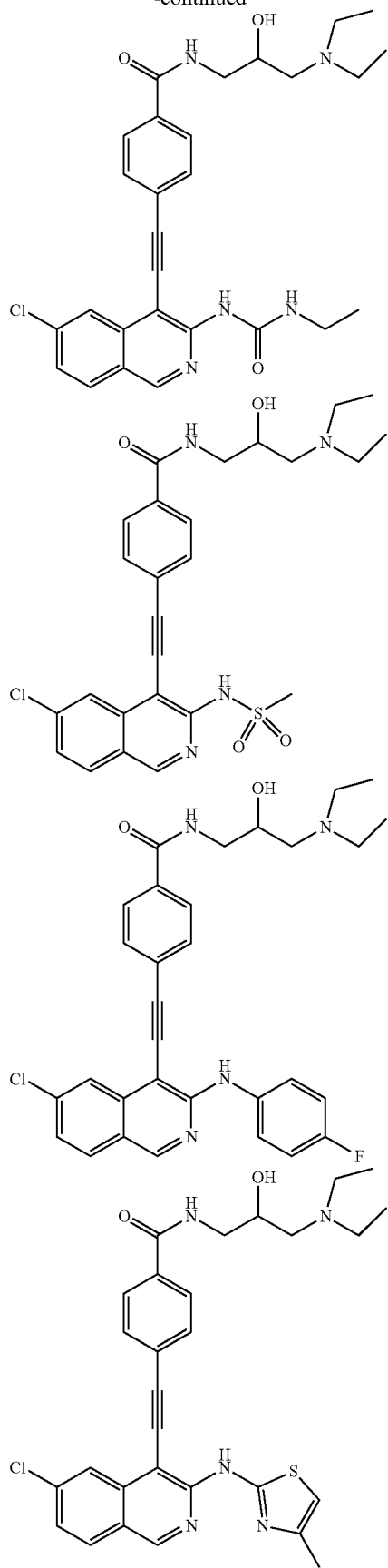

133
-continued
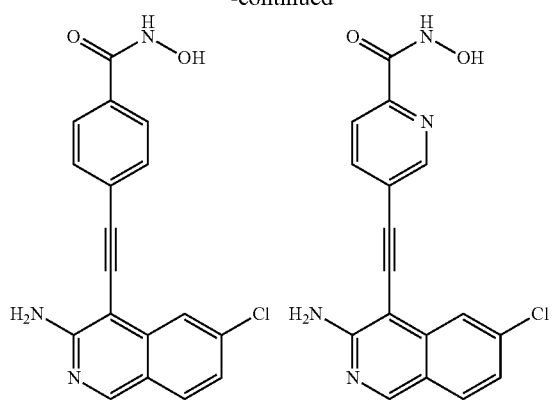
134
-continued
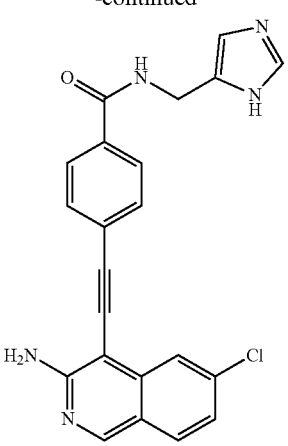
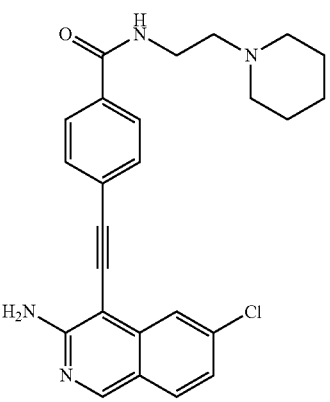
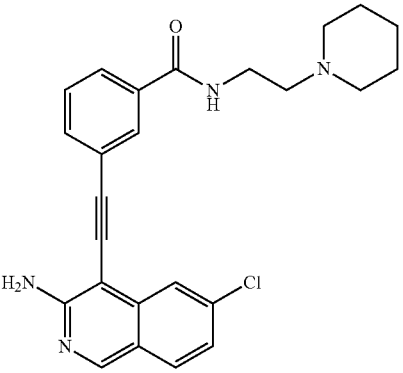
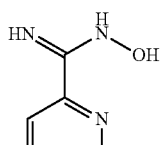
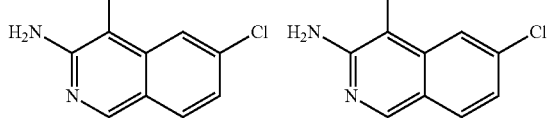

135
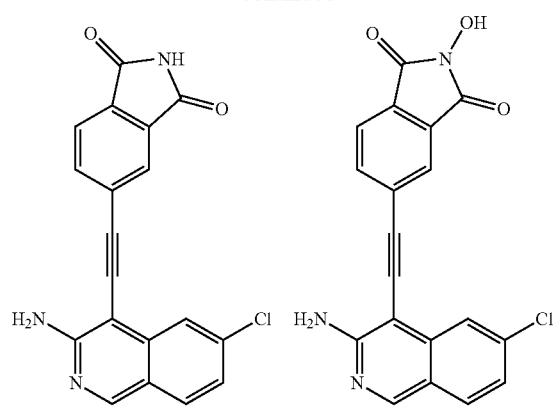
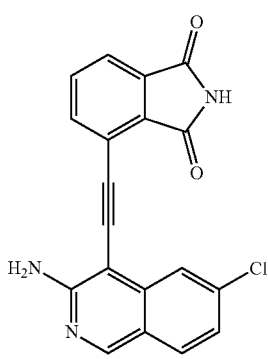
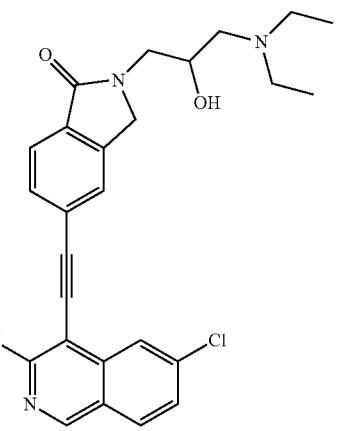
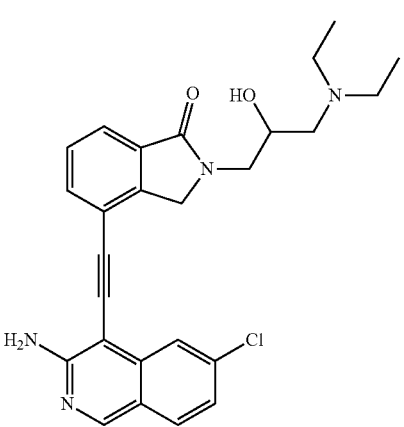
136
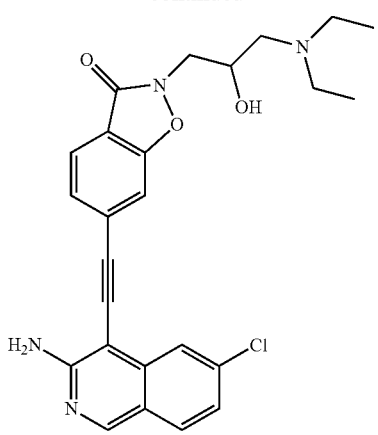
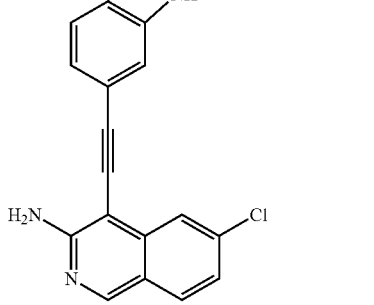
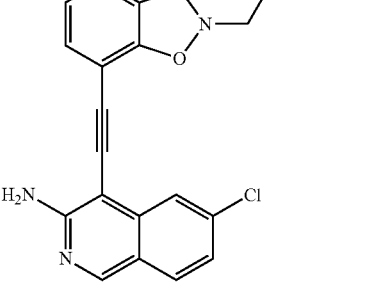
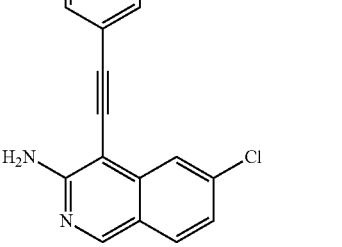

137
-continued
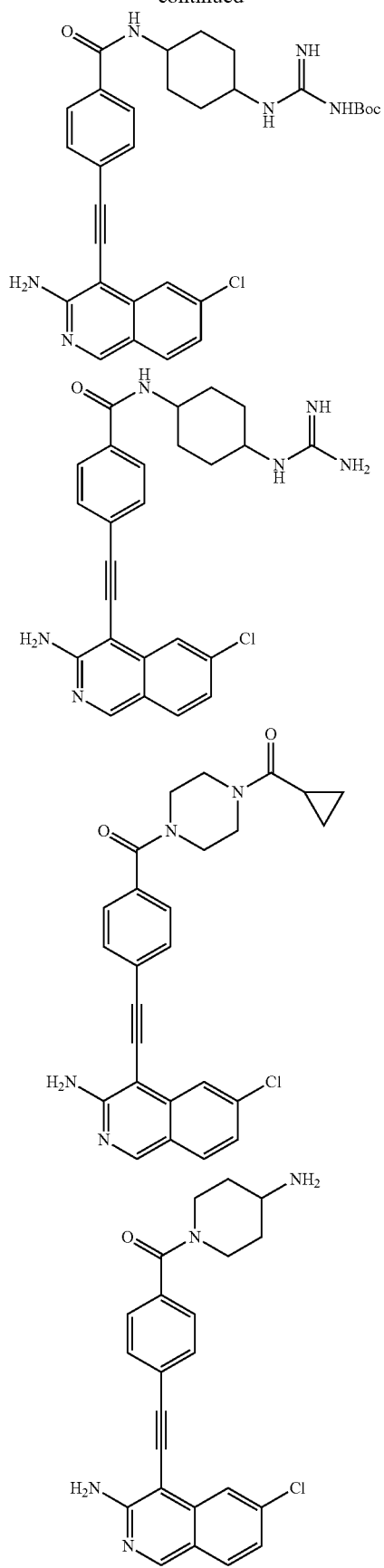
138
-continued
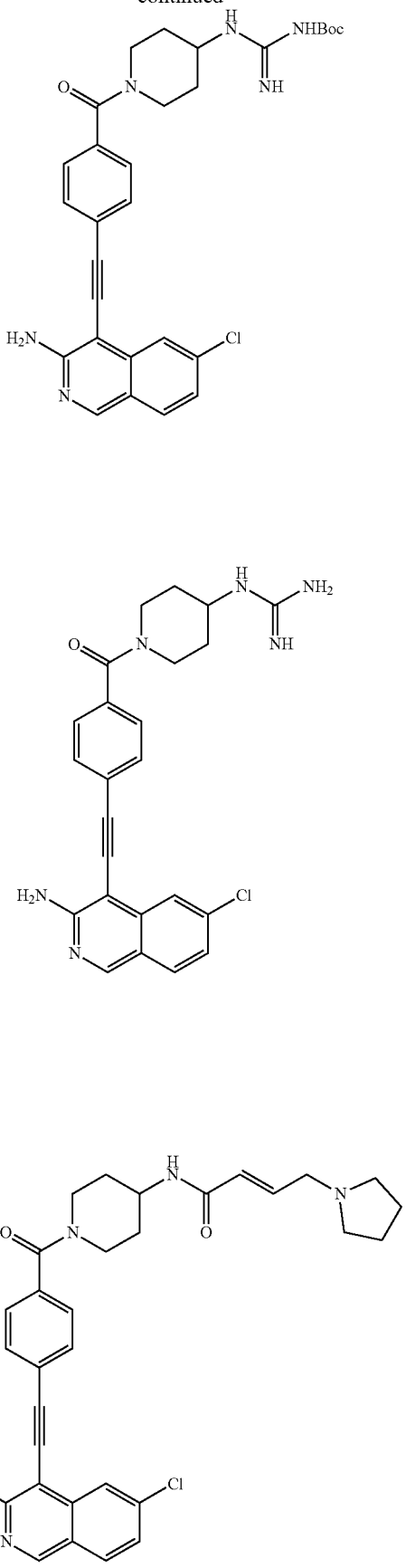

139
-continued
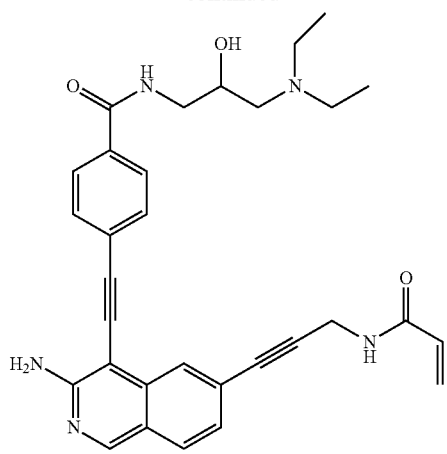
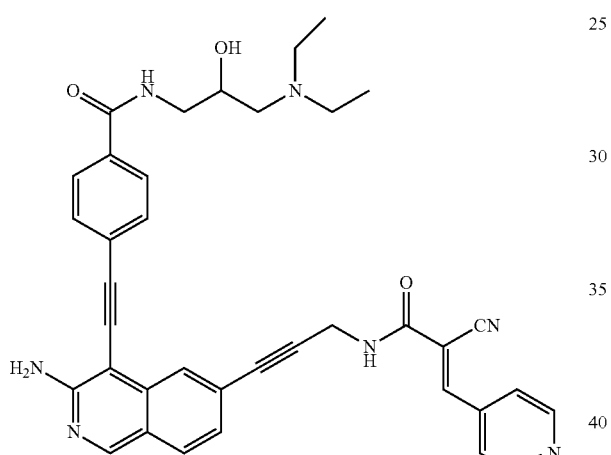
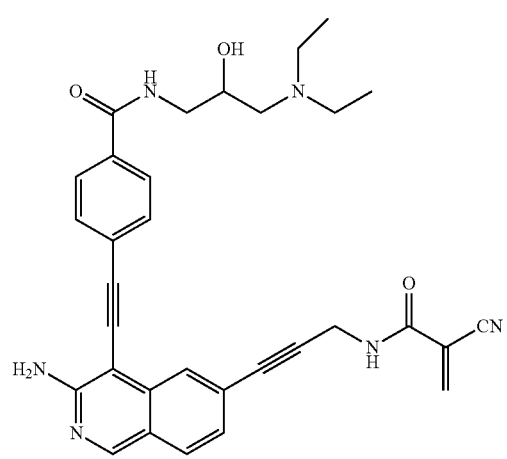
140
-continued
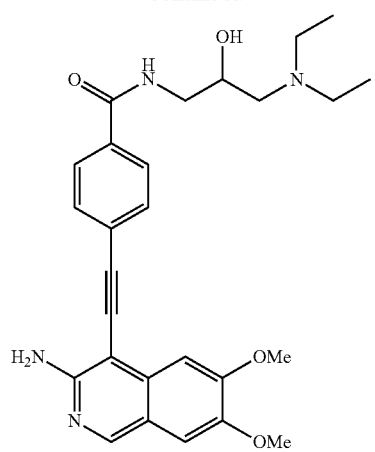
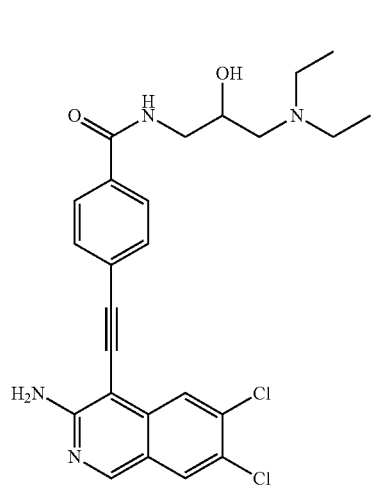
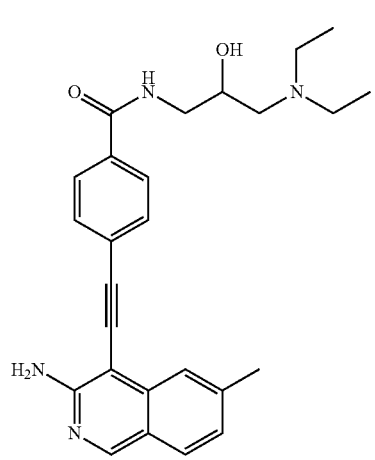

141
-continued
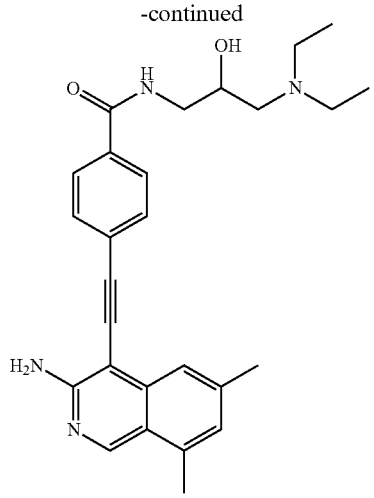
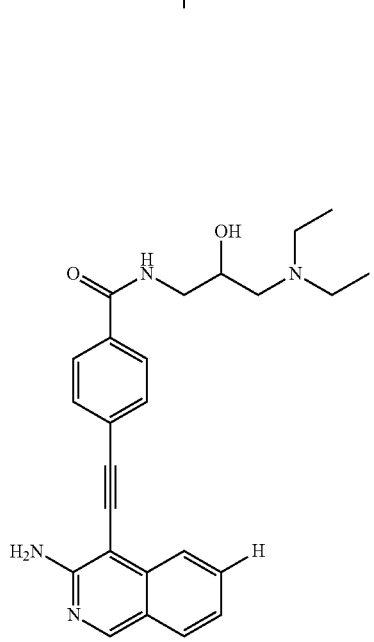

142
-continued
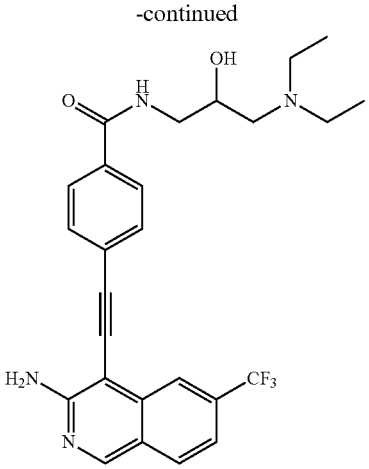
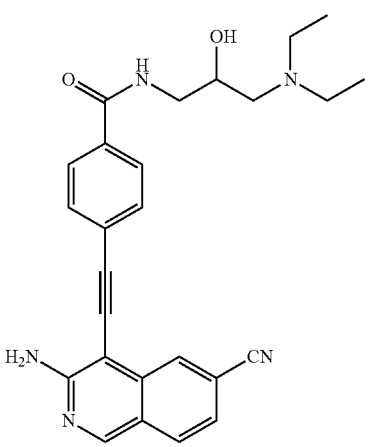
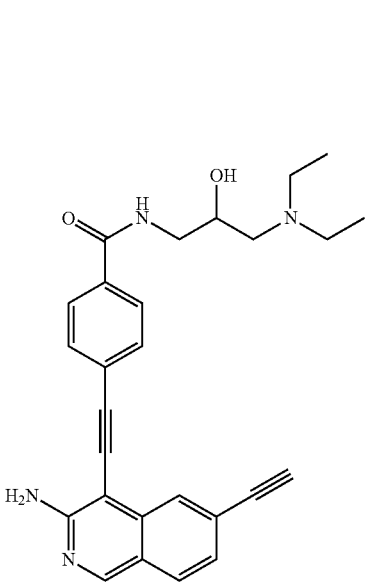

143
-continued
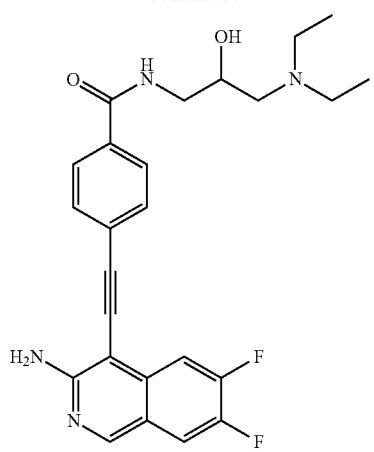
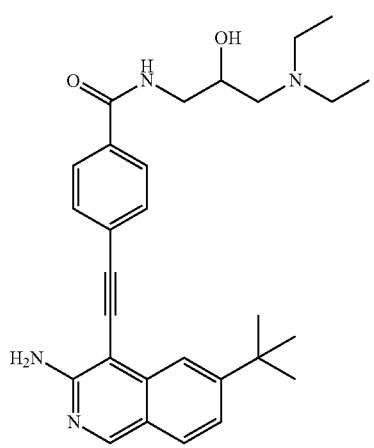
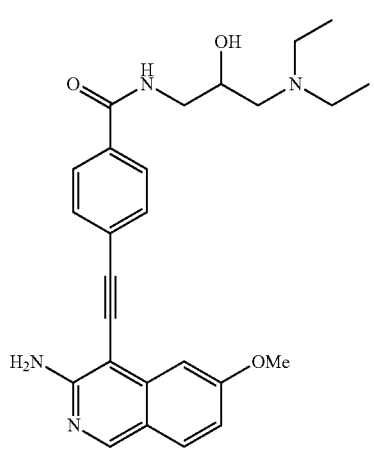
144
-continued
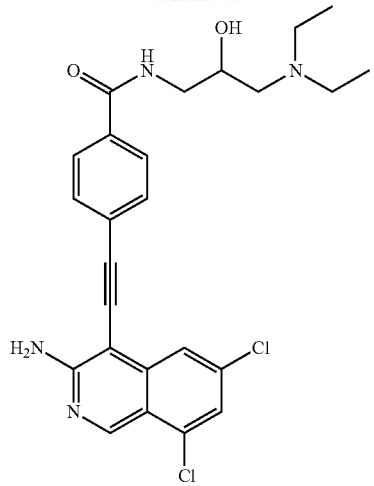
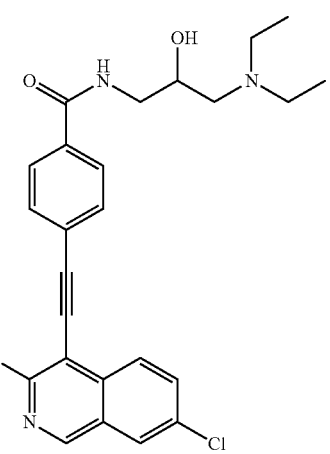
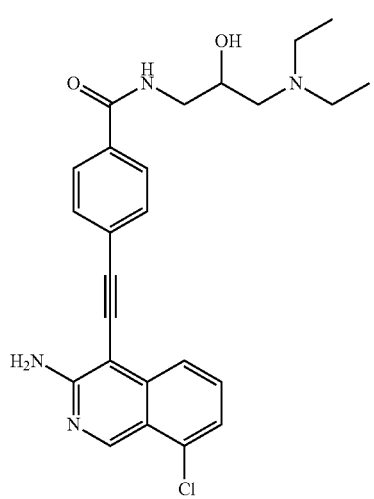

145
-continued
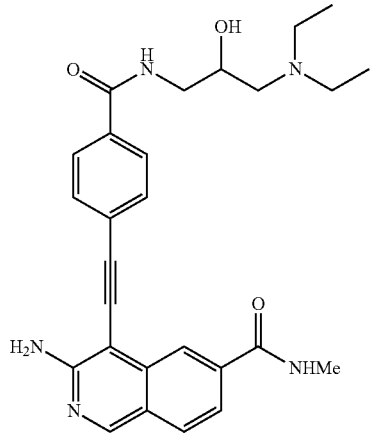 [SMILES: CCN(CC)CC(O)CNC(=O)c1ccc(C#Cc2c(N)ncc3ccc(C(=O)NC)cc23)cc1]
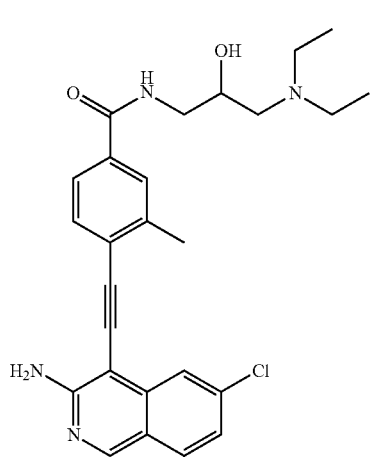
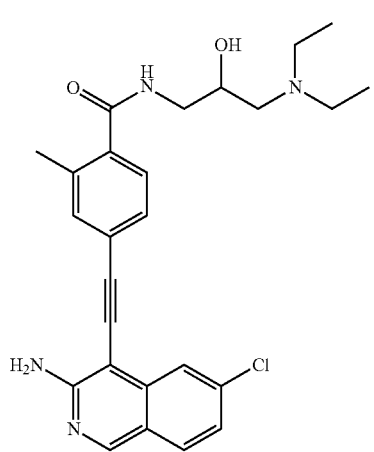
146
-continued
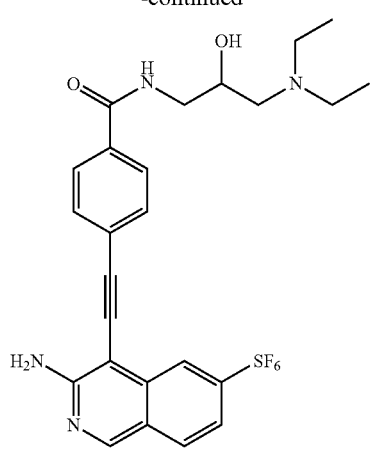
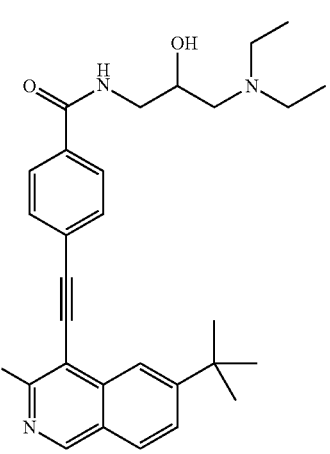
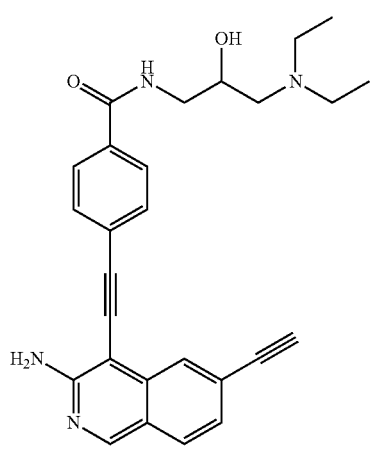

147
-continued
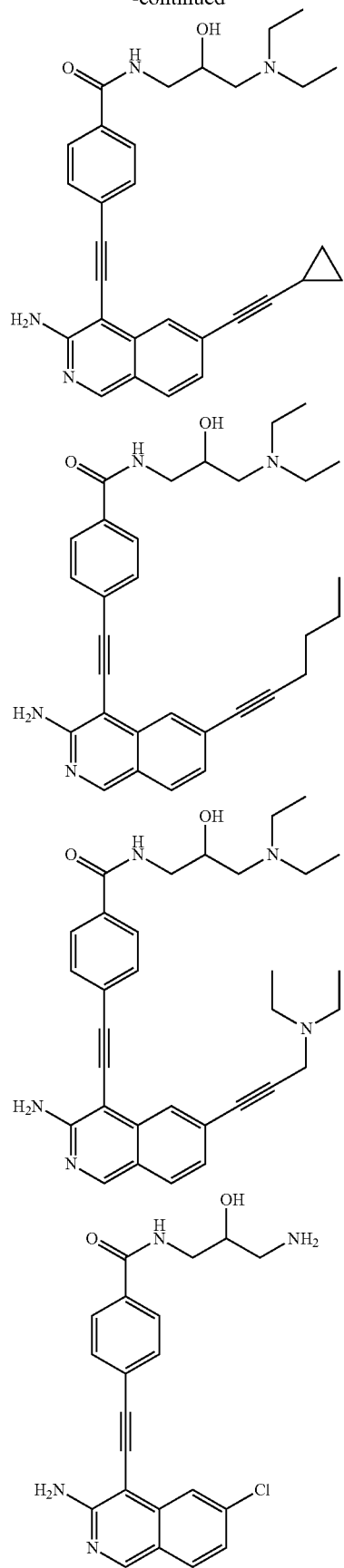
148
-continued
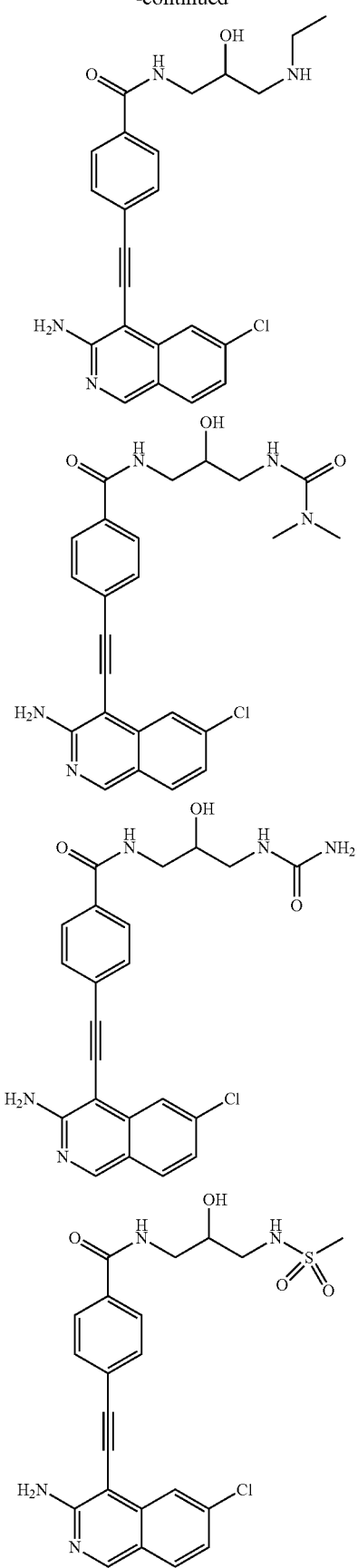

149
-continued
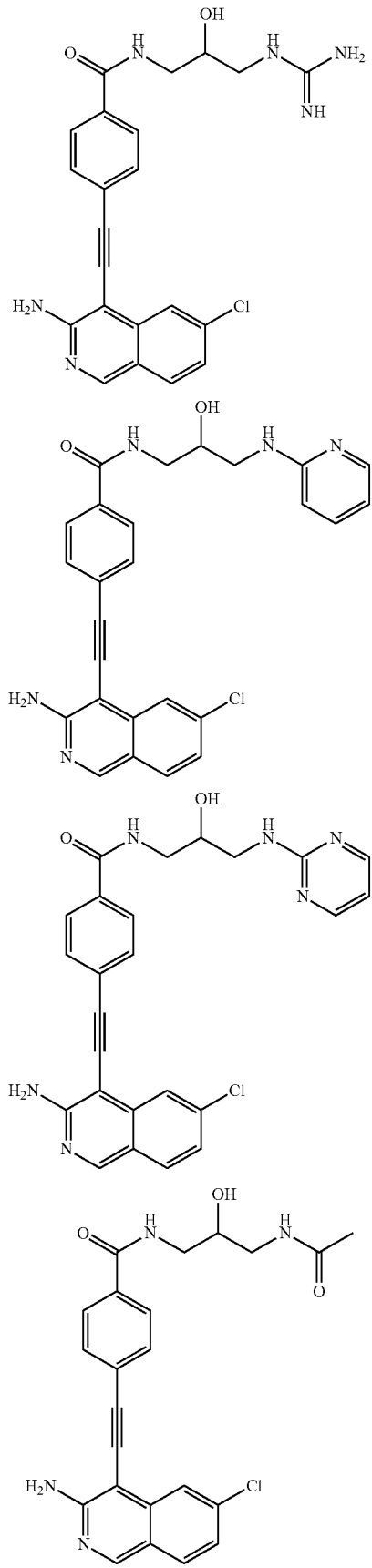
150
-continued
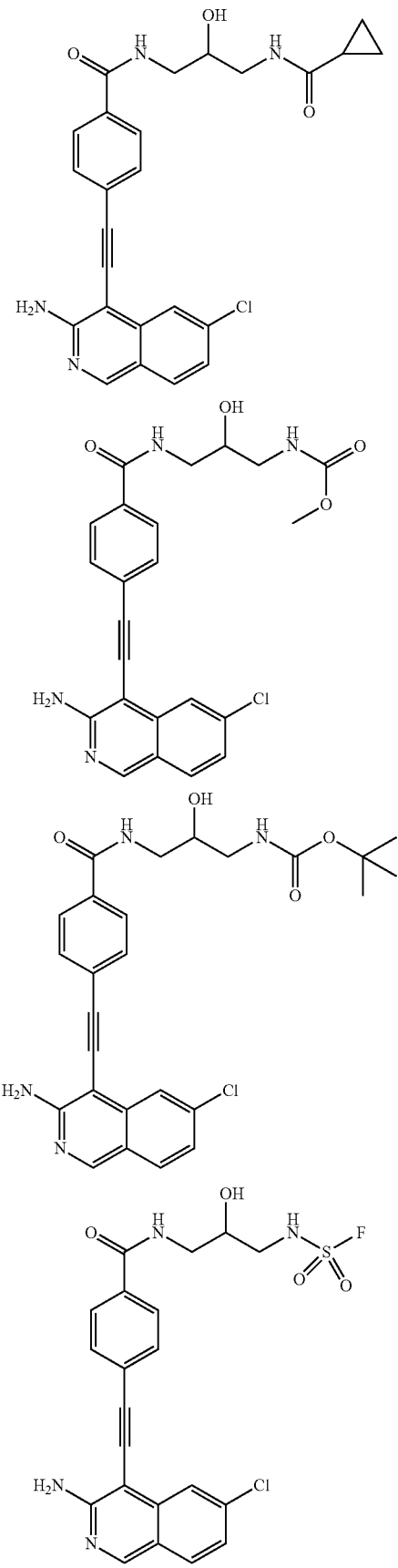

151
-continued
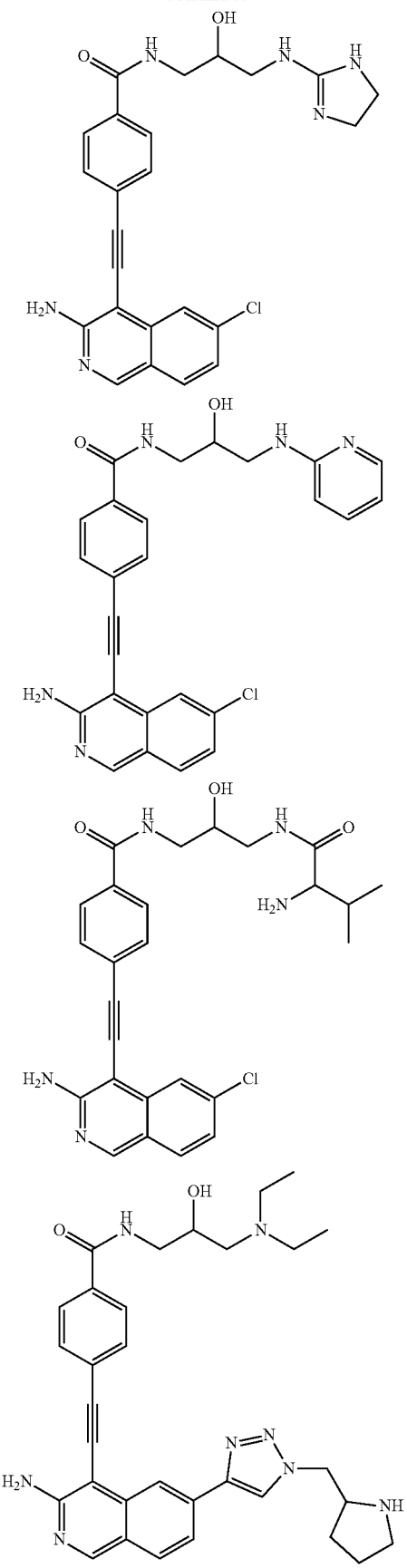
152
-continued
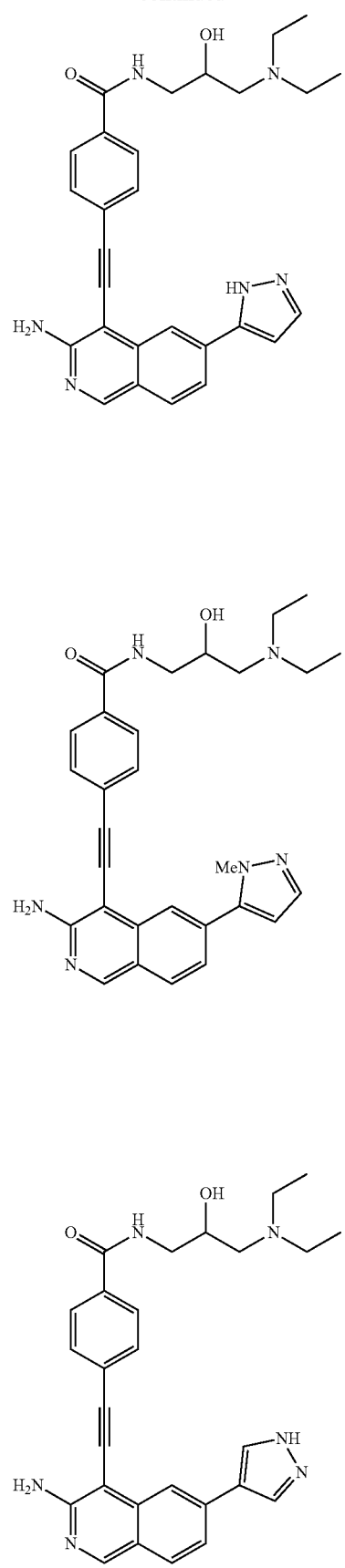

153
-continued
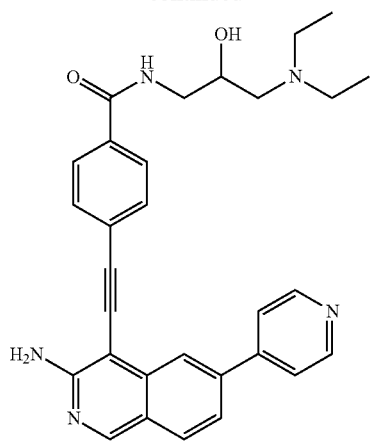
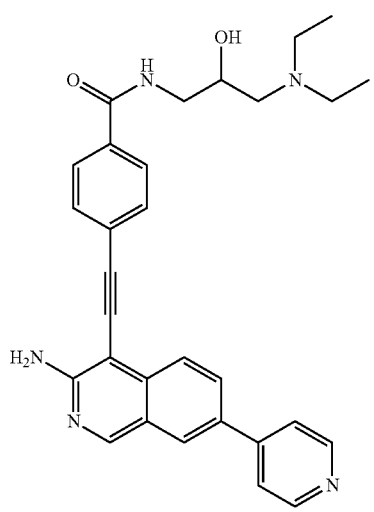
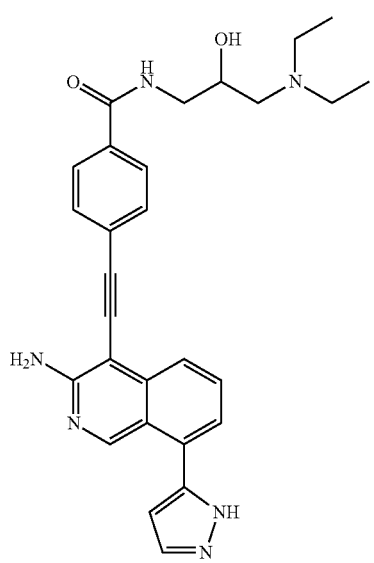
154
-continued
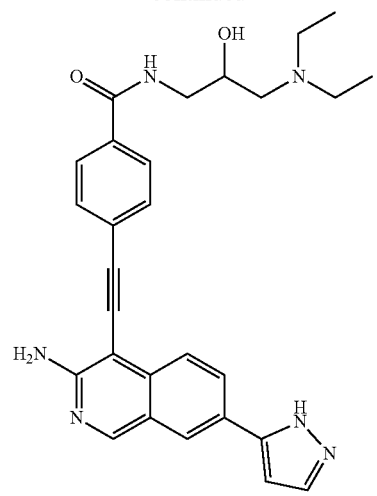 [SMILES: CCN(CC)CC(O)CNC(=O)c1ccc(C#Cc2c(N)ncc3cc(-c4ccn[nH]4)ccc23)cc1]
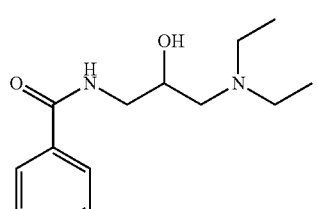
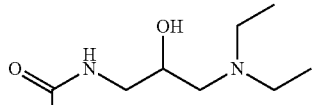
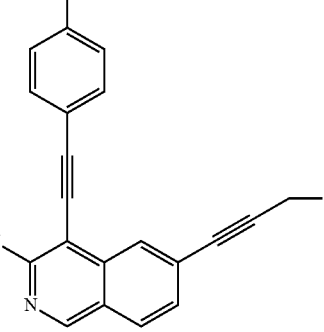

155
-continued
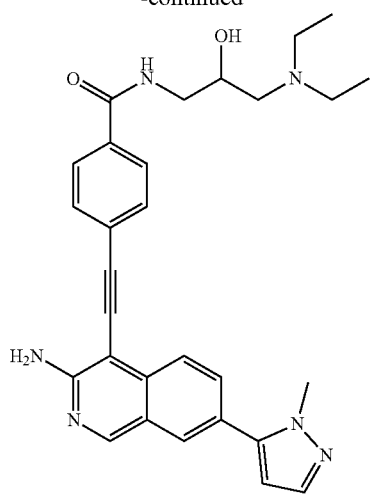
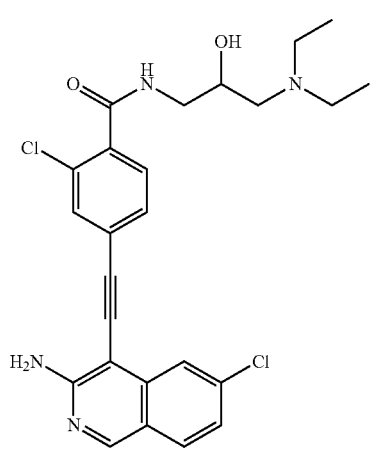
156
-continued
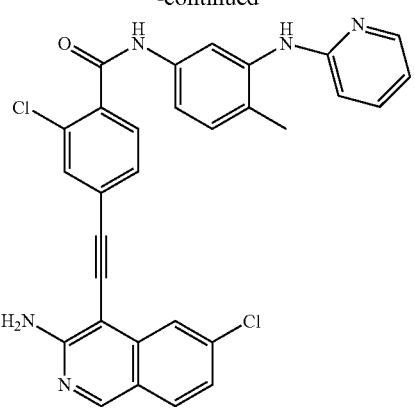
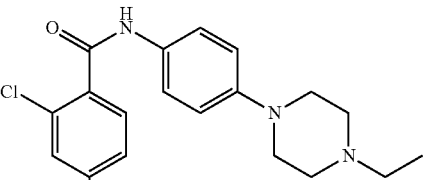
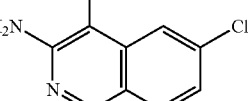
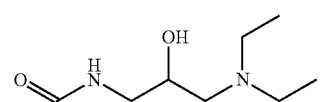
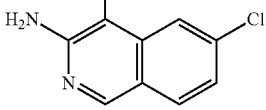
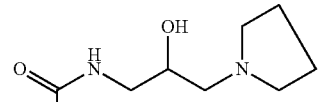

157
-continued
158
-continued
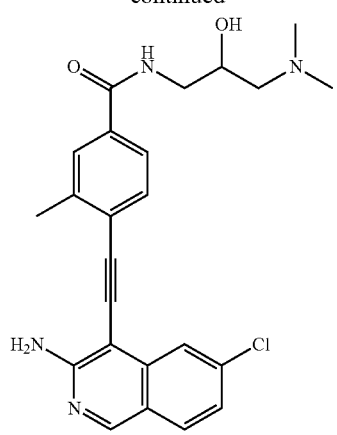
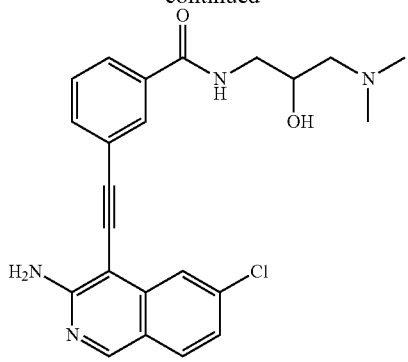
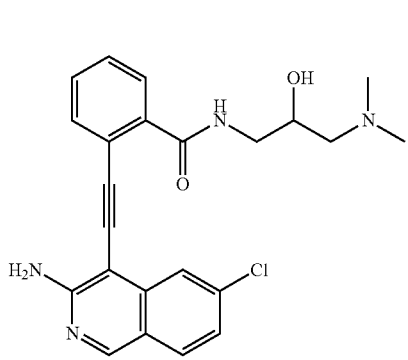
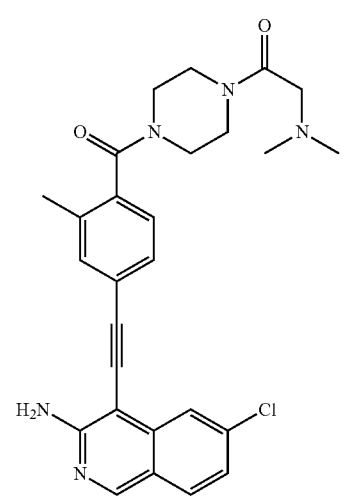

159
-continued
160
-continued
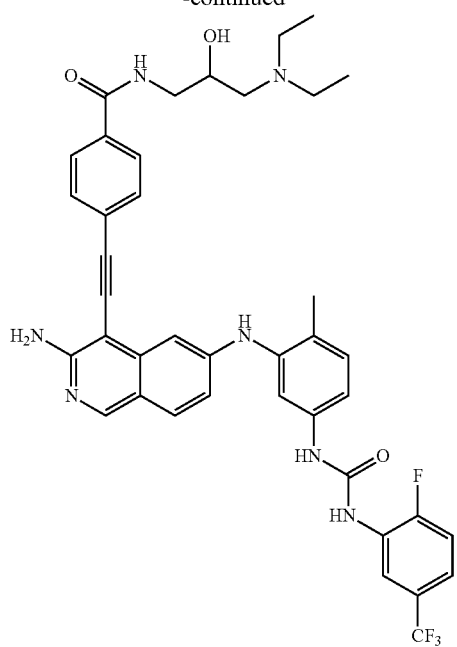
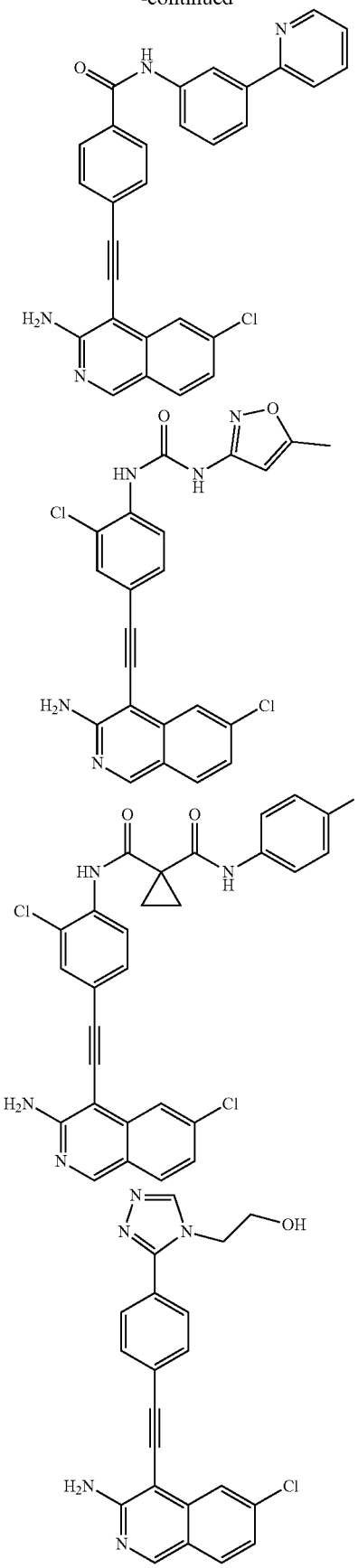

161
-continued
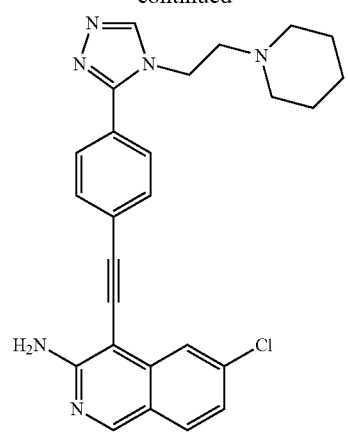
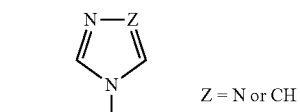
Z = N or CH
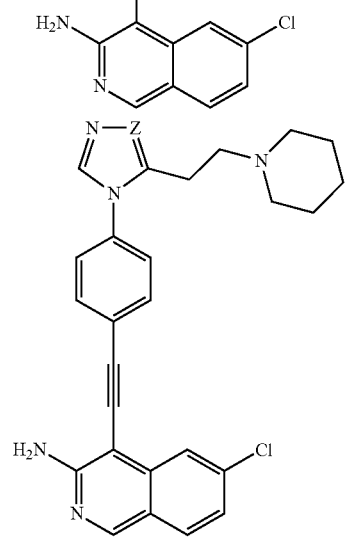
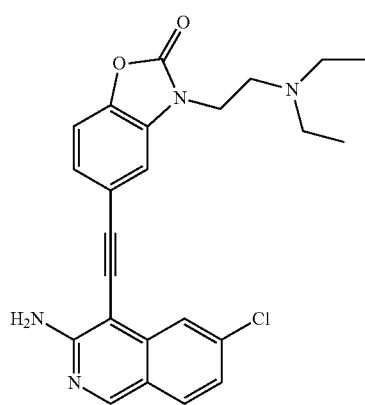
162
-continued
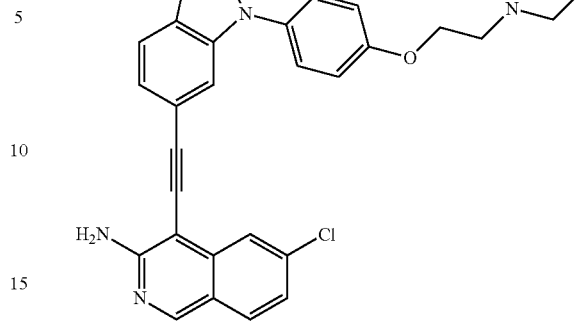
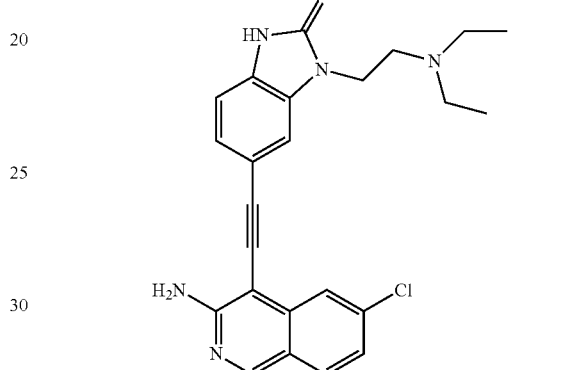
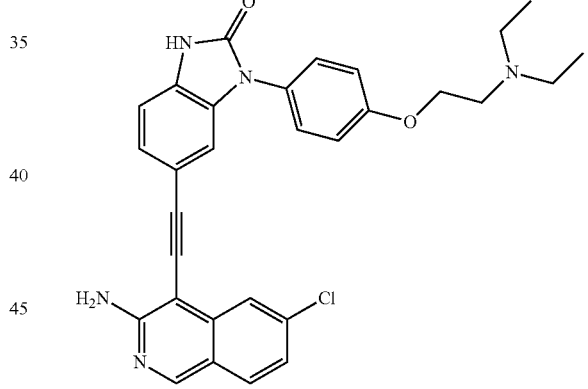
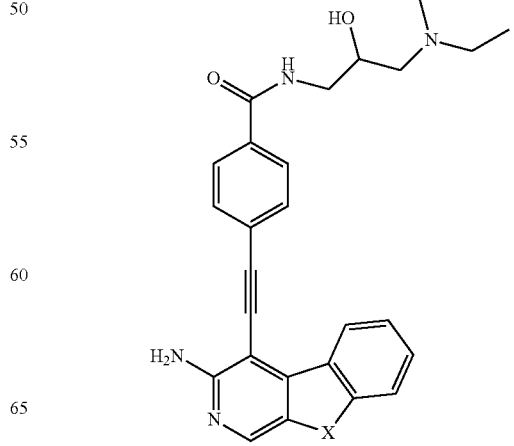

163
-continued
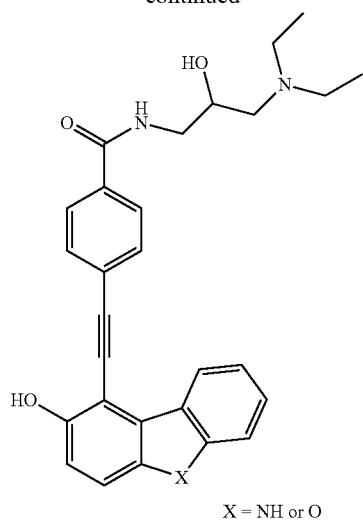
X = NH or O
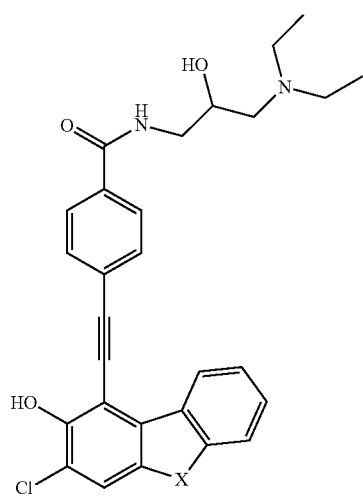
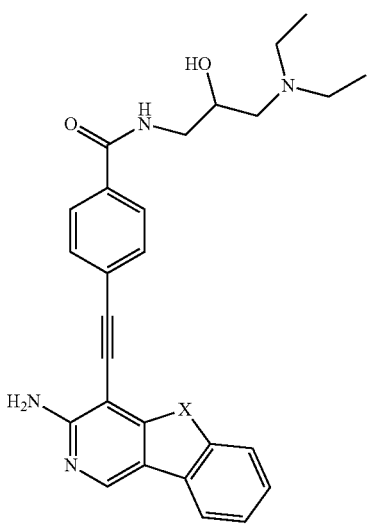
164
-continued
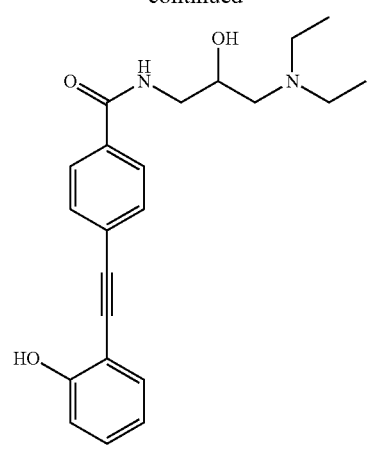
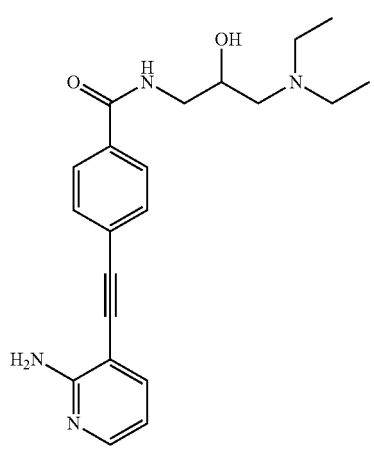
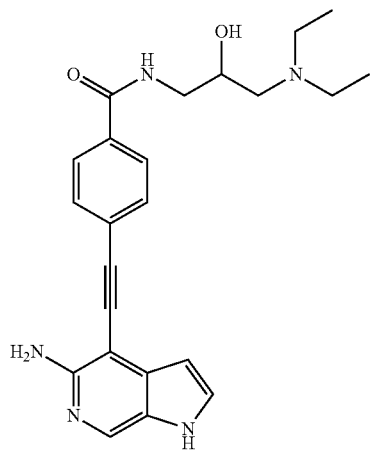

165
-continued
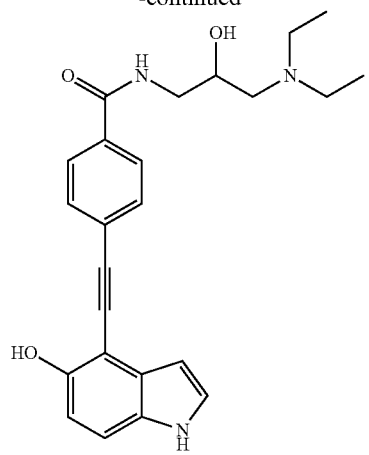
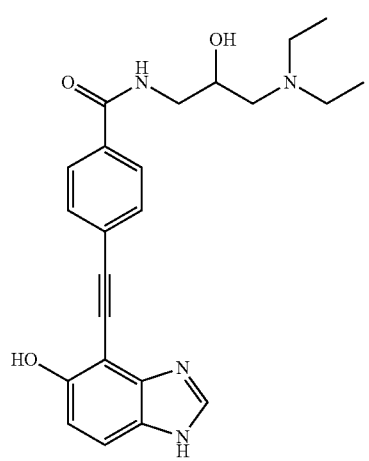
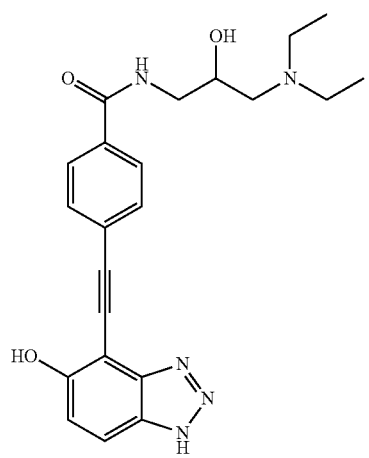
166
-continued
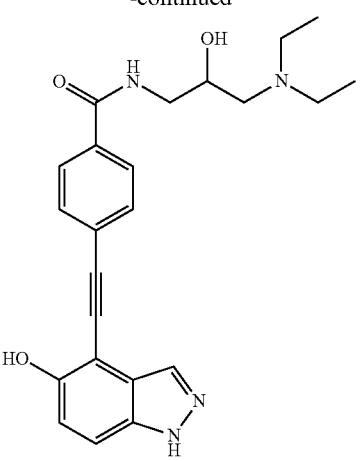
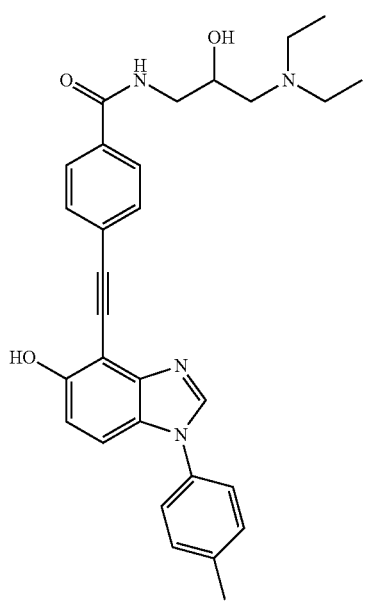
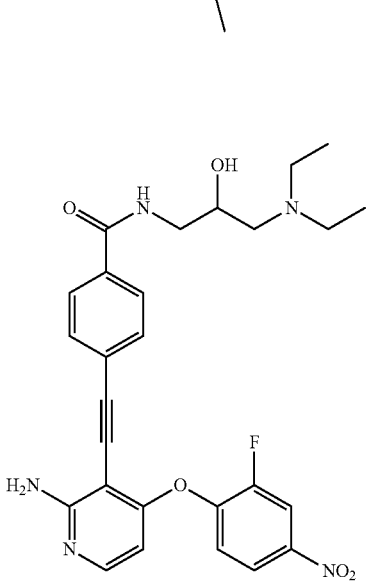

167
-continued
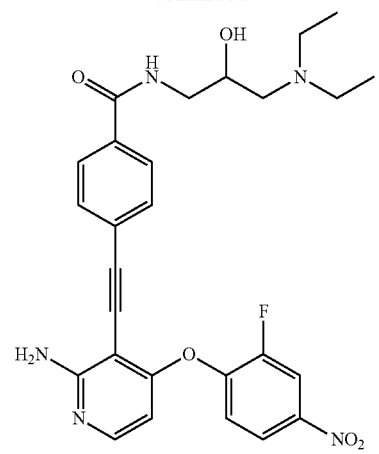
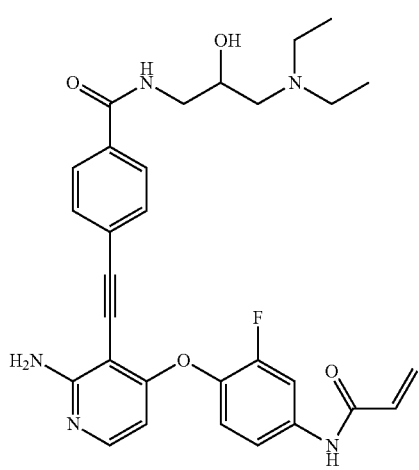
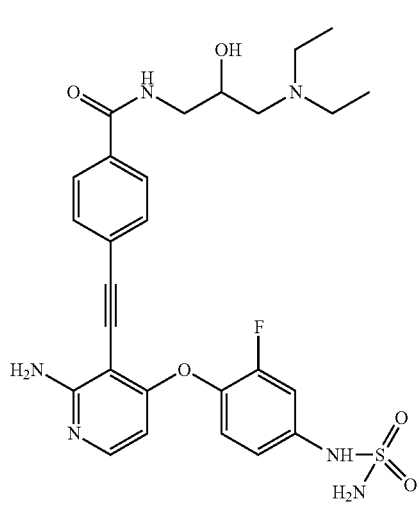
168
-continued
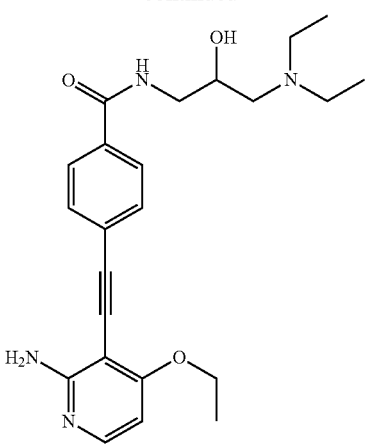
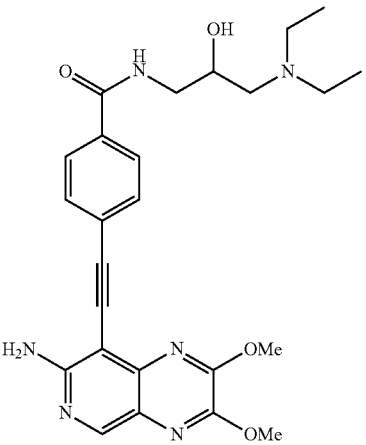
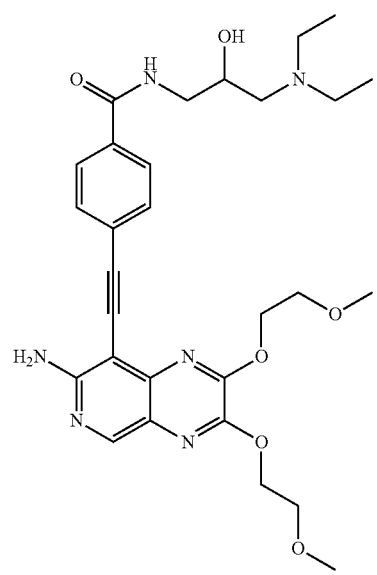

169
-continued
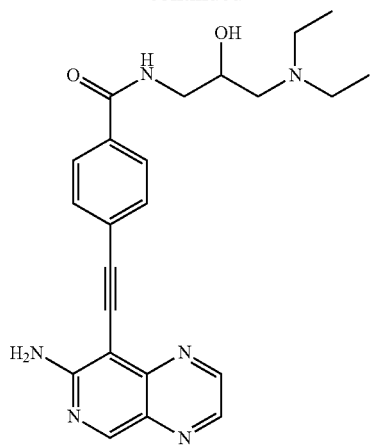
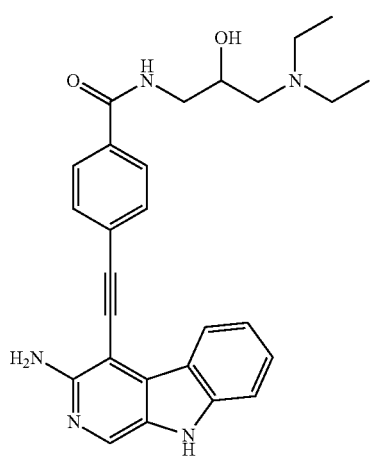
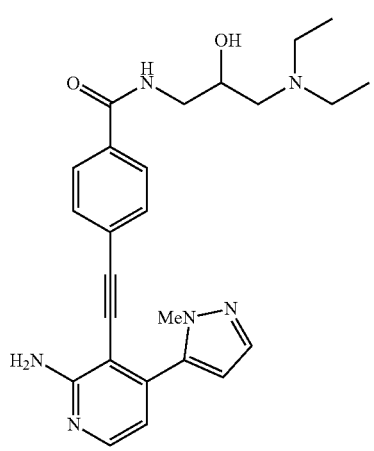
170
-continued
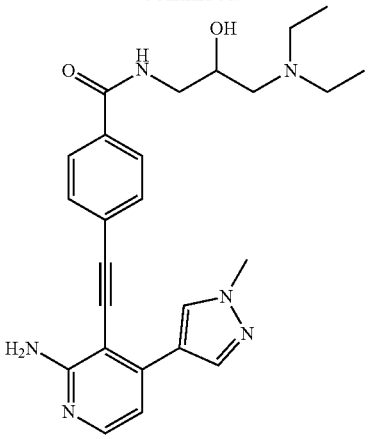
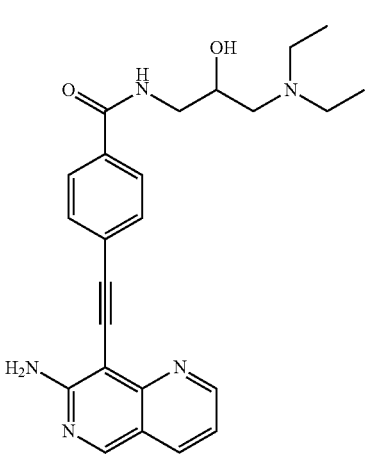
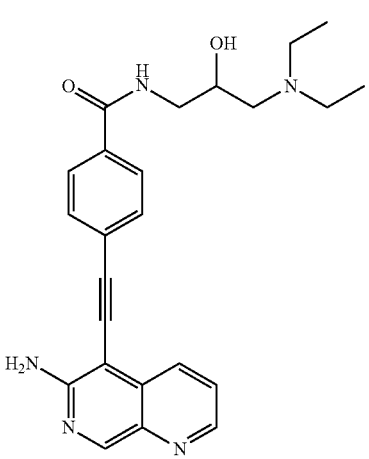

171
-continued
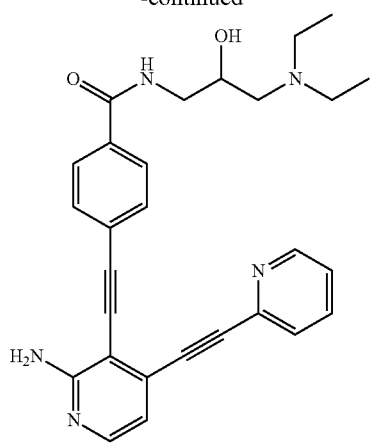
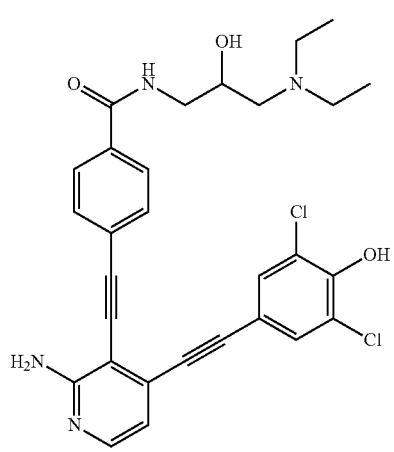
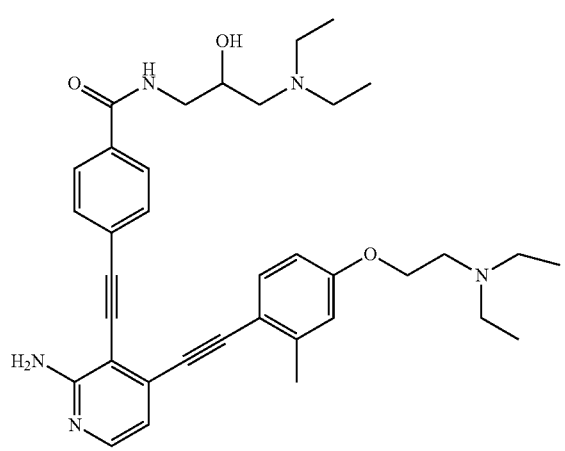
172
-continued
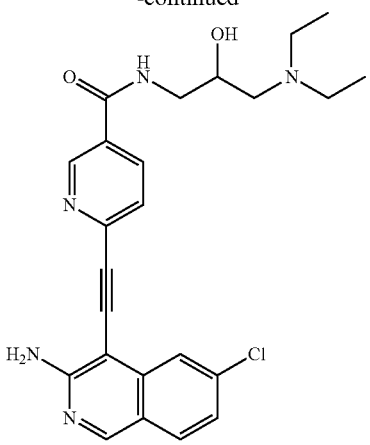
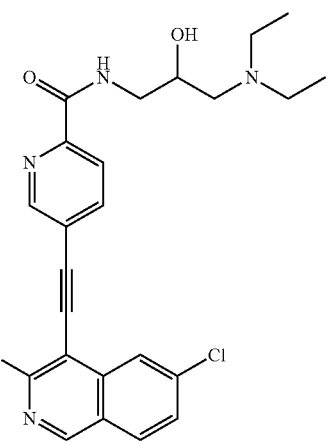
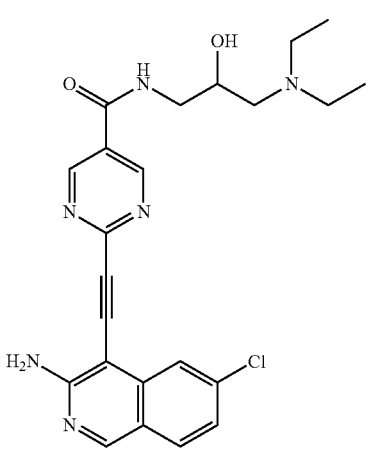

173
-continued
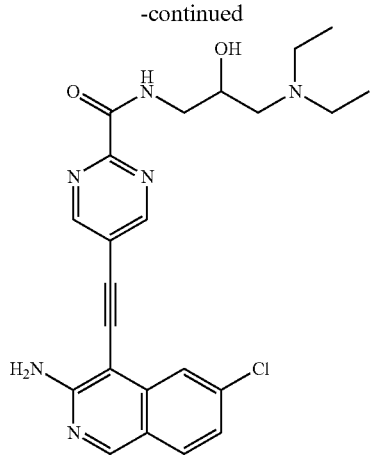
174
-continued
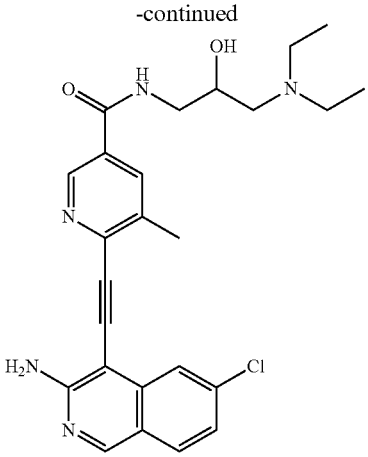
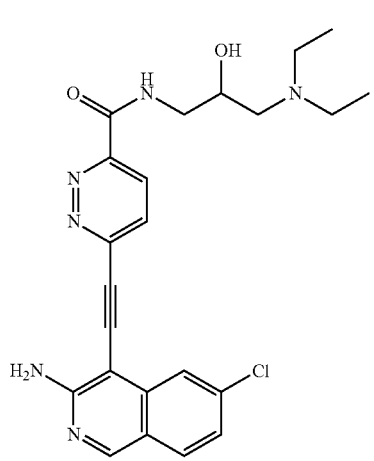

175
-continued
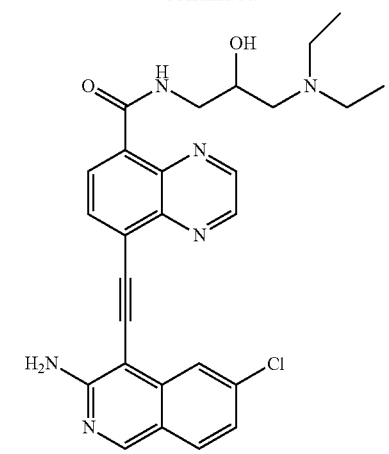
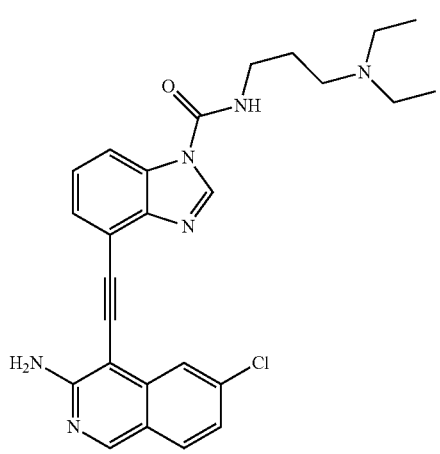
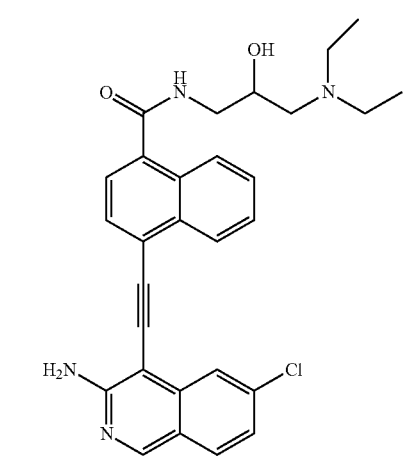
176
-continued
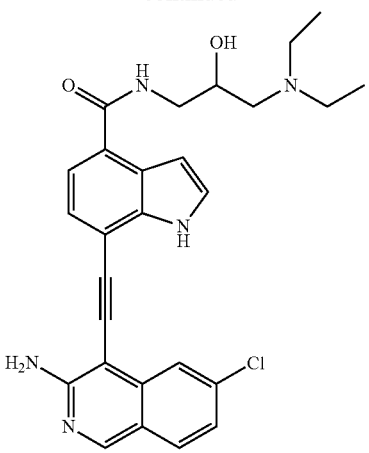
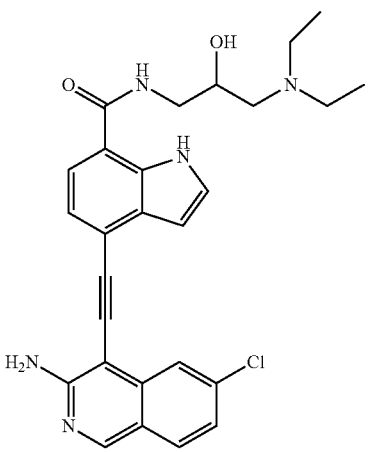
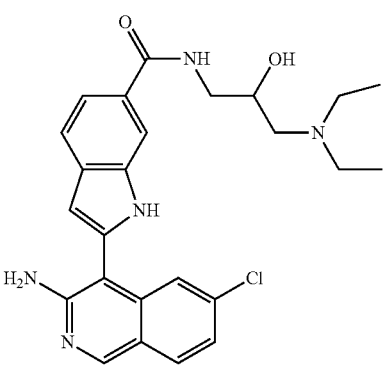
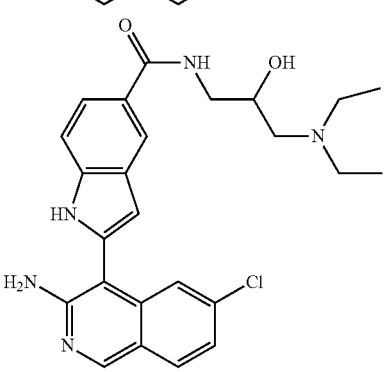

177
-continued
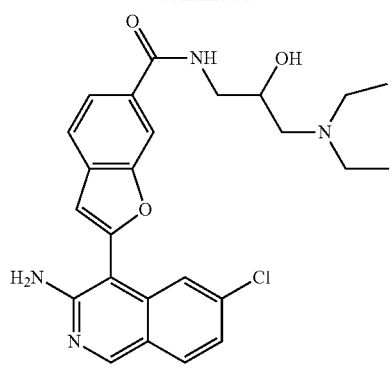
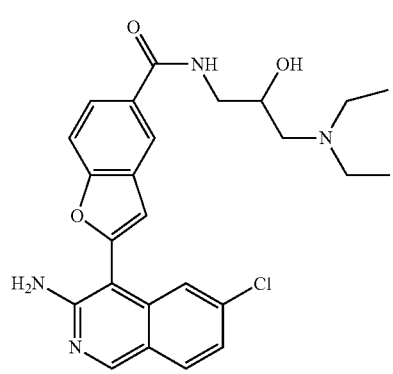
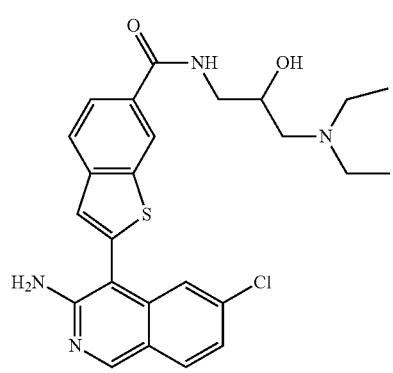
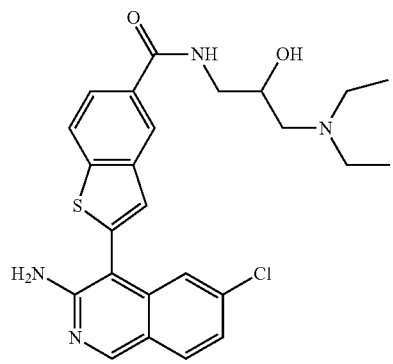
178
-continued
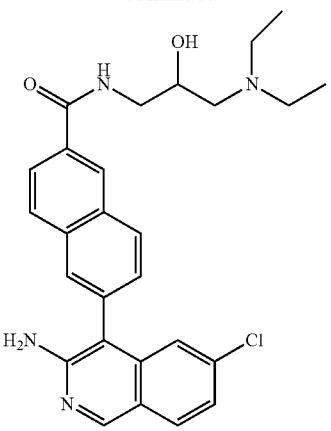
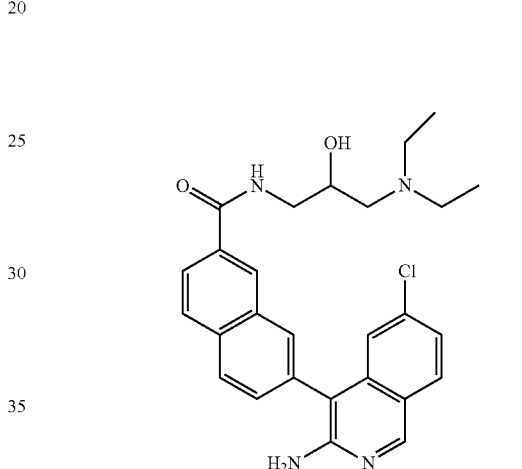
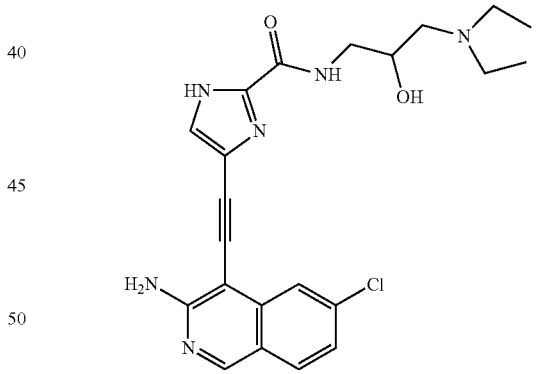
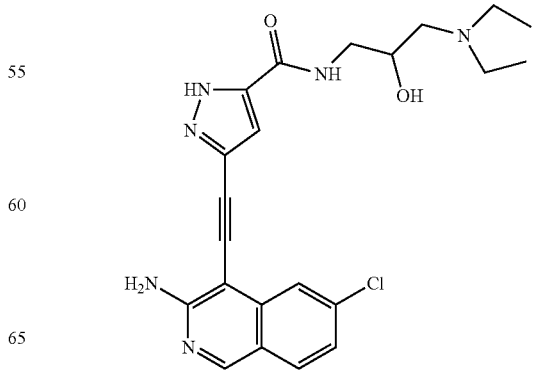

179
-continued
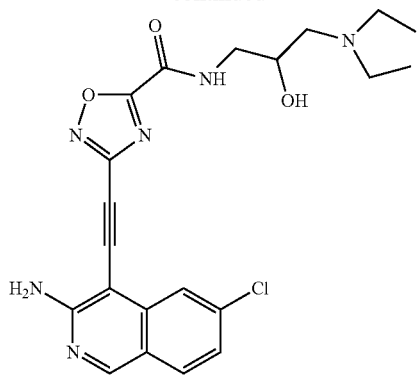
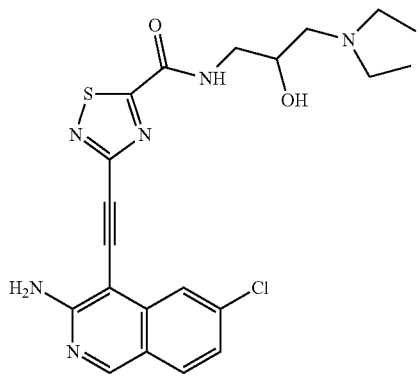
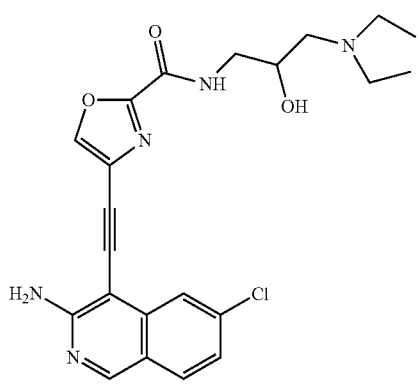
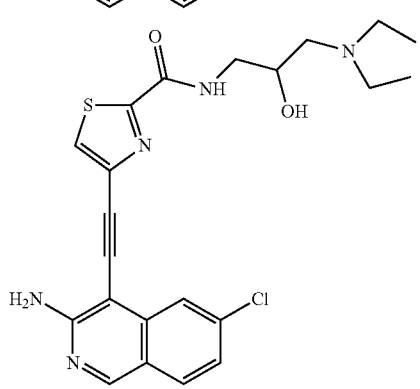
180
-continued
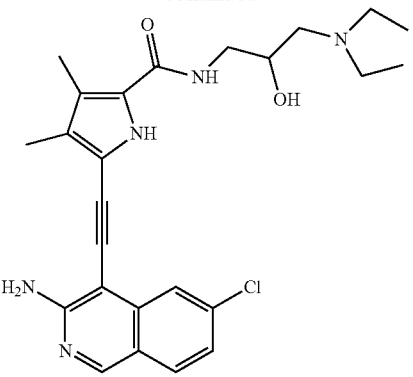
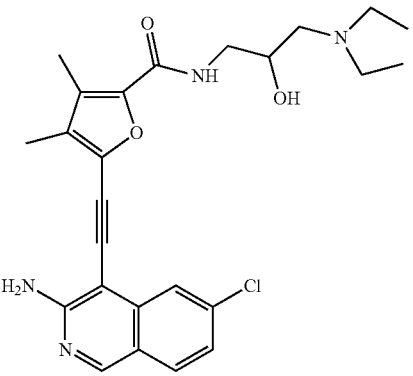
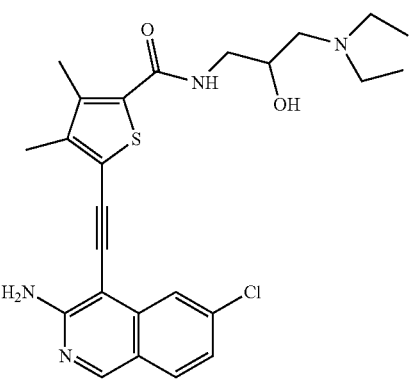
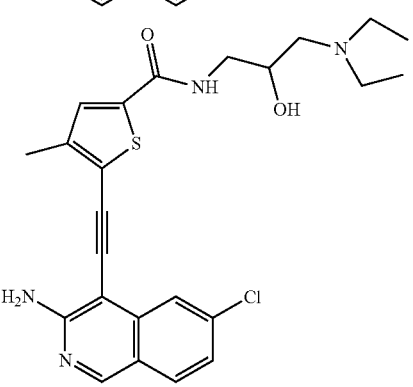

181
-continued
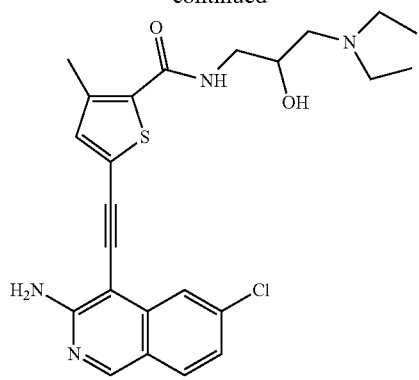
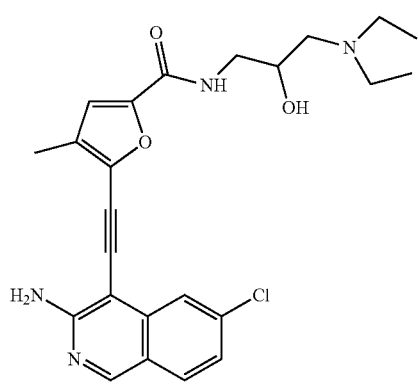
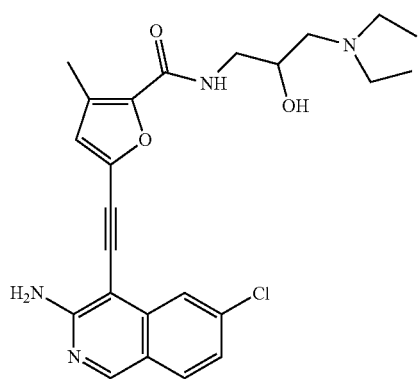
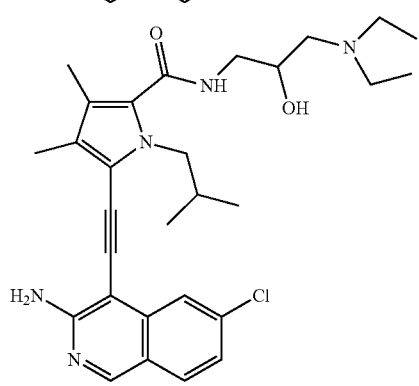
182
-continued
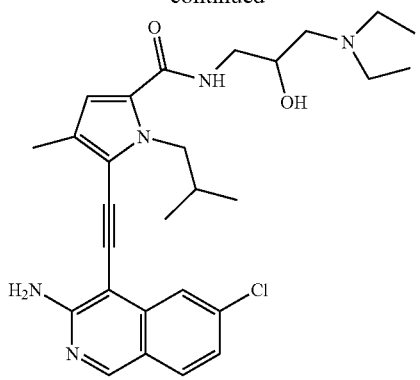
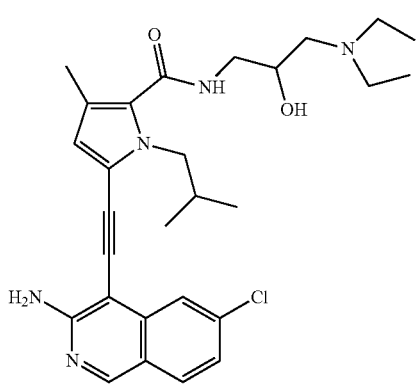
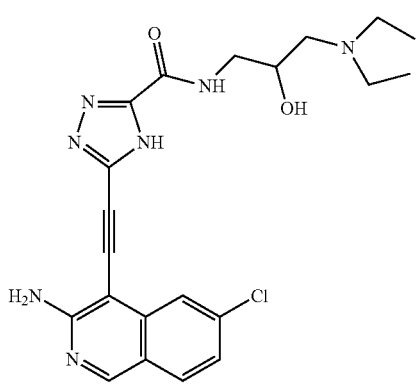
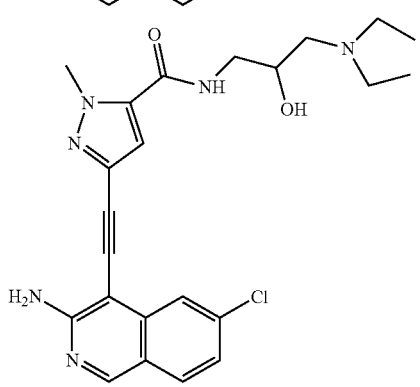

183
-continued
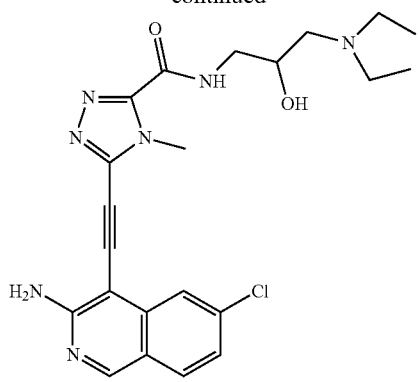
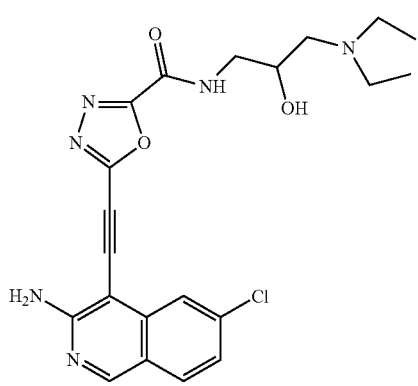
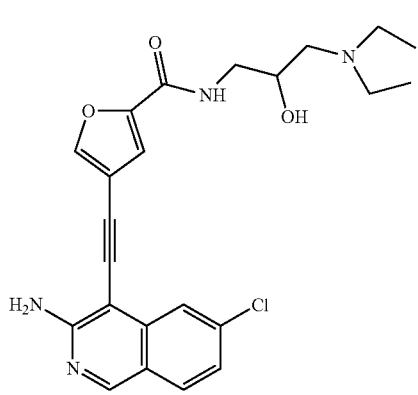
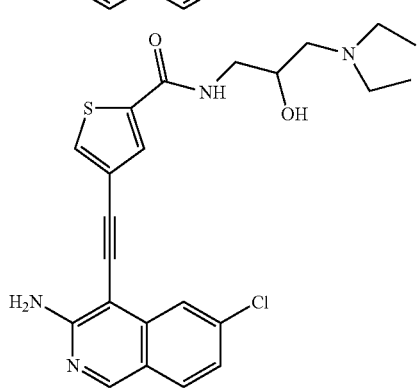
184
-continued
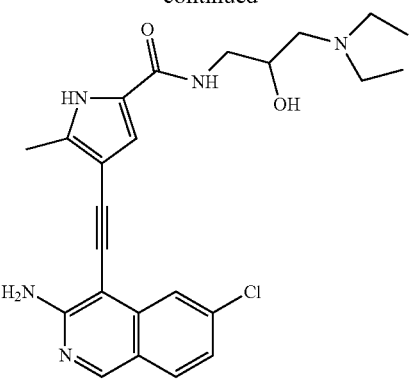
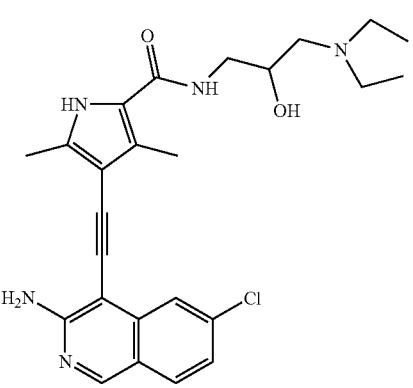
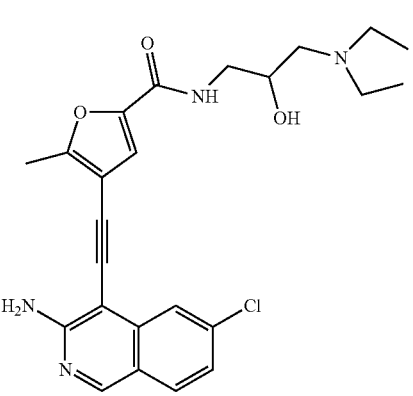
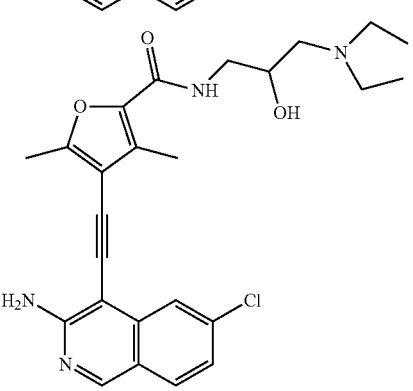

185
-continued
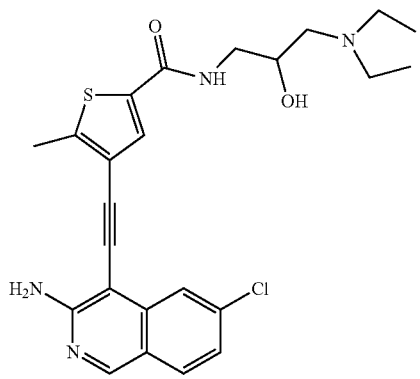
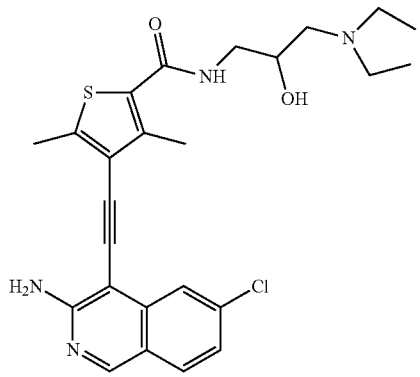
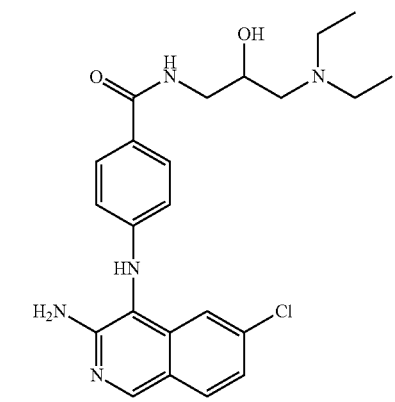
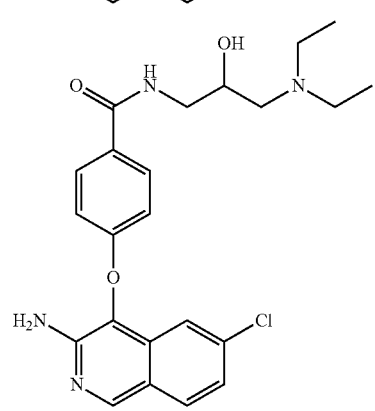
186
-continued
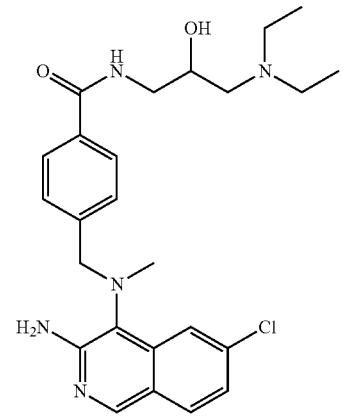
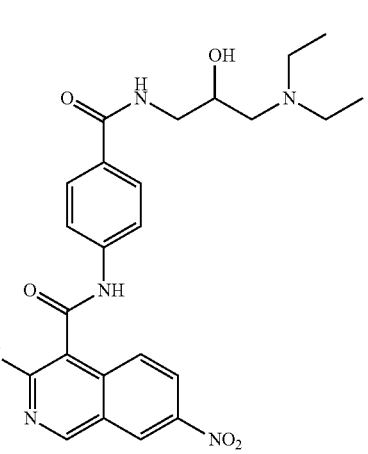
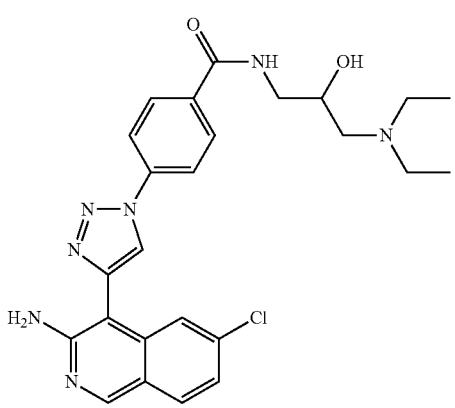
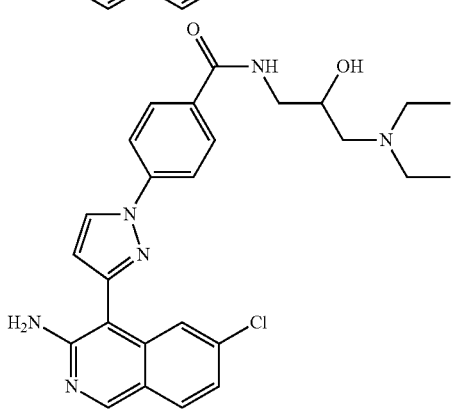

187
-continued
188
-continued
In some embodiments, the compound is the invention is

189
-continued
HSN356c
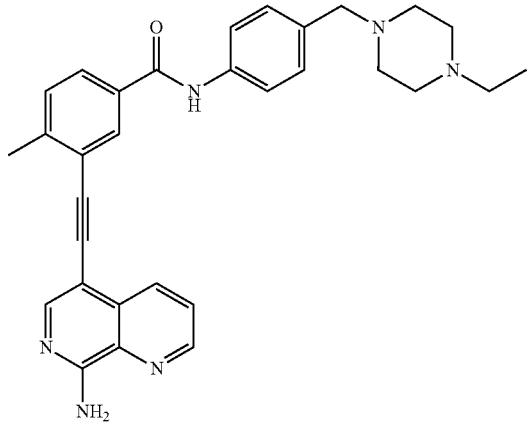
HSN356d
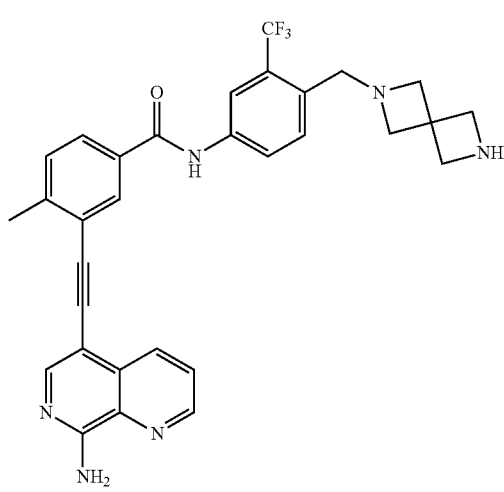
HSN356e
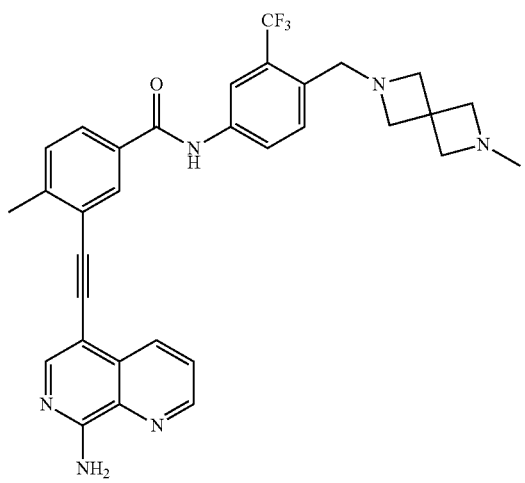
190
-continued
HSN356f
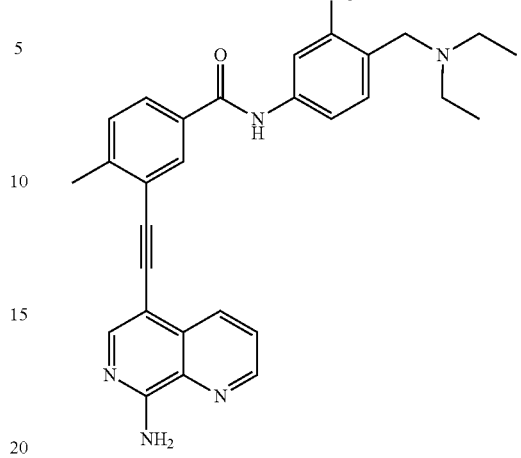
HSN356g
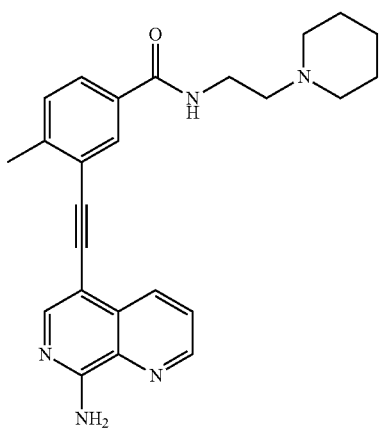
HSN356h
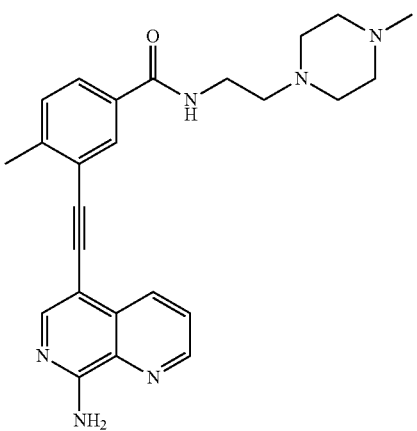

HSN286
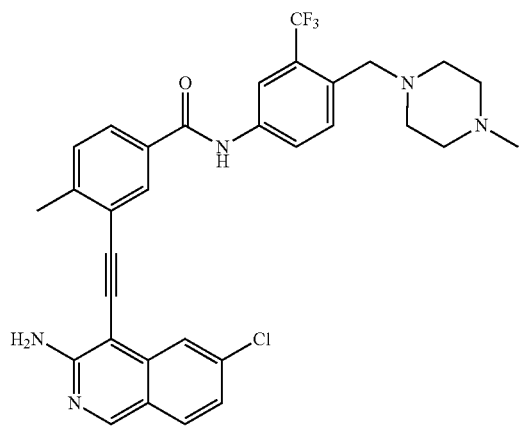
HSN286b
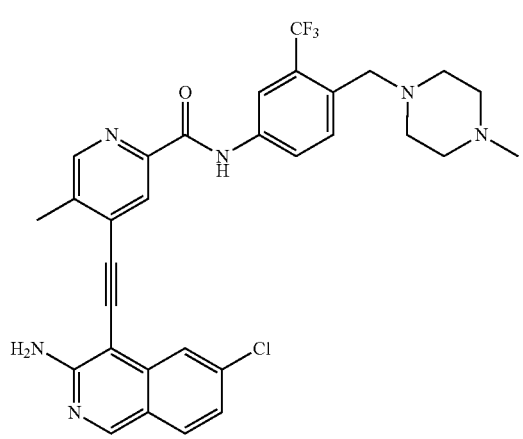
HSN286c
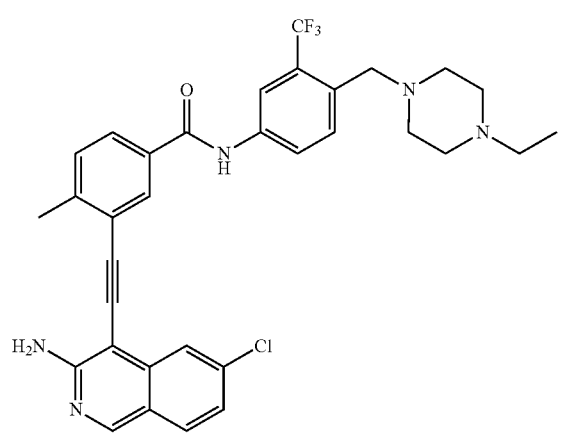
HSN286d
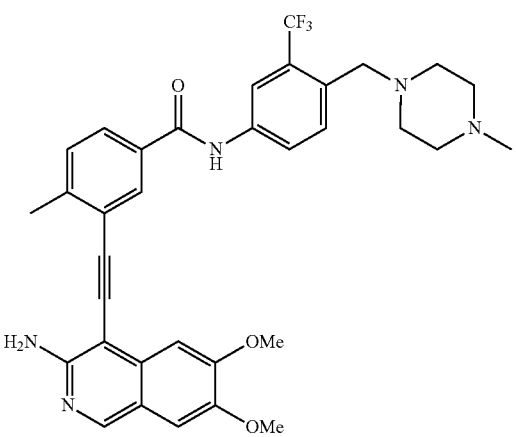
HSN286e
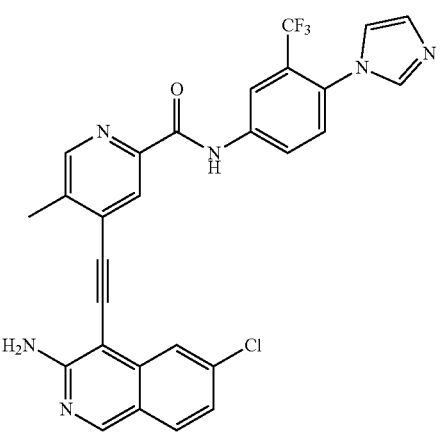
HSN286f
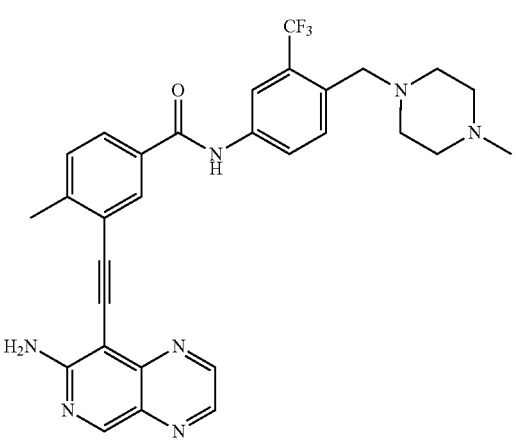

193
-continued
HSN286g
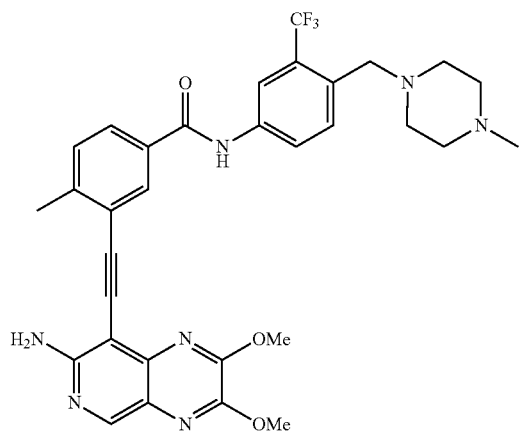
HSN286g
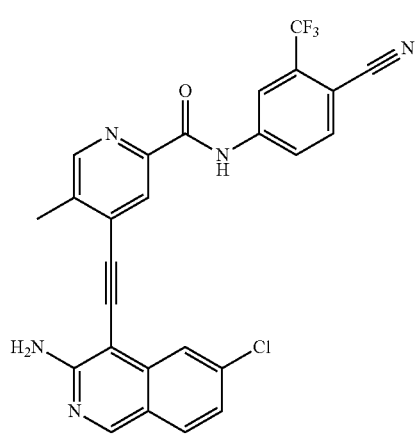
HSN286h
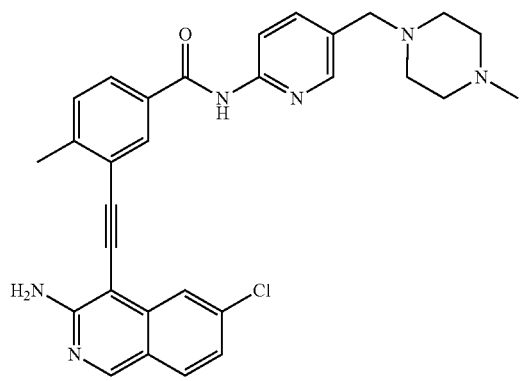
194
-continued
HSN286i
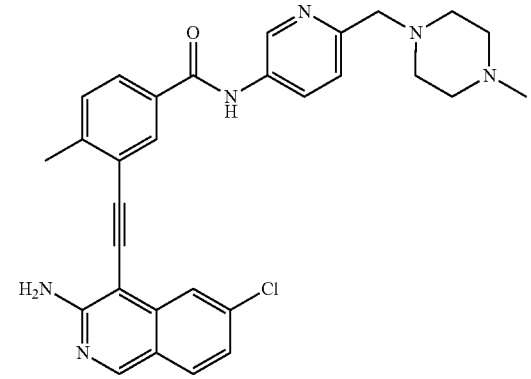
HSN286j
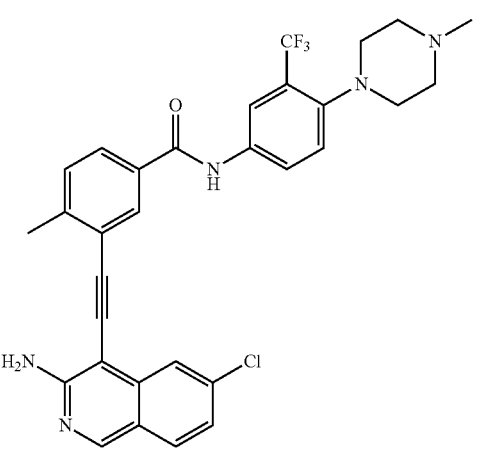
HSN286k
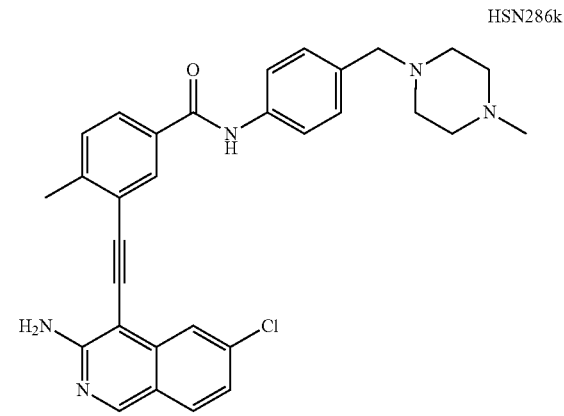

-continued
HSN286l
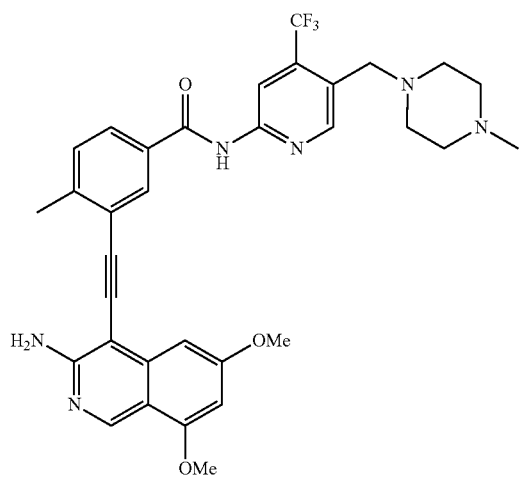
HSN286m
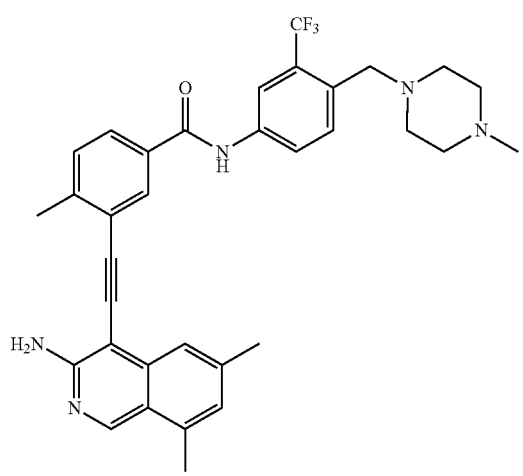
HSN286n
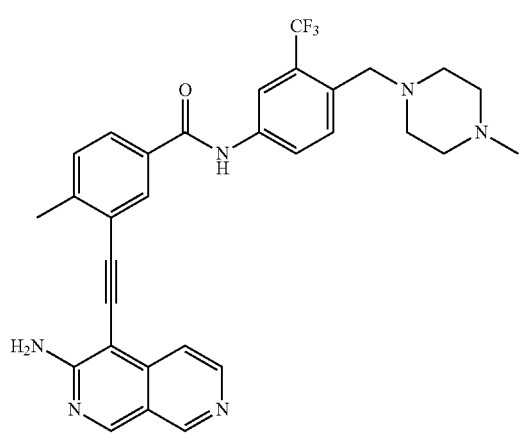
-continued
HSN286o
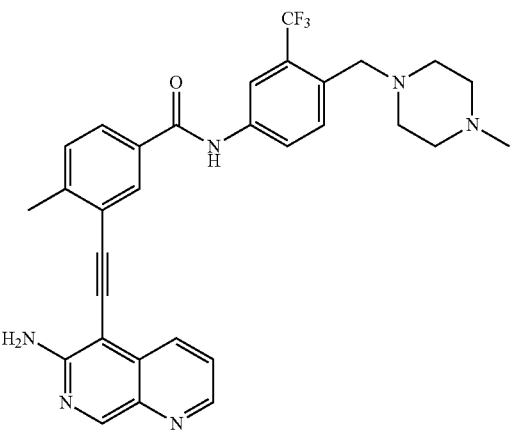
HSN286p
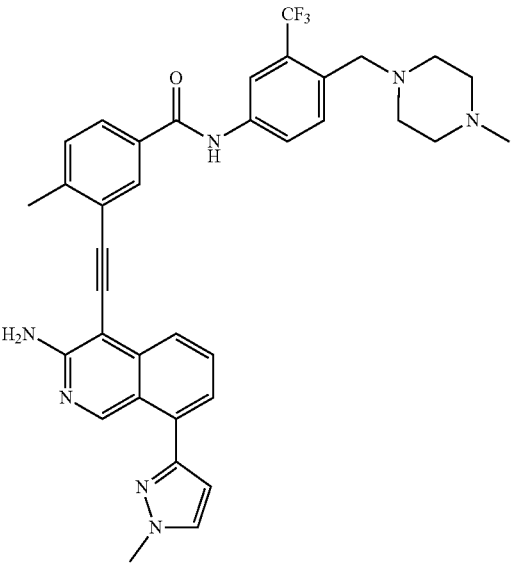
HSN286q
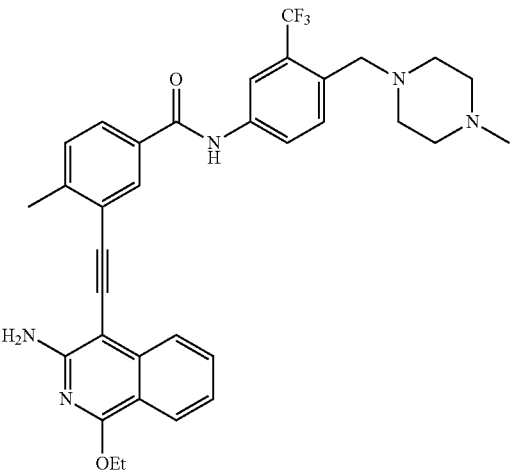

| HSN286r | HSPu002 |
|---|---|
| 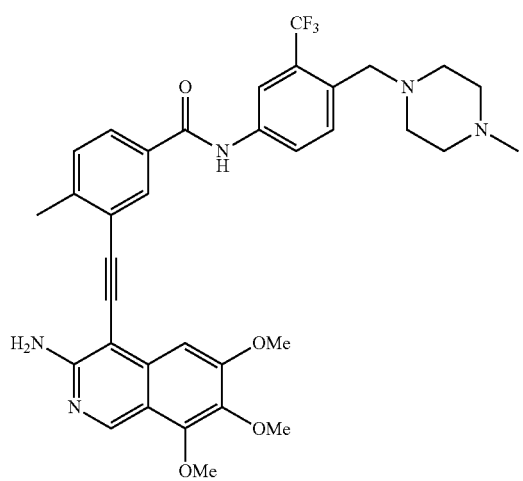 | 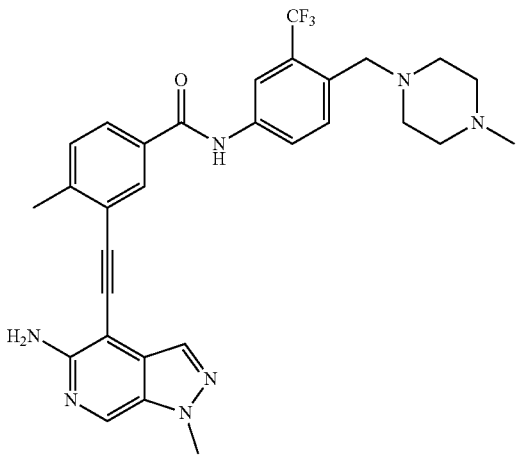 |
| HSN286s | HSPu003 |
|---|---|
| 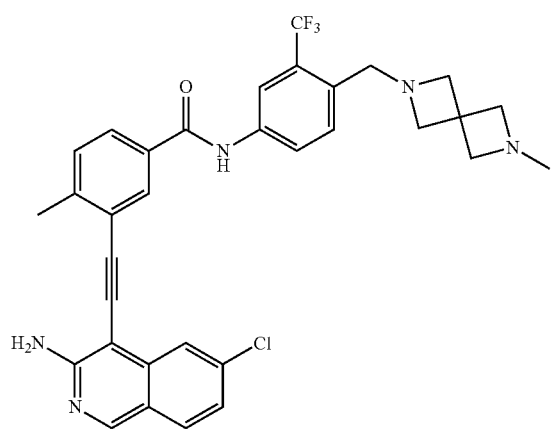 | 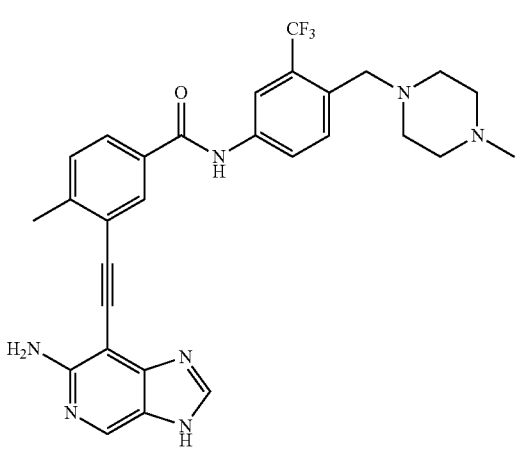 |
| HSPu001 | HSPu004 |
|---|---|
| 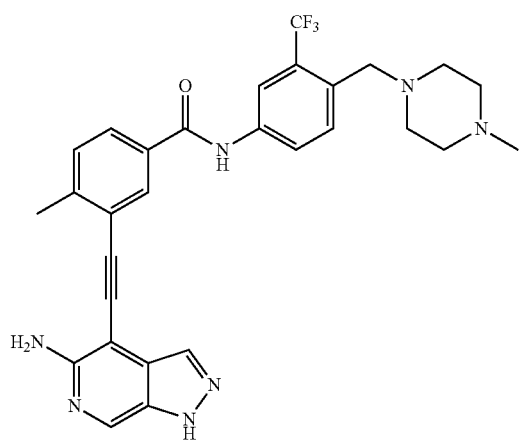 | 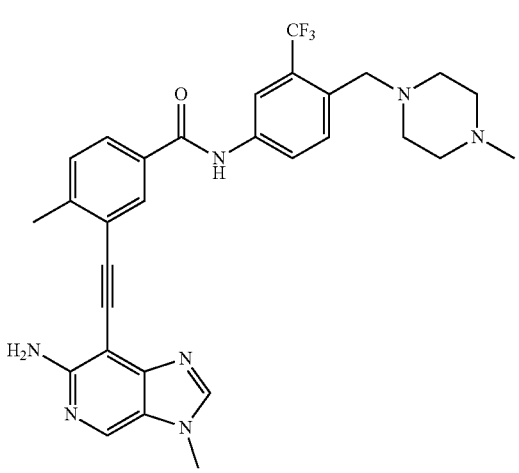 |

199
-continued
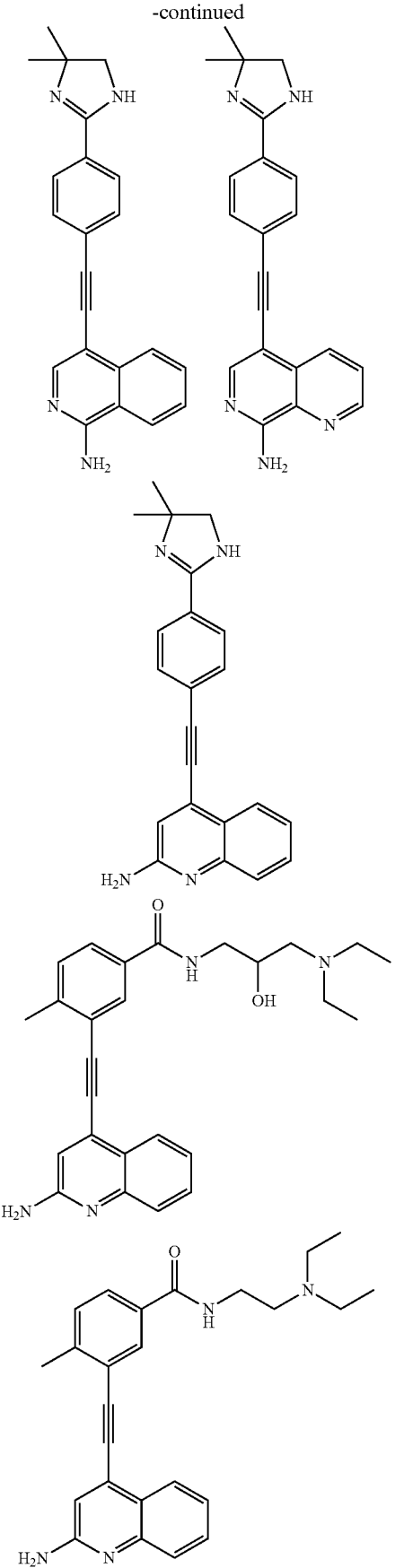
200
-continued
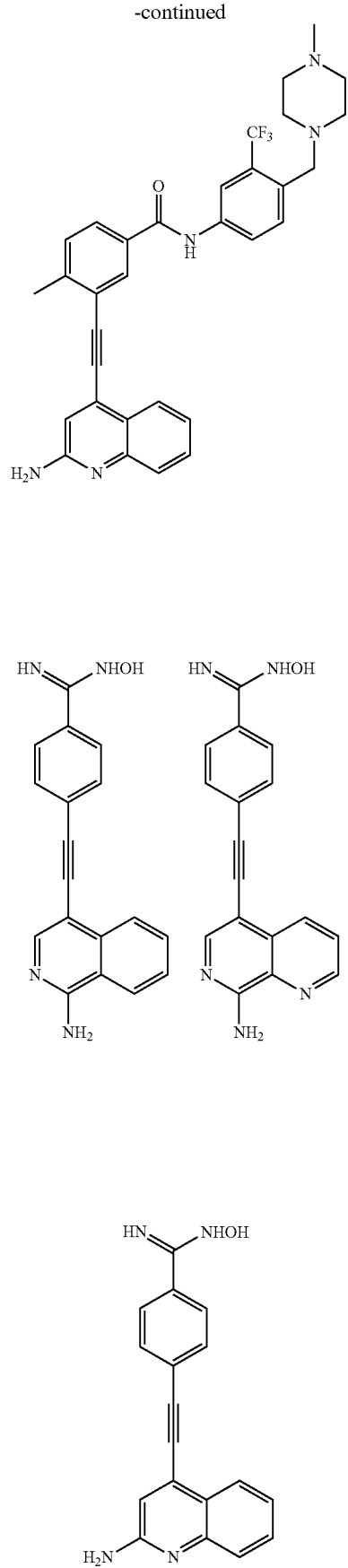

201
-continued
202
-continued
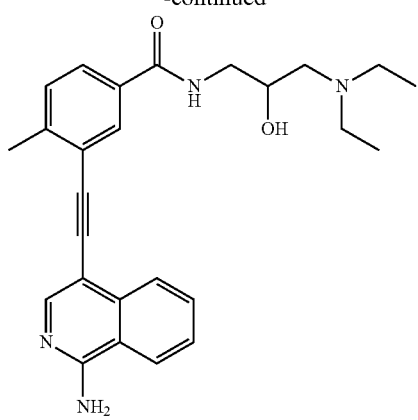
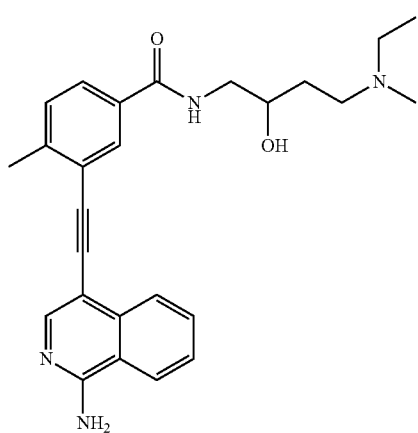
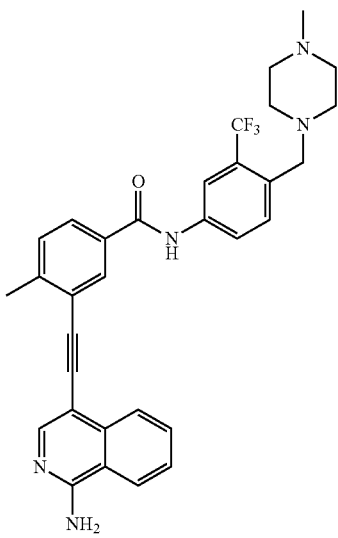
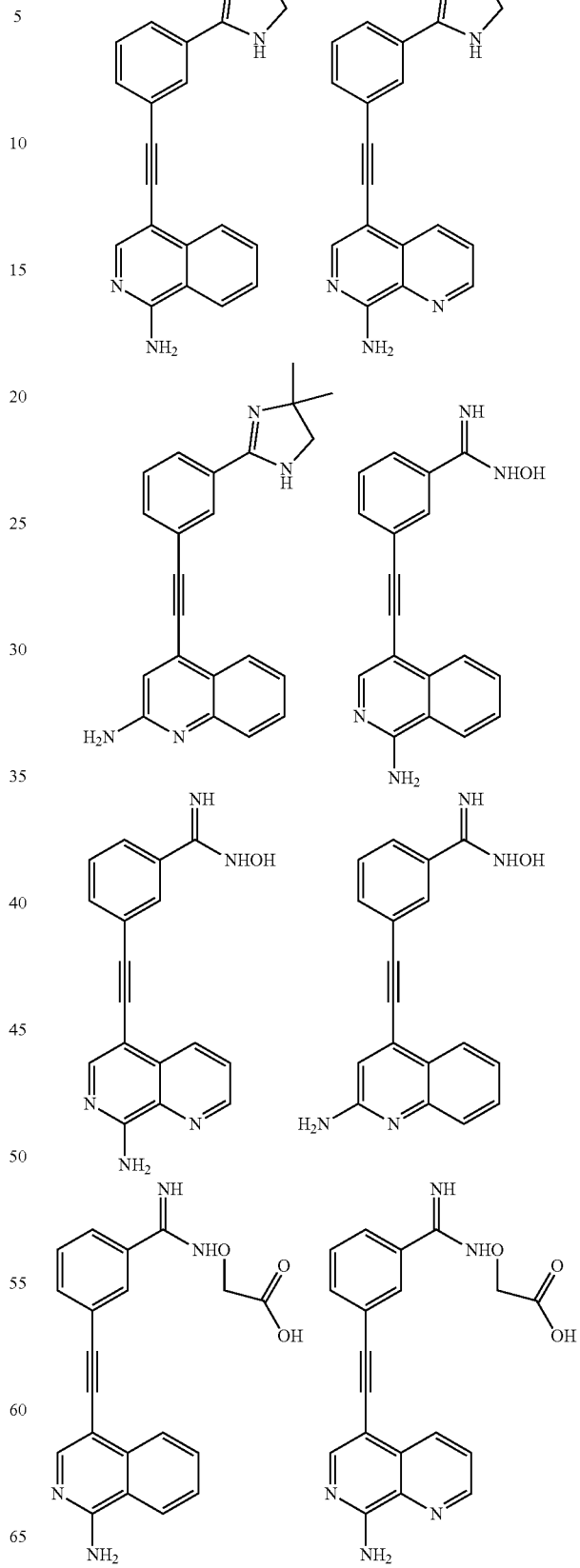

203
-continued
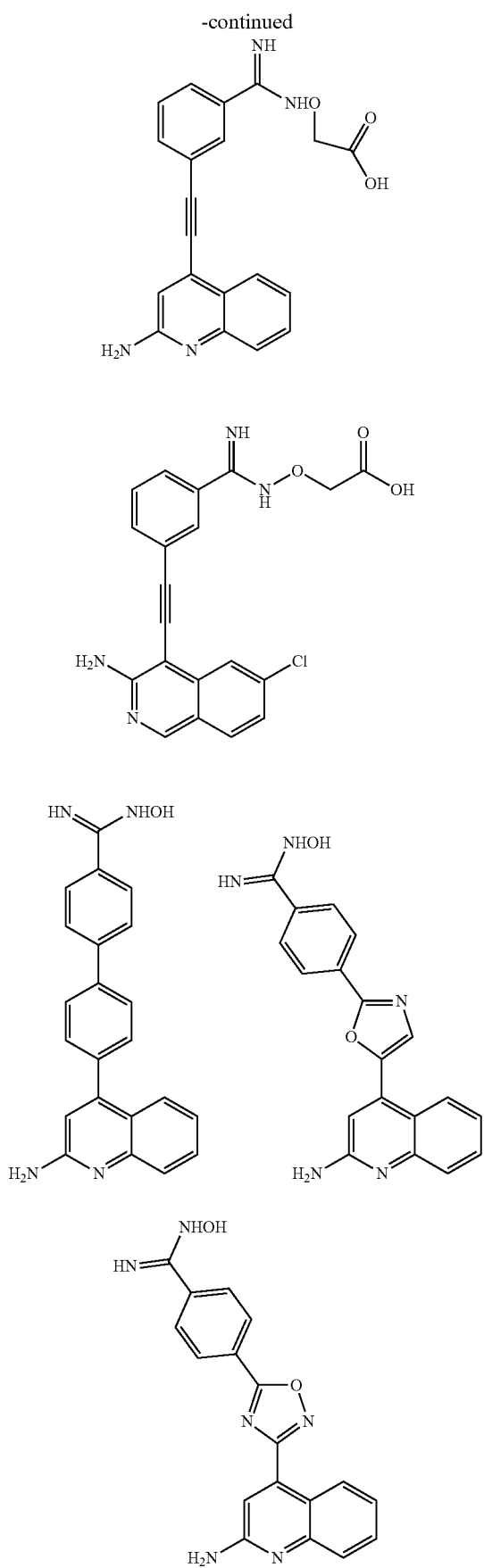
204
-continued
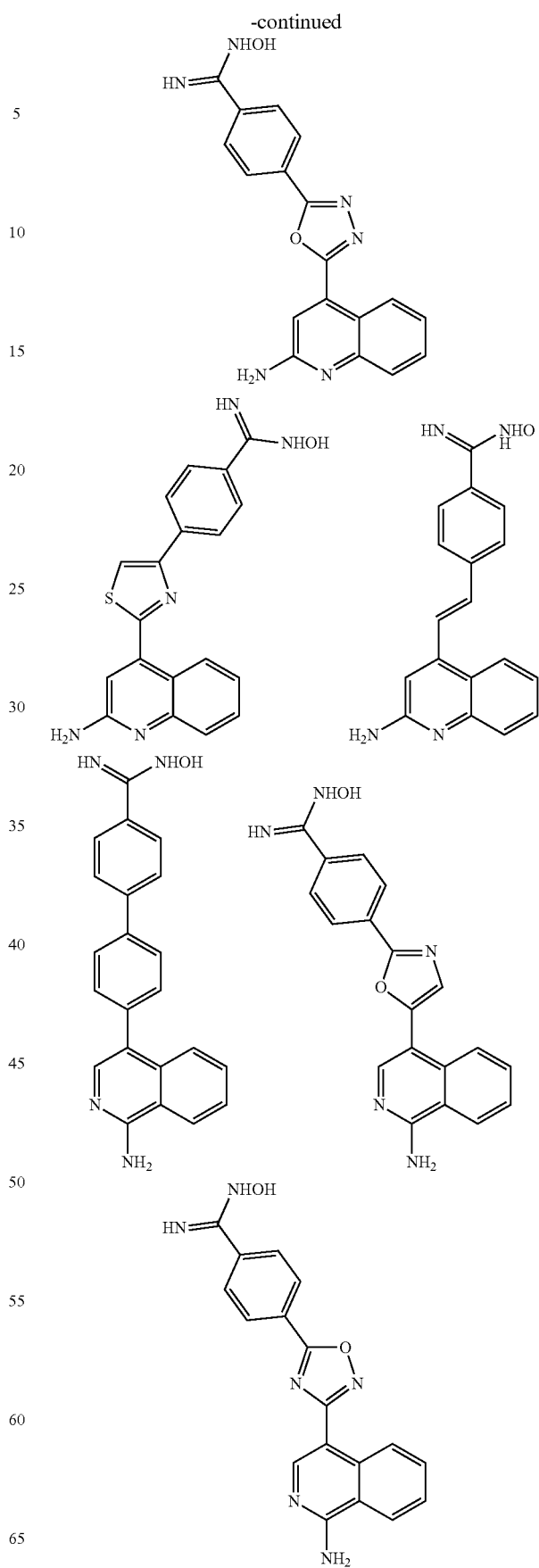

205
-continued
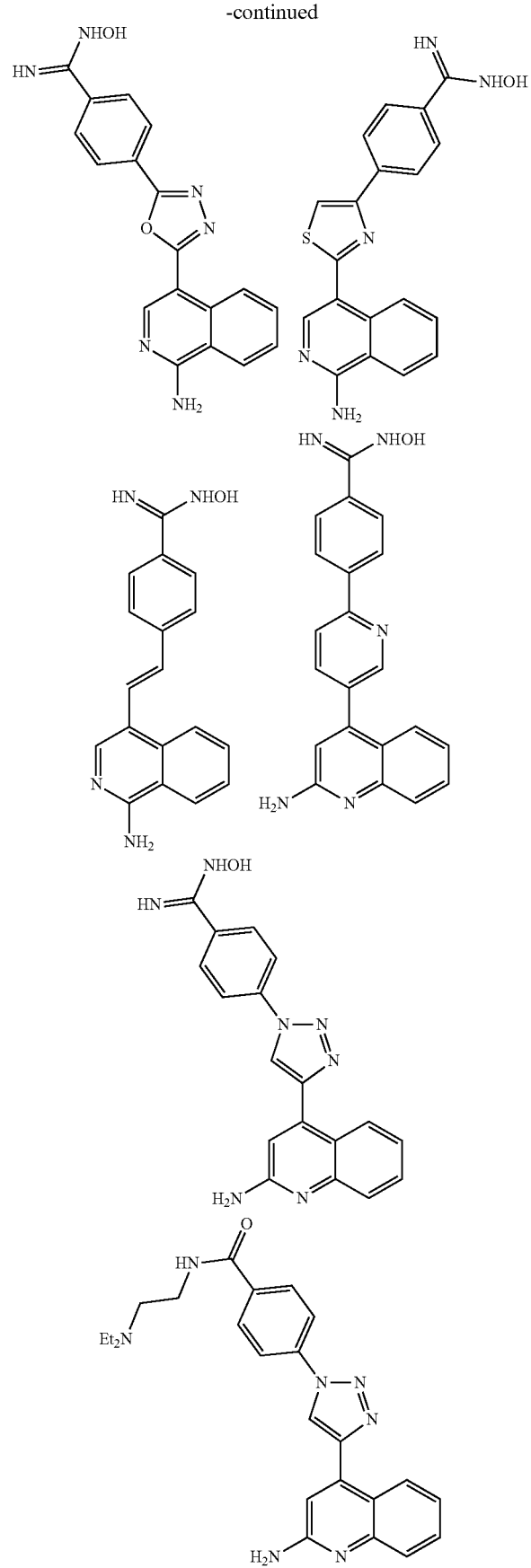
206
-continued
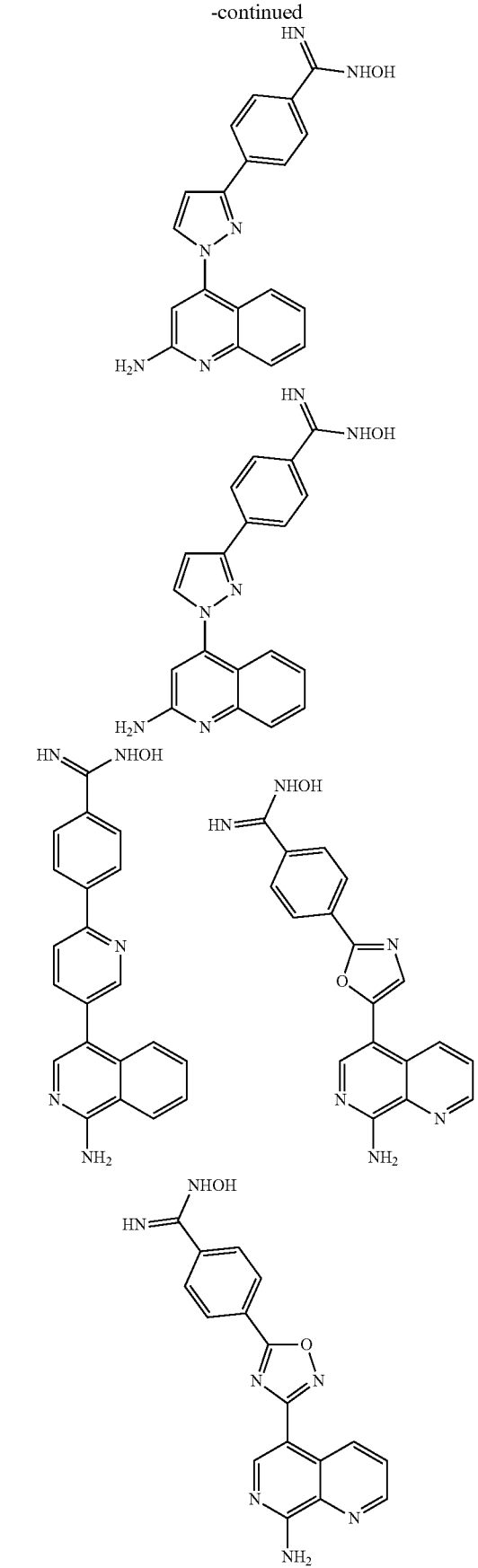

207
-continued
208
-continued
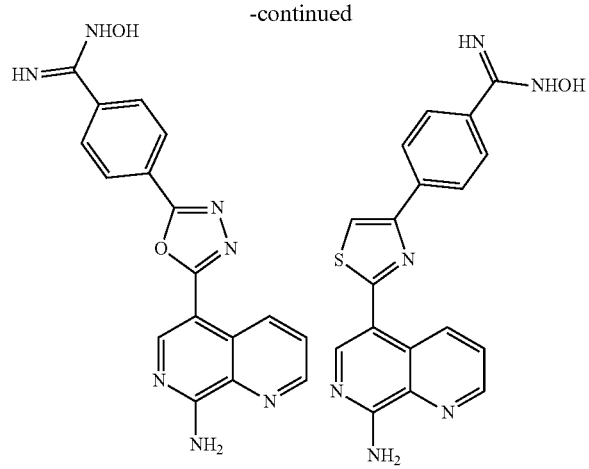
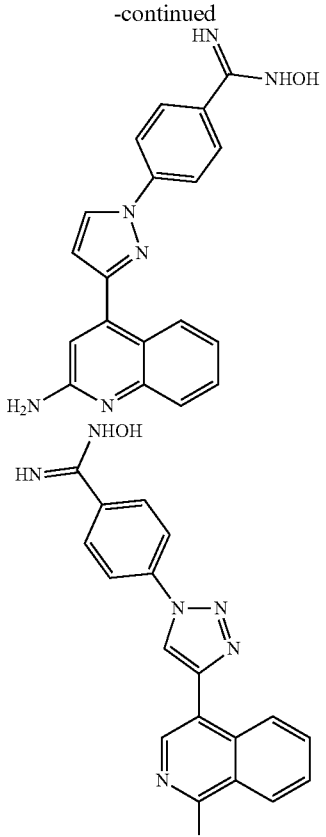
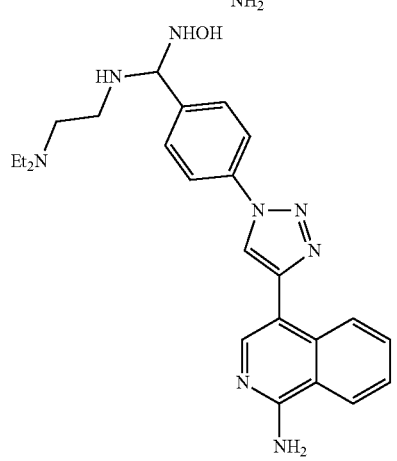
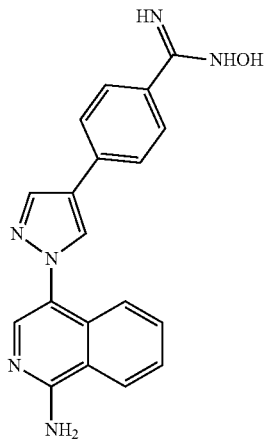

-continued
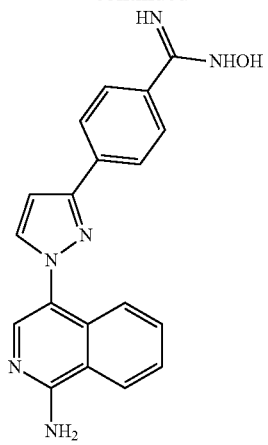
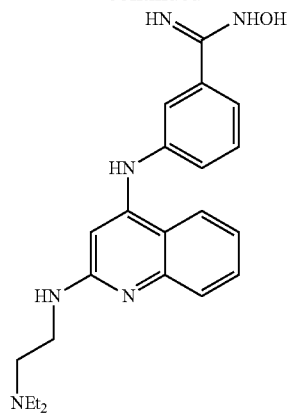
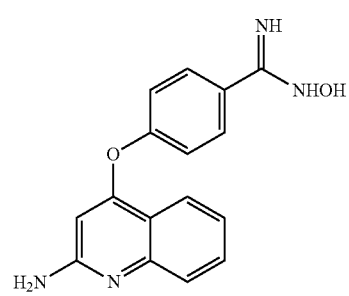
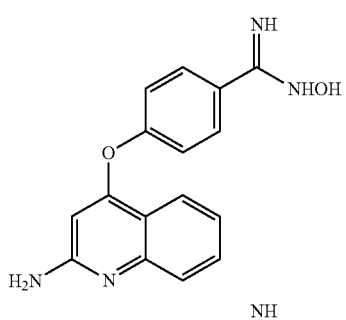
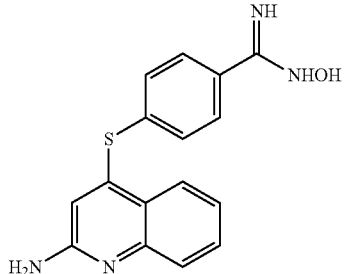
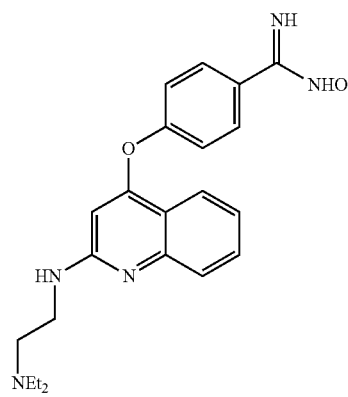
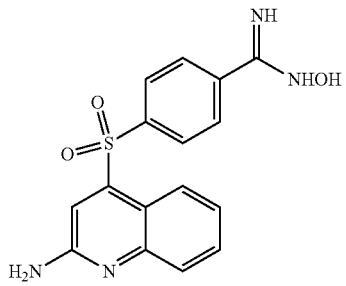
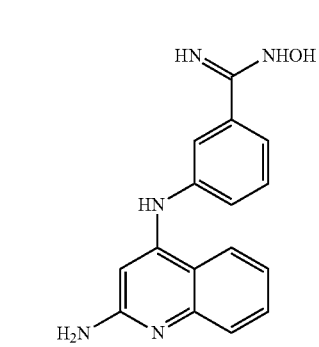
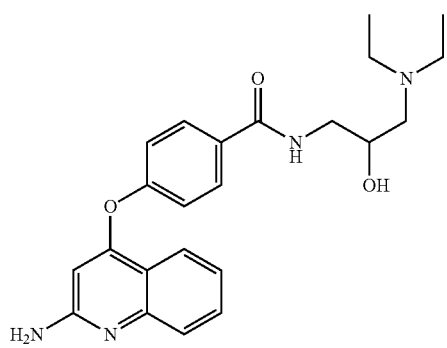

211
-continued
212
-continued
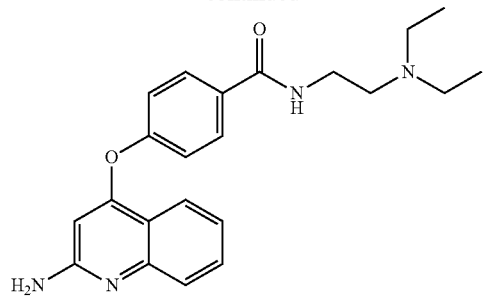
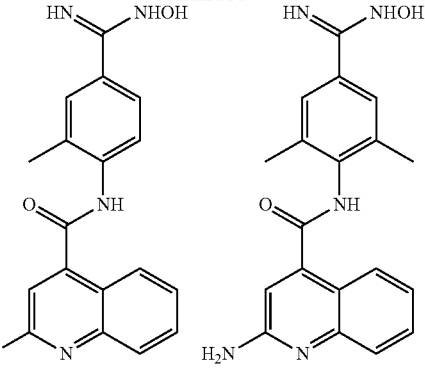
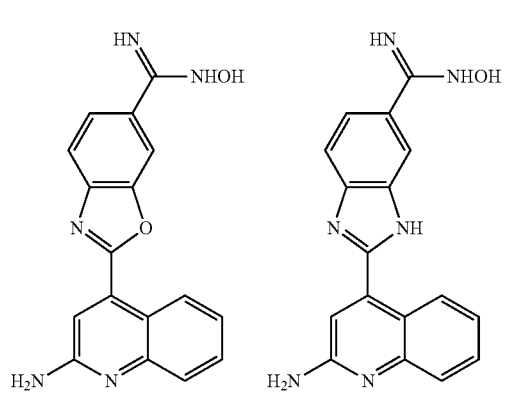
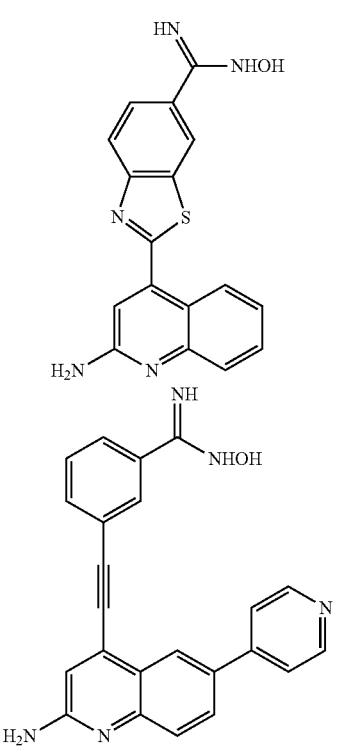

213
-continued
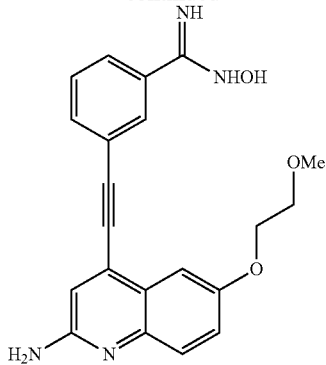
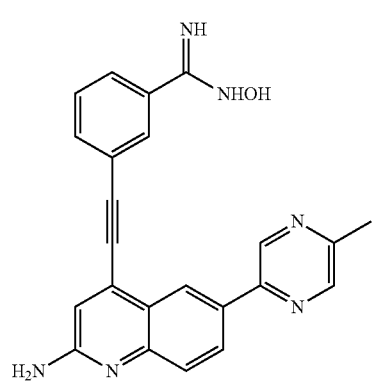
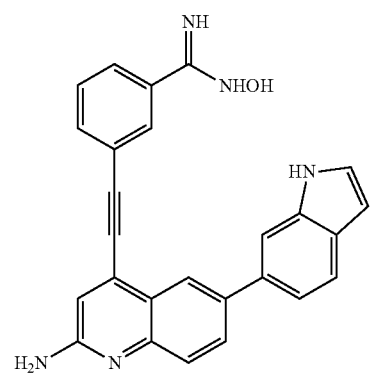
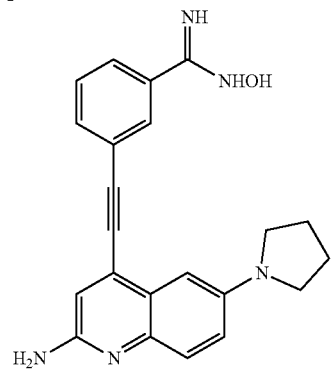
214
-continued
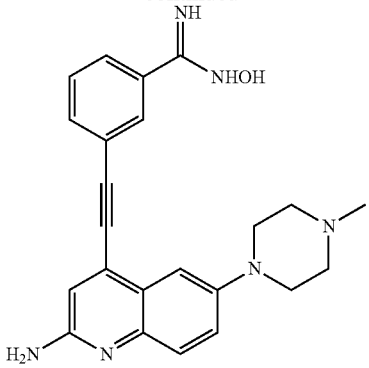
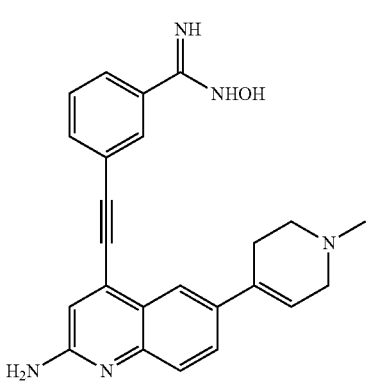
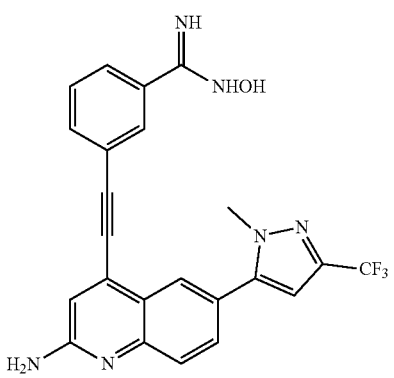
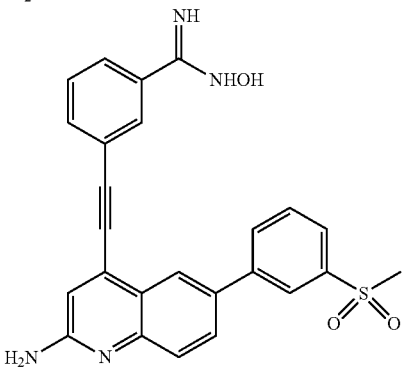

215
-continued
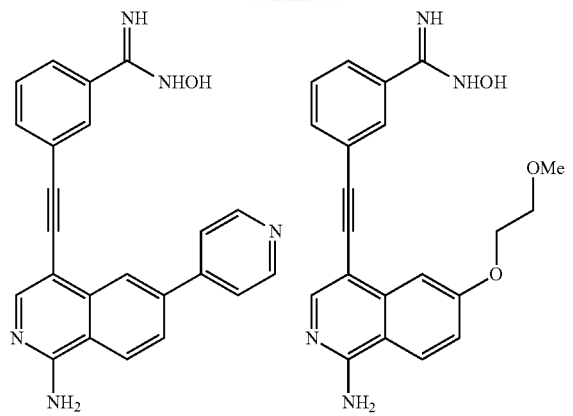
216
-continued
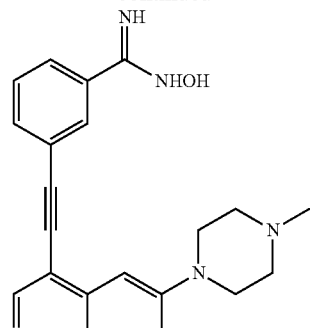
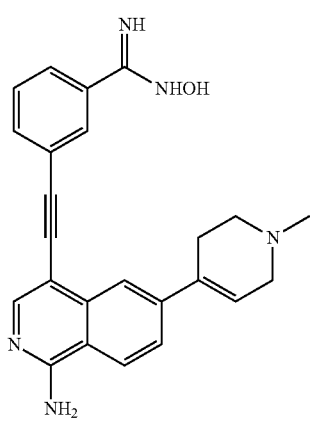
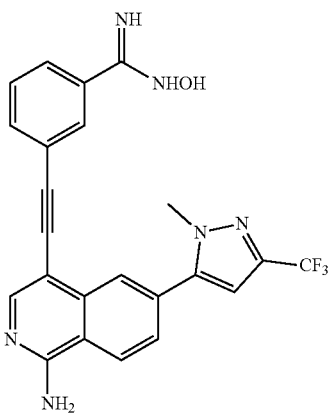
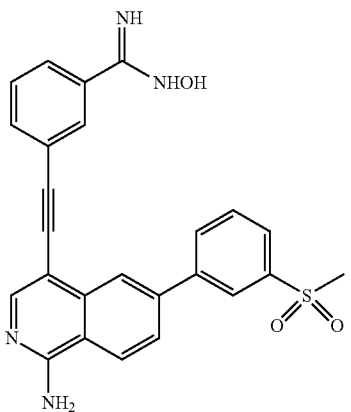

217
-continued
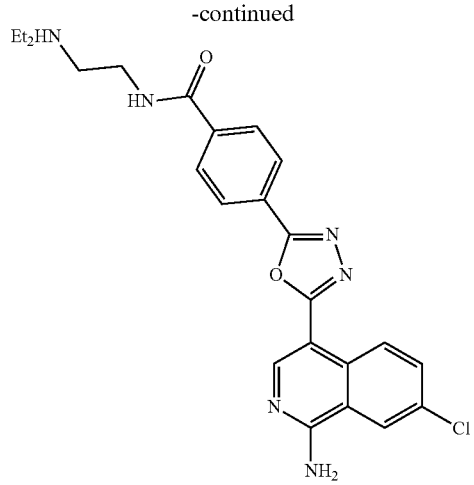
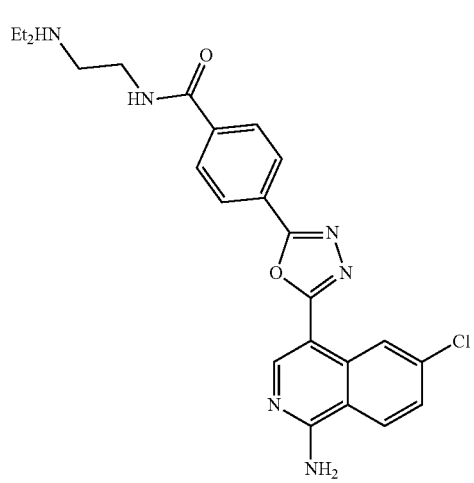
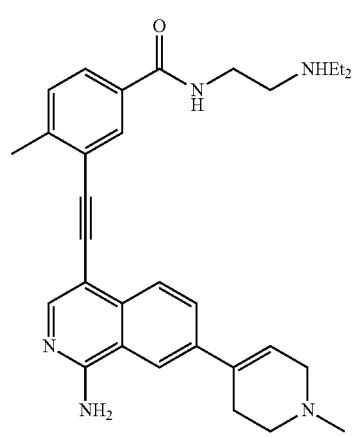
218
-continued
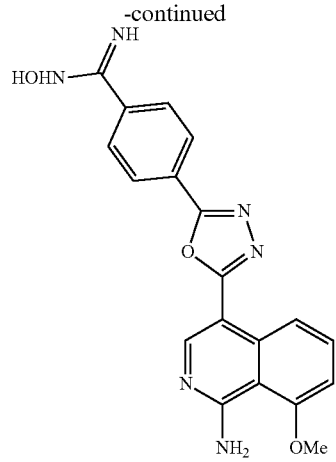
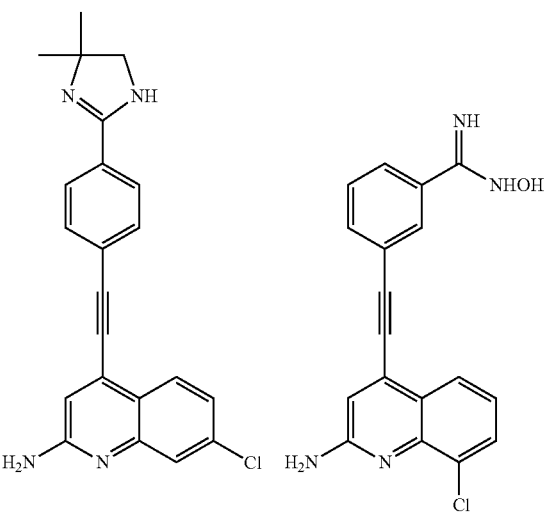
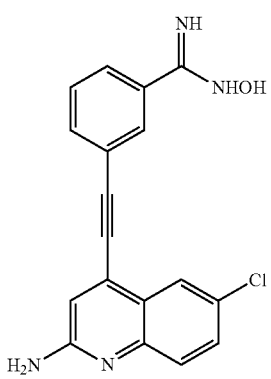

-continued
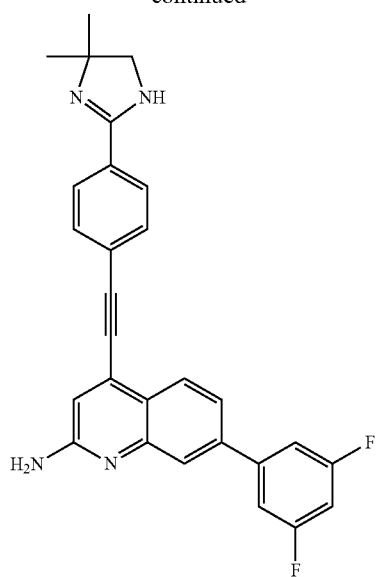
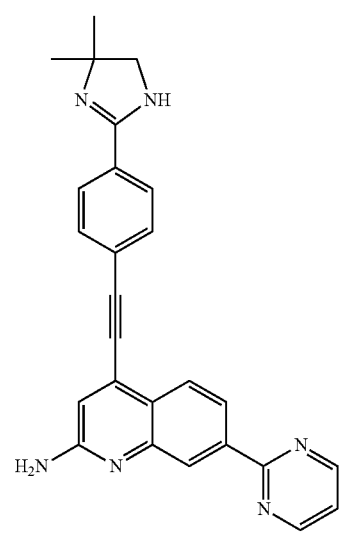 [SMILES: CC1(C)CNC(c2ccc(C#Cc3cc(N)nc4cc(-c5ncccn5)ccc34)cc2)=N1]
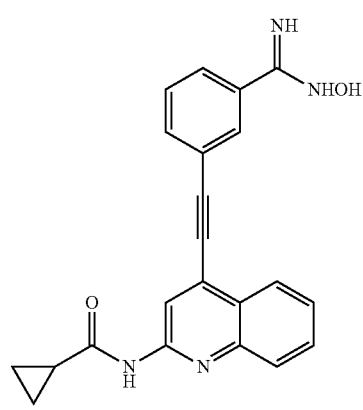
-continued
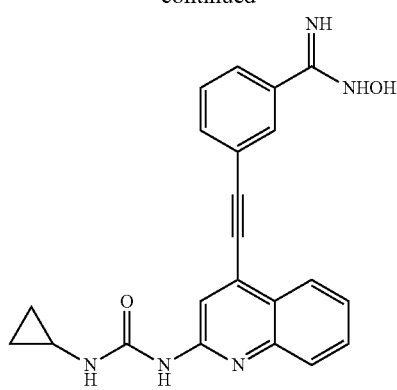
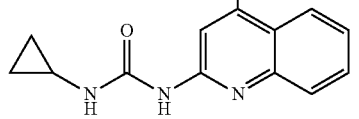
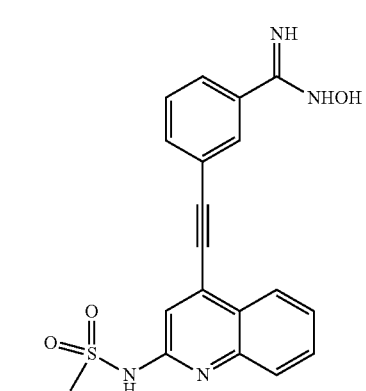
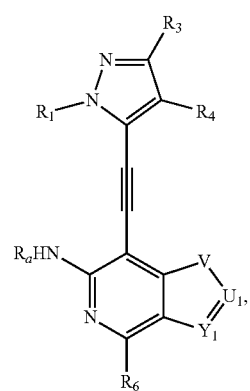

221
-continued
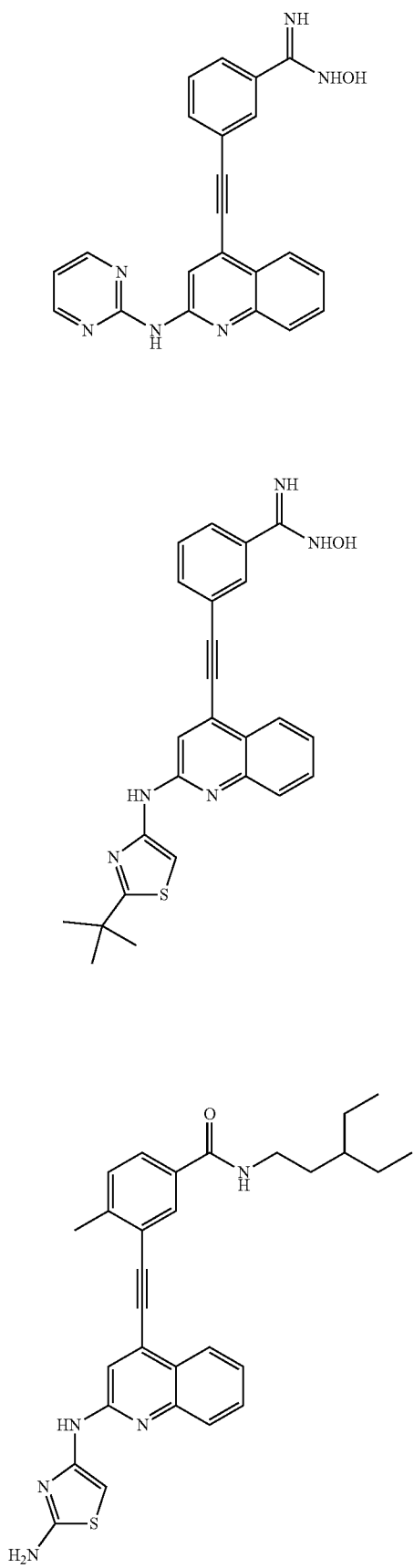
222
-continued
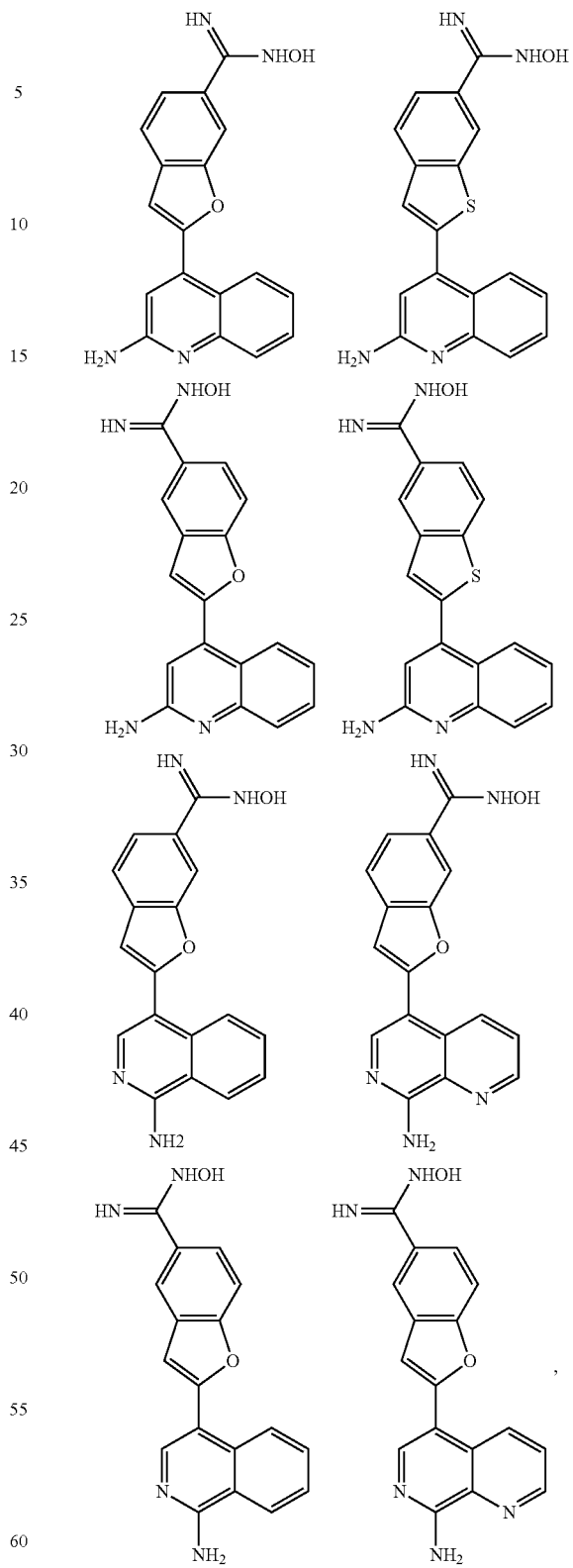
,
or a pharmaceutically acceptable salt, N-oxide, hydrate, solvate, tautomer, or optical isomer thereof.
In some embodiments, the compound of formula (I) of the invention is represented by a compound of formulas $V_a$-$V_f$ (V_a)

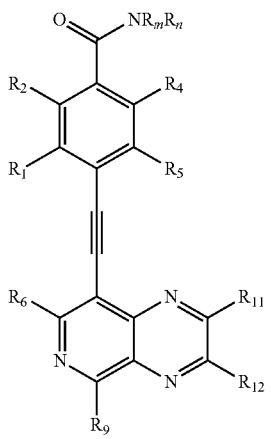

(V_b)

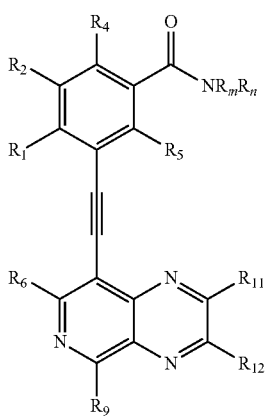

(V_c)

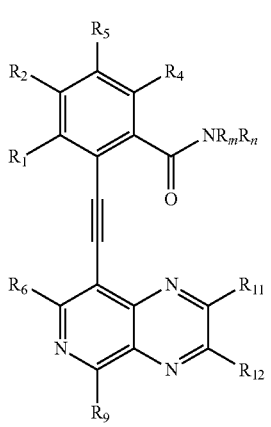

-continued (V_d)

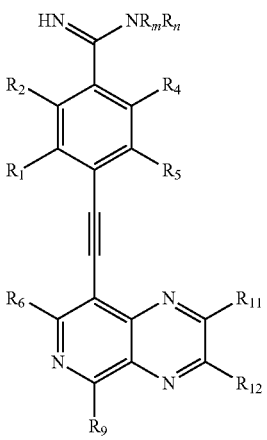

(V_e)

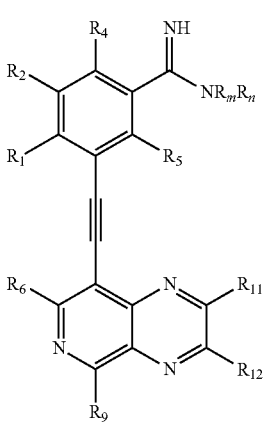

(V_f)

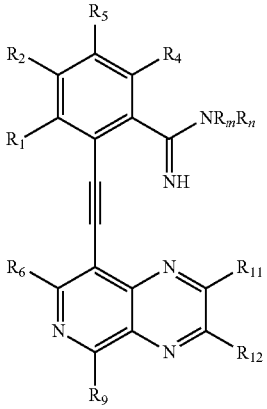

wherein $R_1$, $R_2$, $R_4$, and $R_5$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, NH(CO)-alkyl, NH(CO)$OR_c$, NH(CO)$NR_aR_b$, (CO)$OR_c$, (CO)$NR_aR_b$, $SO_2NR_aR_b$, cycloalkyl, heterocycloalkyl, aryl, or heteroaryl; and $R_{11}$ and $R_{12}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, (CO)$OR_c$, (CO)$NR_aR_b$, $SO_2NR_aR_b$, —C(CH$_3$)(=N—NHC(NH)NH$_2$, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, dialkylamino, —NH(CO)-alkyl, or —NH(CO)— alkenyl.

In some embodiments, the compound of formula (I) of the invention is represented by a compound of formulas VI$_a$-VI$_c$

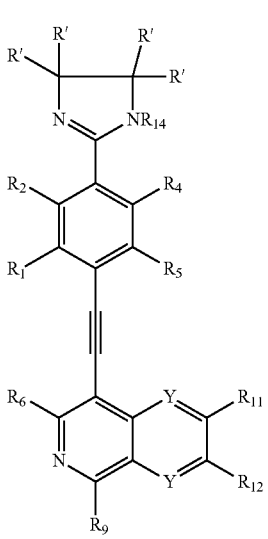

(VI$_a$)

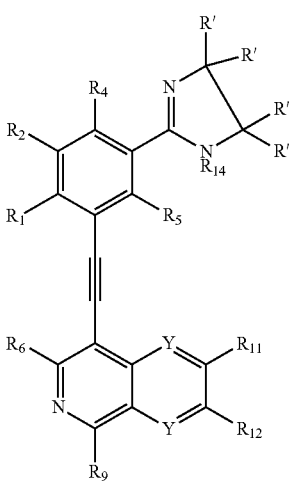

(VI$_b$)

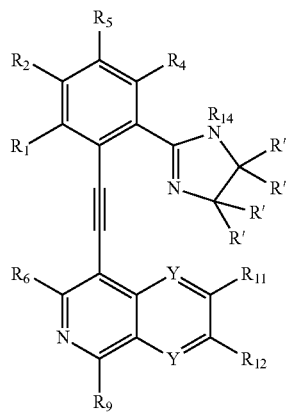

(VI$_c$)

wherein

R', R$_1$, R$_2$, R$_4$, and R$_5$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, NH(CO)-alkyl, NH(CO)OR$_c$, NH(CO)NR$_a$R$_b$, (CO)OR$_c$, (CO)NR$_a$R$_b$, SO$_2$NR$_a$R$_b$, cycloalkyl, heterocycloalkyl, aryl, or heteroaryl, wherein each R' is the same or different;

R$_{11}$ and R$_{12}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, (CO)OR$_c$, (CO)NR$_a$R$_b$, SO$_2$NR$_a$R$_b$, —C(CH$_3$)(=N—NHC(NH)NH$_2$, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, dialkylamino, —NH(CO)-alkyl, or —NH(CO)— alkenyl; and R$_{14}$ is H, alkyl, (CO)-alkyl, (CO)OR$_c$, (CO)NR$_a$R$_b$, or SO$_2$NR$_a$R$_b$.

In some embodiments, the compound of formula (I) of the invention is represented by a compound of formulas VII$_a$-VII$_c$

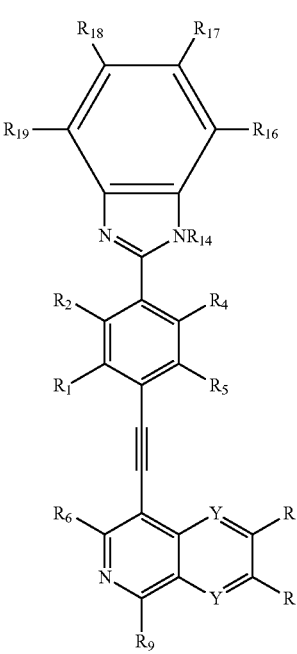

(VII$_a$)

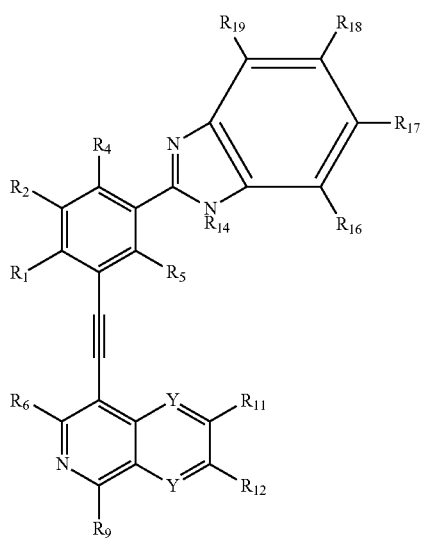

(VII_b)

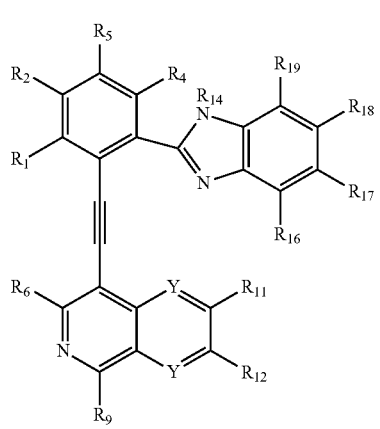

(VII_c)

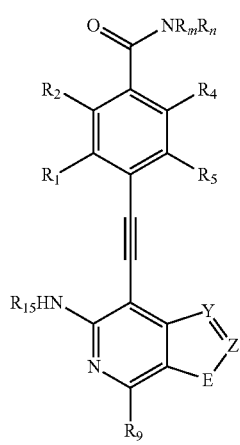

(VIII_a)

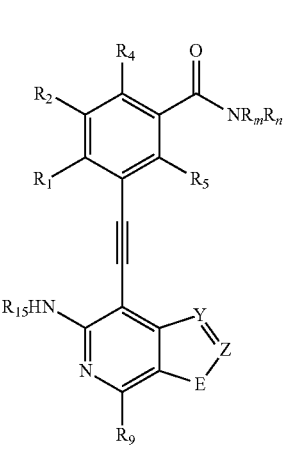

(VIII_b)

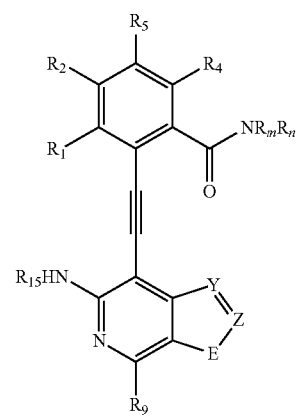

(VIII_c)

wherein

R_1, R_2, R_4, R_5, R_16, R_17, R_18, and R_19 are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR_aR_b, NH(CO)-alkyl, NH(CO)OR_c, NH(CO)NR_aR_b, (CO)OR_c, (CO)NR_aR_b, SO_2NR_aR_b, cycloalkyl, heterocycloalkyl, aryl, or heteroaryl;

R_11 and R_12 are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR_aR_b, (CO)OR_c, (CO)NR_aR_b, SO_2NR_aR_b, —C(CH_3)(=N—NHC(NH)NH_2, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, dialkylamino, —NH(CO)-alkyl, or —NH(CO)— alkenyl; and R_14 is H, alkyl, (CO)-alkyl, (CO)OR_c, (CO)NR_aR_b, or SO_2NR_aR_b.

In some embodiments, the compound of formula (I) of the invention is represented by a compound of formulas VIII_a-VIII_f.

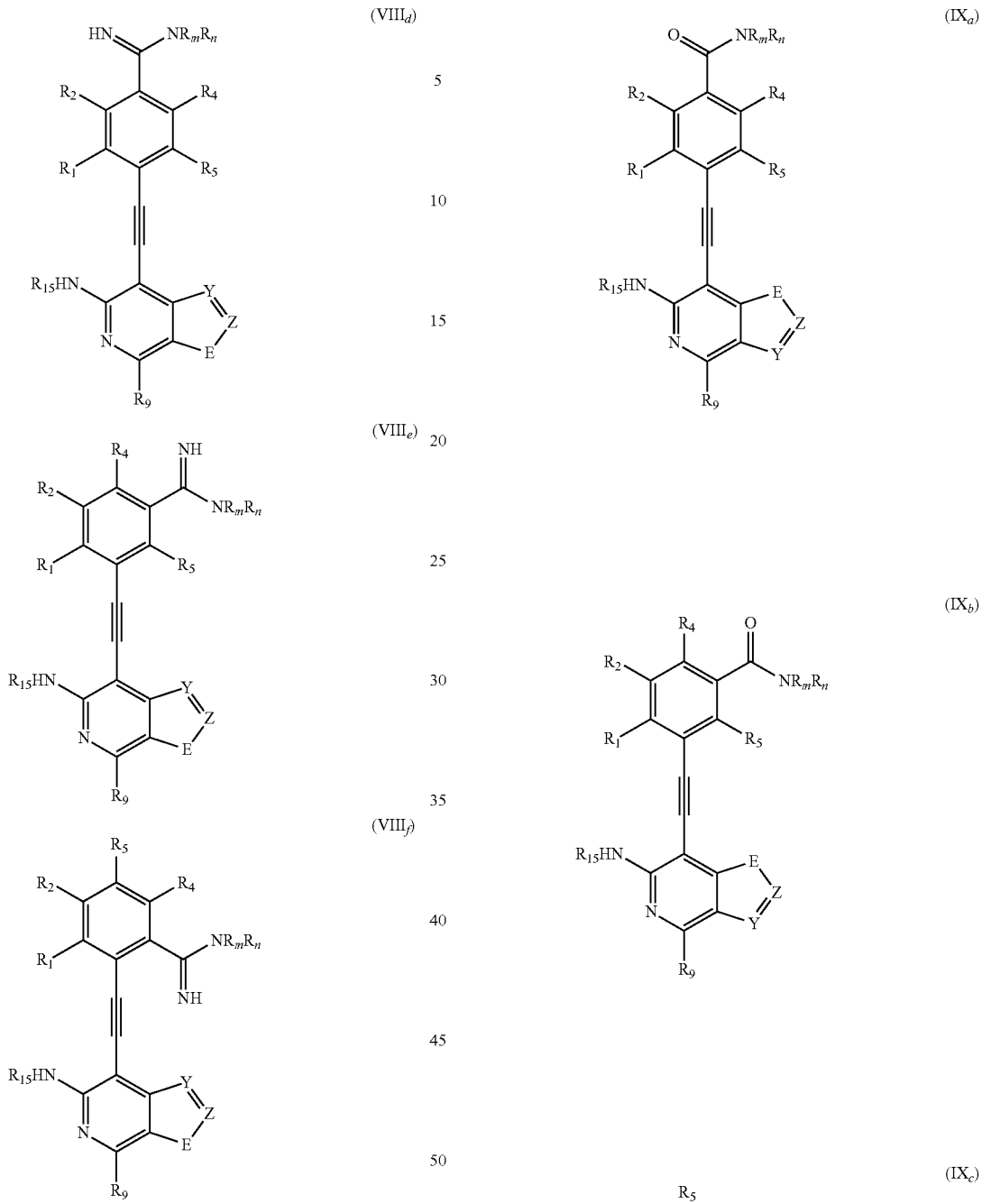

wherein

E is O, S, or $NR_{14}$;

$R_1$, $R_2$, $R_4$, and $R_5$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, NH(CO)-alkyl, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl; and $R_{14}$ and $R_{15}$ are each independently H, alkyl, (CO)-alkyl, $(CO)OR_c$, $(CO)NR_aR_b$, or $SO_2NR_aR_b$.

In some embodiments, the compound of formula (I) of the invention is represented by a compound of formulas $IX_a$-$IX_f$

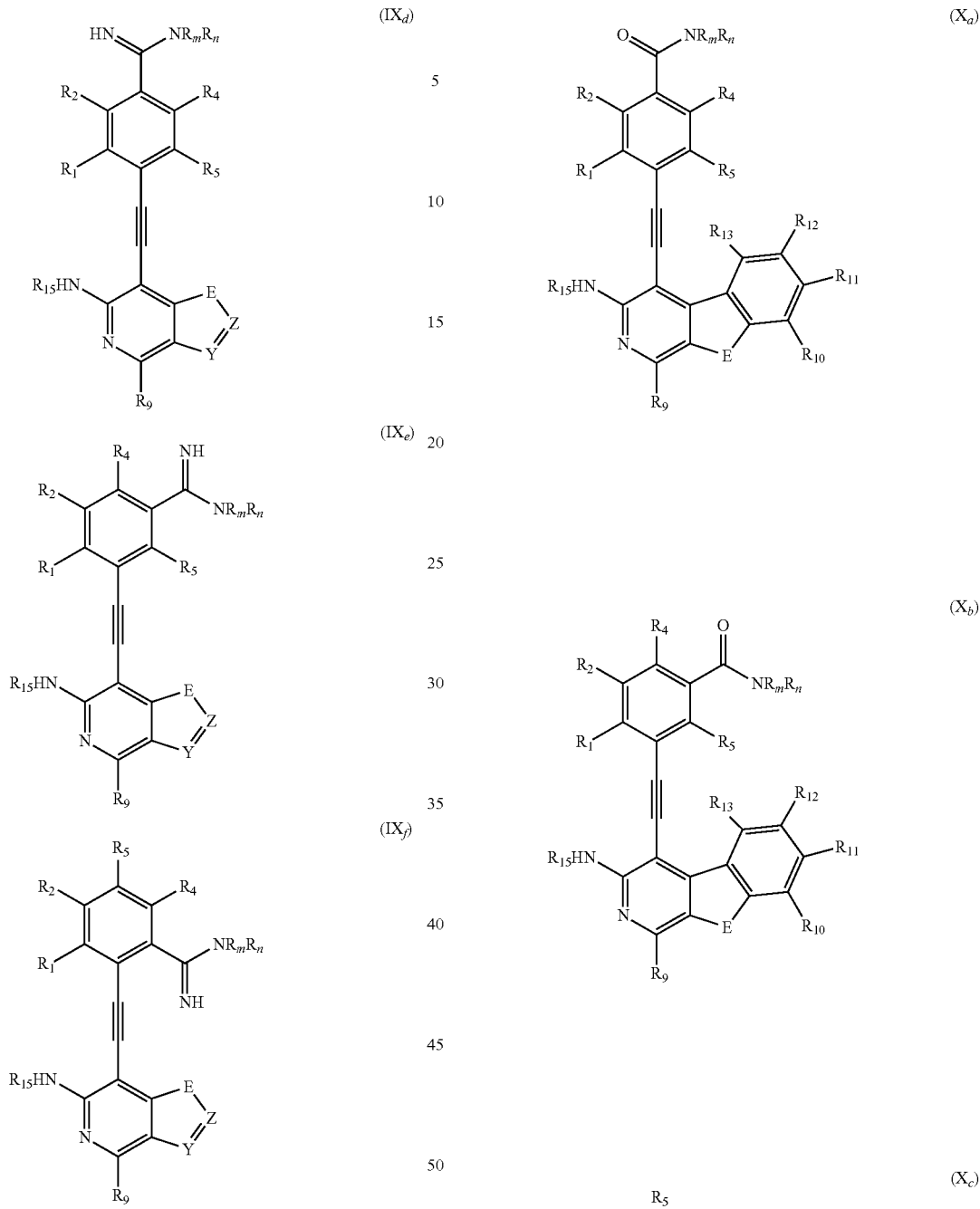

wherein

E is O, S, or NR$_{14}$;

R$_1$, R$_2$, R$_4$, and R$_5$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, NH(CO)-alkyl, NH(CO)OR$_c$, NH(CO)NR$_a$R$_b$, (CO)OR$_c$, (CO)NR$_a$R$_b$, SO$_2$NR$_a$R$_b$, cycloalkyl, heterocycloalkyl, aryl, or heteroaryl; and R$_{14}$ and R$_{15}$ are each independently H, alkyl, (CO)-alkyl, (CO)OR$_c$, (CO)NR$_a$R$_b$, or SO$_2$NR$_a$R$_b$.

In some embodiments, the compound of formula (I) of the invention is represented by a compound of formulas Xa-Xf -continued (X_d)

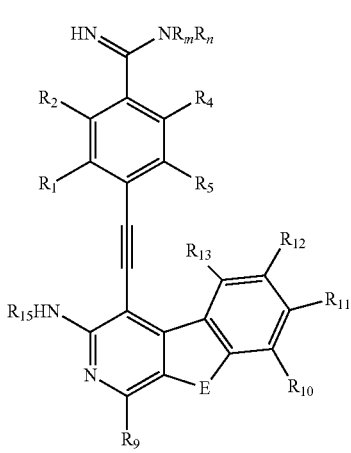

(X_e)

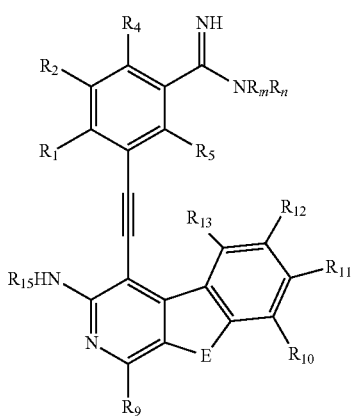

(X_f)

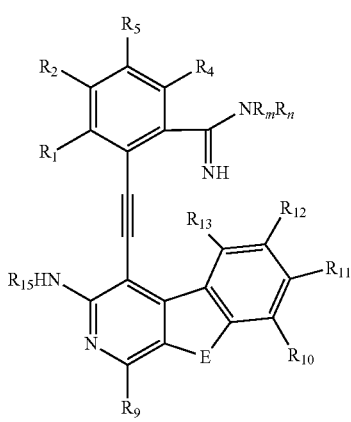

wherein
E is O, S, or NR$_{14}$;
R$_1$, R$_2$, R$_4$, R$_5$, R$_{10}$, and R$_{13}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, NH(CO)-alkyl, NH(CO)OR$_c$, NH(CO)NR$_a$R$_b$, (CO)OR$_c$, (CO)NR$_a$R$_b$, SO$_2$NR$_a$R$_b$, cycloalkyl, heterocycloalkyl, aryl, or heteroaryl;

R$_{11}$ and R$_{12}$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, NR$_a$R$_b$, (CO)OR$_c$, (CO)NR$_a$R$_b$, SO$_2$NR$_a$R$_b$, —C(CH$_3$)(=N—NHC(NH)NH$_2$, cycloalkyl, heterocycloalkyl, aryl, and heteroaryl, wherein alkyl, alkenyl, alkynyl cycloalkyl, heterocycloalkyl, aryl, and heteroaryl are each optionally substituted with amino, alkylamino, dialkylamino, —NH(CO)-alkyl, or —NH(CO)—alkenyl; and R$_{14}$ and R$_{15}$ are each independently H, alkyl, (CO)-alkyl, (CO)OR$_c$, (CO)NR$_a$R$_b$, or SO$_2$NR$_a$R$_b$.

In some embodiments, the compound of formula (I) of the invention is represented by a compound of formulas XIa-XIf (XI$_a$)

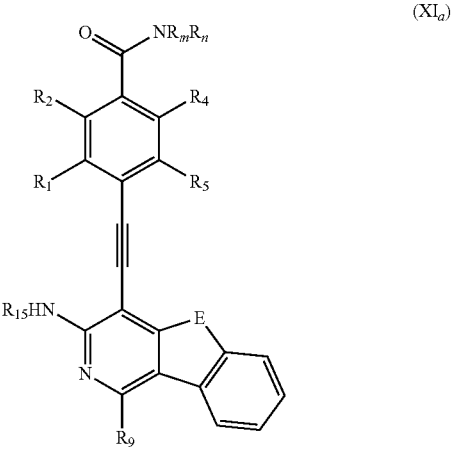

(XI$_b$)

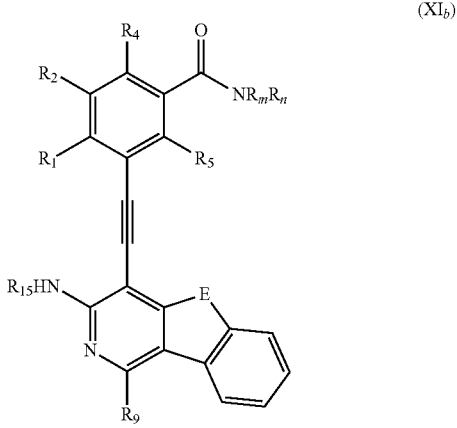

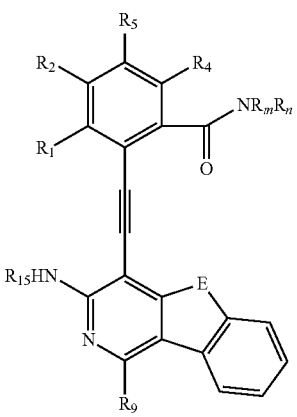

(XI<sub>c</sub>)

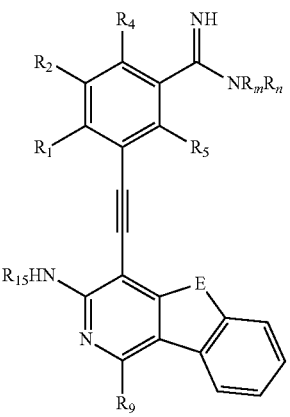

(XI<sub>e</sub>)

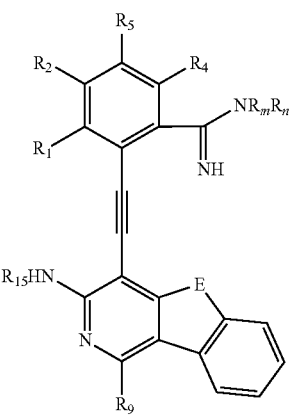

(XI<sub>f</sub>)

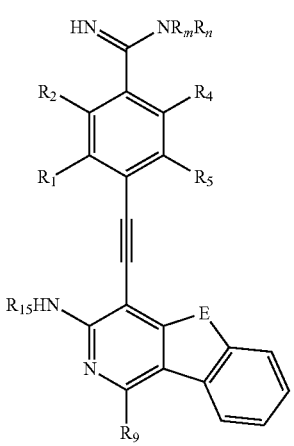

(XI<sub>d</sub>)

wherein

E is O, S, or $NR_{14}$;

$R_1$, $R_2$, $R_4$, and $R_5$ are each independently H, alkyl, alkenyl, alkynyl, halo, nitro, OH, SH, CN, O-alkyl, haloalkyl, O-haloalkyl, S-alkyl, (CO)-alkyl, (CO)-alkenyl, $NR_aR_b$, NH(CO)-alkyl, $NH(CO)OR_c$, $NH(CO)NR_aR_b$, $(CO)OR_c$, $(CO)NR_aR_b$, $SO_2NR_aR_b$, cycloalkyl, heterocycloalkyl, aryl, or heteroaryl; and $R_{14}$ and $R_{15}$ are each independently H, alkyl, (CO)-alkyl, $(CO)OR_c$, $(CO)NR_aR_b$, or $SO_2NR_aR_b$.

The compound of the invention can be prepared by the methods known in the art and the methods in the reaction schemes and experiments as described herein.

Scheme 1 provides a general reaction scheme for the preparation of the compounds of the invention through a halogenation reaction, followed by functionalization.

Scheme 1: Halogenation followed by functionalization

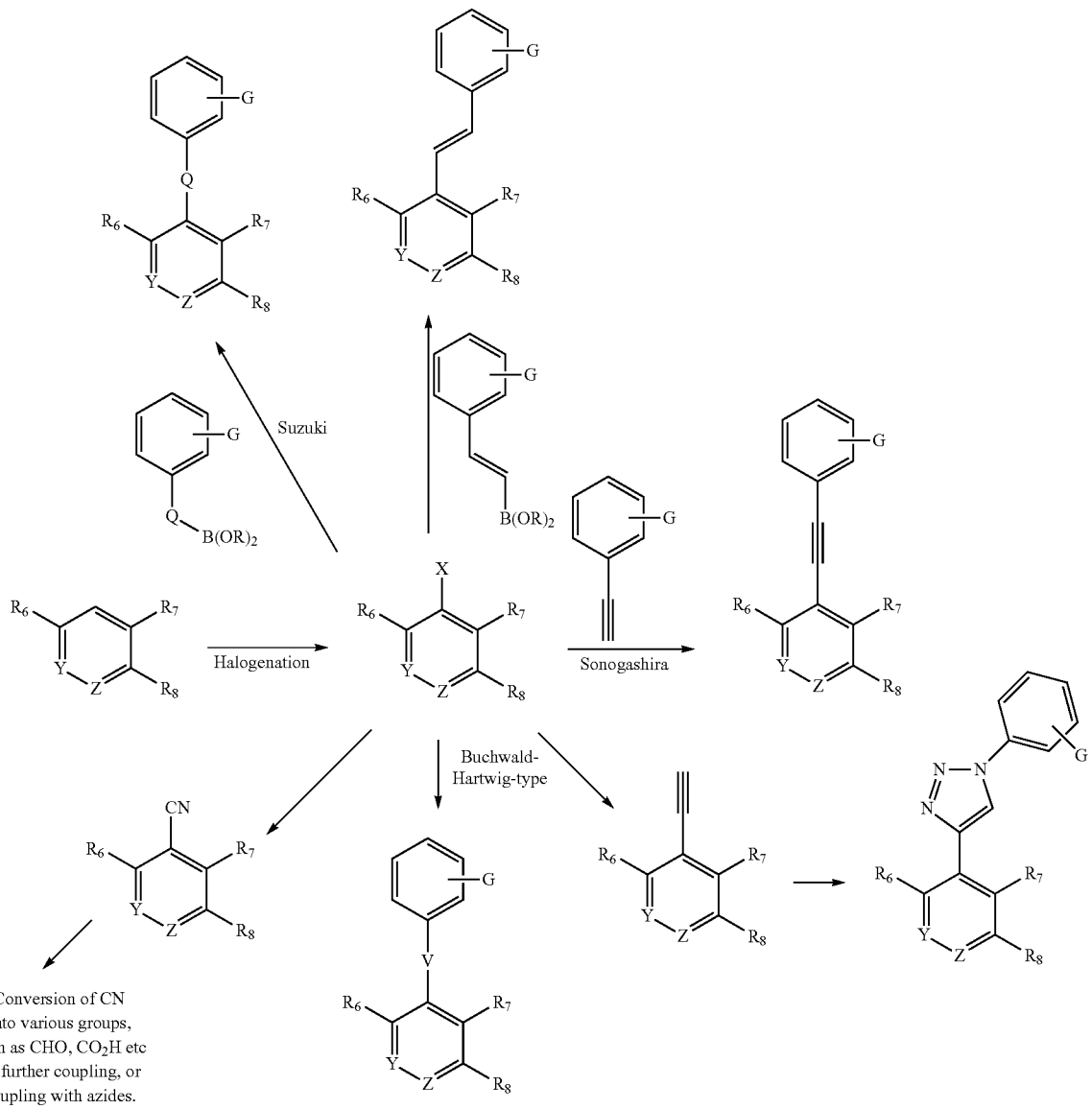

G = cyano, aldehyde or amide
Q = Linker (could be cyclic)
V = R₁NR₂ or R₁OH where R = H, alkyl, aryl, heteroakyl or heteroaryl For alkynes-containing compounds, a compound of the invention can be prepared via Sonogashira methodology as described in Scheme 2.

Scheme 2: Alkynes-containing compounds are prepared via Sonogashira methodology

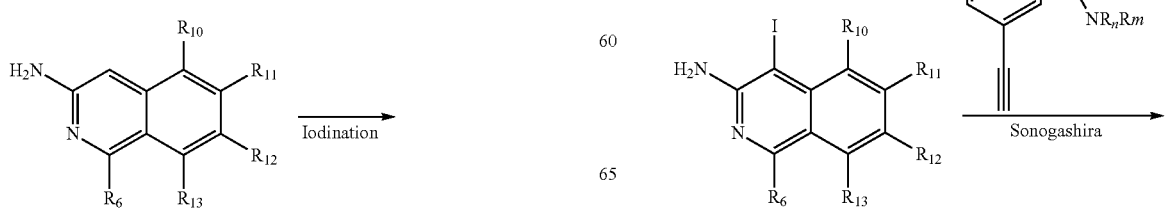

-continued

-continued
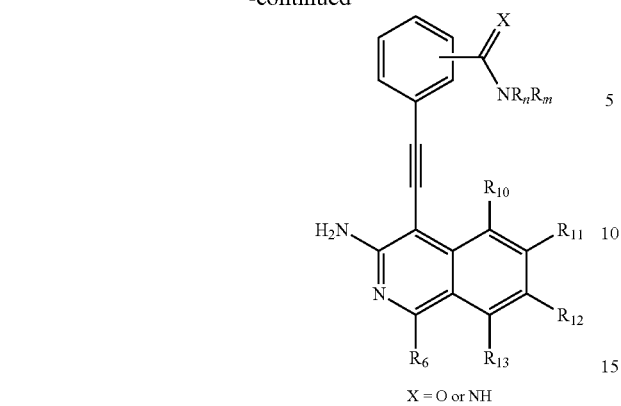
X = O or NH
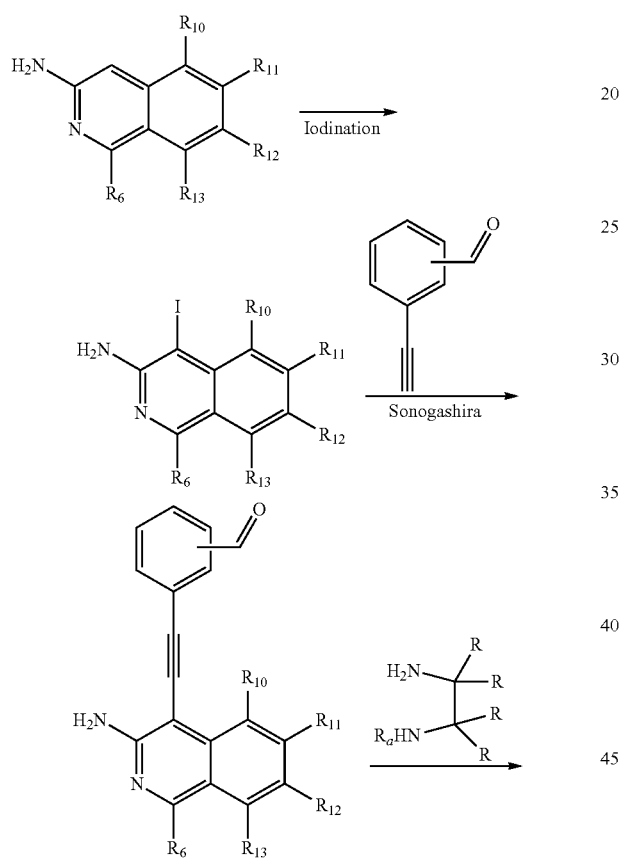
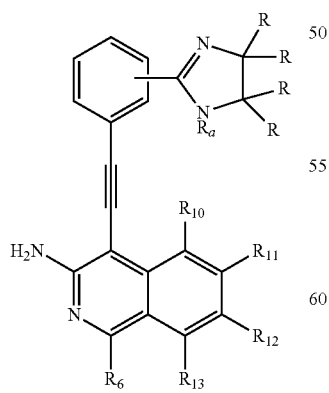
Scheme 3 describes the preparation of a compound of the invention via Suzuki coupling.

Scheme 3: Synthesis via Suzuki coupling
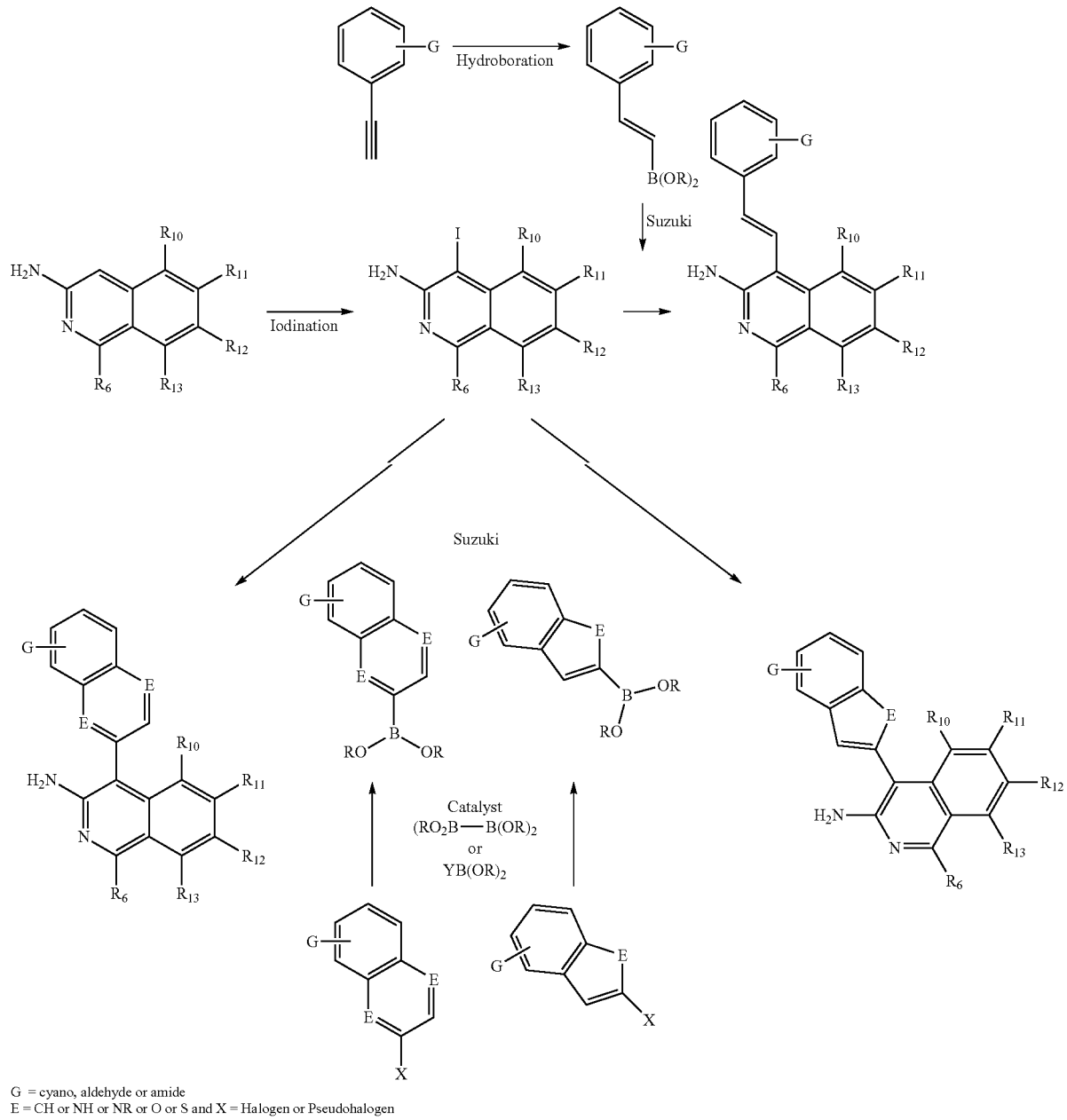
G = cyano, aldehyde or amide
E = CH or NH or NR or O or S and X = Halogen or Pseudohalogen
A compound of the invention can be prepared by functionalization of isoquinoline amine according to Scheme 4.
Scheme 4: Functionalization of isoquinoline amine
A)
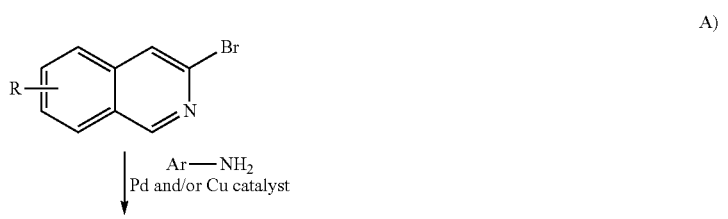

243 -continued 244
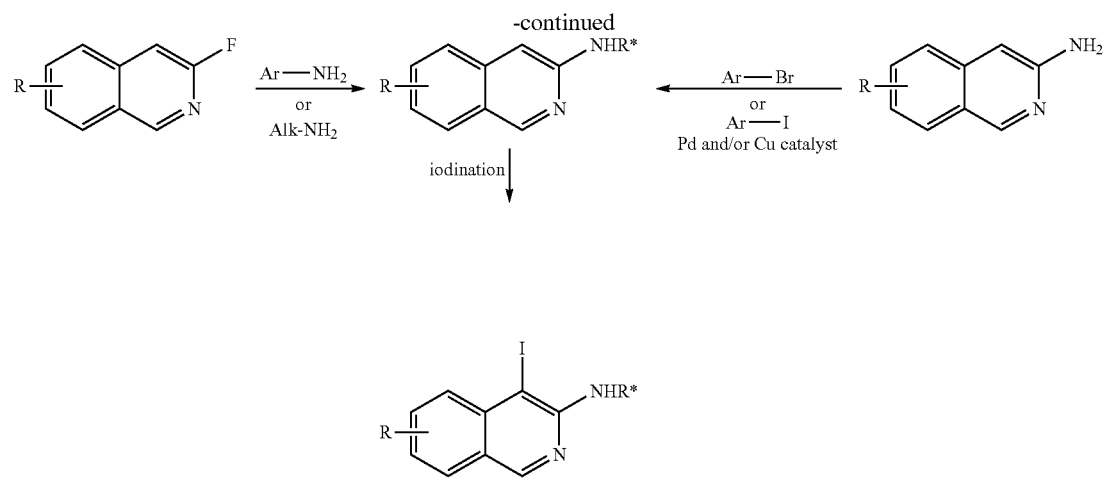
Ar = Aryl
Alk = Alkyl
R* = alkyl or aryl
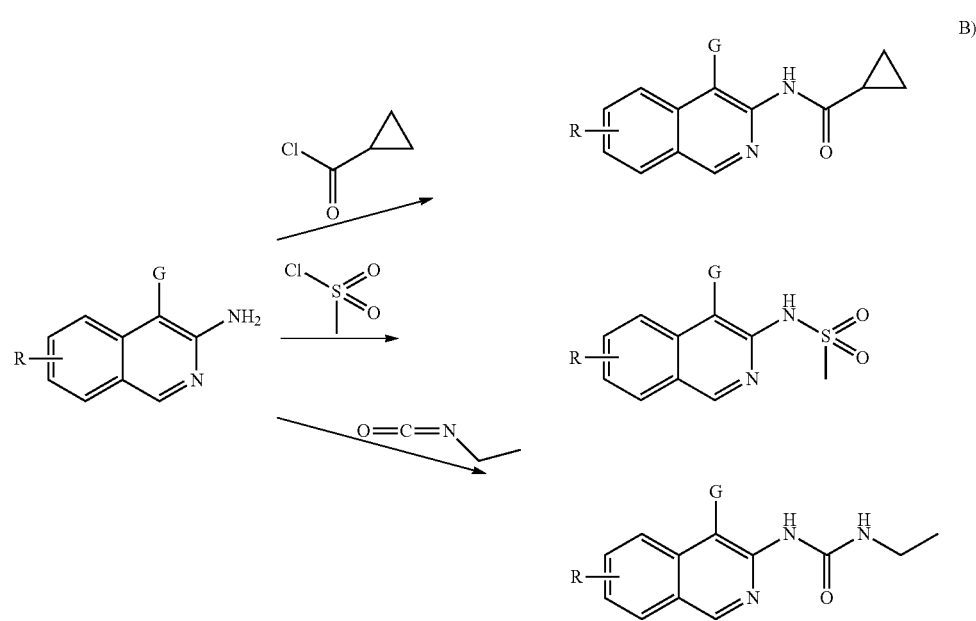
G = H or I Scheme 5 provides a general synthetic strategy for synthesis of functionalized 1-amino or 2-amino or 3-amino isoquinoline, quinoline/quinazoline and isoquinolines using quinoline or isoquinoline or quinazoline amine as nucleophile.
Scheme 5: Synthesis of functionalized 1-amino or 2-amino or 3-amino isoquinoline, quinoline/quinazolne and isoquinolines
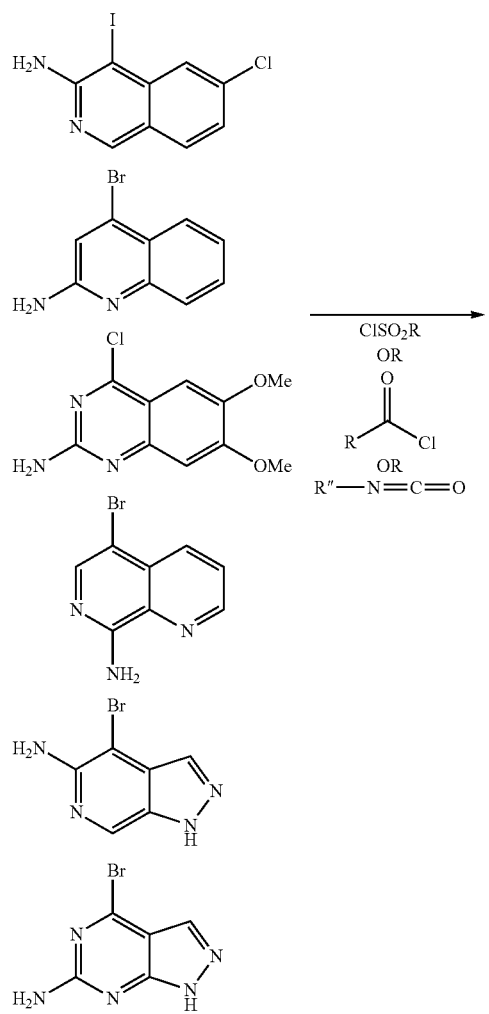

-continued
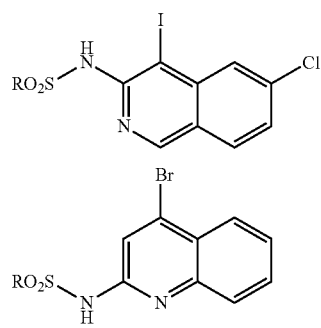
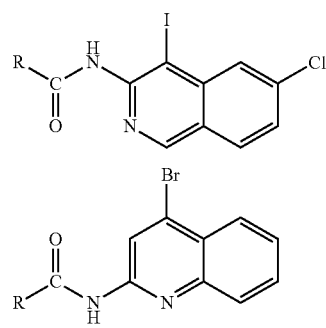
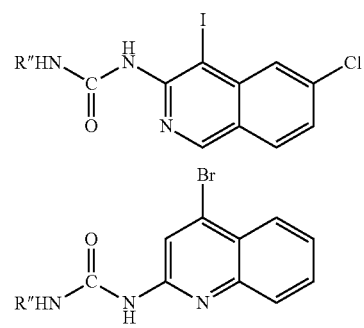
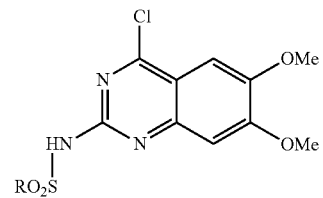
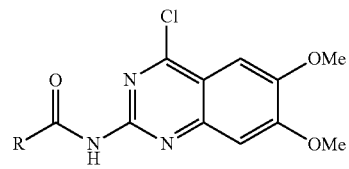
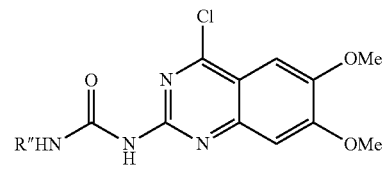
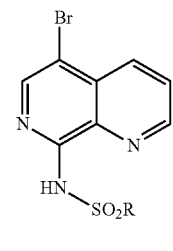
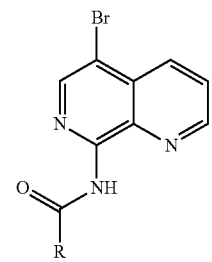
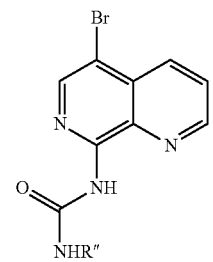
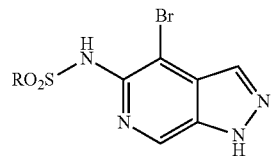
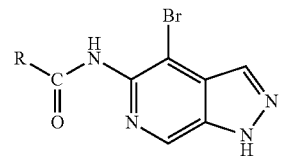
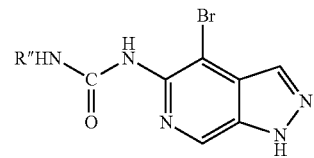
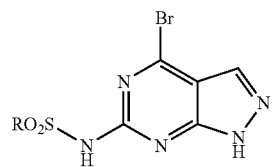
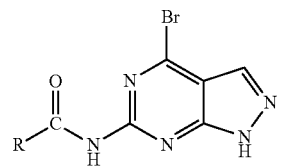
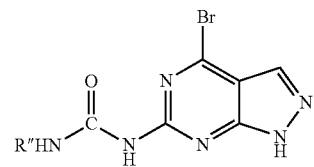

Scheme 6 provides a general synthetic strategy for synthesis of 4-Substituted isoquinolines, quinolones and quinazolines.

Scheme 7 provides synthesis of target compounds via Sonogashira coupling.

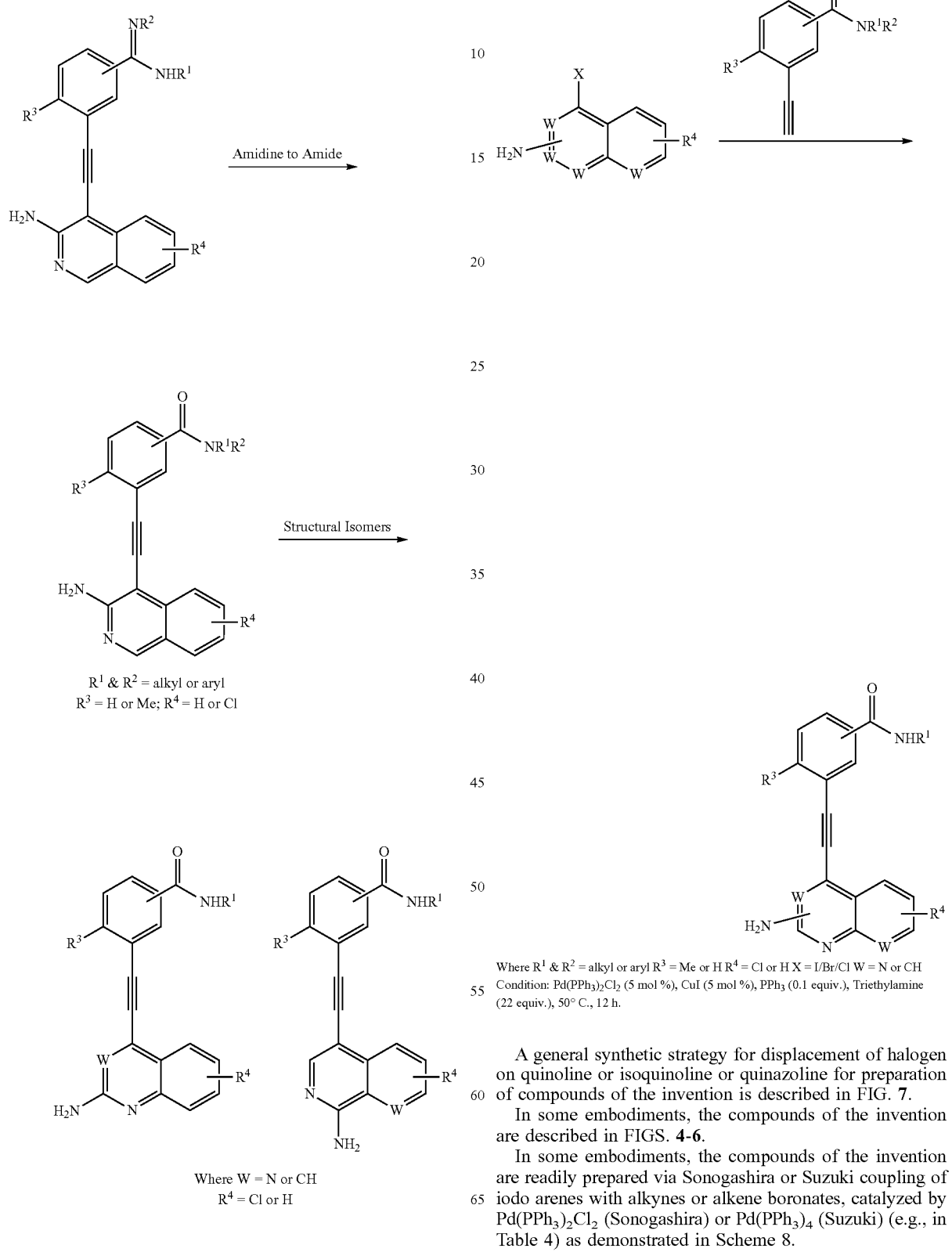

Figure 7:
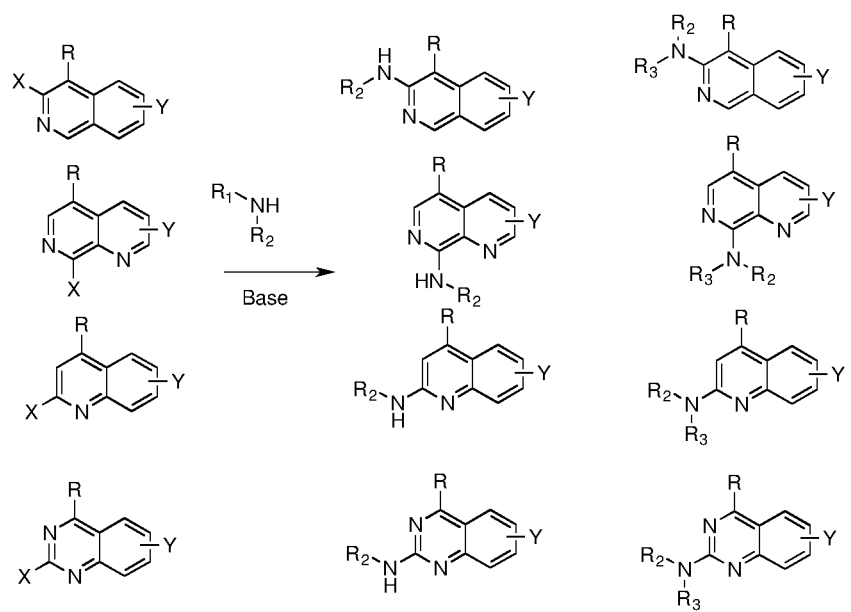
FIG. 7 depicts displacement of halogen on quinolone or isoquinoline or quinazoline for the preparation of the compounds of the invention.

A general synthetic strategy for displacement of halogen on quinoline or isoquinoline or quinazoline for preparation of compounds of the invention is described in FIG. 7.

Figure 4:
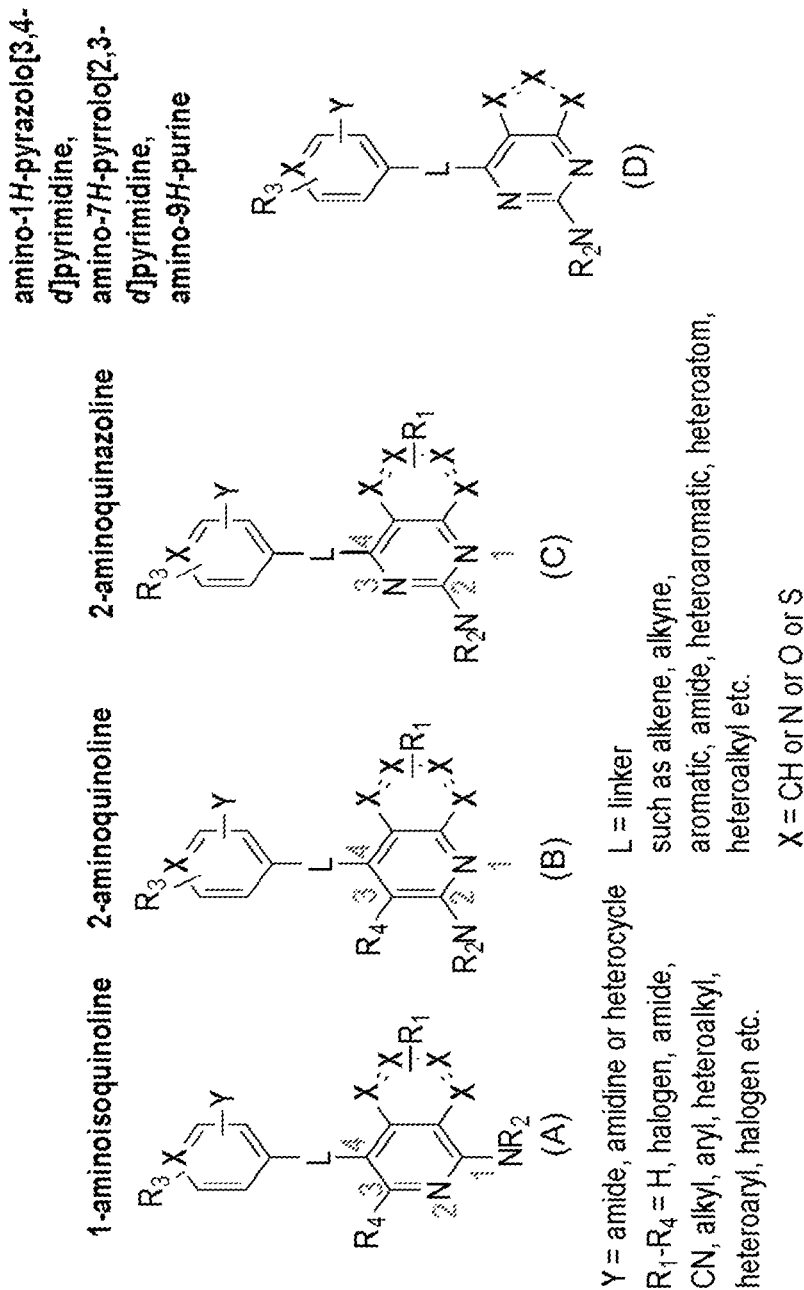
FIG. 4 depicts 4-substituted isoquinoline/quinoline/quinazoline/purine compounds.
Figure 5:
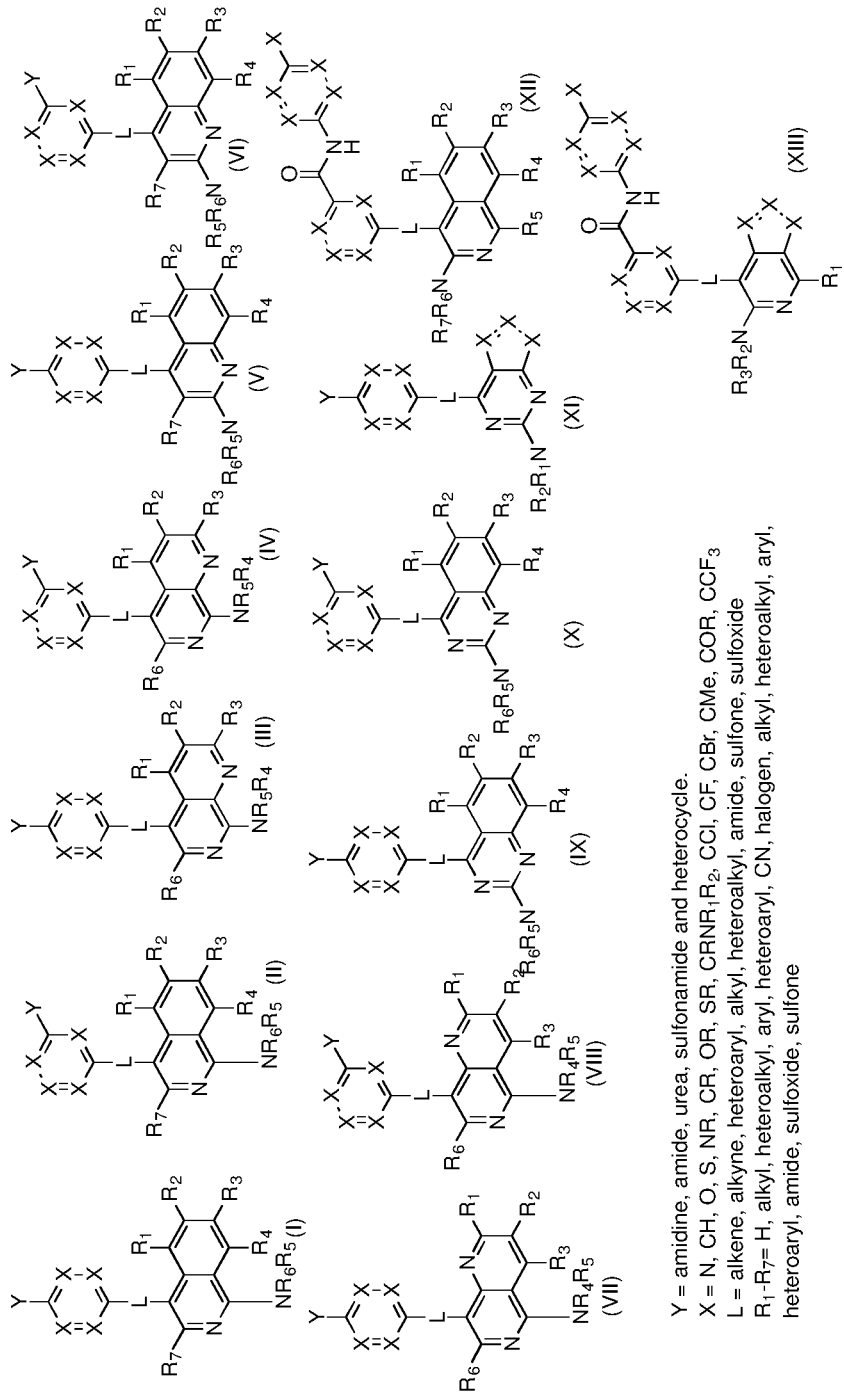
FIG. 5 depicts general structures of the compounds of the invention.
Figure 6:
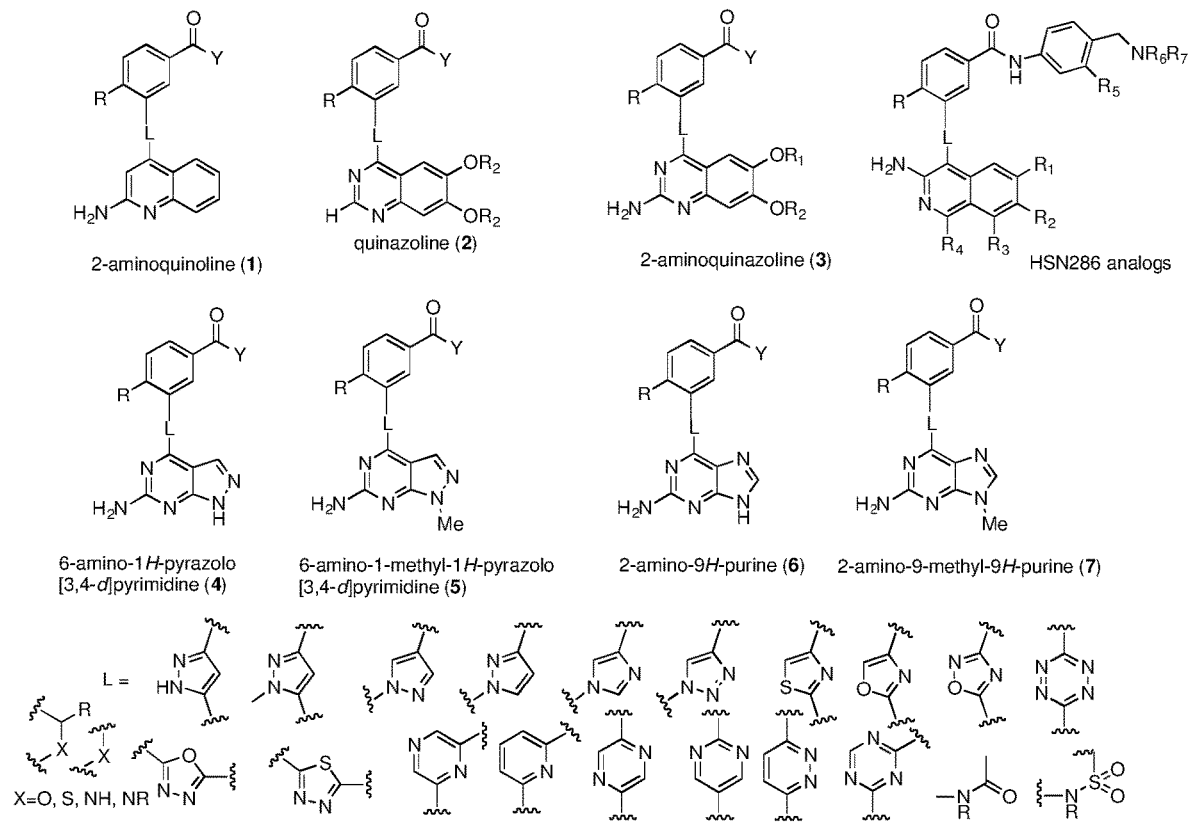
FIG. 6 depicts the compounds of the invention.
Figure 6:
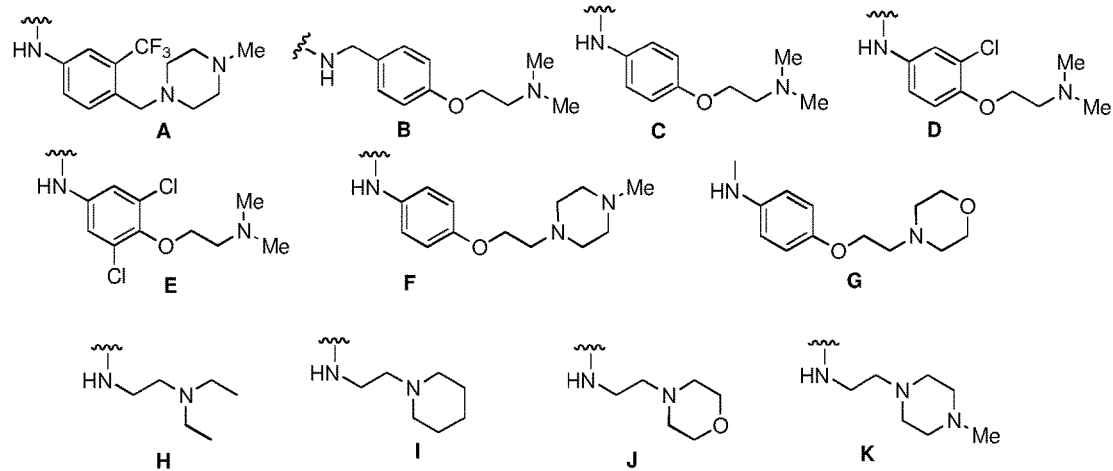

In some embodiments, the compounds of the invention are described in FIGS. 4-6.

In some embodiments, the compounds of the invention are readily prepared via Sonogashira or Suzuki coupling of iodo arenes with alkynes or alkene boronates, catalyzed by $Pd(PPh_3)_2Cl_2$ (Sonogashira) or $Pd(PPh_3)_4$ (Suzuki) (e.g., in Table 4) as demonstrated in Scheme 8.

Scheme 8: Synthesis of alkyne and alkene analogs of the compound of the invention

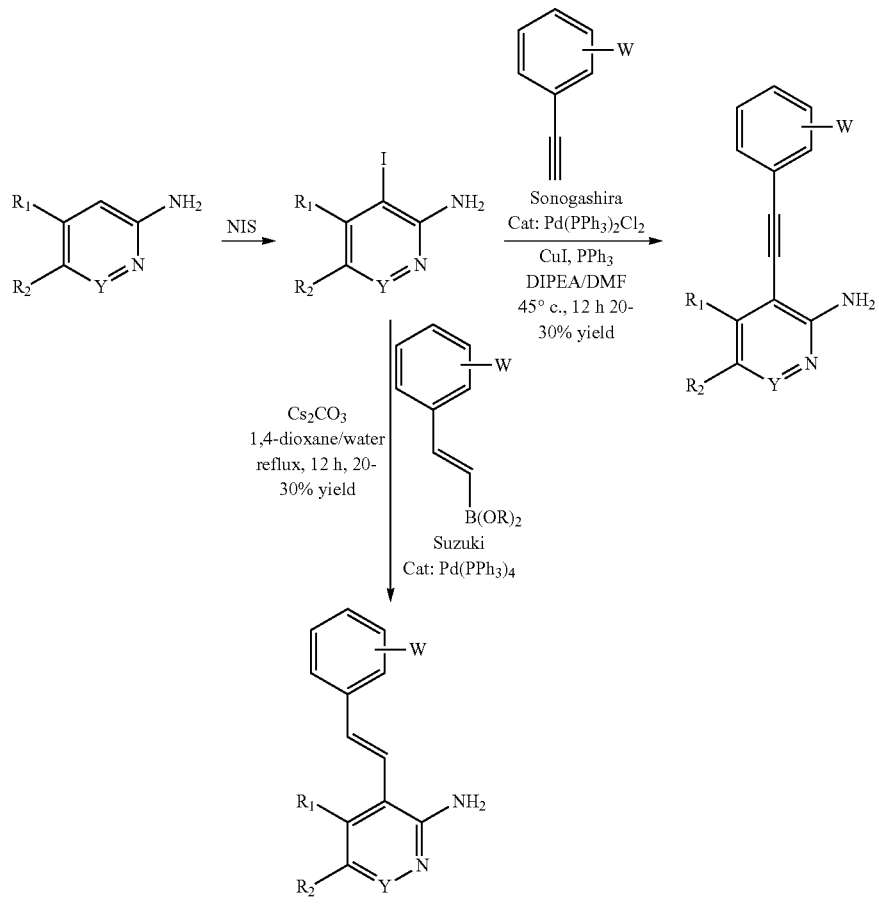

Y = CH or N; W = CN or amidine

NIS (N-iodosuccinimide); DIPEA (diisopropylethylamine); DMF (dimethylformamide)

In the compounds of the invention, the nature and substitution pattern on the amide and amidine head groups remarkably affect the anticancer properties of the compounds. By systematically varying the amide and amidine functionalities, the compounds have been identified that are about two orders of magnitude more potent than the compounds previously reported by Sintim et al. (PCT/US2015/041551).

As described in FIG. 1, in the compounds of the invention, the length of the amide head group, substitution pattern and relative position to the alkyne moiety remarkably affects the anticancer activity against MV4-11 cell line (AML cell line). For example, the nature of the amide group in the molecules shown in FIG. 1 had a dramatic effect on the anticancer activities of the molecules tested.

For example, compounds HSM1669, M731, and HSM1684 differed from each other by a simple methylene group ($CH_2$) yet the anticancer activities against AML are 260 nM (HSM1669), 36 nM (HSM731) and 71 nM (HSM1684). It appears that anticancer potency increases with an additional methylene group (HSM1669 to M731) but then decreases when another methylene group is added (M731 to HSM1684). Further, depending on the nature of the amide linker, the relative positions of the alkyne and amide moieties appear to affect anticancer potencies. For example, the relationship between M731 and HSM1688 (para vs meta substitution) is similar to that between HSD79 and HSD82 but whereas the anticancer activity of M731 is higher than that of HSM1688 (36 nM versus 250 nM; almost a fold difference), and that of HSD79 and HSD82 are similar (108 nM versus 150 nM). This indicates that the effect of substitution pattern of the benzamide part on anticancer activity (para vs. meta vs. ortho) is context dependent.

For the para analogs M731, HSM1692 and HSD79 (analogs differing at the 4*position) the anticancer activities ($IC_{50}$) against MV4-11 are 36 nM, 450 nM, and 108 nM, pointing to the essentiality of a nitrogen group at this 4*position. However, for the meta analogs HSM1688 and HSD82, the IC50 values are 250 nM for HSM1688 (nitrogen at the 4*position) and 150 nM for HSD82 (carbon at the 4*position). Thus, putting a hydroxyl group at the 2-position of M731 (to give HSM1702) remarkably affected the anticancer property (compare IC50 of 36 nM for M731 vs. 3 nM for HSM1702; an order of magnitude difference).

As used herein, all compounds starting with MXC are the same as HSM, N–I=HSN, and DGBI=HSD.

At various places in the present specification, substituents of compounds of the invention are disclosed in groups or in ranges. It is specifically intended that the invention include each and every individual subcombination of the members of such groups and ranges.

For example, the term "$C_{1-5}$ alkyl" is specifically intended to individually disclose methyl, ethyl, $C_3$ alkyl, $C_4$ alkyl, and $C_5$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent. It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as commonly understood to one of ordinary skill in the art.

In some embodiments, the term "about" can allow for a degree of variability in a value or range, for example, within 10%, within 5%, or within 1% of a stated value or of a stated limit of a range.

In some embodiments, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, in some embodiments, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, in some embodiments, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

In some embodiments, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

In some embodiments, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

In some embodiments, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms. In some embodiments, "heteroaryl" may be optionally substituted at any one or more positions capable of bearing a hydrogen atom.

In some embodiments, "heterocycloalkyl" refers to a non-aromatic heterocycle where one or more of the ring-forming atoms are a heteroatom such as an O, N, or S atom. Heterocycloalkyl groups can include mono- or polycyclic (e.g., having 2, 3 or 4 fused rings) ring systems as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. Also included in the definition of heterocycloalkyl are moieties where one or more ring-forming atoms are substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

In some embodiments, "halo" or "halogen" includes fluoro, chloro, bromo, and iodo. A "halogen-substitution" or "halo" substitution designates replacement of one or more hydrogen atoms with F, Cl, Br or I.

In some embodiments, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

It is understood that each of alkyl, cycloalkyl, alkenyl, cycloalkenyl, alkylene, and heterocycle may be optionally substituted with independently selected groups such as alkyl, haloalkyl, hydroxyalkyl, aminoalkyl, carboxylic acid and derivatives thereof, including esters, amides, and nitrites, hydroxy, alkoxy, acyloxy, amino, alky and dialkylamino, acylamino, thio, and the like, and combinations thereof.

In some embodiments, the term "substituted" refers to the replacement of a hydrogen moiety with a non-hydrogen moiety in a molecule or group. It can refer to "mono-substituted" or "poly-substituted." The term "mono-substituted" or "poly-substituted" means substituted with one or more than one substituent up to the valence of the substituted group. For example, a mono-substituted group can be substituted with 1 substituent, and a poly-substituted group can be substituted with 2, 3, 4, or 5 substituents. When a list of possible substituents is provided, the substituents can be independently selected from that group.

The term "optionally substituted," or "optional substituents," as used herein, means that the groups in question are either unsubstituted or substituted with one or more of the substituents specified. When the groups in question are substituted with more than one substituent, the substituents may be the same or different. Such other functional groups illustratively include, but are not limited to, amino, hydroxyl, CN, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, CH, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted. In some embodiments, the functional groups are the substituents described herein for any one of variables. Furthermore, when using the terms "independently," "independently are," and "independently selected from" mean that the groups in question may be the same or different. Certain of the herein defined terms may occur more than once in the structure, and upon such occurrence each term shall be defined independently of the other.

In each of the foregoing and each of the following embodiments, it is to be understood that the formulas also include any and all hydrates and/or solvates of the compound formulas. It is appreciated that certain functional groups, such as the hydroxy, amino, and like groups form complexes and/or coordination compounds with water and/or various solvents, in the various physical forms of the compounds. Accordingly, the above formulas are to be understood to include and represent those various hydrates and/or solvates.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In the case of the compounds which contain an asymmetric carbon atom, the invention relates to the D form, the L form, and D,L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the term "compound" as used herein, is meant to include all stereoisomers, geometric isomers, tautomers, and isotopes of the structures depicted.

In some embodiments, the compound of the invention is substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

In some embodiments, as used herein, the term "therapeutically effective amount" refers to the amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

In addition, it is appreciated that there is an interrelationship of dosages determined for humans and those dosages determined for animals, including test animals (illustratively based on milligrams per meter squared of body surface) as described by Freireich, E. J., et al., Cancer Chemother. Rep. 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). A therapeutically effective amount of the compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of compound per patient body weight. It is appreciated that effective doses may also vary depending on the route of administration, optional excipient usage, and the possibility of co-usage of the compound with other conventional and non-conventional therapeutic treatments, including other anti-tumor agents, radiation therapy, and the like.

In some embodiments, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compound of the present invention also includes "pharmaceutically acceptable salts" of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compound of the invention include the conventional non-toxic salts of the parent compound formed, for example, from non-toxic inorganic or organic acids. The pharmaceutically acceptable salts of the compound of the invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

The pharmaceutically acceptable salts of the compound of the invention can be obtained by converting derivatives which possess tertiary amino groups into the corresponding quaternary ammonium salts in a manner known per se using quaternizing agents. Examples of suitable quaternizing agents are alkyl halides, such as methyl iodide, ethyl bromide, and n-propyl chloride, and also arylalkyl halides, such as benzyl chloride or 2-phenylethyl bromide.

The "subject" used here refers to an animal or a human. In some embodiment, the term "subject" refers to a human. A pharmaceutical composition comprising a compound of claim 1, or a pharmaceutically acceptable salt, N-oxide, hydrate, solvate, tautomer, or optical isomer thereof, and a pharmaceutically acceptable carrier or diluent.

In another aspect, the present invention features a pharmaceutical composition comprising a compound of the invention as described herein, or a pharmaceutically acceptable salt, N-oxide, hydrate, solvate, tautomer, or optical isomer thereof, and a pharmaceutically acceptable carrier or diluent.

In some embodiment, the pharmaceutical composition includes a therapeutically effective amount of the one or more compounds for treating a cancer patient. It is to be understood that the composition may include other component and/or ingredients, including, but not limited to, other therapeutically active compounds, and/or one or more pharmaceutically acceptable carriers, diluents, excipients, and the like.

The term "pharmaceutically acceptable carrier" or "pharmaceutically acceptable diluent" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A therapeutically effective dose of a compound according to the invention is used, in addition to physiologically acceptable carriers, diluents and/or adjuvants for producing a pharmaceutical composition. The dose of the active compound can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are oral, parenteral, intravenous, transdermal, topical, inhalative, intranasal and sublingual preparations. Particular preference is given to using oral, parenteral, e.g. intravenous or intramuscular, intranasal, e.g. dry powder or sublingual preparations of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, are used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavorings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its nontoxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or watermiscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na-N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, a compound of the invention may be administered as a combination therapy with further active agents, e.g. therapeutically active compounds useful in the treatment of cancer, for example, prostate cancer, ovarian cancer, lung cancer, or breast cancer. In some embodiments, the cancer is acute myeloid leukemia, chronic myeloid leukemia, ovarian cancer, cervical cancer, pancreatic cancer, breast cancer, brain cancer, skin cancer, lung cancer, prostate cancer, Lymphoma, Leukemia, colon cancer, head cancer, neck cancer, thyroid cancer, kidney cancer, liver cancer and stomach cancer. For a combination therapy, the active ingredients may be formulated as compositions containing several active ingredients in a single dose form and/or as kits containing individual active ingredients in separate dose forms. The active ingredients used in combination therapy may be coadministered or administered separately.

It is another aspect of the invention that a compound of the invention as described herein is a protein kinase inhibitor. Thus, the present invention features a method of inhibiting a protein kinase, wherein the method comprises contacting the protein kinase with an effective amount of a compound of the invention. In some embodiments, such protein kinase includes, but is not limited to, FLT3 and TrkC. In some embodiments, the protein kinase is Abl, Abl2, AFK, ALK, AMPK_group, ATM, ATR, Aurora A, Aurora B, Axl, BCKDK, BLK, BMPR1B, BMX, Brk, BRSK1, BTK, CaMKIalpha, CaM-KIalpha, CaMKK_group, CaM-KIV, CaM-KKalpha, CaM-KKbeta, CCDPK, CCRK, CDK1, CDK11, CDK2, CDK4, CDK5, CDK6, CDK7, CDK9, CDK_group, CDPK, Chak1, CHK1, CHK2, CK1 alpha, CK1 delta, CK1 epsilon, CK1_group, CK2 alpha, CK2_beta, CK2_group, CLK1, CSF1R, Csk, DAPK1, DAPK2, DAPK3, DAPK_group, DCAMKL1, DMPK_group, DNA-PK, DYRK1A, DYRK1B, DYRK2, DYRK3, eEF2K, Eg3 kinase, EGFR, EIF2AK2, EphA2, EphA3, EphA4, EphA8, EphB1, EphB2, EphB3, EphB5, ErbB2, FAK, Fer, Fes, FGFR1, FGFR3, FGFR4, FGFR_group, Fgr, FLT1, FLT3, FLT4, Fyn, GRK-1, GRK-2, GRK-3, GRK-4, GRK-5, GRK-6, GRK_group, GSK-3alpha, GSK-3beta, GSK-3_group, HCK, HIPK2, HIPK3, HRI, ICK, IGF1R, IKK-alpha, IKK-beta, IKK-epsilon ILK, InsR, IPL1, IRAK1, IRAK4, ITK, JAK1, JAK2, JAK3, JAK_group, JNK_group, KDR, KIS, Kit, KSR1, Lck, LIMK1, LIMK2, LKB1, LOK, Lyn, MAP2K1, MAP2K2, MAP2K3, MAP2K4, MAP2K6, MAP2K7, MAPK2_group, MAP3K1, MAP3K11, MAP3K14, MAP3K5, MAP3K7, MAP3K8, MAPK3_group, MAP4K1, MAP4K2, MAP4K4, MAPK1, MAPK10, MAPK11, MAPK12, MAPK13, MAPK14, MAPK3, MAPK4, MAPK6, MAPK7, MAPK8, MAPK9, MAPK_group, MAPKAPK2, MARK_group, Mer, Met, MHCK, MLCK_group, Mnk1, Mnk2, MOS, MRCKa, MST1, MST3, mTOR, NDR1, NDR2, NEK1, NEK2, NEK6, NEK9, NEK_group, NLK, NuaK1, p37 kinase, p38_group, p70S6K, p70S6Kb, P70S6K_group, PAK1, PAK2, PAK3, PAK5, PAK6, PAK_group, PASK, P-CIP2, PCTAIRE1, PDGFR alpha, PDGFR beta, PDGFR_group, PDHK1, PDHK2, PDHK3, PDHK4, PDK-1, PDK-2, PDK_group, PHK_group, PIK3CA, PIK3CB, PIK3CD, PIK3CG, Pim-1, PKA alpha, Pka_group, PKB beta, PKB_group, PKC alpha, PKC beta, PKC delta, PKC epsilon, PKC eta, PKC gamma, PKC iota, PKC theta, PKC zeta, PKC_group, PKD1, PKD2, PKD3, PKG1/cGK-I, PKG2/cGK-II, PKG2/cGK_group, PKN1, PLK1, PLK2, PLK3, PRP4, PYK2, RAF1, Ret, ROCK1, ROCK2, Ron, RPL10, RSK-1, RSK-2, RSK-3, RSK-5, SDK1, SGK_group, SIK, Sky, Src, Src_group, STLK3, Syk, TBK1, Tec, TESK1, TESK2, TGFbR1, TGFbR2, Tie1, Tie2, Titin kinase, TNK2, TRKA, TRKB, tropomyosin kinase, TSSK3, TXK, Tyk2, TYK2, VRK1, Wee1, Wnk1, WNK1, Yes, ZAP70. In some embodiments, each possibility represents a separate embodiment of the present invention.

It is a further aspect of the invention that a compound of the invention as described herein can be used for treating, inhibiting, suppressing, or reducing the severity of a disease or a disorder associated with a protein kinase, wherein the method comprises administering to the subject in need thereof a therapeutically effective amount of a compound of the invention, or a pharmaceutically acceptable salt, N-oxide, hydrate, solvate, tautomer, or optical isomer thereof. In some embodiments, the protein kinase is one known in the art. In some embodiments, the protein kinase includes, but is not limited to, FLT3 and TrkC. In some embodiments, the protein kinase is Abl, Abl2, AFK, ALK, AMPK_group, ATM, ATR, Aurora A, Aurora B, Axl, BCKDK, BLK, BMPR1B, BMX, Brk, BRSK1, BTK, CaM-KIalpha, CaM-KIIalpha, CaMKK_group, CaM-KIV, CaM-KKalpha, CaM-KKbeta, CCDPK, CCRK, CDK1, CDK11, CDK2, CDK4, CDK5, CDK6, CDK7, CDK9, CDK_group, CDPK, Chak1, CHK1, CHK2, CK1 alpha, CK1 delta, CK1 epsilon, CK1_group, CK2 alpha, CK2_beta, CK2_group, CLK, CSF1R, Csk, DAPK1, DAPK2, DAPK3, DAPK_group, DCAMKL1, DMPK_group, DNA-PK, DYRK1A, DYRK1B, DYRK2, DYRK3, eEF2K, Eg3 kinase, EGFR, EIF2AK2, EphA2, EphA3, EphA4, EphA8, EphB1, EphB2, EphB3, EphB5, ErbB2, FAK, Fer, Fes, FGFR1, FGFR3, FGFR4, FGFR_group, Fgr, FLT1, FLT3, FLT4, Fyn, GRK-1, GRK-2, GRK-3, GRK-4, GRK-5, GRK-6, GRK_group, GSK-3alpha, GSK-3beta, GSK-3_group, HCK, HIPK2, HIPK3, HRI, ICK, IGF1R, IKK-alpha, IKK-beta, IKK-epsilon ILK, InsR, IPL, IRAK1, IRAK4, ITK, JAK1, JAK2, JAK3, JAK_group, JNK_group, KDR, KIS, Kit, KSR1, Lck, LIMK1, LIMK2, LKB1, LOK, Lyn, MAP2K1, MAP2K2, MAP2K3, MAP2K4, MAP2K6, MAP2K7, MAPK2_group, MAP3K1, MAP3K11, MAP3K14, MAP3K5, MAP3K7, MAP3K8, MAPK3_group, MAP4K1, MAP4K2, MAP4K4, MAPK1, MAPK10, MAPK11, MAPK12, MAPK13, MAPK14, MAPK3, MAPK4, MAPK6, MAPK7, MAPK8, MAPK9, MAPK_group, MAPKAPK2, MARK_group, Mer, Met, MHCK, MLCK_group, Mnk1, Mnk2, MOS, MRCKa, MST1, MST3, mTOR, NDR1, NDR2, NEK1, NEK2, NEK6, NEK9, NEK_group, NLK, NuaK1, p37 kinase, p38_group, p70S6K, p70S6Kb, P70S6K_group, PAK1, PAK2, PAK3, PAK5, PAK6, PAK_group, PASK, P-CIP2, PCTAIRE1, PDGFR alpha, PDGFR beta, PDGFR_group, PDHK1, PDHK2, PDHK3, PDHK4, PDK-1, PDK-2, PDK_group, PHK_group, PIK3CA, PIK3CB, PIK3CD, PIK3CG, Pim-1, PKA alpha, Pka_group, PKB beta, PKB_group, PKC alpha, PKC beta, PKC delta, PKC epsilon, PKC eta, PKC gamma, PKC iota, PKC theta, PKC zeta, PKC_group, PKD1, PKD2, PKD3, PKG1/cGK-I, PKG2/cGK-II, PKG2/cGK_group, PKN1, PLK1, PLK2, PLK3, PRP4, PYK2, RAF1, Ret, ROCK1, ROCK2, Ron, RPL10, RSK-1, RSK-2, RSK-3, RSK-5, SDK1, SGK_group, SIK, Sky, Src, Src_group, STLK3, Syk, TBK1, Tec, TESK1, TESK2, TGFbR1, TGFbR2, Tie1, Tie2, Titin kinase, TNK2, TRKA, TRKB, tropomyosin kinase, TSSK3, TXK, Tyk2, TYK2, VRK1, Wee1, Wnk1, WNK1, Yes, ZAP70. In some embodiments, each possibility represents a separate embodiment of the present invention.

In some embodiments, the disease or disorder associated with a protein kinase includes, but is not limited to, cancer, diabetes, malaria, viral infections (such as HIV), cardiovascular and hypertension, CNS and neurodegeneration (such as Alzheimer's, Parkinson, manic depression, supranuclear palsy), osteoporosis, inflammation and autoimmune (such as rheumatoid arthritis, myelofibrosis, inflammatory bowel disease, Crohn's disease, colitis, psoriasis, systemic lupus erythematosus, keratoconjunctivitis sicca), allergy (general allergic disease, allergic asthma, allergic rhinitis). In some embodiments, the disease or disorder associated with a protein kinase is cancer, diabetes, malaria, viral infections, cardiovascular and hypertension, CNS and neurodegeneration, osteoporosis, pulmonary fibrosis, retinitis pigmentosis, Wet macular degeneration, Duchenne muscular dystrophy, diabetic eye disease, inflammation and autoimmune, or allergy. In some embodiments, the disease or disorder associated with a protein kinase is cancer.

In another aspect, the invention is directed to a method of treating, inhibiting, suppressing, or reducing the severity of cancer in a subject in need thereof, wherein the method comprises administering to the subject a therapeutically effective amount of a compound as described herein, or a pharmaceutically acceptable salt, N-oxide, hydrate, solvate, tautomer, or optical isomer thereof, or a pharmaceutical composition containing one or more of the compounds as described herein.

In some embodiments, the invention disclosed herein relates to a method for the treatment of a cancer patient wherein abnormal kinase activities are implicated by administrating a therapeutically effective amount of a compound disclosed herein to the patient in need of relief from said cancer. It is appreciated herein that the compounds described herein may be used alone or in combination with other compounds useful for treating cancer, including those compounds that may be therapeutically effective by the same or different modes of action. It is appreciated herein that the compounds described herein may be used in combination with other compounds that are administered to treat other symptoms of cancer, such as nausea, vomiting, pain, etc.

In some embodiments, the cancer is selected from the group consisting of acute myeloid leukemia, chronic myeloid leukemia, ovarian cancer, cervical cancer, pancreatic cancer, breast cancer, brain cancer, skin cancer, lung cancer, prostate cancer, Lymphoma, Leukemia, colon cancer, head cancer, neck cancer, thyroid cancer, kidney cancer, liver cancer and stomach cancer. In some embodiments, the cancer is acute myeloid leukemia.

It is another aspect of the invention that a compound of the invention as described herein can be used for treating, inhibiting, suppressing, or reducing the severity of cancer in a subject, wherein the method comprises administering to the subject in need thereof a therapeutically effective amount of a compound of the invention, or a pharmaceutically acceptable salt, N-oxide, hydrate, solvate, tautomer, or optical isomer thereof, or a pharmaceutical composition containing one or more of the compounds as described herein. In some embodiments, the cancer that can be treated, inhibited, suppressed, or reduced the severity of by a compound of the invention as described anywhere herein includes, but is not limited to, ovarian cancer, pancreatic cancer, breast cancer, brain cancer, skin cancer, lung cancer, prostate cancer, Lymphoma, Leukemia, colon cancer, head cancer, neck cancer, and stomach cancer. In some embodiments, the cancer that can be treated, inhibited, suppressed, or reduced the severity of by a compound of the invention as described anywhere herein includes, but is not limited to, acute myeloid leukemia, chronic myeloid leukemia, ovarian cancer, cervical cancer, pancreatic cancer, breast cancer, brain cancer, skin cancer, lung cancer, prostate cancer, Lymphoma, Leukemia, colon cancer, head cancer, neck cancer, thyroid cancer, kidney cancer, liver cancer and stomach cancer. In some embodiments, the cander is breast cancer. In other embodiments, the cancer is ovarian cancer. In some embodiments, the cancer is prostate cancer. In some embodiments, the cancer is acute myeloid leukemia.

It is yet another aspect of the invention that a compound of the invention as described herein is a protein kinase inhibitor. The compound of the invention can be used for treating, inhibiting, suppressing, or reducing the severity of a disease or a disorder associated with protein kinase, wherein the method comprises administering to the subject in need thereof a therapeutically effective amount of a compound of invnention, or a pharmaceutically acceptable salt, N-oxide, hydrate, solvate, tautomer, or optical isomer thereof. In some embodiments, the protein kinase is one known in the art. In some embodiments, the protein kinase includes, but is not limited to, FLT3 and TrkC.

In some embodiments, the protein kinase is Abl, Abl2, AFK, ALK, AMPK_group, ATM, ATR, Aurora A, Aurora B, Axl, BCKDK, BLK, BMPR1B, BMX, Brk, BRSK1, BTK, CaM-KIalpha, CaM-KIIalpha, CaMKK_group, CaM-KIV, CaM-KKalpha, CaM-KKbeta, CCDPK, CCRK, CDK1, CDK11, CDK2, CDK4, CDK5, CDK6, CDK7, CDK9, CDK_group, CDPK, Chak1, CHK1, CHK2, CK1 alpha, CK1 delta, CK1 epsilon, CK1_group, CK2 alpha, CK2_beta, CK2_group, CLK1, CSF1R, Csk, DAPK1, DAPK2, DAPK3, DAPK_group, DCAMKL1, DMPK_group, DNA-PK, DYRK1A, DYRK1B, DYRK2, DYRK3, eEF2K, Eg3 kinase, EGFR, EIF2AK2, EphA2, EphA3, EphA4, EphA8, EphB1, EphB2, EphB3, EphB5, ErbB2, FAK, Fer, Fes, FGFR1, FGFR3, FGFR4, FGFR_group, Fgr, FLT1, FLT3, FLT4, Fyn, GRK-1, GRK-2, GRK-3, GRK-4, GRK-5, GRK-6, GRK_group, GSK-3alpha, GSK-3beta, GSK-3_group, HCK, HIPK2, HIPK3, HRI, ICK, IGF1R, IKK-alpha, IKK-beta, IKK-epsilon ILK, InsR, IPL, IRAK1, IRAK4, ITK, JAK1, JAK2, JAK3, JAK_group, JNK_group, KDR, KIS, Kit, KSR1, Lck, LIMK1, LIMK2, LKB1, LOK, Lyn, MAP2K1, MAP2K2, MAP2K3, MAP2K4, MAP2K6, MAP2K7, MAPK2_group, MAP3K1, MAP3K11, MAP3K14, MAP3K5, MAP3K7, MAP3K8, MAPK3_group, MAP4K1, MAP4K2, MAP4K4, MAPK1, MAPK10, MAPK11, MAPK12, MAPK13, MAPK14, MAPK3, MAPK4, MAPK6, MAPK7, MAPK8, MAPK9, MAPK_group, MAPKAPK2, MARK_group, Mer, Met, MHCK, MLCK_group, Mnk1, Mnk2, MOS, MRCKa, MST, MST3, mTOR, NDR, NDR2, NEK, NEK2, NEK6, NEK9, NEK_group, NLK, NuaK1, p37 kinase, p38_group, p70S6K, p70S6Kb, P70S6K_group, PAK1, PAK2, PAK3, PAK5, PAK6, PAK_group, PASK, P-CIP2, PCTAIRE1, PDGFR alpha, PDGFR beta, PDGFR_group, PDHK1, PDHK2, PDHK3, PDHK4, PDK-1, PDK-2, PDK_group, PHK_group, PIK3CA, PIK3CB, PIK3CD, PIK3CG, Pim-1, PKA alpha, Pka_group, PKB beta, PKB_group, PKC alpha, PKC beta, PKC delta, PKC epsilon, PKC eta, PKC gamma, PKC iota, PKC theta, PKC zeta, PKC_group, PKD1, PKD2, PKD3, PKG1/cGK-I, PKG2/cGK-II, PKG2/cGK_group, PKN1, PLK1, PLK2, PLK3, PRP4, PYK2, RAF1, Ret, ROCK1, ROCK2, Ron, RPL10, RSK-1, RSK-2, RSK-3, RSK-5, SDK1, SGK_group, SIK, Sky, Src, Src_group, STLK3, Syk, TBK1, Tec, TESK1, TESK2, TGFbR1, TGFbR2, Tie1, Tie2, Titin kinase, TNK2, TRKA, TRKB, tropomyosin kinase, TSSK3, TXK, Tyk2, TYK2, VRK1, Wee1, Wnk1, WNK1, Yes, ZAP70. In some embodiments, each possibility represents a separate embodiment of the present invention.

In some embodiments, the disease or disorder associated with protein kinase includes those known in the art. In certain embodiments, the disease or disorder associated with protein kinase is cancer, diabetes, malaria, viral infections (such as HIV), cardiovascular and hypertension, CNS and neurodegeneration (such as Alzheimer's, Parkinson, manic depression, supranuclear palsy), osteoporosis, inflammation and autoimmune (such as rheumatoid arthritis, myelofibrosis, inflammatory bowel disease, Crohn's disease, colitis, psoriasis, systemic lupus erythematosus, keratoconjunctivitis sicca), allergy (general allergic disease, allergic asthma, allergic rhinitis). In some embodiments, each possibility represents a separate embodiment of the present invention. In other embodiments, the compound of the invention can be used for treating bacterial infections. In some embodiments, the disease or disorder associated with protein kinase is cancer, diabetes, malaria, viral infections, cardiovascular and hypertension, CNS and neurodegeneration, osteoporosis, pulmonary fibrosis, retinitis pigmentosis, Wet macular degeneration, Duchenne muscular dystrophy, diabetic eye disease, inflammation and autoimmune, or allergy. In some embodiments, the compound of the invention can be used for treating cancer, for example, acute myeloid leukemia, chronic myeloid leukemia, ovarian cancer, cervical cancer, pancreatic cancer, breast cancer, brain cancer, skin cancer, lung cancer, prostate cancer, Lymphoma, Leukemia, colon cancer, head cancer, neck cancer, thyroid cancer, kidney cancer, liver cancer and stomach cancer. In some embodiments, the cancer is breast cancer. In other embodiments, the cancer is ovarian cancer. In some embodiments, the cancer is prostate cancer. In some embodiments, the cancer is acute myeloid leukemia.

It is another aspect of the invention that a compound of the invention can be used for treating, inhibiting, suppressing, or reducing the severity of acute myeloid leukemia in a subject, wherein the method comprises administering to said subject a therapeutically effective amount of a compound of the invention, or a pharmaceutically acceptable salt, N-oxide, hydrate, solvate, tautomer, or optical isomer thereof.

It is a further aspect of the invention the compounds of the invention exhibits low nanomolar IC50 values in the tests for their anticancer properties, which are desired for clinical translation. The compound of the invention is a kinase (especially FLT3, c-Kit, and TrK) inhibitor. For example, the compound of the invention inhibits kinases, such as FLT3, TrkC, and c-Kit at the protein level. In some embodiments, a compound of the invention shows potent anticancer activities (low nanomolar IC50 values) against acute myeloid leukemia. In some embodiments, a compound of the invention is also active against other cancer cell lines, such as pancreatic, breast, and ovarian cancers. In some embodiments, the cancer is acute myeloid leukemia, chronic myeloid leukemia, ovarian cancer, cervical cancer, pancreatic cancer, breast cancer, brain cancer, skin cancer, lung cancer, prostate cancer, Lymphoma, Leukemia, colon cancer, head cancer, neck cancer, thyroid cancer, kidney cancer, liver cancer and stomach cancer. In some embodiments, the cancer is breast cancer. In other embodiments, the cancer is ovarian cancer. In some embodiments, the cancer is prostate cancer. In some embodiments, the cancer is acute myeloid leukemia.

In addition to targeting FLT-3, a compound of the invention also inhibits other protein kinase TrkC as well as c-MyC and Ras oncogenic proteins. Due to the multi-targeting of oncogenic drivers, the compound of the invention has superior performance against AML with mutant FLT-3 than what is known in the art. Moreover, due to its multi targeting nature, a compound of the invention is also effective against other cancer cell lines, for example, ovarian cancer, pancreatic cancer, breast cancer, brain cancer, skin cancer, lung cancer, prostate cancer, Lymphoma, Leukemia, colon cancer, head cancer, neck cancer, and stomach cancer. In some embodiments, the cancer is breast cancer. In some embodiments, the cancer that can be treated, inhibited, suppressed, or reduced the severity of by a compound of the invention as described anywhere herein includes, but is not limited to, acute myeloid leukemia, chronic myeloid leukemia, ovarian cancer, cervical cancer, pancreatic cancer, breast cancer, brain cancer, skin cancer, lung cancer, prostate cancer, Lymphoma, Leukemia, colon cancer, head cancer, neck cancer, thyroid cancer, kidney cancer, liver cancer and stomach cancer. In other embodiments, the cancer is ovarian cancer. In some embodiments, the cancer is prostate cancer. In some embodiments, the cancer is acute myeloid leukemia.

The compound of the invention inhibits the proliferation of several cancer cell lines at nano molar concentrations. Further, the compound of the invention inhibits protein kinase FLT-3 phosphorylation and also inhibits the proliferation of FLT-3 driven cancers, such as MV4-11 (an acute myeloid leukemia) with low (e.g., single digit nanomolar) IC50 values. A compound of the invention as a potent kinase inhibitor can be used to treat cancers, malaria, arthritis, diseases related to the immune system and other diseased states that kinases play key roles in disease establishment or progression.

It will be appreciated by persons skilled in the art that the present invention is not limited by what has been particularly shown and described herein above. Rather the scope of the present invention includes both combinations and sub-combinations of the various features described hereinabove as well as variations and modifications which would occur to persons skilled in the art upon reading the specification and which are not in the prior art.

The details of one or more embodiments of the invention are set forth in the accompa-nying the description below. Other features, objects, and advantages of the invention will be apparent from the description and drawings, and from the claims.

EXAMPLES

Materials and Methods

Solvents and reagents were purchased from commercial vendors and were used without further purification. $^1$H NMR spectra were recorded at 500 MHz, using a Bruker Avance 500 spectrometers with a CryoProbe.

ESI-MS experiments were performed using an Agilent MSD/TOF mass spectrometer at the Bindley Bioscience Center Metabolomics Facility (Purdue University). The instrument was calibrated to a resolution of 10000 with a 10% valley between peaks using the appropriate polypropylene glycol standards.

Analytical thin layer chromatography was carried out on silica gel 60 F254 plastic-backed TLC plates. Compounds were visualized with both short and long wavelength UV light and iodine/silica gel staining unless otherwise specified. Flash column chromatography was performed using Teledyne Isco's Combi-Flash Rf+ with RediSep $R_f$ silica gel disposable flash coumns, 40-60 microns (Catalog #692203304). For purities estimated by HPLC, the major peak accounted for ≥95% of the combined total peak area when monitored by a UV detector at 254 nm unless otherwise specified. All yields refer to isolated compounds.

Quizartinib (>99.5% purity) and crenolanib (>99.5% purity) were purchased from Chemietek.com. Unless otherwise noted, all materials were obtained from commercial suppliers and used as obtained. Solvents were purchased from Sigma and used directly without purification. NMR spectra were recorded on a Bruker 400, 500 or 600 MHz spectrometer at ambient temperature. Chemical shifts are reported in parts per million (δ) and are calibrated using residual undeuterated solvent as an internal reference. Data for 1H NMR spectra are reported as follows: chemical shift (δ ppm) (multiplicity, coupling constant (Hz), integration). Multiplicities are reported as follows: s=singlet, d=doublet, t=triplet, q=quartet, m=multiplet, br=broad, or combinations thereof.

In Vitro Kinase Assays

The Reaction Biology Corporation (www.reactionbiology.com, Malvern, Pa.) HotSpot assay platform was used to measure kinase/inhibitor interactions exactly as previously described. Kinase and substrate were mixed in a buffer containing 20 mM HEPES pH 7.5, 10 mM $MgCl_2$, 1 mM EGTA, 0.02% Brij35, 0.02 mg/mL BSA, 0.1 mM $Na_3VO_4$, 2 mM DTT and 1% DMSO. Single-dose of compounds (500 nM) were then added to each reaction mixture. After 20-minute incubation, ATP (Sigma) and [γ-$^{33}$P] ATP (Perkin Elmer) were added at a final total concentration of 100 iM for addition 2 hours at room temperature, followed by spotting onto P81 ion exchange cellulose chromatography paper (Whatman, Inc.). Filter paper was washed in 0.75% phosphoric acid to remove unincorporated ATP. Percent remaining kinase activity of a vehicle (DMSO) containing kinase reaction was calculated for each kinase/inhibitor pair using Prism 5 (GraphPad).

Docking Method for FLT3

The docking package CANDOCK[1] was used to identify docking poses of HSW630-1 in the binding site of FLT3 kinases. The structure of FLT3 was obtained from the protein databank (PDB#4XUF). The entire protein was considered flexible. No binding site was provided to CANDOCK and the location of this site was determined by the program automatically. CANDOCK used default parameters with interactive flexibility with a maximum iteration of 10 and only the top 2% of the top seed values were used to generate full ligands.

Cell Lines and Culturing

Molm-14 cells were the kind gift of Dr. Mark Levis from Johns Hopkins University. THP-1, MV4-11, K-562 and MRC-5A cells were purchased from ATCC (ATCC, Manassas, Va.). All cell lines were grown in 37° C. with 5% $CO_2$ atmosphere with RPMI 1640 (Life technologies, Carlsbad, Calif.) supplemented with heat-inactivated 10% (V/V) fetal bovine serum. Cell lines were grown and maintained according to ATCC recommendations.

$IC_{50}$ Proliferation Assay

Cell lines were seeded into 96-well plates the afternoon prior to treatment. Approximately 18 hours later, compounds were semi-serially diluted in dimethyl sulfoxide (DMSO) and then growth medium, and added to cells. Plates were incubated for 72 hours prior to addition of Alamar Blue (Life Technologies, Carlsbad, Calif.). Plates were read after 4 additional hours of incubation at 37° C. using a Bio-Tek Synergy HT plate reader (Bio-Tek, Winooski, Vt.). Data was analyzed and graphed using GraphPad Prism Software (Graphpad, La Jolla, Calif.).

Proliferation Inhibition at 100 nM or 1 mM Inhibitor Concentration

To determine inhibition at 100 nM or 1 mM, 96-well plates were seeded the afternoon before treatment. Plates were then treated with compound diluted in dimethyl sulfoxide (DMSO) as well as a DMSO control the following day for 72 hours. After this time the plates were then treated with 10 μL of CellTiter-Blue Cell Viability Assay (Promega, Madison, Wis.) for 4 hours. Then the plates were read on a plate reader (Bio-Tek, Winooski, Vt.). Data was analyzed on Excel as a percent of the DMSO vehicle.

$IC_{50}$ Determination (Proliferation Assay)

Midostaurin hydrate (control compound) was purchased from Sigma-Aldrich (St. Louis, Mo.), >98% HPLC purity and used without further purification. Cell lines were seeded into 96-well plates the afternoon prior to treatment. Approximately 18 hours later, compounds were diluted in dimethyl sulfoxide (DMSO) and added to cells. Plates were incubated for 72 hours and cells viability determined with CellTiter-Blue Cell Viability Assay (Promega, Madison, Wis.). Plates were read after 4 additional hours of incubation at 37° C. using plate reader (Bio-Tek, Winooski, Vt.). Data was analyzed and graphed using GraphPad Prism Software (Graphpad, La Jolla, Calif.).

Western Blotting

Effect of HSW630-1 on protein expression was tested in the MV4-11 leukemia cell line. Total protein extracts were prepared using RIPA buffer (SIGMA) supplemented with Complete Mini™ protease inhibitor and PHOStop™ phosphatase inhibitors (Roche). Equal amounts of proteins (up to 25 μg) were separated on 4-12% NuPAGE gels in 1×MOPS or 1×MES buffer (Invitrogen) and transferred onto PVDF membranes (Millipore). The membrane was blocked with 5% dry milk in 1×TBS/0.1% Tween 20 (TBST) for at least 1 h at room temperature and incubated with human specific primary antibodies: FLT3, Phospho-FLT3, c-Myc (Cell Signaling Technologies), KRAS (Santa Cruz), or mouse anti-β-actin (SIGMA) overnight at 4° C. The membrane was washed 3 times in TBST and incubated with a horseradish peroxidase-conjugated secondary anti-rabbit or anti-mouse antibody (Cell Signaling Technologies) for 1 h at room temperature. Blots were again washed and the signal was detected with SuperSignal West Femto Chemiluminescent Substrate (Pierce) and exposed to HyBlot CL® autoradiography film (Denville).

Example 1

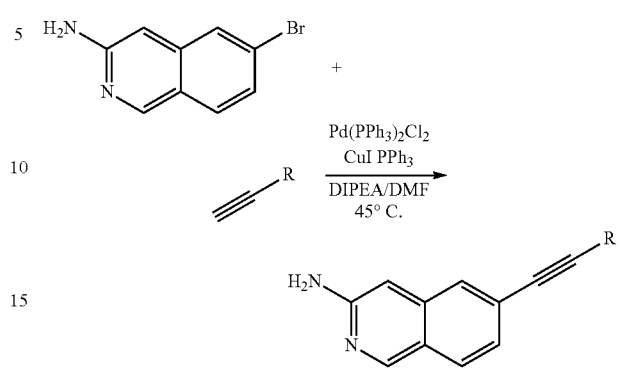

In a 50 ml round bottom flask, 50 mg 6-bromo-isoquinolin-3-amine, 10 mol % Bis(triphenylphosphine)palladium (II) dichloride, 10 mol % triphenylphosphine were added, purged with nitrogen three times before 5 ml anhydrous DMF was added. Stirred at 45° C., stirred for another 5 minutes before the corresponding alkyne was added via syringe in 1ml anhydrous DMF in 2 minutes. 2 ml DIPEA was added and stirred overnight. After TCL showed the reaction was completed, equal volume of distilled water was added, and extracted with DCM three times (50 ml*3), washed with brine and dried with anhydrous sodium sulfate, removed solvents. Pure product was obtained by Combi-flash using 100% DCM to 35% MeOH.

Example 1A:
6-(3,3-dimethylbut-1-yn-1-yl)isoquinolin-3-amine

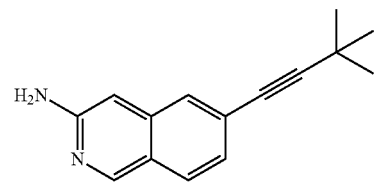 [SMILES: CC(C)(C)C#Cc1ccc2cnc(N)cc2c1]

$^1$H NMR (500 MHz, DMSO) δ 8.78 (d, J=19.0 Hz, 1H), 7.80-7.64 (m, 1H), 7.53 (s, 1H), 7.09 (ddd, J=97.0, 8.5, 1.5 Hz, 1H), 6.55 (d, J=3.7 Hz, 1H), 6.05 (d, J=62.4 Hz, 2H), 1.28 (s, 9H). LR-MS(ESI) m/z calcd for $C_{15}H_{16}N_2$ ([M+H]$^+$) 225.1 found 225.3.

Example 1B:
6-(hexa-1,5-diyn-1-yl)isoquinolin-3-amine

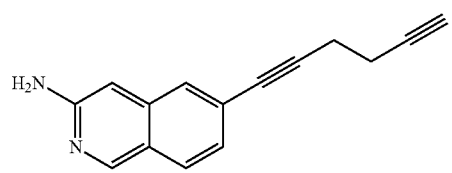 [SMILES: C#CCCC#Cc1ccc2cnc(N)cc2c1]

LR-MS(ESI) m/z calcd for $C_{15}H_{12}N_2$ ([M+H]$^+$) 221.1 found 221.1.

Example 1C: 6-(cyclopropylethynyl)isoquinolin-3-amine

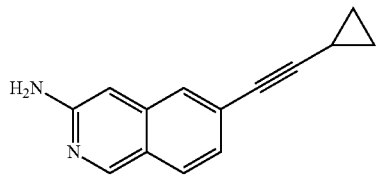 [SMILES: Nc1cc2cc(C#CC3CC3)ccc2cn1]

LR-MS(ESI) m/z calcd for $C_{14}H_{12}N_2$ ([M+H]$^+$) 209.1 found 209.1.

Example 1D: 6-(3-(diethylamino)prop-1-yn-1-yl)isoquinolin-3-amine

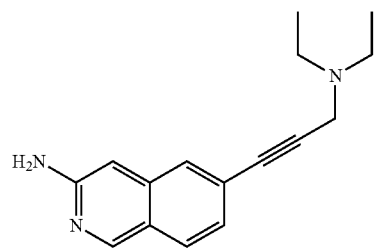 [SMILES: CCN(CC)CC#Cc1ccc2cnc(N)cc2c1]

$^1$H NMR (500 MHz, CDCl$_3$) δ 7.72-7.63 (m, 2H), 7.54 (dd, J=7.6, 1.2 Hz, 1H), 7.46 (td, J=7.6, 2.8 Hz, 1H), 7.26 (s, 1H), 3.50 (s, 2H), 2.56 (d, J=7.2 Hz, 4H), 1.07 (t, J=7.2 Hz, 6H). LR-MS(ESI) m/z calcd for $C_{16}H_{19}N_3$ ([M+H]$^+$) 254.2 found 254.2.

Example 1E: 6-(hex-1-yn-1-yl)isoquinolin-3-amine

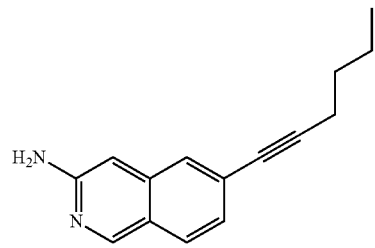 [SMILES: CCCCC#Cc1ccc2cnc(N)cc2c1]

LR-MS(ESI) m/z calcd for $C_{15}H_{16}N_2$ ([M+H]$^+$) 225.1 found 225.6.

Example 1F: 6-ethynylisoquinolin-3-amine

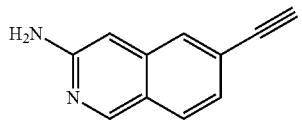

LR-MS(ESI) m/z calcd for $C_{11}H_8N_2$ ([M+H]$^+$) 169.1 found 169.5.

Example 1G: tert-butyl (3-(3-aminoisoquinolin-6-yl)prop-2-yn-1-yl)carbamate

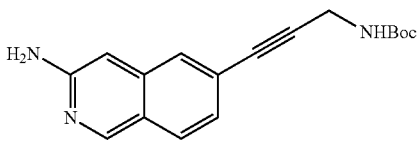 [SMILES: CC(C)(C)OC(=O)NCC#Cc1ccc2cnc(N)cc2c1]

$^1$H NMR (500 MHz, MeOD) δ 8.72 (s, 1H), 7.97 (s, 1H), 7.81-7.45 (m, 3H), 7.15 (dd, J=8.5, 1.1 Hz, 1H), 6.71 (s, 1H), 4.08 (s, 2H), 1.47 (s, 9H); $^{13}$C NMR (126 MHz, DMSO) δ 157.45, 155.76, 151.79, 138.47, 128.62, 127.88, 124.22, 124.08, 121.69, 97.05, 89.51, 82.19, 78.78, 30.65, 28.66. LR-MS(ESI) m/z calcd for $C_{17}H_{19}N_3O_2$ ([M+H]$^+$) 298.1 found 298.4.

Example 1H: 6-(3-aminoprop-1-yn-1-yl)isoquinolin-3-amine

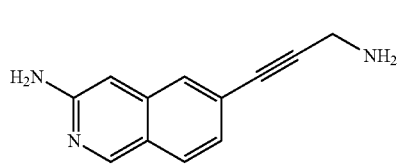 [SMILES: NCC#Cc1ccc2cnc(N)cc2c1]

LR-MS(ESI) m/z calcd for $C_{12}H_{11}N_3$ ([M+H]$^+$) 198.0 found 198.6.

Example 1I: 6-(3-aminoisoquinolin-6-yl)hex-5-ynenitrile

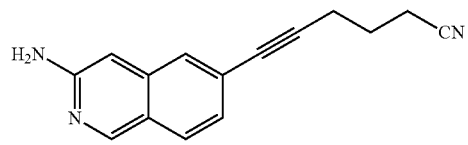 [SMILES: N#CCCCC#Cc1ccc2cnc(N)cc2c1]

LR-MS(ESI) m/z calcd for $C_{15}H_{13}N_3$ ([M+H]$^+$) 236.1 found 236.6.

Example 2

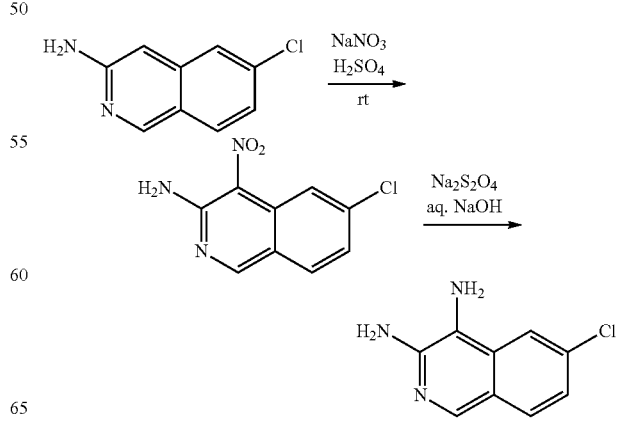

To a 50 ml round bottom flask, 1 eq 6-chloro-isoquinolin-3-amine was dissolved in concentrated sulfuric acid at room temperature, after stirred the mixture for 5 minutes, sodium nitrate was added all at once, and the mixture was stirred overnight. After TLC showed the reaction was completed, 100 ml cooled water was added, and extracted with DCM three times (50 ml*3), washed with brine and dried with anhydrous sodium sulfate, removed solvents. The crude product was directly treated with 100 ml aqueous sodium hydroxide and 5 eq of sodium dithionite was added and the mixture was stirred overnight. After TLC showed the reaction was completed, equal volume of distilled water was added, and extracted with DCM three times (50 ml*3), washed with brine and dried with anhydrous sodium sulfate, removed solvents. Pure product was obtained by Combi-flash using 100% DCM to 35% MeOH.

Example 2A: 6-chloro-4-nitroisoquinolin-3-amine

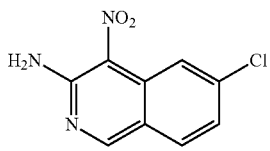

LR-MS(ESI) m/z calcd for $C_9H_6ClN_3O_2$ ([M+H]$^+$) 224.1 found 224.4.

Example 2B: 6-chloroisoquinoline-3,4-diamine

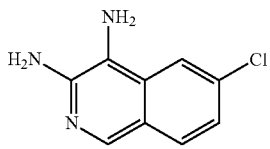 [SMILES: Nc1ncc2ccc(Cl)cc2c1N]

LR-MS(ESI) m/z calcd for $C_9H_8ClN_3$ ([M+H]$^+$) 194.0 found 194.2.

Example 3: pyrido[3,4-b]pyrazin-7-amine

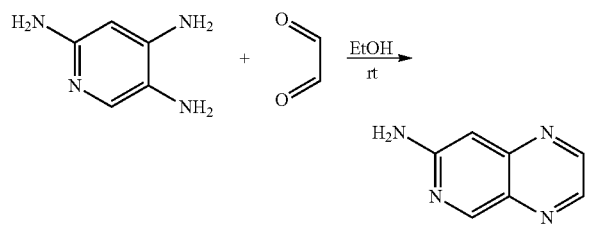

To a 50 ml round bottom flask, 1 eq pyridine-2,4,5-triamine was dissolved in anhydrous ethanol at room temperature, after stirred the mixture for 5 minutes, oxalaldehyde was added all at once, and the mixture was stirred overnight. After TLC showed the reaction was completed, 100 ml cooled water was added, and extracted with DCM three times (50 ml*3), washed with brine and dried with anhydrous sodium sulfate, removed solvents. Pure product was obtained by Combi-flash using 100% DCM to 35% MeOH.

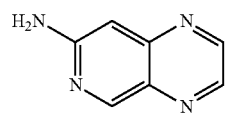

LR-MS(ESI) m/z calcd for $C_7H_6N_4$ ([M+H]$^+$) 147.0 found 147.1.

Example 4: 3-aminoisoquinoline-6-carbonitrile

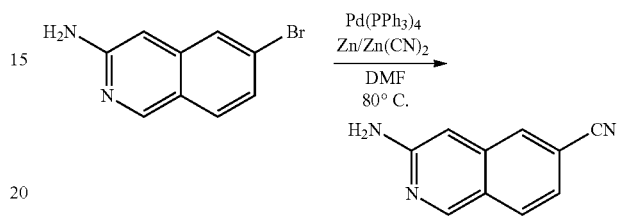

In a 50 ml round bottom flask, 50 mg 6-bromo-isoquinolin-3-amine, 10 mol % tetrakis(triphenylphosphine)palladium(0), 1 mol % zinc, 1.5 eq zinc cyanide were added, purged with nitrogen three times before 5 ml anhydrous DMF was added. Stirred at 80° C. overnight. After TCL shows the reaction is completed, equal volume of distilled water was added, and extracted with DCM three times (50 ml*3), washed with brine and dried with anhydrous sodium sulfate, removed solvents. Pure product was obtained by Combi-flash using 100% DCM to 35% MeOH.

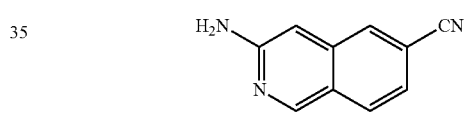

$^1$H NMR (500 MHz, DMSO) δ 8.95 (s, 1H), 8.18 (s, 1H), 7.67-7.50 (m, 2H), 7.35 (dd, J=8.4, 1.3 Hz, 1H), 6.69 (s, 1H), 6.32 (s, 2H); LR-MS(ESI) m/z calcd for $C_{10}H_7N_3$ ([M+H]$^+$) 170.1 found 170.6.

Example 5

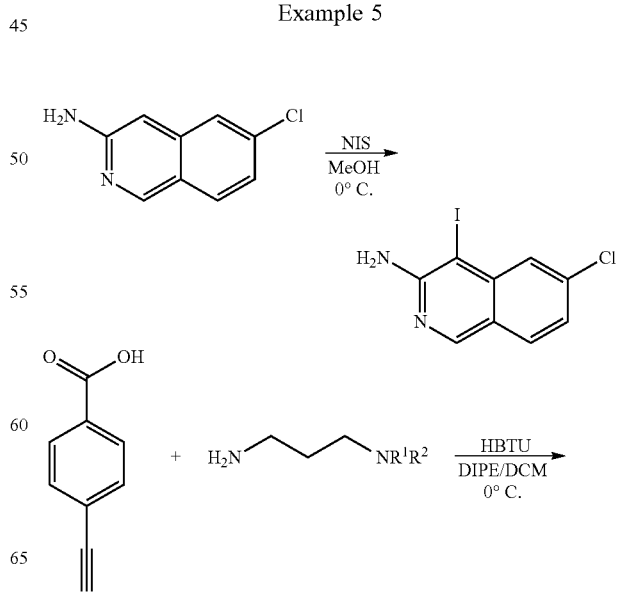

-continued

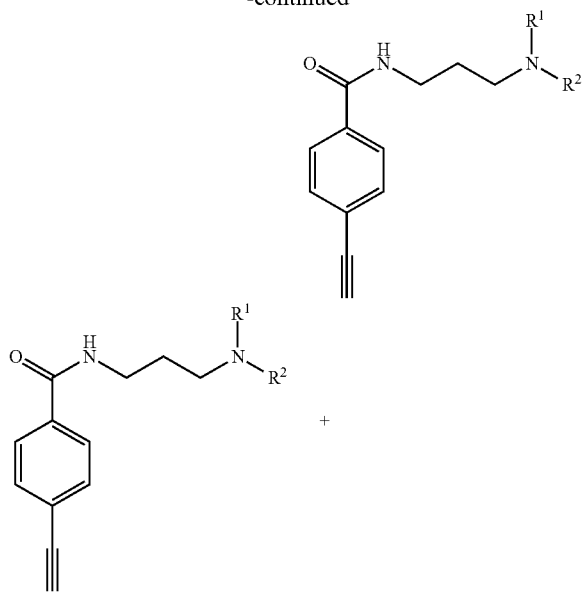

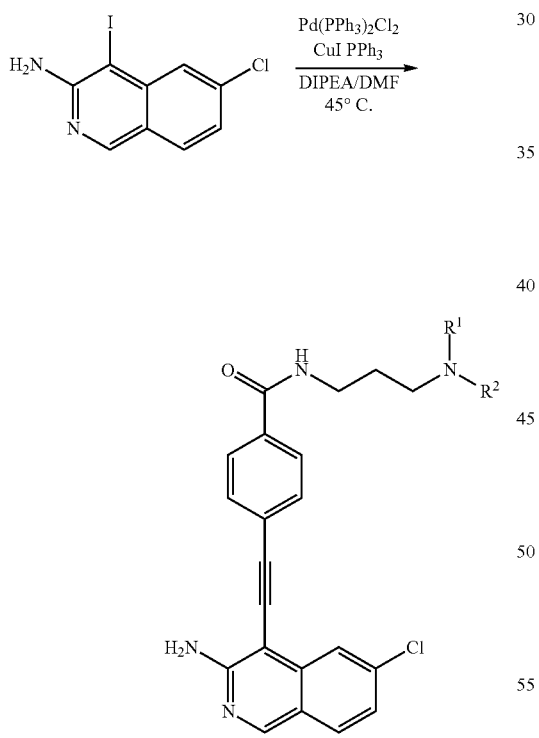

In a 250 ml round bottom flask, 579 mg 1 eq 6-chloroisoquinolin-3-amine was dissolved in 150 ml anhydrous MeOH at 0° C. and stirred for 5 minutes before 675 mg NIS was added in portions slowly in 10 minutes. Stop the reaction by remove all solvents when TLC showed the reaction was completed (usually within 15 minutes). 420 mg 6-chloro-4-iodoisoquinolin-3-amine was obtained either by flash column or Combi-flash using 100% hexane-100% ethyl acetate.

In a 100 ml round bottom flask, 290 mg 1 eq 4-ethynyl-benzoic acid was dissolved in 50 ml anhydrous DCM at 0° C., 800 mg of HBTU was added and stirred for another 10 minutes before 1.1 eq of the corresponding amine was added. After 30 seconds, 1 eq. of DIPEA was added and the mixture was stirred overnight. After TLC showed the reaction was completed, stop the reaction by adding equal volume of distilled water. Extracted with DCM three times (50 ml*3), washed with brine and dried with anhydrous sodium sulfate, removed solvents. Pure benzamide was obtained by Combi-flash using 100% DCM to 20% MeOH.

In a 50 ml round bottom flask, 50 mg 6-chloro-4-iodo-isoquinolin-3-amine, 10 mol % Bis(triphenylphosphine)palladium(II) dichloride, 10 mol % triphenylphosphine were added, purged with nitrogen three times before 5 ml anhydrous DMF was added. Stirred at 45° C. for another 5 minutes before the corresponding benzamide was added via syringe in 1ml anhydrous DMF in 2 minutes. 2 ml DIPEA was added and stirred overnight. After TCL shows the reaction is completed, equal volume of distilled water was added, and extracted with DCM three times (50 ml*3), washed with brine and dried with anhydrous sodium sulfate, removed solvents. Pure product was obtained by Combi-flash using 100% DCM to 35% MeOH.

Example 5A:
4-ethynyl-N-(3-morpholinopropyl)benzamide

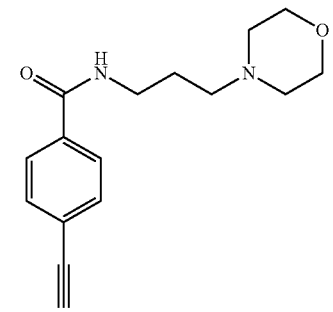 [SMILES: C#Cc1ccc(C(=O)NCCCN2CCOCC2)cc1]

LR-MS(ESI) m/z calcd for $C_{16}H_{20}N_2O_2$ ([M+H]$^+$) 273.2, found. 273.8.

Example 5B:
N-(3-(dimethylamino)propyl)-3-ethynylbenzamide

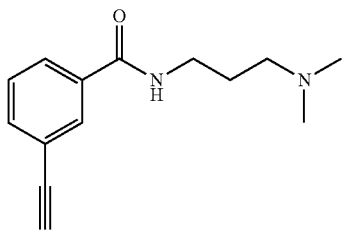 [SMILES: C#Cc1cccc(C(=O)NCCCN(C)C)c1]

LR-MS(ESI) m/z calcd for $C_{14}H_{18}N_2O$ ([M+H]$^+$) 231.1, found 231.6.

Example 5C: 4-ethynyl-N-(3-(4-methylpiperazin-1-yl)propyl)benzamide

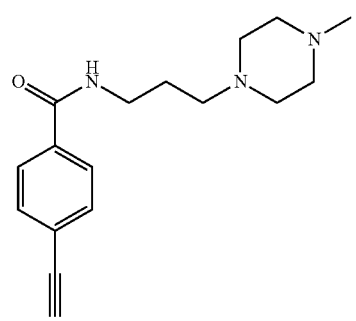 [SMILES: C#Cc1ccc(C(=O)NCCCN2CCN(C)CC2)cc1]

LR-MS(ESI) m/z calcd for $C_{17}H_{23}N_3O$ ([M+H]$^+$) 286.1, found 286.4.

Example 5D: 4-ethynyl-N-(4-((4-methylpiperazin-1-yl)methyl)phenyl)benzamide

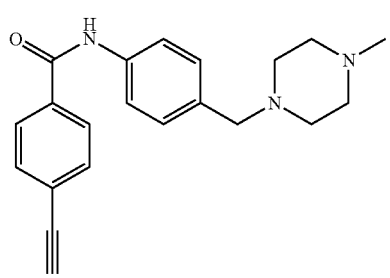 [SMILES: C#Cc1ccc(C(=O)Nc2ccc(CN3CCN(C)CC3)cc2)cc1]

LR-MS(ESI) m/z calcd for $C_{21}H_{23}N_3O$ ([M+H]$^+$) 334.2, found 334.4.

Example 5E: N-(2-(dimethylamino)ethyl)-4-ethynylbenzamide

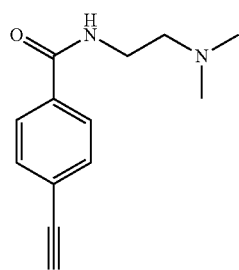 [SMILES: C#Cc1ccc(C(=O)NCCN(C)C)cc1]

LR-MS(ESI) m/z calcd for $C_{13}H_{16}N_2O$ ([M+H]$^+$) 217.1, found 217.2.

Example 5F: 4-ethynyl-N-(3-(pyrrolidin-1-yl)propyl)benzamide

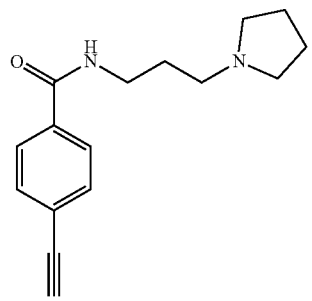 [SMILES: C#Cc1ccc(C(=O)NCCCN2CCCC2)cc1]

LR-MS(ESI) m/z calcd for $C_{16}H_{20}N_2O$ ([M+H]$^+$) 257.1, found 257.3.

Example 5G: 4-ethynyl-N-(3-(piperidin-1-yl)propyl)benzamide

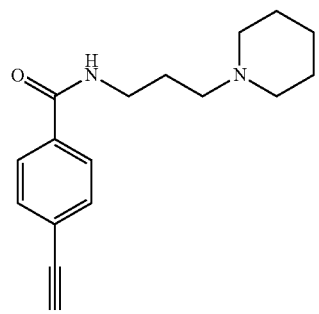 [SMILES: C#Cc1ccc(C(=O)NCCCN2CCCCC2)cc1]

LR-MS(ESI) m/z calcd for $C_{17}H_{22}N_2O$ ([M+H]$^+$) 271.2, found 271.6.

Example 5H: N-(5-(dimethylamino)pentyl)-4-ethynylbenzamide

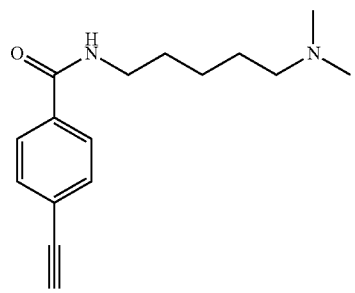 [SMILES: C#Cc1ccc(C(=O)NCCCCCN(C)C)cc1]

LR-MS(ESI) m/z calcd for $C_{16}H_{22}N_2O$ ([M+H]$^+$) 259.2, found 259.6.

Example 5I:
4-ethynyl-N-(3-methoxypropyl)benzamide

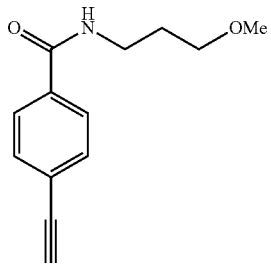 [SMILES: C#Cc1ccc(C(=O)NCCCOC)cc1]

¹H NMR (500 MHz, CDCl₃) δ 7.73 (d, J=8.5 Hz, 2H), 7.54 (d, J=8.5 Hz, 2H), 3.62-3.51 (m, 4H), 3.39 (s, 3H), 1.90 (dd, J=6.5, 5.5 Hz, 2H); ¹³C NMR (126 MHz, CDCl₃) δ 166.40, 134.78, 132.22, 126.82, 125.06, 82.61, 79.31, 72.19, 58.99, 39.01, 28.58. LR-MS(ESI) m/z calcd for C₁₃H₁₅NO₂ ([M+H]⁺) 218.1, found 218.3.

Example 5J: tert-butyl 4-(3-(4-ethynylbenzamido)propyl)piperazine-1-carboxylate

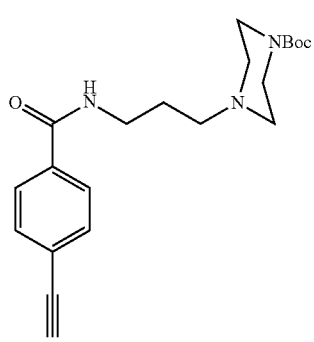 [SMILES: C#Cc1ccc(C(=O)NCCCN2CCN(C(=O)OC(C)(C)C)CC2)cc1]

LR-MS(ESI) m/z calcd for C₂₁H₂₉N₃O₃ ([M+H]⁺) 217.1, found 271.3.

Example 5K: N-(3-(dimethylamino)-2-hydroxypropyl)-4-ethynylbenzamide

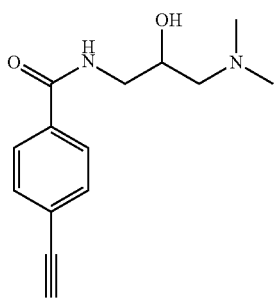 [SMILES: C#Cc1ccc(C(=O)NCC(O)CN(C)C)cc1]

LR-MS(ESI) m/z calcd for C₁₄H₁₈N₂O₂ ([M+H]⁺) 217.1, found 217.5.

Example 5L: 4-ethynyl-N-(2-hydroxy-3-(piperidin-1-yl)propyl)benzamide

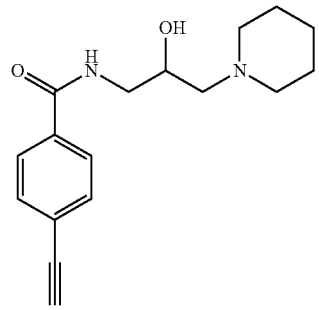 [SMILES: C#Cc1ccc(C(=O)NCC(O)CN2CCCCC2)cc1]

LR-MS(ESI) m/z calcd for C₁₇H₂₂N₂O₂ ([M+H]⁺) 287.2, found 287.4.

Example 5M: 2-ethynyl-N-(3-(piperidin-1-yl)propyl)benzamide

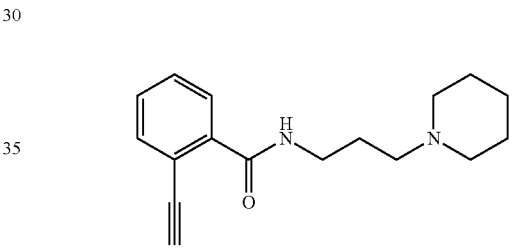

LR-MS(ESI) m/z calcd for C₁₇H₂₂N₂O ([M+H]⁺) 271.1, found 270.2.

Example 5N: 4-ethynyl-N-(4-methyl-3-((4-(pyridin-3-yl)pyrimidin-2-yl)amino)phenyl)benzamide

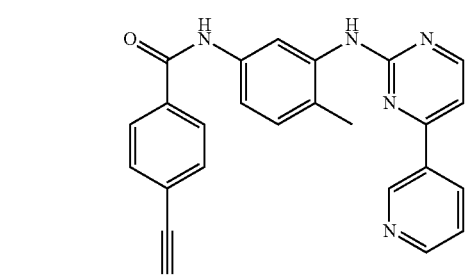 [SMILES: C#Cc1ccc(C(=O)Nc2ccc(C)c(Nc3nccc(-c4cccnc4)n3)c2)cc1]

LR-MS(ESI) m/z calcd for C₂₅H₁₉N₅O ([M+H]⁺) 406.2, found 406.4.

Example 5O: 4-ethynyl-N-(2-(piperidin-1-yl)ethyl)benzamide

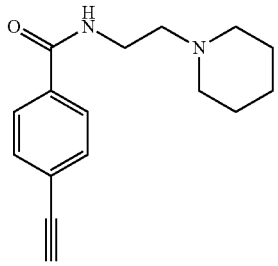 [SMILES: C#Cc1ccc(C(=O)NCCN2CCCCC2)cc1]

$^1$H NMR (500 MHz, Chloroform-d) δ 7.74 (d, J=8.2 Hz, 2H), 7.53 (d, J=8.2 Hz, 2H), 7.13 (s, 1H), 3.52 (q, J=5.7 Hz, 2H), 3.18 (s, 1H), 2.56 (t, J=6.0 Hz, 2H), 2.45 (s, 4H), 1.59 (p, J=5.6 Hz, 4H), 1.46 (t, J=6.0 Hz, 2H); $^{13}$C NMR (126 MHz, CDCl$_3$) δ 166.53, 134.67, 132.24, 126.97, 125.14, 82.87, 79.34, 56.94, 54.24, 36.38, 25.89, 24.22.

Example 5P: N-(4-aminophenethyl)-4-ethynylbenzamide

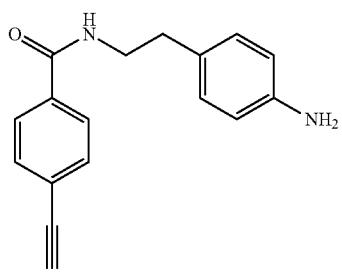 [SMILES: C#Cc1ccc(C(=O)NCCc2ccc(N)cc2)cc1]

$^1$H NMR (500 MHz, Chloroform-d) δ 7.64 (d, J=8.4 Hz, 2H), 7.51 (d, J=8.5 Hz, 2H), 7.01 (d, J=8.3 Hz, 2H), 6.66 (d, J=8.3 Hz, 2H), 6.11 (s, 1H), 3.65 (q, J=6.6 Hz, 2H), 3.18 (s, 1H), 2.81 (t, J=6.8 Hz, 2H); $^{13}$C NMR (126 MHz, CDCl$_3$) δ 166.57, 145.01, 134.71, 132.29, 129.66, 128.54, 126.80, 125.22, 115.50, 82.78, 79.40, 41.37, 34.72.

Example 5Q: tert-butyl (1-(4-ethynylbenzoyl)piperidin-4-yl)carbamate

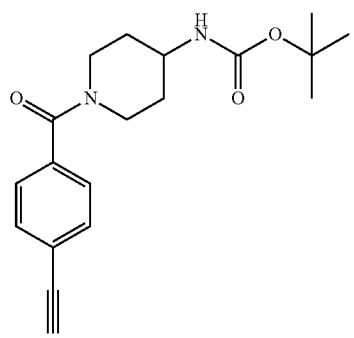 [SMILES: C#Cc1ccc(C(=O)N2CCC(NC(=O)OC(C)(C)C)CC2)cc1]

$^1$H NMR (500 MHz, Chloroform-d) δ 7.51 (d, J=8.1 Hz, 2H), 7.33 (d, J=8.3 Hz, 2H), 4.57-4.59 (2H), 3.69 (s, 2H), 3.14 (s, 1H), 3.08 (s, 1H), 2.95 (s, 1H), 1.99 (d, J=47.4 Hz, 2H), 1.44-1.25 (11H); $^{13}$C NMR (126 MHz, CDCl$_3$) δ 169.60, 155.05, 136.10, 132.26, 126.91, 123.63, 82.81, 79.67, 78.71, 47.88, 33.11, 32.15, 28.39.

Example 5R: tert-butyl (1-(3-ethynylbenzoyl)piperidin-4-yl)carbamate

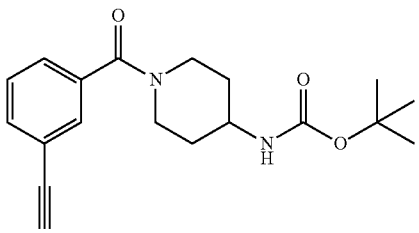 [SMILES: C#Cc1cccc(C(=O)N2CCC(NC(=O)OC(C)(C)C)CC2)c1]

$^1$H NMR (500 MHz, Chloroform-d) δ 7.52 (dd, J=6.0, 2.3 Hz, 1H), 7.49 (s, 1H), 7.40-7.32 (m, 2H), 4.59-4.49 (NH & NH—CH, 2H), 3.69 (s, 2H), 3.11 (s, C≡C—H & N—CH$_a$H$_b$, 2H), 2.96 (s, N—CH$_a$H$_b$, 1H), 2.05-1.94 (2H), 1.45-1.28 (—(CH$_3$)$_3$ & CH$_2$, 11H); $^{13}$C NMR (126 MHz, CDCl$_3$) δ 169.33, 155.04, 136.23, 133.24, 130.38, 128.67, 127.16, 122.62, 82.71, 79.67, 78.23, 47.89, 38.63, 32.15, 28.39.

Example 5S: [1,4'-bipiperidin]-1'-yl(4-ethynylphenyl)methanone

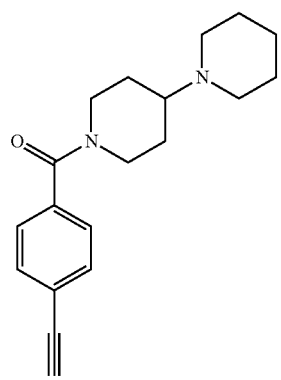 [SMILES: C#Cc1ccc(C(=O)N2CCC(N3CCCCC3)CC2)cc1]

$^1$H NMR (500 MHz, Chloroform-d) δ 7.50 (d, J=7.8 Hz, 2H), 7.34 (d, J=8.1 Hz, 2H), 4.72 (s, 1H), 3.73 (s, 1H), 3.13 (s, 1H), 2.98 (s, 1H), 2.74 (s, 1H), 2.53 (s, 5H), 1.93 (s, 1H), 1.77 (s, 1H), 1.63-1.40 (m, 7H); $^{13}$C NMR (126 MHz, CDCl$_3$) δ 169.41, 136.33, 132.23, 126.90, 123.49, 82.85, 78.62, 62.54, 50.29, 26.18, 24.55.

Example 5T: N-(4-(2-(dimethylamino)ethoxy)benzyl)-4-ethynylbenzamide

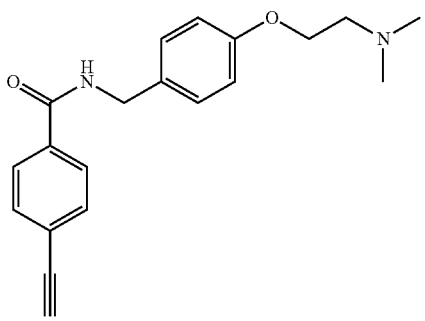 [SMILES: C#Cc1ccc(C(=O)NCc2ccc(OCCN(C)C)cc2)cc1]

¹H NMR (500 MHz, Chloroform-d) δ 7.73 (d, J=8.4 Hz, 2H), 7.51 (d, J=8.3 Hz, 2H), 7.24 (d, J=8.5 Hz, 2H), 6.87 (d, J=8.5 Hz, 2H), 6.53 (t, J=5.7 Hz, 1H), 4.54 (d, J=5.5 Hz, 2H), 4.06 (t, J=5.7 Hz, 2H), 3.18 (s, 1H), 2.76 (t, J=5.6 Hz, 2H), 2.36 (s, 6H); ¹³C NMR (126 MHz, CDCl₃) δ 166.46, 158.31, 134.42, 132.27, 130.28, 129.31, 126.98, 125.34, 114.85, 82.76, 79.52, 65.83, 58.17, 45.76, 43.69.

Example 5U: 3-ethynyl-N-(2-(piperidin-1-yl)ethyl)benzamide

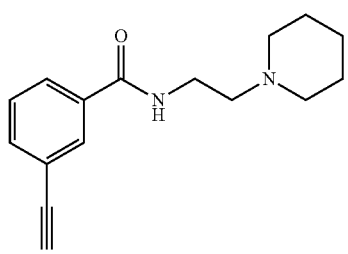 [SMILES: C#Cc1cccc(C(=O)NCCN2CCCCC2)c1]

¹H NMR (500 MHz, Chloroform-d) δ 8.85 (s, 1H), 8.10 (s, 1H), 8.03 (dd, J=7.8, 1.5 Hz, 1H), 7.55 (dd, J=7.5, 1.4 Hz, 1H), 7.36 (t, J=7.8 Hz, 1H), 3.85 (q, J=5.5 Hz, 2H), 3.19 (t, J=5 Hz, 2H), 3.08 (bs, 5H), 1.97 (s, 4H), 1.61 (s, 2H); ¹³C NMR (126 MHz, CDCl₃) δ 166.99, 135.09, 133.60, 131.58, 128.62, 127.79, 122.51, 82.82, 78.10, 57.71, 54.32, 34.83, 22.86, 22.08.

Example 5V: N-(2-(1H-imidazol-4-yl)ethyl)-4-ethynylbenzamide

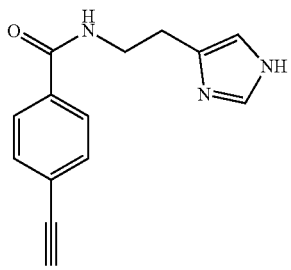 [SMILES: C#Cc1ccc(C(=O)NCCc2c[nH]cn2)cc1]

¹H NMR (500 MHz, DMSO-d₆) δ 8.66 (t, J=5.6 Hz, 1H), 7.82 (d, J=8.3 Hz, 2H), 7.60-7.49 (m, 3H), 6.82 (s, 1H), 4.36 (s, 1H), 3.50-3.43 (m, 2H), 2.74 (t, J=7.5 Hz, 2H); ¹³C NMR (126 MHz, DMSO) δ 165.73, 135.16, 135.12, 132.11, 127.89, 124.76, 117.11, 83.38, 83.27, 27.29.

Example 5W: tert-butyl-4-(4-ethynylbenzamido)cyclohexyl)carbamate

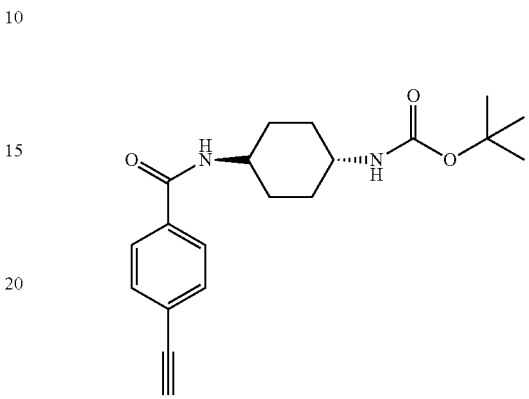

¹H NMR (500 MHz, DMSO-d₆) δ 8.31 (d, J=7.9 Hz, 1H), 7.82 (d, J=7.9 Hz, 2H), 7.53 (d, J=7.9 Hz, 2H), 6.75 (d, J=8.0 Hz, 1H), 4.36 (s, 1H), 3.74-3.61 (m, 1H), 3.18 (m, 1H), 1.81-1.73 (m, 4H), 1.36 (m, 11H), 1.26-1.14 (m, 2H); ¹³C NMR (126 MHz, DMSO) δ 165.07, 155.33, 135.19, 132.00, 128.02, 124.69, 83.40, 83.23, 77.87, 49.04, 48.30, 31.91, 31.44, 28.74.

Example 5X: Bis-Boc-4-ethynyl-N-(4-guanidinocyclohexyl)benzamide

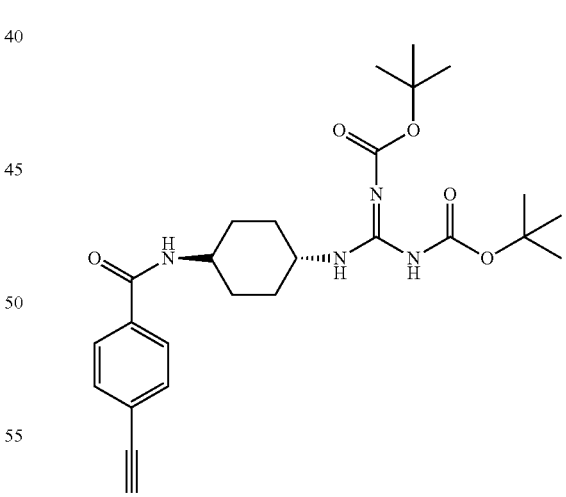

¹H NMR (500 MHz, Chloroform-d) δ 11.53 (s, 1H), 8.27 (d, J=8.3 Hz, 1H), 7.71 (d, J=8.0 Hz, 2H), 7.54 (d, J=8.3 Hz, 2H), 5.90 (d, J=7.9 Hz, 1H), 3.99 (d, J=45.1 Hz, 1H), 3.19 (s, 1H), 2.15-2.10 (m, 4H), 1.50 (d, J=4.7 Hz, 18H), 1.38 (q, J=5.2, 4.6 Hz, 4H); ¹³C NMR (126 MHz, CDCl₃) δ 165.99, 163.78, 155.58, 153.30, 134.70, 132.29, 126.86, 125.29, 83.15, 82.77, 79.45, 79.25, 48.23, 48.14, 31.54, 31.50, 28.32, 28.12.

Example 6

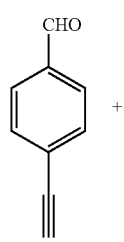

+

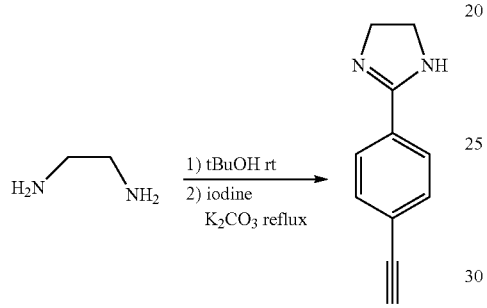

To a 50 ml round bottom, 1 eq 4-ethynylbenzaldehyde was dissolved in tBuOH and 1 eq of the corresponding diamine was added all at once, stirred for 1 hour at room temperature. 1.1 eq of iodine and 3 eq of potassium carbonate were added and the mixture was reflux overnight. After TCL shows the reaction is completed, equal volume of distilled water was added, and extracted with DCM three times (50 ml*3), washed with brine and dried with anhydrous sodium sulfate, removed solvents. Pure product was obtained by Combi-flash using 100% DCM to 35% MeOH.

Example 7: 4-cyclopropyl-2-(4-ethynylphenyl)-4,5-dihydro-1H-imidazole

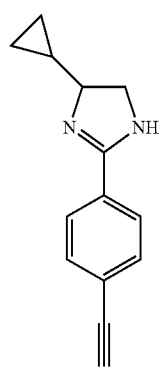 [SMILES: C#Cc1ccc(C2=NC(C3CC3)CN2)cc1]

LR-MS(ESI) m/z calcd for $C_{14}H_{14}N_2$ ([M+H]$^+$) 211.1 found 211.3.

Example 8: 2-(4-ethynylphenyl)-4,5-dihydro-1H-imidazole

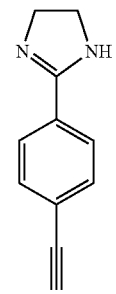

LR-MS(ESI) m/z calcd for $C_{11}H_{10}N_2$ ([M+H]$^+$) 171.1 found 171.3.

Example 9: 1-(2-(2-(4-ethynylphenyl)-4,5-dihydro-1H-imidazol-1-yl)ethyl)piperidine

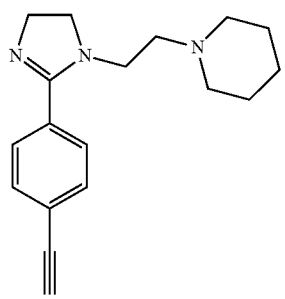 [SMILES: C#Cc1ccc(C2=NCCN2CCN2CCCCC2)cc1]

LR-MS(ESI) m/z calcd for $C_{18}H_{23}N_3$ ([M+H]$^+$) 282.2 found 282.4.

Example 10: 4-(2-(2-(4-ethynylphenyl)-4,5-dihydro-1H-imidazol-1-yl)ethyl)morpholine

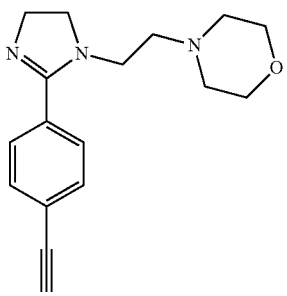 [SMILES: C#Cc1ccc(C2=NCCN2CCN2CCOCC2)cc1]

LR-MS(ESI) m/z calcd for $C_{17}H_{21}N_3O$ ([M+H]$^+$) 211.1 found 211.3.

Example 11: 2-(4-ethynylphenyl)-4,4-dimethyl-4,5-dihydro-1H-imidazole

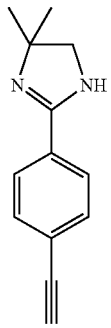

LR-MS(ESI) m/z calcd for $C_{13}H_{14}N_2$ ([M+H]$^+$) 199.1 found 199.2.

Example 12: 4-((3-amino-6-chloroisoquinolin-4-yl)ethynyl)-N-(3-morpholinopropyl)benzamide

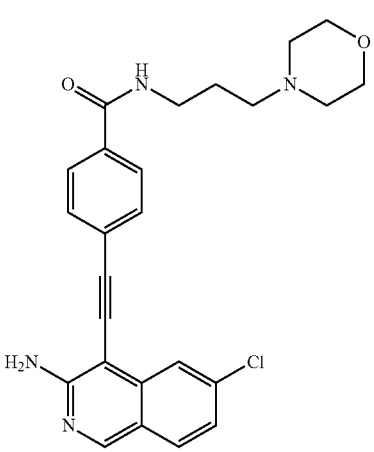 [SMILES: Nc1ncc2ccc(Cl)cc2c1C#Cc1ccc(C(=O)NCCCN2CCOCC2)cc1]

$^1$H NMR (500 MHz, MeOD) δ 8.79 (s, 1H), 7.93-7.82 (m, 4H), 7.76 (d, J=8.4 Hz, 2H), 7.25 (dd, J=8.6, 1.9 Hz, 1H), 3.72 (t, J=4.6 Hz, 4H), 3.47 (t, J=6.9 Hz, 2H), 2.58-2.49 (m, 6H), 1.93-1.81 (m, 2H); $^{13}$C NMR (125 MHz, MeOD) δ 167.91, 157.55, 151.88, 138.75, 138.03, 133.81, 131.01, 130.33, 127.09, 126.33, 123.67, 121.30, 120.77, 99.21, 90.21, 84.49, 66.25, 56.38, 53.35, 38.16, 25.52; LR-MS(ESI) m/z calcd for $C_{25}H_{26}ClN_4O_2$ ([M+H]$^+$) 449.2, found 449.3.

Example 13: 4-((3-amino-6-chloroisoquinolin-4-yl)ethynyl)-N-(4-((4-methylpiperazin-1-yl)methyl)phenyl)benzamide

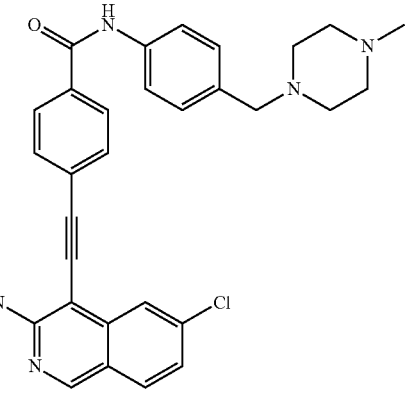

$^1$H NMR (500 MHz, DMSO) δ 10.34 (s, 1H), 8.91 (s, 1H), 8.03 (d, J=8.3 Hz, 2H), 7.96-7.85 (m, 3H), 7.74 (d, J=8.4 Hz, 2H), 7.32-7.20 (m, 3H), 6.88 (s, 2H), 3.43 (s, 2H), 2.63-2.31 (m, 8H), 2.24 (s, 3H); $^{13}$C NMR (125 MHz, DMSO) δ 165.16, 158.79, 153.44, 138.78, 138.45, 137.47, 134.50, 131.64, 129.62, 128.32, 126.51, 123.54, 121.35, 120.76, 120.63, 99.58, 88.35, 86.33, 61.88, 54.71, 52.25, 45.47; LR-MS(ESI) m/z calcd for $C_{30}H_{29}ClN_5O$ ([M+H]$^+$) 510.2, found 510.5.

Example 14: 6-chloro-4-((4-(4,5-dihydro-1H-imidazol-2-yl)phenyl)ethynyl)isoquinolin-3-amine

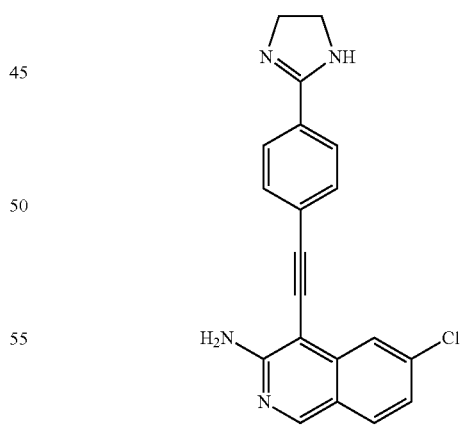

$^1$H NMR (500 MHz, DMSO) δ 8.92 (s, 1H), 7.96 (d, J=8.6 Hz, 1H), 7.93-7.81 (m, 5H), 7.28 (dd, J=8.6, 1.8 Hz, 1H), 6.85 (s, 2H), 3.68 (s, 4H); $^{13}$C NMR (125 MHz, DMSO) δ 163.73, 158.70, 153.30, 138.73, 137.42, 131.64, 131.56, 129.45, 127.78, 125.60, 123.52, 121.33, 120.61, 99.69, 88.45, 85.91, 49.51; LR-MS(ESI) m/z calcd for $C_{20}H_{15}ClN_4$ ([M+H]$^+$) 347.1, found 347.4.

Example 15: 3-((3-amino-6-chloroisoquinolin-4-yl)ethynyl)-N-(3-(dimethylamino)propyl)benzamide

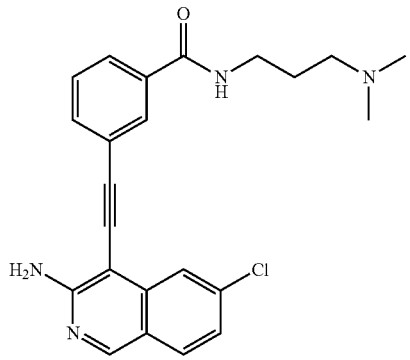 [SMILES: CN(C)CCCNC(=O)c1cccc(C#Cc2c(N)ncc3ccc(Cl)cc23)c1]

$^1$H NMR (500 MHz, DMSO) δ 8.90 (s, 1H), 8.64 (t, J=5.4 Hz, 1H), 8.16 (s, 1H), 7.92 (dd, J=18.9, 8.2 Hz, 2H), 7.86 (d, J=1.3 Hz, 1H), 7.82 (d, J=7.9 Hz, 1H), 7.52 (t, J=7.7 Hz, 1H), 7.26 (dd, J=8.6, 1.9 Hz, 1H), 6.82 (s, 2H), 3.30 (dd, J=12.8, 6.7 Hz, 2H), 2.35 (t, J=7.1 Hz, 2H), 2.19 (s, 6H), 1.73-1.60 (m, 2H); $^{13}$C NMR (125 MHz, DMSO) δ 165.99, 158.69, 153.15, 138.77, 137.37, 135.51, 134.23, 131.58, 130.35, 129.09, 127.53, 123.49, 123.45, 121.30, 120.63, 99.47, 88.53, 84.37, 57.13, 45.32, 38.16, 27.21; LR-MS (ESI) m/z calcd for $C_{23}H_{24}ClN_4O$ ([M+H]$^+$) 407.2, found 407.2.

Example 16: 4-((3-amino-6-chloroisoquinolin-4-yl)ethynyl)-N-(3-(pyrrolidin-1-yl)propyl)benzamide

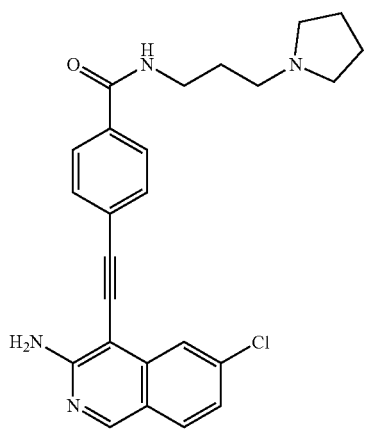 [SMILES: Nc1ncc2ccc(Cl)cc2c1C#Cc1ccc(C(=O)NCCCN2CCCC2)cc1]

$^1$H NMR (500 MHz, MeOD) δ 8.80 (s, 1H), 7.97-7.84 (m, 4H), 7.77 (dd, J=5.8, 4.1 Hz, 2H), 7.26 (dd, J=8.7, 2.0 Hz, 1H), 3.50 (t, J=6.8 Hz, 2H), 3.33 (dt, J=3.3, 1.6 Hz, 4H), 2.86-2.80 (m, 2H), 1.94 (d, J=3.6 Hz, 6H); $^{13}$C NMR (125 MHz, MeOD) δ 168.08, 157.58, 151.92, 138.76, 138.05, 133.59, 131.02, 130.36, 127.13, 126.43, 123.68, 121.30, 120.79, 99.19, 90.18, 84.55, 53.68, 53.37, 37.58, 27.33, 22.74; LR-MS(ESI) m/z calcd for $C_{25}H_{26}ClN_4O$ ([M+H]$^+$) 433.2, found 433.4.

Example 17: 4-((3-amino-6-chloroisoquinolin-4-yl)ethynyl)-N-(3-(4-methylpiperazin-1-yl)propyl)benzamide

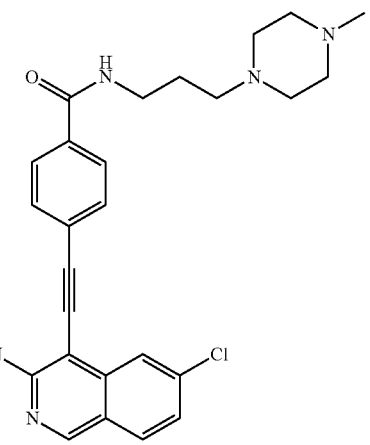

$^1$H NMR (500 MHz, MeOD) δ 8.76 (s, 1H), 7.90-7.87 (m, 1H), 7.87-7.84 (m, 2H), 7.82 (d, J=8.6 Hz, 1H), 7.75-7.71 (m, 2H), 7.22 (dd, J=8.6, 2.0 Hz, 1H), 3.44 (t, J=6.9 Hz, 2H), 2.77-2.37 (m, 10H), 2.28 (s, 3H), 1.83 (dd, J=14.5, 7.2 Hz, 2H); $^{13}$C NMR (125 MHz, MeOD) δ 167.90, 157.57, 151.90, 138.77, 138.05, 133.85, 131.03, 130.36, 127.13, 126.34, 123.68, 121.32, 120.79, 99.23, 90.21, 84.51, 55.88, 54.24, 52.27, 44.56, 38.25, 25.80; LR-MS(ESI) m/z calcd for $C_{26}H_{29}ClN_5O$ ([M+H]$^+$) 462.2, found 462.2.

Example 18: 4-((3-amino-6-chloroisoquinolin-4-yl)ethynyl)-N-(3-(piperidin-1-yl)propyl)benzamide

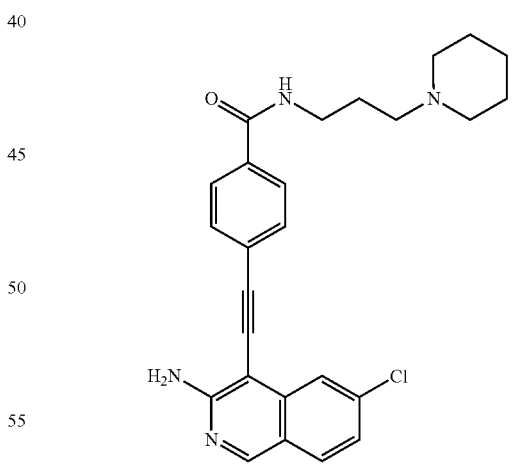

$^1$H NMR (500 MHz, MeOD) δ 8.81 (s, 1H), 7.95 (s, 1H), 7.93 (d, J=1.9 Hz, 2H), 7.87 (d, J=8.8 Hz, 1H), 7.78 (d, J=8.5 Hz, 2H), 7.27 (dd, J=8.6, 2.0 Hz, 1H), 3.54 (t, J=6.6 Hz, 2H), 3.33 (dt, J=3.3, 1.6 Hz, 6H), 3.22-3.17 (m, 2H), 1.91 (s, 6H); $^{13}$C NMR (125 MHz, MeOD) δ 168.53, 157.63, 152.01, 137.98, 133.10, 131.06, 130.41, 127.33, 125.30, 123.70, 121.29, 117.28, 110.55, 99.15, 90.11, 86.23, 84.74, 54.45, 52.95, 36.48, 24.18, 22.99, 21.36; LR-MS(ESI) m/z calcd for $C_{26}H_{28}ClN_4O$ ([M+H]$^+$) 447.2, found 447.3.

Example 19: 4-((3-amino-6-chloroisoquinolin-4-yl)ethynyl)-N-(5-(dimethylamino)pentyl)benzamide

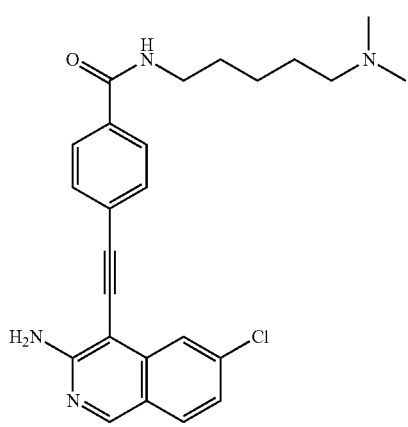 [SMILES: CN(C)CCCCCNC(=O)c1ccc(C#Cc2c(N)ncc3ccc(Cl)cc23)cc1]

¹H NMR (500 MHz, MeOD) δ 7.92 (s, 1H), 7.90 (s, 1H), 7.86 (d, J=8.7 Hz, 1H), 7.76 (d, J=8.3 Hz, 1H), 7.43 (s, 2H), 7.26 (dd, J=8.6, 1.9 Hz, 1H), 3.45 (t, J=6.9 Hz, 2H), 3.21-3.12 (m, 2H), 2.91 (s, 6H), 1.82 (dt, J=12.0, 8.0 Hz, 2H), 1.77-1.68 (m, 2H), 1.49 (dt, J=15.0, 7.7 Hz, 2H); ¹³C NMR (125 MHz, MeOD) δ 167.99, 157.58, 151.86, 138.75, 138.05, 133.79, 131.02, 130.40, 127.16, 126.31, 125.93, 124.96, 123.70, 121.29, 99.25, 84.50, 57.52, 44.62, 42.04, 39.07, 28.53, 23.85, 23.35; LR-MS(ESI) m/z calcd for C₂₅H₂₈ClN₄O ([M+H]⁺) 435.2, found 435.3.

Example 20: 4-((3-amino-6-chloroisoquinolin-4-yl)ethynyl)-N-(3-(dimethylamino)-2-hydroxypropyl)benzamide

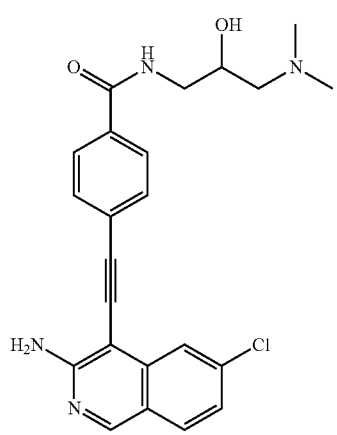 [SMILES: CN(C)CC(O)CNC(=O)c1ccc(C#Cc2c(N)ncc3ccc(Cl)cc23)cc1]

¹H NMR (500 MHz, MeOD) δ 8.79 (s, 1H), 7.92 (s, 2H), 7.90 (s, 1H), 7.85 (d, J=8.7 Hz, 1H), 7.76 (d, J=8.4 Hz, 2H), 7.25 (dd, J=8.6, 1.9 Hz, 1H), 4.05-3.94 (m, 1H), 3.55 (dd, J=13.6, 4.8 Hz, 1H), 3.42-3.35 (m, 1H), 2.47-2.43 (m, 2H), 2.33 (s, 6H); ¹³C NMR (125 MHz, MeOD) δ 168.24, 157.56, 151.88, 138.76, 138.05, 133.69, 131.00, 130.34, 127.18, 126.38, 123.67, 121.30, 120.78, 99.22, 90.21, 84.49, 67.43, 63.23, 44.75, 44.70; LR-MS(ESI) m/z calcd for C₂₃H₂₄ClN₄O₂ ([M+H]⁺) 423.2, found 423.3.

Example 21: 4-((3-amino-6-chloroisoquinolin-4-yl)ethynyl)benzonitrile

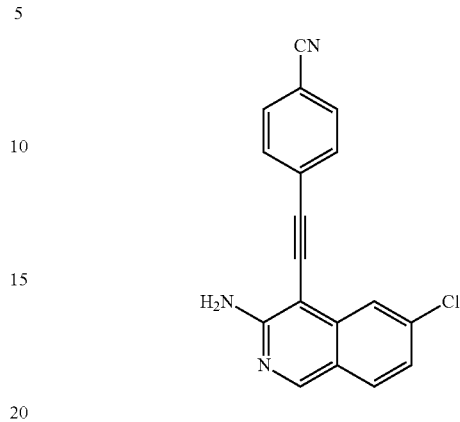

1H NMR (500 MHz, MeOD) δ 8.84 (s, 1H), 7.94 (d, J=1.6 Hz, 1H), 7.89 (d, J=8.7 Hz, 1H), 7.85 (d, J=8.4 Hz, 2H), 7.80 (d, J=8.4 Hz, 2H), 7.28 (dd, J=8.6, 1.9 Hz, 1H); LR-MS (ESI) m/z calcd for C₁₈H₁₁ClN₃ ([M+H]⁺) 304.1, found 304.1.

Example 22: 2-((3-amino-6-chloroisoquinolin-4-yl)ethynyl)-N-(3-(piperidin-1-yl)propyl)benzamide

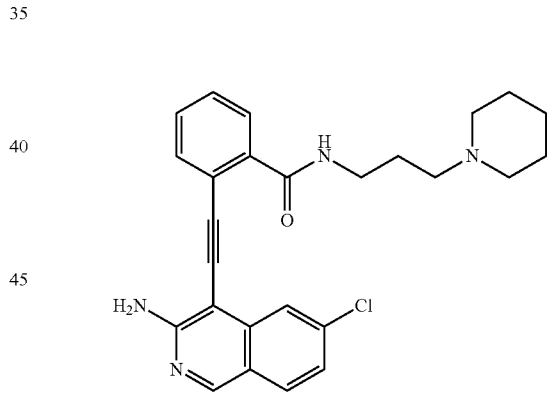

¹H NMR (500 MHz, DMSO) δ 8.90 (d, J=0.4 Hz, 1H), 8.61 (s, 1H), 7.98 (d, J=2.0 Hz, 1H), 7.93 (d, J=8.6 Hz, 1H), 7.88 (dd, J=7.7, 0.9 Hz, 1H), 7.58-7.50 (m, 2H), 7.46 (td, J=7.5, 1.3 Hz, 1H), 7.26 (dd, J=8.6, 2.0 Hz, 1H), 6.92 (s, 2H), 2.51 (dt, J=3.6, 1.8 Hz, 3H), 2.30-2.21 (m, 2H), 2.16 (s, 4H), 1.71-1.59 (m, 2H), 1.42-1.30 (m, 4H), 1.27 (d, J=4.7 Hz, 2H); ¹³C NMR (126 MHz, DMSO) δ 168.30, 159.29, 153.12, 138.80, 138.68, 137.32, 132.81, 131.37, 130.23, 128.44, 127.80, 123.43, 121.69, 121.39, 120.54, 98.53, 88.83, 87.85, 56.93, 54.41, 39.65, 39.48, 38.55, 26.68, 26.00, 24.55.

Example 23: 4-((3-amino-6-chloroisoquinolin-4-yl)ethynyl)-N-(3-(1,3-dioxoisoindolin-2-yl)propyl)benzamide

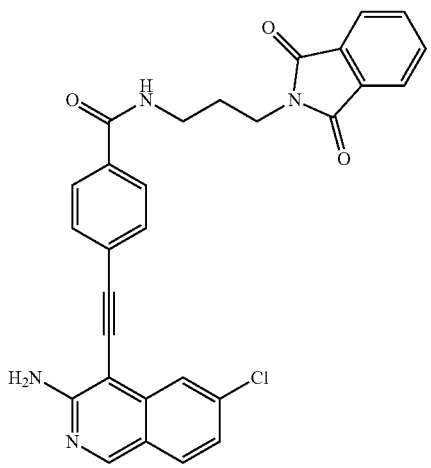 [SMILES: Nc1ncc2ccc(Cl)cc2c1C#Cc1ccc(C(=O)NCCCN2C(=O)c3ccccc3C2=O)cc1]

1H NMR (500 MHz, DMSO) δ 8.92 (d, J=0.8 Hz, 1H), 7.96 (d, J=8.6 Hz, 1H), 7.92-7.77 (m, 8H), 7.71 (d, J=8.4 Hz, 1H), 7.29 (dd, J=8.6, 2.0 Hz, 1H), 6.85 (s, 2H), 3.65 (d, J=7.2 Hz, 2H), 3.30 (s, 2H), 1.89 (q, J=7.1 Hz, 2H); LR-MS(ESI) m/z calcd for $C_{29}H_{22}ClN_4O_3$ ([M+H]$^+$) 509.1, found 509.4.

Example 24: 4-((3-amino-6-chloroisoquinolin-4-yl)ethynyl)-N-(3-aminopropyl)benzamide

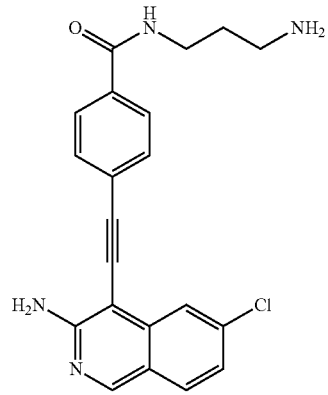 [SMILES: NCCCNC(=O)c1ccc(C#Cc2c(N)ncc3ccc(Cl)cc23)cc1]

$^1$H NMR (500 MHz, MeOD) δ 8.71 (s, 1H), 7.93 (d, J=1.9 Hz, 1H), 7.88-7.79 (m, 2H), 7.73 (d, J=8.6 Hz, 1H), 7.69-7.61 (m, 2H), 7.21 (dd, J=8.6, 2.0 Hz, 1H), 3.45 (t, J=6.7 Hz, 2H), 3.34-3.29 (m, 2H), 1.79-1.72 (m, 2H); $^{13}$C NMR (125 MHz, MeOD) δ 168.26, 157.20, 151.91, 139.19, 138.80, 134.19, 131.71, 130.49, 127.61, 126.43, 124.90, 122.52, 121.36, 100.08, 91.97, 85.03, 37.61, 33.97, 29.93, 25.19; LR-MS(ESI) m/z calcd for C21H19ClN4ONa 378.12, found 401.30.

Example 25: tert-butyl ((1r,4r)-4-(4-((3-amino-6-chloroisoquinolin-4-yl)ethynyl)benzamido)cyclohexyl)carbamate

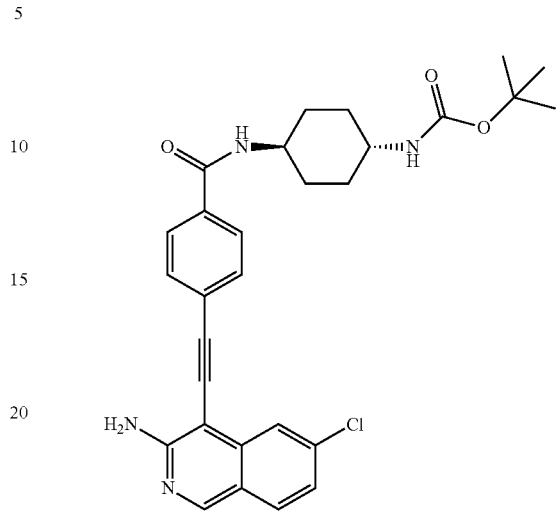

$^1$H NMR (500 MHz, Methanol-d$_4$) δ 8.77 (s, 1H), 7.91-7.86 (m, 3H), 7.83 (d, J=8.6 Hz, 1H), 7.73 (d, J=8.3 Hz, 2H), 7.33 (d, J=8.8 Hz, 2H), 7.23 (dd, J=8.6, 2.0 Hz, 1H), 6.97 (d, J=8.7 Hz, 1H), 4.53 (s, 2H), 4.29-4.16 (m, 2H), 3.23 (t, J=5.3 Hz, 2H), 2.70 (s, 6H); $^{13}$C NMR (126 MHz, MeOD) δ 167.81, 157.59, 157.41, 151.93, 138.77, 138.06, 133.75, 131.87, 131.04, 130.38, 128.70, 127.21, 126.40, 123.69, 121.31, 120.80, 114.31, 99.24, 90.21, 84.52, 63.25, 56.96, 43.32, 42.63.

Example 26: tert-butyl (1-(4-((3-amino-6-chloroisoquinolin-4-yl)ethynyl)benzoyl)piperidin-4-yl)carbamate

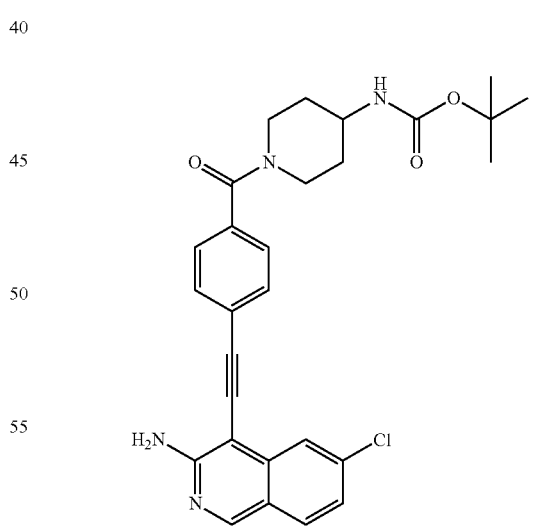

$^1$H NMR (500 MHz, DMSO-d$_6$) δ 8.90 (s, 1H), 7.94 (d, J=8.6 Hz, 1H), 7.85 (d, J=2.0 Hz, 1H), 7.81 (d, J=8.3 Hz, 2H), 7.40 (dd, J=8.4, 3.0 Hz, 2H), 7.26 (dd, J=8.7, 1.9 Hz, 1H), 6.88 (d, J=8.0 Hz, 1H), 6.82 (s, 2H), 4.29 (s, 1H), 3.09 (s, 1H), 1.75 (d, J=41.7 Hz, 3H), 1.37 (d, J=2.5 Hz, 11H); $^{13}$C NMR (126 MHz, DMSO) δ 168.85, 158.68, 155.29, 153.24, 138.78, 137.40, 136.17, 133.07, 131.82, 127.42, 124.44, 123.50, 121.32, 120.62, 99.47, 88.47, 85.12, 78.13, 55.38, 47.59, 40.50, 40.43, 40.33, 40.16, 40.00, 39.83, 39.66, 39.50, 28.72.

Example 27: 4-((3-amino-6-chloroisoquinolin-4-yl)ethynyl)-N-methyl-N-(3-(pyrrolidin-1-yl)propyl)benzamide

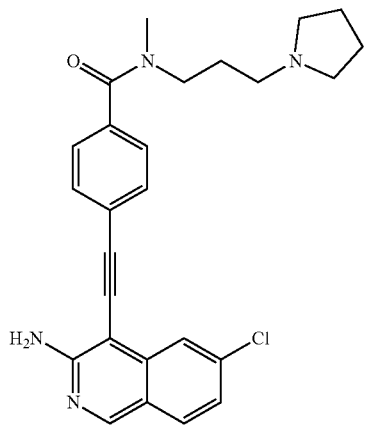 [SMILES: CN(CCCN1CCCC1)C(=O)c1ccc(C#Cc2c(N)ncc3ccc(Cl)cc23)cc1]

¹H NMR (500 MHz, Methanol-d₄) δ 8.78 (s, 1H), 7.90 (s, 1H), 7.85 (d, J=8.6 Hz, 1H), 7.78-7.74 (m, 2H), 7.50 (d, J=7.7 Hz, 1H), 7.46 (d, J=7.8 Hz, 1H), 7.24 (dd, J=8.6, 2.1 Hz, 1H), 3.61 (t, J=7.1 Hz, 1H), 3.31 (t, J=1.9 Hz, 3H), 3.10 (s, 1H), 2.87-2.71 (m, 3H), 2.42 (s, 2H), 2.27 (t, J=7.7 Hz, 1H), 2.06-1.96 (m, 1H), 1.85-1.67 (m, 3H), 1.65-1.50 (m, 3H), 1.45 (s, 1H), 1.27 (s, 1H); ¹³C NMR (126 MHz, MeOD) δ 171.93, 157.57, 151.87, 138.80, 138.04, 135.93, 135.54, 131.28, 131.14, 130.39, 127.00, 126.68, 124.89, 123.68, 121.31, 120.81, 99.13, 90.22, 83.82, 55.35, 53.78, 53.65, 48.12, 47.94, 47.77, 47.60, 47.44, 47.27, 47.09, 45.25, 36.78, 31.99, 29.36, 24.83, 24.30, 23.39, 22.82, 22.67.

Example 28: tert-butyl ((1r,4r)-4-(4-((3-amino-6-chloroisoquinolin-4-yl)ethynyl)benzamido)cyclohexyl)carbamate

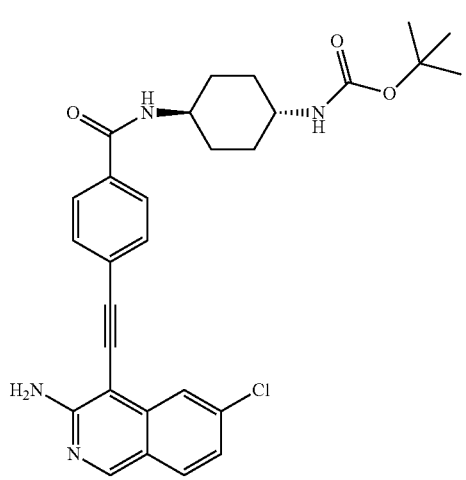 [SMILES: CC(C)(C)OC(=O)N[C@H]1CC[C@H](NC(=O)c2ccc(C#Cc3c(N)ncc4ccc(Cl)cc34)cc2)CC1]

¹H NMR (500 MHz, DMSO-d₆) δ 8.90 (s, 1H), 8.29 (d, J=7.9 Hz, 1H), 7.94 (d, J=8.6 Hz, 1H), 7.91-7.85 (m, 3H), 7.83 (d, J=8.1 Hz, 2H), 7.26 (d, J=8.6 Hz, 1H), 6.84 (s, 2H), 6.74 (d, J=8.0 Hz, 1H), 3.71 (dt, J=7.7, 3.8 Hz, 1H), 1.83 (d, J=13.4 Hz, 1H), 1.37 (s, 11H), 1.25 (dd, J=23.9, 12.4 Hz, 2H). ¹³C NMR (126 MHz, DMSO) δ 165.22, 158.74, 155.35, 153.34, 138.76, 137.43, 134.36, 131.51, 127.88, 125.95, 123.53, 121.34, 120.63, 99.62, 88.41, 85.90, 77.87, 49.10, 48.33, 40.50, 40.33, 40.16, 40.00, 39.83, 39.66, 39.50, 31.96, 31.51, 28.75.

Example 29: 4-((3-amino-6-chloroisoquinolin-4-yl)ethynyl)-N-(4-aminophenethyl)benzamide

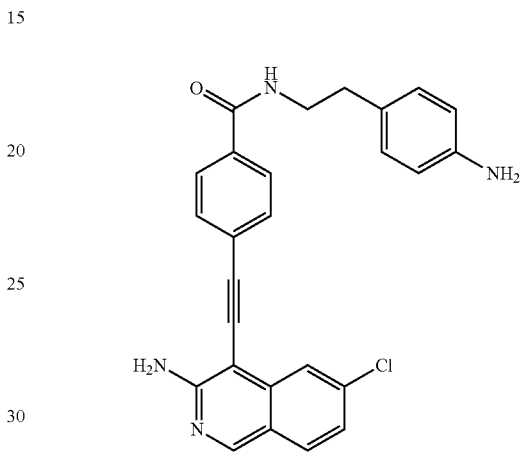

¹H NMR (500 MHz, DMSO-d₆) δ 8.90 (s, 1H), 8.59 (t, J=5.6 Hz, 1H), 7.94 (d, J=8.6 Hz, 1H), 7.90-7.80 (m, 5H), 7.26 (dd, J=8.7, 2.1 Hz, 1H), 6.93-6.78 (m, 4H), 6.49 (d, J=8.2 Hz, 2H), 4.84 (s, 2H), 3.43-3.36 (m, 2H), 2.69-2.63 (m, 2H); ¹³C NMR (126 MHz, DMSO) δ 165.82, 158.74, 153.34, 147.29, 138.77, 137.44, 134.38, 132.91, 131.61, 129.49, 127.75, 126.79, 125.97, 123.53, 121.35, 120.63, 114.48, 99.60, 88.43, 85.90, 41.99, 34.92.

Example 30: [1,4'-bipiperidin]-1'-yl(4-((3-amino-6-chloroisoquinolin-4-yl)ethynyl)phenyl)methanone

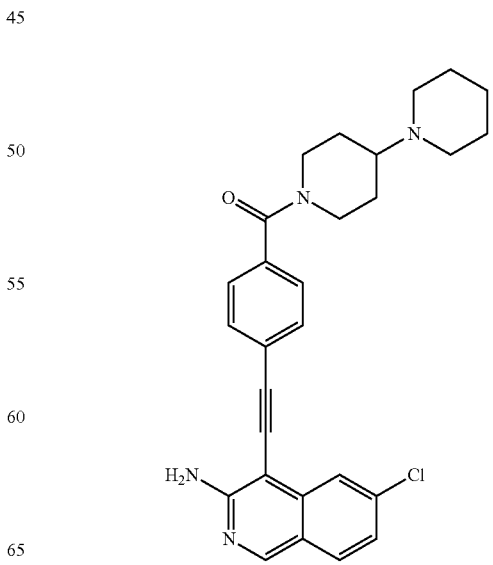

¹H NMR (500 MHz, Methanol-d₄) δ 8.79 (s, 1H), 7.91 (d, J=12.6 Hz, 1H), 7.88-7.81 (m, 1H), 7.78-7.72 (m, 2H), 7.48 (d, J=8.3 Hz, 2H), 7.25 (d, J=8.3 Hz, 1H), 4.74 (s, 1H), 3.85 (s, 1H), 3.17 (s, 1H), 2.82 (d, J=33.4 Hz, 6H), 2.07 (s, 1H), 1.93 (s, 1H), 1.72-1.53 (m, 8H); ¹³C NMR (126 MHz, MeOD) δ 170.27, 157.59, 151.86, 138.83, 138.07, 135.31, 131.20, 130.31, 126.91, 124.93, 123.74, 121.37, 120.93, 99.16, 90.41, 83.88, 62.58, 49.95, 48.11, 47.94, 47.77, 47.60, 47.43, 47.26, 47.09, 24.78, 23.31.

Example 31: (4-((3-amino-6-chloroisoquinolin-4-yl)ethynyl)phenyl)(4-aminopiperidin-1-yl)methanone

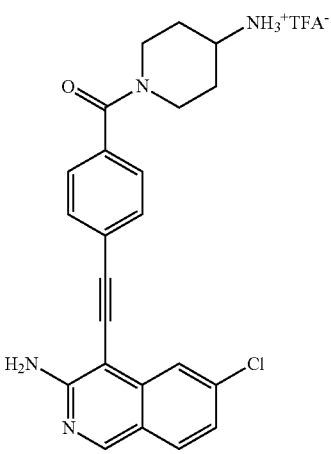

¹H NMR (500 MHz, DMSO-d₆) δ 8.90 (s, 1H), 8.53 (s, 1H), 8.15 (s, 3H), 7.94 (d, J=8.6 Hz, 1H), 7.83 (d, J=8.5 Hz, 2H), 7.42 (d, J=8.3 Hz, 2H), 7.26 (m, 1H), 6.84 (s, 2H), 4.46 (s, 1H), 3.31 (s, 1H), 2.87 (s, 1H), 2.48 (d, J=2.7 Hz, 2H), 1.99 (s, 1H), 1.91-1.87 (m, 1H), 1.47 (s, 2H); ¹³C NMR (126 MHz, DMSO) δ 169.10, 158.67, 153.30, 138.78, 137.43, 135.77, 131.85, 131.62, 127.45, 124.63, 123.52, 121.29, 120.60, 99.44, 88.41, 85.23, 47.82, 40.40, 40.33, 40.23, 40.07, 39.90, 39.73, 39.57, 39.40

Example 32: 4-((3-amino-6-chloroisoquinolin-4-yl)ethynyl)-N-(2-(piperidin-1-yl)ethyl)benzamide

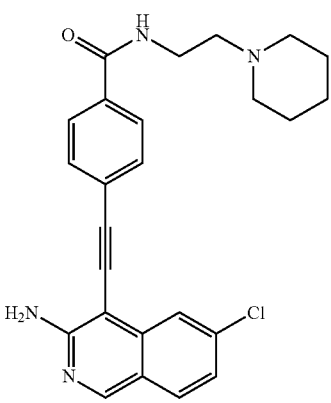 [SMILES: Nc1ncc2ccc(Cl)cc2c1C#Cc1ccc(C(=O)NCCN2CCCCC2)cc1]

¹H NMR (500 MHz, DMSO-d₆) δ 8.90 (s, 1H), 8.48 (s, 1H), 7.93 (d, J=8.6 Hz, 1H), 7.90 (d, J=8.2 Hz, 2H), 7.87 (d, J=2.0 Hz, 1H), 7.83 (d, J=8.1 Hz, 2H), 7.26 (dd, J=8.6, 2.1 Hz, 1H), 6.71 (s, 2H), 3.45 (s, 2H), 3.2 (s, 2H), 2.59 (s, 4H), 1.56 (s, 4H), 1.41 (s, 2H); ¹³C NMR (126 MHz, DMSO) δ 166.08, 158.73, 153.28, 138.80, 137.45, 134.28, 131.59, 131.53, 127.82, 126.09, 123.57, 121.38, 120.73, 99.62, 88.62, 85.96, 57.62, 54.17, 25.44, 23.93.

Example 33: N-(2-(1H-imidazol-4-yl)ethyl)-4-((3-amino-6-chloroisoquinolin-4-yl)ethynyl)benzamide

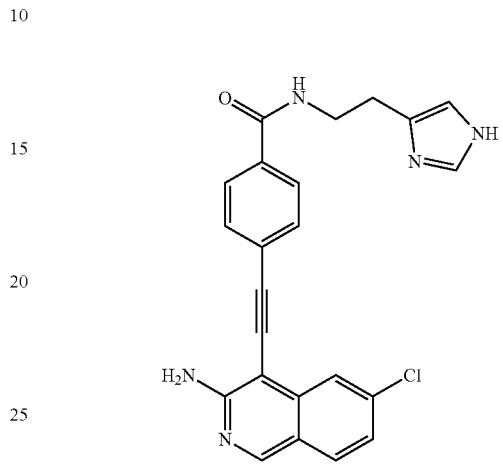

¹H NMR (500 MHz, DMSO-d₆) δ 8.90 (s, 1H), 8.69 (t, J=5.6 Hz, 1H), 7.94 (d, J=8.6 Hz, 1H), 7.91-7.82 (m, 5H), 7.68 (s, 1H), 7.26 (dd, J=8.6, 2.1 Hz, 1H), 6.88 (d, J=9.5 Hz, 3H), 3.54-3.43 (m, 2H), 2.78 (t, J=7.5 Hz, 2H); ¹³C NMR (126 MHz, DMSO) δ 165.89, 158.75, 153.37, 138.76, 137.44, 135.09, 134.77, 134.22, 131.62, 127.76, 126.05, 123.53, 121.34, 120.60, 117.03, 99.59, 88.35, 85.96, 27.18.

Example 34: 4-((3-amino-6-chloroisoquinolin-4-yl)ethynyl)-N-((1r,4r)-4-aminocyclohexyl)benzamide

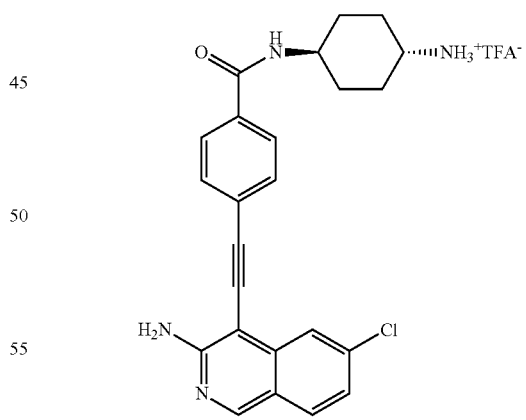

¹H NMR (500 MHz, DMSO-d₆) δ 8.90 (s, 1H), 8.38 (d, J=7.7 Hz, 1H), 8.02-7.92 (m, 4H), 7.91-7.81 (m, 5H), 7.27 (dd, J=8.7, 1.8 Hz, 1H), 6.84 (s, 2H), 3.72 (s, 1H), 2.99 (s, 1H), 1.94 (d, J=34.4 Hz, 4H), 1.42 (q, J=9.1, 8.4 Hz, 4H); ¹³C NMR (126 MHz, DMSO) δ 165.37, 153.37, 138.76, 137.43, 134.24, 131.52, 127.91, 126.03, 123.53, 121.32, 120.63, 118.96, 116.57, 99.60, 88.38, 85.96, 49.13, 47.87, 30.33, 29.72.

Example 35: 4-((3-amino-6-chloroisoquinolin-4-yl)ethynyl)-N-(4-(2-(dimethylamino)ethoxy)benzyl)benzamide

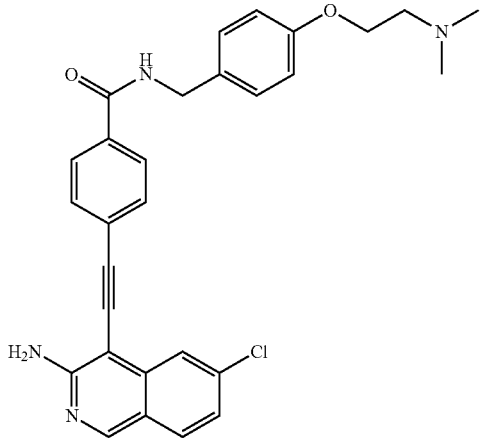 [SMILES: CN(C)CCOc1ccc(CNC(=O)c2ccc(C#Cc3c(N)ncc4ccc(Cl)cc34)cc2)cc1]

¹H NMR (500 MHz, Methanol-d₄) δ 8.77 (s, 1H), 7.91-7.86 (m, 3H), 7.83 (d, J=8.6 Hz, 1H), 7.73 (d, J=8.3 Hz, 2H), 7.33 (d, J=8.8 Hz, 2H), 7.23 (dd, J=8.6, 2.0 Hz, 1H), 6.97 (d, J=8.7 Hz, 1H), 4.53 (s, 2H), 4.29-4.16 (m, 2H), 3.23 (t, J=5.3 Hz, 2H), 2.70 (s, 6H); ¹³C NMR (126 MHz, MeOD) δ 167.81, 157.59, 157.41, 151.93, 138.77, 138.06, 133.75, 131.87, 131.04, 130.38, 128.70, 127.21, 126.40, 123.69, 121.31, 120.80, 114.31, 99.24, 90.21, 84.52, 63.25, 56.96, 43.32, 42.63.

Example 36: N-(2-(1H-imidazol-4-yl)ethyl)-3-((3-amino-6-chloroisoquinolin-4-yl)ethynyl)benzamide

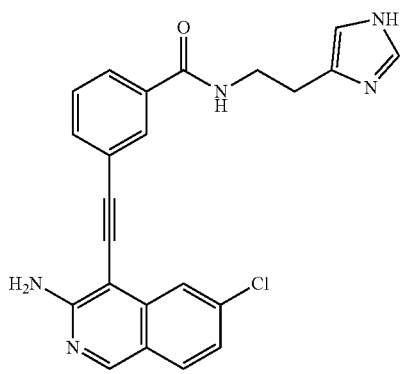 [SMILES: Nc1ncc2ccc(Cl)cc2c1C#Cc1cccc(C(=O)NCCc2c[nH]cn2)c1]

¹H NMR (500 MHz, DMSO-d₆) δ 8.90 (s, 1H), 8.69 (t, J=5.6 Hz, 1H), 8.17 (d, J=1.8 Hz, 1H), 7.95-7.81 (m, 4H), 7.53 (dd, J=16.1, 8.2 Hz, 2H), 7.26 (dd, J=8.6, 2.1 Hz, 1H), 6.82 (d, J=12.8 Hz, 3H), 3.50 (td, J=7.6, 5.6 Hz, 2H), 2.78 (t, J=7.5 Hz, 2H); ¹³C NMR (126 MHz, DMSO) δ 166.01, 158.68, 153.15, 138.77, 137.40, 135.50, 135.15, 134.26, 131.58, 130.39, 129.10, 127.53, 123.51, 123.45, 121.31, 120.63, 99.47, 88.54, 84.38, 40.47, 40.30, 40.14, 40.05, 39.97, 39.80, 39.64, 39.47, 27.35.

Example 37: 3-((3-amino-6-chloroisoquinolin-4-yl)ethynyl)-N-(3-(dimethylamino)-2-hydroxypropyl)benzamide

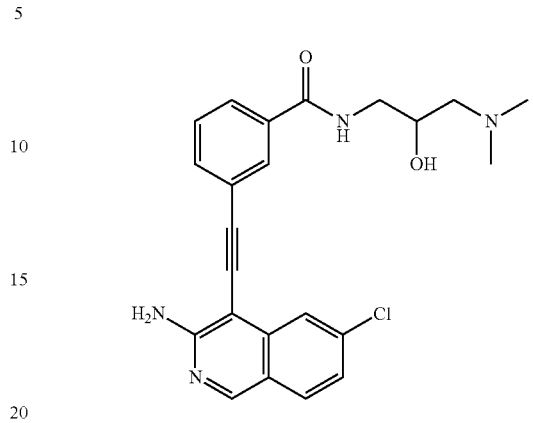

¹H NMR (500 MHz, DMSO-d₆) δ 8.90 (s, 1H), 8.64 (t, J=5.7 Hz, 1H), 8.22 (d, J=1.8 Hz, 1H), 7.98-7.81 (m, 4H), 7.52 (t, J=7.8 Hz, 1H), 7.26 (dd, J=8.6, 2.1 Hz, 1H), 6.81 (s, 2H), 5.09 (s, 1H), 3.89-3.83 (m, 1H), 3.42 (dt, J=13.4, 5.5 Hz, 1H), 3.23-3.16 (m, 1H), 2.54 (dd, J=12.4, 5.0 Hz, 1H), 2.45 (dd, J=12.6, 7.6 Hz, 1H), 2.34 (s, 6H); ¹³C NMR (126 MHz, DMSO) δ 166.28, 158.70, 153.17, 138.76, 137.38, 135.32, 134.31, 131.60, 130.51, 129.08, 127.68, 123.51, 123.42, 121.30, 120.63, 99.47, 88.53, 84.38, 66.77, 63.21, 45.55, 45.00.

Example 38: BisBoc-1-(1-(4-((3-amino-6-chloroisoquinolin-4-yl)ethynyl)benzoyl)piperidin-4-yl)guanidine

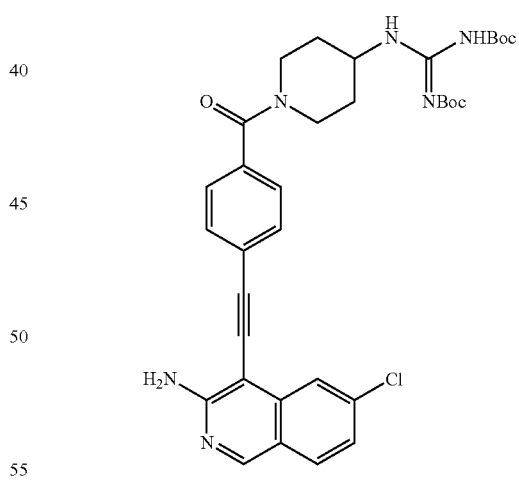

¹H NMR (500 MHz, Methanol-d₄) δ 8.73 (s, 1H), 7.85 (d, J=2.0 Hz, 1H), 7.78 (d, J=8.6 Hz, 1H), 7.71 (d, J=8.3 Hz, 2H), 7.45 (d, J=8.1 Hz, 2H), 7.19 (dd, J=8.6, 2.1 Hz, 1H), 4.50 (s, 1H), 4.18 (q, J=4.1 Hz, 1H), 3.70 (s, 1H), 3.24 (s, 1H), 3.08 (s, 1H), 2.08 (s, 1H), 1.96 (s, 1H), 1.49 (d, J=25.7 Hz, 20H); ¹³C NMR (126 MHz, MeOD) δ 170.34, 163.15, 157.51, 155.43, 152.89, 151.81, 138.72, 137.98, 135.23, 131.22, 130.31, 126.90, 124.85, 123.66, 121.34, 120.74, 99.19, 90.27, 83.89, 83.30, 79.08, 48.13, 47.96, 47.80, 47.63, 47.45, 47.37, 47.28, 47.11, 31.72, 30.94, 27.20, 26.86.

Example 39: General Isoquinoline Synthesis

The majority of isoquinolines used are commercially available but can also be synthesized following the scheme below.

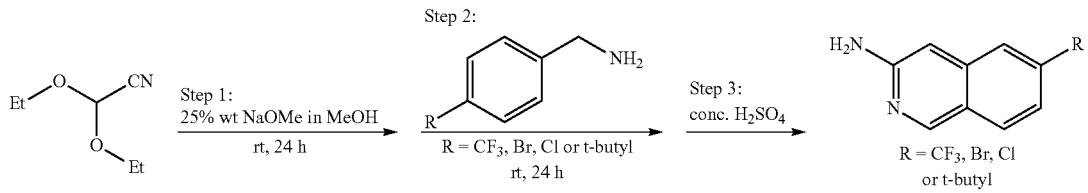

General Procedure for Synthesizing Isoquinolines:

Diethoxyacetonitrile (15.5 mmol, 1 eq) was added to sodium methoxide solution, 25% w/t in methanol and stirred for 24 hours at rt. Corresponding amine (0.9 eq) was added and stirred for additional 24 hours at rt. The reaction mixture was then concentrated under vacuum. The flask was then placed on ice, followed by addition of concentrated sulfuric acid to reach final concentration as 1 M. The reaction was allowed to stir for additional 48 hours and then neutralized by 4 M potassium hydroxide solution to pH~7. The resulting precipitate was collected and extracted with $CH_2Cl_2$ for three times. The combined organic layers were washed with brine, dried over $Na_2SO_4$ and concentrated under reduced pressure. Crude product was subject to purification by silica gel column chromatography.

Example 39A: 6-(trifluoromethyl)isoquinolin-3-amine

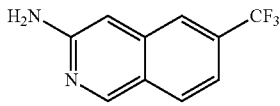 [SMILES: Nc1cc2cc(C(F)(F)F)ccc2cn1]

Following the described general procedure, brown solid was obtained. $^1$H NMR (400 MHz, MeOD) δ 8.84 (s, 1H), 7.92 (d, J=8.8 Hz, 1H), 7.83 (s, 1H), 7.31-7.29 (m, 1H), 6.84 (s, 1H). $^{13}$C NMR (100 MHz, MeOD) δ 158.36, 152.70, 139.69, 133.63, 133.32, 133.00, 132.68, 130.74, 126.98, 124.99, 124.28, 123.63, 123.58, 118.73, 118.70, 100.92. LRMS (ESI$^+$) [M+H] calcd for $C_{10}H_8F_3N_2$ 213.1, found 213.4.

Example 39B: 6-(tert-butyl)isoquinolin-3-amine

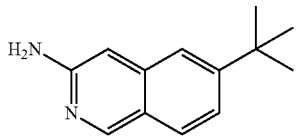

Following the described general procedure, brown solid (370 mg, 13% yield) was obtained. $^1$H NMR (500 MHz, MeOD) δ 8.67 (s, 1H), 7.72 (d, J=8.8 Hz, 1H), 7.46 (s, 1H), 7.36-7.34 (m, 1H), 6.80 (s, 1H), 1.37 (s, 9H). $^{13}$C NMR (126 MHz, MeOD) δ 157.62, 155.86, 151.94, 141.81, 130.20, 129.78, 129.36, 124.15, 121.35, 102.05, 124.28, 36.86, 32.10. LRMS (ESI$^+$) [M+H] calcd for $C_{13}H_{17}N_2$ 201.1, found 201.2.

Example 39C: 6-bromoisoquinolin-3-amine

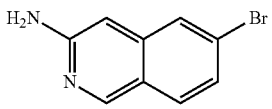

Following the described general procedure, brown solid was obtained. $^1$H NMR (500 MHz, D$^6$-DMSO) δ 8.79 (s, 1H), 7.78 (s, 1H), 7.71 (d, J=8.6 Hz, 1H), 7.20 (d, J=8.4 Hz, 1H), 6.54 (s, 1H), 6.10 (s, 2H). $^{13}$C NMR (126 MHz, DMSO) δ 157.62, 152.25, 140.12, 130.54, 126.41, 124.95, 124.69, 121.13, 96.35.

Example 39D: 6-chloroisoquinolin-3-amine

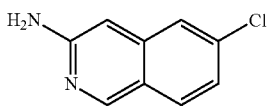 [SMILES: Nc1cc2cc(Cl)ccc2cn1]

Following the described general procedure, brown solid was obtained. $^1$H NMR (500 MHz, D$^6$-DMSO) δ 8.80 (s, 1H), 7.79 (d, J=8.6 Hz, 1H), 7.60 (s, 1H), 7.08 (d, J=8.4 Hz, 1H), 6.55 (s, 1H), 6.10 (s, 2H). $^{13}$C NMR (126 MHz, DMSO) δ 157.68, 152.13, 139.71, 135.50, 130.58, 123.11, 122.47, 121.02, 96.56.

Example 40: General Procedure for Amide Coupling

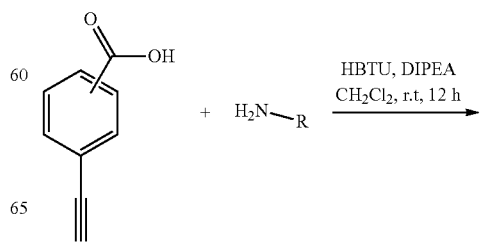

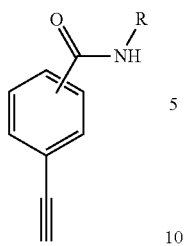

To a solution of ethynyl benzoic acid (200 mg, 1.37 mmol, 1 equiv) in CH$_2$Cl$_2$ (10 mL) at 0° C. was added HBTU (623 mg, 1.64 mmol, 1.2 equiv), amine (1.64 mmol, 1.2 equiv) and DIPEA (0.67 mL, 4.11 mmol, 3 equiv). The reaction was moved to room temperature and stirred for 12 h. Subsequently, reaction mixture was diluted with CH$_2$Cl$_2$ (40 mL) and washed with water (2×40 mL). The combined organic layer were dried over anhydrous sodium sulphate, filtered and concentrated in vacuo to obtain crude compound. The compound was purified by flash column chromatography.

Example 41: General Procedure for Sonogashira Coupling

A solution of iodo, bromo or chloro compound (100 mg, 0.33 mmol, 1 equiv), Pd catalyst (5 mol %), CuI (5 mol %) and Triphenylphosphine (10 mg, 0.04 mmol, 0.1 equiv) in Triethylamine (1 mL, 7.2 mmol, 22 equiv) was de-oxygenated using steam of Argon gas. A de-oxygenated solution of alkyne (0.49 mmol, 1.5 equiv) in DMF (3 mL) was added slowly over a period of 15 min to the solution and the reaction temperature was increased to 70° C. and allowed to stir 12 h. The reaction was quenched by addition of NH$_4$Cl (5 mL) at room temperature. The crude compound was extracted using EtOAc (3×40 mL). Combined organic layers were dried over anhydrous sodium sulphate, filtered and concentrated in vacuo. The pure product was obtained by flash column chromatography.

Example 42: N$^1$-(4-bromoquinolin-2-yl)-N$^2$,N$^2$-diethylethane-1,2-diamine

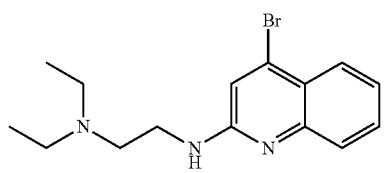 [SMILES: CCN(CC)CCNc1cc(Br)c2ccccc2n1]

2,4-dibromoquinoline (550 mg), N$^2$,N$^2$-diethylethane-1,2-diamine (240 mg), Cs$_2$CO$_3$ (650 mg) and DMSO (4 mL) were placed in a round bottle and the mixture was heated to 150° C. for 12h. The mixture was cooled to room temperature and purified using flash chromatography. $^1$H NMR (500 MHz, CDCl$_3$) δ 7.92 (d, J=8.3 Hz, 1H), 7.79 (d, J=8.3 Hz, 1H), 7.72-7.65 (m, 1H), 7.49 (td, J=7.8, 3.7 Hz, 1H), 6.55 (s, 1H), 6.46 (s, 1H), 3.29 (d, J=4.7 Hz, 2H), 2.87 (t, J=6.0 Hz, 2H), 2.67 (m, 6H), 1.14 (s, 6H). $^{13}$C NMR (126 MHz, CDCl$_3$) δ 151.10, 148.16, 143.39, 129.85, 128.80, 125.00, 119.99, 118.15, 101.86, 50.29, 46.41, 40.90, 11.96.

Example 43: Compound HSN225

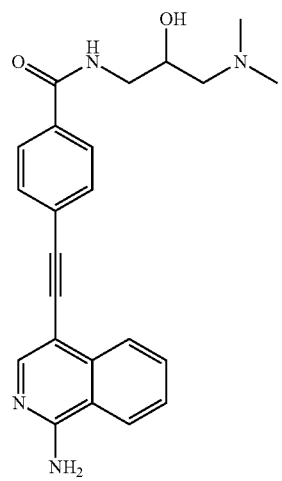 [SMILES: CN(C)CC(O)CNC(=O)c1ccc(C#Cc2cnc(N)c3ccccc23)cc1]

$^1$H NMR (500 MHz, DMSO-d$_6$) δ 8.52 (t, J=5.7 Hz, 1H), 8.27 (d, J=8.3 Hz, 1H), 8.15 (s, 1H), 8.10 (d, J=7.8 Hz, 1H), 7.89 (d, J=8.4 Hz, 2H), 7.78 (t, J=7.6 Hz, 1H), 7.67 (d, J=8.4 Hz, 2H), 7.57 (t, J=7.0 Hz, 1H), 7.38 (s, 2H), 4.73 (s, 1H), 3.76 (s, 1H), 3.42 (dt, J=13.2, 5.3 Hz, 1H), 3.15 (t, J=6.1 Hz, 1H), 2.27 (dd, J=12.4, 5.9 Hz, 1H), 2.23-2.20 (m, 1H), 2.17 (s, 6H); $^{13}$C NMR (126 MHz, DMSO) δ 166.08, 158.20, 147.78, 136.41, 134.02, 131.56, 131.16, 128.03, 126.78, 126.29, 124.93, 116.72, 102.89, 93.24, 89.28, 67.52, 64.33, 46.35, 45.28; HRMS (ESI$^+$): calcd. for C$_{23}$H$_{25}$N$_4$O$_2$ (MH$^+$) 389.1978, found 389.2018.

Example 44: 4-((4-(4,5-dihydro-1H-imidazol-2-yl)phenyl)ethynyl)isoquinolin-1-amine (HSM1795)

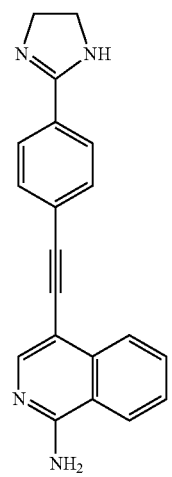 [SMILES: Nc1ncc(C#Cc2ccc(C3=NCCN3)cc2)c2ccccc12]

$^1$H NMR (500 MHz, DMSO) δ 8.27 (d, J=8.3 Hz, 1H), 8.17-8.06 (m, 2H), 7.85 (d, J=7.9 Hz, 2H), 7.77 (t, J=7.5 Hz, 1H), 7.63 (d, J=7.9 Hz, 2H), 7.57 (d, J=7.5 Hz, 1H), 7.37 (s, 2H), 6.97 (s, 1H), 3.34 (s, 4H); $^{13}$C NMR (126 MHz, DMSO) δ 163.54, 158.16, 147.64, 136.44, 131.55, 131.16, 130.38, 127.82, 126.78, 125.34, 124.94, 116.75, 103.03, 93.42, 88.87, 55.48, 44.89; HR-MS(ESI) m/z calcd for C$_{20}$H$_{17}$N$_4$ ([M+H]$^+$) 313.1453, found 313.1455.

Example 45: 4-((4-(4,5-dihydro-1H-imidazol-2-yl)phenyl)ethynyl)quinolin-2-amine (HSM1803)

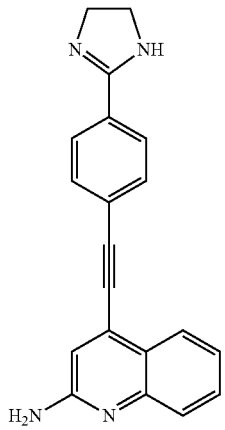 [SMILES: Nc1cc(C#Cc2ccc(C3=NCCN3)cc2)c2ccccc2n1]

$^1$H NMR (500 MHz, DMSO) δ 8.03 (dd, J=8.1, 0.8 Hz, 1H), 7.91 (d, J=8.4 Hz, 2H), 7.76 (d, J=8.4 Hz, 2H), 7.57-7.44 (m, 2H), 7.26 (ddd, J=8.1, 6.7, 1.4 Hz, 1H), 7.00 (s, 1H), 6.59 (s, 2H), 3.62 (s, 4H); $^{13}$C NMR (126 MHz, DMSO) δ 163.40, 158.16, 148.49, 132.19, 131.72, 130.37, 129.10, 127.95, 126.24, 125.64, 123.57, 122.52, 122.00, 115.50, 96.07, 86.97; HR-MS(ESI) m/z calcd for $C_{20}H_{17}N_4$ ([M+H]$^+$) 313.1453, found 313.1487.

Example 46: 4-((2-amino-6,7-dimethoxyquinazolin-4-yl)ethynyl)benzonitrile (HSN364)

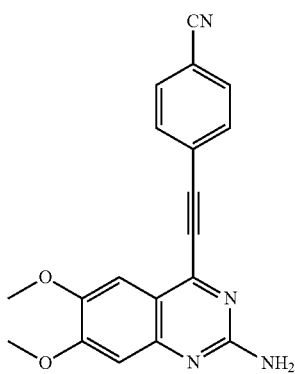 [SMILES: COc1cc2nc(N)nc(C#Cc3ccc(C#N)cc3)c2cc1OC]

$^1$H NMR (500 MHz, DMSO-d$_6$) δ 7.96 (q, J=8.5 Hz, 4H), 7.28 (s, 1H), 6.87 (s, 1H), 6.61 (s, 2H), 3.90 (d, J=1.1 Hz, 6H); $^{13}$C NMR (126 MHz, DMSO) δ 160.53, 156.96, 150.97, 148.83, 147.55, 133.48, 133.27, 125.91, 118.74, 115.15, 112.82, 104.86, 103.86, 93.27, 89.06, 56.41, 56.07.

Example 47: 4-((4-(4,4-dimethyl-4,5-dihydro-1H-imidazol-2-yl)phenyl)ethynyl)-1-methylisoquinolin-3-amine (HSN370)

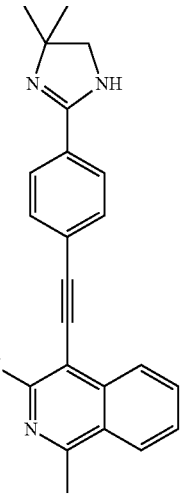

$^1$H NMR (500 MHz, Methanol-d$_4$) δ 8.01 (d, J=7.9 Hz, 2H), 7.82 (d, J=8.0 Hz, 2H), 7.71 (d, J=7.9 Hz, 2H), 7.63 (t, J=7.9 Hz, 1H), 7.33-7.28 (m, 1H), 3.58 (s, 2H), 2.81 (s, 3H), 1.38 (s, 6H); $^{13}$C NMR (126 MHz, MeOD) δ 159.31, 155.78, 138.09, 132.19, 131.08, 130.90, 127.89, 127.26, 126.88, 126.16, 123.20, 122.87, 121.33, 98.53, 89.81, 85.93, 62.63, 60.86, 27.24, 20.69.

Example 48: 4-((4-(4,4-dimethyl-4,5-dihydro-1H-imidazol-2-yl)phenyl)ethynyl)-6,7-dimethoxyquinazolin-2-amine (HSN335)

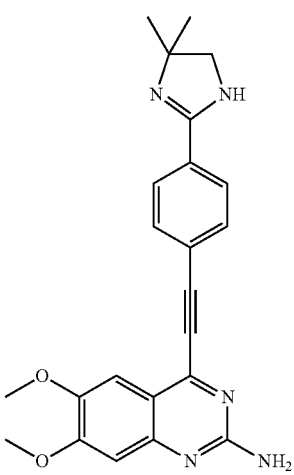 [SMILES: COc1cc2nc(N)nc(C#Cc3ccc(C4=NC(C)(C)CN4)cc3)c2cc1OC]

$^1$H NMR (500 MHz, DMSO-d$_6$) δ 8.03 (d, J=9.9 Hz, 3H), 7.97 (d, J=8.3 Hz, 1H), 7.93 (s, 1H), 7.30 (s, 1H), 6.88 (s, 1H), 6.61 (s, 2H), 3.91 (d, J=5.2 Hz, 6H), 3.77 (s, 2H), 1.46 (s, 3H), 1.44 (s, 3H); $^{13}$C NMR (126 MHz, DMSO) δ 162.00, 160.54, 156.99, 150.99, 148.86, 147.57, 133.71, 133.39, 129.33, 126.80, 126.12, 115.15, 104.90, 93.45, 89.08, 62.12, 57.30, 56.45, 56.15, 27.94.

Example 49: 3-((2-amino-6,7-dimethoxyquinazolin-4-yl)ethynyl)-4-methylbenzonitrile (HSN368)

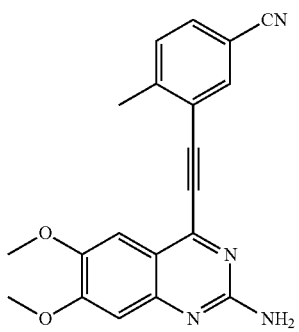 [SMILES: COc1cc2nc(N)nc(C#Cc3cc(C#N)ccc3C)c2cc1OC]

$^1$H NMR (500 MHz, DMSO-d$_6$) δ 8.19 (d, J=1.6 Hz, 1H), 7.87 (d, J=1.8 Hz, 1H), 7.62 (d, J=8.0 Hz, 1H), 7.30 (s, 1H), 6.88 (s, 1H), 6.62 (s, 2H), 3.89 (d, J=8.4 Hz, 6H), 2.66 (s, 3H); $^{13}$C NMR (126 MHz, DMSO) δ 160.55, 156.88, 150.90, 149.12, 147.52, 146.97, 136.34, 133.89, 131.60, 122.56, 118.50, 115.11, 110.06, 104.88, 103.93, 91.52, 91.36, 56.05, 46.02, 21.44.

Example 50: Compound HSG33

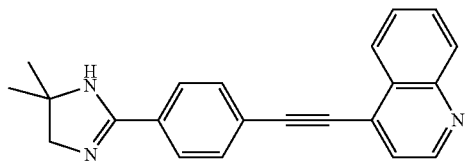 [SMILES: CC1(C)CN=C(c2ccc(C#Cc3ccnc4ccccc34)cc2)N1]

$^1$H NMR (500 MHz, Methanol-d$_4$) δ 8.90 (d, J=4.5 Hz, 1H), 8.43 (dd, J=8.5, 1.4 Hz, 1H), 8.11 (dt, J=8.5, 0.9 Hz, 1H), 8.03-7.93 (m, 4H), 7.88 (ddd, J=8.4, 6.9, 1.4 Hz, 1H), 7.80-7.76 (m, 2H), 3.90 (s, 2H), 1.58 (s, 6H); $^{13}$C NMR (126 MHz, Methanol-d$_4$) δ 164.44, 150.83, 148.75, 133.95, 131.87, 129.97, 129.69, 129.25, 128.76, 126.90, 125.44, 124.58, 97.95, 89.29, 63.32, 58.53, 27.92.

Example 51: Compound HSG39

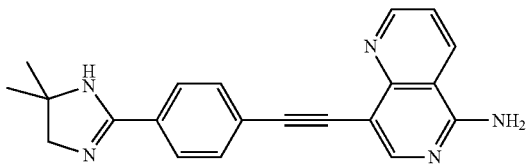 [SMILES: CC1(C)CN=C(c2ccc(C#Cc3cnc(N)c4cccnc34)cc2)N1]

$^1$H NMR (500 MHz, Methanol-d$_4$) δ 9.02 (dd, J=4.4, 1.7 Hz, 1H), 8.66 (dd, J=8.4, 1.7 Hz, 1H), 8.32 (s, 1H), 7.82 (q, J=8.2 Hz, 4H), 7.61 (dd, J=8.4, 4.4 Hz, 1H), 5.12 (s, 1H), 3.71 (s, 2H), 1.46 (s, 6H); $^{13}$C NMR (126 MHz, Methanol-d$_4$) δ 164.13, 161.49, 159.71, 155.45, 152.66, 151.48, 134.89, 132.41, 130.64, 128.36, 127.87, 122.96, 114.17, 107.49, 94.02, 88.07, 49.85, 28.75; HRMS (M+H): Calc. 342.1640, Observed 342.1715.

Example 52: Compound HSG42

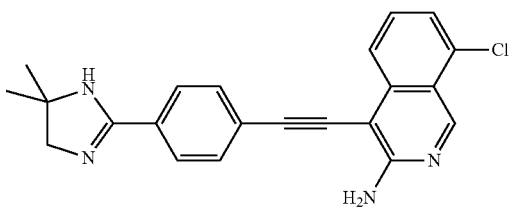 [SMILES: CC1(C)CN=C(c2ccc(C#Cc3c(N)ncc4c(Cl)cccc34)cc2)N1]

$^1$H NMR (500 MHz, Methanol-d$_4$) δ 9.24-8.97 (m, 1H), 7.91 (dt, J=8.5, 0.9 Hz, 1H), 7.86-7.76 (m, 2H), 7.77-7.66 (m, 2H), 7.52 (dd, J=8.5, 7.4 Hz, 1H), 7.29 (dd, J=7.4, 0.9 Hz, 1H), 3.52 (s, 2H), 1.35 (s, 6H); $^{13}$C NMR (126 MHz, MeOD) δ 163.98, 158.77, 149.57, 140.95, 134.17, 132.71, 132.40, 130.81, 128.54, 127.13, 124.58, 123.58, 120.72, 100.91, 92.85, 85.89, 64.15, 62.96, 28.73.

Example 53: Compound HSG43

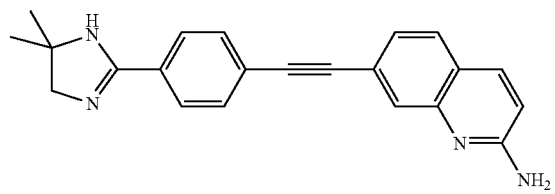 [SMILES: CC1(C)CN=C(c2ccc(C#Cc3ccc4ccc(N)nc4c3)cc2)N1]

$^1$H NMR (500 MHz, Methanol-d$_4$) δ 7.92 (d, J=8.9 Hz, 1H), 7.85 (d, J=1.9 Hz, 1H), 7.82-7.77 (m, 2H), 7.63 (dd, J=8.6, 1.9 Hz, 1H), 7.61-7.56 (m, 2H), 7.51 (d, J=8.7 Hz, 1H), 6.86 (d, J=8.9 Hz, 1H), 3.51 (s, 2H), 1.34 (s, 6H); $^{13}$C NMR (126 MHz, MeOD) δ 164.02, 161.48, 160.37, 148.44, 139.04, 133.44, 132.41, 132.35, 131.00, 128.47, 127.32, 125.80, 124.28, 117.56, 114.36, 92.45, 89.03, 28.75; HRMS (M+H): Calc. 341.1688, Observed 341.1769.

Example 54: Compound HSG47

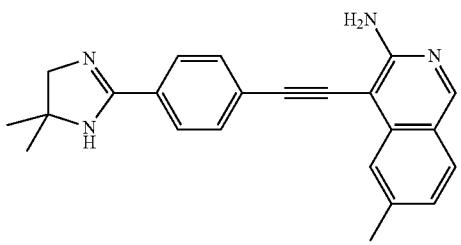 [SMILES: Cc1ccc2cnc(N)c(C#Cc3ccc(C4=NCC(C)(C)N4)cc3)c2c1]

$^1$H NMR (500 MHz, Methanol-d$_4$) δ 8.77-8.53 (m, 1H), 7.86-7.78 (m, 2H), 7.74 (dt, J=1.7, 0.9 Hz, 1H), 7.72-7.64 (m, 3H), 7.12 (dd, J=8.3, 1.6 Hz, 1H), 3.52 (s, 2H), 2.51 (d, J=1.0 Hz, 3H), 1.35 (s, 6H); $^{13}$C NMR (126 MHz, MeOD) δ 163.57, 157.57, 152.04, 143.52, 139.34, 132.07, 130.30, 129.16, 128.21, 126.93, 126.67, 122.82, 122.27, 100.25, 92.73, 86.20, 78.93, 78.86, 78.67, 78.41, 63.84, 62.72, 30.43, 28.72, 22.56; HRMS (M+H): Calc. 355.1844, Observed 355.1916.

Example 55: Compound HSG74

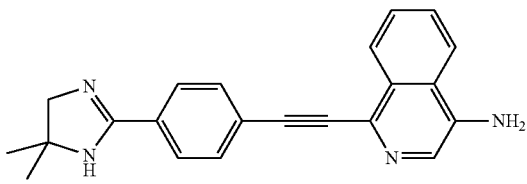 [SMILES: CC1(C)CN=C(c2ccc(C#Cc3ncc(N)c4ccccc34)cc2)N1]

$^1$H NMR (500 MHz, Methanol-d$_4$) δ 8.36-8.24 (m, 1H), 8.06-7.98 (m, 1H), 7.84 (s, 1H), 7.78-7.73 (m, 2H), 7.65-7.59 (m, 4H), 3.45 (s, 2H), 1.28 (s, 6H); $^{13}$C NMR (126 MHz, MeOD) δ 163.89, 142.29, 132.54, 131.14, 131.06, 130.87, 130.11, 129.52, 128.56, 127.66, 127.45, 126.74, 126.16, 122.66, 92.31, 90.05, 64.17, 63.00.

Example 56: Compound HSG001

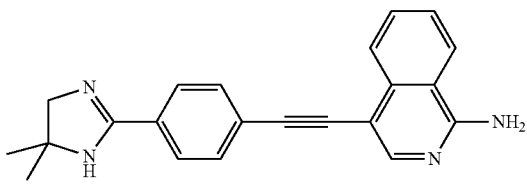 [SMILES: CC1(C)CN=C(c2ccc(C#Cc3cnc(N)c4ccccc34)cc2)N1]

$^1$H NMR (500 MHz, Methanol-d$_4$) δ 8.23-8.14 (m, 2H), 8.08 (s, 1H), 7.87-7.78 (m, 3H), 7.70-7.64 (m, 2H), 7.60 (ddd, J=8.3, 6.9, 1.2 Hz, 1H), 5.49 (s, 2H), 3.57 (s, 2H), 1.38 (s, 6H); $^{13}$C NMR (126 MHz, MeOD) δ 164.54, 159.39, 147.42, 137.83, 134.32, 132.91, 132.66, 131.63, 129.47, 128.04, 125.99, 125.24, 122.89, 118.25, 111.11, 105.33, 93.32, 91.86, 63.17, 58.59, 27.93.

Example 57: Compound HSG82

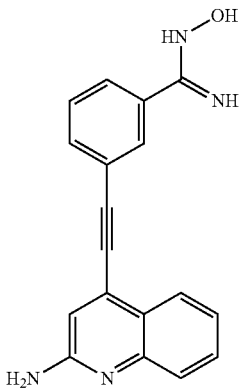 [SMILES: N=C(NO)c1cccc(C#Cc2cc(N)nc3ccccc23)c1]

$^1$H NMR (500 MHz, DMSO-d$_6$) δ 9.79 (s, 1H), 8.05 (dd, J=8.1, 1.4 Hz, 1H), 7.99 (d, J=1.8 Hz, 1H), 7.81 (dt, J=7.9, 1.4 Hz, 1H), 7.72 (dt, J=7.7, 1.3 Hz, 1H), 7.60-7.46 (m, 3H), 7.29 (ddd, J=8.1, 6.7, 1.4 Hz, 1H), 7.01 (s, 1H), 6.60 (s, 2H), 5.97 (s, 2H); $^{13}$C NMR (126 MHz, DMSO) δ 157.63, 149.91, 147.89, 133.96, 132.08, 129.91, 128.82, 128.77, 128.57, 126.52, 125.69, 125.12, 122.07, 121.55, 121.32, 114.96, 95.87, 85.10, 54.92.

Example 58: Compound HSG83

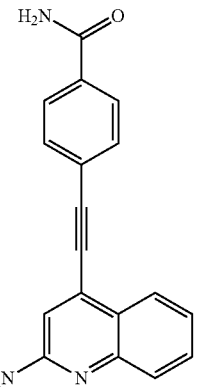

$^1$H NMR (500 MHz, DMSO-d$_6$) δ 8.12 (s, 1H), 8.05 (dd, J=8.1, 1.4 Hz, 1H), 8.03-7.92 (m, 2H), 7.87-7.75 (m, 2H), 7.56-7.50 (m, 3H), 7.28 (ddd, J=8.1, 6.7, 1.4 Hz, 1H), 7.02 (s, 1H), 6.60 (s, 2H); $^{13}$C NMR (126 MHz, DMSO) δ 166.98, 157.65, 147.98, 134.78, 131.73, 129.92, 128.52, 127.92, 125.75, 125.16, 124.13, 122.08, 121.49, 115.12, 109.23, 95.34, 86.75.

Example 59: 3-((2-aminoquinolin-4-yl)ethynyl)-N-(4-(2-(dimethylamino)ethoxy)benzyl)-4-methylbenzamide (HSN316)

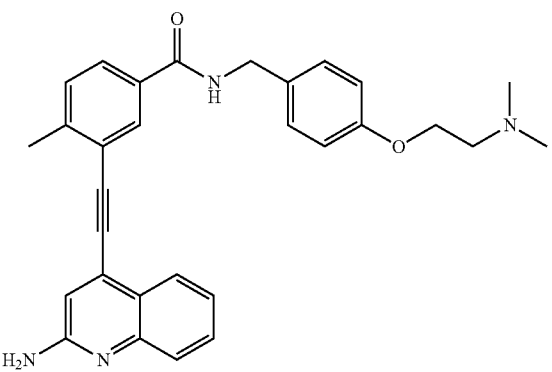 [SMILES: Cc1ccc(C(=O)NCc2ccc(OCCN(C)C)cc2)cc1C#Cc1cc(N)nc2ccccc12]

$^1$H NMR (500 MHz, DMSO-d$_6$) δ 9.07 (t, J=6.0 Hz, 1H), 8.17 (d, J=1.9 Hz, 1H), 8.03 (dd, J=8.1, 1.4 Hz, 1H), 7.88 (dd, J=8.0, 2.0 Hz, 1H), 7.59-7.46 (m, 3H), 7.28 (ddd, J=8.1, 6.6, 1.5 Hz, 1H), 7.23 (d, J=8.6 Hz, 2H), 7.02 (s, 1H), 6.88 (d, J=8.7 Hz, 2H), 6.57 (s, 2H), 4.40 (d, J=5.9 Hz, 2H), 3.99 (t, J=5.8 Hz, 2H), 2.59 (s, 5H), 2.18 (s, 6H); $^{13}$C NMR (126 MHz, DMSO) δ 165.40, 158.17, 157.90, 148.52, 143.70, 132.80, 131.97, 131.21, 130.43, 130.34, 129.23, 129.14, 128.96, 126.28, 125.47, 122.53, 121.92, 121.84, 115.57, 114.74, 94.59, 89.81, 66.22, 58.13, 45.98, 42.62, 20.93.

Example 60: Compound HSN303

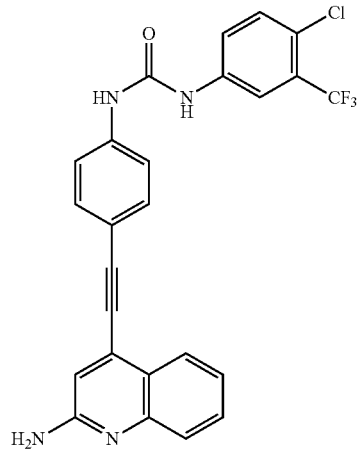 [SMILES: Nc1cc(C#Cc2ccc(NC(=O)Nc3ccc(Cl)c(C(F)(F)F)c3)cc2)c2ccccc2n1]

¹H NMR (500 MHz, DMSO-d₆) δ 9.25 (s, 1H), 9.16 (s, 1H), 8.11 (d, J=2.4 Hz, 1H), 8.02 (d, J=8.1 Hz, 1H), 7.69-7.56 (m, 6H), 7.54-7.50 (m, 2H), 7.25 (t, J=7.3 Hz, 1H), 6.96 (s, 1H), 6.53 (s, 2H); ¹³C NMR (126 MHz, DMSO) δ 158.16, 152.64, 148.49, 141.06, 139.56, 133.74, 133.20, 132.51, 130.23, 129.63, 127.31, 127.07, 126.22, 125.66, 123.74, 123.06, 122.38, 122.18, 118.90, 117.44, 115.11, 97.07, 84.72; HRMS (ESI⁺): calcd. for C₂₅H₁₇ClF₃N4O (MH⁺) 481.1043, found 481.1034.

Example 61: Compound HSN285

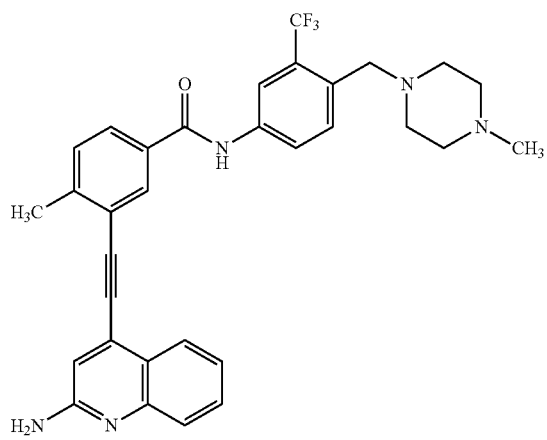 [SMILES: Cc1ccc(C(=O)Nc2ccc(CN3CCN(C)CC3)c(C(F)(F)F)c2)cc1C#Cc1cc(N)nc2ccccc12]

¹H NMR (500 MHz, DMSO-d₆) δ 10.56 (s, 1H), 8.29 (d, J=1.9 Hz, 1H), 8.21 (d, J=2.2 Hz, 1H), 8.06 (dd, J=8.0, 1.3 Hz, 2H), 7.97 (dd, J=8.0, 2.0 Hz, 1H), 7.70 (d, J=8.5 Hz, 1H), 7.61-7.48 (m, 3H), 7.29 (ddd, J=8.1, 6.6, 1.6 Hz, 1H), 7.05 (s, 1H), 6.59 (s, 2H), 3.55 (s, 2H), 3.15 (s, 2H), 2.63 (s, 3H), 2.37 (s, 6H), 2.14 (s, 3H); ¹³C NMR (126 MHz, DMSO) δ 165.06, 158.17, 148.54, 144.50, 138.60, 132.83, 132.59, 131.69, 131.59, 130.59, 130.36, 129.40, 129.19, 127.74, 126.30, 125.50, 124.00, 122.55, 121.99, 121.92, 117.76, 115.63, 94.42, 90.11, 57.92, 55.19, 53.15, 49.06, 46.17, 21.04; HRMS (ESI⁺): calcd. for C₃₂H₃₁F₃N₅O (MH⁺) 558.2481, found 558.2479.

Example 62: 4-((4-(4,4-dimethyl-4,5-dihydro-1H-imidazol-2-yl)-3-fluorophenyl)ethynyl)quinolin-2-amine (HSM1856)

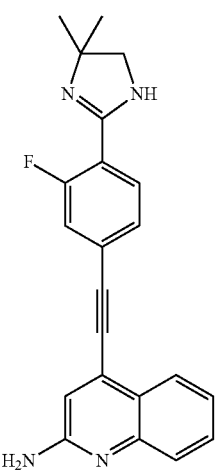 [SMILES: CC1(C)CNC(c2ccc(C#Cc3cc(N)nc4ccccc34)cc2F)=N1]

¹H NMR (500 MHz, DMSO) δ 8.08 (d, J=8.0 Hz, 1H), 7.89 (d, J=7.8 Hz, 1H), 7.75 (s, 1H), 7.58-7.47 (m, 2H), 7.29 (dd, J=10.9, 4.0 Hz, 1H), 7.05 (s, 1H), 6.66 (s, 2H), 3.61 (s, 2H), 1.38 (s, 6H); ¹³C NMR (126 MHz, DMSO) δ 160.58, 157.18, 147.84, 140.91, 131.91, 131.34, 130.86, 128.05, 127.64, 125.57, 124.22, 122.68, 122.44, 105.95, 94.97, 87.12, 29.08.

Example 63: 4-(5-(2-aminoquinolin-4-yl)-1,3,4-oxadiazol-2-yl)-N-hydroxybenzimidamide (HSM1860)

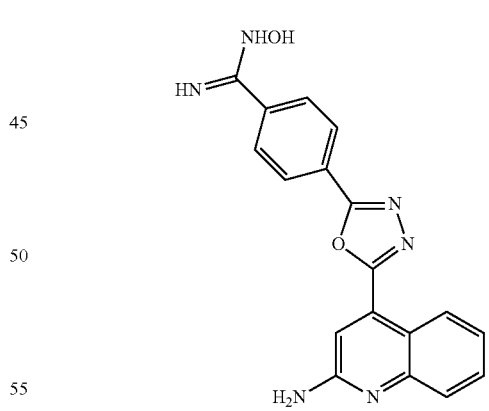

¹H NMR (500 MHz, DMSO) δ 9.92 (d, J=9.2 Hz, 1H), 8.80 (dd, J=17.4, 8.5 Hz, 1H), 8.23-8.05 (m, 2H), 8.00-7.92 (m, 2H), 7.63-7.55 (m, 2H), 7.39-7.26 (m, 1H), 6.86-6.73 (m, 2H), 6.10-5.90 (m, 2H); ¹³C NMR (126 MHz, DMSO) δ 164.26, 163.24, 158.07, 150.41, 149.43, 137.22, 130.31, 128.79, 127.17, 126.73, 126.57, 126.02, 123.66, 123.12, 118.17, 113.60.

Example 64: 3-((2-amino-6,7-dimethoxyquinazolin-4-yl)amino)benzonitrile (HSN295)

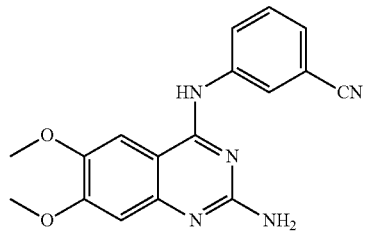

$^1$H NMR (500 MHz, DMSO-d$_6$) δ 10.79 (s, 1H), 8.36 (s, 1H), 8.14 (s, 2H), 7.90 (s, 2H), 7.75-7.53 (m, 2H), 7.00 (s, 1H), 3.92 (s, 6H); HRMS (ESI$^+$): calcd. for C$_{17}$H$_{16}$N$_5$O$_2$ (MH$^+$) 322.1304, found 322.1314.

Example 65: 3-((2-amino-6,7-dimethoxyquinazolin-4-yl)amino)-N-hydroxybenzimidamide (HSN301)

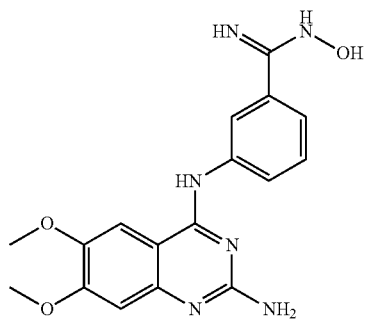

$^1$H NMR (500 MHz, DMSO-d$_6$) δ 9.79 (s, 1H), 9.62 (s, 1H), 8.02-7.88 (m, 2H), 7.82 (s, 1H), 7.43 (dt, J=7.8, 1.5 Hz, 1H), 7.40-7.35 (m, 1H), 6.81 (d, J=28.2 Hz, 3H), 5.79 (s, 2H), 3.87 (s, 6H); $^{13}$C NMR (126 MHz, DMSO) δ 158.43, 157.29, 155.27, 151.25, 146.28, 139.16, 134.27, 128.75, 124.18, 121.69, 120.61, 104.28, 103.53, 102.56, 56.70, 56.20; HRMS (ESI$^+$): calcd. for C$_{17}$H$_{19}$N$_6$O$_3$ (MH$^+$) 355.1519, found 355.1515.

Example 66: N-(4-((2-amino-6,7-dimethoxyquinazolin-4-yl)amino)phenyl)-3-(piperidin-1-yl)propanamide (HSN304)

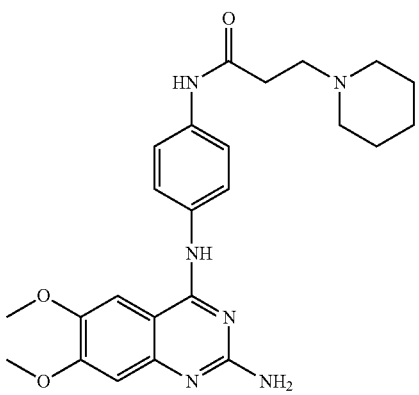

$^1$H NMR (500 MHz, DMSO-d$_6$) δ 10.57 (s, 1H), 10.53 (s, 1H), 8.09 (s, 1H), 7.69 (q, J=8.7 Hz, 6H), 6.96 (s, 1H), 3.90 (s, 6H), 3.32 (t, J=5.1 Hz, 6H), 3.22 (s, 2H), 2.94 (t, J=7.4 Hz, 2H), 1.89-1.67 (m, 4H); $^{13}$C NMR (126 MHz, DMSO) δ 168.38, 158.76, 155.79, 154.43, 147.14, 136.86, 133.30, 125.16, 119.70, 105.48, 103.00, 99.20, 74.35, 60.46, 58.49, 57.06, 56.53, 52.63, 31.05, 22.92, 21.87; HRMS (ESI$^+$): calcd. for C$_{24}$H$_{31}$N$_6$O$_3$ (MH$^+$) 451.2458, found 451.2452.

Example 67: 4-((2-amino-6,7-dimethoxyquinazolin-4-yl)(methyl)amino)-N-hydroxybenzimidamide (HSN318)

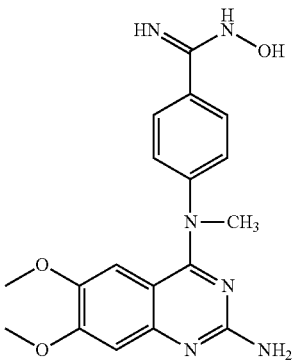

$^1$H NMR (500 MHz, DMSO-d$_6$) δ 9.60 (s, 1H), 7.65 (d, J=8.6 Hz, 2H), 7.13 (d, J=8.6 Hz, 2H), 6.69 (s, 1H), 6.20 (s, 1H), 6.13 (s, 2H), 5.78 (s, 2H), 3.77 (s, 3H), 3.45 (s, 3H), 3.13 (s, 3H); $^{13}$C NMR (126 MHz, DMSO) δ 162.04, 159.86, 154.14, 151.52, 150.71, 149.48, 144.06, 130.25, 127.08, 124.86, 106.11, 105.37, 105.15, 55.84, 54.91, 41.42.

Example 68: 3-((2-amino-6,7-dimethoxyquinazolin-4-yl)ethynyl)-N-(4-(2-(dimethylamino)ethoxy)benzyl)-4-methylbenzamide (HSN317)

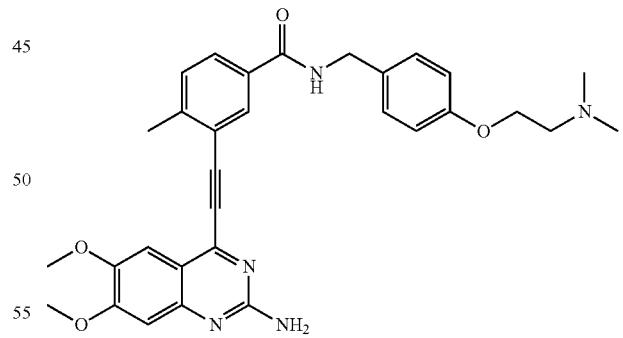

$^1$H NMR (500 MHz, DMSO-d$_6$) δ 9.08 (t, J=5.9 Hz, 1H), 8.20 (d, J=1.9 Hz, 1H), 7.91 (dd, J=8.0, 1.9 Hz, 1H), 7.50 (d, J=8.1 Hz, 1H), 7.32 (s, 1H), 7.23 (d, J=8.6 Hz, 2H), 6.94-6.82 (m, 3H), 6.57 (s, 2H), 4.39 (d, J=5.8 Hz, 2H), 4.00 (t, J=5.8 Hz, 2H), 3.90 (s, 3H), 3.87 (s, 3H), 2.64 (s, 3H), 2.58 (t, J=5.8 Hz, 2H), 2.18 (s, 6H); $^{13}$C NMR (126 MHz, DMSO) δ 165.27, 160.60, 157.92, 156.78, 150.80, 149.56, 147.42, 144.21, 132.93, 131.91, 131.79, 130.59, 129.58, 129.14, 121.11, 115.01, 114.74, 104.91, 103.96, 93.55, 90.21, 66.24, 58.14, 56.39, 55.91, 46.00, 42.63, 20.97.

Example 69: Compound HSN325

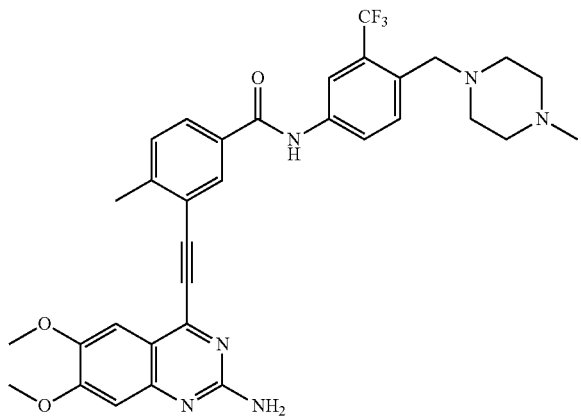

¹H NMR (500 MHz, DMSO-d₆) δ 10.58 (s, 1H), 8.33 (d, J=1.9 Hz, 1H), 8.20 (d, J=2.2 Hz, 1H), 8.06 (d, J=8.6 Hz, 1H), 8.00 (dd, J=8.0, 2.0 Hz, 1H), 7.70 (d, J=8.5 Hz, 1H), 7.58 (d, J=8.1 Hz, 1H), 7.34 (s, 1H), 6.88 (s, 1H), 6.59 (s, 2H), 3.90 (d, J=7.0 Hz, 6H), 3.56 (s, 2H), 2.68 (s, 3H), 2.42 (s, 8H), 2.22 (s, 3H); ¹³C NMR (126 MHz, DMSO) δ 164.87, 160.60, 156.81, 150.83, 149.49, 147.45, 145.04, 138.64, 132.83, 132.46, 132.10, 131.75, 130.75, 130.05, 123.94, 121.26, 117.71, 115.03, 104.91, 103.95, 93.31, 90.47, 57.80, 56.40, 55.94, 54.94, 52.74, 45.72, 21.08.

Example 70: 4-((6-chloro-3-(cyclopropanecarboxamido)isoquinolin-4-yl)ethynyl)-N-(2-(piperidin-1-yl)ethyl)benzamide (HSN329)

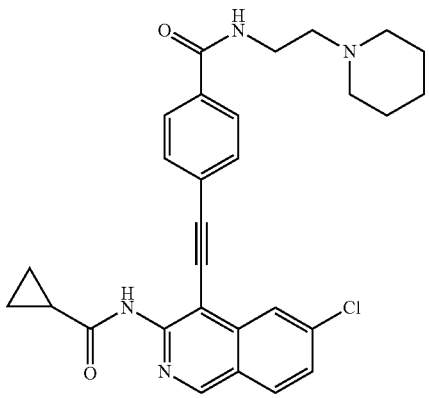 [SMILES: O=C(NCCN1CCCCC1)c1ccc(C#Cc2c(NC(=O)C3CC3)ncc3ccc(Cl)cc23)cc1]

¹H NMR (500 MHz, Chloroform-d) δ 8.80 (s, 1H), 7.99 (d, J=1.9 Hz, 1H), 7.77 (m, 3H), 7.71 (d, J=8.4 Hz, 1H), 7.66 (d, J=8.4 Hz, 2H), 7.25 (d, J=2.0 Hz, 1H), 4.05 (t, J=6.2 Hz, 2H), 2.60 (s, 2H), 2.46-2.33 (bs, 4H), 1.43-1.33 (m, 6H), 1.24-1.22 (m, 1H), 1.06 (m, 2H), 0.67 (m, 2H); ¹³C NMR (126 MHz, CDCl₃) δ 177.24, 173.16, 157.02, 152.12, 138.68, 138.29, 136.20, 131.63, 131.29, 130.06, 129.42, 126.83, 124.68, 122.36, 121.32, 99.58, 85.80, 57.62, 54.47, 29.71, 25.70, 24.19, 18.50, 11.76, 9.43.

Example 71: 1-(3-((2-aminoquinolin-4-yl)ethynyl)phenyl)-3-(4-chloro-3-(trifluoromethyl)phenyl)urea (HSN333)

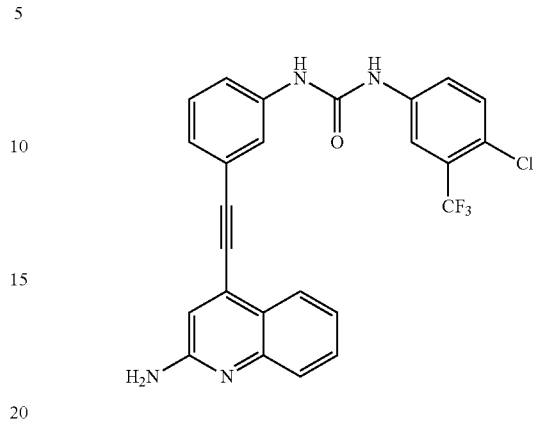

¹H NMR (500 MHz, DMSO-d₆) δ 9.25 (s, 1H), 9.03 (s, 1H), 8.11 (d, J=2.6 Hz, 1H), 8.01 (d, J=8.1 Hz, 1H), 7.87 (s, 1H), 7.65 (dd, J=8.7, 2.5 Hz, 1H), 7.61 (d, J=8.8 Hz, 1H), 7.53 (d, J=5.5 Hz, 2H), 7.49 (d, J=8.0 Hz, 1H), 7.40 (t, J=7.8 Hz, 1H), 7.34 (d, J=7.5 Hz, 1H), 7.27 (t, J=7.2 Hz, 1H), 7.03 (s, 1H), 6.58 (s, 2H); ¹³C NMR (126 MHz, DMSO) δ 158.13, 152.89, 148.48, 140.17, 139.66, 132.48, 130.31, 129.96, 129.21, 127.30, 127.06, 126.30, 126.18, 125.52, 124.36, 123.72, 122.98, 122.49, 122.26, 122.19, 121.82, 120.46, 117.40, 96.54, 85.25.

Example 72: 3-((8-amino-1,7-naphthyridin-5-yl)ethynyl)-4-methyl-N-(4-((4-methylpiperazin-1-yl)methyl)-3-(trifluoromethyl)phenyl)benzamide (HSN356)

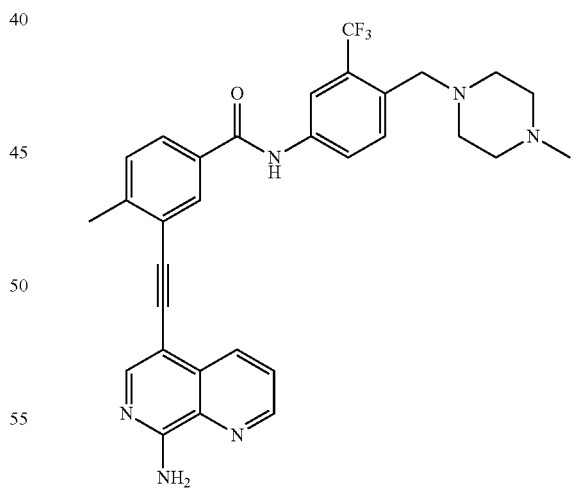

¹H NMR (500 MHz, DMSO-d₆) δ 10.57 (s, 1H), 8.88 (dd, J=4.3, 1.6 Hz, 1H), 8.46 (dd, J=8.3, 1.6 Hz, 1H), 8.28-8.19 (m, 3H), 8.08 (d, J=8.5 Hz, 1H), 7.89 (dd, J=8.0, 2.0 Hz, 1H), 7.85 (dd, J=8.4, 4.2 Hz, 1H), 7.69 (d, J=8.5 Hz, 1H), 7.53 (s, 1H), 7.50 (d, J=8.1 Hz, 1H), 3.57 (s, 2H), 2.60 (s, 3H), 2.48 (bs, merged with DMSO, 8H), 2.29 (s, 3H); ¹³C NMR (126 MHz, DMSO) δ 165.32, 158.56, 149.70, 148.18, 143.41, 138.78, 133.14, 132.64, 132.52, 132.21, 131.73, 131.36, 130.82, 130.33, 128.05, 127.99, 127.75, 127.06, 124.00, 123.42, 117.76, 102.11, 91.74, 90.52, 57.69, 54.64, 52.27, 45.89, 21.19.

Example 73: 3-((8-amino-1,7-naphthyridin-5-yl) ethynyl)-N-(4-(2-(dimethylamino)ethoxy)benzyl)-4-methylbenzamide (HSN357)

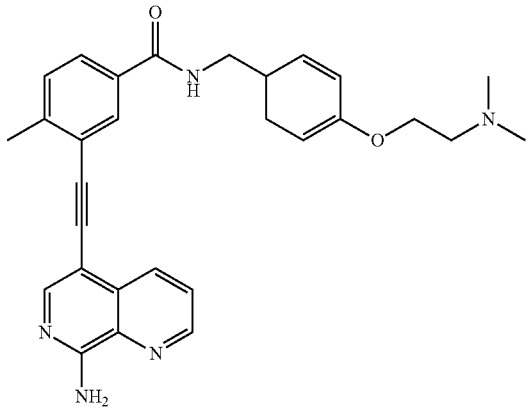

$^1$H NMR (500 MHz, DMSO-d$_6$) δ 9.02 (t, J=6.0 Hz, 1H), 8.87 (dd, J=4.2, 1.6 Hz, 1H), 8.42 (dd, J=8.4, 1.6 Hz, 1H), 8.21 (s, 1H), 8.09 (d, J=1.8 Hz, 1H), 7.84 (dd, J=8.4, 4.2 Hz, 1H), 7.78 (dd, J=8.0, 1.9 Hz, 1H), 7.51 (s, 2H), 7.42 (d, J=8.0 Hz, 1H), 7.23 (d, J=8.6 Hz, 2H), 6.88 (d, J=8.7 Hz, 2H), 4.39 (d, J=5.9 Hz, 2H), 4.00 (t, J=5.8 Hz, 2H), 2.61 (t, J=5.8 Hz, 2H), 2.56 (s, 3H), 2.20 (s, 6H); $^{13}$C NMR (126 MHz, DMSO) δ 165.64, 158.51, 157.85, 149.68, 148.09, 142.60, 133.08, 132.67, 132.52, 132.08, 131.34, 130.43, 130.16, 129.13, 127.58, 127.04, 123.25, 114.73, 102.18, 91.86, 90.14, 66.09, 58.05, 45.89, 42.58, 21.08.

Example 74: 3-((1-aminoisoquinolin-4-yl)ethynyl)-4-methyl-N-(4-((4-methylpiperazin-1-yl)methyl)-3-(trifluoromethyl)phenyl)benzamide (HSN334)

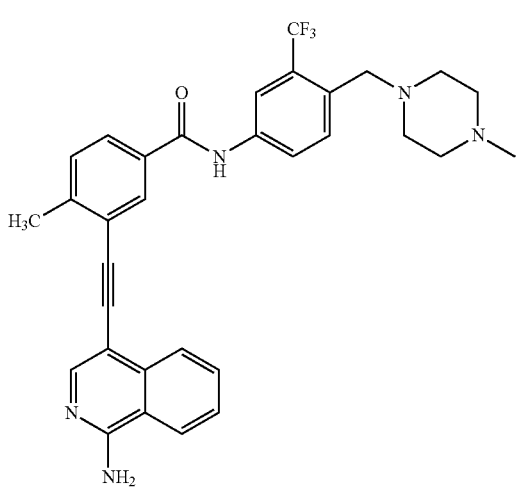

$^1$H NMR (500 MHz, DMSO-d$_6$) δ 10.52 (s, 1H), 8.29 (d, J=8.3 Hz, 1H), 8.21 (d, J=2.2 Hz, 1H), 8.19 (s, 2H), 8.11 (d, J=8.7 Hz, 1H), 8.06 (d, J=8.5 Hz, 1H), 7.86 (dd, J=7.9, 1.9 Hz, 1H), 7.80 (t, J=7.5 Hz, 1H), 7.69 (d, J=8.5 Hz, 1H), 7.57 (t, J=7.6 Hz, 1H), 7.50 (d, J=8.0 Hz, 1H), 7.38 (s, 2H), 3.55 (s, 2H), 3.15 (d, J=3.7 Hz, 1H), 2.61 (s, 3H), 2.37 (s, 7H), 2.14 (s, 3H); $^{13}$C NMR (126 MHz, DMSO) δ 165.34, 158.17, 147.70, 143.30, 138.67, 136.38, 132.66, 132.52, 131.68, 131.60, 130.62, 130.33, 127.87, 126.77, 125.00, 124.78, 123.99, 123.69, 117.74, 116.76, 103.16, 91.94, 91.71, 57.93, 55.20, 53.18, 46.20, 21.20.

Example 75: Compound HSN286

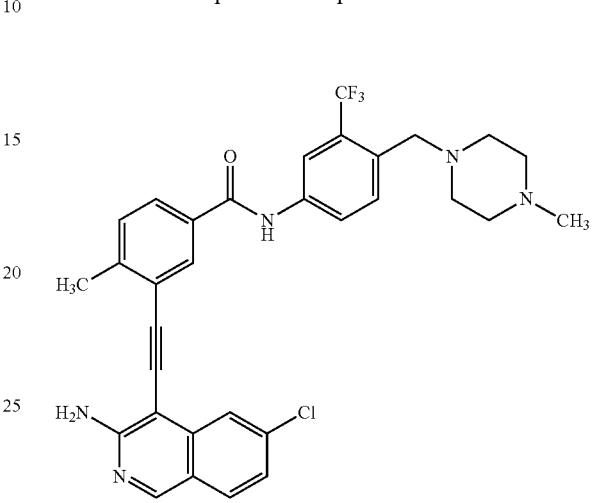

$^1$H NMR (500 MHz, DMSO-d$_6$) δ 10.54 (s, 1H), 8.92 (d, J=0.8 Hz, 1H), 8.38 (d, J=2.0 Hz, 1H), 8.21 (d, J=2.2 Hz, 1H), 8.05 (dd, J=8.5, 2.2 Hz, 1H), 7.96 (d, J=8.6 Hz, 1H), 7.88 (dd, J=8.0, 2.0 Hz, 2H), 7.70 (d, J=8.6 Hz, 1H), 7.51 (d, J=8.1 Hz, 1H), 7.28 (dd, J=8.6, 2.0 Hz, 1H), 6.78 (s, 2H), 3.55 (s, 2H), 3.15 (d, J=3.8 Hz, 1H), 2.63 (s, 3H), 2.37 (s, 7H), 2.16 (s, 3H); $^{13}$C NMR (126 MHz, DMSO) δ 165.55, 158.55, 153.20, 143.27, 138.74, 138.69, 137.39, 132.82, 132.47, 131.70, 131.64, 131.49, 130.20, 128.05, 127.74, 125.90, 123.93, 123.48, 121.34, 120.68, 117.69, 98.17, 88.78, 88.59, 57.89, 55.14, 53.07, 46.08, 21.28; HRMS (ESI$^+$): calcd. for C$_{32}$H$_{30}$F$_3$N$_5$O (MH$^+$) 592.2091, found 592.2091.

Example 76: 3-((3-aminoisoquinolin-4-yl)ethynyl)-4-methyl-N-(4-((4-methylpiperazin-1-yl)methyl)-3-(trifluoromethyl)phenyl)benzamide (HSN352)

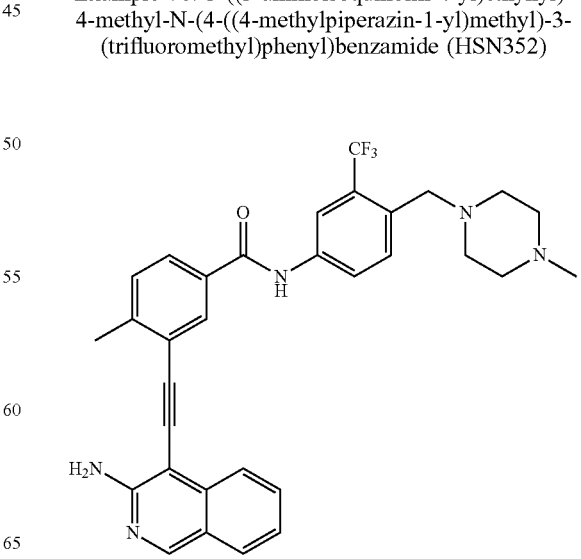

¹H NMR (500 MHz, DMSO-d₆) δ 10.54 (s, 1H), 8.90 (s, 1H), 8.36 (d, J=1.9 Hz, 1H), 8.21 (s, 1H), 8.06 (d, J=8.5 Hz, 1H), 7.95 (d, J=8.4 Hz, 1H), 7.91 (d, J=8.1 Hz, 1H), 7.87 (dd, J=7.9, 2.0 Hz, 1H), 7.69 (t, J=7.7 Hz, 2H), 7.51 (d, J=8.0 Hz, 1H), 7.28 (d, J=7.8 Hz, 1H), 6.55 (s, 2H), 3.56 (s, 2H), 3.37 (s, 1H), 2.64 (s, 3H), 2.38 (bs, 7H), 2.17 (s, 3H); ¹³C NMR (126 MHz, DMSO) δ 165.57, 158.02, 153.10, 143.26, 138.70, 137.86, 132.79, 132.46, 132.20, 131.72, 131.37, 130.19, 129.16, 127.93, 127.75, 123.95, 123.66, 123.15, 122.71, 122.45, 97.88, 89.69, 89.38, 57.88, 55.11, 53.02, 46.02, 21.37.

Example 77: 3-((3-amino-8-chloroisoquinolin-4-yl)ethynyl)-4-methyl-N-(4-((4-methylpiperazin-1-yl)methyl)-3-(trifluoromethyl)phenyl)benzamide (HSN353)

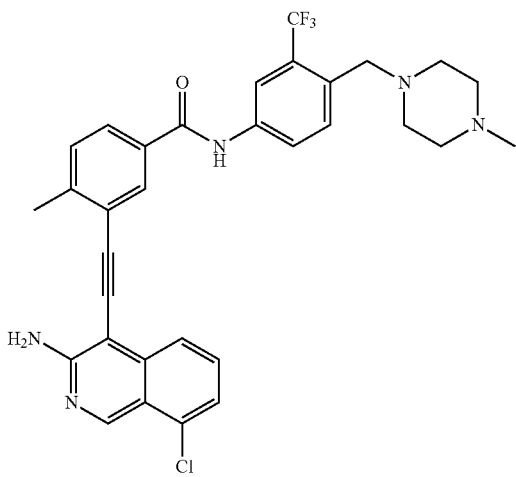

¹H NMR (500 MHz, DMSO-d₆) δ 10.53 (s, 1H), 9.10 (s, 1H), 8.37 (d, J=2.0 Hz, 1H), 8.20 (d, J=2.2 Hz, 1H), 8.05 (dd, J=8.5, 2.2 Hz, 1H), 7.94 (d, J=8.5 Hz, 1H), 7.88 (dd, J=8.0, 2.0 Hz, 1H), 7.70 (d, J=8.5 Hz, 1H), 7.63 (dd, J=8.5, 7.4 Hz, 1H), 7.51 (d, J=8.0 Hz, 1H), 7.38 (dd, J=7.4, 0.9 Hz, 1H), 6.82 (s, 2H), 3.56 (s, 2H), 2.63 (s, 3H), 2.39 (s, 8H), 2.18 (s, 3H); ¹³C NMR (126 MHz, DMSO) δ 165.53, 158.44, 148.96, 143.46, 139.61, 138.69, 132.79, 132.62, 132.44, 132.38, 131.72, 131.57, 130.20, 128.14, 125.89, 123.94, 123.45, 123.38, 122.60, 118.91, 117.70, 117.65, 98.37, 90.06, 88.65, 57.86, 55.07, 52.96, 45.96, 21.37.

Example 78: Compound HSN247

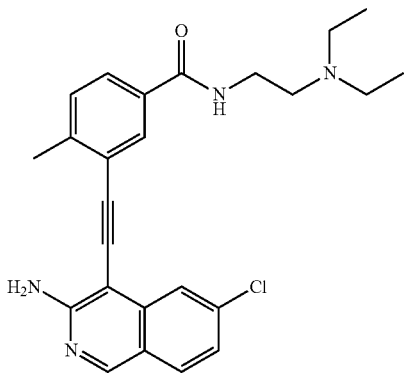 [SMILES: CCN(CC)CCNC(=O)c1ccc(C)c(C#Cc2c(N)ncc3ccc(Cl)cc23)c1]

¹H NMR (500 MHz, Methanol-d₄) δ 8.73 (s, 1H), 8.05 (d, J=2.0 Hz, 1H), 7.88 (d, J=1.9 Hz, 1H), 7.79 (d, J=8.7 Hz, 1H), 7.71 (dd, J=7.9, 2.0 Hz, 1H), 7.37 (d, J=8.0 Hz, 1H), 7.20 (dd, J=8.7, 2.0 Hz, 1H), 3.54 (t, J=7.0 Hz, 2H), 2.86-2.78 (m, 2H), 2.74 (q, J=7.2 Hz, 4H), 2.60 (s, 3H), 1.13 (t, J=7.2 Hz, 6H); ¹³C NMR (126 MHz, MeOD) δ 167.88, 157.31, 151.62, 142.91, 138.56, 137.95, 131.86, 130.31, 130.09, 129.53, 126.86, 123.66, 123.18, 121.37, 120.81, 98.11, 90.75, 87.08, 51.21, 46.89, 36.67, 19.97, 9.87; HRMS (ESI⁺): calcd. for C₂₅H₂₈ClN₄O (MH⁺) 435.1952, found 435.1952.

Example 79: Compound HSN248

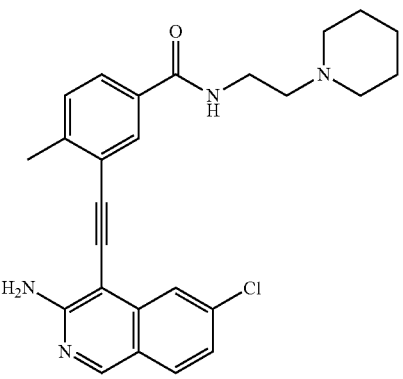 [SMILES: Cc1ccc(C(=O)NCCN2CCCCC2)cc1C#Cc1c(N)ncc2ccc(Cl)cc12]

¹H NMR (500 MHz, Methanol-d₄) δ 8.67 (s, 1H), 8.00 (d, J=2.0 Hz, 1H), 7.81 (d, J=2.0 Hz, 1H), 7.72 (d, J=8.6 Hz, 1H), 7.67 (dd, J=7.9, 2.0 Hz, 1H), 7.30 (d, J=8.0 Hz, 1H), 7.14 (dd, J=8.6, 1.9 Hz, 1H), 3.54 (t, J=6.9 Hz, 2H), 2.62 (t, J=6.9 Hz, 2H), 2.55 (bs, 7H), 1.63 (p, J=5.6 Hz, 4H), 1.48 (s, 2H); ¹³C NMR (126 MHz, MeOD) δ 167.67, 157.22, 151.52, 142.74, 138.47, 137.87, 131.86, 130.23, 130.03, 129.45, 126.84, 123.62, 123.11, 121.39, 120.76, 98.20, 90.85, 87.12, 57.54, 54.11, 36.37, 25.05, 23.61, 20.02; HRMS (ESI⁺): calcd. for C₂₆H₂₈ClN₄O (MH⁺) 447.1952, found 447.1946.

Example 80: 3-((3-amino-1-methylisoquinolin-4-yl)ethynyl)-4-methyl-N-(4-((4-methylpiperazin-1-yl)methyl)-3-(trifluoromethyl)phenyl)benzamide (HSN375)

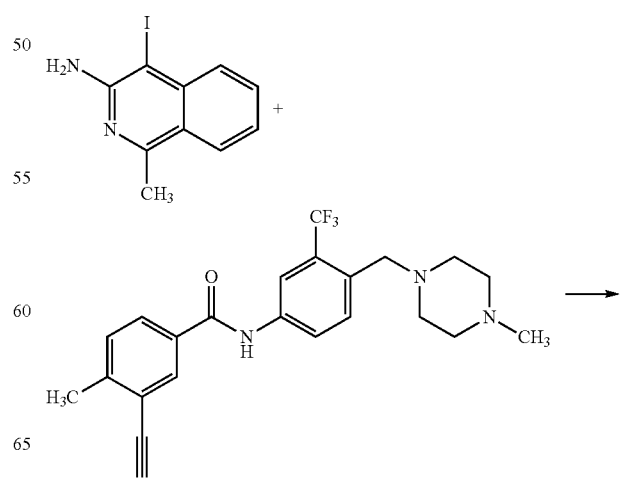

319

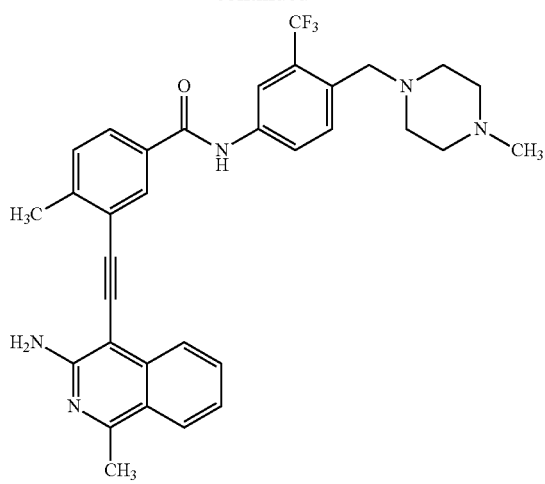

¹H NMR (500 MHz, DMSO-d₆) δ 10.53 (s, 1H), 8.34 (d, J=1.9 Hz, 1H), 8.21 (d, J=2.2 Hz, 1H), 8.06 (d, J=7.9 Hz, 1H), 8.02 (d, J=8.3 Hz, 1H), 7.97 (d, J=8.4 Hz, 1H), 7.85 (dd, J=7.9, 2.0 Hz, 1H), 7.70 (d, J=8.5 Hz, 1H), 7.66 (t, J=7.6 Hz, 1H), 7.50 (d, J=8.1 Hz, 1H), 7.28 (ddd, J=8.2, 6.8, 1.2 Hz, 1H), 6.44 (s, 2H), 3.58 (s, 2H), 2.77 (s, 3H), 2.63 (s, 3H), 2.57-2.37 (bs, 8H, merged with solvent), 2.29 (s, 3H); ¹³C NMR (126 MHz, DMSO) δ 165.60, 159.76, 156.89, 143.08, 138.78, 138.07, 132.75, 132.23, 131.77, 131.73, 131.19, 130.17, 127.73, 127.17, 123.95, 123.85, 123.29, 122.93, 121.10, 117.68, 97.47, 89.85, 88.16, 57.72, 54.77, 52.44, 49.07, 22.52, 21.39.

Example 81: 3-((3-amino-6-methylisoquinolin-4-yl) ethynyl)-4-methyl-N-(4-((4-methylpiperazin-1-yl) methyl)-3-(trifluoromethyl)phenyl)benzamide (HSN379)

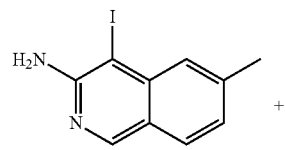

320

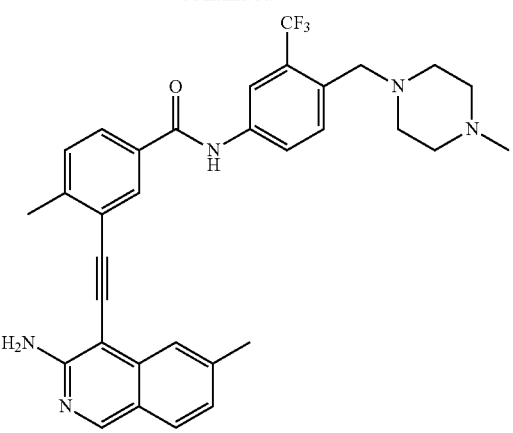 [SMILES: Cc1ccc(C(=O)Nc2ccc(CN3CCN(C)CC3)c(C(F)(F)F)c2)cc1C#Cc1c(N)ncc2ccc(F)cc12]

¹H NMR (500 MHz, DMSO-d₆) δ 10.54 (s, 1H), 8.81 (d, J=0.7 Hz, 1H), 8.35 (d, J=2.0 Hz, 1H), 8.21 (d, J=2.2 Hz, 1H), 8.05 (dd, J=8.5, 2.2 Hz, 1H), 7.87 (dd, J=8.0, 2.0 Hz, 1H), 7.80 (d, J=8.3 Hz, 1H), 7.74-7.72 (m, 1H), 7.70 (d, J=8.6 Hz, 1H), 7.51 (d, J=8.1 Hz, 1H), 7.13 (dd, J=8.3, 1.5 Hz, 1H), 6.48 (s, 2H), 3.56 (s, 2H), 2.65 (s, 3H), 2.47 (s, 3H), 2.37 (bs, 8H), 2.15 (s, 3H); ¹³C NMR (126 MHz, DMSO) δ 165.58, 158.09, 152.60, 143.24, 142.22, 138.70, 138.16, 132.79, 132.50, 131.72, 131.33, 130.21, 129.01, 127.88, 125.91, 125.34, 123.94, 123.74, 121.73, 120.96, 117.69, 97.80, 89.57, 89.32, 57.92, 55.20, 53.16, 46.19, 22.50, 21.33.

Example 82: 3-((3-amino-6-chloroisoquinolin-4-yl) ethynyl)-4-methyl-N-(4-(4-methyl-1H-imidazol-1-yl)-3-(trifluoromethyl)phenyl)benzamide (HSN380)

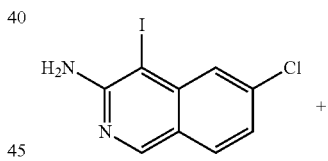

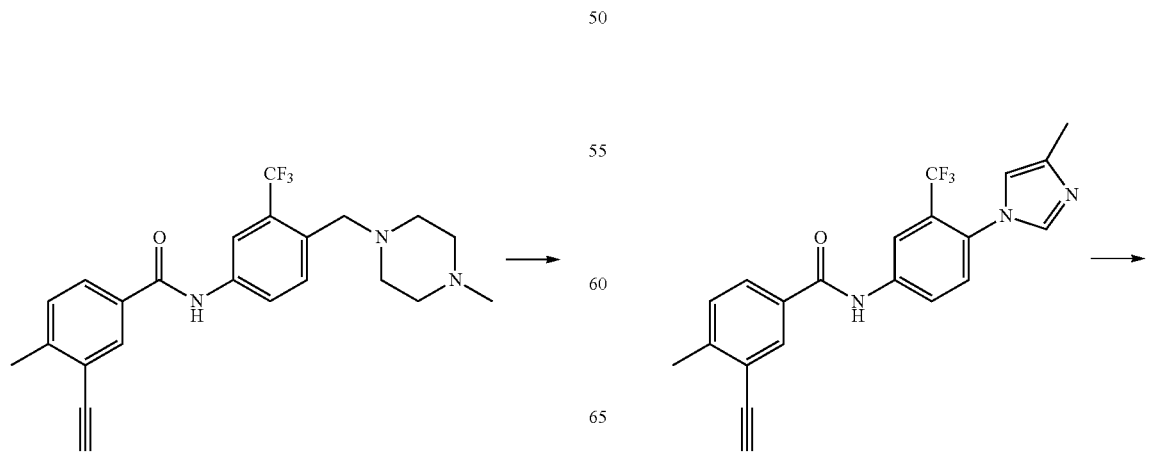

321

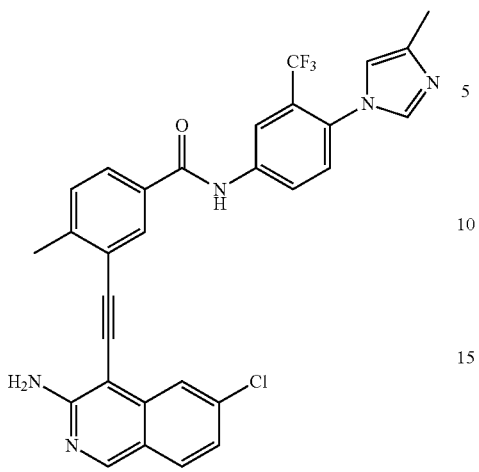

¹H NMR (500 MHz, DMSO-d₆) δ 10.73 (s, 1H), 8.93 (s, 1H), 8.40 (d, J=2.0 Hz, 1H), 8.30 (s, 1H), 8.15 (s, 1H), 7.96 (d, J=8.6 Hz, 1H), 7.89 (q, J=1.3, 0.7 Hz, 2H), 7.73 (s, 1H), 7.54 (d, J=8.1 Hz, 1H), 7.49 (s, 1H), 7.28 (dd, J=8.6, 2.0 Hz, 1H), 6.93 (d, J=22.1 Hz, 1H), 6.79 (s, 2H), 2.65 (s, 3H), 2.17 (s, 3H); ¹³C NMR (126 MHz, DMSO) δ 165.82, 162.76, 158.57, 153.26, 151.29, 143.66, 141.74, 138.75, 138.43, 137.41, 132.46, 131.66, 131.50, 131.20, 130.34, 128.07, 125.19, 123.59, 123.51, 121.32, 120.68, 115.35, 114.71, 112.14, 108.27, 103.70, 98.06, 88.71, 21.31, 14.07.

322

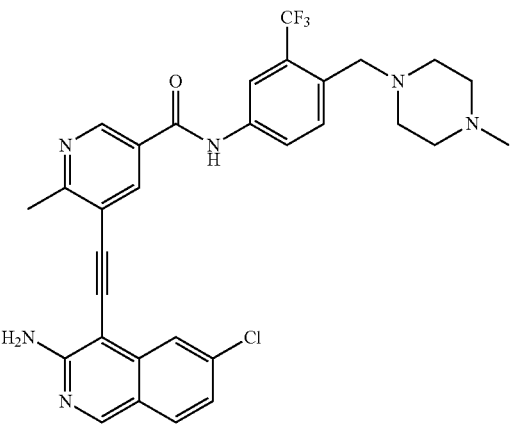

¹H NMR (500 MHz, DMSO-d₆) δ 10.71 (s, 1H), 8.95 (d, J=2.3 Hz, 1H), 8.94 (s, 1H), 8.71 (d, J=2.3 Hz, 1H), 8.19 (d, J=2.2 Hz, 1H), 8.04 (dd, J=8.5, 2.2 Hz, 1H), 7.96 (d, J=8.6 Hz, 1H), 7.87 (d, J=2.0 Hz, 1H), 7.72 (d, J=8.5 Hz, 1H), 7.29 (dd, J=8.6, 2.0 Hz, 1H), 6.92 (s, 2H), 3.56 (s, 2H), 2.84 (s, 3H), 2.38 (s, 8H), 2.17 (s, 3H); ¹³C NMR (126 MHz, DMSO) δ 164.32, 162.10, 158.88, 153.71, 147.25, 138.80, 138.65, 138.39, 137.55, 132.83, 131.81, 131.70, 128.17, 127.81, 125.85, 123.97, 123.55, 121.28, 120.62, 119.14, 117.69, 96.27, 90.91, 88.11, 57.88, 55.13, 53.06, 46.07, 24.37.

Example 83: 5-((3-amino-6-chloroisoquinolin-4-yl)ethynyl)-6-methyl-N-(4-((4-methylpiperazin-1-yl)methyl)-3-(trifluoromethyl)phenyl)nicotinamide (HSN387)

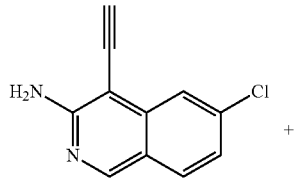

+

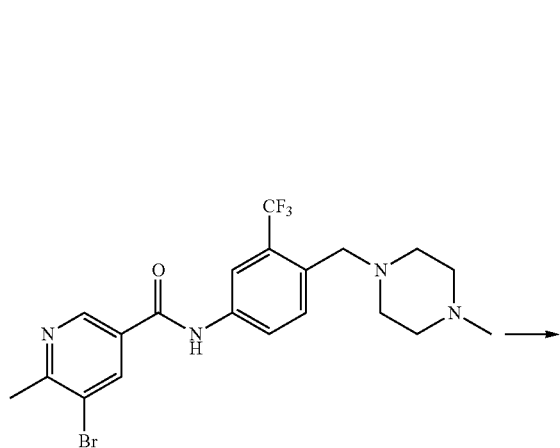

Example 84: 3-((3-amino-6-chloroisoquinolin-4-yl)ethynyl)-N-(3,5-dichloro-4-(2-(dimethylamino)ethoxy)phenyl)-4-methylbenzamide (HSN391)

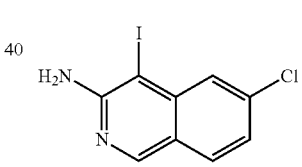

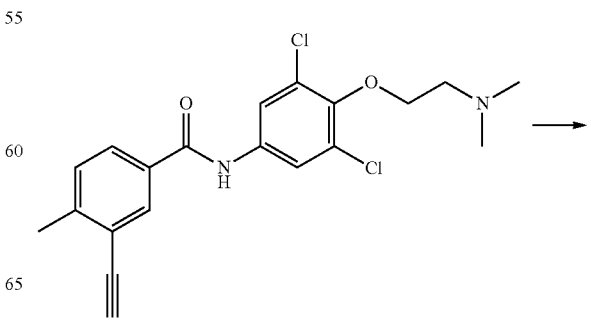

-continued

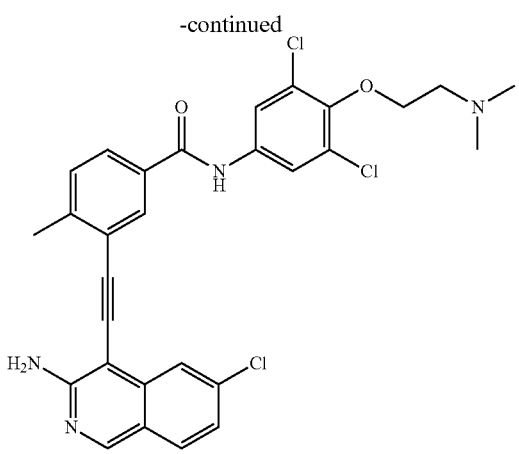

¹H NMR (500 MHz, DMSO-d₆) δ 10.47 (s, 1H), 8.92 (s, 1H), 8.34 (d, J=1.9 Hz, 1H), 7.96 (d, J=8.7 Hz, 1H), 7.94 (s, 2H), 7.88 (d, J=1.9 Hz, 1H), 7.84 (dd, J=8.0, 2.0 Hz, 1H), 7.52 (d, J=8.1 Hz, 1H), 7.28 (dd, J=8.6, 2.0 Hz, 1H), 6.79 (s, 2H), 4.02 (t, J=5.9 Hz, 2H), 2.68 (t, J=5.9 Hz, 2H), 2.63 (s, 3H), 2.23 (s, 6H); ¹³C NMR (126 MHz, DMSO) δ 165.52, 158.57, 153.24, 147.01, 146.90, 143.45, 138.75, 137.40, 136.77, 132.60, 131.66, 131.46, 130.27, 128.63, 128.50, 128.02, 123.52, 121.33, 120.70, 113.72, 98.09, 88.73, 72.09, 58.71, 45.95, 21.29.

Example 85: 3-((3-amino-6-chloroisoquinolin-4-yl)ethynyl)-N-(6-(2-(dimethylamino)ethoxy)pyridin-3-yl)-4-methylbenzamide (HSN392)

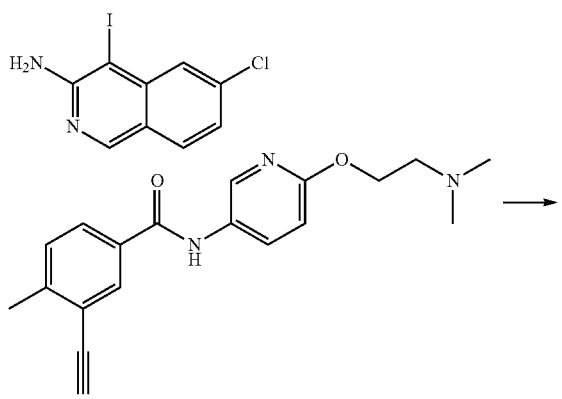

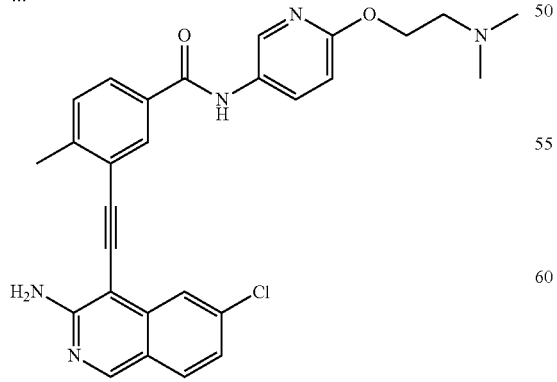

¹H NMR (500 MHz, DMSO-d₆) δ 10.32 (s, 1H), 8.92 (s, 1H), 8.50 (d, J=2.7 Hz, 1H), 8.36 (d, J=1.8 Hz, 1H), 8.03 (dd, J=8.9, 2.7 Hz, 1H), 7.96 (d, J=8.6 Hz, 1H), 7.89 (s, 1H), 7.86 (d, J=7.9 Hz, 1H), 7.50 (d, J=8.0 Hz, 1H), 7.28 (dd, J=8.6, 2.0 Hz, 1H), 6.82 (d, J=8.9 Hz, 1H), 6.79 (s, 2H), 4.30 (t, J=5.9 Hz, 2H), 2.63 (s, 3H), 2.59 (t, J=5.9 Hz, 2H), 2.19 (s, 6H); ¹³C NMR (126 MHz, DMSO) δ 165.24, 159.98, 158.55, 153.20, 143.06, 139.32, 138.75, 137.39, 133.09, 132.85, 131.66, 131.42, 130.36, 130.18, 127.96, 123.50, 121.34, 120.68, 110.71, 98.21, 88.80, 88.55, 63.90, 58.13, 45.98, 21.27.

Example 86: 3-((3-amino-6,7-dichloroisoquinolin-4-yl)ethynyl)-4-methyl-N-(4-((4-methylpiperazin-1-yl)methyl)-3-(trifluoromethyl)phenyl)benzamide (HSN393)

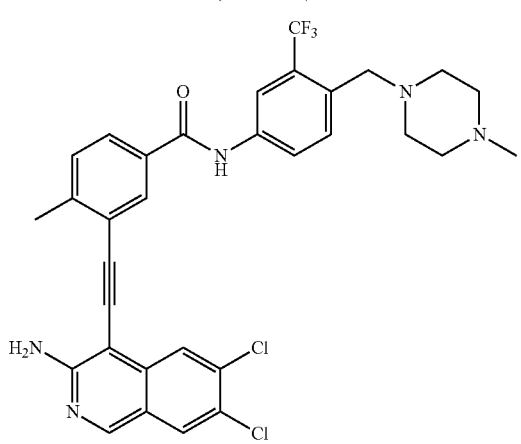

¹H NMR (500 MHz, DMSO-d₆) δ 10.53 (s, 1H), 8.91 (s, 1H), 8.38 (d, J=1.9 Hz, 1H), 8.27 (s, 1H), 8.20 (d, J=2.2 Hz, 1H), 8.05 (d, J=7.1 Hz, 2H), 7.88 (dd, J=7.9, 2.0 Hz, 1H), 7.70 (d, J=8.5 Hz, 1H), 7.51 (d, J=8.1 Hz, 1H), 6.91 (s, 2H), 3.55 (s, 2H), 2.63 (s, 3H), 2.37 (s, 8H), 2.15 (s, 3H); ¹³C NMR (126 MHz, DMSO) δ 165.55, 158.60, 152.47, 143.36, 138.68, 137.06, 135.39, 132.84, 132.50, 131.72, 131.59, 130.67, 130.21, 128.14, 127.75, 124.96, 124.01, 123.94, 123.34, 121.29, 117.68, 98.38, 88.45, 88.16, 57.91, 55.17, 53.11, 46.13, 21.27.

Example 87: 3-((3-amino-6-fluoroisoquinolin-4-yl)ethynyl)-4-methyl-N-(4-((4-methylpiperazin-1-yl)methyl)-3-(trifluoromethyl)phenyl)benzamide (HSN394)

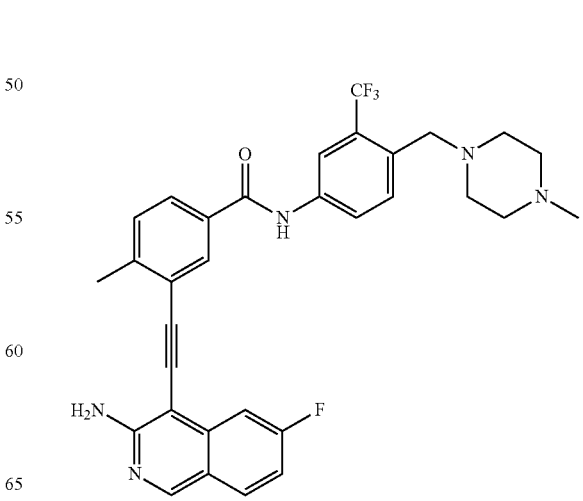

¹H NMR (500 MHz, Methanol-d₄) δ 8.93 (s, 1H), 8.37 (d, J=1.9 Hz, 1H), 8.25 (d, J=2.2 Hz, 1H), 8.10-8.02 (m, 2H), 7.95 (dd, J=8.0, 2.0 Hz, 1H), 7.81 (d, J=8.4 Hz, 1H), 7.66 (dd, J=10.6, 2.4 Hz, 1H), 7.57 (d, J=8.0 Hz, 1H), 7.19 (td, J=8.8, 2.5 Hz, 1H), 3.69 (s, 2H), 2.74 (s, 3H), 2.56 (s, 8H), 2.35 (s, 3H); ¹³C NMR (126 MHz, MeOD) δ 165.94, 163.90, 157.90, 152.39, 143.40, 139.79, 138.30, 132.68, 132.55, 132.45, 132.37, 131.40, 130.88, 129.95, 127.77, 123.71, 123.45, 117.68, 113.24, 113.04, 109.71, 106.14, 105.96, 98.05, 88.03, 57.65, 54.78, 52.42, 44.91, 20.48.

Example 87: 3-((2-amino-6,7-dimethoxyquinazolin-4-yl)ethynyl)-N-(3,5-dichloro-4-(2-(dimethylamino)ethoxy)phenyl)-4-methylbenzamide (HSN400)

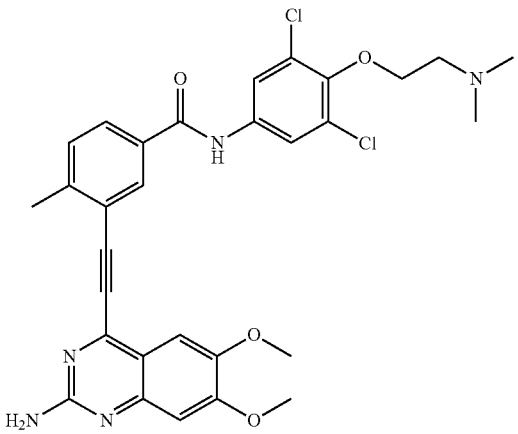

¹H NMR (500 MHz, DMSO-d₆) δ 10.49 (s, 1H), 8.29 (s, 1H), 7.97 (dd, J=8.1, 1.9 Hz, 1H), 7.94 (s, 2H), 7.58 (d, J=8.1 Hz, 1H), 7.33 (s, 1H), 6.88 (s, 1H), 6.58 (s, 2H), 4.03 (t, J=5.9 Hz, 2H), 3.90 (d, J=7.5 Hz, 6H), 2.70 (t, J=5.9 Hz, 2H), 2.67 (s, 3H), 2.24 (s, 6H); ¹³C NMR (126 MHz, DMSO) δ 164.81, 160.60, 156.82, 150.85, 149.47, 147.46, 147.06, 145.21, 136.68, 132.59, 132.09, 130.80, 130.00, 128.50, 121.33, 120.74, 115.04, 104.91, 103.95, 93.22, 90.54, 71.98, 58.65, 56.41, 55.95, 45.88, 21.10.

Example 88: 3-((2-amino-6,7-dimethoxyquinazolin-4-yl)ethynyl)-N-(6-(2-(dimethylamino)ethoxy)pyridin-3-yl)-4-methylbenzamide (HSN401)

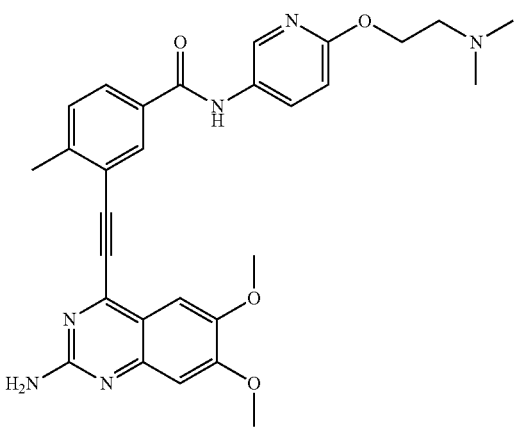

¹H NMR (500 MHz, DMSO-d₆) δ 10.37 (s, 1H), 8.50 (d, J=2.7 Hz, 1H), 8.31 (d, J=2.0 Hz, 1H), 8.04 (dd, J=8.9, 2.7 Hz, 1H), 7.99 (dd, J=8.0, 2.0 Hz, 1H), 7.57 (d, J=8.1 Hz, 1H), 7.34 (s, 1H), 6.88 (s, 1H), 6.83 (d, J=8.9 Hz, 1H), 6.59 (s, 2H), 4.31 (t, J=5.9 Hz, 2H), 3.90 (s, 3H), 3.89 (s, 3H), 2.68 (s, 3H), 2.60 (s, 2H), 2.20 (s, 6H); ¹³C NMR (126 MHz, DMSO) δ 164.54, 160.61, 160.02, 156.82, 150.84, 149.52, 147.46, 144.83, 139.33, 133.08, 132.86, 132.03, 130.73, 130.29, 129.97, 121.24, 115.04, 110.71, 104.92, 103.96, 93.38, 90.46, 63.86, 58.09, 56.41, 55.96, 45.94, 21.08.

Example 89: 3-((2-amino-9-methyl-9H-purin-6-yl)ethynyl)-4-methyl-N-(4-((4-methylpiperazin-1-yl)methyl)-3-(trifluoromethyl)phenyl)benzamide (HSN403)

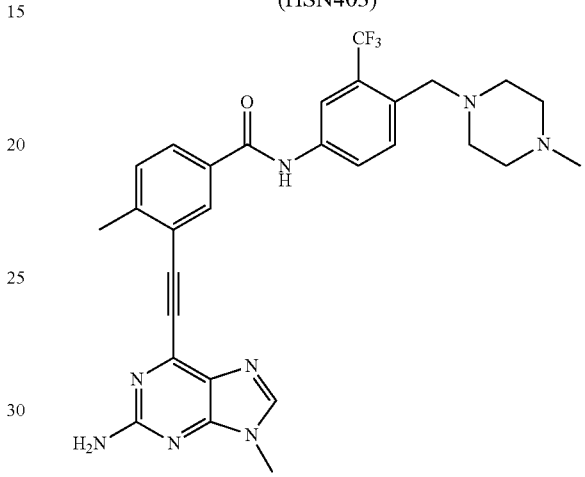

¹H NMR (500 MHz, Methanol-d₄) δ 8.20 (s, 1H), 8.12 (s, 2H), 7.94 (d, J=7.6 Hz, 1H), 7.88 (d, J=9.2 Hz, 1H), 7.73 (d, J=8.4 Hz, 1H), 7.41 (d, J=8.1 Hz, 1H), 3.71 (s, 3H), 3.64 (s, 2H), 2.73-2.43 (11H), 2.34 (s, 3H); ¹³C NMR (126 MHz, MeOD) δ 165.96, 160.53, 145.12, 140.63, 137.87, 132.48, 132.25, 131.53, 131.14, 129.77, 128.84, 128.53, 127.15, 125.42, 123.53, 121.30, 117.67, 117.62, 94.14, 87.90, 57.44, 54.52, 52.07, 44.38, 28.40, 19.54.

Example 90: 4-((3-amino-6-chloroisoquinolin-4-yl)ethynyl)-5-methyl-N-(4-((4-methylpiperazin-1-yl)methyl)-3-(trifluoromethyl)phenyl)picolinamide (HSN404)

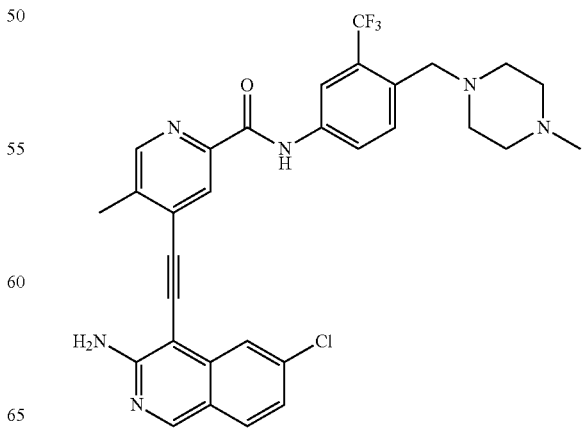

¹H NMR (500 MHz, DMSO-d₆) δ 10.94 (s, 1H), 8.96 (s, 1H), 8.69 (s, 1H), 8.57 (s, 1H), 8.38 (d, J=2.2 Hz, 1H), 8.16 (d, J=7.9 Hz, 1H), 7.97 (d, J=8.6 Hz, 1H), 7.87 (s, 1H), 7.69 (d, J=8.5 Hz, 1H), 7.29 (dd, J=8.6, 2.0 Hz, 1H), 7.11 (s, 2H), 3.55 (s, 2H), 2.65 (s, 3H), 2.38 (s, 8H), 2.16 (s, 3H); ¹³C NMR (126 MHz, DMSO) δ 163.27, 159.25, 154.54, 149.38, 148.11, 139.01, 138.02, 137.74, 137.12, 132.94, 132.73, 131.78, 131.60, 124.35, 124.17, 123.57, 121.26, 120.59, 117.99, 96.18, 94.13, 87.32, 57.90, 55.17, 53.11, 46.12, 18.19.

Example 91: 3-((6,7-dimethoxyquinazolin-4-yl)ethynyl)-4-methyl-N-(4-((4-methylpiperazin-1-yl)methyl)-3-(trifluoromethyl)phenyl)benzamide (HSN405)

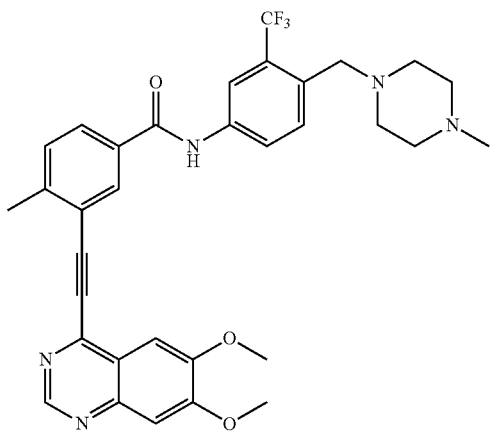

¹H NMR (500 MHz, DMSO-d₆) δ 10.56 (s, 1H), 9.09 (s, 1H), 8.38 (s, 1H), 8.20 (s, 1H), 8.03 (dd, J=16.2, 8.2 Hz, 2H), 7.70 (d, J=8.5 Hz, 1H), 7.59 (d, J=8.0 Hz, 1H), 7.56 (s, 1H), 7.40 (s, 1H), 4.02 (s, 3H), 4.00 (s, 3H), 3.55 (s, 2H), 2.71 (s, 3H), 2.39 (bs, 8H), 2.15 (s, 3H); ¹³C NMR (126 MHz, DMSO) δ 164.82, 156.92, 153.87, 151.69, 148.28, 147.81, 145.23, 138.58, 132.86, 132.61, 132.23, 131.73, 130.80, 130.29, 123.96, 121.18, 121.07, 117.70, 107.19, 103.15, 95.41, 90.31, 57.90, 56.40, 55.16, 53.10, 46.12, 21.12.

Example 92: 3-((2-amino-9H-purin-6-yl)ethynyl)-4-methyl-N-(4-((4-methylpiperazin-1-yl)methyl)-3-(trifluoromethyl)phenyl)benzamide (HSN408)

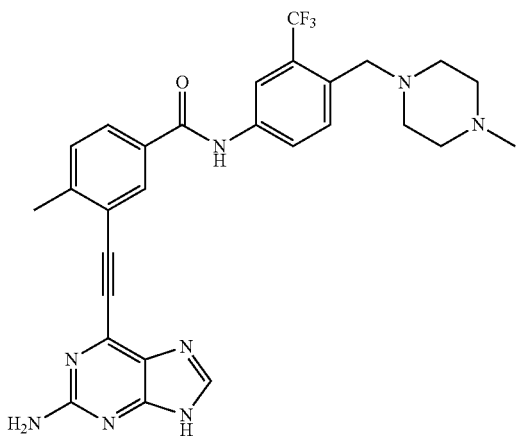

¹H NMR (500 MHz, DMSO-d₆) δ 10.58 (s, 1H), 8.25 (s, 1H), 8.21 (d, J=2.2 Hz, 1H), 8.11 (s, 1H), 8.06 (d, J=8.5 Hz, 1H), 7.98 (dd, J=8.0, 1.9 Hz, 1H), 7.70 (d, J=8.5 Hz, 1H), 7.55 (d, J=8.1 Hz, 1H), 6.52 (s, 2H), 3.56 (s, 2H), 2.60 (s, 3H), 2.38 (s, 8H), 2.17 (s, 3H). ¹³C NMR (126 MHz, DMSO) δ 164.93, 160.92, 155.15, 145.09, 142.20, 140.44, 138.62, 132.73, 132.55, 131.71, 131.57, 130.64, 129.74, 128.07, 127.74, 125.89, 124.01, 121.53, 117.74, 92.44, 90.21, 57.88, 55.12, 53.03, 46.04, 20.84.

Example 93: 3-((2-amino-6,7-dimethoxyquinazolin-4-yl)ethynyl)-N-(3-chloro-4-(2-(dimethylamino)ethoxy)phenyl)-4-methylbenzamide (HSN409)

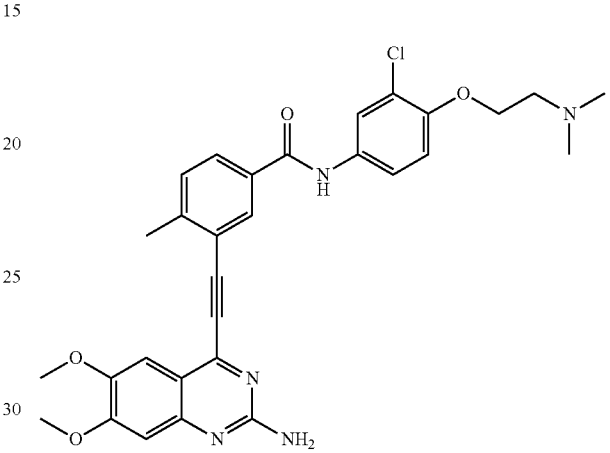

¹H NMR (500 MHz, DMSO-d₆) δ 10.32 (s, 1H), 8.29 (d, J=2.0 Hz, 1H), 7.98 (dd, J=8.0, 1.9 Hz, 1H), 7.94 (d, J=2.5 Hz, 1H), 7.66 (dd, J=9.0, 2.6 Hz, 1H), 7.56 (d, J=8.1 Hz, 1H), 7.34 (s, 1H), 7.17 (d, J=9.0 Hz, 1H), 6.88 (s, 1H), 6.59 (s, 2H), 4.12 (t, J=5.7 Hz, 2H), 3.90 (s, 3H), 3.89 (s, 3H), 2.67 (s, 5H), 2.25 (s, 6H); ¹³C NMR (126 MHz, DMSO) δ 164.36, 160.60, 156.81, 150.83, 150.60, 149.52, 147.45, 144.77, 133.25, 133.06, 132.02, 130.69, 129.94, 122.36, 121.30, 121.22, 120.59, 115.04, 114.40, 104.91, 103.96, 93.40, 90.44, 67.84, 57.93, 56.40, 55.95, 46.10, 21.07.

Example 93: 3-((3-amino-6-chloroisoquinolin-4-yl)ethynyl)-4-methyl-N-(4-((4-methylpiperazin-1-yl)methyl)phenyl)benzamide (HSN415)

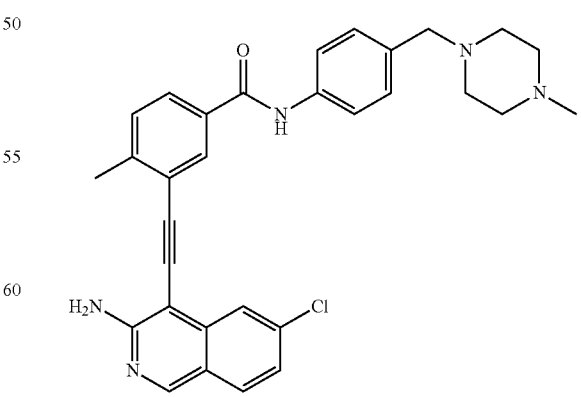

¹H NMR (500 MHz, DMSO-d₆) δ 10.26 (s, 1H), 8.92 (s, 1H), 8.35 (s, 1H), 7.96 (d, J=8.6 Hz, 1H), 7.89 (d, J=2.0 Hz,

1H), 7.85 (dd, J=8.0, 2.0 Hz, 1H), 7.72 (d, J=8.4 Hz, 2H), 7.49 (d, J=8.0 Hz, 1H), 7.28 (dd, J=8.6, 2.0 Hz, 1H), 7.26 (d, J=8.2 Hz, 2H), 6.78 (s, 2H), 3.43 (s, 2H), 2.63 (s, 3H), 2.42 (bs, 8H), 2.23 (s, 3H). $^{13}$C NMR (126 MHz, DMSO) δ 165.21, 158.53, 153.18, 142.89, 138.75, 138.46, 137.38, 133.34, 131.66, 131.44, 130.12, 129.62, 128.01, 123.50, 123.37, 121.34, 120.68, 120.63, 98.27, 88.83, 88.49, 61.93, 54.85, 52.42, 45.44, 21.25.

Example 94: 6-((3-amino-6-chloroisoquinolin-4-yl)ethynyl)-5-methyl-N-(4-((4-methylpiperazin-1-yl)methyl)-3-(trifluoromethyl)phenyl)picolinamide (HSN416)

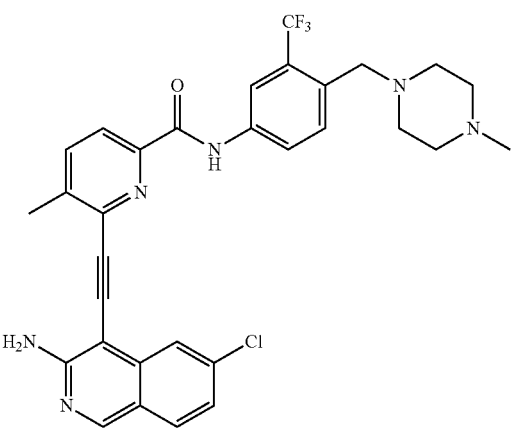

$^{1}$H NMR (500 MHz, DMSO-d$_6$) δ 10.85 (s, 1H), 8.98 (s, 1H), 8.35 (d, J=2.2 Hz, 1H), 8.17 (d, J=8.5 Hz, 1H), 8.06-8.00 (m, 2H), 7.99 (d, J=8.6 Hz, 1H), 7.94 (s, 1H), 7.72 (d, J=8.6 Hz, 1H), 7.31 (dd, J=8.6, 2.0 Hz, 1H), 6.88 (s, 2H), 3.57 (s, 2H), 2.66 (s, 3H), 2.38 (s, 8H), 2.16 (s, 3H); $^{13}$C NMR (126 MHz, DMSO) δ 163.02, 159.17, 154.71, 148.08, 141.92, 139.53, 139.39, 138.90, 137.89, 137.71, 132.82, 131.75, 131.67, 124.16, 123.76, 121.94, 121.42, 120.71, 117.96, 97.81, 88.52, 87.59, 57.90, 55.13, 53.07, 46.07, 19.94.

Example 95: 3-((6-amino-1H-pyrazolo[3,4-d]pyrimidin-4-yl)ethynyl)-4-methyl-N-(4-((4-methylpiperazin-1-yl)methyl)-3-(trifluoromethyl)phenyl)benzamide (HSN422)

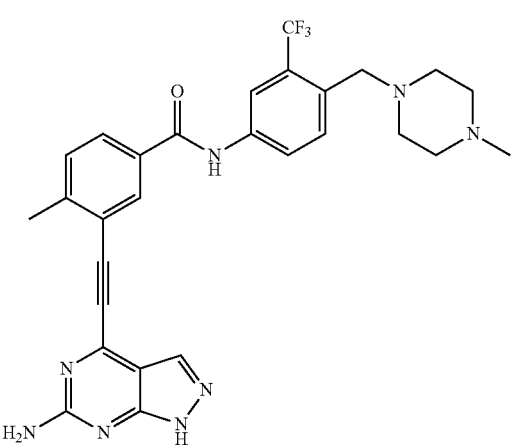

$^{1}$H NMR (500 MHz, DMSO-d$_6$) δ 10.55 (s, 1H), 8.31 (d, J=2.0 Hz, 1H), 8.20 (d, J=2.2 Hz, 1H), 8.07 (d, J=1.2 Hz, 1H), 8.05 (dd, J=8.5, 2.3 Hz, 1H), 7.99 (dd, J=8.0, 2.0 Hz, 1H), 7.70 (d, J=8.6 Hz, 1H), 7.57 (d, J=8.1 Hz, 1H), 6.91 (s, 2H), 3.55 (s, 2H), 2.61 (s, 3H), 2.38 (s, 8H), 2.15 (s, 3H); $^{13}$C NMR (126 MHz, DMSO) δ 164.93, 162.69, 157.33, 145.26, 138.57, 133.48, 132.88, 132.64, 132.14, 131.73, 130.69, 130.15, 125.89, 124.00, 120.96, 109.69, 108.67, 92.11, 90.25, 57.92, 55.19, 53.15, 46.17, 20.90.

Example 96: 3-((6-amino-1-methyl-1H-pyrazolo[3,4-d]pyrimidin-4-yl)ethynyl)-4-methyl-N-(4-((4-methylpiperazin-1-yl)methyl)-3-(trifluoromethyl)phenyl)benzamide (HSN423)

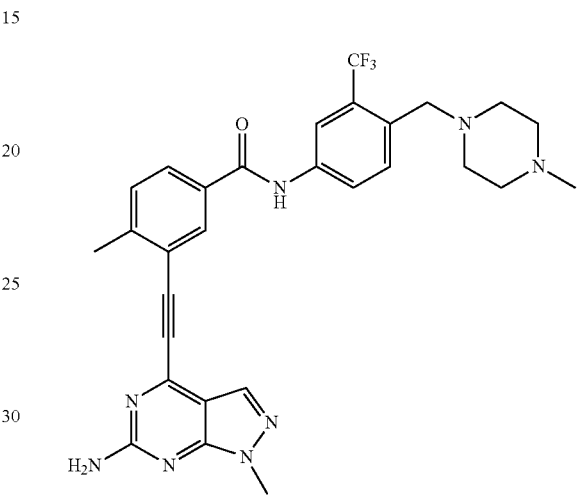

$^{1}$H NMR (500 MHz, DMSO-d$_6$) δ 10.57 (s, 1H), 8.32 (d, J=2.0 Hz, 1H), 8.21 (d, J=2.2 Hz, 1H), 8.09 (s, 1H), 8.05 (dd, J=8.5, 2.2 Hz, 1H), 8.00 (dd, J=8.0, 2.0 Hz, 1H), 7.70 (d, J=8.5 Hz, 1H), 7.57 (d, J=8.1 Hz, 1H), 7.06 (s, 2H), 3.80 (s, 3H), 3.56 (s, 2H), 2.60 (s, 3H), 2.40 (s, 8H), 2.20 (s, 3H); $^{13}$C NMR (126 MHz, DMSO) δ 164.92, 162.68, 155.49, 145.39, 145.30, 138.61, 132.87, 132.58, 132.23, 131.74, 130.69, 130.21, 127.76, 125.88, 124.00, 120.86, 117.74, 109.03, 92.39, 90.05, 57.83, 55.00, 52.83, 45.83, 33.58, 20.90.

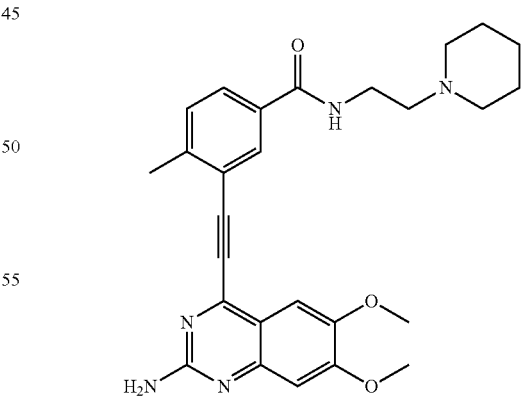

Example 97: 3-((2-amino-6,7-dimethoxyquinazolin-4-yl)ethynyl)-4-methyl-N-(2-(piperidin-1-yl)ethyl)benzamide (HSN432)

$^{1}$H NMR (500 MHz, Chloroform-d) δ 8.79 (s, 1H), 7.98 (d, J=1.9 Hz, 1H), 7.82 (dd, J=8.9, 5.6 Hz, 1H), 7.65 (dd, J=7.9, 2.0 Hz, 1H), 7.61 (dd, J=10.4, 2.5 Hz, 1H), 7.37 (d, J=8.0 Hz, 1H), 7.07 (td, J=8.6, 2.4 Hz, 1H), 6.52 (s, 1H), 5.25 (bs, 2H), 3.61 (q, J=5.9 Hz, 2H), 3.18-3.03 (m, 8H), 2.81 (t, J=6.1 Hz, 2H), 2.64 (s, 3H); $^{13}$C NMR (126 MHz, CDCl$_3$) δ 166.75, 156.68, 151.74, 143.25, 132.13, 131.61, 131.53, 130.30, 130.06, 126.71, 123.56, 120.38, 114.22, 114.01, 107.15, 106.96, 98.35, 87.81, 55.53, 50.81, 37.01, 29.71, 21.30.

Example 98: 3-((2-amino-6,7-dimethoxyquinazolin-4-yl)ethynyl)-4-methyl-N-(2-(piperidin-1-yl)ethyl)benzamide (HSN433)

$^1$H NMR (500 MHz, DMSO-d$_6$) δ 8.50 (t, J=5.6 Hz, 1H), 8.15 (d, J=1.9 Hz, 1H), 7.86 (dd, J=8.0, 1.9 Hz, 1H), 7.49 (d, J=8.1 Hz, 1H), 7.32 (s, 1H), 6.87 (s, 1H), 6.58 (s, 2H), 3.90 (s, 3H), 3.88 (s, 3H), 3.36 (q, J=6.6 Hz, 2H), 2.63 (s, 3H), 2.42 (t, J=7.1 Hz, 2H), 2.36 (bs, 4H), 1.47 (p, J=5.6 Hz, 4H), 1.36 (bs, 2H); $^{13}$C NMR (126 MHz, DMSO) δ 165.27, 160.60, 156.79, 150.80, 149.57, 147.43, 144.10, 133.07, 131.65, 130.54, 129.48, 121.07, 115.01, 104.91, 103.96, 93.56, 90.21, 58.14, 56.40, 55.93, 54.57, 37.52, 26.07, 24.52, 20.97.

Example 99: 3-((6,7-dimethoxyquinazolin-4-yl)ethynyl)-4-methyl-N-(2-(piperidin-1-yl)ethyl)benzamide (HSN434)

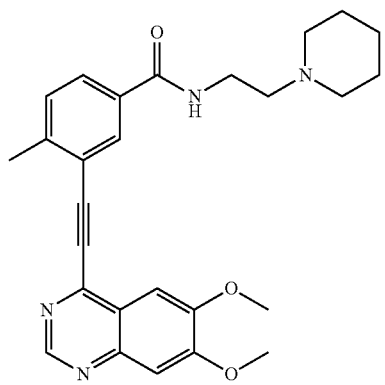 [SMILES: COc1cc2ncnc(C#Cc3cc(C(=O)NCCN4CCCCC4)ccc3C)c2cc1OC]

$^1$H NMR (500 MHz, Chloroform-d) δ 9.14 (s, 1H), 8.16 (d, J=1.9 Hz, 1H), 7.81 (dd, J=8.0, 1.9 Hz, 1H), 7.57 (s, 1H), 7.38 (d, J=8.0 Hz, 1H), 7.33 (s, 1H), 7.25 (s, 1H), 4.08 (s, 3H), 4.08 (s, 3H), 3.59 (q, J=5.4 Hz, 2H), 2.70 (s, 3H), 2.65 (t, J=5.9 Hz, 2H), 2.54 (s, 4H), 1.67-1.63 (m, 4H), 1.48 (bs, 2H); $^{13}$C NMR (126 MHz, CDCl$_3$) δ 166.27, 156.49, 153.78, 151.27, 148.58, 148.39, 144.26, 132.64, 131.68, 130.08, 128.56, 121.63, 121.53, 106.82, 103.20, 95.62, 89.89, 57.22, 56.58, 56.37, 54.35, 36.31, 25.54, 24.04, 21.09.

Example 100: 3-((8-amino-1,7-naphthyridin-5-yl)ethynyl)-N-(3-fluoro-4-(4-methylpiperazin-1-yl)phenyl)-4-methylbenzamide (HSN445)

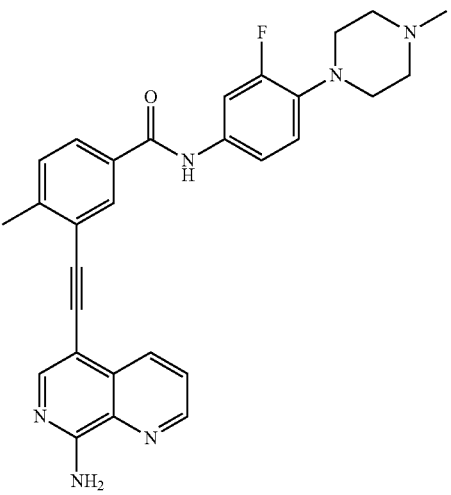

$^1$H NMR (500 MHz, DMSO-d$_6$) δ 10.29 (s, 1H), 8.88 (dd, J=4.2, 1.6 Hz, 1H), 8.46 (dd, J=8.4, 1.6 Hz, 1H), 8.24 (s, 1H), 8.16 (d, J=2.0 Hz, 1H), 7.88-7.82 (m, 2H), 7.69 (dd, J=15.1, 2.4 Hz, 1H), 7.52 (s, 2H), 7.50-7.45 (m, 2H), 7.06-6.99 (m, 1H), 2.98 (s, 4H), 2.59 (s, 3H), 2.48 (s, 4H, merged with DMSO peak), 2.23 (s, 3H); $^{13}$C NMR (126 MHz, DMSO) δ 164.82, 158.56, 153.76, 149.71, 148.18, 143.13, 136.19, 134.41, 133.14, 132.97, 132.53, 131.37, 130.69, 130.28, 127.94, 127.07, 123.37, 119.55, 116.79, 109.07, 102.13, 91.80, 90.46, 55.12, 50.58, 46.15, 21.17.

Example 101: 3-((2-amino-6,7-dimethoxyquinazolin-4-yl)ethynyl)-N-(3-fluoro-4-(4-methylpiperazin-1-yl)phenyl)-4-methylbenzamide (HSN446)

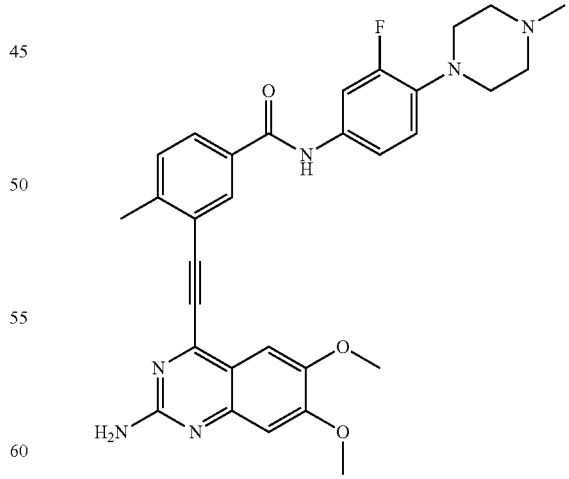

$^1$H NMR (500 MHz, DMSO-d$_6$) δ 10.34 (s, 1H), 8.29 (d, J=2.0 Hz, 1H), 7.98 (dd, J=8.0, 2.0 Hz, 1H), 7.70 (dd, J=15.1, 2.4 Hz, 1H), 7.57 (d, J=8.1 Hz, 1H), 7.46 (dd, J=8.7, 1.5 Hz, 1H), 7.34 (s, 1H), 7.07-6.98 (m, 1H), 6.88 (s, 1H), 6.59 (s, 2H), 3.91 (s, 3H), 3.89 (s, 3H), 2.97 (s, 4H), 2.67 (s,

3H), 2.46 (s, 4H), 2.21 (s, 3H); ¹³C NMR (126 MHz, DMSO) δ 164.36, 160.61, 156.81, 153.74, 150.83, 149.52, 147.46, 144.75, 136.25, 133.13, 132.01, 130.70, 129.97, 121.20, 119.57, 116.74, 115.04, 109.03, 108.82, 104.92, 103.97, 93.41, 90.43, 56.41, 55.96, 55.18, 50.66, 46.26, 21.07.

Example 102: 3-((2-amino-6,7-dimethoxyquinazolin-4-yl)ethynyl)-N-(4-(2-(dimethylamino)ethoxy)phenyl)-4-methylbenzamide (HSN447)

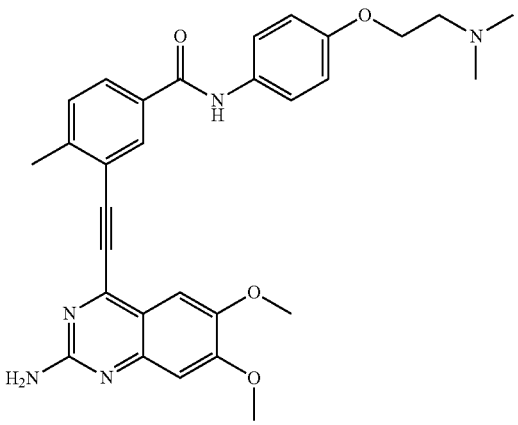

¹H NMR (500 MHz, DMSO-d₆) δ 10.21 (s, 1H), 8.29 (d, J=1.9 Hz, 1H), 7.98 (dd, J=8.0, 2.0 Hz, 1H), 7.67 (d, J=9.1 Hz, 2H), 7.56 (d, J=8.1 Hz, 1H), 7.35 (s, 1H), 6.93 (d, J=9.1 Hz, 2H), 6.88 (s, 1H), 6.59 (s, 2H), 4.02 (t, J=5.9 Hz, 2H), 3.91 (s, 3H), 3.89 (s, 3H), 2.67 (s, 3H), 2.60 (t, J=5.8 Hz, 2H), 2.20 (s, 6H); ¹³C NMR (126 MHz, DMSO) δ 164.16, 160.61, 156.81, 155.32, 150.83, 149.56, 147.45, 144.50, 133.44, 132.55, 132.00, 130.64, 129.92, 122.38, 121.15, 115.04, 114.84, 104.92, 103.98, 93.52, 90.37, 66.42, 58.22, 56.41, 55.96, 46.06, 21.04.

Example 103: 5-((8-amino-1,7-naphthyridin-5-yl)ethynyl)-6-methyl-N-(4-((4-methylpiperazin-1-yl)methyl)-3-(trifluoromethyl)phenyl)nicotinamide (HSN459)

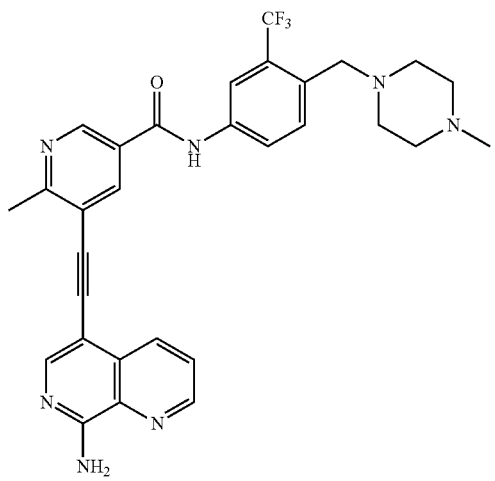

¹H NMR (500 MHz, DMSO-d₆) δ 10.68 (s, 1H), 8.94 (d, J=2.3 Hz, 1H), 8.88 (dd, J=4.2, 1.6 Hz, 1H), 8.51 (d, J=2.2 Hz, 1H), 8.47 (dd, J=8.3, 1.6 Hz, 1H), 8.27 (s, 1H), 8.20 (d, J=2.2 Hz, 1H), 8.04 (dd, J=8.5, 2.2 Hz, 1H), 7.72 (d, J=8.5 Hz, 1H), 7.60 (s, 2H), 3.56 (s, 2H), 2.81 (s, 3H), 2.39 (s, 8H), 2.19 (s, 3H); ¹³C NMR (126 MHz, DMSO) δ 164.07, 162.31, 158.81, 149.79, 148.63, 147.41, 138.39, 137.88, 133.13, 132.79, 132.48, 131.80, 131.35, 127.97, 127.14, 124.00, 118.93, 117.74, 101.58, 92.83, 90.00, 57.84, 55.05, 52.93, 45.94, 24.30.

Example 104: 5-((1-aminoisoquinolin-4-yl)ethynyl)-6-methyl-N-(4-((4-methylpiperazin-1-yl)methyl)-3-(trifluoromethyl)phenyl)nicotinamide (HSN461)

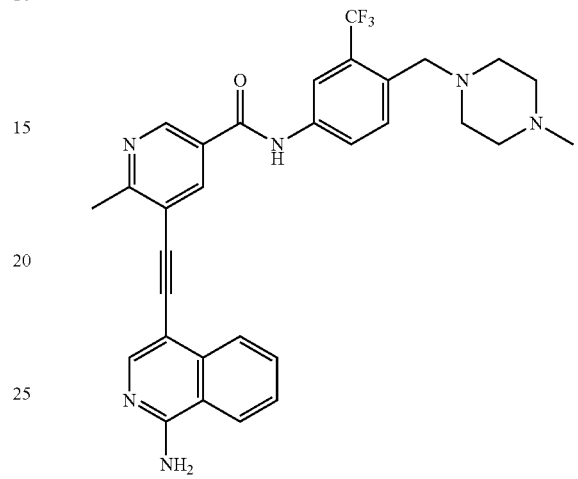

¹H NMR (500 MHz, DMSO-d₆) δ 10.66 (s, 1H), 8.93 (d, J=2.3 Hz, 1H), 8.48 (d, J=2.3 Hz, 1H), 8.29 (d, J=8.1 Hz, 1H), 8.22 (s, 1H), 8.20 (d, J=2.2 Hz, 1H), 8.11 (d, J=8.1 Hz, 1H), 8.04 (dd, J=8.4, 2.2 Hz, 1H), 7.81 (ddd, J=8.1, 6.9, 1.2 Hz, 1H), 7.72 (d, J=8.5 Hz, 1H), 7.58 (ddd, J=8.3, 6.9, 1.3 Hz, 1H), 7.45 (s, 2H), 3.56 (s, 2H), 2.81 (s, 3H), 2.37 (s, 8H), 2.14 (s, 3H); ¹³C NMR (126 MHz, DMSO) δ 164.08, 162.21, 158.42, 148.15, 147.27, 138.36, 137.64, 136.33, 132.87, 131.78, 131.71, 127.95, 126.86, 125.03, 124.74, 124.00, 119.15, 117.74, 116.71, 102.62, 94.26, 89.98, 57.91, 55.20, 53.18, 46.21, 24.30.

Example 105: 2-((8-amino-1,7-naphthyridin-5-yl)ethynyl)-5-methyl-N-(4-((4-methylpiperazin-1-yl)methyl)-3-(trifluoromethyl)phenyl)thiazole-4-carboxamide (HSN482)

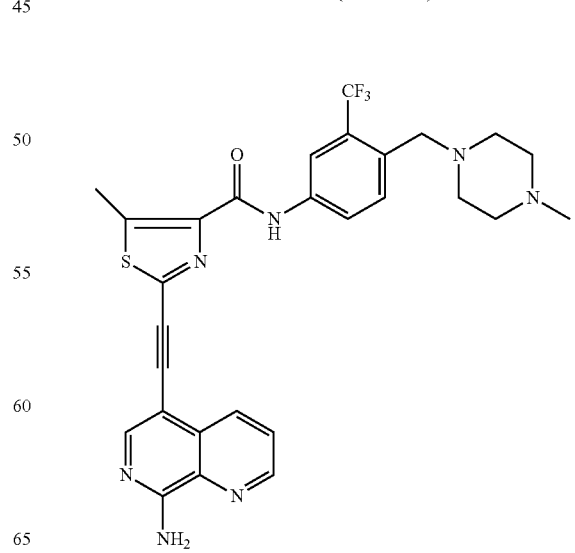

¹H NMR (500 MHz, Methanol-d₄) δ 8.85 (dd, J=4.3, 1.6 Hz, 1H), 8.41 (dd, J=8.3, 1.6 Hz, 1H), 8.19 (d, J=2.2 Hz, 1H), 8.16 (s, 1H), 7.89 (dd, J=8.5, 2.2 Hz, 1H), 7.77 (dd, J=8.4, 4.2 Hz, 1H), 7.72 (d, J=8.5 Hz, 1H), 3.64 (s, 2H), 2.85 (s, 3H), 2.54 (s, 8H), 2.32 (s, 3H); ¹³C NMR (126 MHz, MeOD) δ 160.63, 158.73, 149.46, 147.71, 143.98, 143.00, 137.35, 132.56, 132.43, 131.13, 128.57, 126.49, 123.10, 117.26, 101.20, 90.03, 85.49, 57.45, 54.54, 52.12, 44.43, 11.54.

Example 106: 4-((1-aminoisoquinolin-4-yl)ethynyl)-3-methyl-N-(4-((4-methylpiperazin-1-yl)methyl)-3-(trifluoromethyl)phenyl)benzamide (HSN485)

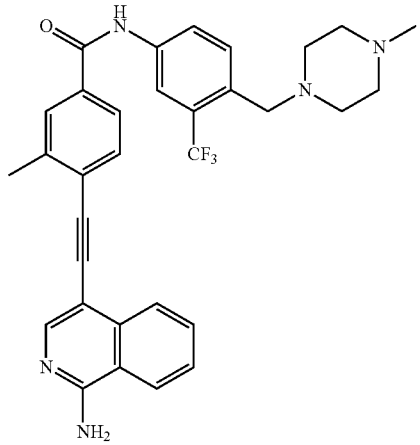

¹H NMR (500 MHz, Methanol-d₄) δ 8.18 (t, J=8.7 Hz, 2H), 8.11 (d, J=21.9 Hz, 2H), 7.93 (d, J=8.5 Hz, 1H), 7.88 (s, 1H), 7.80 (t, J=8.4 Hz, 2H), 7.75 (d, J=8.5 Hz, 1H), 7.65 (d, J=8.0 Hz, 1H), 7.59 (t, J=7.8 Hz, 1H), 3.64 (s, 2H), 2.66 (s, 3H), 2.51 (s, 8H), 2.29 (s, 3H); ¹³C NMR (126 MHz, MeOD) δ 166.84, 157.63, 145.29, 139.48, 137.88, 136.44, 133.42, 132.59, 131.24, 131.15, 131.10, 128.31, 127.22, 126.52, 124.78, 124.69, 123.78, 123.57, 117.71, 116.91, 104.82, 92.18, 91.36, 57.51, 54.59, 52.29, 44.58, 19.87.

Example 107: 4-((3-amino-6-chloroisoquinolin-4-yl)ethynyl)-3-methyl-N-(4-((4-methylpiperazin-1-yl)methyl)-3-(trifluoromethyl)phenyl)benzamide (HSN486)

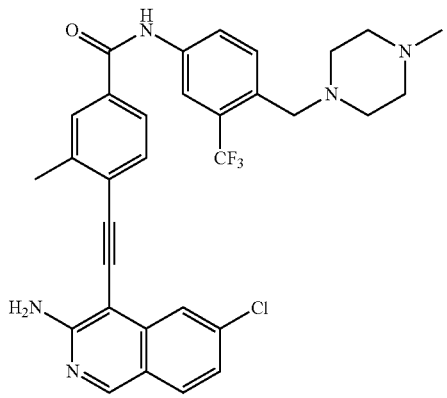

¹H NMR (500 MHz, Methanol-d₄) δ 8.79 (s, 1H), 8.14 (s, 1H), 7.95 (m, 2H), 7.90 (s, 1H), 7.85 (d, J=8.7 Hz, 1H), 7.81 (dd, J=8.0, 1.8 Hz, 1H), 7.76 (m, 2H), 7.25 (dd, J=8.7, 2.0 Hz, 1H), 3.67 (s, 2H), 2.69 (s, 3H), 2.61 (bs, 8H), 2.40 (s, 3H); ¹³C NMR (126 MHz, MeOD) δ 166.72, 157.47, 151.95, 139.46, 138.68, 138.09, 137.94, 133.86, 132.42, 131.49, 131.19, 130.41, 128.39, 126.61, 124.88, 123.71, 123.59, 121.38, 120.85, 117.78, 98.24, 90.49, 88.94, 57.39, 54.44, 51.86, 44.17, 20.04.

Example 108: 4-((1-aminoisoquinolin-4-yl)ethynyl)-N-(4-((4-methylpiperazin-1-yl)methyl)-3-(trifluoromethyl)phenyl)benzamide (HSN489)

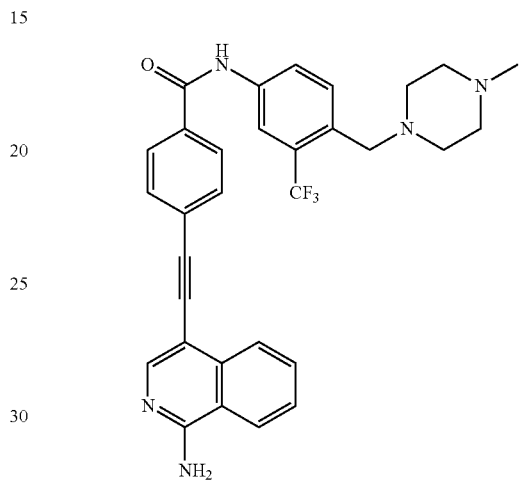

¹H NMR (500 MHz, Methanol-d₄) δ 8.18 (t, J=9.3 Hz, 2H), 8.13 (d, J=2.3 Hz, 1H), 8.08 (s, 1H), 7.98 (d, J=8.6 Hz, 2H), 7.94 (dd, J=8.4, 2.3 Hz, 1H), 7.81 (ddd, J=8.2, 6.9, 1.2 Hz, 1H), 7.76 (d, J=8.5 Hz, 1H), 7.71 (d, J=8.6 Hz, 2H), 7.60 (ddd, J=8.3, 7.0, 1.3 Hz, 1H), 3.65 (s, 2H), 2.52 (s, 8H), 2.30 (s, 3H); ¹³C NMR (126 MHz, MeOD) δ 166.67, 157.66, 145.36, 137.86, 136.51, 133.47, 132.65, 131.18, 131.12, 130.88, 128.83, 127.54, 126.53, 124.72, 123.75, 123.61, 117.76, 116.90, 104.56, 92.42, 88.07, 57.50, 54.58, 52.27, 44.56.

Example 109: 4-((3-amino-6-chloroisoquinolin-4-yl)ethynyl)-N-(4-((4-methylpiperazin-1-yl)methyl)-3-(trifluoromethyl)phenyl)benzamide (HSN490)

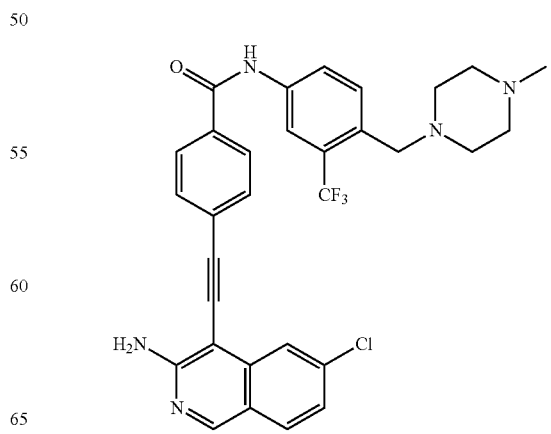

¹H NMR (500 MHz, DMSO-d₆) δ 10.56 (s, 1H), 8.92 (s, 1H), 8.21 (s, 1H), 8.06 (s, 1H), 8.04 (d, J=8.3 Hz, 2H), 7.99-7.91 (m, 3H), 7.89 (s, 1H), 7.70 (d, J=8.5 Hz, 1H), 7.28 (dd, J=8.6, 2.0 Hz, 1H), 6.89 (s, 2H), 3.56 (s, 2H), 2.38 (s, 8H), 2.17 (s, 3H); ¹³C NMR (126 MHz, DMSO) δ 165.49, 158.82, 153.50, 138.78, 138.64, 137.48, 133.93, 132.55, 131.71, 131.61, 128.35, 126.85, 124.05, 123.56, 121.34, 120.62, 117.77, 99.50, 88.25, 86.55, 57.88, 55.11, 53.02, 46.03.

Example 110: 3-((8-amino-1,7-naphthyridin-5-yl)ethynyl)-4-methyl-N-(4-(morpholinomethyl)-3-(trifluoromethyl)phenyl)benzamide (HSN514)

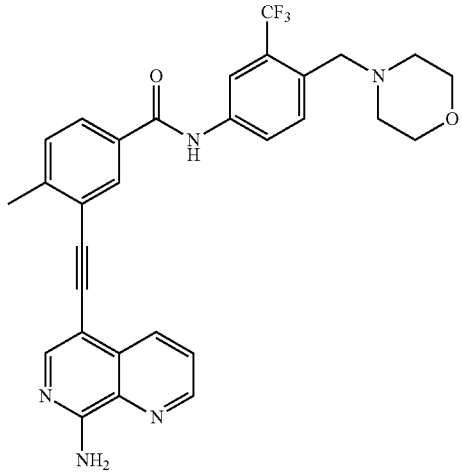 [SMILES: Cc1ccc(C(=O)Nc2ccc(CN3CCOCC3)c(C(F)(F)F)c2)cc1C#Cc1cnc(N)c2ncccc12]

¹H NMR (500 MHz, DMSO-d₆) δ 10.53 (s, 1H), 8.88 (d, J=4.3 Hz, 1H), 8.45 (d, J=8.4 Hz, 1H), 8.24 (s, 1H), 8.21 (d, J=8.8 Hz, 2H), 8.09-8.04 (m, 1H), 7.87 (d, J=9.2 Hz, 1H), 7.86-7.82 (m, 1H), 7.72 (d, J=8.5 Hz, 1H), 7.53 (s, 2H), 7.51 (d, J=8.0 Hz, 1H), 3.62-3.52 (m, 6H), 2.60 (s, 3H), 2.37 (s, 4H); ¹³C NMR (126 MHz, DMSO) δ 165.33, 158.56, 149.71, 148.19, 143.43, 138.75, 133.12, 132.67, 132.52, 132.00, 131.83, 131.35, 130.78, 130.34, 128.04, 127.84, 127.06, 125.88, 123.94, 123.42, 117.74, 102.10, 91.74, 90.53, 66.69, 58.33, 53.76, 21.19.

Example 111: 3-((8-amino-1,7-naphthyridin-5-yl)ethynyl)-N-(4-((4-ethylpiperazin-1-yl)methyl)-3-(trifluoromethyl)phenyl)-4-methylbenzamide (HSN515)

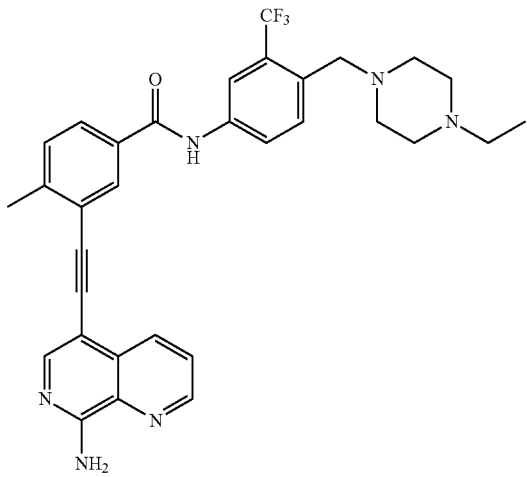 [SMILES: CCN1CCN(Cc2ccc(NC(=O)c3ccc(C)c(C#Cc4cnc(N)c5ncccc45)c3)cc2C(F)(F)F)CC1]

¹H NMR (500 MHz, DMSO-d₆) δ 10.52 (s, 1H), 8.88 (dd, J=4.2, 1.6 Hz, 1H), 8.46 (dd, J=8.3, 1.6 Hz, 1H), 8.24 (s, 1H), 8.20 (dd, J=4.0, 2.1 Hz, 2H), 8.06 (dd, J=8.5, 2.2 Hz, 1H), 7.86 (ddd, J=12.6, 8.1, 3.1 Hz, 2H), 7.70 (d, J=8.5 Hz, 1H), 7.53 (s, 2H), 7.51 (d, J=8.1 Hz, 1H), 3.55 (s, 2H), 2.60 (s, 3H), 2.47-2.23 (bs, 10H), 0.97 (t, J=7.1 Hz, 3H); ¹³C NMR (126 MHz, DMSO) δ 165.32, 158.57, 149.71, 148.19, 143.42, 138.65, 133.12, 132.69, 132.52, 131.67, 131.36, 130.79, 130.34, 128.03, 127.71, 127.07, 123.98, 123.72, 123.42, 117.73, 102.10, 91.74, 90.53, 57.93, 53.27, 52.82, 52.03, 21.19, 12.45.

Example 112: 5-((1-aminoisoquinolin-4-yl)ethynyl)-1-methyl-N-(4-((4-methylpiperazin-1-yl)methyl)-3-(trifluoromethyl)phenyl)-1H-pyrazole-3-carboxamide (HSN516)

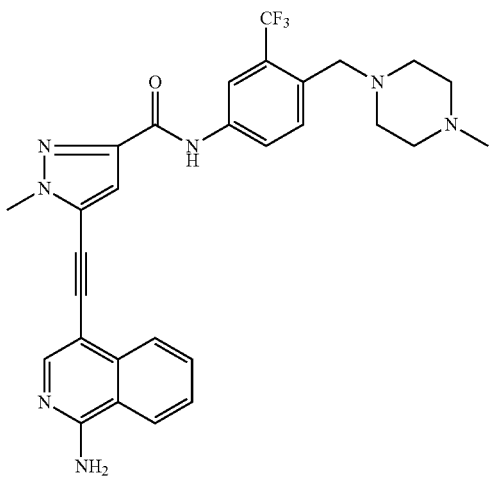

¹H NMR (500 MHz, DMSO-d₆) δ 10.50 (s, 1H), 8.31-8.27 (m, 2H), 8.23 (s, 1H), 8.06 (dd, J=8.5, 2.2 Hz, 1H), 8.03 (d, J=8.3 Hz, 1H), 7.79 (ddd, J=8.2, 6.9, 1.2 Hz, 1H), 7.66 (d, J=8.5 Hz, 1H), 7.58 (ddd, J=8.3, 6.9, 1.2 Hz, 1H), 7.50 (s, 2H), 7.13 (s, 1H), 4.10 (s, 3H), 3.55 (s, 2H), 2.39 (bs, 8H), 2.19 (s, 3H); ¹³C NMR (126 MHz, DMSO) δ 160.11, 158.62, 148.44, 145.71, 138.34, 136.18, 132.29, 131.82, 131.59, 128.01, 126.93, 125.04, 124.68, 123.96, 117.70, 116.61, 110.76, 101.63, 95.36, 80.85, 57.85, 55.06, 52.93, 45.94, 38.36.

Example 113: 3-((6-amino-4-cyanopyridin-3-yl)ethynyl)-4-methyl-N-(4-((4-methylpiperazin-1-yl)methyl)-3-(trifluoromethyl)phenyl)benzamide (HSN517)

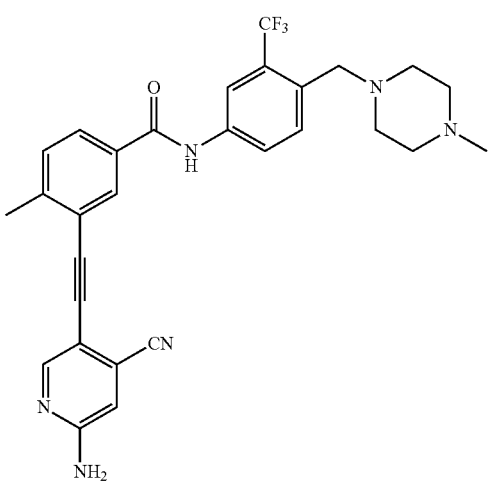

$^1$H NMR (500 MHz, DMSO-d$_6$) δ 10.53 (s, 1H), 8.38 (d, J=0.7 Hz, 1H), 8.19 (d, J=2.3 Hz, 1H), 8.09 (d, J=2.0 Hz, 1H), 8.04 (dd, J=8.5, 2.2 Hz, 1H), 7.89 (dd, J=8.0, 2.0 Hz, 1H), 7.69 (d, J=8.5 Hz, 1H), 7.49 (d, J=8.1 Hz, 1H), 7.07 (s, 2H), 6.84 (d, J=0.8 Hz, 1H), 3.55 (s, 2H), 2.54 (s, 3H), 2.38 (s, 8H), 2.18 (s, 3H); $^{13}$C NMR (126 MHz, DMSO) δ 165.18, 159.51, 153.13, 143.94, 138.63, 132.70, 132.49, 131.71, 130.83, 130.43, 128.54, 127.74, 123.98, 122.52, 122.29, 117.69, 116.64, 111.01, 106.74, 92.10, 89.37, 57.86, 55.09, 52.99, 46.00, 20.93.

Example 114: General Procedure for Preparation of Compounds in Table 4

6-chloroisoquinolin-3-amine (3.2 mmol) was iodinated by N-Iodosuccinimide (675 mg) and purified by flash column (part 1). 4-ethynylbenzaldehyde (1 eq) was dissolved in tert-butyl alcohol and the corresponding diamine (1 eq) was added and stirred for 1 hour at room temperature. 1.1 eq of iodine and 3 eq of potassium carbonate were added and the mixture was reflux overnight. Crude product was subject to column purification (part 2). Pure part 1 (50 mg), 10 mol % Bis(triphenylphosphine)palladium(II) dichloride, 10 mol % triphenylphosphine were added, purged with nitrogen three times before anhydrous DMF (5 mL) was added. The reaction mixture was stirred at 45° C. for another 5 minutes before the corresponding pure part 2 (1.1 eq) was added via syringe in 1 ml anhydrous DMF in 2 minutes. DIPEA (2 mL) was subsequently added and stirred overnight. Crude product was subject to column purification.

Example 115: Synthesis Procedure for HSM1859

Following the same procedure above, 6-chloroisoquinolin-3-amine (3.2 mmol) was iodinated by N-Iodosuccinimide (675 mg) and purified by flash column. To a solution of iodo compound (1 equiv), Pd(PPh$_3$)$_4$ (20 mol %) and cesium carbonate (1 equiv) in 1,4-dioxane/water (1 mL) were de-oxygenated using steam of Argon gas. A de-oxygenated solution of 4-vinylbenzonitrile (0.49 mmol, 1.5 equiv) in DMF (3 mL) was added slowly over a period of 15 min to the solution and the reaction temperature was increased to 70° C. and allowed to stir 12 h. The reaction was quenched by addition of water (5 mL) at room temperature and subject to flash column purification. After purification, it was dissolved in 2 mL absolute ethanol and 1 mL of hydroxylamine solution was added and reflux for 6 hours. After TLC showed complete consumption of starting material, ethanol was removed in vacuo and pure product was obtained by flash column chromatography.

Example 116: 6-chloro-4-((4-(4,5-dihydro-1H-imidazol-2-yl)phenyl)ethynyl)isoquinolin-3-amine (HSM1651)

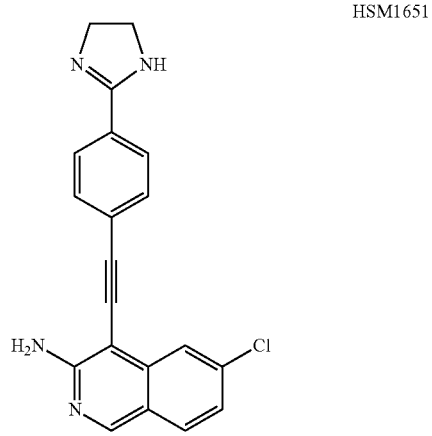 [SMILES: Nc1ncc2ccc(Cl)cc2c1C#Cc1ccc(C2=NCCN2)cc1]

Following the described general procedure IV, yellow solid was obtained. $^1$H NMR (500 MHz, DMSO-d6) δ 8.92 (s, 1H), 7.96 (d, J=8.6 Hz, 1H), 7.93-7.81 (m, 5H), 7.28 (dd, J=8.6, 1.8 Hz, 1H), 6.85 (s, 2H), 3.68 (s, 4H); $^{13}$C NMR (125 MHz, DMSO-d6) δ 163.73, 158.70, 153.30, 138.73, 137.42, 131.64, 131.56, 129.45, 127.78, 125.60, 123.52, 121.33, 120.61, 99.69, 88.45, 85.91, 49.51; HRMS (ESI$^+$) [M+H] calcd for C$_{20}$H$_{16}$ClN$_4$ 347.1063, found 347.1057.

Example 117: 6-chloro-4-((4-(1-(2-(piperidin-1-yl)ethyl)-4,5-dihydro-1H-imidazol-2-yl)phenyl)ethynyl)isoquinolin-3-amine

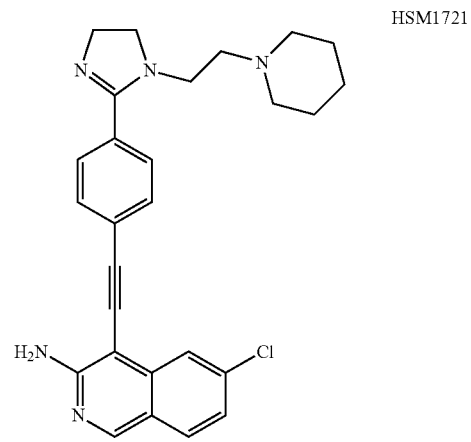 [SMILES: Nc1ncc2ccc(Cl)cc2c1C#Cc1ccc(C2=NCCN2CCN2CCCCC2)cc1]

Following the described general procedure IV, yellow solid was obtained. $^1$H NMR (500 MHz, DMSO-d6) δ 8.93 (s, 1H), 7.99-7.78 (m, 6H), 7.29 (dd, J=8.6, 2.0 Hz, 1H), 6.86 (s, 2H), 3.53-3.46 (m, 2H), 3.42 (dd, J=7.9, 3.1 Hz, 2H), 3.25-3.16 (m, 2H), 2.38 (dd, J=24.1, 22.3 Hz, 6H), 1.55-1.47 (m, 4H), 1.39 (s, 2H); $^{13}$C NMR (126 MHz, DMSO-d6) δ 206.36, 166.05, 158.59, 157.55, 153.58, 138.92, 137.12, 133.90, 131.37, 128.40, 126.15, 123.15, 121.23, 120.71, 99.32, 88.09, 86.12, 72.35, 67.21, 60.93, 54.76, 45.46, 32.08, 26.11, 23.84; HRMS (ESI$^+$) [M+H] calcd for $C_{27}H_{29}ClN_5$ 458.2111, found 458.2110.

Example 118: 6-chloro-4-((4-(4-cyclopropyl-4,5-dihydro-1H-imidazol-2-yl)phenyl)ethynyl)isoquinolin-3-amine

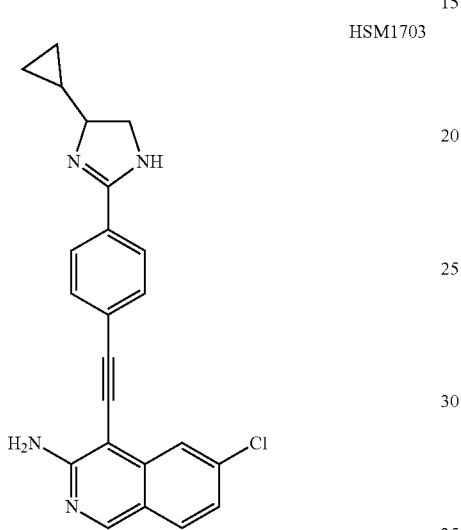

HSM1703

Following the described general procedure IV, yellow solid was obtained. 1H NMR (500 MHz, MeOD) δ 8.83 (s, 1H), 7.88 (ddd, J=62.4, 45.2, 5.0 Hz, 6H), 7.29 (dd, J=8.7, 1.9 Hz, 1H), 4.05-3.90 (m, 1H), 3.67 (dd, J=11.9, 8.0 Hz, 1H), 3.53 (dd, J=18.2, 7.9 Hz, 1H), 1.10-0.98 (m, 1H), 0.66-0.29 (m, 4H). HRMS (ESI$^+$) [M+H] calcd for $C_{23}H_{20}ClN_4$ 387.1376, found 387.1.

Example 119: 6-chloro-4-((4-(4,4-dimethyl-4,5-dihydro-1H-imidazol-2-yl)phenyl)ethynyl)isoquinolin-3-amine

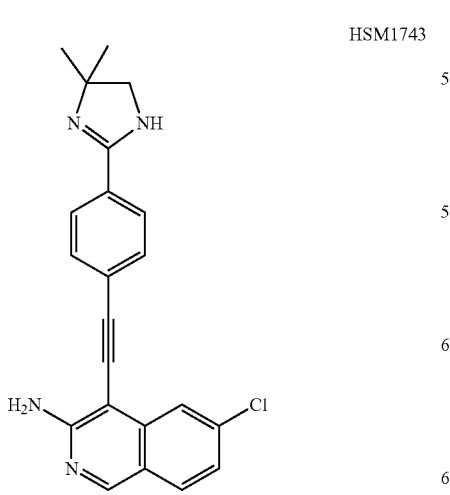

HSM1743

Following the described general procedure IV, yellow solid was obtained. $^1$H NMR (500 MHz, MeOD) δ 8.75 (s, 1H), 7.88 (d, J=1.2 Hz, 1H), 7.81 (d, J=7.4 Hz, 3H), 7.70 (d, J=8.2 Hz, 2H), 7.22 (dd, J=8.7, 1.9 Hz, 1H), 3.53 (s, 2H), 1.35 (s, 6H); $^{13}$C NMR (126 MHz, MeOD) δ 162.62, 157.51, 151.80, 138.75, 138.02, 131.01, 130.32, 129.49, 127.18, 125.73, 123.67, 121.34, 120.78, 99.38, 90.34, 84.27, 62.77, 61.61, 27.34; HRMS (ESI$^+$) [M+H] calcd for $C_{22}H_{20}ClN_4$ 350.1376, found 375.1368.

Example 120: 4-((4-(4,5-dihydro-1H-imidazol-2-yl)phenyl)ethynyl)-1H-pyrrolo[2,3-c]pyridin-5-amine

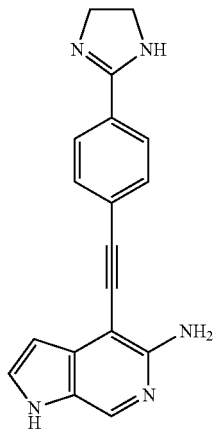

HSM1781

Following the described general procedure IV, yellow solid was obtained. $^1$H NMR (500 MHz, MeOD) δ 8.27 (s, 1H), 7.90 (d, J=8.5 Hz, 2H), 7.79 (d, J=8.5 Hz, 2H), 7.53 (d, J=2.9 Hz, 1H), 6.50 (dd, J=2.8, 0.7 Hz, 1H), 3.96 (s, 4H); $^{13}$C NMR (126 MHz, MeOD) δ 165.52, 153.08, 143.40, 136.88, 133.96, 132.14, 131.63, 131.27, 128.33, 128.20, 127.85, 99.54, 96.35, 87.85, 41.16; HRMS (ESI$^+$) [M+H] calcd for $C_{18}H_{16}N_5$ 302.1406, found 302.1399.

Example 121: 4-((4-(4,5-dihydro-1H-imidazol-2-yl)phenyl)ethynyl)cinnolin-3-amine

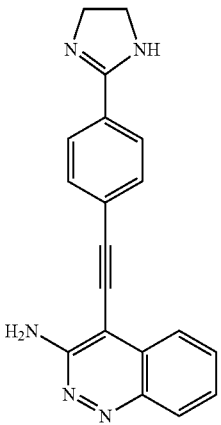

HSM1796

Following the described general procedure IV, yellow solid was obtained. $^1$H NMR (500 MHz, DMSO-d6) δ 8.19 (d, J=8.5 Hz, 1H), 8.03 (d, J=2.1 Hz, 1H), 7.91 (d, J=11.9 Hz, 3H), 7.75-7.68 (m, 1H), 7.56-7.48 (m, 1H), 7.11 (d, J=17.1 Hz, 3H), 3.62 (s, 4H); $^{13}$C NMR (126 MHz, DMSO-d6) δ 163.46, 157.83, 145.17, 132.88, 132.59, 132.25, 131.49, 130.35, 127.69, 127.32, 126.36, 125.17, 124.06, 123.77, 103.13, 94.50, 83.62, 41.23; HRMS(ESI$^+$) [M+H] calcd for $C_{19}H_{16}N_5$ 314.1406, found 314.1396.

Example 122: 4-((3-amino-6-chloroisoquinolin-4-yl)ethynyl)benzonitrile

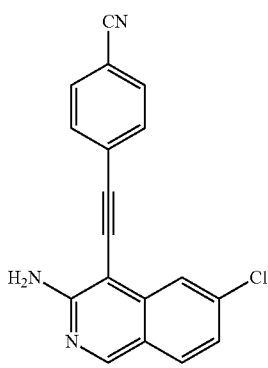

HSM1611

Following the described general procedure IV, yellow solid was obtained. $^1$H NMR (500 MHz, DMSO-d6) δ 8.91 (s, 1H), 7.91 (ddd, J=12.4, 9.9, 5.0 Hz, 6H), 7.26 (d, J=8.6 Hz, 1H), 6.95 (s, 2H); $^{13}$C NMR (126 MHz, DMSO-d6) δ 159.04, 153.96, 138.83, 137.63, 132.78, 132.41, 131.61, 128.36, 123.61, 121.33, 120.58, 119.18, 110.60, 98.86, 88.51, 87.73; HRMS (ESI$^+$) [M+H] calcd for $C_{18}H_{11}ClN_3$ 304.0642, found 304.1411.

Example 123: 4-((4-(4,5-dihydro-1H-imidazol-2-yl)phenyl)ethynyl)isoquinoline

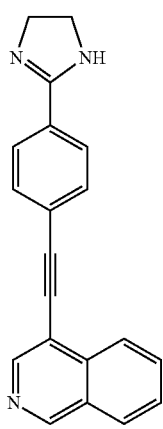

HSM1813

Following the described general procedure IV, yellow solid was obtained. $^1$H NMR (500 MHz, DMSO-d6) δ 9.37 (s, 1H), 8.79 (s, 1H), 8.35 (d, J=8.2 Hz, 1H), 8.24 (d, J=8.0 Hz, 1H), 7.96 (dd, J=19.4, 7.8 Hz, 3H), 7.81 (dd, J=13.7, 7.7 Hz, 3H), 3.65 (s, 4H); $^{13}$C NMR (126 MHz, DMSO-d6) δ 163.43, 153.15, 146.66, 134.95, 132.48, 131.96, 131.31, 128.96, 128.85, 127.93, 127.85, 124.84, 124.02, 115.01, 96.65, 86.36, 50.06. HRMS (ESI$^+$) [M+H] calcd for $C_{20}H_{16}N_3$ 298.1344, found 298.1341.

Example 124: 3-((3-amino-6-chloroisoquinolin-4-yl)ethynyl)-N-hydroxybenzimidamide

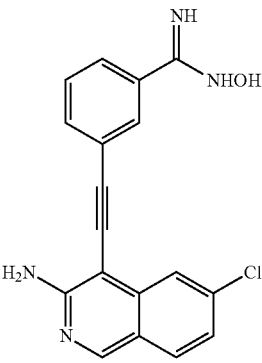

HSM1819

Following the described general procedure IV, yellow solid was obtained. $^1$H NMR (500 MHz, DMSO-d6) δ 9.75 (s, 1H), 8.92 (s, 1H), 8.04 (s, 1H), 7.96 (d, J=8.6 Hz, 1H), 7.88 (s, 1H), 7.78 (d, J=7.5 Hz, 1H), 7.72 (d, J=7.8 Hz, 1H), 7.46 (t, J=7.7 Hz, 1H), 7.28 (d, J=8.5 Hz, 1H), 6.80 (s, 2H), 5.93 (s, 2H); $^{13}$C NMR (126 MHz, DMSO-d6) δ 158.57, 153.00, 150.66, 138.73, 137.33, 134.15, 132.13, 131.55, 128.89, 128.65, 125.84, 123.48, 123.22, 121.31, 120.63, 99.88, 88.73, 83.91. HRMS (ESI$^+$) [M+H] calcd for $C_{18}H_{14}ClN_4O$, 337.0856, found 337.0873.

Example 125: 4-((3-amino-6-chloroisoquinolin-4-yl)ethynyl)-N-hydroxybenzimidamide

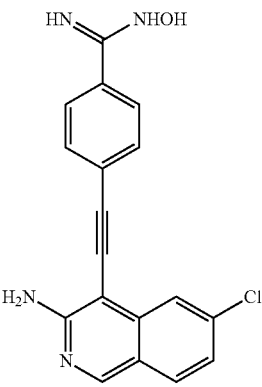

HSM1820

Following the described general procedure IV, yellow solid was obtained. $^1$H NMR (500 MHz, DMSO-d6) δ 9.79 (s, 1H), 8.91 (s, 1H), 7.95 (d, J=8.6 Hz, 1H), 7.88 (d, J=1.4 Hz, 1H), 7.80-7.72 (m, 4H), 7.27 (dd, J=8.6, 1.9 Hz, 1H), 6.80 (s, 2H), 5.90 (s, 2H); $^{13}$C NMR (126 MHz, DMSO-d6) δ 158.53, 153.00, 150.71, 138.69, 137.32, 133.41, 131.53, 125.81, 123.66, 123.47, 121.35, 120.62, 99.94, 88.76, 84.85. HRMS (ESI$^+$) [M+H] calcd for $C_{18}H_{14}ClN_4O$, 337.0856, found 337.0865.

Example 126: (E)-4-(2-(3-amino-6-chloroisoquinolin-4-yl)vinyl)-N-hydroxybenzimidamide

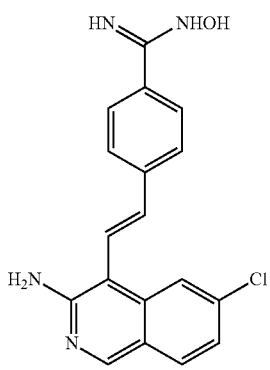

HSM1859

Following the described synthesis procedure V, yellow solid was obtained. $^1$H NMR 500 MHz, DMSO-d6) δ 9.66 (d, J=6.2 Hz, 1H), 8.88-8.75 (m, 1H), 7.89 (dt, J=17.8, 5.5 Hz, 2H), 7.77-7.63 (m, 4H), 7.33 (t, J=17.4 Hz, 1H), 7.28-7.09 (m, 1H), 7.06-6.94 (m, 1H), 6.24 (s, 2H), 5.83 (s, 2H), $^{13}$C NMR (126 MHz, DMSO-d6) δ 154.75, 151.48, 151.00, 138.28, 136.75, 136.24, 134.02, 132.80, 131.32, 126.82, 125.88, 122.80, 122.59, 121.50, 121.20, 104.46, HRMS (ESI$^+$) [M+H] calcd for $C_{18}H_{16}ClN_4O$, 339.1013, found 339.1010.

Example 127: Activity Studies Against AML Cell Line, MV4-11

Cells were added to 96 well plates at 2000 cells per well for adherent lines and 4000 cells per well for suspension lines and kept in an incubator overnight. The following day the plates were treated with compounds to give rise to the final concentrations of; 100 μM, 10 μM, 5 μM 1 μM, 500 nM, 100 nM, 10 nM, 10 pM. The plates were then stored in the incubator for 72 hours. On the third day the cells were assayed with 20 μL of CellTiter-Blue Cell Viability Assay per well and were incubated for 4 hours. After 4 hours' fluorescence intensity was taken on a plate reader: Excitation: 560/10 Emission: 590/10. IC$_{50}$ analysis was performed on GraphPad Prism 7.

TABLE 1

Selected IC50 values against AML cell line, MV4-11

| Compound | IC50 against MV4-11/uM |
|---|---|
| HSM1661 | 0.016 |
| HSM1611 | 0.840 |
| HSM1617 | 0.770 |
| HSM1651 | 0.008 |
| HSM1688 | 0.250 |
| HSM1669 | 0.260 |
| M731 | 0.036 |
| HSM1674 | 0.110 |
| HSM1673 | 0.011 |
| HSM1692 | 0.450 |
| HSM1693 | 0.030 |
| HSM1702 | 0.003 |
| HSM1683 | 0.003 |
| HSM1684 | 0.071 |
| HSM1690 | 3.090 |
| HSM1717 | 0.050 |

TABLE 1-continued

Selected IC50 values against AML cell line, MV4-11

| Compound | IC50 against MV4-11/uM |
|---|---|
| HSM1721 | 0.015 |
| HSM1725 | 0.008 |
| HSN105 | 0.061 |
| HSN122 | 0.009 |
| HSN129 | 0.008 |
| HSN135 | 0.033 |
| HSN136 | 0.095 |
| HSN137 | 0.006 |
| HSD48 | 0.028 |

TABLE 2

IC50 against MV4-11 (AML cell line)

| Compound | IC50 (nM) |
|---|---|
| HSM1683 | 42.1 ± 1.3 |
| HSM1693 | 14.8 ± 1.4 |
| HSM1702 | 5.5 ± 1.3 |
| HSM1662 | 6.2 ± 1.3 |
| HSM1673 | 25.0 ± 1.4 |

Example 128: In Vitro Kinase Assays

The Reaction Biology Corporation (www.reactionbiology.com, Malvern, Pa.) HotSpot assay platform was used to measure kinase/inhibitor interactions exactly as previously described. Kinase and substrate were mixed in a buffer containing 20 mM HEPES pH 7.5, 10 mM MgCl$_2$, 1 mM EGTA, 0.02% Brij35, 0.02 mg/mL BSA, 0.1 mM Na$_3$VO$_4$, 2 mM DTT and 1% DMSO. Single-dose of compounds (500 nM) were then added to each reaction mixture. After 20-minute incubation, ATP (Sigma) and [γ-$^{33}$P] ATP (Perkin Elmer) were added at a final total concentration of 100 μM for addition 2 hours at room temperature, followed by spotting onto P81 ion exchange cellulose chromatography paper (Whatman, Inc.). Filter paper was washed in 0.75% phosphoric acid to remove unincorporated ATP. Percent remaining kinase activity of a vehicle (DMSO) containing kinase reaction was calculated for each kinase/inhibitor pair using Prism 5 (GraphPad). At a concentration of 500 nM, HSM1856 inhibits 70% of BTK (IBruton's tyrosine kinase) activity and HSN325 blocks 96% of RET activity.

IC$_{50}$ proliferation assay—Cell lines and primary cells were seeded into 96-well plates the afternoon prior to treatment. Approximately 18 hours later, compounds were semi-serially diluted in dimethyl sulfoxide (DMSO) and then growth medium, and added to cells. Plates were incubated for 72 hours prior to addition of Alamar Blue (Life Technologies, Carlsbad, Calif.). Plates were read after 4 additional hours of incubation at 37° C. using a Bio-Tek Synergy HT plate reader (Bio-Tek, Winooski, Vt.). Data was analyzed and graphed using GraphPad Prism Software (Graphpad, La Jolla, Calif.). Experimental results are summarized in Table 3.

TABLE 3

Anti-Tumor Activities of Selected Compound

| Compound | Cell line - MV4-11 | Cell line - K562 |
|---|---|---|
| HSN248 | 0.225 μM | 0.007 μM |
| HSN178 | 0.171 μM | 1.443 μM |
| HSN247 | 0.154 μM | 0.025 μM |
| HSM1702 | 0.071 μM | 5.057 μM |
| HSN315 | 0.54 μM | 0.203 μM |
| HSN316 | 0.759 μM | 0.759 μM |
| HSN317 | n/a* | 1.483 μM |
| HSN285 | 0.722 μM | 1.102 μM |
| HSN286 | 0.0004 μM | n/a |
| HSN325 | 0.135 μM | 0.444 μM |
| HSN334 | 0.001 μM | 0.006 μM |
| HSN353 | 0.003 μM | 0.005 μM |
| HSN352 | 0.003 μM | 0.002 μM |
| HSN356 | 0.0004 μM | 0.002 μM |
| HSM1795 | 0.1 μM | n/a |
| HSM1856 | 0.025 μM | n/a |

*n/a: not determined.

IC50 (proliferation inhibition) against leukemia cell lines MV4-11 and K562. HSM1856 also inhibited MiaPaca-2 and HLY-1 with IC50 of 0.4 and 0.08 aM respectively. MiaPaca-2 (Pancreatic cell line), HLY-1 (Lymphoma cell line), MV4-11 (AML cell line) and K562 (CML cell line).

Example 129: Inhibition of FLT3, FLT3 ITD and FLT3 D835Y

Figure 8A:
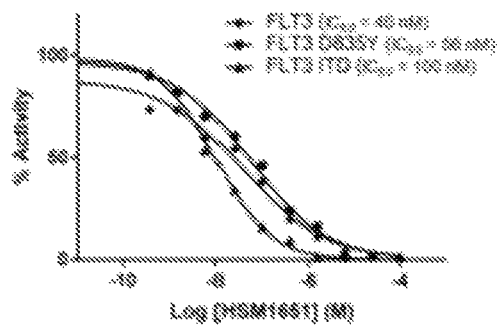
FIGS. 8A, 8B, and 8C depict dose-response curves and Western Blot analyses.

The compounds of the invention are aFLT3 inhibitors (Table 4 for percentage enzymatic inhibition at 0.5 μM compounds). Detailed characterization of one of HSM1651 revealed that it inhibited FLT3, FLT3 ITD and FLT3 D835Y with $IC_{50}$ values of 40 nM, 100 nM and 56 nM respectively (FIG. 8A).

TABLE 4

FLT3 inhibition profile and anti-proliferative activities of the compounds of the invnvention against different leukemia cancer cell lines.

| Entry | Structure | % Inhibition of kinases FLT3 at 500 nM | Anti-proliferative effects in leukemia panel (μM) MV4-11[a] MOLM14[b] THP-1[c] K-562[d] HL60[e] |
|---|---|---|---|
| 1 | 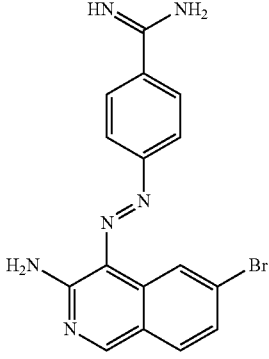 HSW630-1 | 92 | 0.15 ± 0.01[a]<br>0.15 ± 0.01[b]<br>1.20 ± 0.20[c]<br>3.00 ± 0.96[d] |
| 2 | 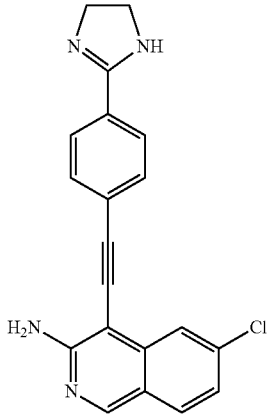 HSM1651 | 60 | 0.05 ± 0.01[a]<br>0.11 ± 0.02[b]<br>1.85 ± 0.92[c]<br>1.39 ± 0.01[d]<br>3.05 ± 0.07[e] |

TABLE 4-continued
FLT3 inhibition profile and anti-proliferative activities of the compounds of the innvention against different leukemia cancer cell lines.
| Entry | Structure | % Inhibition of kinases FLT3 at 500 nM | Anti-proliferative effects in leukemia panel (μM) MV4-11[a] MOLM14[b] THP-1[c] K-562[d] HL60[e] |
|---|---|---|---|
| 3 | 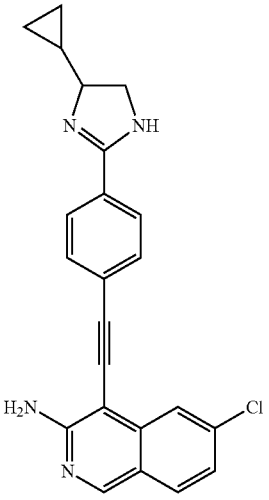<br>HSM1703 | 43 | 0.30 ± 0.20[a]<br>0.10 ± 0.02[b] |
| 4 | 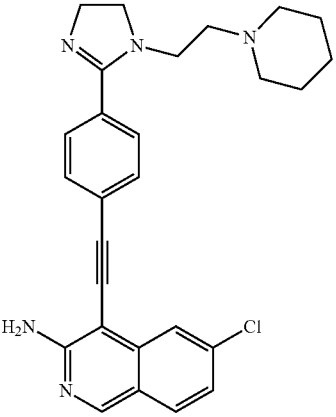<br>HSM1721 | 51 | 0.08 ± 0.02[a]<br>0.30 ± 0.08[b] |

TABLE 4-continued

FLT3 inhibition profile and anti-proliferative activities of the compounds of the innvention against different leukemia cancer cell lines.

| Entry | Structure | % Inhibition of kinases FLT3 at 500 nM | Anti-proliferative effects in leukemia panel (μM) MV4-11[a] MOLM14[b] THP-1[c] K-562[d] HL60[e] |
|---|---|---|---|
| 5 | HSM1743 | 56 | 0.07 ± 0.02[a]<br>0.30 ± 0.01[b] |
| 6 | HSM1781 | 1 | >5[a]<br>>5[b] |
| 7 | HSM1611 | 34 | >5[a]<br>>5[b] |

TABLE 4-continued

FLT3 inhibition profile and anti-proliferative activities of the compounds of the innvention against different leukemia cancer cell lines.

| Entry | Structure | % Inhibition of kinases FLT3 at 500 nM | Anti-proliferative effects in leukemia panel (μM) MV4-11[a] MOLM14[b] THP-1[c] K-562[d] HL60[e] |
|---|---|---|---|
| 8 | HSM1796 | 6 | >5[a] >5[b] |
| 9 | HSM1798 | 21 | >5[a] >5[b] |
| 10 | HSM1813 | 36 | >5[a] >5[b] |

TABLE 4-continued

FLT3 inhibition profile and anti-proliferative activities of the compounds of the innvention against different leukemia cancer cell lines.

| Entry | Structure | % Inhibition of kinases FLT3 at 500 nM | Anti-proliferative effects in leukemia panel (μM) MV4-11[a] MOLM14[b] THP-1[c] K-562[d] HL60[e] |
|---|---|---|---|
| 11* | HSM1820 | 61 | 0.04 ± 0.01[a]<br>0.05 ± 0.03[b] |
| 12* | HSM1819 | 54 | 0.02 ± 0.01[a]<br>0.06 ± 0.01[b] |
| 13* | HSM1859 | 41 | 0.35 ± 1.17[a] |

TABLE 4-continued

FLT3 inhibition profile and anti-proliferative activities of the compounds of the innvention against different leukemia cancer cell lines.

| Entry | Structure | % Inhibition of kinases FLT3 at 500 nM | Anti-proliferative effects in leukemia panel (µM) MV4-11[a] MOLM14[b] THP-1[c] K-562[d] HL60[e] |
|---|---|---|---|
| 14 | 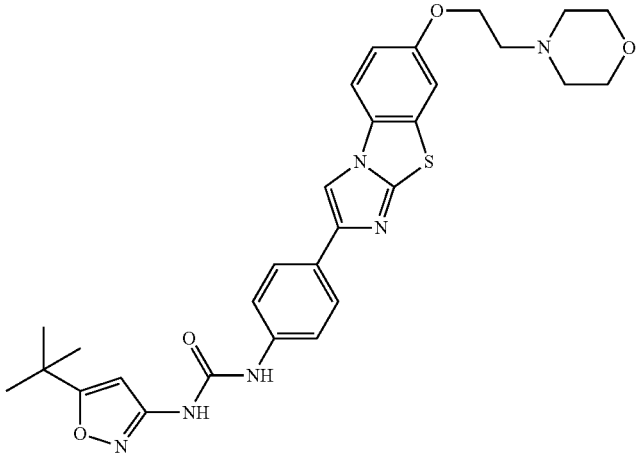 Quizartinib | 98 | 0.001 ± 0.001[a]<br>0.001 ± 0.001[b] |
| 15 | 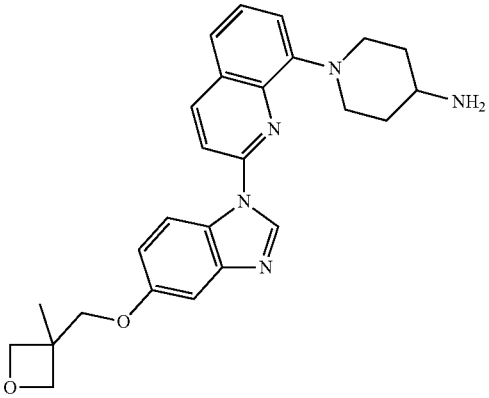 Crenolanib | 99 | 0.005 ± 0.001[a]<br>0.004 ± 0.001[b] |

[a-e]these correlate the cell lines tested to respective IC$_{50}$.
*hydroxyamidines may be acting as prodrugs of amidines in these cellular assays.

Example 130: Inhibition of c-Kit and TrkC Enzymes

The compounds of the invention inhibited c-Kit and TrkC enzymes. Table 5 provides % inhibition of TrkC/c-Kit activities by compounds with stable linkers at concentration of 500 nM, in the presence of 100 pM radiolabeled ATP.

TABLE 5

% Inhibition of Trkc/C-Kit Activities

| Entry | Compound name | % inhibition of TrkC at 500 nM | % inhibition of c-Kit at 500 nM |
|---|---|---|---|
| 1 | HSW630-1 | 99% | 68% |
| 2 | HSM1651 | 64% | 83% |
| 3 | HSM1703 | 49% | 60% |
| 4 | HSM1721 | 52% | 80% |
| 5 | HSM1743 | 44% | 78% |
| 7 | HSM1611 | 16% | 63% |
| 8 | HSM1796 | 7% | 3% |
| 9 | HSM1798 | 11% | 15% |
| 10 | HSM1813 | 17% | 39% |
| 11 | HSM1820 | 74% | 86% |
| 12 | HSM1819 | 80% | 82% |
| 13 | HSM1859 | 42% | 62% |

Figure 8B:
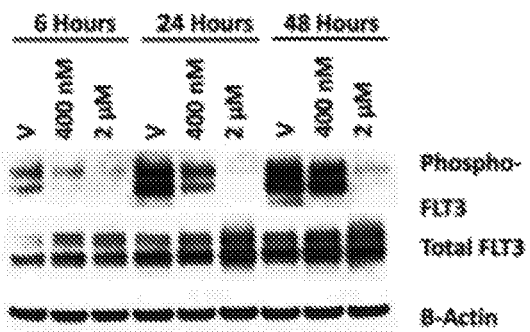
Figure 8C:
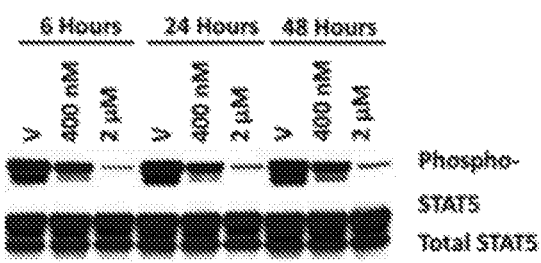
Figure 9:
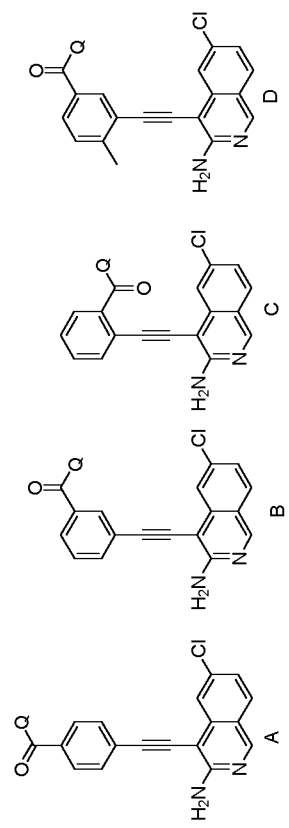
FIG. 9 depicts representative examples of compounds synthesized.
Figure 9:
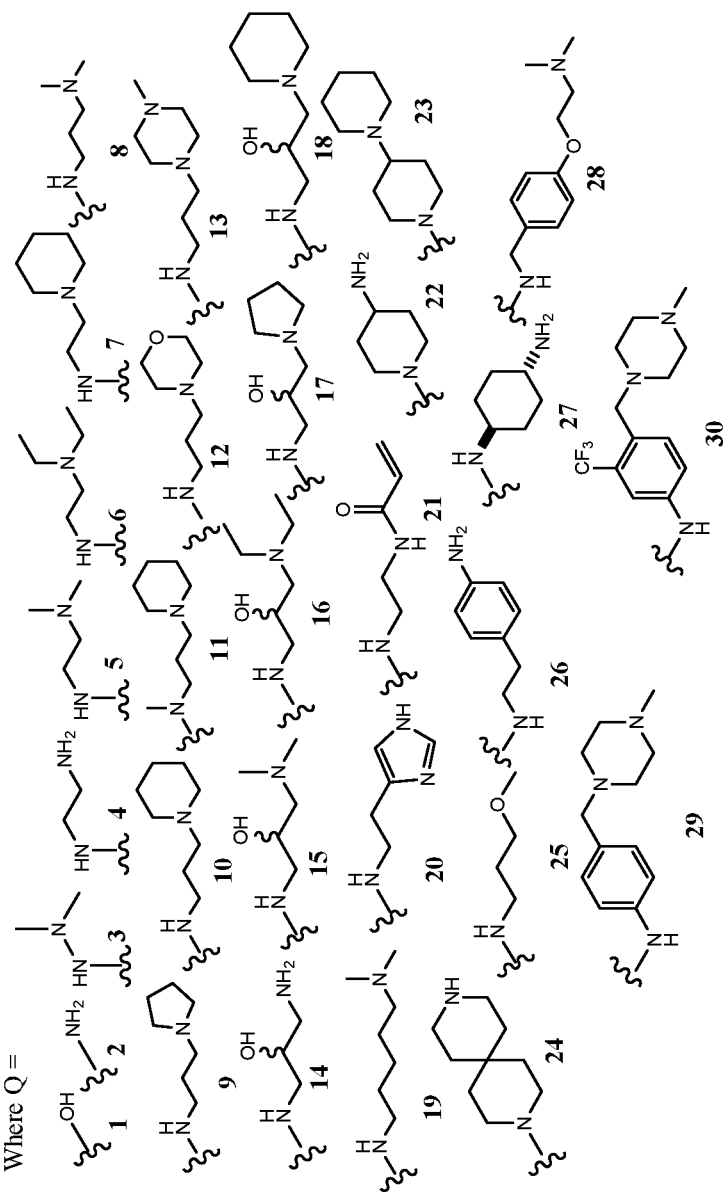

The compounds of the invention could also potently inhibit AML cell lines (Table 5). Western analysis of MV4-11, treated with HSM1651, revealed that FLT3 phosphorylation as well as the downstream STAT5 phosphorylation were reduced in the presence of HSM1651 (FIGS. 8B and 8C). A few of the alkyne analogs have respectable anti-proliferative properties (HSM1819 has an $IC_{50}$ value of 20 nM, which is only four times less potent than crenolanib ($IC_{50}$=5 nM), which proceeded to clinical trials). Regarding structure-activity-relationship studies of the alkyne/alkene analogs, it appears that modifications to the isoquinoline ring greatly affected both kinase inhibition and anti-proliferative activity. For the alkyne series, HSM1813 (H at 3-position and also lacking Cl at 6-position) was not a potent inhibitor of MV4-11 proliferation (Table 5, entry 10). HSM1651 (amino at 3-position and Cl at 6-position) is a good inhibitor of MV4-11 and MOLM-14 proliferation whereas compounds HSM1781, 1798 and 1796, which differed from HSM1651 at the isoquinoline part, are ineffective anti-proliferative agents in AML cell lines. The amidine group also appears to be important for anti-proliferative activity. The cyano analog HSM1611 is ineffective against MV4-11 and MOLM-14 whereas the hydroxyamidine analog (HSM1819), which is derived from HSM1611, is a very potent anti-proliferative in AML cell lines. The hydroxyamidine HSM1819 inhibits FLT3 and FLT3 ITD with IC50 of 217 and 240 nM, respectively, in vitro. HSM1820, another hydroxyamidine analogue, inhibits FLT3 and FLT3 ITD with IC50 of 359 and 350 nM, respectively, in vitro.

Example 131: Antiproliferative Activity Studies

Antiproliferative activities against AML cell line, MV4-11 (a FLT3-driven cell line) and three other solid tumors (MCF7, breast; HCT116, colon and HeLa) have been investigated (Tables 6A and 6B and FIG. 10).

Figure 10:
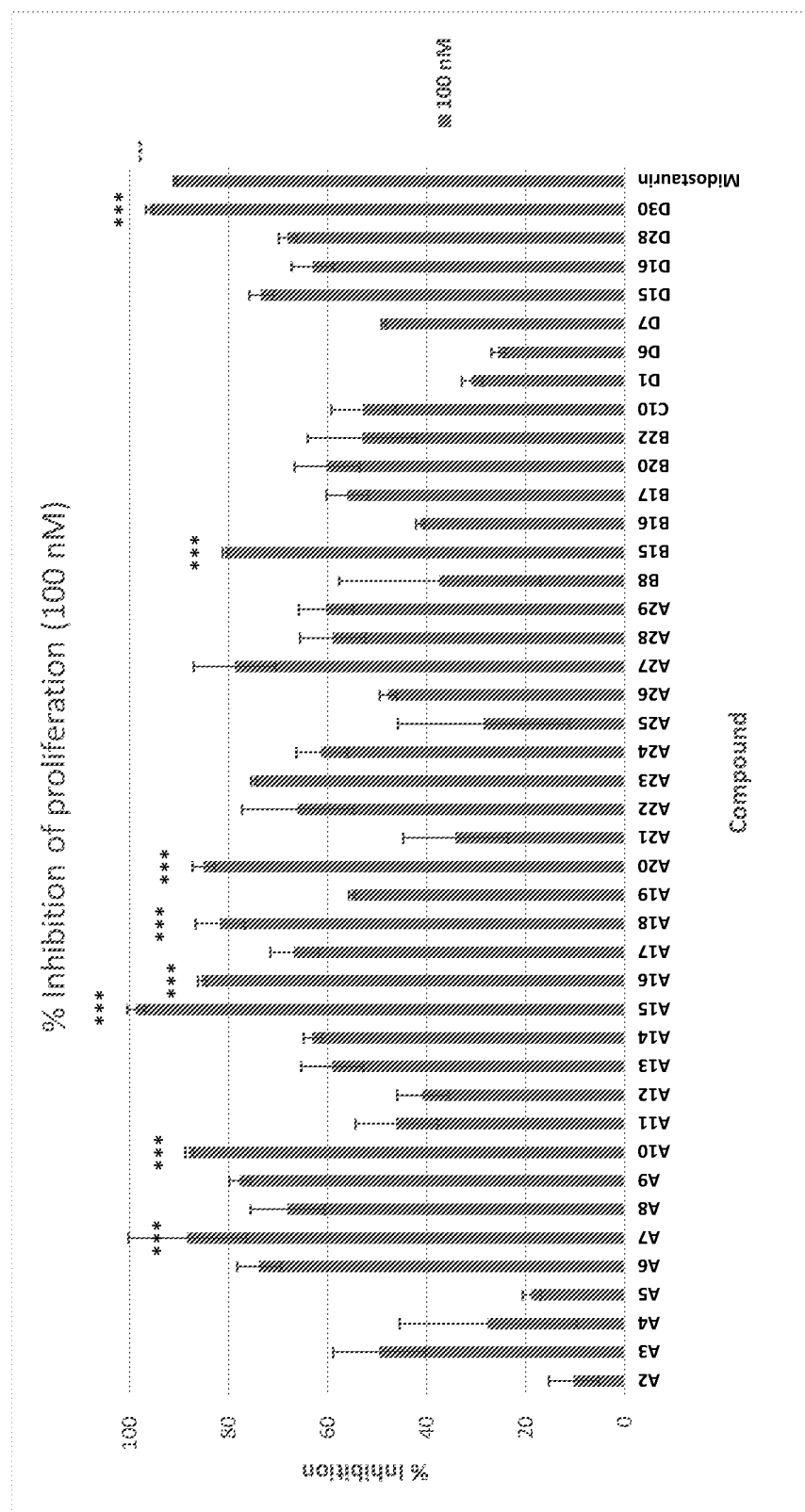
FIG. 10 depicts the percentage inhibition of proliferation in MV4-11 cell line with various analogs (100 nM). Table 2 provides $IC_{50}$ values for selected compounds D7, D15, D6, A15, D28, D30 and midostaurin (compounds are described in FIG. 9).

From these cell proliferation studies, MV4-11 appeared to be more sensitive to the compounds than the other cell lines (Table 6A). At 1 pM, most of the compounds could inhibit MV4-11 significantly. To identify group of compounds potently inhibiting cancer cell proliferation, a lower concentration of compounds (100 nM) were used to screen against MV4-11 (FIG. 10). From these experiments, potent amide compounds A7, A10, A15, A16, A18, A20, B15 and D30 (as indicated by ***, FIG. 10) were selected. At 100 nM, these selected compounds inhibited MV4-11 at similar levels to midostaurin, a pan kinase inhibitor that recently completely a Phase III clinical trials (FIG. 10). Typically amides that contain basic amines are included in compound libraries to improve aqueous solubility but it appears that the presence of a basic amine in the side chain of the compounds also facilitated the actual inhibition of MV4-11 proliferation. For example, compounds A1, A2, A21 and A25, which did not have a basic amine side chain, were inactive against MV4-11 whereas many of the other compounds containing a basic amine chain were active against MV4-11. Stability of the active compounds, in the presence of mouse liver microsomes revealed that compounds with the D substitution pattern (such as D30) preformed much better in the liver microsomal stability assay compared to the other analogs.

Example 132: Proliferation Inhibition ($IC_{50}$) Against MV4-11 and MOLM-14

Compound D30 contains 1-methyl-4-(2-(trifluoromethyl)benzyl)piperazine group, which is found in many kinase inhibitors, including ponatinib. Ponatinib, which is used to treat imatinib-resistant CML, has been shown to inhibit FLT3-driven AML. Unfortunately ponatinib causes adverse cardiovascular effects (Gainor, J. F., et al. Oncologist, 20 (8), 847-848 (2015)) and it is now given with a black box

TABLE 6A

Percent Inhibition of cancer cell line proliferation in the presence of compounds (1 μM)

| | Compound | | | | | | | | | | | | | | | | | |
|---|---|---|---|---|---|---|---|---|---|---|---|---|---|---|---|---|---|---|
| | HSN 210 | HSN 204 | HSM 1669 | HSM 1812 | HSN 137 | HSM 1673 | HSM 1683 | HSN 105 | HSM 1610 | HSM 1674 | HSN 177 | HSM 1702 | HSN 184 | HSM 1750 | HSN 145 | HSN 139 | HSN 135 | HSM 1773 |
| code | A3 | A4 | A5 | A6 | A7 | A9 | A10 | A11 | A12 | A13 | A14 | A15 | A16 | A17 | A20 | A22 | A23 | A24 |
| MV-4-11 | 100 | 77 | 83 | 92 | 99 | 98 | 95 | 88 | 90 | 93 | 91 | 99 | 97 | 93 | 99 | 95 | 100 | 93 |
| HCT116 | 6 | 21 | 46 | 17 | 60 | 28 | 10 | 40 | 39 | 14 | 15 | 33 | 38 | 20 | 35 | 32 | 21 | 24 |
| HeLa | 16 | 22 | 20 | 97 | 20 | 38 | 49 | 1 | 20 | 8 | 1 | 17 | 51 | 11 | 11 | 35 | 0 | 24 |
| MCF-7 | 1 | 20 | 98 | 100 | 74 | 56 | 57 | 12 | 29 | 36 | 46 | 100 | 92 | 17 | 6 | 60 | 35 | 43 |

TABLE 6B

Percent Inhibition of cancer cell line proliferation in the presence of compounds (1 μM)

Figure 11:
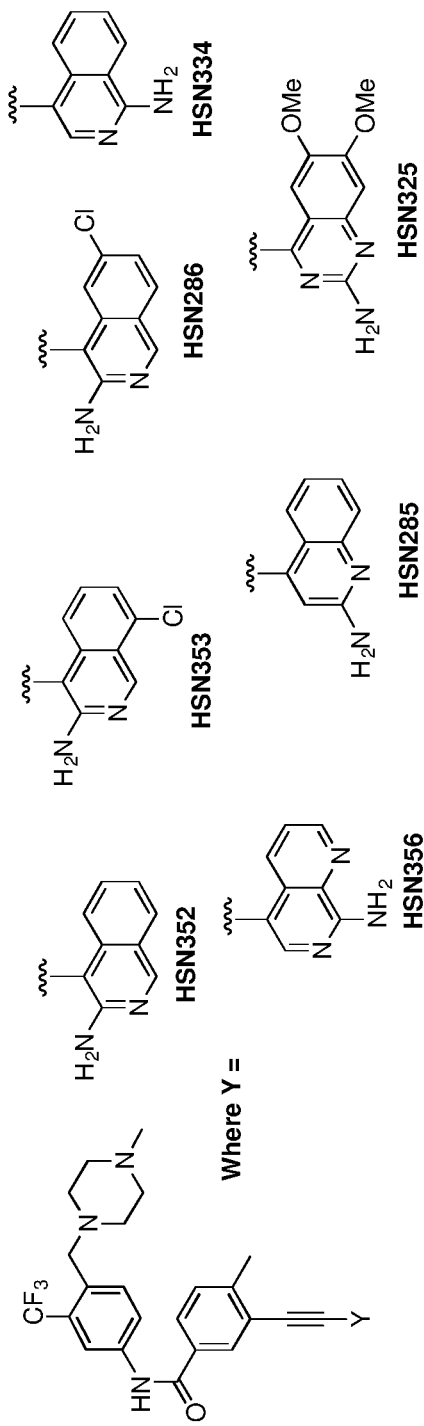
FIG. 11 depicts D30 analogs that were synthesized to investigate the influence of the quinoline/quinazoline/isoquinoline core on anticancer activity and kinase inhibition.

| | Compound | | | | | | | | | | | | | | | | | |
|---|---|---|---|---|---|---|---|---|---|---|---|---|---|---|---|---|---|---|
| | HSM 1692 | HSN 136 | HSN 129 | HS N99 | HSM 1661 | HSM 1688 | HSN 161 | HSN 189 | HSM 1751 | HSN 157 | HSN 174 | HSM 1717 | HSN 247 | HSN 248 | HSN 178 | HSN 185 | HSN 315 | HSN 286 |
| code | A25 | A26 | A27 | A28 | A29 | B8 | B15 | B16 | B17 | B20 | B22 | C10 | D6 | D7 | D15 | D16 | D28 | D30 |
| MV-4-11 | 81 | 86 | 99 | 97 | 90 | 74 | 97 | 95 | 91 | 96 | 85 | 82 | 58 | 98 | 98 | 97 | 83 | 99 |
| HCT116 | 29 | 38 | 29 | 20 | 0 | 43 | 18 | 7 | 32 | 12 | 28 | 33 | 54 | 76 | 97 | 67 | 66 | 100 |
| HeLa | 0 | 0 | 22 | 6 | 1 | 64 | 70 | 18 | 23 | 33 | 10 | 2 | 100 | 100 | 100 | 99 | 100 | 100 |
| MCF-7 | 22 | 33 | 37 | 42 | 96 | 33 | 91 | 49 | 47 | 21 | 40 | 76 | 100 | 100 | 100 | 100 | 100 | 100 | warning and as a last resort drug against CML (Talbert, D. R., et al., *Toxicol. Sci,* 143 (1), 147-155 (2015). In 2014 it was withdrawn from the US market due to blood clotting and cardiovascular adverse effects and therefore it might not be an ideal drug to advance for AML treatment (especially for elderly patients). Therefore further analogs of D30 were investigated if the kinase selectivity of compounds containing the 1-methyl-4-(2-(trifluoromethyl)benzyl)piperazine group could be modulated via a judicious substitution on the isoquinoline core or use of isoquinoline isomers. Compounds HSN352, HSN353, HSN334, HSN356, HSN285 and HSN325 (containing 3-aminoisoquinoline, 1-aminoisoquinoline, 2-aminoquinoline and 2-aminoquinazoline, FIG. 11) were prepared via the Sonogashira coupling. These compounds' proliferation inhibition ($IC_{50}$) against MV4-11 and MOLM-14 (FLT3-driven AML cell lines) were determined (Table 6B).

HSN286 had an $IC_{50}$ against MV-4-11 and MOLM-14 of 0.5 nM and 0.7 nM respectively (Table 7). 1-Aminoisoquinoline analogs, HSN334 and HSN356, were also potent proliferation inhibitors of MV4-11 and MOLM-14. The degrees of AML proliferation inhibition by the isoquinoline compounds were similar to (or even slightly better than) midostaurin (Table 7). In general, there was a good correlation between the percentage inhibition of FLT3 enzymatic reaction (obtained as percentage inhibition at 500 nM compound, Reaction Biology) and the inhibition of AML cell lines MV4-11 and MOLM-14 proliferation. Not all of the aminoquinoline compounds were potent inhibitors of the AML cell lines proliferation. For example, HSN248, HSN178, HSN247, MXC1702 and HSN315 that also contained the 2-aminoquinoline core were only moderate inhibitors of AML proliferation or FLT3 enzymatic activity. However, the 1-methyl-4-(2-(trifluoromethyl)benzyl)piperazine moiety (FIG. 11) is not the sole determinant of FLT3 inhibition. The 2-aminoquinolines and quinazoline analogs, HSN285 and HSN325, both contain this moiety but they were neither potent inhibitors of FLT3 nor active against MV4-11 or MOLM-14 cell lines. Therefore it appears that the potencies of these compounds are due to the combined or synergistic effects of the 1-methyl-4-(2-(trifluoromethyl)benzyl)piperazine moiety (found in ponatinib) and the aminoisoquinoline moiety.

TABLE 7

$IC_{50}$ (proliferation) and FMS-like tyrosein kinase 3 inhibition of activity

| Compound | % inhibition of FLT3 activity (500 nM) | $IC_{50}$ (nM) MV-4-11 | $IC_{50}$ (nM) MOLM14 |
|---|---|---|---|
| HSN248 (D7) | 73% | 181 ± 6.5 | 180 ± 7.8 |
| HSN178 (D15) | 66% | 144 ± 2.6 | 187 ± 5.5 |
| HSN247 (D6) | 74% | 154 ± 7.1 | 129 ± 8.2 |
| HSM1702 (A15) | 66% | 71 ± 1.1 | 102 ± 11 |
| HSN315 (D28) | 32% | 549 ± 7.4 | 523 ± 6.4 |
| HSN285 | 28% | 721 ± 5.8 | 415 ± 6.9 |
| HSN286 (D30) | 97% | 0.49 ± 0.02 | 0.72 ± 0.02 |
| HSN325 | 33% | 135 ± 5.87 | 456 ± 15 |
| HSN334 | 99% | 1.38 ± 0.1 | 1.61 ± 0.02 |
| HSN353 | 94% | 3.45 ± 0.04 | 1.97 ± 0.1 |
| HSN352 | 93% | 3.09 ± 0.1 | 3.01 ± 0.1 |
| HSN356 | 98% | 0.42 ± 0.02 | 0.62 ± 0.02 |
| Midostaurin | 98%[a] | 18.5 ± 2.5 | 7.37 ± 0.1 |

[a]% FLT3 inhibition at 412 nM.

Example 133: Selectivity

Figure 12:
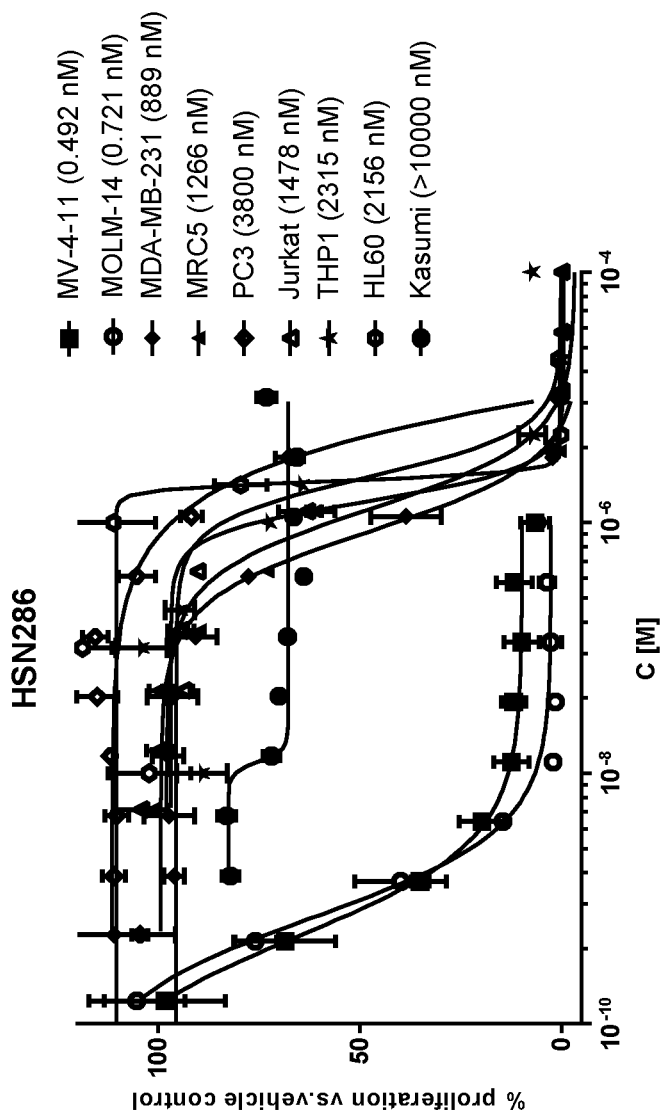
FIG. 12 depicts HSN286 (D30) activity against FLT3-driven MV4-11 and MOLM-14 but not other cancer cell lines and normal cell line, MRC5.

To test for selectivity, HSN286 was tested against various other cancer lines as well as a normal cell line (MRC5, lung fibroblast cell line) (FIG. 12). When tested against Kasumi-1, a non-FLT3 AML line, the $IC_{50}$ of HSN286 was determined to be over 10000 nM. The $IC_{50}$ values for compound HSN286 against HL60, an acute promyelocytic leukemia cell line and THP1 (another non-FLT3-driven AML line) were 2156 nM and 2315 nM respectively (i.e. more than 2000× less active against these cell lines when compared to FLT3-driven cell lines MV4-11 or MOLM-14). In addition, the $IC_{50}$ of compound HSN286 against MRC5 is 1266 nM (over 1000× less compared to $IC_{50}$ for MV4-11 or MOLM-14). It therefore appears that HSN286 is selective (at least amongst the cell lines tested) for FLT3-driven leukemia.

Example 134: Docking to Inactive Conformater

Figure 13:
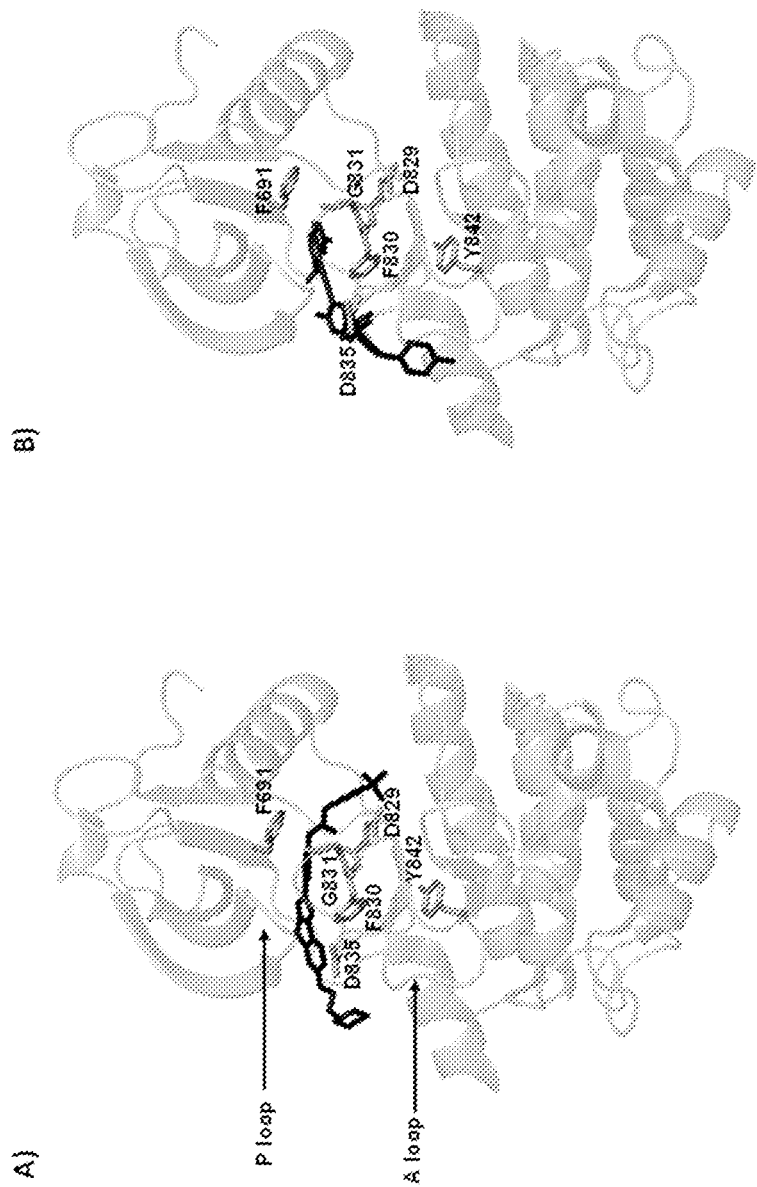
FIG. 13 depicts docked quizartinib bound to the inactive form of wild-type FLT3 (A) and docked HSN286 bound to the inactive form of wild-type FLT3 (B). PDB #4xuf. Docking was done with Autodock Vina. The docked quizartinib matched the ligand in the crystal struture of FLT3/quizartinib. Key residues D835, Y842 and F691 which when mutated block binding of FLT3 inhibitors are shown as sticks.
Figure 14:
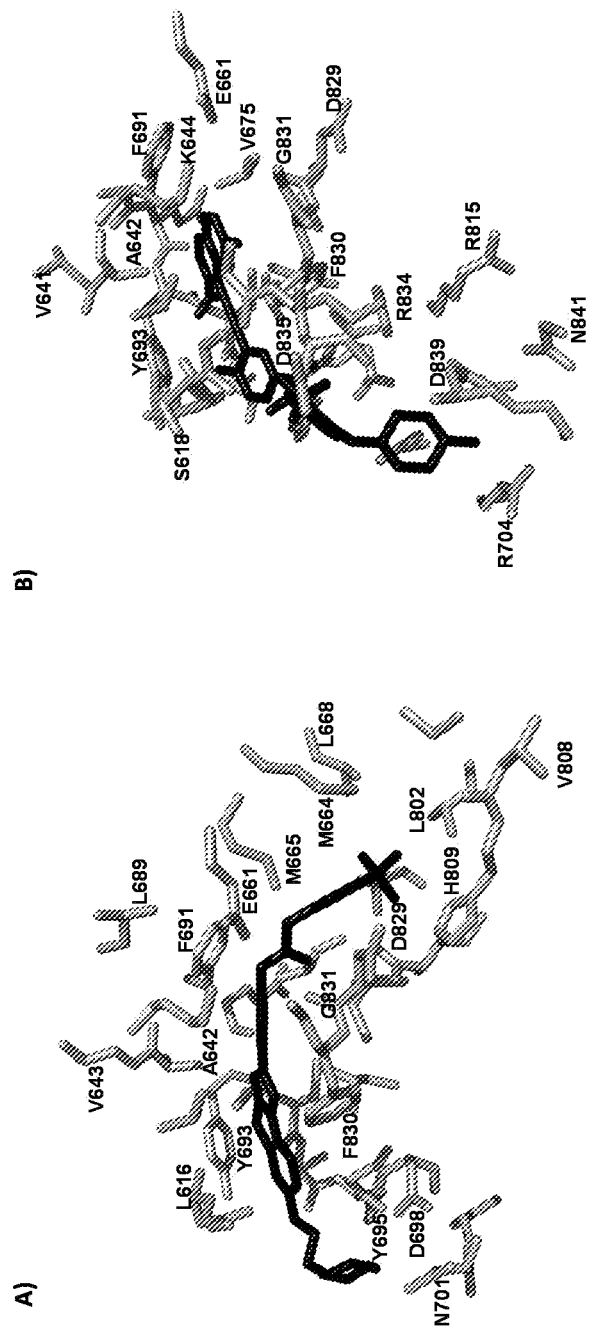
FIG. 14 depicts FLT3 residues that are within 6 Å of quizartinib in the docked structure (A) and FLT3 residues that are within 6 Å of HSN286 in the docked structure (B).
Figure 15:
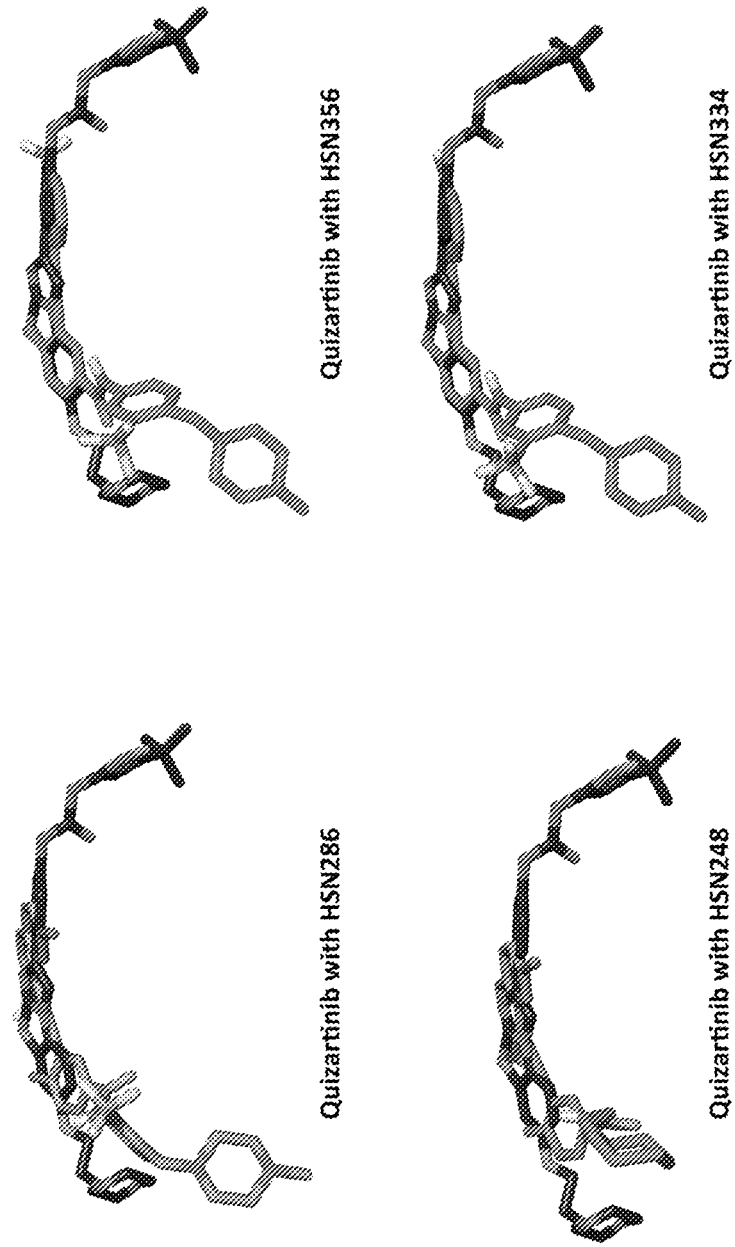
FIG. 15 depicts overlays of FLT3 binding mode of quizartinib and the compounds of the invention.

Docking [25] of HSN 286, 334, 356 and 248 to the inactive conformer of FLT3 (a crystal structure of the potent FLT3 inhibitor, quizartinib, was solved in complex with FLT3, PDB #4xuf), revealed that the compounds bind to both the ATP binding site and neighboring site (FIG. 13). The binding of the compounds partly overlap with the quizartinib binding site, but there are some differences in the binding modes (FIGS. 14 and 15).

Example 135: Binding with FLT3 Secondary Mutations

Although the current drugs on the market or in clinical trials are relatively successful in killing the AML leukemia cells, they currently are unable to deal with secondary mutations that occur after TKI treatment, such as FLT3 (D385V). The binding of HSN286, HSN336, HSN334, HSN248 and HSN247 with several FLT3 secondary mutations (Table 8) was investigated. Interestingly, HSN356 could bind to FLT3 (D835V) with a $K_d$ of 19 nM, whereas a similar compound, HSN334, was a poor binder of FLT3 (D835V) with a $K_d$ of 120 nM (Table 8).

TABLE 8

$K_d$ for isoquinoline analogs binding to FLT3, FLT3-ITD, and FLT3 (D835V), determined via DiscoverX $K_d$ Elect service

| | HSN286 | HSN356 | HSN334 | HSN178 | HSN248 |
|---|---|---|---|---|---|
| FLT3 | 6.5 nM | 1.3 nM | 5.1 nM | 53 nM | 47 nM |
| FLT 3 (IDT) | 27.6 nM | 6.7 nM | 19 nM | 450 nM | 330 nM |
| FLT3 (D835V) | 120 nM | 19 nM | 120 nM | ND | ND |

Example 136: Inhibition of Src-Family Kinases

Most kinase inhibitors that have found clinical success have been multikinase inhibitors. For example, sorafenib, used to treat kidney cancer, hepatocellular carcinoma and radioiodine-resistant thyroid cancers, also inhibits several kinases, such as RAF, MEK, ERK, VEGFR, PDGFR, FLT3, c-KIT, FGFR-1, DDR2. Dasatinib, another multikinase inhibitor is a first line treatment for CML and Ph$^+$ ALL inhibits multitudes of kinase. This includes BCR-ABL, YES, EPHA8, c-KIT, SRC, LCK, DDR2, FRK, FYN, ARG, BTK, HCK. Despite the promiscuity of these multikinase inhibitors, safe and tolerable doses have been found for cancer treatment. The successes of these multikinase inhibitors could be derived, in part, from the simultaneous inhibition of different kinases axes.

Further, it was investigated if HSN286 and its analogs also inhibited other cancer-related kinases. In addition to FLT3, the Src-family kinases (such as BLK, FGR, FYN, HCK, LYN, SRC and YES) have been shown to play critical roles in leukemia. Lopez et al. recently demonstrated that CDK6 overexpression in FTL3-ITD positive AML is achieved via the Src-family kinase, HCK (Lopez, S., et al., *Oncotarget*, 7 (23), 51163-51173 (2016)). HCK is expressed more in human primary leukemic stem cells than in human normal hematopoietic stem cells. A study showed that when HCK is targeted with small molecules the drug resistance is reduced (Ishikawa, F. el al., *Sci. Transl. Med.*, 5 (181), 181 (2013)). Other protein kinases such as SYK, BRAF, p38 (p38MAPK), PDGFRα/β, FGFR1, RET, FLT4, Tie2 have also been linked to leukemia. All this data further strengthen the consensus in the field that leukemia is a heterogeneous disease and hence targeting the aforementioned multiple kinase pathways could lead to a better outcome. Thus, it was tested if HSN286 and analogs were also targeting kinases that play critical roles in AML. The kinase screening services Reaction Biology and DiscoverX were used to characterize the inhibition of kinase activity (enzymatic activity in the presence of 500 nM of compounds). HSN286 and analogs potently inhibit FLT3 and the Src-family kinases but not other kinases such as Aurora A, CDK6 or PIK3Ca. (Table 9). The inhibition of the Src-kinase family could be important clinically because these kinases are downstream of FLT3. In the event of FLT3 mutation, the inhibition of the Src-family kinases could still lead to proliferation inhibition.

TABLE 9

$K_d$ (nM) determined via DiscoverX $K_d$ Elect service

| Kinase | HSN286 | HSN356 |
|---|---|---|
| AURKA | >30000 | 5100 |
| BLK | 3.9 | 1.2 |
| CDK6 | 28000 | ND |
| CDK9 | 2300 | ND |
| FAK | 5100 | 4700 |
| FGR | 7 | 7.9 |
| FLT3 | 7.2 | 1.3 |
| FYN | 28 | 38 |
| HCK | 3.6 | 2.5 |
| KIT | 42 | 7.2 |
| LYN | 11 | 5.4 |
| PIK3CA | 26000 | >30000 |
| PIM1 | 11000 | 19000 |
| PLK1 | >30000 | 9600 |
| SRC | 16 | 15 |

Example 137: Inhibition of FLT3 Kinase Enzymatic Activity by Midostaurin

Figure 16:
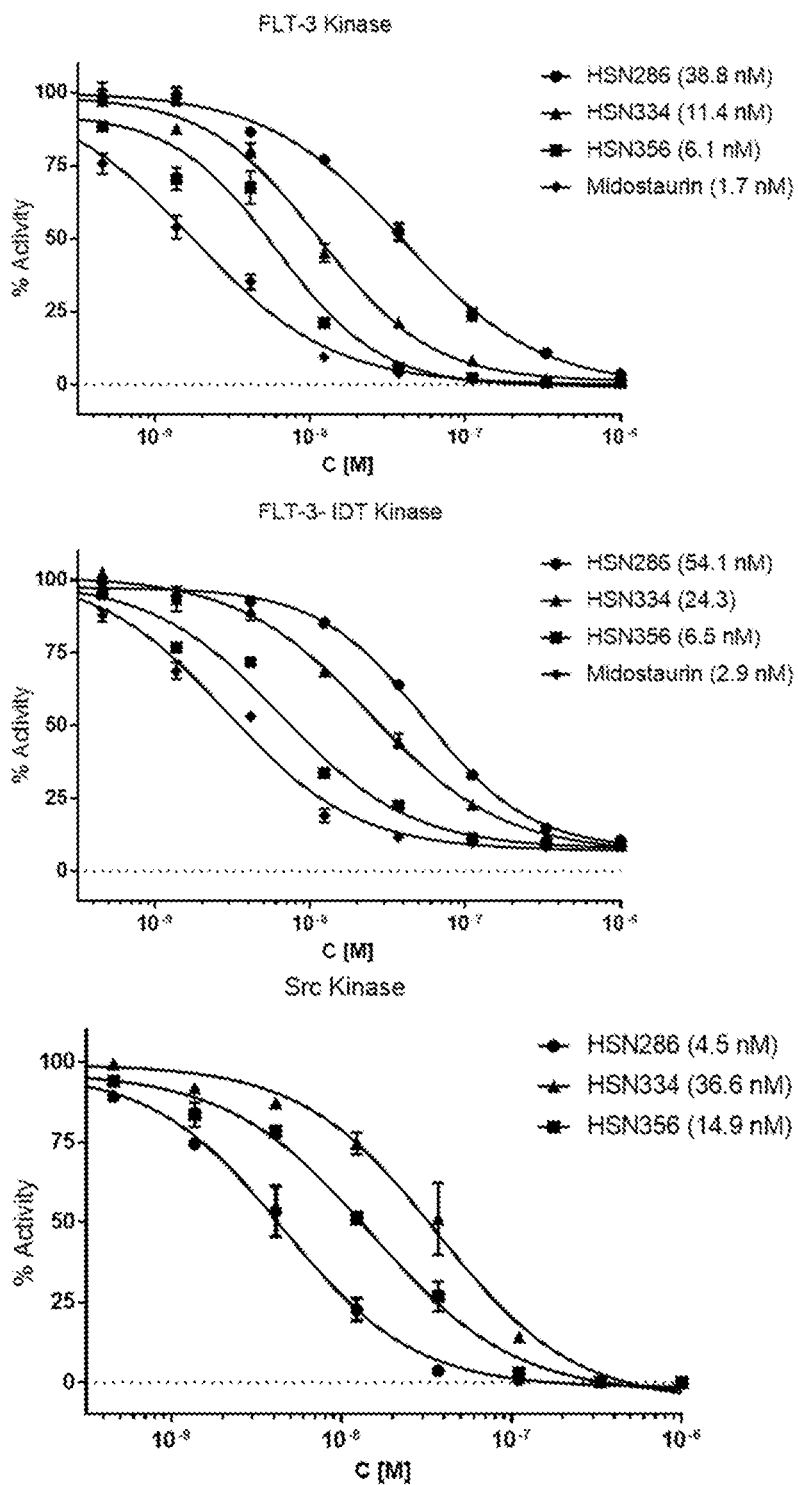
FIG. 16 depicts enzymatic inhibiton of FLT3, FLT3 ITD and Src Kinases, respectively, by the compounds of the invention.

In addition to the binding assays (Table 9), $IC_{50}$ values for the inhibition of FLT3 kinase enzymatic activity by midostaurin, HSN286, 334 and 356 were determined. All of the four compounds could inhibit FLT3 with low nanomolar values, although midostaurin and HSN356 were better than HSN286 and HSN334 (FIG. 16). Midostaurin and HSN356 inhibited FLT3 and FLT3 ITD with single digit $IC_{50}$ values. However in the case of Src kinase, HSN286 was the most potent ($IC_{50}$ of 4.5 nM). HSN356 is also an effective inhibitor of Src kinase with a $IC_{50}$ of 14.9 nM.

Example 138: Phosphorylation of FLT3 and SRC Kinase

Figure 17A:
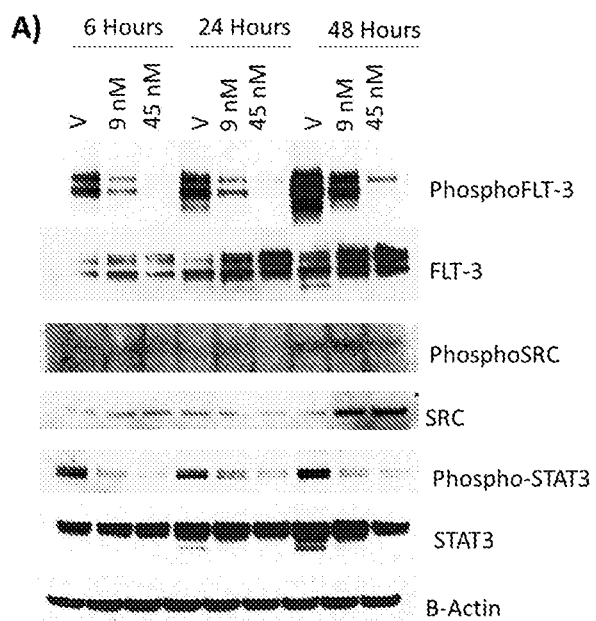
FIGS. 17A and 17B depict Western Blot analysis after treating MV4-11 with HSN286.
Figure 17B:
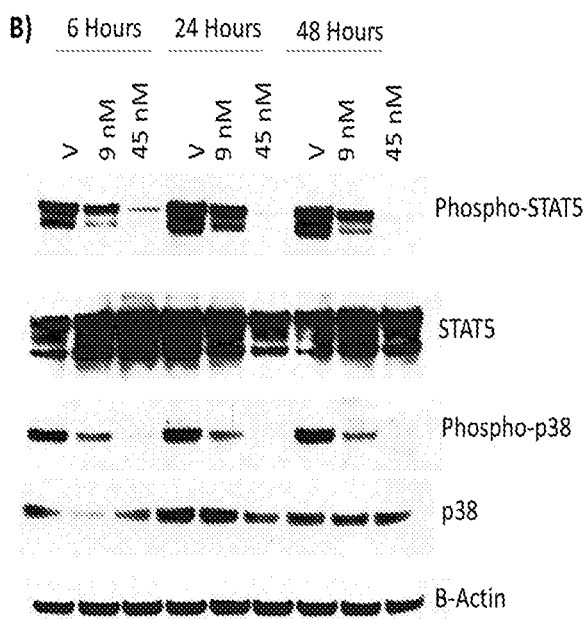

To determine if the phosphorylation of FLT3, SRC kinase and downstream effectors or kinases (such as STAT3 [44], STAT5 [45] and p-38 [46]) could be affected by the compounds, Western Blot analysis was performed on total protein obtained from MV4-11 treated with HSN286 for FLT3/phosphorylated FLT3, STAT5/phosphorylated STAT5, STAT3/phosphorylated STAT3 as well as SRC kinase/phosphorylated SRC and p-38/phosphorylated p-38 to ascertain that one could indeed target FLT3 and associated signaling axis in cells (target engagement or confirmation, FIG. 17). In line with the in-vitro kinase inhibition data, the phosphorylation of FLT3, STAT5, STAT3 and p-38 could be inhibited by HSN286 (FIG. 17). The level of SRC kinase increased over time (amount at the 48 h time point is greater than at the 6 and 24 h time points). Unfortunately the bands for the phosphorylated SRC kinase are blurred despite repeated attempts to get clearer bands. Despite the technical challenge with the phospho-SRC Western, it is conclusive that at the 48 h time point, the level of unphosphorylated SRC kinase increases as the compound HSN286 is added (compare band corresponding to vehicle to 9 and 45 nM HSN286 in FIG. 17). From the above Western analyses, it is confirmed that the proliferation inhibition of MV4-11 is due to the inhibition of FLT3 signaling axis.

The compounds of the invention are novel FLT3 inhibitors which can inhibit the problematic D835 secondary mutants. 4-alkyne substituted aminoisoquinolines (readily obtained via Sonogashira coupling) but not the related quinolines, were potent FLT3 and SRC-kinase inhibitors. Extensive structure-activity relationship (SAR) studies revealed that the FLT3 inhibition profiles and anti-proliferative activities against FLT3-driven cancer cell lines, MV4-11 and MOLM-14 were dictated by the substitution pattern and nature of benzamide. The SAR studies have led to the identification of 3-amino and 1-aminoisoquinoline benzamides, compounds D30 (HSN286), HSN334 and HSN356 as potent FLT3 kinase inhibitors. Some of these novel kinase inhibitors also inhibit the proliferation of FLT3-driven AML cell lines at concentrations as low as 500 pM. In addition to FLT3, the compounds were identified that also inhibit the Src-family kinases and FGFR kinases. It is also shown that one could combine different isoquinolines with 1-methyl-4-(2-(trifluoromethyl)benzyl)piperazine group (a privileged moiety in kinase inhibitors) to develop analogs that have different kinase selectivities (a kind of "plug-and-play" strategy). This has unveiled a new class of aminoisoquinoline benzamide kinase inhibitors, which have a high potential for clinical translation.

Example 139: Binding Constant of the Compounds of the Invention

Figure 18:
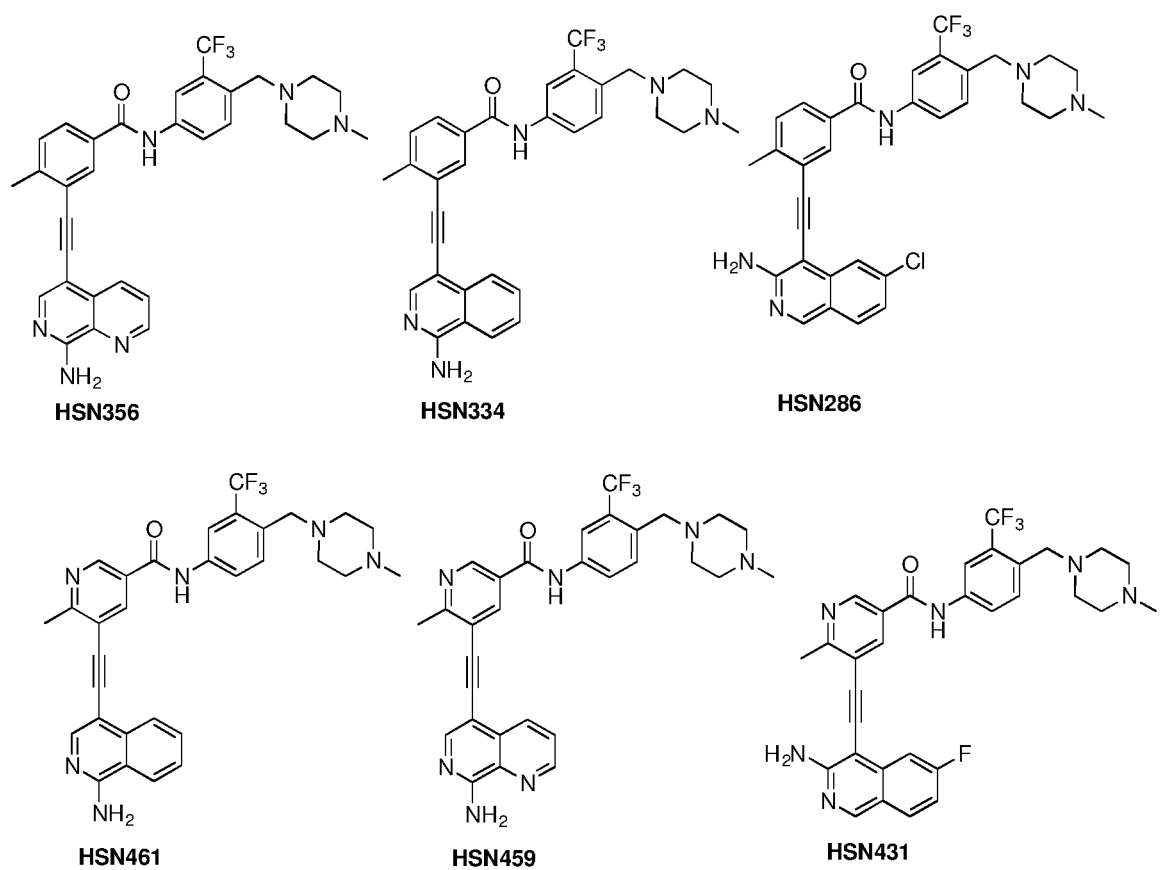
FIG. 18 depicts compounds of the invention with different substitution pattern.

Substitution pattern of aminoisoquinolines play important role in kinase binding, in-vitro and in-vivo efficacy of compounds (FIG. 18). Table 10 provides the binding constant, $K_d$ (DiscoverX KdElect) of compounds against FLT3, ABL1 and clinically relevant mutants that lead to drug resistance.

TABLE 10

Binding constant of compounds of the invention ($K_d$ unit = nM)

| Compound | FLT3 (ITD) | FLT3 (ITD, F691L) | ABL1 phosphorylated | ABL1 non-phosphorylated | ABL1 (T315I) non-phosphorylated |
|---|---|---|---|---|---|
| HSN356 | 6.7 | 28 | 1.2 | 2.5 | 2.4 |
| HSN334 | 19 | nd | 12 | 4.4 | nd |

TABLE 10-continued

Binding constant of compounds of the invention ($K_d$ unit = nM)

| Compound | FLT3 (ITD) | FLT3 (ITD, F691L) | ABL1 phosphor-ylated | ABL1 non-phosphor-ylated | ABL1 (T315I) non-phosphor-ylated |
|---|---|---|---|---|---|
| HSN286 | 26 | 110 | 7.9 | 7.2 | 29 |
| HSN461 | 7.9 | 91 | nd | nd | nd |
| HSN459 | 5.6 | 17 | nd | nd | nd |
| HSN431 | 4.8 | 57 | nd | nd | nd |
| HSN248 | 330 | 100 | 2.2 | 0.29 | 520 |

From the data in the $K_d$ Table 10, it is clear that it is possible to tune the activity of the claimed compounds towards a specific kinase or drug-resistant mutant. These compounds can therefore be developed against drug-resistant AML (such as AML harboring FLT3 (ITD, F691L) mutation or CML (harboring T315I) mutation.

Example 140: Percentage Kinase Inhibition Data

Figure 19:
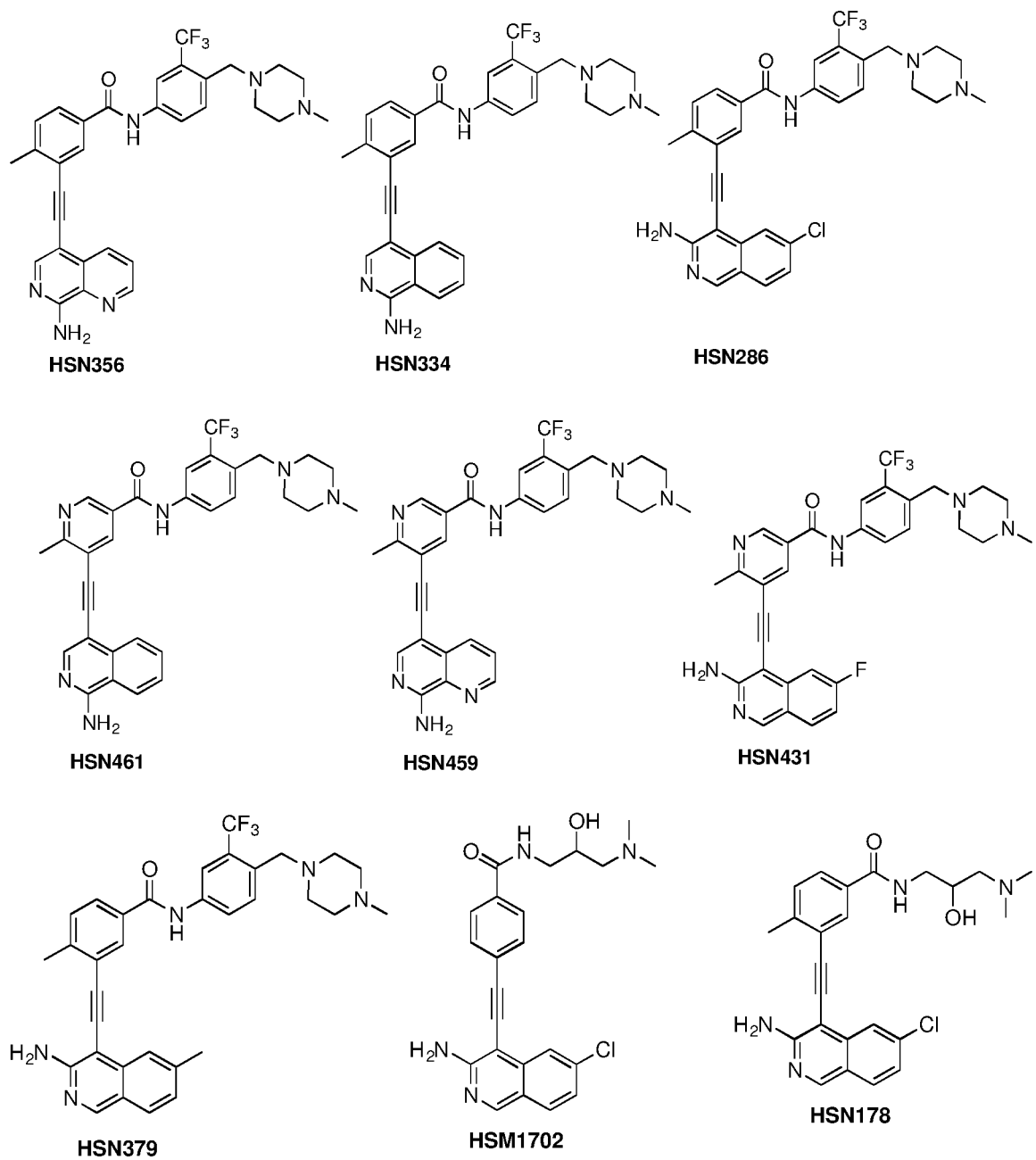
FIG. 19 depicts compounds of the invention with different substitution pattern.

To further illustrate the tenability of the claimed compounds, the inhibition of enzymatic activities of several kinases was evaluated by compounds that differ in substitution pattern (FIG. 19 and Tables 11-16) (500 nM of compounds were used, (Reaction Biology, Malvern, Pa.).

TABLE 11

Percentage Kinase Inhibition Data: HSN286, HSN325 and HSM1702

| | HSN286 | HSN325 | HSM1702 |
|---|---|---|---|
| AKT1 | 0 | 0 | 13 |
| AKT2 | 3 | 0 | 18 |
| ALK | 0 | 2 | 7 |
| Aurora A | 0 | 0 | 19 |
| AXL | 3 | 3 | 0 |
| BLK | 100 | 30 | 10 |
| BRAF | 97 | 38 | 3 |
| BRK | 92 | 0 | 18 |
| BTK | 41 | 4 | 5 |
| c-MER | 0 | 0 | 6 |
| c-Met | 20 | 15 | 4 |
| c-Src | 99 | 30 | 9 |
| CDK1/cyclin E | 0 | 0 | 13 |
| CDK2/cyclin A | 0 | 0 | 18 |
| CDK4/cyclin D1 | 0 | 0 | 16 |
| CDK6/cyclin D3 | 7 | 0 | 50 |
| CDK9/cyclin K | 24 | 7 | 53 |
| CDK9/cyclin T1 | 0 | 0 | 41 |
| CDK9/cyclin T2 | 0 | 0 | 65 |
| CSK | 93 | 0 | 1 |
| CTK/MATK | 0 | 5 | 0 |
| DDR2 | 77 | 81 | 0 |
| DNA-PK | 0 | 0 | ND |
| EGFR | 44 | 0 | 0 |
| EPHA3 | 96 | 6 | 0 |
| EPHA5 | 96 | 30 | 4 |
| EPHB2 | 96 | 3 | 5 |
| ERBB2/HER2 | 25 | 4 | 0 |
| ERBB4/HER4 | 71 | 7 | 0 |
| ERK1 | 0 | 0 | 5 |
| FAK/PTK2 | 0 | 0 | 6 |
| FER | 0 | 12 | 0 |
| FGFR1 | 98 | 58 | 11 |
| FGR | 100 | 39 | 6 |
| FLT1/VEGFR1 | 86 | 42 | 0 |
| FLT3 | 97 | 34 | 66 |
| FLT4/VEGFR3 | 98 | 42 | 10 |

TABLE 11-continued

Percentage Kinase Inhibition Data: HSN286, HSN325 and HSM1702

| | HSN286 | HSN325 | HSM1702 |
|---|---|---|---|
| FMS | 99 | 93 | 35 |
| FRK/PTK5 | 95 | 49 | 0 |
| FYN | 100 | 10 | 16 |
| HCK | 95 | 18 | 2 |
| HIPK1 | 0 | 0 | 42 |
| IGF1R | 0 | 0 | 3 |
| IKKa/CHUK | 36 | 6 | 0 |
| IR | 16 | 9 | 9 |
| IRR/INSRR | 0 | 0 | 10 |
| ITK | 0 | 1 | 0 |
| JAK2 | 67 | 0 | 0 |
| JNK1 | 7 | 0 | 0 |
| KDR/VEGFR2 | 95 | 90 | 9 |
| KSR1 | 0 | 0 | 0 |
| LRRK2 | 6 | 0 | 40 |
| LYN | 98 | 69 | 6 |
| LYN B | 95 | 35 | 0 |
| MEK1 | 0 | 2 | 0 |
| MEKK1 | 6 | 4 | 4 |
| MELK | 27 | 0 | 12 |
| MKK7 | 0 | 6 | 0 |
| MST4 | 0 | 0 | 0 |
| MUSK | 13 | 0 | 35 |
| P38a/MAPK14 | 81 | 5 | 0 |
| PAK1 | 0 | 0 | 1 |
| PDGFRa | 93 | 53 | 48 |
| PDK1/PDHK1 | 0 | 1 | 0 |
| PIM1 | 0 | 0 | 34 |
| PKCa | 5 | 5 | 3 |
| PKD2/PRKD2 | 7 | 0 | 6 |
| RAF1 | 94 | 92 | 5 |
| RET | 100 | 96 | 15 |
| ROCK1 | 0 | 3 | 0 |
| RON/MST1R | 0 | 0 | 0 |
| ROS/ROS1 | 10 | 0 | 15 |
| RSK2 | 0 | 0 | 7 |
| SYK | 0 | 0 | 4 |
| TAOK1 | 0 | 0 | 12 |
| TGFBR2 | 15 | 0 | 0 |
| TIE2/TEK | 97 | 47 | 8 |
| TRKB | 79 | 0 | 40 |
| TRKC | 91 | 4 | 81 |
| TYK2 | 0 | 0 | 2 |
| YES/YES1 | 100 | 41 | 13 |
| ZAP70 | 0 | 0 | 0 |

Other Percentage Kinase Inhibition Data: HSN286, HSN325 and HSM1702

HSN286 c-kit (61), DAPK1 (9), FGFR2 (96), FGFR3 (88), FGFR4 (82), MEKK2 (52), PDGFRb (96), RIPK2 (25), RIPK3 (96), RIPK4 (32); HSM1702 c-kit (83).

TABLE 12

Percentage Kinase Inhibition Data on HSN334, HSN356 and HSN285

| | HSN334 | HSN356 | HSN285 |
|---|---|---|---|
| AKT1 | 0 | 0 | 0 |
| ALK | 0 | 0 | 1 |
| AXL | 5 | 4 | 0 |
| BRAF | 96 | 100 | 64 |
| BTK | 46 | 65 | 0 |
| c-kit | 73 | 87 | 31 |
| c-MER | 0 | 0 | 3 |
| c-Met | 14 | 15 | 23 |
| EGFR | 61 | 59 | 0 |
| EPHA5 | 97 | 96 | 0 |
| EPHB2 | 98 | 100 | 3 |
| ERBB2/HER2 | 31 | 64 | 0 |
| FGFR1 | 96 | 96 | 0 |
| FGR | 100 | 99 | 0 |

TABLE 12-continued

Percentage Kinase Inhibition Data on HSN334, HSN356 and HSN285

|  | HSN334 | HSN356 | HSN285 |
|---|---|---|---|
| FLT1/VEGFR1 | 79 | 94 | 3 |
| FLT3 | 100 | 99 | 28 |
| FLT4/VEGFR3 | 79 | 94 | 6 |
| KDR/VEGFR2 | 94 | 97 | 15 |
| PDGFRa | 86 | 92 | 30 |
| PKCa | 0 | 0 | 6 |
| RAF1 | 96 | 100 | 90 |
| ROS/ROS1 | 0 | 0 | 0 |
| TIE2/TEK | 99 | 100 | 0 |
| TRKB | 41 | 75 | 0 |
| TRKC | ND | 59 | 0 |
| YES/YES1 | 100 | 100 | 0 |

Other Percentage Kinase Inhibition Data: HSN334, HSN356 and HSN285
HSN334 RET (100);
HSN356 RET (100);
HSN285 c-Src (0), DAPK (14), FGFR2 (0), FGFR3 (0), FGFR4 (0), MEKK2 (0), PDGFRb (46), RIPK2 (0), RIPK3 (0), RIPK4 (25).

TABLE 13

Percentage Kinase Inhibition Data: HSN248

|  | HSN248 |
|---|---|
| c-kit | 93 |
| c-Src | 23 |
| FGFR1 | 9 |
| FLT3 | 73 |
| RET | 52 |
| TRKC | 83 |

TABLE 14

Percentage Kinase Inhibition Data: HSN178

|  | HSN178 |
|---|---|
| c-Src | 1 |
| FGFR1 | 3 |
| FLT3 | 67 |
| RET | 0 |

TABLE 15

Percentage Kinase Inhibit ion Data: HSN247

|  | HSN247 |
|---|---|
| c-kit | 86 |
| c-Src | 3 |
| FGFR1 | 6 |
| FET3 | 75 |
| RET | 3 |
| TRKC | 77 |

TABLE 16

Percentage Kinase Inhibition Data: HSN353 and HSN352

|  | HSN353 | HSN352 |
|---|---|---|
| c-kit | 82 | 78 |
| c-Src | 98 | 100 |
| FGFR1 | 93 | 100 |
| FLT3 | 94 | 93 |

Example 141: In Vivo Efficacy Study

Figure 20:
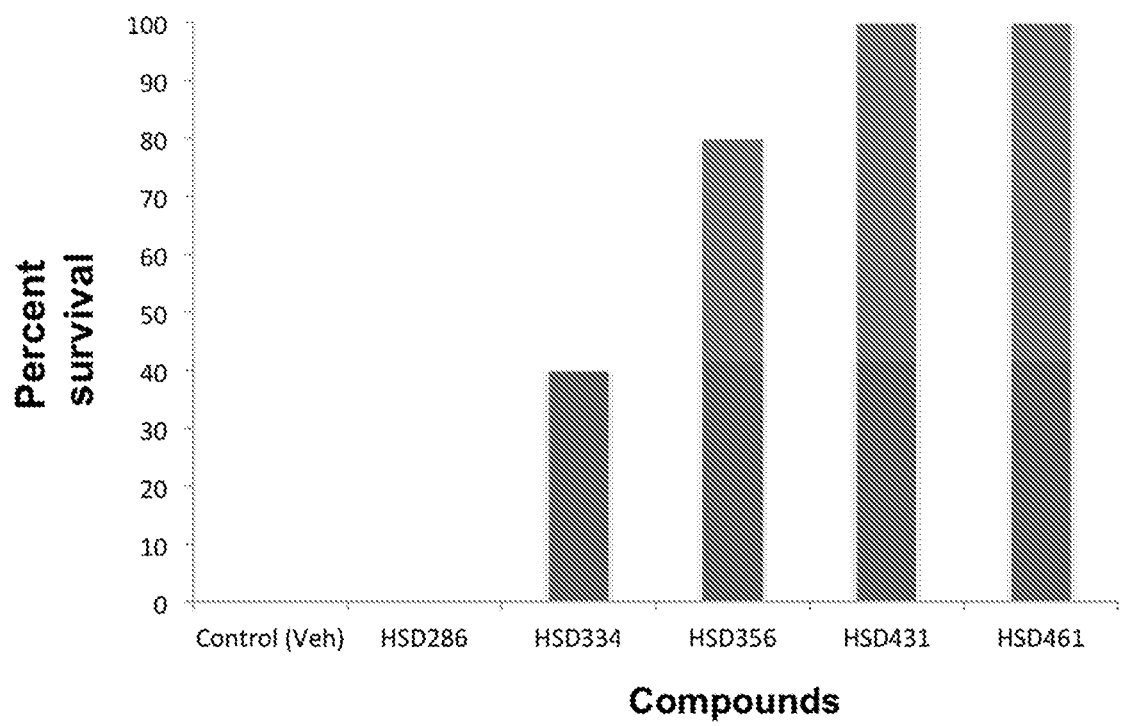
FIG. 20 depicts the percent survival at day 60 of NSG mice injected with AML cell line MV4-11 and treated with various compounds at 25 mg/Kg, 3×/week.

The in-vitro efficacies of HSN356, HSN334, HSN286, HSN461 and HSN431 against AML cell line MV4-11 are similar (all have IC50<1 nM against MV4-11) yet the compounds have differing potencies in-vivo. For example HSN286 and HSN286 are both 3-aminoisoquinolines but HSN286 is not efficacious in-vivo whereas HSN431 is efficacious (FIG. 20). Also HSN334 only differs from HSN356 and HSN461 via a carbon to nitrogen but the percent survival of mice injected with MV4-11 cell lines of HSN334 is different from both HSN356 and HSN461.

Method: Six week old female NSG mice were injected intravenously with $1\times10^6$ logarithimically growing MV4-11 cells expressing luciferase (MV4-11). Luciferase expressing leukemia cells were imaged using the IVIS Xenogen system (Perkin Elmer, Waltham Mass.). On day of imaging, mice are injected IP with 150 mg/kg luciferin (Perkin Elmer, Waltham, Mass.), anaesthetized and then placed in imaging chamber. Maximal luminescence is recorded and then averaged among each treatment group. Ten days post cell injection, mice were imaged and then sorted into groups so that leukemic burden was similar and dosing started. Mice were dosed either with vehicle (10% DMSO/10% Tween 20/80% saline) or 25 mg/kg of compounds three times per week for the duration of the experiment. Mice were weighed and observed five days per week and imaged once per week.

Example 142: Activity Against Lung Cancer

In addition to AML, the compounds of the invention are also active against several other cancers. For example the claimed compounds are active against lung cancer (Table 17). This is to be expected since the compounds can be tuned to inhibit different kinases, which drive specific tumors (Tables 11-16).

TABLE 17

IC50 against NCI H1703 (NSCLC)/nM

| Compound | IC50 against NCI H1703 (NSCLC)/nM |
|---|---|
| HSN356 | 88 |
| HSN379 | 13 |
| HSN334 | 98 |
| HSN286 | 50 |
| HSN459 | 38 |
| HSN461 | 157 |
| HSN431 | 247 |

Example 143: Inhibition of Proliferation of K562 Cell Lines (CML)

The compounds of the invention potently inhibit proliferation of K562 cell lines (CML) (Table 18).

TABLE 18

| Inhibition of Proliferation of K562 Cell Lines (CML) | |
|---|---|
| HSL41 | 30.1 ± 0.19 nM |
| HSL45 | 25.3 ± 0.1 nM |
| HSL58 | 94.5 ± 0.1 nM |
| HSN178 | 1443 ± 0.21 nM |
| HSN285 | 1102 ± 0.08 nM |
| HSN316 | 913 ± 0.1 nM |
| HSN334 | 6.1 ± 0.1 nM |
| HSN356 | 1.8 ± 0.03 nM |
| HSL43 | 10.1 ± 0.1 nM |
| HSL47 | 161.1 ± 0.11 nM |
| HSL64 | 1932 ± 0.41 nM |
| HSN247 | 25.7 ± 0.31 nM |
| HSN286 | 3.5 ± 0.02 nM |
| HSN317 | 1483 ± 0.1 nM |
| HSN352 | 2.4 ± 0.06 nM |
| HSN375 | 8.8 ± 0.4 nM |
| HSL44 | 43.5 ± 0.14 nM |
| HSL56 | 95.4 ± 0.23 nM |
| HSM1702 | 5057 ± 0.45 nM |
| HSN248 | 7.0 ± 0.1 nM |
| HSN315 | 203 ± 0.1 nM |
| HSN325 | 44 ± 0.1 nM |
| HSN353 | 5.2 ± 0.02 nM |
| HSN393 | 7.3 ± 0.04 nM |

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be.

What is claimed is:

1. A compound represented by a formula of HSN608:

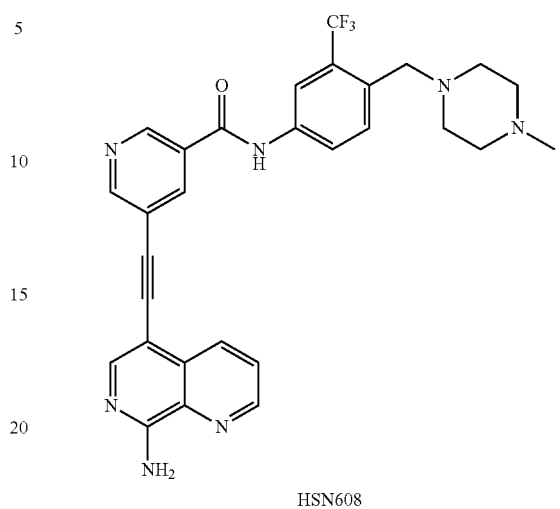

HSN608 or a pharmaceutically acceptable salt, N-oxide, hydrate, solvate, tautomer or optical isomer thereof.

2. A pharmaceutical composition comprising a compound of claim 1, or a pharmaceutically acceptable salt, N-oxide, hydrate, solvate, tautomer, or optical isomer thereof, and a pharmaceutically acceptable carrier or diluent.

* * * * *